(12) United States Patent
Eden et al.

(10) Patent No.: US 11,450,406 B2
(45) Date of Patent: *Sep. 20, 2022

(54) COMPUTATIONAL ANALYSIS OF BIOLOGICAL DATA USING MANIFOLD AND A HYPERPLANE

(71) Applicant: MeMed Diagnostics Ltd., Tirat HaCarmel (IL)

(72) Inventors: Eran Eden, Haifa (IL); Kfir Oved, Hof HaCarmel (IL); Roy Navon, Tel-Aviv (IL); Assaf Cohen-Dotan, Natania (IL); Olga Boico, Haifa (IL)

(73) Assignee: MeMed Diagnostics Ltd., Tirat HaCarmel (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/998,006

(22) Filed: Aug. 20, 2020

(65) Prior Publication Data
US 2020/0388347 A1    Dec. 10, 2020

Related U.S. Application Data

(60) Division of application No. 16/355,984, filed on Mar. 18, 2019, now Pat. No. 11,081,206, which is a
(Continued)

(51) Int. Cl.
*G16B 5/20* (2019.01)
*G16B 5/00* (2019.01)
(Continued)

(52) U.S. Cl.
CPC ............ *G16B 5/20* (2019.02); *G06F 17/18* (2013.01); *G16B 5/00* (2019.02); *G16B 20/00* (2019.02);
(Continued)

(58) Field of Classification Search
CPC .................. G06N 33/56983; G01N 33/56911
See application file for complete search history.

(56) References Cited

U.S. PATENT DOCUMENTS

| | | | |
|---|---|---|---|
| 5,639,617 A | 6/1997 | Bohuon | |
| 5,910,421 A | 6/1999 | Small, Jr. et al. | |

(Continued)

FOREIGN PATENT DOCUMENTS

| | | |
|---|---|---|
| CN | 1656378 | 8/2005 |
| CN | 101208602 | 6/2008 |

(Continued)

OTHER PUBLICATIONS

Communication Pursuant to Article 94(3) EPC dated Nov. 12, 2020 From the European Patent Office Re. Application No. 17759389.4. (6 Page).

(Continued)

*Primary Examiner* — Nicholas J Tobergte

(57) ABSTRACT

A method of analyzing biological data containing expression values of a plurality of polypeptides in the blood of a subject. The method comprises: calculating a distance between a segment of a curved line and an axis defined by a direction, the distance being calculated at a point over the curved line defined by a coordinate along the direction. The method further comprises correlating the distance to the presence of, absence of, or likelihood that the subject has, a bacterial infection. The coordinate is defined by a combination of the expression values, wherein at least 90% of the segment is between a lower bound line and an upper bound line.

24 Claims, 66 Drawing Sheets

Specification includes a Sequence Listing.

Related U.S. Application Data continuation of application No. 15/503,439, filed as application No. PCT/IL2015/050823 on Aug. 12, 2015, now Pat. No. 10,303,846.

(60) Provisional application No. 62/105,938, filed on Jan. 21, 2015, provisional application No. 62/037,180, filed on Aug. 14, 2014.

(51) Int. Cl.

| | | |
|---|---|---|
| *G16B 20/00* | (2019.01) | |
| *G16B 40/00* | (2019.01) | |
| *G16B 20/20* | (2019.01) | |
| *G16B 40/30* | (2019.01) | |
| *G16B 25/10* | (2019.01) | |
| *G16B 40/20* | (2019.01) | |
| *G16H 50/50* | (2018.01) | |
| *G06F 17/18* | (2006.01) | |
| *G16B 25/00* | (2019.01) | |
| *G01N 33/569* | (2006.01) | |

(52) U.S. Cl.
CPC ............ *G16B 20/20* (2019.02); *G16B 25/10* (2019.02); *G16B 40/00* (2019.02); *G16B 40/20* (2019.02); *G16B 40/30* (2019.02); *G16H 50/50* (2018.01); *G01N 33/56911* (2013.01); *G01N 33/56983* (2013.01); *G16B 25/00* (2019.02); *Y02A 90/10* (2018.01)

(56) References Cited

U.S. PATENT DOCUMENTS

| | | |
|---|---|---|
| 6,077,665 A | 6/2000 | Welrich et al. |
| 6,136,526 A | 10/2000 | Venge |
| 6,210,661 B1 | 4/2001 | Enssle et al. |
| 6,709,855 B1 | 3/2004 | Stanton et al. |
| 6,756,483 B1 | 6/2004 | Bergmann et al. |
| 6,953,435 B2 | 10/2005 | Kondo et al. |
| 7,115,717 B2 | 10/2006 | Mori et al. |
| 7,132,246 B2 | 11/2006 | Bergmann et al. |
| 7,153,662 B2 | 12/2006 | Bergmann et al. |
| 7,157,081 B2 | 1/2007 | Bergmann et al. |
| 7,598,031 B2 | 10/2009 | Lew |
| 7,629,116 B2 | 12/2009 | Ott |
| 7,892,539 B2 | 2/2011 | Winoto et al. |
| 8,021,836 B2 | 9/2011 | Kolopp-Sarda et al. |
| 8,465,951 B2 | 6/2013 | Rao et al. |
| 8,507,210 B2 | 8/2013 | Bergmann et al. |
| 8,563,476 B2 | 10/2013 | Lillard, Jr. |
| 8,697,370 B2 | 4/2014 | Kas et al. |
| 8,821,876 B2 | 9/2014 | Ginsburg et al. |
| 9,034,328 B2 | 5/2015 | Takahashi |
| 9,709,565 B2 | 7/2017 | Eden et al. |
| 9,726,668 B2 | 8/2017 | Oved et al. |
| 9,850,539 B2 | 12/2017 | Tsalik et al. |
| 10,209,260 B2 | 2/2019 | Oved et al. |
| 10,303,846 B2 * | 5/2019 | Eden ............... G16B 25/10 |
| 10,502,739 B2 | 12/2019 | Oved et al. |
| 10,859,574 B2 | 12/2020 | Oved et al. |
| 2004/0038201 A1 | 2/2004 | Nau et al. |
| 2004/0043379 A1 | 3/2004 | Hashimoto et al. |
| 2004/0171013 A1 | 9/2004 | Lilius et al. |
| 2005/0227223 A1 | 10/2005 | Miyawaki |
| 2005/0233395 A1 | 10/2005 | Weiser et al. |
| 2006/0052278 A1 | 3/2006 | Powell |
| 2006/0099628 A1 | 5/2006 | Ching et al. |
| 2006/0246495 A1 | 11/2006 | Garrett et al. |
| 2007/0015172 A1 | 1/2007 | Zhang et al. |
| 2007/0184460 A1 | 8/2007 | Ching et al. |
| 2007/0231816 A1 | 10/2007 | Chaussabel et al. |
| 2007/0281319 A1 | 12/2007 | Kolopp-Sarda et al. |
| 2008/0020379 A1 | 1/2008 | Agan et al. |
| 2008/0064113 A1 | 3/2008 | Goix et al. |
| 2008/0171323 A1 | 7/2008 | Banchereau et al. |
| 2009/0155180 A1 | 6/2009 | Jump et al. |
| 2009/0203534 A1 | 8/2009 | Hossain et al. |
| 2010/0028874 A1 | 2/2010 | Ramachandran et al. |
| 2010/0068147 A1 | 3/2010 | Hibberd et al. |
| 2010/0143372 A1 | 6/2010 | Yao et al. |
| 2010/0267569 A1 | 10/2010 | Salmon et al. |
| 2010/0297611 A1 | 11/2010 | Sambursky et al. |
| 2011/0059858 A1 | 3/2011 | Kas et al. |
| 2011/0117563 A1 | 5/2011 | Filipowicz et al. |
| 2011/0166166 A1 | 7/2011 | Henkin |
| 2011/0183856 A1 | 7/2011 | Agan et al. |
| 2011/0275542 A1 | 11/2011 | Eden et al. |
| 2011/0312534 A1 | 12/2011 | Kayser et al. |
| 2013/0309168 A1 | 11/2013 | Ho |
| 2014/0127827 A1 | 5/2014 | Kim et al. |
| 2014/0206016 A1 | 7/2014 | Lozano Sanchez et al. |
| 2014/0227324 A1 | 8/2014 | Robinson et al. |
| 2015/0017630 A1 | 1/2015 | Oved et al. |
| 2016/0153993 A1 | 6/2016 | Eden et al. |
| 2017/0030909 A1 | 2/2017 | Oved et al. |
| 2017/0234873 A1 | 8/2017 | Oved et al. |
| 2017/0235871 A1 | 8/2017 | Eden et al. |
| 2017/0269081 A1 | 9/2017 | Oved et al. |
| 2018/0074057 A1 | 3/2018 | Eden et al. |
| 2019/0011456 A1 | 1/2019 | Oved et al. |
| 2019/0041388 A1 | 2/2019 | Oved et al. |
| 2019/0085378 A1 | 3/2019 | Eden et al. |
| 2019/0120837 A1 | 4/2019 | Eden et al. |
| 2019/0161813 A1 | 5/2019 | Oved et al. |
| 2019/0237156 A1 | 8/2019 | Eden et al. |
| 2019/0242894 A1 | 8/2019 | Oved et al. |
| 2019/0242895 A1 | 8/2019 | Eden et al. |
| 2019/0271709 A1 | 9/2019 | Eden et al. |
| 2019/0339189 A1 | 11/2019 | Takeda et al. |
| 2020/0088728 A1 | 3/2020 | Oved et al. |
| 2020/0124593 A1 | 4/2020 | Oved et al. |
| 2020/0393463 A1 | 12/2020 | Oved et al. |
| 2020/0400668 A1 | 12/2020 | Eden et al. |
| 2022/0011320 A1 | 1/2022 | Eden et al. |
| 2022/0042994 A1 | 2/2022 | Oved et al. |

FOREIGN PATENT DOCUMENTS

| | | |
|---|---|---|
| CN | 101479389 | 7/2009 |
| CN | 101523217 | 9/2009 |
| CN | 101541976 | 9/2009 |
| CN | 101611314 | 12/2009 |
| CN | 101617056 | 12/2009 |
| CN | 101617230 | 12/2009 |
| CN | 101622364 | 1/2010 |
| CN | 101790687 | 7/2010 |
| CN | 101932940 | 12/2010 |
| CN | 102081101 | 6/2011 |
| CN | 102257386 | 11/2011 |
| CN | 102301002 | 12/2011 |
| CN | 102858991 | 1/2013 |
| CN | 103097891 | 5/2013 |
| CN | 103119444 | 5/2013 |
| CN | 104126125 | 10/2014 |
| CN | 104204803 | 12/2014 |
| CN | 104204808 | 12/2014 |
| CN | 104969071 | 10/2015 |
| CN | 105556308 | 5/2016 |
| EP | 1489416 | 12/2004 |
| JP | 2005-106694 | 4/2005 |
| JP | 2007-518062 | 7/2007 |
| JP | 2008-502908 | 1/2008 |
| JP | 2011-069696 | 4/2011 |
| KR | 10-2016-0072626 | 6/2016 |
| RU | 2007122617 | 12/2008 |
| RU | 2011111875 | 10/2012 |
| UA | 78641 | 3/2013 |
| UA | 92843 | 9/2014 |
| WO | WO 95/29404 | 11/1995 |
| WO | WO 99/33965 | 7/1999 |
| WO | WO 99/60171 | 11/1999 |
| WO | WO 01/14535 | 3/2001 |
| WO | WO 2004/108899 | 12/2004 |

(56) References Cited

FOREIGN PATENT DOCUMENTS

| | | |
|---|---|---|
| WO | WO2005/033327 | 4/2005 |
| WO | WO 2006/009702 | 1/2006 |
| WO | WO 2007/011412 | 1/2007 |
| WO | WO 2007/088355 | 8/2007 |
| WO | WO 2007/127801 | 11/2007 |
| WO | WO 2008/024642 | 2/2008 |
| WO | WO 2009/015821 | 2/2009 |
| WO | WO 2009/021521 | 2/2009 |
| WO | WO 2009/025743 | 2/2009 |
| WO | WO 2009/077864 | 6/2009 |
| WO | WO 2009/100907 | 8/2009 |
| WO | WO 2009/130176 | 10/2009 |
| WO | WO 2009/158521 | 12/2009 |
| WO | WO 2010/056637 | 5/2010 |
| WO | WO 2011/008349 | 1/2011 |
| WO | WO 2011/017682 | 2/2011 |
| WO | WO 2011/132086 | 10/2011 |
| WO | WO 2013/040062 | 3/2013 |
| WO | WO 2013/117746 | 8/2013 |
| WO | WO 2014/006408 | 1/2014 |
| WO | WO 2014/008545 | 1/2014 |
| WO | WO 2014/049255 | 4/2014 |
| WO | WO 2014/117873 | 8/2014 |
| WO | WO 2015/048098 | 4/2015 |
| WO | WO 2016/024278 | 2/2016 |
| WO | WO 2016/059636 | 4/2016 |
| WO | WO 2016/079219 | 5/2016 |
| WO | WO 2016/092554 | 6/2016 |
| WO | WO 2017/149547 | 9/2017 |
| WO | WO 2017/149548 | 9/2017 |
| WO | WO 2017/221255 | 12/2017 |
| WO | WO 2018/011795 | 1/2018 |
| WO | WO 2018/011796 | 1/2018 |
| WO | WO 2018/060998 | 4/2018 |
| WO | WO 2018/060999 | 4/2018 |

OTHER PUBLICATIONS

Official Action dated Nov. 23, 2020 From the US Patent and Trademark Office Re. U.S. Appl. No. 16/355,984. (9 pages).
Notification of Office Action and Search Report dated Jun. 3, 2021 From the State Intellectual Property Office of the People's Republic of China Re. Application No. 20180014541.1 and Its Translation Into English. (17 Pages).
Notice of Reasons for Rejection dated Apr. 20, 2021 From the Japan Patent Office Re. Application No. 2020-021606 and Its Translation Into English. (9 Pages).
Official Action dated May 5, 2021 From the US Patent and Trademark Office Re. U.S. Appl. No. 16/336,528. (108 Pages).
Second Notice of Allowance dated May 12, 2021 From the US Patent and Trademark Office Re. U.S. Appl. No. 16/355,984. (32 Pages).
Brost et al. "Differential Expression of the TRAIL/TRAIL-receptor System in Patients with Inflammatory Bowel Disease", Pathology—Rescarch and Practice, 206(1):43-50, Jan. 15, 2010.
European Search Report and the European Search Opinion dated Jul. 14, 2021 From the European Patent Office Re. Application No. 21170448.1. (6 Pages).
Notice of Allowance Dated and Interview Summary dated Jul. 19, 2021 from the US Patent and Trademark Office Re. U.S. Appl. No. 16/687,726. (24 pages).
Translation dated Jul. 22, 2021 of Notification of Office Action dated Jul. 13, 2021 From the State Intellectual Property Office of the People's Republic of China Re. Application No. 20180781584.9. (2 Pages).
Translation dated Jul. 27, 2021 of Notification of Office Action dated Jul. 2, 2021 From the State Intellectual Property Office of the People's Republic of China Re. Application No. 201780055014.5. (12 Pages).
Official Action dated Nov. 4, 2020 From the US Patent and Trademark Office Re. U.S. Appl. No. 16/238,582. (37 Pages).

Patent Examination Report dated Feb. 8, 2021 From the Australian Government, IP Australia Re. Application No. 2015302870. (4 Pages).
Final Official Action dated Sep. 3, 2021 From the US Patent and Trademark Office Re. U.S. Appl. No. 16/316,631. (37 Pages).
Final Official Action dated Sep. 8, 2020 from the US Patent and Trademark Office Re. U.S. Appl. No. 16/687,726. (28 pages).
Restriction Official Action dated Sep. 10, 2020 from the US Patent and Trademark Office Re. U.S. Appl. No. 16/316,631. (6 pages).
Communication Pursuant to Article 94(3) EPC dated Mar. 17, 2021 From the European Patent Office Re. Application No. 15868614.7. (5 Pages).
Final Official Action dated Jun. 15, 2021 From the US Patent and Trademark Office Re. U.S. Appl. No. 16/334,033. (36 Pages).
Notice of Reason(s) for Rejection dated Jun. 15, 2021 From the Japan Patent Office Re. Application No. 2020-109710 and Its Translation Into English. (12 Pages).
Notification of Office Action dated Sep. 1, 2021 From the State Intellectual Property Office of the People's Republic of China Re. Application No. 201780014568.0 and Its Translation Into English. (7 Pages).
Communication Pursuant to Article 94(3) EPC dated Sep. 25, 2020 From the European Patent Office Re. Application No. 17827122.7. (5 Pages).
European Search Report and the European Search Opinion dated Sep. 28, 2020 From the European Patent Office Re. Application No. 20164056.2. (10 Pages).
Interview Summary dated Oct. 14, 2020 from the US Patent and Trademark Office Re. U.S. Appl. No. 16/081,906. (3 pages).
Official Action dated Oct. 20, 2020 From the US Patent and Trademark Office Re. U.S. Appl. No. 16/081,069. (112 Pages).
ThermoFisher Scientific "Interferon Alpha Inducible Protein 27: IFI27", ThermoFisher Scientific, Product Details, 2 P., 2020.
ThermoFisher Scientific "Interferon Induced Protein 44 Like: IFI44L", ThermoFisher Scientific, Product Details, 2 P., 2020.
ThermoFisher Scientific "TaqMan Gene Expression Assay Solutions: Proven 5' Nuclease-Based Real-Time PCR Chemistry", Thermo Fisher Scientific, Applied Biosystems, 11 P., 2015.
Zaas et al. Supplementary Materials for "A Host-Based RT-PCR Gene Expression Signature to Identify Acute Respiratory Viral Infection", Science Translational Medicine, 5(203): 203ra126-1-203ra126-21, Sep. 18, 2013.
Notification of Office Action and Search Report dated Jul. 2, 2021 From the State Intellectual Property Office of the People's Republic of China Re. Application No. 201780055014.5. (23 Pages).
Notification of Office Action and Search Report dated Jul. 13, 2021 From the State Intellectual Property Office of the People's Republic of China Re. Application No. 20180781584.9 and an English Summary. (4 Pages).
Interview Summary dated Feb. 1, 2021 From the US Patent and Trademark Office Re. U.S. Appl. No. 16/687,726. (2 Pages).
Examination Report Under Sections 12 & 13 of the Patents Act, 1970 and the Patents Rules, 2003 dated Mar. 31, 2021 From the Government of India, Intellectual Property India, Patents, Designs, Trade Marks, Geographical Indications, The Patent Office Re. Application No. 201727005513. (7 Pages).
Notice of Allowance dated Apr. 19, 2021 from the US Patent and Trademark Office Re. U.S. Appl. No. 16/238,582. (22 pages).
Bloos et al. "Rapid Diagnosis of Sepsis"; Virulence, 5(1): 154-160, 2014.
Henriquez-Camacho et al. "Biomarkers for Sepsis"; BioMed Research International, 547818: 6 pages, 2014.
Notification of Office Action and Search Report dated Feb. 20, 2021 From the State Intellectual Property Office of the People's Republic of China Re. Application No. 201780014568.0. (9 Pages).
Requisition by the Examiner dated Jul. 30, 2021 From the Innovation, Science and Economic Development Canada, Canadian Intellectual Property Office Re. Application No. 2,954,601. (4 Pages).
Notification of Office Action dated Mar. 5, 2021 From the State Intellectual Property Office of the People's Republic of China Re. Application No. 201810781584.9 and Its Translation of Office Action Into English. (13 Pages).

(56) References Cited

OTHER PUBLICATIONS

Official Action dated Mar. 9, 2021 From the US Patent and Trademark Office Re. U.S. Appl. No. 16/316,631. (121 Pages).
Official Action dated Mar. 10, 2021 From the US Patent and Trademark Office Re. U.S. Appl. No. 16/081,906. (127 Pages).
Shair et al. "Epstein-Barr Vitus Latent Membrane Protein-1 Effects on Junctional Plakoglobin and Induction of a Cadherin Switch", Cancer Research, Cell, Tumor, and Stem Cell Biology, 69(14): 5734-5742, Jul. 15, 2009.
European Search Report and the European Search Opinion dated Oct. 6, 2021 From the European Patent Office Re. Application No. 21178885.6. (10 Pages).
Notification of Office Action and Search Report dated Aug. 3, 2021 From the State Intellectual Property Office of the People's Republic of China Re. Application No. 201780055347.8 and Its Translation of Office Action Into English. (526Pages).
Zhang et al. "Expression of Tumor Necrosis Factor-Related Apoptosis-Inducing Ligand in Serum of Severe Hepatitis Patients with Nosocomial Infections and its Clinical Significance", Chinese Journal of Nosocomiology, 24, Abstract, 2012.
Advisory Action Before the Filing of an Appeal Brief dated Dec. 23, 2019 From the US Patent and Trademark Office Re. U.S. Appl. No. 16/157,193. (3 pages).
Applicant-Initiated Interview Summary dated Jul. 6, 2016 From the US Patent and Trademark Office Re. U.S. Appl. No. 14/377,887.
Applicant-Initiated Interview Summary dated Feb. 10, 2020 From the US Patent and Trademark Office Re. U.S. Appl. No. 16/157,193. (3 pages).
Applicant-Initiated Interview Summary dated Jul. 17, 2015 From the US Patent and Trademark Office Re. U.S. Appl. No. 13/090,893.
Applicant-Initiated Interview Summary dated Feb. 22, 2017 From the US Patent and Trademark Office Re. U.S. Appl. No. 14/377,887. (3 Pages).
Applicant-Initiated Interview Summary dated Oct. 26, 2017 From the US Patent and Trademark Office Re. U.S. Appl. No. 15/237,728. (3 pages).
Applicant-Initiated Interview Summary dated Jul. 30, 2018 From the US Patent and Trademark Office Re. U.S. Appl. No. 15/641,400. (3 pages).
Communication Pursuant to Article 94(3) EPC dated Jun. 4, 2020 From the European Patent Office Re. Application No. 17759388.6. (3 Pages).
Communication Pursuant to Article 94(3) EPC dated May 7, 2019 From the European Patent Office Re. Application No. 15831781.8. (3 Pages).
Communication Pursuant to Article 94(3) EPC dated Dec. 9, 2016 From the European Patent Office Re. Application No. 13703112.6. (4 Pages).
Communication Pursuant to Article 94(3) EPC dated Oct. 9, 2018 From the European Patent Office Re. Application No. 11748712.4. (8 Pages).
Communication Pursuant to Article 94(3) EPC dated Jun. 17, 2016 From the European Patent Office Re. Application No. 11748712.4.
Communication Pursuant to Article 94(3) EPC dated Mar. 25, 2020 From the European Patent Office Re. Application No. 18162713.4. (5 Pages).
Communication Pursuant to Article 94(3) EPC dated May 25, 2020 From the European Patent Office Re. Application No. 11748712.4. (7 Pages).
Communication Pursuant to Article 94(3) EPC dated Mar. 27, 2020 From the European Patent Office Re. Application No. 15868614.7. (6 Pages).
Communication Pursuant to Article 94(3) EPC dated Jul. 31, 2019 From the European Patent Office Re. Application No. 18162713.4. (4 Pages).
European Search Report and the European Search Opinion dated May 16, 2018 From the European Patent Office Re. Application No. 18162713.4. (7 Pages).
Examination Report dated Oct. 6, 2017 From the Australian Government, IP Australia Re. Application No. 2013217935. (2 Pages).
Examination Report dated May 29, 2019 From the Australian Government, IP Australia Re. Application No. 2018202302. (5 Pages).
Examination Report Under Sections 12 & 13 of the Patents Act, 1970 and the Patents Rules, 2003 dated Oct. 21, 2019 From the Government of India, Intellectual Property India, Patents, Designs, Trade Marks, Geographical Indications Re. Application No. 9122/DELNP/2012 (5 Pages).
Examination Report Under Sections 12 & 13 of the Patents Act, 1970 and the Patents Rules, 2003 dated Mar. 26, 2018 From the Government of India, Intellectual Property India, Patents, Designs, Trade Marks, Geographical Indications Re. Application No. 9122/DELNP/2012. (7 Pages).
Examination Report Under Sections 12 & 13 of the Patents Act, 1970 and the Patents Rules, 2003 dated Nov. 30, 2018 From the Government of India, Intellectual Property India, Patents, Designs, Trade Marks, Geographical Indications Re. Application No. 1780/MUMNP/2014. (7 Pages).
Examiner-Initiated Interview Summary dated Nov. 27, 2017 From the US Patent and Trademark Office Re. U.S. Appl. No. 15/518,491. (2 pages).
Hearing Notice dated Jul. 16, 2019 From the Government of India, Patent Office, Intellectual Property Building Re. Application No. 1780/MUMNP/2014. (3 Pages).
International Preliminary Report on Patentability dated Apr. 11, 2019 From the International Bureau of WIPO Re. Application No. PCT/IL2017/051088. (6 Pages).
International Preliminary Report on Patentability dated Apr. 11, 2019 From the International Bureau of WIPO Re. Application No. PCT/IL2017/051089. (7 Pages).
International Preliminary Report on Patentability dated Sep. 13, 2018 From the International Bureau of WIPO Re. Application No. PCT/IL2017/050270. (7 Pages).
International Preliminary Report on Patentability dated Sep. 13, 2018 From the International Bureau of WIPO Re. Application No. PCT/IL2017/050271. (9 Pages).
International Preliminary Report on Patentability dated Jun. 22, 2017 From the International Bureau of WIPO Re. Application No. PCT/IL2015/051201. (7 Pages).
International Preliminary Report on Patentability dated Feb. 23, 2017 From the International Bureau of WIPO Re. Application No. PCT/IL2015/050823. (7 Pages).
International Preliminary Report on Patentability dated Jan. 24, 2019 From the International Bureau of WIPO Re. Application No. PCT/IL2017/050780. (9 Pages).
International Preliminary Report on Patentability dated Jan. 24, 2019 From the International Bureau of WIPO Re. Application No. PCT/IL2017/050781. (7 Pages).
International Preliminary Report on Patentability dated Apr. 27, 2017 From the International Bureau of WIPO Re. Application No. PCT/IL2015/051024. (7 Pages).
International Search Report and the Written Opinion dated Mar. 12, 2012 From the International Searching Authority Re. Application No. PCT/IB2011/001299.
International Search Report and the Written Opinion dated Sep. 14, 2017 From the International Searching Authority Re. Application No. PCT/IL2017/050781. (12 Pages).
International Search Report and the Written Opinion dated Jun. 15, 2017 From the International Searching Authority Re. Application No. PCT/IL2017/050270. (13 Pages).
International Search Report and the Written Opinion dated Jun. 15, 2017 From the International Searching Authority Re. Application No. PCT/IL2017/050271. (16 Pages).
International Search Report and the Written Opinion dated Sep. 18, 2017 From the International Searching Authority Re. Application No. PCT/IL2017/050780. (15 Pages).
International Search Report and the Written Opinion dated Jan. 20, 2016 From the International Searching Authority Re. Application No. PCT/IL2015/051024.
International Search Report and the Written Opinion dated Feb. 22, 2016 From the International Searching Authority Re. Application No. PCT/IL2015/051201.

(56) References Cited

OTHER PUBLICATIONS

International Search Report and the Written Opinion dated Dec. 25, 2017 From the International Searching Authority Re. Application No. PCT/IL2017/051088. (9 Pages).
International Search Report and the Written Opinion dated Dec. 28, 2017 From the International Searching Authority Re. Application No. PCT/IL2017/051089. (10 Pages).
International Search Report and the Written Opinion dated Nov. 29, 2015 From the International Searching Authority Re. Application No. PCT/IL2015/050823.
International Search Report dated Apr. 5, 2013 From the International Searching Authority Re. Application No. PCT/EP2013/052619.
Notice of Non-Compliant Amendment dated Aug. 4, 2015 From the US Patent and Trademark Office Re. U.S. Appl. No. 13/090,893.
Notice of Reason for Rejection dated Nov. 12, 2019 From the Japan Patent Office Re. Application No. 2017-126712 and an English Summary. (3 Pages).
Notice of Reason for Rejection dated Aug. 20, 2019 From the Japan Patent Office Re. Application No. 2017-507867 and Its Translation Into English. (5 Pages).
Notice of Reasons for Rejection dated Nov. 1, 2016 From the Japan Patent Office Re. Application No. 2014-556086 and Its Translation Into English. (12 Pages).
Notice of Reasons for Rejection dated Apr. 2, 2019 From the Japan Patent Office Re. Application No. 2017-126712 and Its Translation Into English. (8 Pages).
Notice of Reasons for Rejection dated Jun. 19, 2018 From the Japan Patent Office Re. Application No. 2017-126712 and Its Translation Into English. (9 Pages).
Notice on Office Action and the Search Report dated Feb. 25, 2015 From The State Intellectual Property Office of the People's Republic of China Re. Application No. 201180030792.1 and Its Translation Into English.
Notification of Lack of Unity and Search Report dated Jan. 21, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (12 Pages).
Notification of Office Action and Search Report dated Mar. 4, 2016 From the State Intellectual Property Office of the People's Republic of China Re. Application No. 201380019055.0.
Notification of Office Action and Search Report dated Jan. 11, 2019 From the State Intellectual Property Office of the People's Republic of China Re. Application No. 201580055946.0. (5 Pages).
Notification of Office Action and Search Report dated Feb. 13, 2017 From the State Intellectual Property Office of the People's Republic of China Re. Application No. 201380019055.0 and Its Translation of Office Action Into English. (10 Pages).
Notification of Office Action and Search Report dated Feb. 19, 2019 From the State Intellectual Property Office of the People's Republic of China Re. Application No. 201580075265.0 and a Summary of the Notification of Office Action Into English. (7 Pages).
Notification of Office Action and Search Report dated Jun. 19, 2018 From the State Intellectual Property Office of the People's Republic of China Re. Application No. 201580075265.0 and its English Summary. (14 Pages).
Notification of Office Action and Search Report dated Jul. 28, 2020 From the State Intellectual Property Office of the People's Republic of China Re. Application No. 201810781584.9 and Its Translation of Office Action Into English.
Notification of Office Action and Search Report dated Oct. 30, 2017 From the State Intellectual Property Office of the People's Republic of China Re. Application No. 201610817276.8. (10 Pages).
Notification of Office Action dated Jul. 2, 2019 From the State Intellectual Property Office of the People's Republic of China Re. Application No. 201580075265.0. (3 Pages).
Notification of Office Action dated Jul. 3, 2015 From the State Intellectual Property Office of the People's Republic of China Re. Application No. 201380019055.0.
Notification of Office Action dated Jun. 3, 2019 From the China National Intellectual Property Administration Re. Application No. 201610817276.8 and Its Translation Into English. (10 Pages).
Notification of Office Action dated Aug. 4, 2016 From the State Intellectual Property Office of the People's Republic of China Re. Application No. 201380019055.0 and Its Translation Into English.
Notification of Office Action dated May 6, 2014 From The State Intellectual Property Office of the People's Republic of China Re. Application No. 201180030792.1 and Its Translation Into English.
Notification of Office Action dated Jun. 20, 2018 From the State Intellectual Property Office of the People's Republic of China Re. Application No. 201580055946.0 and Its Summary in English. (5 Pages).
Notification of Office Action dated Jan. 21, 2016 From The State Intellectual Property Office of the People's Republic of China Re. Application No. 201180030792.1 and Its Translation Into English.
Notification of Office Action dated Aug. 22, 2019 From the State Intellectual Property Office of the People's Republic of China Re. Application No. 201580055946.0. (3 Pages).
Notification of Office Action dated Aug. 25, 2017 From the State Intellectual Property Office of the People's Republic of China Re. Application No. 201380019055.0. (6 Pages).
Notification of Office Action dated Aug. 28, 2015 From The State Intellectual Property Office of the People's Republic of China Re. Application No. 201180030792.1 and Its Translation Into English.
Notification of Office Action dated Aug. 30, 2018 From the State Intellectual Property Office of the People's Republic of China Re. Application No. 201610817276.8 and Its Translation Into English. (22 Pages).
Notification of Reexamination dated Jan. 12, 2018 From the State Intellectual Property Office of the People's Republic of China Re. Application No. 2013800190and Its Machine Translation into English.
Office Action dated Feb. 18, 2019 From the Israel Patent Office Re. Application No. 250585 and Its Translation Into English. (6 Pages).
Office Action dated Nov. 28, 2019 From the Israel Patent Office Re. Application No. 254095 and Its Translation Into English. (7 Pages).
Office Action dated Feb. 29, 2016 From the Israel Patent Office Re. Application No. 233998 and Its Translation Into English.
Office Action dated Jul. 30, 2020 From the Israel Patent Office Re. Application No. 261529 and Its Translation Into English. (5 Pages).
Office Action dated Jul. 30, 2020 From the Israel Patent Office Re. Application No. 261530 and Its Translation Into English. (5 Pages).
Official Action dated Sep. 1, 2015 From the US Patent and Trademark Office Re. U.S. Appl. No. 13/090,893.
Official Action dated Feb. 3, 2020 From the US Patent and Trademark Office Re. U.S. Appl. No. 16/355,984. (24 pages).
Official Action dated Apr. 4, 2016 From the US Patent and Trademark Office Re. U.S. Appl. No. 13/090,893.
Official Action dated Jan. 4, 2019 From the US Patent and Trademark Office Re. Application No. 151713,722. (72 pages).
Official Action dated Mar. 5, 2020 From the US Patent and Trademark Office Re. U.S. Appl. No. 15/713,722. (24 pages).
Official Action dated Feb. 6, 2018 From the US Patent and Trademark Office Re. U.S. Appl. No. 15/503,439. (63 pages).
Official Action dated Nov. 7, 2016 From the US Patent and Trademark Office Re. U.S. Appl. No. 13/090,893. (26 pages).
Official Action dated Jun. 10, 2013 From the US Patent and Trademark Office Re. U.S. Appl. No. 13/090,893.
Official Action dated Apr. 12, 2018 From the US Patent and Trademark Office Re. U.S. Appl. No. 15/518,491. (59 pages).
Official Action dated Aug. 12, 2015 From the US Patent and Trademark Office Re. U.S. Appl. No. 14/377,887.
Official Action dated May 12, 2017 From the US Patent and Trademark Office Re. U.S. Appl. No. 15/237,728. (27 pages).
Official Action dated Apr. 13, 2016 From the US Patent and Trademark Office Re. U.S. Appl. No. 14/377,887.
Official Action dated Mar. 13, 2014 From the US Patent and Trademark Office Re. U.S. Appl. No. 13/090,893.

(56) References Cited

OTHER PUBLICATIONS

Official Action dated Apr. 15, 2019 From the US Patent and Trademark Office Re. U.S. Appl. No. 15/237,728. (16 Pages).
Official Action dated Dec. 15, 2016 From the US Patent and Trademark Office Re. U.S. Appl. No. 14/377,887. (22 pages).
Official Action dated May 15, 2018 From the US Patent and Trademark Office Re. U.S. Appl. No. 15/237,728. (55 pages).
Official Action dated May 15, 2020 from the US Patent and Trademark Office Re. U.S. Appl. No. 16/238,582. (92 pages).
Official Action dated Oct. 15, 2019 From the US Patent and Trademark Office Re. Application No. 151713,722. (57 Pages).
Official Action dated Nov. 16, 2018 From the US Patent and Trademark Office Re. U.S. Appl. No. 15/503,439. (41 pages).
Official Action dated Sep. 16, 2019 From the US Patent and Trademark Office Re. U.S. Appl. No. 16/355,984. (44 pages).
Official Action dated Dec. 17, 2018 From the US Patent and Trademark Office Re. U.S. Appl. No. 15/237,728. (39 pages).
Official Action dated Nov. 18, 2016 From the US Patent and Trademark Office Re. U.S. Appl. No. 15/237,728. (33 pages).
Official Action dated Sep. 18, 2019 From the US Patent and Trademark Office Re. U.S. Appl. No. 16/157,193. (30 pages).
Official Action dated Apr. 23, 2019 From the US Patent and Trademark Office Re. U.S. Appl. No. 16/157,193. (47 pages).
Official Action dated Oct. 24, 2019 From the US Patent and Trademark Office Re. U.S. Appl. No. 15/531,747. (37 Pages).
Official Action dated Jan. 26, 2017 From the US Patent and Trademark Office Re. U.S. Appl. No. 15/015,309. (45 pages).
Official Action dated Mar. 26, 2015 From the US Patent and Trademark Office Re. U.S. Appl. No. 13/090,893.
Official Action dated Mar. 26, 2020 from the US Patent and Trademark Office Re. U.S. Appl. No. 16/687,726. (47 pages).
Official Action dated Apr. 30, 2018 From the US Patent and Trademark Office Re. U.S. Appl. No. 15/641,400. (62 pages).
Official Action dated Mar. 30, 2018 From the US Patent and Trademark Office Re. U.S. Appl. No. 15/531,747. (67 pages).
Official Action ated Mar. 31, 2020 from the US Patent and Trademark Office Re. U.S. Appl. No. 15/531,747. (21 pages).
Official Action dated May 7, 2020 from the US Patent and Trademark Office Re. U.S. Appl. No. 16/157,193. (23 pages).
Partial European Search Report and Provisional Opinion dated Jun. 25, 2020 From the European Search Report Re. Application No. 20164056.2. (11 Pages).
Request for Examination dated Jun. 18, 2019 From the Federal Government Institution, Federal Institute of Industrial Property of the Federal Service for Intellectual Property, Patents and Trade Marks of the Russian Federation Re. Application No. 2017107750 and Its Translation of Office Action into English. (11 Pages).
Requisition by the Examiner dated Oct. 4, 2019 From the Innovation, Science and Economic Development Canada, Canadian Intellectual Property Office Re. Application No. 2,863,819. (3 Pages).
Requisition by the Examiner dated Nov. 9, 2018 From the Innovation, Science and Economic Development Canada, Canadian Intellectual Property Office Re. Application No. 2,796,666. (3 Pages).
Requisition by the Examiner dated Jan. 18, 2018 From the Innovation, Science and Economic Development Canada, Canadian Intellectual Property Office Re. Application No. 2,796,666. (5 Pages).
Requisition by the Examiner dated Feb. 21, 2019 From the Innovation, Science and Economic Development Canada, Canadian Intellectual Property Office Re. Application No. 2,863,819. (8 Pages).
Restriction Official Action dated Nov. 2, 2017 From the US Patent and Trademark Office Re. U.S. Appl. No. 15/531,747. (9 pages).
Restriction Official Action dated Dec. 5, 2019 From the US Patent and Trademark Office Re. U.S. Appl. No. 16/081,906. (9 pages).
Restriction Official Action dated Nov. 8, 2018 From the US Patent and Trademark Office Re. U.S. Appl. No. 16/157,193. (5 pages).
Restriction Official Action dated May 10, 2018 From the US Patent and Trademark Office Re. U.S. Appl. No. 15/713,722. (6 Pages).
Restriction Official Action dated Feb. 13, 2013 From the US Patent and Trademark Office Re. U.S. Appl. No. 13/090,893.
Restriction Official Action dated May 15, 2015 From the US Patent and Trademark Office Re. U.S. Appl. No. 14/377,887.
Restriction Official Action dated Apr. 2, 2020 from the US Patent and Trademark Office Re. U.S. Appl. No. 16/081,069. (7 pages).
Restriction Official Action dated Nov. 29, 2019 From the US Patent and Trademark Office Re. U.S. Appl. No. 16/238,582. (7 pages).
Restriction Official Action dated Jul. 30, 2020 from the US Patent and Trademark Office Re. U.S. Appl. No. 16/081,906. (7 pages).
Restriction Official Action dated Aug. 31, 2017 From the US Patent and Trademark Office Re. U.S. Appl. No. 15/518,491. (6 pages).
Search Report and Opinion dated Dec. 10, 2019 From the Servico Publico Federal, Ministerio da Economia, Institute National da Propriedade Industrial do Brasil Re. Application No. BR112017002884-0 and Its Translation Into English. (7 Pages).
Search Report and Opinion dated Aug. 20, 2019 From the Servi?o Publico Federal, Ministerio da Economia, Institute National da Propriedade Industrial do Brasil Re. Application No. BR112014 019733-4 and Its Summary in English. (4 Pages).
Search Report dated May 6, 2014 From The State Intellectual Property Office of the People s Republic of China Re. Application No. 201180030792.1 and Its Translation Into English.
Second Notice of Allowance dated Dec. 12, 2018 From the US Patent and Trademark Office Re. U.S. Appl. No. 15/641,400. (7 pages).
Supplementary European Search Report and the European Search Opinion dated May 4, 2020 From the European Patent Office Re. Application No. 17855163.6. (9 Pages).
Supplementary European Search Report and the European Search Opinion dated Mar. 15, 2018 From the European Patent Office Re. Application No. 15831781.8. (11 Pages).
Supplementary European Search Report and the European Search Opinion dated Sep. 17, 2018 From the European Patent Office Re. Application No. 15868614.7. (18 Pages).
Supplementary European Search Report and the European Search Opinion dated Feb. 18, 2020 From the European Patent Office Re. Application No. 17827121.9. (5 Pages).
Supplementary European Search Report and the European Search Opinion dated May 18, 2020 From the European Patent Office Re. Application No. 17855164.4. (13 Pages).
Supplementary European Search Report and the European Search Opinion dated Jan. 21, 2020 From the European Patent Office Re. Application No. 17827122.7.
Supplementary European Search Report and the European Search Opinion dated Jan. 28, 2020 From the European Patent Office Re. Application No. 17759389.4. (11 Pages).
Supplementary European Search Report and the European Search Opinion dated Sep. 30, 2019 From the European Patent Office Re. Application No. 17759388.6. (11 Pages).
Supplementary Partial European Search Report and the European Provisional Opinion dated Jun. 1, 2018 From the European Patent Office Re. Application No. 15868614.7. (23 Pages).
Supplementary Partial European Search Report and the European Provisional Opinion dated Oct. 24, 2019 From the European Patent Office Re. Application No. 17759389.4. (15 Pages).
Translation dated Sep. 4, 2017 of Notification of Office Action dated Aug. 25, 2017 From the State Intellectual Property Office of the People's Republic of China Re. Application No. 201380019055.0.
Translation dated Apr. 5, 2016 of Notification of Office Action dated Mar. 4, 2016 From the State Intellectual Property Office of the People's Republic of China Re. Application No. 201380019055.0.
Translation dated Jul. 10, 2019 of Notification of Office Action dated Jul. 2, 2019 From the State Intellectual Property Office of the People's Republic of China Re. Application No. 201580075265.0. (1 Page).
Translation dated Sep. 11, 2019 of Notification of Office Action dated Aug. 22, 2019 From the State Intellectual Property Office of the People's Republic of China Re. Application No. 201580055946. 0. (1 Page).

(56) References Cited

OTHER PUBLICATIONS

Translation dated Mar. 20, 2019 of Notification of Office Action dated Feb. 19, 2019 From the State Intellectual Property Office of the People's Republic of China Re. Application No. 201580075265.0. (5 Pages).
Translation dated Nov. 21, 2019 of Reason for Rejection From the Japanese Patent Office Re. Application No. 2017-126712. (2 Pages).
Translation dated Sep. 21, 2015 of Office Action dated Jul. 3, 2015 From the State Intellectual Property Office of the People's Republic of China Re. Application No. 201380019055.0.
Translation dated Sep. 22, 2019 of Search Report and Opinion dated Aug. 20, 2019 From the Servi?o Publico Federal, Ministerio da Economia, Institute Nacional da Propriedade Industrial do Brasil Re. Application No. BR112014019733-4 and Its Summary in English. (4 Pages).
Translation dated Jan. 30, 2019 of Notification of Office Action dated Jan. 11, 2019 From the State Intellectual Property Office of the People's Republic of China Re. Application No. 201580055946.0. (1 Page).
Translation of Notification of Office Action and Search Report dated Oct. 30, 2017 From the State Intellectual Property Office of the People's Republic of China Re. Application No. 201610817276.8. (16 Pages).
Alexander et al. "*Staphylococcus aureus* and *Salmonella enterica* Serovar Dublin Induce Tumor Necrosis Factor-Related Apoptosis-Inducing Ligand Expression by Normal Mouse and Human Osteoblasts", Infection and Immunity, 69(3): 1581-1586, Mar. 2001.
Ali et al. "Reliability of Serum Procalcitonin Concentrations for the Diagnosis of Sepsis in Neonates", Egypt Journal of lmmunology, 15(1): 75-84, 2008. Abstract only.
Bai et al. "A New Early Diagnostic Marker for Inflammatory Diseases—sTREM-1", International Journal of Pathology and Clinical Medicine, 27(1): 73-76, Feb. 2007.
Barnhart et al. "Changes in Cellular mRNA Stability, Splicing, and Polyadenylation Through HuR Protein Sequestration by A Cytoplasmic RNA Virus", Cell Reports, XP055621573, 5(4): 909-917, Nov. 27, 2013.
Becker et al. "Procalcitonin in Sepsis and Systemic Inflammation: a Harmful Biomarker and a Therapeutic Target", British Journal of Pharmacology, 159: 253-264, 2010.
Biezeveld et al. "Sustained Activation of Neutrophils in the Course of Kawasaki Disease: An Association with Matrix Metalloproteinases", Clinical & Experimental Immunology 141(1): 183-188, Jul. 2005.
Boldrick et al. "Stereotyped and Specific Gene Expression Programs in Human Innate Immune Responses to Bacteria", Proc. Natl. Acad. Sci. USA, PNAS, 99(2): 972-977, Jan. 22, 2002.
Borjesson et al. "Insights Into Pathogen Immune Evasion Mechanisms: Anaplasma Phagocytophilum Fails to Induce an Apoptosis Differentiation Program in Human Neutrophils", The Jurnal of Immunology, 174: 6364-6372, 2005.
Boser et al. "A Training Algorithm for Optimal Margin Classifiers", Proceedings of the 5th Annual ACM Workshop on Computational Learning Theory, COLT'92, Pittsburgh, PA, USA, Jul. 27-29, 1992, p. 144-152, Jul. 27, 1992.
Cai et al. "The Study on the Relationship Between PCT and CRP in Infective Diseases", Journ al of Qiqihar University of Medicine, 32(5): 696-697, 2011.
Calvano et al. "A Network-Based Analysis of Systemic Inflammation in Humans", Nature, 437: 1032-1037, Oct. 13, 2005.
Carrol et al. "The Diagnostic and Prognostic Accuracy of Five Markers of Serious Bacterial Infection in Malawian Children With Sign of Severe Infection", PLoS ONE, 4(8): e6621-1-e6621-8, Aug. 2009.
Chagan-Yasutan et al. "Persistent Elevation of Plasma Osteopontin Levels in HIV Patients Despite Highly Active Antiretroviral Therapy", The Tohoku Journal of Experimental Medicine, 218(4): 285-292, Aug. 2009.
Chaussabel et al. "Analysis of Significance Patterns Identifies Ubiquitous and Disease-Specific Gene-Expression Signatures in Patient Peripheral Blood Leukocytes", Annals of the New York Academy of Sciences, 1062: 146-154, 2005.
Chen et al. "Discordant Protein and mRNA Expression in Lung Adenocarcinomas", Molecular & Cellular Proteomics: MCP, 1(4): 304-313, Apr. 2002.
Chieux et al. "MxA Protein in Capillary Blood of Children With Viral Infections", Journal of Medical Virology, 59: 547-551, 1999.
Chieux et al. "The MxA Protein Levels in Whole Blood Lysates of Patients With Various Viral Infections", Journal of Virological Methods, 70: 183-191, 1998.
Consiglio et al. "BEAT: Bioinformatics Exon Array Tool to Store, Analyze and Visualize Affymetrix GeneChip Human Exon Array Data From Disease Experiments", BMC Bioinformatics, XP021117755, 13(Suppl.4): S21-1-S21-14, Mar. 28, 2012.
Corada et al. "Monoclonal Antibodies Directed to Different Regions of Vascular Endothelial Cadherin Extracellular Domain Affect Adhesion and Clustering of the Protein and Modulate Endothelial Permeability", Blood, 97(6): 1679-1684, Mar. 15, 2001.
Cowland et al. "Molerular Charaderization and Pattern of Tissue Expression of the Gene for Neutrophil Gelatinase-Associated Upocalin from Humans", Genomics, 45:17-23,1997.
Cristianini et al. "An Introduction to Support Vector Machines and Other Kernel-Based Learning Methods: Contents", Cambridge University Press, 4 P., 2000.
Crowe et al. "Quantitative lmmunocytofluorographic Analysis of CD4 Surface Antigen Expression and HIV Infection of Human Peripheral Blood Monocyte/Macrophages", Aids Research and Human Retroviruses, 3(2): 135-145, 1987.
Cummins et al. "The TRAIL to Viral Pathogenesis: The Good, the Bad and the Ugly", Current Molecular Medicine, XP055056835, 9(4): 495-505, May 1, 2009.
Dirke et al. "TRAIL and DcR1 Expressions are Differentially Regulated in the Pancreatic Islets of STZ—Versus CY-AppHed NOD Mice", Experimental Diabetes Research, Article ID 625813, pp. 1-11, 2011.
Duda et al. "Contents", Pattern Classification, 2nd Ed., 11 P., 2001.
Eberl et al. "A Rapid Crosstalk of Human gamma delta T Cells and Monocytes Drives the Acute Inflammation in Bacterial Infections", PLOS Pathogens 5(2): 1-16, 2009.
Falschlehner et al. "Following TRAIL'S Path in the Immune System", Immunology, XP055056763, 127(2): 145-154, Jun. 1, 2009. Chapter TRAIL in Viral and Bacterial Infections'.
Feezor et al. "Molecular Characterization of the Acute Inflammatory Response to Infections With Gram-Negaitve Versus Gram-Positive Bacteria", Infection and Immunity, 71(10): 5803-5813, Oct. 2003.
Forde et al. "The Beneficial Pleiotropic Effects of Tumour Necrosis Factor-Related Apoptosis-Inducing Ligand (TRAIL) Within the Vasculature: A Review of the Evidence", Atherosclerosis, XP029468976, 247: 87-96, Available Online Feb. 9, 2016.
Furey et al. "Support Vector Machine Classification and Validation of Cancer Tissue Samples Using Microarray Expression Data", Bioinformatics, 16(10): 906-914, Oct. 2000.
Greenspan et al. "Defining Epitopes: It's Not as Easy as It Seems". Nature Biotechnology, 17: 936-937, Oct. 1999.
Halminen et al. "Expression of MxA Protein in Blood Lymphocytes Discriminates Between Viral and Bacterial Infections in Febrile Children", Pediatric Research, 41(5): 647-650, May 1997.
Hanley et al. "A Method of Comparing the Areas Under Receiver Operating Characteristics Curves Derived From the Same Cases", Radiology, 148(3): 839-843, Sep. 1983.
Hastie et al. "The Elements of Statistical Learning: Data Mining, Inference, and Prediction", Springer Series in Statistics, 2nd Ed., p. 1-745, 2001.
Herzig et al. "The Role of CXCL10 in the Pathogenesis of Experimental Septic Shock", Critical Care, 18(3): 1-18, 2014.
Hinson et al. "Viperin Is Highly Induced in Neutrophils and Macrophages during Acute and Chronic Lymphocytic Choriomeningitis Virus Infection", The Journal of Immunology, 184:5723-5731, 2010.
Hoffmann et al. "TRAIL Limits Excessive Host Immune Responses in Bacterial Meningitis", JCI The Journal of Clinical Investigation, 117(7): 2004-2013, Jul. 2, 2007.

(56) References Cited

OTHER PUBLICATIONS

Holland et al. "STAT3 Mutations in the Hyper-IgE Syndrome", The New England Journal of Medicine, 357(16): 1608-1619, Oct. 18, 2007.
Janols et al. "Lymphocyte and Monocyte Flow Cytometry Immunophenotyping as a Diagnostic Tool in Uncharacteristic Inflammatory Disorders", BMC Infectious Diseases, XP002663504, 10(205): 1-9, 2010. Abstract.
Jenner et al. "Insights Into Host Responses Against Pathogens From Transcriptional Profiling", Nature Review Microbiology, 3: 281-294, Apr. 2005.
Ju et al. "Research Progress of Some Inflammatory Markers in Infectious Diseases", Chinese Journal of Practical Internal Medicine, 30(Suppl.1): 80-81, Jun. 2010.
Kaizer et al. "Gene Expression in Peripheral Blood Mononuclear Cells From Children With Diabetes", The Journal of Clinical Endocrinology & Metabolism, 92(9): 3705-3711, 2007.
Kawada et al. "Analysis of Gene-Expression Profiles by Oligonucleotide Microarray in Children With Influenza", Journal of General Virology, 87: 1677-1683, 2006.
Kichev et al. "Tumor Necrosis Factor-Related Apoptosis-Inducing Ligand (TRAiL) Signaling and Cell Death in the Immature Central Nervous System after Hypoxia-Ischemia and Inflammation", Journal of Biological Chemistry 289(13): 9430-9439, 2014.
Kohavi et al. "Wrappers for Feature Subset Selection", Artifical Intelligence. 97: 273-324, 1997.
Kotelkin et al. "Respiratory Syncytial Virus Infections Sensitizes Cells to Apoptosis Mediated by Tumor Necrosis Factor-Related Apoptosis-Inducing Ligand", Journal of Virology, XP055056816, 77(17): 9156-9172, Aug. 12, 2003. Fig.5B.
Lampe et al. "Expression of the Interferon-Induced MxA Protein in Viral Encephalitis", Neuropathology and Applied Neurobiology, 29(3): 273-279, May 27, 2003.
Le Roux "Les Examens a Visee Etiologique Dans les Pneumopathies Communautaires de l'Enfant (Hors Imagerie) [Laboratory Investigations in Acute Lower Respiratory Tract Infections in Children]", Archives de Pediatrie, XP002663501, 5(Suppl.1): 28S-32S, 1998. Abstract.
Leibovici et al. "The Benefit of Appropriate Empirical Antibiotic Treatment in Patients with Bloodstream Infection", Journal of Internal Medicine, 244(5): 379-386, Nov. 1, 1998.
Liabeuf et al. "The Circulating Soluble TRAIL, Is a Negative Marker for Inflammation Inversely Associated With the Mortality Risk in Chronic Kidney Disease Patients", Nephrology Dialysis Transplantation, XP055497900, 25(8): 2596-2602, Advance Access Publication Feb. 26, 2010. Abstract, p. 2597, Right col., 2nd Para, Figs.2, 3.
Liu et al. "Early Days: Genomics and Human Responses to Infection", Current Opinion in Microbiology, 9: 312-319, Available Online May 6, 2006.
Lloyd et al. "Modelling The Human Immune Response: Performance of a 1011 Human Antibody Repertoire Against a Broad Panel of Therapeutically Relevant Antigens", Protein Engineering, Design & Selection 22(3): 159-168, Oct. 29, 2008.
Ludwig et al. "Tumor Necrosis Factor Related Apoptosis Inducing Ligand: A Novell Mechanism for Bacillus Calmette Guerin Induced Antitumor Activity" Cancer Research 64: 3386-3390,May 15, 2004.
Malcolm et al. "Microarrays Analysis of Lipopolysaccharide-Treated Human Neutrophils", American Journal of Physiology, Lung Cellular & Molecular Physiology, 284(4): L663-L670, First Published Dec. 20, 2002.
Mount "Bioinformatics: Sequence and Genome Analysis", Chaps. 1-10: 1-564, 2001.
Nakabayashi et al. "MxA-Based Recognition of Viral Illness in Febrile Children by a Whole Blood Assay", Pediatric Research, 60(6): 770-774, 2006.
Neu et al. "Expression of Tumor Necrosis Factor-Alpha-Related Apoptosis-Inducing Ligand and Its Proapoptotic Receptors Is Down-Regulated during Gastric Infection with Virulent cagA+/vacAs1+ Helicobacter pylori Strains", The Journal of Infectious Diseases 191(4): 571-578, Feb. 15, 2005.
Ng et al. "IP-10 Is an Early Diagnostic Marker for Identification of Late-Onset Bacterial Infection in Preterm Infants", Pediatric Research, 61(1): 93-98, 2007.
Niederman "Biological Markers to Determine Eligibility in Trials for Community-Acquired Pneumonia: A Focus on Procalcitonin", Clinical Infectious Diseases, XP002670357, 47(Suppl.3): S127-S132, Dec. 2008.
Niessner et al. "Prognostic Value of Apoptosis Markers in Advanced Heart Failure Patients", European Heart Journal, XP055497907, 30(7): 789-796, Published Online Feb. 4, 2009. Abstract, Table 2, Fig.2.
Oda et al. "A Comprehensive Map of the Toll-Like Receptor Signaling Network", Molecular Systems Biology, 2(2006.0015): 1-20, Apr. 18, 2006.
Oved et al. "A Novel Host-Proteome Signature for Distinguishing Between Acute Bacterial and Viral Infections", PLOS ONE, XP055456891, 10(3): e0120012-1-e120012-18, Mar. 18, 2015. Figs. 3C, 4.
Padlan "X-Ray Crystallography Of Antibodies", Advances In Protein Chemistry, 49: 57-133; 1996.
Paul et al. "Systematic Review and Meta-Analysis of the Efficacy of Appropriate Empiric Antibiotic Therapy for Sepsis", Antimicrobial Agents and Chemotherapy, 54(11): 4851-4863, Nov. 2010.
Pepe et al. "Combining Diagnostic Test Results to Increase Accuracy", Biostatistics, XP055033234, 1(2): 123-140, Jun. 2000.
Povoa et al. "C-Reactive Protein, an Early Marker of Community-Acquired Sepsis Resolution: a Multi-Center Prospective Observational Study", Critical Care, 15(4): 1-10, 2011.
Radom-Aizik et al. "Effects of 30 Min. of Aerobic Exercise on Gene Expression in Human Neutrophils", Journal of Applied Physiology, 104: 236-243, 2008.
Ramilo et al. "Gene Expression Patterns in Blood Leukocytes Discriminate Patients With Acute Infections", Blood, 109(5): 2066-2077, Mar. 1, 2007.
RayBiotech "Mouse L308 Array, Membrane [AAM-BLM-1]1-Series-308-Label-Based-Mouse-Cytok", RayBiotech, XP055473187, Retrieved From the Internet, 7 P., May 7, 2018.
Rosseau et al. "Comparative Transcriptional Profiling of the Lung Reveals Shared and Distinct Features of Streptococcus pneumoniae and Influenza A Virus Infection", Immunology, 120: 380-391, 2006.
Rudikoff et al. "Single Amino Acid Substitution Altering Antigen-Binding Specificity", PNAS, 79(6): 1979-1983, Mar. 1982.
Sasaki et al. "Differentiating Between Bacterial and Viral Infection by Measuring Both C-Reactive Protein and 2'-5'-Oligoadenylate Synthetase as Inflammatory Markers", Journal of Infection and Chemotherapy, XP055696216, 8(1): 76-80. Mar. 2002.
Secchiero et al. "Potential Prognostic Significance of Decreased Serum Levels of TRAIL After Acute Myocardial Infarction", PLoS ONE, XP055056988, 4(2): e4442-1-e4442-6, Feb. 16, 2009. Fig.1.
Shimetani et al. "Levels of Three Inflammation Markers, C-Reactive Protein, Serum Amyloid A Protein and Procalcitonin, in the Serum and Cerebrospinal Fluid of Patients With Meningitis", Scandinavian Journal of Clinical and Laboratory Investigation, XP008113027, 61(7): 567-574, 2001. Abstract.
Shommu et al. "Metabolomic and Inflammatory Mediator Based Biomarker Profiling as a Potential Novel Method to Aid Pediatric Appendicitis Identification", PLOS ONE, XP055692841, 13(3): e0193563-1-e0193563-13, Mar. 12, 2018.
Singer et al. "The Third International Consensus Definitions for Sepsis and Septic Shock (Sepsis-3)", Journal of the American Medical Association, JAMA, 315(8): 801-810, Feb. 23, 2016. Box 3, Fig.
Smith et al. "Quantitative Assessment of Human Whole Blood RNA as a Potential Biomarker for Infectious Disease", Analyst, 132: 1200-1209, First Published Oct. 31, 2007.
Sukumaran et al. "Early Transcriptional Response of Human Neutrophils to Anaplasma Phagocytophilum Infection", Infection and Immunity, 73(12): 8089-8099, Dec. 1, 2005.

(56) References Cited

OTHER PUBLICATIONS

Sullivan Pepe et al. "Combining Diagnostic Test Results to Increase Accuracy", Biostatistics, XP055033234, 1(2): 123-140, Jun. 1, 2000. Abstract, Section 2.4.
Tang et al. "Gene-Expression Profiling of Gram-Positive and Gram-Negative Sepsis in Critically I11 Patients", Critical Care Medicine, 36(4): 1125-1128, 2008.
Tang et al. "Hvpoxic Preconditioning Enhances the Benefit of Cardiac Progenitor Cell Therapy for Treatment of Myocardial Infarction by Inducing CXCR4 Expression", Circulation Research, XP055473182, 104(10): 1209-1216, May 22, 2009. Online Table 1.
Tang et al. "The Use of Gene-Expression Profiling to Identify Candidate Genes in Human Sepsis", American Journal of Respiratory and Critical Care Medicine, 176: 676-684, Originally Published Jun. 15, 2007.
Thivierge et al. "Eukaryotic Elongation Factor 1A Interacts With Turnip Mosaic Virus RNA-Dependent RNA Polymerase and VPg-Pro in Virus-Induced Vesicles", Virology, XP002663503, 377(1): 216-225, Jul. 2008. Abstract, p. 220, r-h col., Para 3—p. 222, r-h col., Para 1.
Tian et al. "Soluble Tumor Necrosis Factor Related Apoptosis Inducing Ligand Level as a Predictor of Severity of Sepsis and the Risk of Mortality in Septic Patients", PLOS One, XP055497898, 8(12): e82204-1-e82204-5, Dec. 12, 2013. 'Study Design' Para, 'Inclusion Criteria' Para, Table 1, Figs.1, 3, Abstract, Table 1.
Tisato et al. "Low Circulating TRAIL Levels Are Associated with Increase of Resistin and Lipocalin-2/ngal Adipokines in Postmenopausal Women", Mediators of Inflammation, Article ID 5356020, 8 Pages, 2017.
Torkkola "Feature Extraction by Non-Parametric Mutual Information Maximization", Journal of Machine Learning Research, 3: 1415-1438, Mar. 2003.
Tsuji "TRAILing Gastrointestinal Pathogenesis", Journal of Gastroenterology and Hepatology, 18(7): 753-755, Published Online Jun. 10, 2003.
Tworoger et al. "Collection, Processing, and Storage of Biological Samples in Epidemiologic Studies: Sex Hormones. Carotenoids, Inflammatory Markers, and Proteomics as Examples", Cancer Epidemiol Biomarkers and Prevention, 15(9): 1578-1581, Sep. 2006.
UCSC "UCSC Browser on Human Feb. 2009 (GRCh37/hg19) Assembly: Showing Location of Probes on the Affymetrix ExonChip Binding to Exons of ANKRD22", UCSC Browser, XP055621243, Retrieved From the Internet, 7 P., Jan. 2009.
UCSC "UCSC Genome Browser on Human Feb. 2009 (GRCh37/hg19) Assembly: Showing Location of Probes on the Affymetrix ExonChip Binding to Exons of AIM2", UCSC Browser, XP055621240, Retrieved From the Interent, 8 P., Jan. 2009.
Vapnik "Statistical Learning Theory", Adaptive and Learning Systems for Signal Processing, Communications, and Control, p. 1-732, 1998. Part I.
Vapnik "Statistical Learning Theory", Adaptive and Learning Systems for Signal Processing, Communications, and Control, p. 1-732, 1998. Part II.
Vapnik "Statistical Learning Theory", Adaptive and Learning Systems for Signal Processing, Communications, and Control, p. 1-732, 1998. Part III.
Vapnik "Statistical Learning Theory", Adaptive and Learning Systems for Signal Processing, Communications, and Control, p. 1-732, 1998. Part IV.
Vogel et al. "Sequence Signatures and mRNA Concentration can Explain Two-Thirds of Protein Abundance Variation in a Human Cell Line", Molecular Systems Biology, 6(Art.400): 1-9, Published Online Aug. 24, 2010.
Wang et al. "Rotavirus Infection Alters Peripheral T-Cell Homeostasis in Children With Acute Diarrhea", Journal of Virology, 81(8): 3904-3912, Apr. 2007.
Whiteside et al. "Role of Human Natural Killer Cells in Health and Disease", Clinical and Diagnostic Laboratory Immunology, 1(2): 125-133, Mar. 31, 1994.

Xu et al. "Lipocalins as Biochemical Markers of Disease", Biochimica et Biophysica Acta, XP002376345, 1482(1): 298-307, Oct. 18, 2000. Abstract, Sections 3, 5, p. 303, col. 2—p. 304, col. 1, Bridging Para, p. 304, cols. 1-2, Bidging Para, Fig.1, Table 1.
Yamaji et al. "Sinificance of Eukaryotic Translation Elongation Factor 1A in Tobacco Mosaic Vims Infection", Archives of Virology, XP002663502, 155(2): 263-268, Feb. 2010. Abstract.
Yeung et al. "Serum Cytokines in Differentiating Between Viral and Bacterial Enterocolitis", Annals of Tropical Paediatrics, 24(4): 337-343. Published Online Jul. 18, 2013.
Zaas et al. "A Host-Based RT-PCR Gene Expression Signature to Identify Acute Respiratory Viral Infection", Science Translational Medicine, 5(203): 203ra126-1-203ra126-19, Sep. 18, 2013.
Zaas et al. "Gene Expression Signatures Diagnose Influenza and Other Symptomatic Respiratory Viral Infections in Humans", Cell Host & Microbe, XP002670360, 6(3): 207-217, Sep. 17, 2009. Abstract, p. 212, 1-h col., p. 213, 1-h col., Fig.4.
Zaas et al. "The Current Epidemiology and Clinical Decisions Surrounding Acute Respiratory Infections", Trends in Molecular Medicine, XP055522333, 20(10): 579-588, Published Online Sep. 5, 2014.
Zhu et al. "Use of Differential Display Analysis to Assess the Effect of Human Cytomegalovirus Infection on the Accumulation of Cellular RNAs: Induction of Interferon-Responsive RNAs", Proc. Natl. Acad. Sci. USA, XP002088235, 94(25): 13985-13990, Dec. 9, 1997. Abstract, Fig.2.
Zilliox et al. "Gene Expression Changes in Peripheral Blood Mononuclear Cells During Measles Virus Infection". Clinical and Vaccine Immunology, 14(7): 918-923, Jul. 2007.
Ju et al. "Research Progress of Some Inflammatory Markers in Infectious Diseases", Chinese Journal of Practical Internal Medicine, 30(Suppl.1): 80-81, Jun. 2010. With an English Translation.
Communication Pursuant to Article 94(3) EPC dated Jun. 2, 2021 From the European Patent Office Re. Application No. 17827121.9. (5 Pages).
Official Action dated Dec. 30, 2020 from the US Patent and Trademark Office Re. U.S. Appl. No. 16/334,033. (112 pages).
Requisition by the Examiner dated Dec. 7, 2020 From the Innovation, Science and Economic Development Canada, Canadian Intellectual Property Office Re. Application No. 2,863,819. (4 Pages).
Restriction Official Action dated Dec. 9, 2020 from the LIS Patent and Trademark Office Re. U.S. Appl. No. 16/336,528. (7 pages).
Bone et al. "Definitions for Sepsis and Organ Failure and Guidelines for the Use of Innovative Therapies in Sepsis", Chest, 101(6): 1644-1655, 1992.
Kang et al. "Low serum TNF-Related Apoptosis-Inducing Ligand (TRAIL) Levels Are Associated with Acute Ischemic Stroke Severity", Atherosclerosis, 240: 228-233, 2015.
Michowitz et al. "The Involvement of Tumor Necrosis Factor-Related Apoptosis-Inducing Ligand (TRAIL) in Atherosclerosis.", Journal of the American College of Cardiology, 45(7): 1018-1024, 2005.
Osmancik et al. "Prognostic Value of TNF-Related Apoptosis Inducing Ligand (TRAIL) in Acute Coronary Syndrome Patients", PLoS One, 8(2): e53860, 2013.
Volpato et al. "Association of Tumor Necrosis Factor-Related Apoptosis-Inducing Ligand with Total and Cardiovascular Mortality in Older Adults", Atherosclerosis, 215:452-458, 2011.
Communication Pursuant to Article 94(3) EPC dated Aug. 18, 2020 From the European Patent Office Re. Application No. 11748712.4. (3 Pages).
Restriction Official Action dated Mar. 29, 2021 From the US Patent and Trademark Office Re. U.S. Appl. No. 16/081,069. (8 Pages).
Final Official Action dated Sep. 10, 2021 from the US Patent and Trademark Office Re. U.S. Appl. No. 16/081,069. (61 pages).
Affymetrix "Whole-Transcript Expression Analysis", Asymetrix, 8 pages, 2007.
New England Biolabs "New England Biolabs Catalog", New England Biolabs, 1-4 pages, 1996.
Rothstein et al. "Chronic Inhibition of Superoxide Dismutase Produces Apoptotic Death of Spinal Neurons", PNAS, (10): 4155-4159, May 1994.

(56) References Cited

OTHER PUBLICATIONS

Final Official Action dated Nov. 29 together with Interview Summary dated Nov. 14, 2021 from US Patent and Trademark Office Re. U.S. Appl. No. 16/081,906. (45 pages).
Interview Summary dated Dec. 3, 2021 from US Patent and Trademark Office Re. U.S. Appl. No. 16/081,069. (3 pages).
Ioannidis et al. "Plasticity and Virus Specifity of the Airway Epithelial Cell Immune Response During Respiratory Virus Infection", Journal of Virology. 86(10): 5422-36, Mar. 7, 2012.
Requisition by the Examiner dated Nov. 5, 2021 From the Innovation, Science and Economic Development Canada, Canadian Intellectual Property Office Re. Application No. 2,968,650. (7 Pages).
English Translation dated Feb. 16, 2022 of Grounds of Reason of Rejection dated Jan. 27, 2022 From the Korean Intellectual Property Office Re. Application No. 10-2017-7007002. (6 Pages).
Interview Summary dated Feb. 22, 2022 from US Patent and Trademark Office Re. U.S. Appl. No. 16/081,706. (2 pages).
Notification of Office Action dated Jan. 24, 2022 From the State Intellectual Property Office of the People's Republic of China Re. Application No. 201780014568.0 and its Translation into English. (9 Pages).
Notice of Allowance dated Jan. 5, 2022 from US Patent and Trademark Office Re. U.S. Appl. No. 16/316,631. (9 pages).
Notification of Office Action dated Dec. 3, 2021 From the State Intellectual Property Office of the People's Republic of China Re. Application No. 201780055014.5 and Its Translation Into English. (5 Pages).
Notification of Office Action and Search Report dated Dec. 23, 2021 From the State Intellectual Property Office of the People's Republic of China Re. Application No. 201780014541.1 and Its Translation of Office Action Into English. (14 Pages).
Grounds of Reason of Rejection dated Jan. 27, 2022 From the Korean Intellectual Property Office Re. Application No. 10-2017-7007002. (6 Pages).
Notice of Allowance dated Feb. 7, 2022 from US Patent and Trademark Office Re. U.S. Appl. No. 16/336,528. (46 pages).
Requisition by the Examiner dated Feb. 9, 2022 From the Innovation, Science and Economic Development Canada, Canadian Intellectual Property Office Re. Application No. 2,954,601. (3 Pages).
Restriction Official Action dated Feb. 4, 2022 from US Patent and Trademark Office Re. U.S. Appl. No. 17/007,095. (6 pages).
Notice of Reason(s) for Rejection dated Dec. 7, 2021 From the Japan Patent Office Re. Application No. 2020-021606 and Its Translation Into English. (11 Pages).
Advisory Action dated Dec. 20, 2021 from US Patent and Trademark Office Re. U.S. Appl. No. 16/081,069. (7 pages).
Notification of Office Action and Search Report dated Sep. 30, 2021 From the State Intellectual Property Office of the People's Republic of China Re. Application No. 201780073531.5 and Its Translation of Office Action Into English. (14 Pages).
Zhang "Research Progress of Interferon-Inducible Protein 10 and Its Effect in Newborn Infection Diagnosis", Chinese Journal of Neonatology. 4: 60-62, Jul. 15, 2013.
Notice of Reason(s) for Rejection dated Dec. 14, 2021 From the Japan Patent Office Re. Application No. 2020-109710 and Its Translation Into English. (7 Pages).
Examination Report dated Feb. 19, 2022 From the Servico Publico Federal, Ministerio da Economia, Institute Nacional da Propriedade Industrial do Brasil RE Application No. BR112014 019733.4. (4 Pages).
Interview Summary dated Apr. 29, 2022 from US Patent and Trademark Office Re. U.S. Appl. No. 16/081,906. (2 pages).
Notice of Allowance dated Mar. 17, 2022 from US Patent and Trademark Office Re. U.S. Appl. No. 16/334,033. (29 pages).
Notification of Office Action and Search Report dated Mar. 15, 2022 From the State Intellectual Property Office of the People's Republic of China Re. Application No. 201780055347.8 and Its Translation of Office Action Into English. (28 Pages).
Altmann et al. "Elevated Cardiac Troponin I in Sepsis and Septic Shock: No Evidence for Thrombus Associated Myocardial Necrosis", PLOSE One, 5(2): 1-5, 2010.
Ammann et al. "Elevation of Troponin I in Sepsis and Septic Shock". Intensive Care Medicine, 27: 965-969, May 16, 2001.
Arshed et al. "Elevated Troponin I in the Absence of Coronary Artery Disease: A Case Report with Review of Literature", Journal of Clinical Medicine Research, 7(10): 820-824, Aug. 23, 2015.
Bessiere et al. "Prognostic Value of Troponins in Sepsis: a Meta-Analysis", Intensive Care Medicine, 39: 1181-1189, Apr. 18, 2018.
Gaedtke et al. "Elevated Troponin is Associated with Mortality in Severe Sepsis and Septic Shock Patients", American Journal of Respiratory and Critical Care Medicine, 189: 1-2, 2014.
Sheyin et al. "The Prognostic Significance of Troponin Elevation in Patients with Sepsis: A Meta-Analysis", Heart & Lung, 44(1): 75-81, Jan.-Feb. 2015.
Wu "Increased Troponin in patients with Sepsis and Septic Shock: Myocardial Necrosis or Reversible Myocardial Depression", Intensive Care Medicine, 27: 959-961, 2001.
Communication of Notices of Opposition (R79(1) EPC) dated May 4, 2022 From the European Patent Office Re. Application No. 17759388.6. (1 Page).
English Translation dated May 10, 2022 of Examination Report dated Apr. 14, 2022 From the Servico Publico Federal, Ministerio da Economia, Instituto Nacional da Propriedade Industrial do Brasil RE Application No. BR11 2017 002884 0. (3 Pages).
Examination Report dated Apr. 14, 2022 From the Servico Publico Federal, Ministerio da Economia, Institute Nacional da Propriedade Industrial do Brasil RE Application No. BR11 2017 002884 0 together with an English Summary and Pending Claims. (8 Pages).
Notice of Allowance dated May 17, 2022 From the US Patent and Trademark Office Re. U.S. Appl. No. 16/081,906. (14 Pages).
Notification of Office Action and Search Report dated Apr. 20, 2022 From the State Intellectual Property Office of the People's Republic of China Re. Application No. 201780073531.5 and Its Translation Into English including Claims.. (31 Pages).
Opposition to European Patent No. 3423589 Memed Diagnostics Ltd. on Behalf of J.A. Kemp LLP dated Apr. 21, 2022 From the European Patent Office Re. Application No. 17759388.6. (31 Pages).
Chaussabel et al. "Assessing the Human Immune System Through Blood Transcriptomics", BMC Biology, 8: 84-1-84-14, Jul. 1, 2010.
De la Grange et al. "A New Advance in Alternative Splicing Databases: From Catalogue to Detailed Analysis of Regulation of Expression and Function of Human Alternative Splicing Variants", BMC Bioinformatics, 8: 180-1-180-14, Jun. 4, 2007.
Hu et al. "Gene Expression Profiles in Febrile Children With Defined Viral and Bacterial Infection", Proc. Natl. Acad. Sci. USA, PNAS, 110(31): 12792-12797, Published Online Jul. 15, 2013.
Qian et al. "Identification of Genes Critical for Resistance to Infection by West Nile Virus Using RNA-Seq Analysis", Viruses, 5(7): 1664-1681, Jul. 8, 2013.
UCSC "Human Gene IFI27 (ENST00000621160.5) From Gencode V39", UCSC Browser, Retrieved From the Internet, 3 Pages, Last Updated Jan. 17, 2022.
UCSC "Human Gene IFIT1 (ENST00000371804.4) From Gencode V39", UCSC Browser, Retrieved From the Internet, 4 Pages, Last Updated Jan. 17, 2022.
UCSC "UCSC Genome Browser on Human (GRCh38/hg38)", UCSC Browser, Retrieved From the Internet, 1 Page, Apr. 14, 2022.
Summons to attend Oral Proceedings Pursuant to Rule 115(1) EPC dated Jun. 10, 2022 From the European Patent Office Re. Application No. 17759389.4, (5 Pages).
Notification of Office Action dated May 11, 2022 From the State Intellectual Property Office of the People's Republic of China Re. Application No. 201780014541.1 and Its Translation Into English. (11 Pages).
Official Action dated Jun. 9, 2022 from US Patent and Trademark Office Re. U.S. Appl. No. 17/007,095. (118 pages).
Requisition by the Examiner dated Jun. 7, 2022 From the Innovation, Science and Economic Development Canada, Canadian Intellectual Property Office Re. Application No. 2,968,650. (3 Pages).

\* cited by examiner

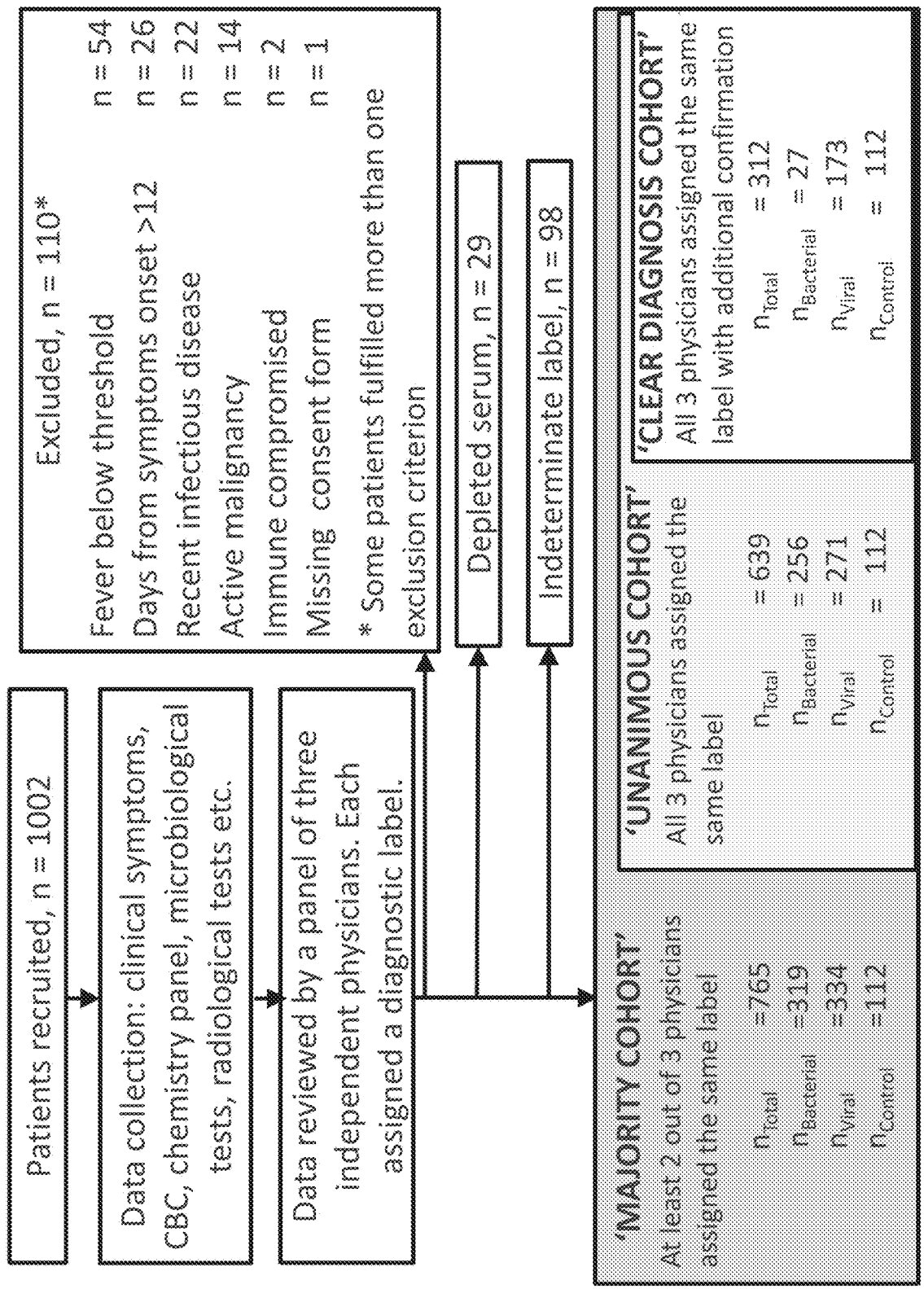

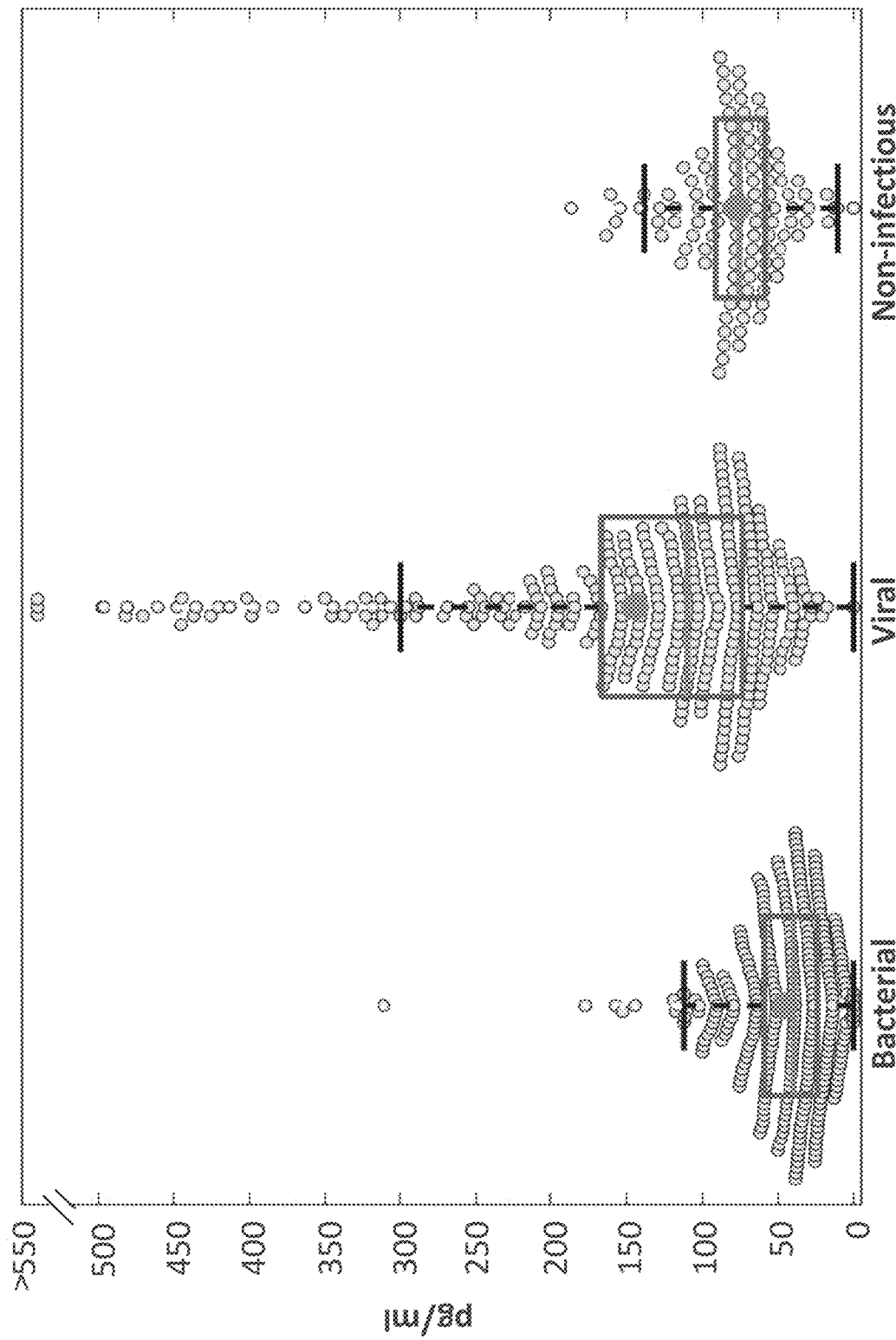

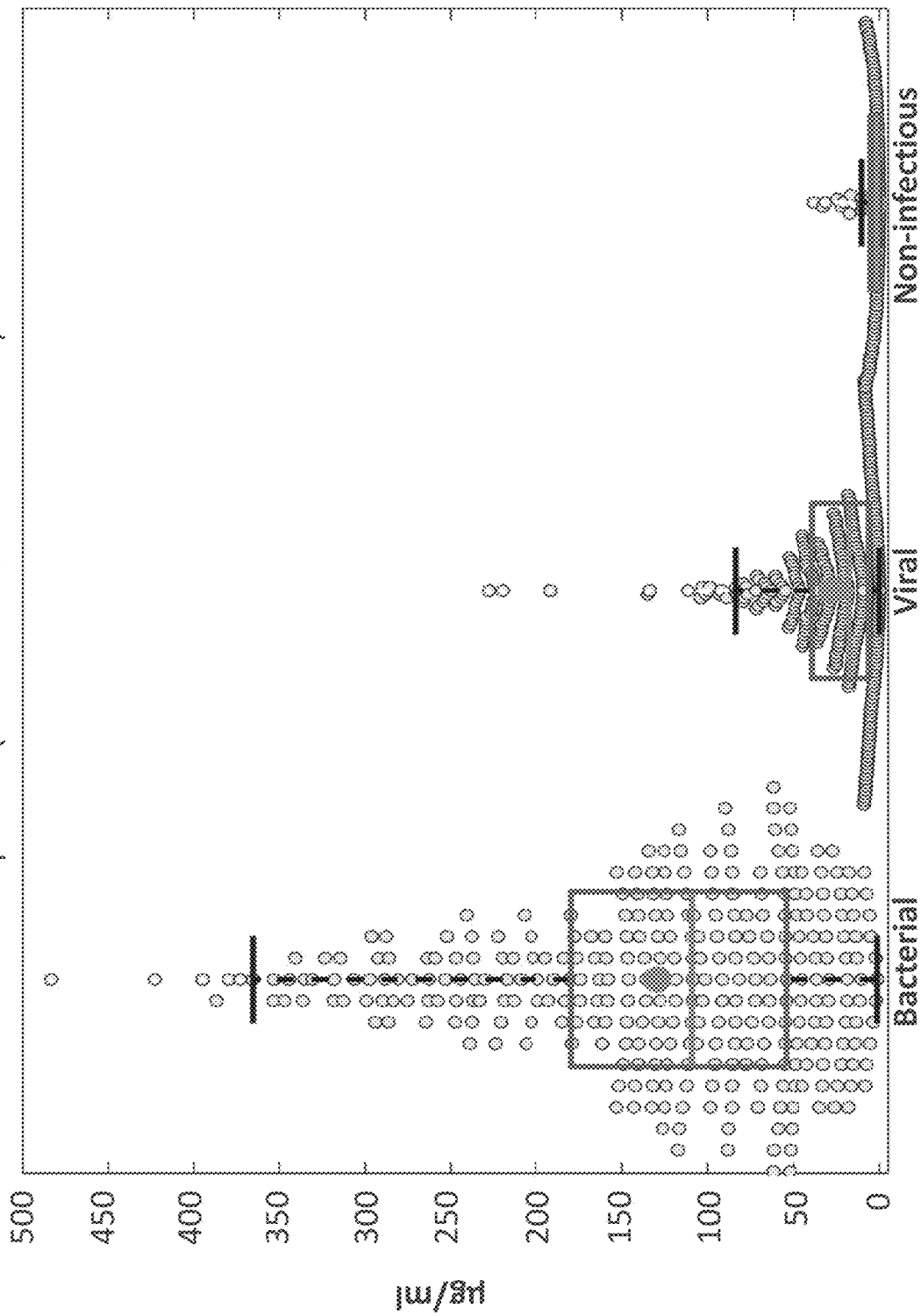

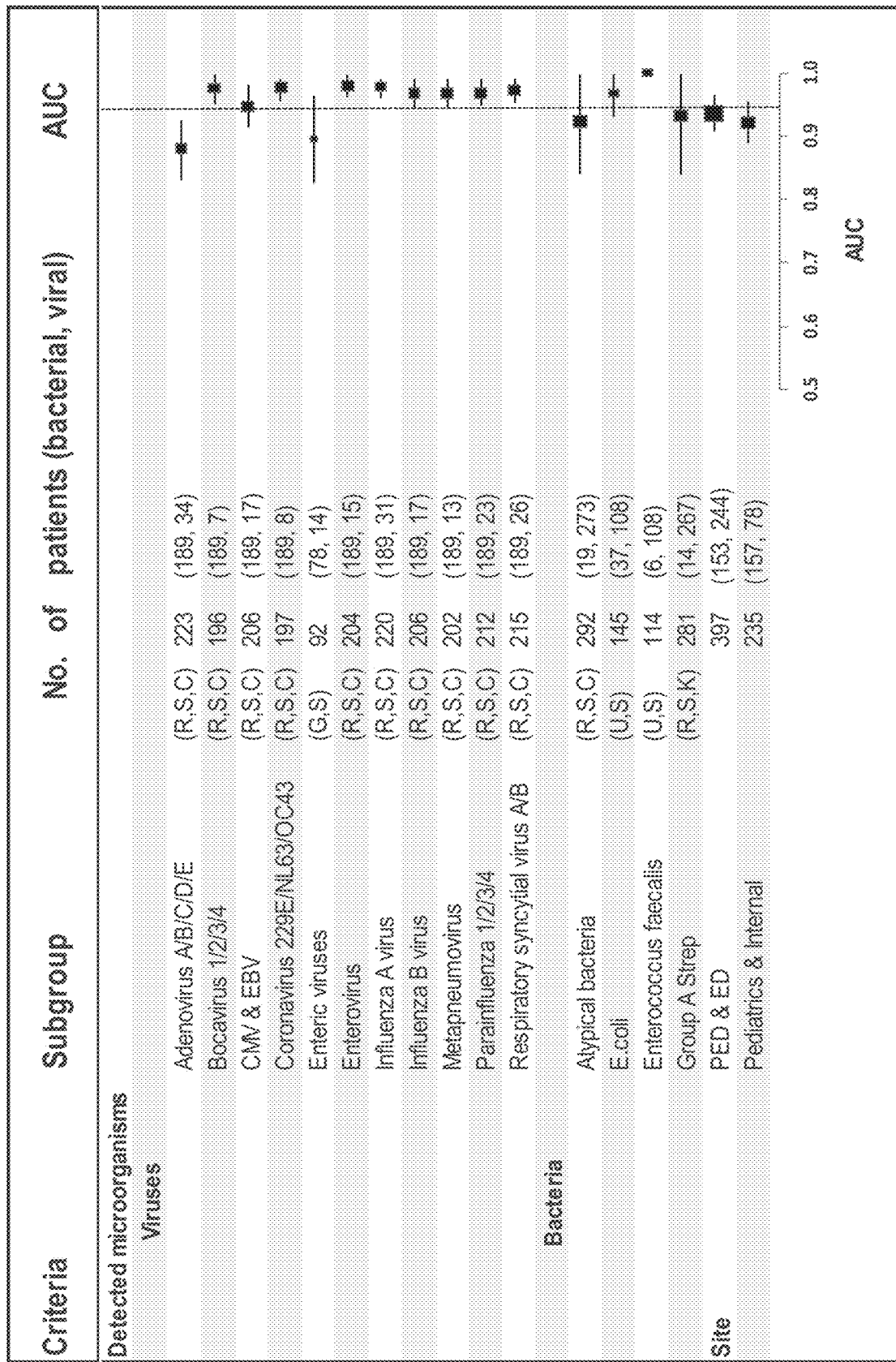
FIG. 4- cont.

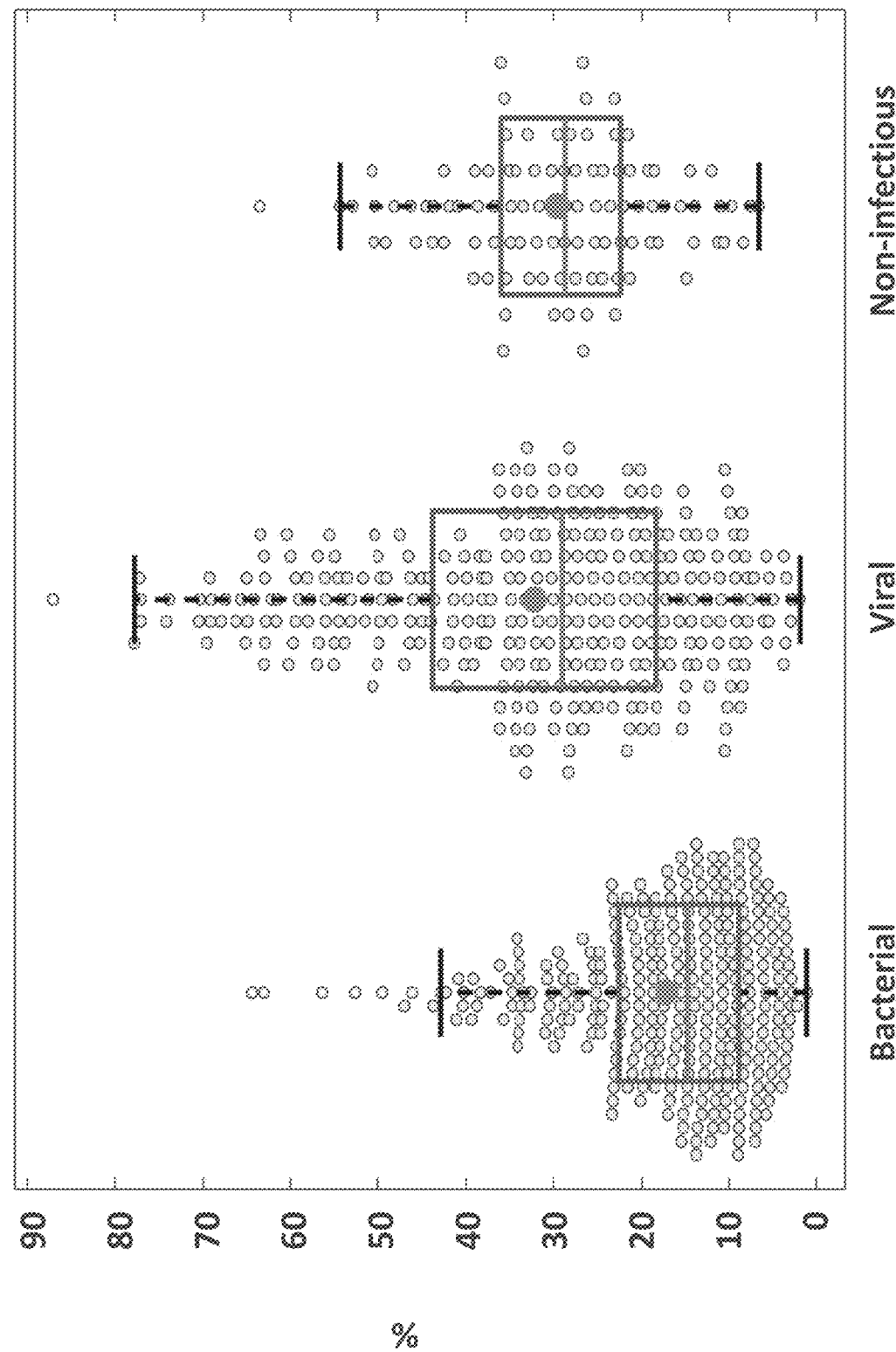

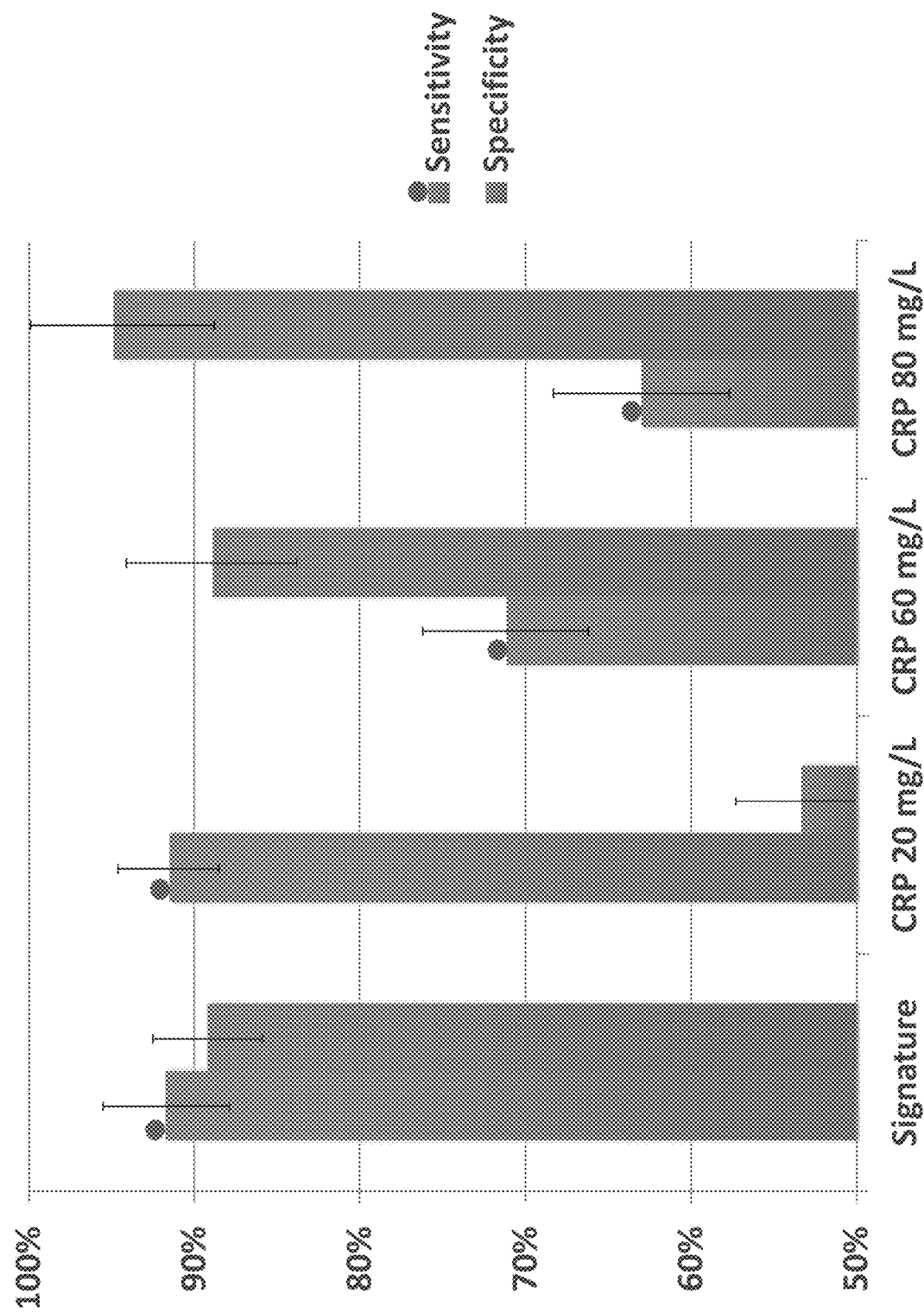

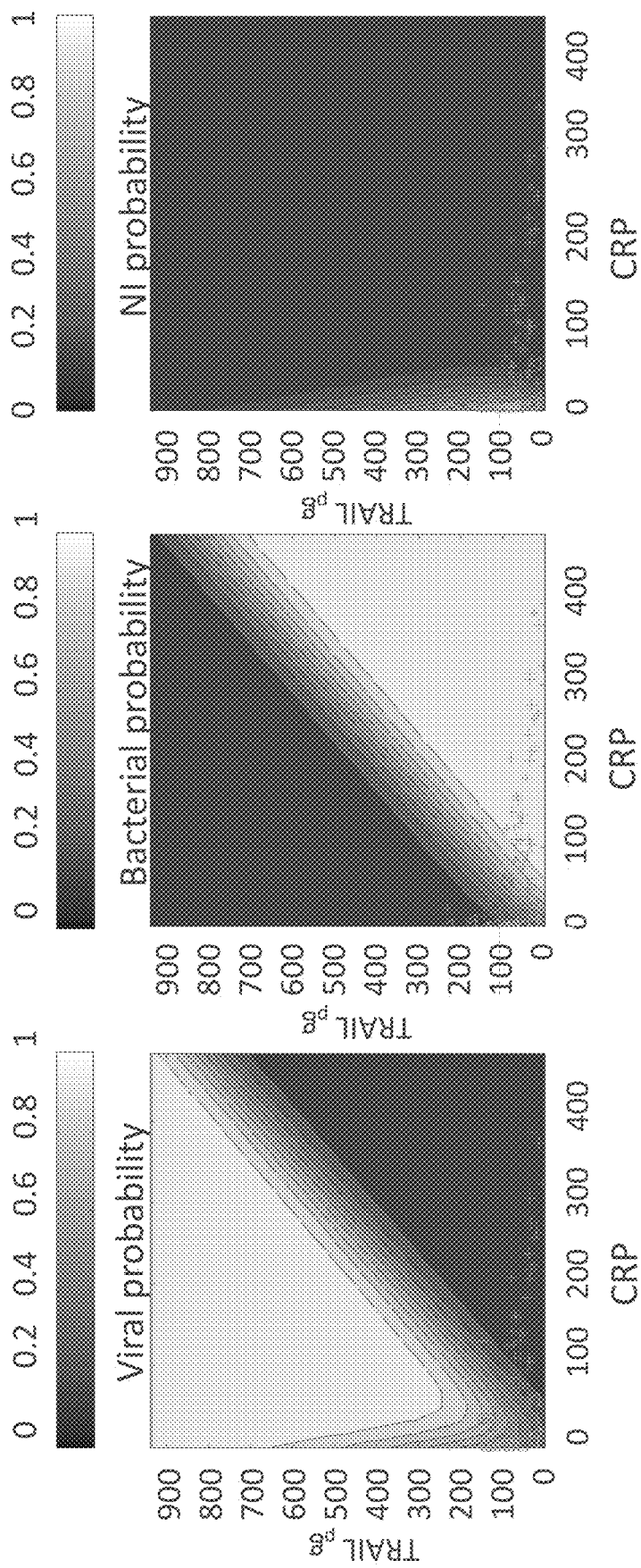

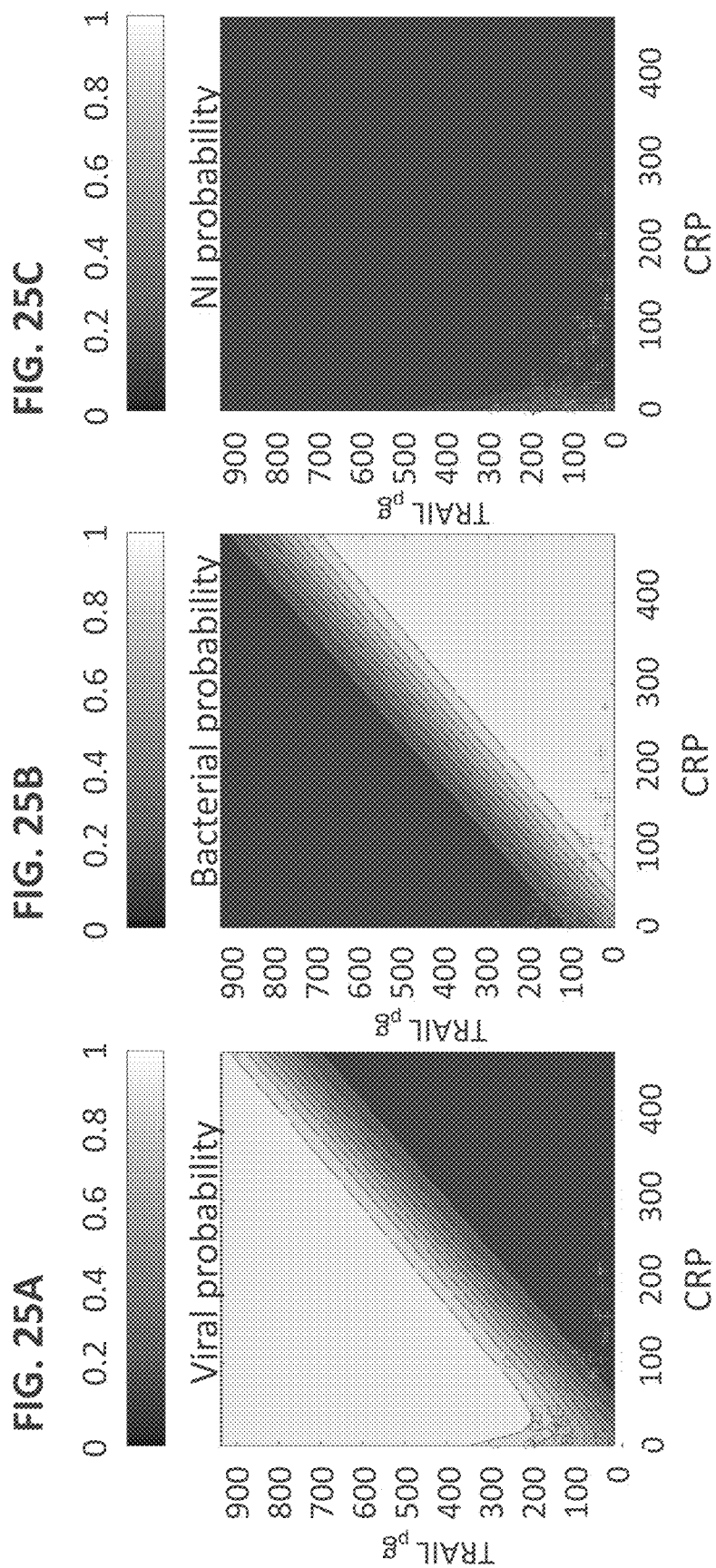

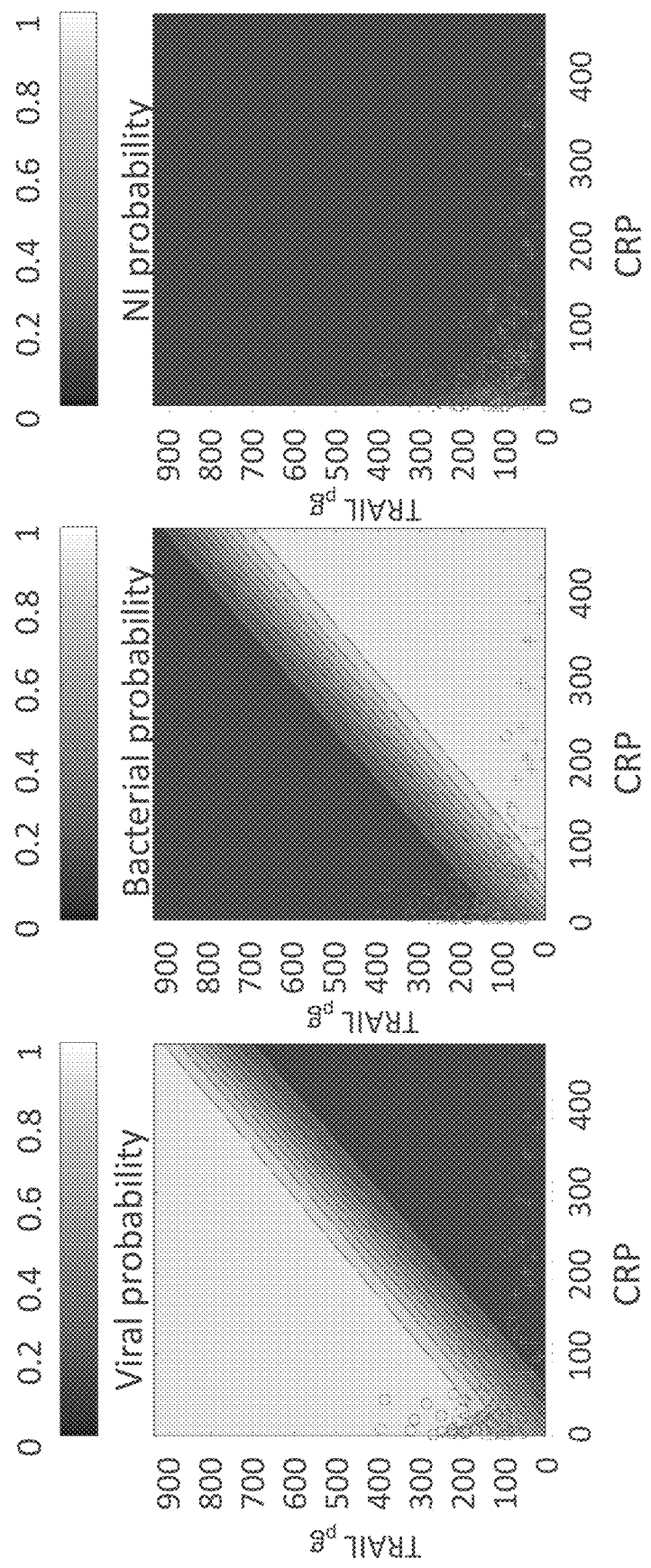

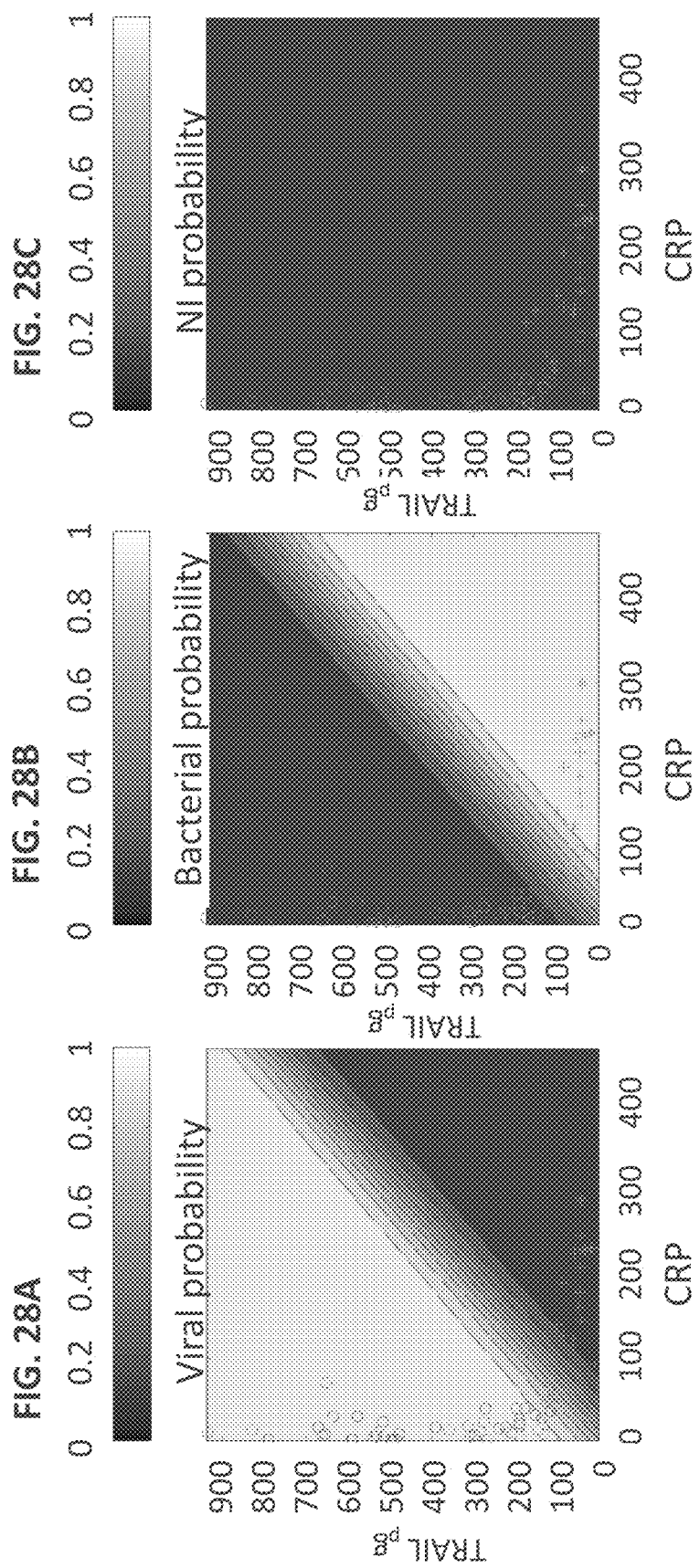

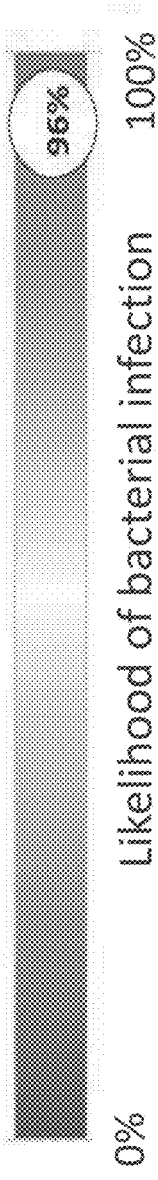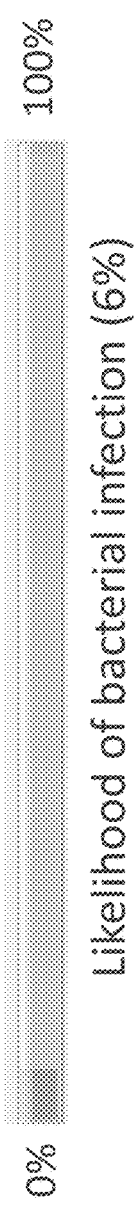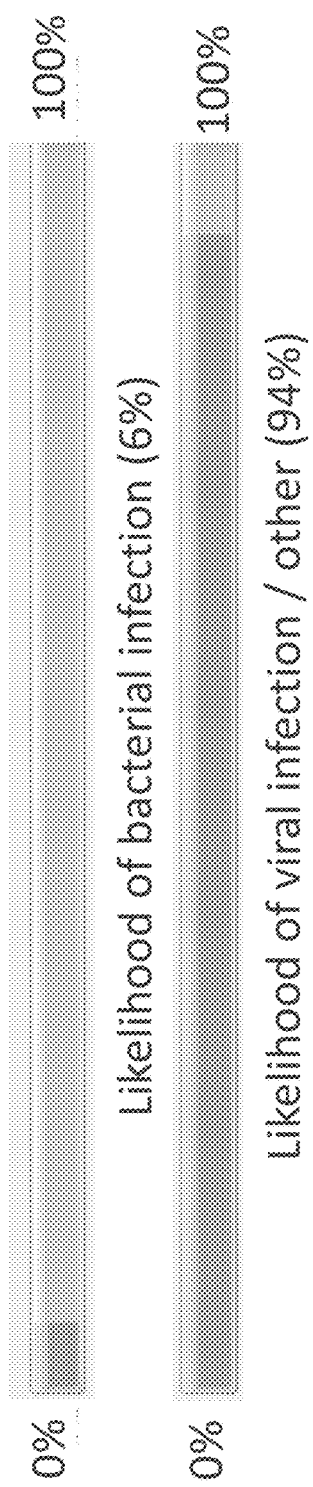
FIG. 29A
FIG. 29B
FIG. 29C

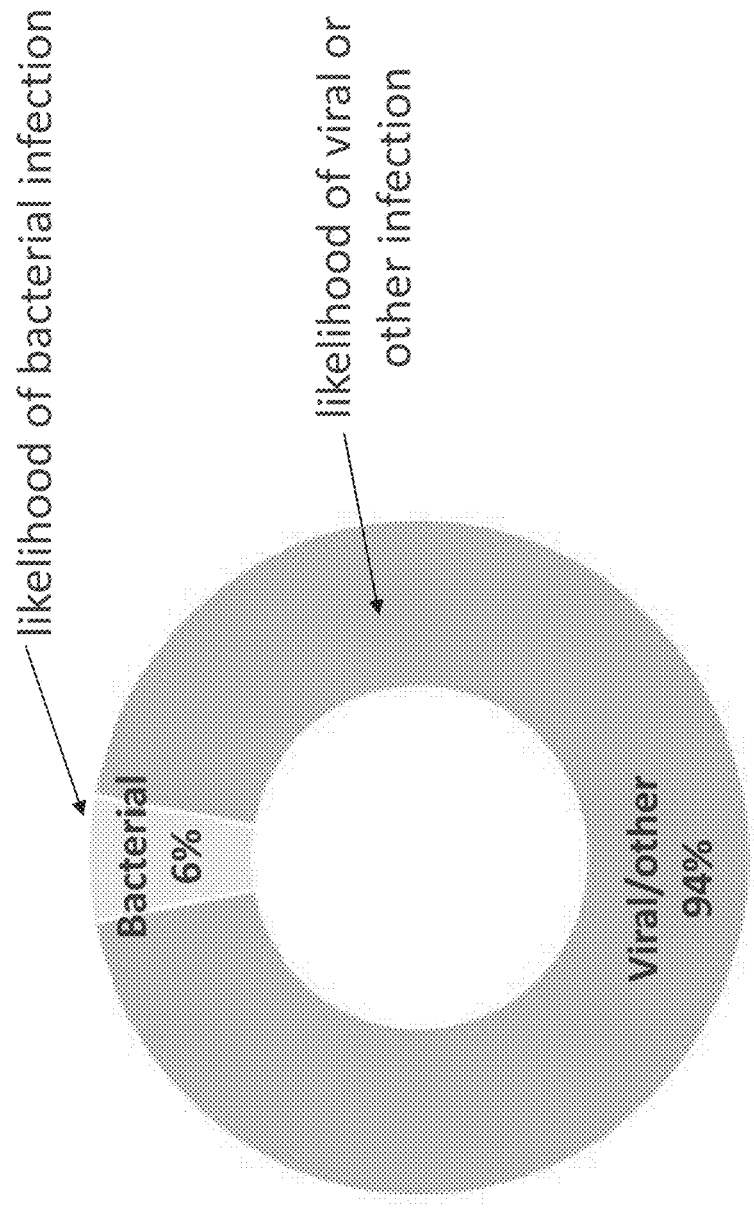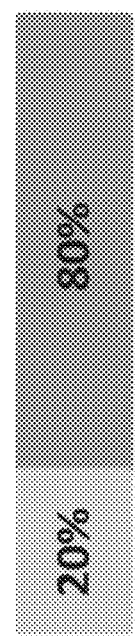
FIG. 29D
FIG. 29E

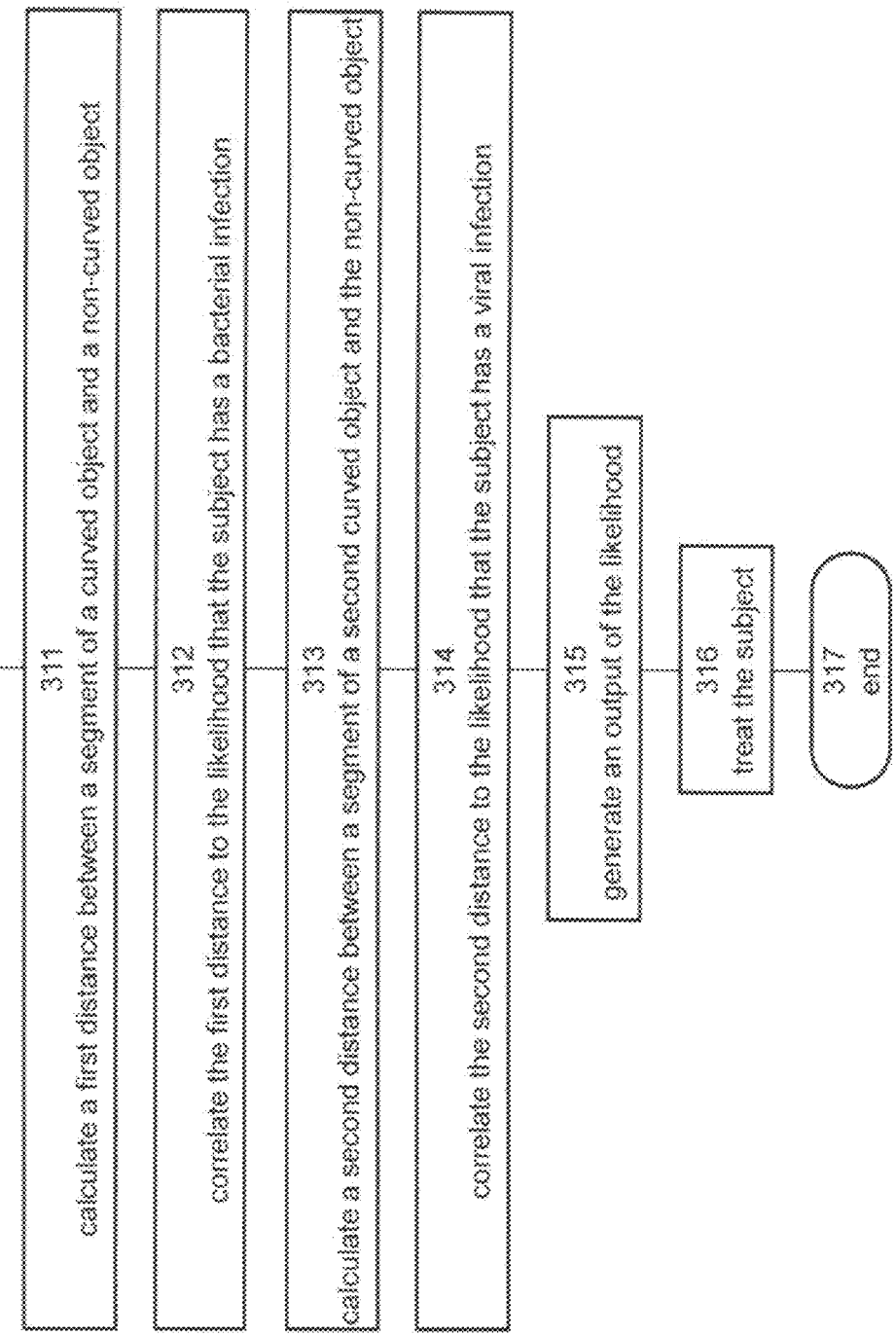

SEQUENCE LISTING

<160> NUMBER OF SEQ ID NOS: 38

<210> SEQ ID NO 1
<211> LENGTH: 1953
<212> TYPE: DNA
<213> ORGANISM: Homo sapiens

<400> SEQUENCE: 1

| | | | | | |
|---|---|---|---|---|---|
| acagaaccca | gaaaaacaac | tcattcgctt | tcatttcctc | actgactata | aaagaataga | 60 |
| gaaggaaggg | cttcagtgac | cggctgcctg | gctgacttac | agcagtcaga | ctctgacagg | 120 |
| atcatggcta | tgatggaggt | ccagggggga | cccagcctgg | gacagacctg | cgtgctgatc | 180 |
| gtgatcttca | cagtgctcct | gcagtctctc | tgtgtggctg | taacttacgt | gtactttacc | 240 |
| aacgagctga | agcagatgca | ggacaagtac | tccaaaagtg | gcattgcttg | tttcttaaaa | 300 |
| gaagatgaca | gttattggga | ccccaatgac | gaagagagta | tgaacagccc | ctgctggcaa | 360 |
| gtcaagtggc | aactccgtca | gctcgttaga | aagatgattt | tgagaacctc | tgaggaaacc | 420 |
| atttctacag | ttcaagaaaa | gcaacaaaat | atttctcccc | tagtgagaga | aagaggtcct | 480 |
| cagagagtag | cagctcacat | aactgggacc | agaggaagaa | gcaacacatt | gtcttctcca | 540 |
| aactccaaga | atgaaaaggc | tctgggccgc | aaaataaact | cctgggaatc | atcaaggagt | 600 |
| gggcattcat | tcctgagcaa | cttgcacttg | aggaatggtg | aactggtcat | ccatgaaaaa | 660 |
| gggttttact | acatctattc | ccaaacatac | tttcgatttc | aggaggaaat | aaaagaaaac | 720 |
| acaaagaacg | acaaacaaat | ggtccaatat | atttacaaat | acacaagtta | tcctgaccct | 780 |
| atattgttga | tgaaaagtgc | tagaaatagt | tgttggtcta | aagatgcaga | atatggactc | 840 |
| tattccatct | atcaagggg | aatatttgag | cttaaggaaa | atgacagaat | ttttgtttct | 900 |
| gtaacaaatg | agcacttgat | agacatggac | catgaagcca | gttttttgg | ggcctttta | 960 |
| gttggctaac | tgacctggaa | agaaaaagca | ataacctcaa | agtgactatt | cagttttcag | 1020 |
| gatgatacac | tatgaagatg | tttcaaaaaa | tctgaccaaa | acaaacaaac | agaaaacaga | 1080 |
| aaacaaaaaa | acctctatgc | aatctgagta | gagcagccac | aaccaaaaaa | ttctacaaca | 1140 |
| cacactgttc | tgaaagtgac | tcacttatcc | caagagaatg | aaattgctga | agatctttc | 1200 |
| aggactctac | ctcatatcag | tttgctagca | gaaatctaga | agactgtcag | cttccaaaca | 1260 |
| ttaatgcaat | ggttaacatc | ttctgtcttt | ataatctact | ccttgtaaag | actgtagaag | 1320 |
| aaagagcaac | aatccatctc | tcaagtagtg | tatcacagta | gtagcctcca | ggtttcctta | 1380 |
| agggacaaca | tccttaagtc | aaaagagaga | agaggcacca | ctaaaagatc | gcagtttgcc | 1440 |
| tggtgcagtg | gctcacacct | gtaatcccaa | cattttggga | acccaaggtg | ggtagatcac | 1500 |
| gagatcaaga | gatcaagacc | atagtgacca | acatagtgaa | accccatctc | tactgaaagt | 1560 |
| acaaaaatta | gctgggtgtg | ttggcacatg | cctgtagtcc | cagctacttg | agaggctgag | 1620 |
| gcaagagaat | tgtttgaacc | cgggaggcag | aggttgcagt | gtggtgagat | catgccacta | 1680 |
| cactccagcc | tggcgacaga | gcgagacttg | gtttcaaaaa | aaaaaaaaaa | aaaaacttca | 1740 |
| gtaagtacgt | gttattttt | tcaataaaat | tctattacag | tatgtcatgt | ttgctgtagt | 1800 |
| gctcatattt | attgttgttt | ttgttttagt | actcacttgt | ttcataatat | caagattact | 1860 |
| aaaaatgggg | gaaaagactt | ctaatctttt | tttcataata | tctttgacac | atattacaga | 1920 |
| agaaataaat | ttcttacttt | taatttaata | tga | | | 1953 |

<210> SEQ ID NO 2
<211> LENGTH: 1805

```
<212> TYPE: DNA
<213> ORGANISM: Homo sapiens

<400> SEQUENCE: 2
acagaaccca gaaaaacaac tcattcgctt tcatttcctc actgactata aaagaatcaga     60 gaaggaaggg cttcagtgac cggctgcctg gctgacttac agcagtcaga ctctgacagg    120
atcatggcta tgatggaggt ccagggggga cccagcctgg acagacctg cgtgctgatc     180 gtgatcttca cagtgctcct gcagtctctc tgtgtggctg taacttacgt gtactttacc    240
aacgagctga agcagatgca ggacaagtac tccaaaagtg gcattgcttg tttcttaaaa    300
gaagatgaca gttattggga ccccaatgac aagagagta tgaacagccc ctgctggcaa     360
gtcaagtggc aactccgtca gctcgttaga aagactccaa gaatgaaaag gctctgggcc    420
gcaaaataaa ctcctgggaa tcatcaagga gtgggcattc attcctgagc aacttgcact    480
tgaggaatgg tgaactggtc atccatgaaa aagggtttta ctacatctat tcccaaacat    540
actttcgatt tcaggaggaa ataaaagaaa acacaaagaa cgacaaacaa atggtccaat    600
atatttacaa atacacaagt tatcctgacc ctatattgtt gatgaaaagt gctagaaata    660
gttgttggtc taaagatgca gaatatgac tctattccat ctatcaaggg ggaatatttg     720
agcttaagga aaatgacaga attttttgttt ctgtaacaaa tgagcacttg atagacatgg    780
accatgaagc cagttttttt ggggcctttt tagttggcta actgacctgg aaagaaaaag    840
caataacctc aaagtgacta ttcagttttc aggatgatac actatgaaga tgtttcaaaa    900
aatctgacca aaacaaacaa acagaaaaca gaaaacaaaa aaacctctat gcaatctgag    960
tagagcagcc acaaccaaaa aattctacaa cacacactgt tctgaaagtg actcacttat   1020
cccaagagaa tgaaattgct gaaagatctt tcaggactct acctcatatc agtttgctag   1080
cagaaatcta gaagactgtc agcttccaaa cattaatgca atggttaaca tcttctgtct   1140
ttataatcta ctccttgtaa agactgtaga agaaagagca acaatccatc tctcaagtag   1200
tgtatcacag tagtagcctc caggtttcct taagggacaa catccttaag tcaaaagaga   1260
gaagaggcac cactaaaaga tcgcagtttg cctggtgcag tggctcacac ctgtaatccc   1320
aacattttgg gaacccaagg tgggtagatc acgagatcaa gagatcaaga ccatagtgac   1380
caacatagtg aaaccccatc tctactgaaa gtacaaaaat tagctgggtg tgttggcaca   1440
tgcctgtagt cccagctact tgagaggctg aggcaagaga attgtttgaa cccgggaggc   1500
agaggttgca gtgtggtgag atcatgccac tacactccag cctggcgaca gagcgagact   1560
tggtttcaaa aaaaaaaaaa aaaaaaactt cagtaagtac gtgttatttt tttcaataaa   1620
attctattac agtatgtcat gtttgctgta gtgctcatat ttattgttgt ttttgtttta   1680
gtactcactt gtttcataat atcaagatta ctaaaaatgg gggaaaagac ttctaatctt   1740
tttttcataa tatctttgac acatattaca gaagaaataa atttcttact tttaatttaa   1800
tatga                                                              1805

<210> SEQ ID NO 3
<211> LENGTH: 1334
<212> TYPE: DNA
<213> ORGANISM: Homo sapiens

<400> SEQUENCE: 3
atttcctcac tgactataaa agaatagaga aggaagggct tcagtgaccg gctgcctggc     60
tgacttacag cagtcagact ctgacaggat catggctatg atggaggtcc aggggggacc    120
```

|  |  |  |  |  | |
|---|---|---|---|---|---|
| cagcctggga | cagacctgcg | tgctgatcgt | gatcttcaca | gtgctcctgc | agtctctctg | 180 |
| tgtggctgta | acttacgtgt | actttaccaa | cgagctgaag | cagtttgcag | aaaatgattg | 240 |
| ccagagacta | atgtctgggc | agcagacagg | gtcattgctg | ccatcttgaa | gtctaccttg | 300 |
| ctgagtctac | cctgctgacc | tcaagcccca | tcaaggactg | gttgaccctg | cctagacaa | 360 |
| ccaccgtgtt | tgtaacagca | ccaagagcag | tcaccatgga | aatccacttt | tcagaaccaa | 420 |
| gggcttctgg | agctgaagaa | caggcaccca | gtgcaagagc | tttcttttca | gaggcacgca | 480 |
| aatgaaaata | atccccacac | gctaccttct | gcccccaatg | cccaagtgtg | gttagttaga | 540 |
| gaatatagcc | tcagcctatg | atatgctgca | ggaaactcat | attttgaagt | ggaaaggatg | 600 |
| ggaggaggcg | ggggagacgt | atcgtattaa | ttatcattct | tggaataacc | acagcacctc | 660 |
| acgtcaaccc | gccatgtgtc | tagtcaccag | cattggccaa | gttctatagg | agaaactacc | 720 |
| aaaattcatg | atgcaagaaa | catgtgaggg | tggagagagt | gactggggct | tcctctctgg | 780 |
| atttctattg | ttcagaaatc | aatatttatg | cataaaaagg | tctagaaaga | gaaacaccaa | 840 |
| aatgacaatg | tgatctctag | atggtatgat | tatgggtact | ttttttcctt | tttattttc | 900 |
| tatattttac | aaattttcta | cagggaatgt | tataaaaata | tccatgctat | ccatgtataa | 960 |
| ttttcataca | gatttaaaga | acacagcatt | tttatatagt | cttatgagaa | acaaccata | 1020 |
| ctcaaaatta | tgcacacaca | cagtctgatc | tcacccctgt | aaacaagaga | tatcatccaa | 1080 |
| aggttaagta | ggaggtgaga | atatagctgc | tattagtggt | gtttttgttt | tgttttttgtg | 1140 |
| atttacttat | ttagttttttg | gagggttttt | tttttctttt | agaaaagtgt | tctttacttt | 1200 |
| tccatgcttc | cctgcttgcc | tgtgtatcct | gaatgtatcc | aggctttata | aactcctggg | 1260 |
| taataatgta | gctacattaa | cttgttaacc | tcccatccac | ttatacccag | gaccttactc | 1320 |
| aattttccag | gttc |  |  |  |  | 1334 |

<210> SEQ ID NO 4
<211> LENGTH: 281
<212> TYPE: PRT
<213> ORGANISM: Homo sapiens

<400> SEQUENCE: 4

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160
```

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 5
<211> LENGTH: 101
<212> TYPE: PRT
<213> ORGANISM: Homo sapiens

<400> SEQUENCE: 5

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Thr Pro Arg Met Lys Arg
                85                  90                  95

Leu Trp Ala Ala Lys
            100

<210> SEQ ID NO 6
<211> LENGTH: 65
<212> TYPE: PRT
<213> ORGANISM: Homo sapiens

<400> SEQUENCE: 6

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Phe Ala Glu Asn
        35                  40                  45

Asp Cys Gln Arg Leu Met Ser Gly Gln Gln Thr Gly Ser Leu Leu Pro
    50                  55                  60

Ser
65

<210> SEQ ID NO 7

<211> LENGTH: 223
<212> TYPE: PRT
<213> ORGANISM: Homo sapiens

<400> SEQUENCE: 7

Gln Asp His Gly Tyr Asp Gly Pro Gly Gly Thr Gln Pro Gly Thr
1               5                   10                  15

Asp Leu Arg Ala Asp Arg Asp Leu His Ser Ala Pro Ala Val Ser Leu
            20                  25                  30

Cys Gly Cys Asn Leu Arg Val Leu Tyr Gln Arg Ala Glu Ala Glu Lys
        35                  40                  45

Gln Gln Asn Ile Ser Pro Leu Val Arg Glu Arg Gly Pro Gln Arg Val
50                  55                  60

Ala Ala His Ile Thr Gly Thr Arg Gly Arg Ser Asn Thr Leu Ser Ser
65                  70                  75                  80

Pro Asn Ser Lys Asn Glu Lys Ala Leu Gly Arg Lys Ile Asn Ser Trp
                85                  90                  95

Glu Ser Ser Arg Ser Gly His Ser Phe Leu Ser Asn Leu His Leu Arg
            100                 105                 110

Asn Gly Glu Leu Val Ile His Glu Lys Gly Phe Tyr Tyr Ile Tyr Ser
        115                 120                 125

Gln Thr Tyr Phe Arg Phe Gln Glu Glu Ile Lys Glu Asn Thr Lys Asn
130                 135                 140

Asp Lys Gln Met Val Gln Tyr Ile Tyr Lys Tyr Thr Ser Tyr Pro Asp
145                 150                 155                 160

Pro Ile Leu Leu Met Lys Ser Ala Arg Asn Ser Cys Trp Ser Lys Asp
                165                 170                 175

Ala Glu Tyr Gly Leu Tyr Ser Ile Tyr Gln Gly Gly Ile Phe Glu Leu
            180                 185                 190

Lys Glu Asn Asp Arg Ile Phe Val Ser Val Thr Asn Glu His Leu Ile
        195                 200                 205

Asp Met Asp His Glu Ala Ser Phe Phe Gly Ala Phe Leu Val Gly
210                 215                 220

<210> SEQ ID NO 8
<211> LENGTH: 178
<212> TYPE: PRT
<213> ORGANISM: Homo sapiens

<400> SEQUENCE: 8

Lys Glu Lys Gln Gln Asn Ile Ser Pro Leu Val Arg Glu Arg Gly Pro
1               5                   10                  15

Gln Arg Val Ala Ala His Ile Thr Gly Thr Arg Gly Arg Ser Asn Thr
            20                  25                  30

Leu Ser Ser Pro Asn Ser Lys Asn Glu Lys Ala Leu Gly Arg Lys Ile
        35                  40                  45

Asn Ser Trp Glu Ser Ser Arg Ser Gly His Ser Phe Leu Ser Asn Leu
50                  55                  60

His Leu Arg Asn Gly Glu Leu Val Ile His Glu Lys Gly Phe Tyr Tyr
65                  70                  75                  80

Ile Tyr Ser Gln Thr Tyr Phe Arg Phe Gln Glu Glu Ile Lys Glu Asn
                85                  90                  95

Thr Lys Asn Asp Lys Gln Met Val Gln Tyr Ile Tyr Lys Tyr Thr Ser
            100                 105                 110

Tyr Pro Asp Pro Ile Leu Leu Met Lys Ser Ala Arg Asn Ser Cys Trp
        115                 120                 125

```
Ser Lys Asp Ala Glu Tyr Gly Leu Tyr Ser Ile Tyr Gln Gly Gly Ile
    130                 135                 140

Phe Glu Leu Lys Glu Asn Asp Arg Ile Phe Val Ser Val Thr Asn Glu
145                 150                 155                 160

His Leu Ile Asp Met Asp His Glu Ala Ser Phe Phe Gly Ala Phe Leu
                165                 170                 175

Val Gly

<210> SEQ ID NO 9
<211> LENGTH: 2421
<212> TYPE: DNA
<213> ORGANISM: Homo sapiens

<400> SEQUENCE: 9
caccctcatg agccccgggt acgtttaact attgagggcc aggaaattgc cttcctcctg      60
gacactggcg cagccttctc agggttaatc tcctgtcctg gatgactgtc ttcaaggtcc     120
gttaccaccc gaggaatcct gggacagcct ataaccaggc atttctccca catcctcagt     180
tgtaattgag agactttaat cttttcacat gccttttttg ttattcctga aagtcccaca     240
cccttattaa ggagggatat attagccaag gctggagcta ttatctacat gaatatgggg     300
aaaaagttac ccatttgctg tcccctactt gaggagggaa tcaaccctga agtctgggca     360
ttggaaggac aatttggaag ggcaaaaaat gcctgcccag tccaaatcag gttaaaagat     420
cccaccactt ttccgtatca aaggcaatat cccttaaggc ctgaagctca taaaggatta     480
tagaatattg ttaaacattt aaaagctcaa ggcttagtga ggaaatgcag cagtccctgc     540
aacaccccag ttctaggagt acaaaaacca acagtcagt ggagactagt gcaagatctt      600
agactcatta atgaggcagt aattcctcta tatccagttg tacccaaccc ctataccctg     660
ctctctcaaa taccagggga agcagaatgg ttcacggttc tggacctcaa ggatgccttc     720
ttctttattc ccctgcactc tgactcccag ttttctcttg cttttgagga tcccacagac     780
cacacgtccc aacttacaca gatggtcttg ccccaagggt ttagggatag ccctcatctg     840
tttggtcagg cactggccca agatctatag gccacttctc aagtccaggc actctggtcc     900
ttcaatatgt ggatgattta cttttggcta ccagtttgga agcctcgtgc cagcaggcta     960
ctctggatct cttgaacttt ctggctaatc aagggtacaa ggtgtctagg tcgaaggccc    1020
agctttgcct acagcaggtt aaatatctaa gcctaatctt agccaaaggg accagggccc    1080
tcagcaagga atgaatacag cctatactgg cttatcctca ccctaagaca ttaaaacagt    1140
tgcggggatt ccttggaatt actggctttt gctgactatg gatctccaga tacagcgaga    1200
cagccaggcc cctctatact ctaatcaagg aaacccagag ggcaaatact catctagtcg    1260
aaagggaacc agaggcagaa acagccttca aaagcttaaa gcaggctcta gtacaagctc    1320
cagctttaag ccttcccaca ggacagaact tctctttata catcacagag agagccaaga    1380
tagctcttgg agtccttaga ctcgtgggac aaccccacaa ccagtggcat acctaagtaa    1440
ggaaattgat gtagtagcaa aaggctggcc tcactgttta agggtagttg cagcagcggc    1500
cgtcttagcg tcagaggcta tcagaataat acaaggaaag gatctcactg tctggactac    1560
tcatgatgta aatggcatac taggtgccaa aggaagttta tggctatcag acaaccgcct    1620
cttagatgcc aggcactact ccttgaggga ctggtgctta aaatatgcac gtgcgtggcc    1680
ctcaaccctg ccacttttct cccagaggat ggggaaccaa ttgagcatga ctgccaacaa    1740
attatagtcc agacttatgc cgcccgagat gatctcttag aagtccccctt aactaatcct    1800
```

```
gaccttaacc tatataccga cggaagttca tttgtggaga atgggatacg aagggcaggt    1860
tacgccatag tgatgtaacc acacttgaaa gcaagcctct tcccccaggg accagtgccc    1920
agttagcaga actagtggca cttacccgag ccttagaact gggaaaggga aaaagaataa    1980
atgtgtatac agataacaag tatgcttatc taatcctaca tgcccatgct gcaatatgga    2040
aagaatggga gttcctaacc tctgggaacc ccgctggat gccacaggga agttatggag     2100
ttattgcaca tggtgcagga acccaaagag gtgggagtct acactacca aggccatcaa     2160 aatgggaagg agaggggaga acagcagcat aagcggctgg cagaggtagg gaaagaccag    2220
caagaaggaa agagagaaag agaaagtcag agaaagagac agagagagga agagacagag    2280
agacagaacg ttaaagaggg tgtcagaaac agagacaaac aaaaggagtc agaaagaagg    2340
acagacacag aaagtcaaag agagagttaa aagagagga agagacaaag aagtcgaaga     2400
gagaaagaga gagatggaag t                                              2421
```

<210> SEQ ID NO 10
<211> LENGTH: 2421
<212> TYPE: DNA
<213> ORGANISM: Homo sapiens

<400> SEQUENCE: 10

```
ctttgcagat aaatatggca cactagcccc acgttttctg agacattcct caattgctta     60
gacatattct gagcctacag cagaggaacc tccagtctca gcaccatgaa tcaaactgcc    120
attctgattt gctgccttat ctttctgact ctaagtggca ttcaaggtaa ggaacatcaa    180
aggatactta atttgtaaaa tgagaaatag gaataggtat aaattctaaa aatacagaaa    240
taatgtattt gtaaaagttt cactgcatgc ttataaataa gagggaaata atagagatt    300 ccctcagatc ataaaactta tatgaattga agtgagagaa acaaatagaa taagagaaag    360
agaaggaaaa agggaaggag gacagaagag atggggaaga gggaggatag agagagaaaa    420
tgtgagggaa tgcggacaga gatgagatac agatacttcc ttacctaact aagctcaatg    480
aaccacatga actgtgctta agggtttgac tttataatca acaagctgca attcttttct    540
tccagataat caactcttta atcatttaca gttgtgttat gatgtgatcc attcctcctc    600
agattaagtg actatttgct gatatgggga tataggttct gctaaatacc accagtctac    660
attaaatgcc taaatgaac actgtgctaa ccttctctgc tgttcctctt ttcctacagg     720
agtacctctc tctagaactg tacgctgtac ctgcatcagc attagtaatc aacctgttaa    780
tccaaggtct ttagaaaaac ttgaaattat tcctgcaagc caattttgtc cacgtgttga    840
gatcatgtga gtgaaatccc atctgattat cacttccctg gttgtaatta tatactgtat    900
taaatatgta atgataataa aaaagatca gtaagggtt tgtgatgatt ctaaaactaa      960
tgtacagcaa acaaaaacat gcagagtgaa acttaaatgt ctgacttcag aactgcgtat   1020
gccatctgtt ttattgaccc aacacagttt taaatatttt catccctatt tatttctaca   1080
gtgctacaat gaaaaagaag ggtgagaaga gatgtctgaa tccagaatcg aaggccatca   1140
agaatttact gaaagcagtt agcaaggaaa ggtaggtttg ctgttgcctg cagaagaatt   1200
gctctttagg aaacggcaat cttgggagtc agaaatactt gcattgtggt ttgctgtgca   1260
atcgctggtt taaagtatg ttaccaccac gccctcccct acctccattt atttaaatgc    1320
tgaggcacca tcttgtgtga taagtatcag aagttaccct gattaccagt caaccttgaa   1380
gtacagctat aactatctaa gcaaaactga caacatttc cccaagtctt tcatggttga   1440
```

| | |
|---|---|
| aaaaagcaac cccctataatc cataatgaat gcatagcagc aggaaagctc agttatctat | 1500 |
| tctatgaact cggtactttc caaacacaac ccaatctgaa gccagagtca gactatcaca | 1560 |
| cttttatatc cccttttctct tcttacaggt ctaaaagatc tccttaaaac cagaggggag | 1620 |
| caaaatcgat gcagtgcttc caaggatgga ccacacagag gctgcctctc ccatcacttc | 1680 |
| cctacatgga gtatatgtca agccataatt gttcttagtt tgcagttaca ctaaaaggtg | 1740 |
| accaatgatg gtcaccaaat cagctgctac tactcctgta ggaaggttaa tgttcatcat | 1800 |
| cctaagctat tcagtaataa ctctaccctg gcactataat gtaagctcta ctgaggtgct | 1860 |
| atgttcttag tggatgttct gaccctgctt caaatatttc cctcacctttt cccatcttcc | 1920 |
| aagggtacta aggaatcttt ctgctttggg gtttatcaga attctcagaa tctcaaataa | 1980 |
| ctaaaaggta tgcaatcaaa tctgcttttt aaagaatgct cttactttca tggacttcca | 2040 |
| ctgccatcct cccaaggggc ccaaattctt tcagtggcta cctacataca attccaaaca | 2100 |
| catacaggaa ggtagaaata tctgaaaatg tatgtgtaag tattcttatt taatgaaaga | 2160 |
| ctgtacaaag tagaagtctt agatgtatat atttcctata ttgttttcag tgtacatgga | 2220 |
| ataacatgta attaagtact atgtatcaat gagtaacagg aaaattttaa aaatacagat | 2280 |
| agatatatgc tctgcatgtt acataagata aatgtgctga atggttttca aaataaaaat | 2340 |
| gaggtactct cctggaaata ttaagaaaga ctatctaaat gttgaaagat caaaaggtta | 2400 |
| ataaagtaat tataactaag a | 2421 |

<210> SEQ ID NO 11
<211> LENGTH: 2421
<212> TYPE: DNA
<213> ORGANISM: Homo sapiens

<400> SEQUENCE: 11

| | |
|---|---|
| agatgacttt tttctatttta tatttaataa gatgatgaac ccttcttgca ttcccgaaat | 60 |
| aaacctcaac tgttacagtg ttttattctt ttaatatgta cgaagtacat gttaagcaag | 120 |
| ttatttccta agcagcccca caaactgggc actactacca tcctgctctg cccctccctc | 180 |
| actctacttc agccacttca gccacaatgg cctctcctca ctgcccctct gatgcaccaa | 240 |
| gcttgttctc acctcaggaa tgtgcaacac ctgccagact tgctgttccc cggagcctcc | 300 |
| atccccagat atcctcatat atcatcctcc tcttcatttg tgtctctgct tacatatgac | 360 |
| ctatttacag aagcctttcc tgtctacccc ccatgaaata gaaatcgcat tccaatcttg | 420 |
| tctctacccc aatgctgttt cattttgtct gtagcaattg tcatcatctc atatatattc | 480 |
| acatgtggaa aatacacaaa atgtttaact tcttttaatt tacattccat ttccccatga | 540 |
| attgaagctc catgacagcg gagattttc tctgctttcc ctgttgctca cttcccagca | 600 |
| ccaagagcag gcctggcaca tgggaagtac ttactattta ttgaatggat gaatgaacaa | 660 |
| atgaatgaat ggatacttat tttacacata agaaaactga agcttataga aattaagtaa | 720 |
| ctaaaatcac acagaagcac agctgaaact aaaacctacg tctaactttc aattcctgac | 780 |
| ccttaaccat taaaacaaat gacaggtgac tttaggccac tgaaaatgct catataatct | 840 |
| tatgaattct aaagcacaag ttaatcacac cattgattga aagtctgagg aatactgtat | 900 |
| agacaagccc ctgtacaagg taagcaaaag aatcagagga tggcctccaa agaattccct | 960 |
| ggacattatg ggaattacat tgttagcctt cctactgata cccataagcc tcacagcaag | 1020 |
| catcatgaag ctgtgacctt catctgcaca tgcccttgta tacccaaaag ataaaactgg | 1080 |
| atgcttcagg gccgaatggc caataaacac gtgtttatta ctggcatggg cagacacaca | 1140 |

```
tactgaaagt accatttccc agcggactag ccatattatg atcagtacag acactaaaga    1200
tttagctttg aaaaaactat ttgctcttcc aaagctgaag aatcttctgt gatttcaaca    1260
ggcaagttac agtcaggtat tcttaatgtt cttttcctcc tctctcactg ggatactttc    1320
tttccttcag acaacgtcaa gcgaaaaaca aaatttcaca aatctccatt tctgacacta    1380
aacagtacag tatctttatt ttttttataa tttaatcaaa ccctgtattt tagaactgtg    1440
gggctgatcc aacattgcaa tgtgtcacat ttaattccat caatgtaaag cataatgagc    1500
aaagattaag gtagtgaggc ataactaaat gttttgaacc tgtgaatttc aaaagcaagg    1560
cccatttgtg ttattttcta aatagtaaat aaaatcattt ccaacatttt cactatcaaa    1620
ttacagtaat ttttccacca gtacacactt gaggaaagcc acaaaaagac ttttccaaca    1680
gttcattctg ttattgctca taaccttcta aatacttctc ctcattggct tctattcaaa    1740
ggtaaatgga aagcagtaaa atttatggaa aatatattca actgcttaaa atacatcaac    1800
caaaaaaaag attttagagc tgtattatga gttgtgaaat tgcattgcct tcacttacct    1860
ttcagtttca ctggtaggta acaaaactga cagactggtc aagttccaaa acatccccta    1920
tatagagcct gactcttcca tctcaaattc tcaccttggt caaggccaga gtaaacacct    1980
gtccttcaca tttttacaca acatcacttt gtatgctaca aatataagct ttcataccag    2040
ggaggaagca aattccagga cactggaaac atttctgctc tcttaaacca gtctgttgat    2100
tgttcccttg actttctcag ctgtcaggat agtgaaagga ggaaaactgc aaaactgtaa    2160
agtataacct gataagtttg ccctttaagc ttttcacaca gagagaggta aaataaaact    2220
caagtctaag gtttaaaatt gagctatgaa tattatattc tagcactaga caaaaatgtt    2280
gcaagatttt aataaaataa gattattaaa atcaattttt acatttcatg ggccaaggag    2340
agacatcaaa gaatgtttaa ctaacatttt aaagatacta tactttataa agttaagaag    2400
aaaaatgaca actgcaccag t                                              2421

<210> SEQ ID NO 12
<211> LENGTH: 1227
<212> TYPE: DNA
<213> ORGANISM: Homo sapiens

<400> SEQUENCE: 12
ctttgcagat aaatatggca cactagcccc acgttttctg agacattcct caattgctta     60
gacatattct gagcctacag cagaggaacc tccagtctca gcaccatgaa tcaaactgcc    120
attctgattt gctgccttat cttcctgact ctaagtggca ttcaaggagt acctctctct    180
agaactgtac gctgtacctg catcagcatt agtaatcaac ctgttaatcc aaggtcttta    240 gaaaacttg aaattattcc tgcaagccaa ttttgtccac gtgttgagat cattgctaca    300
atgaaaaaga agggtgagaa gagatgtctg aatccagaat cgaaggccat caagaattta    360
ctgaaagcag ttagcaagga aaggtctaaa agatctcctt aaaaccagag gggagcaaaa    420
tcgatgcagt gcttccaagg atggaccaca cagaggctgc ctctcccatc acttccctac    480
atggagtata tgtcaagcca taattgttct tagtttgcag ttacactaaa aggtgaccaa    540
tgatggtcac caaatcagct gctactactc ctgtaggaag gttaatgttc atcatcctaa    600
gctattcagt aataactcta ccctggcact ataatgtaag ctctactgag gtgctatgtt    660
cttagtggat gttctgaccc tgcttcaaat atttccctca cctttcccat cttccaaggg    720
tactaaggaa tctttctgct ttggggttta tcagaattct cagaatctca ataactaaa     780
```

| | |
|---|---|
| aggtatgcaa tcaaatctgc tttttaaaga atgctcttta cttcatggac ttccactgcc | 840 |
| atcctcccaa ggggcccaaa ttctttcagt ggctacctac atacaattcc aaacacatac | 900 |
| aggaaggtag aaatatctga aaatgtatgt gtaagtattc ttatttaatg aaagactgta | 960 |
| caaagtagaa gtcttagatg tatatatttc ctatattgtt ttcagtgtac atggaataac | 1020 |
| atgtaattaa gtactatgta tcaatgagta acaggaaaat tttaaaaata cagatagata | 1080 |
| tatgctctgc atgttacata agataaatgt gctgaatggt tttcaaaata aaaatgaggt | 1140 |
| actctcctgg aaatattaag aaagactatc taaatgttga aagatcaaaa ggttaataaa | 1200 |
| gtaattataa ctaagaaaaa aaaaaaa | 1227 |

<210> SEQ ID NO 13
<211> LENGTH: 98
<212> TYPE: PRT
<213> ORGANISM: Homo sapiens

<400> SEQUENCE: 13

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 14
<211> LENGTH: 2301
<212> TYPE: DNA
<213> ORGANISM: Homo sapiens

<400> SEQUENCE: 14

| | |
|---|---|
| aaggcaagag atctaggact tctagcccct gaactttcag ccgaatacat cttttccaaa | 60 |
| ggagtgaatt caggcccttg tatcactggc agcaggacgt gaccatggag aagctgttgt | 120 |
| gtttcttggt cttgaccagc ctctctcatg cttttggcca gacaggtaag ggccacccca | 180 |
| ggctatggga gagatttgat ctgaggtatg ggggtggggt ctaagactgc atgaacagtc | 240 |
| tcaaaaaaaa aaaaaaaaga ctgtatgaac agaacagtgg agcatccttc atggtgtgtg | 300 |
| tgtgtgtgtg tgtgtgtgtg tgtgtgtgtg tggtgtgtaa ctggagaagg ggtcagtctg | 360 |
| tttctcaatc ttaaattcta tacgtaagtg aggggataga tctgtgtgat ctgagaaacc | 420 |
| tctcacattt gcttgttttt ctggctcaca gacatgtcga ggaaggcttt tgtgtttccc | 480 |
| aaagagtcgg atacttccta tgtatccctc aaagcaccgt taacgaagcc tctcaaagcc | 540 |
| ttcactgtgt gcctccactt ctacacggaa ctgtcctcga cccgtgggta cagtattttc | 600 |
| tcgtatgcca ccaagagaca agacaatgag attctcatat tttggtctaa ggatatagga | 660 |
| tacagtttta cagtgggtgg gtctgaaata ttattcgagg ttcctgaagt cacagtagct | 720 |
| ccagtacaca tttgtacaag ctgggagtcc gcctcaggga tcgtggagtt ctgggtagat | 780 |
| gggaagccca gggtgaggaa gagtctgaag aagggataca ctgtggggc agaagcaagc | 840 |

```
atcatcttgg ggcaggagca ggattccttc ggtgggaact ttgaaggaag ccagtccctg    900
gtgggagaca ttggaaatgt gaacatgtgg gactttgtgc tgtcaccaga tgagattaac    960
accatctatc ttggcgggcc cttcagtcct aatgtcctga actggcgggc actgaagtat   1020
gaagtgcaag gcgaagtgtt caccaaaccc cagctgtggc cctgaggccc agctgtgggt   1080
cctgaaggta cctcccggtt ttttacaccg catgggcccc acgtctctgt ctctggtacc   1140
tcccgctttt ttacactgca tggttcccac gtctctgtct ctgggccttt gttccctat    1200 atgcattgca ggcctgctcc accctcctca gcgcctgaga atggaggtaa agtgtctggt   1260
ctgggagctc gttaactatg ctgggaaacg gtccaaaaga atcagaattt gaggtgtttt   1320
gttttcattt ttatttcaag ttggacagat cttggagata atttcttacc tcacatagat   1380
gagaaaacta acacccagaa aggagaaatg atgttataaa aaactcataa ggcaagagct   1440
gagaaggaag cgctgatctt ctatttaatt ccccacccat gaccccaga aagcaggagg    1500 gcattgccca cattcacagg gctcttcagt ctcagaatca ggacactggc caggtgtctg   1560
gtttgggtcc agagtgctca tcatcatgtc atagaactgc tgggcccagg tctcctgaaa   1620
tgggaagccc agcaatacca cgcagtccct ccactttctc aaagcacact ggaaaggcca   1680
ttagaattgc cccagcagag cagatctgct ttttttccag agcaaaatga agcactaggt   1740
ataaatatgt tgttactgcc aagaacttaa atgactggtt tttgtttgct tgcagtgctt   1800
tcttaatttt atggctcttc tgggaaactc ctccccttt ccacacgaac cttgtggggc    1860
tgtgaattct ttcttcatcc ccgcattccc aatataccca ggccacaaga gtggacgtga   1920
accacagggt gtcctgtcag aggagcccat ctcccatctc cccagctccc tatctggagg   1980
atagttggat agttacgtgt tcctagcagg accaactaca gtcttcccaa ggattgagtt   2040
atggactttg ggagtgagac atcttcttgc tgctggattt ccaagctgag aggacgtgaa   2100
cctgggacca ccagtagcca tcttgtttgc cacatggaga gagactgtga ggacagaagc   2160
caaactggaa gtggaggagc caagggattg acaaacaaca gagccttgac cacgtggagt   2220
ctctgaatca gccttgtctg gaaccagatc tacacctgga ctgcccaggt ctataagcca   2280
ataaagcccc tgtttacttg a                                              2301
```

<210> SEQ ID NO 15
<211> LENGTH: 2301
<212> TYPE: DNA
<213> ORGANISM: Homo sapiens

<400> SEQUENCE: 15

```
aggaattgaa ctcagctctg ccccaagcgg acctaataga catctacaga actctccacc      60
ccaaatcaac agaatataca ttttttttcag caccacacca cacctattcc aaaattgatc    120
acatagttgg cagtaaagct ctcctcagca aatgtaaagg aacagaaatt ataacaaact    180
atctctcaga ccacagtgca atcaaattag aactcagaat taagaatctc actcaaaacc    240
gcacaactac atggaaactg aacaacctgc ttctgaatga ctactgggta cataatgaaa    300
tgaaggcaga aataaagatg ttcttttgaaa tgaacaagaa caaacacaca acataccaga    360
atctctggga cgcattcaaa gcagtgtgta gagggaaatt tatagcacta aatgcccaca    420
agagaaagca ggaaacatcc aaaattgaca tcctaacatc acagttaaaa gaactagaaa    480
agcaagagca aacacattca aaagctagca gaaggcaaga gataactaaa atcagagcag    540
aactgaagga aatagagaca caaaaaccct tcaaaaaatt aatgaatcca ggagctggtt    600
```

| | |
|---|---|
| ttttgaaagg atcaacaaaa tagatagacc actagcaaga ctaataaaga aaaaagaga | 660 |
| gaagaatcaa atagacacaa taaaaaaatg ataaagggga tatcaccacc gatcccacgg | 720 |
| aaatacaaac taccatcaga gaatactaca acacctcta cgcaaataaa ctagaaaatc | 780 |
| aagaagaaat ggataaattc ctcgacacat acactctccc aagactaaac caggaagaag | 840 |
| ttgaatctct gaatagacca ataacaggat atgaaattgt ggcaataatc aatacettac | 900 |
| caacaaaaaa gagtccagga ccagatggat tcacagccga attctaccag aggtacaagg | 960 |
| aggaactggt accattcctt ctgaaactat tccaatcaat agaaaagag ggaatcctcc | 1020 |
| ctaactcatt ttatgaggcc agcatcattc tgataccaaa gccgggcaga gacacaacca | 1080 |
| aaaagagaa ttttagacca atcaatatcc ttgatgaaca ttgatgcaaa atcctcaat | 1140 |
| aaatactgc caaaccaaat ccagcagcac atcaaaagc ttatccacca tgatcaagtg | 1200 |
| ggcttcatcc ctgggatgca aggctggttc aatatacgca atcaataaa tgtaatccag | 1260 |
| catataaaca gagccaaaga caaaaaccac atgattatct caatagatgc agaaaagacc | 1320 |
| tttgacaaaa ttcaacaacc cttcatgctc aaaactctca ataaattagg tattgatggg | 1380 |
| acgtatttca aaataataag agctatctat gacaaaccca cagccaatat catactgaat | 1440 |
| gggcaaaaac tggaagtatt cactttgaaa actggcacaa gacagggatg ccctctctca | 1500 |
| ccactcctat tcaacatagt gttggaagtt ctggccaggg caattaggca ggagaaggaa | 1560 |
| ataagggta ttcaattagg aaaagaggaa gtcaaattgt ccctgtttgc agacgacatg | 1620 |
| attgtatatc tagaaaaccc cattgtctca gcccaaaatc tccttaagca gataagcaac | 1680 |
| ttcagcaaaa tctcaggata caaatcaat gtacaaaaat cacaagcatt cttatacacc | 1740 |
| aacaacagac aaacagagag ccaaatcatg agtgaaatcc cattcacaat tgctttaaag | 1800 |
| agaataaaat acctaggaat ccaacttaca agggatgtga aggacctctt caaggagaac | 1860 |
| tacaaaccac tgctcaatga aataaagag gataaaaaca atggaagaa cattccatgc | 1920 |
| tcatgggtag aagaatcaa tatcatgaaa atggccatac tgcccaaggt aatttacaga | 1980 |
| ttcaatgcca tccccatcaa gctaccaatg cctttcttca cagaattgga aaaaactatt | 2040 |
| tttagttcat atggaaccaa aaaagagccc gcattgccaa gtcaatccta agccaaaaga | 2100 |
| acaaagctgg aggcatcaca ctacctgact tcaaactata ctacaaggct acagtaacca | 2160 |
| aaacagcatg gtactggaac caaaacagag atatagatca atggaacaga acagagccct | 2220 |
| caaaattaat gccacatatc tacaactatc tgatctttga caaacctgag aaaaaccagc | 2280 |
| aatgggaaa ggattcccca t | 2301 |

<210> SEQ ID NO 16
<211> LENGTH: 2024
<212> TYPE: DNA
<213> ORGANISM: Homo sapiens

<400> SEQUENCE: 16

| | |
|---|---|
| aaggcaagag atctaggact tctagcccct gaactttcag ccgaatacat cttttccaaa | 60 |
| ggagtgaatt caggcccttg tatcactggc agcaggacgt gaccatggag aagctgttgt | 120 |
| gtttcttggt cttgaccagc ctctctcatg cttttggcca gacagacatg tcgaggaagg | 180 |
| cttttgtgtt tcccaaagag tcggatactt cctatgtatc cctcaaagca ccgttaacga | 240 |
| agcctctcaa agccttcact gtgtgcctcc acttctacac ggaactgtcc tcgacccgtg | 300 |
| ggtacagtat tttctcgtat gccaccaaga gacaagacaa tgagattctc atattttggt | 360 |
| ctaaggatat aggatacagt tttacagtgg gtgggtctga aatattattc gaggttcctg | 420 |

```
aagtcacagt agctccagta cacatttgta caagctggga gtccgcctca gggatcgtgg    480
agttctgggt agatgggaag cccagggtga ggaagagtct gaagaaggga tacactgtgg    540
gggcagaagc aagcatcatc ttggggcagg agcaggattc cttcggtggg aactttgaag    600
gaagccagtc cctggtggga gacattggaa atgtgaacat gtgggacttt gtgctgtcac    660
cagatgagat taacaccatc tatcttggcg ggcccttcag tcctaatgtc ctgaactggc    720
gggcactgaa gtatgaagtg caaggcgaag tgttcaccaa accccagctg tggccctgag    780
gcccagctgt gggtcctgaa ggtacctccc ggttttttac accgcatggg ccccacgtct    840
ctgtctctgg tacctcccgc ttttttacac tgcatggttc ccacgtctct gtctctgggc    900
ctttgttccc ctatatgcat tgcaggcctg ctccaccctc ctcagcgcct gagaatggag    960
gtaaagtgtc tggtctggga gctcgttaac tatgctggga acggtccaa aagaatcaga   1020
atttgaggtg ttttgttttc attttatttt caagttggac agatcttgga gataatttct   1080
tacctcacat agatgagaaa actaacaccc agaaaggaga aatgatgtta taaaaaactc   1140
ataaggcaag agctgagaag gaagcgctga tcttctattt aattccccac ccatgacccc   1200
cagaaagcag gagggcattg cccacattca cagggctctt cagtctcaga atcaggacac   1260
tggccaggtg tctggtttgg gtccagagtg ctcatcatca tgtcatagaa ctgctgggcc   1320
caggtctcct gaaatgggaa gcccagcaat accacgcagt ccctccactt tctcaaagca   1380
cactggaaag gccattagaa ttgccccagc agagcagatc tgctttttt ccagagcaaa   1440
atgaagcact aggtataaat atgttgttac tgccaagaac ttaaatgact ggttttgtt   1500
tgcttgcagt gctttcttaa ttttatggct cttctgggaa actcctcccc ttttccacac   1560
gaaccttgtg gggctgtgaa ttctttcttc atccccgcat tcccaatata cccaggccac   1620
aagagtggac gtgaaccaca gggtgtcctg tcagaggagc ccatctccca tctccccagc   1680
tccctatctg gaggatagtt ggatagttac gtgttcctag caggaccaac tacagtcttc   1740
ccaaggattg agttatggac tttgggagtg agacatcttc ttgctgctgg atttccaagc   1800
tgagaggacg tgaacctggg accaccagta gccatcttgt ttgccacatg gagagagact   1860
gtgaggacag aagccaaact ggaagtggag gagccaaggg attgacaaac aacagagcct   1920
tgaccacgtg gagtctctga atcagccttg tctggaacca gatctacacc tggactgccc   1980
aggtctataa gccaataaag cccctgttta cttgaaaaaa aaaa                    2024
```

<210> SEQ ID NO 17
<211> LENGTH: 224
<212> TYPE: PRT
<213> ORGANISM: Homo sapiens

<400> SEQUENCE: 17

```
Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
```

|  |  |  |  | 85 |  |  |  | 90 |  |  |  | 95 |  |  |
|---|---|---|---|---|---|---|---|---|---|---|---|---|---|---|
| Gly | Ser | Glu | Ile | Leu | Phe | Glu | Val | Pro | Glu | Val | Thr | Val | Ala | Pro | Val |
|  |  |  | 100 |  |  |  |  | 105 |  |  |  |  | 110 |  |  |
| His | Ile | Cys | Thr | Ser | Trp | Glu | Ser | Ala | Ser | Gly | Ile | Val | Glu | Phe | Trp |
|  |  |  | 115 |  |  |  |  | 120 |  |  |  |  | 125 |  |  |
| Val | Asp | Gly | Lys | Pro | Arg | Val | Arg | Lys | Ser | Leu | Lys | Lys | Gly | Tyr | Thr |
|  | 130 |  |  |  |  | 135 |  |  |  |  | 140 |  |  |  |  |
| Val | Gly | Ala | Glu | Ala | Ser | Ile | Ile | Leu | Gly | Gln | Glu | Gln | Asp | Ser | Phe |
| 145 |  |  |  |  | 150 |  |  |  |  | 155 |  |  |  |  | 160 |
| Gly | Gly | Asn | Phe | Glu | Gly | Ser | Gln | Ser | Leu | Val | Gly | Asp | Ile | Gly | Asn |
|  |  |  |  | 165 |  |  |  |  | 170 |  |  |  |  | 175 |  |
| Val | Asn | Met | Trp | Asp | Phe | Val | Leu | Ser | Pro | Asp | Glu | Ile | Asn | Thr | Ile |
|  |  |  | 180 |  |  |  |  | 185 |  |  |  |  | 190 |  |  |
| Tyr | Leu | Gly | Gly | Pro | Phe | Ser | Pro | Asn | Val | Leu | Asn | Trp | Arg | Ala | Leu |
|  |  |  | 195 |  |  |  |  | 200 |  |  |  |  | 205 |  |  |
| Lys | Tyr | Glu | Val | Gln | Gly | Glu | Val | Phe | Thr | Lys | Pro | Gln | Leu | Trp | Pro |
|  | 210 |  |  |  |  | 215 |  |  |  |  | 220 |  |  |  |  |

<210> SEQ ID NO 18
<211> LENGTH: 26803
<212> TYPE: DNA
<213> ORGANISM: Homo sapiens

<400> SEQUENCE: 18

| cttgctctgt | cacccaggct | ggagtgcagt | gctgtgatca | tggttcactg | cagccttgaa | 60 |
| ctcctgggct | ctggcaatcc | tcctgcctga | gccttctgag | tagctgagac | tatagatatg | 120 |
| ggccaccaca | cctggctaat | ttttaatttt | ttttagtaga | gatgaagtct | tgctatgttg | 180 |
| accaggcttg | tgggagttca | gtcaggctgg | tggaaaaaat | tttaaagata | gttataagaa | 240 |
| atagacacaa | accttcttgt | aaggctggag | agggtttaca | ttgcttcagt | aacagatttg | 300 |
| gctgaaagca | gcctaatcct | ctctaccttt | agctgatagc | aaaaatgaaa | ataacaaggg | 360 |
| aatgtgagga | agtttatcta | aatagcttgc | ttactcatgt | ggtcctaaaa | ccaaactttg | 420 |
| atcaacctca | ggtgcataat | tgctctctac | tcagggggtg | agcaatgtta | attaccctct | 480 |
| agtggtgttt | actcgagacc | tttgtcattt | aatctgtatt | aaataaatgt | gaactttgct | 540 |
| agcttattga | ggtgatgctc | cagatgcaga | gcagagcccc | ttagccagac | tgacaggcaa | 600 |
| aatatctgtg | tcagtgtatg | tctctcatcc | atcactggtt | cagggtctgc | gggctggatt | 660 |
| cctgcacagg | ctggtcttga | actcctgggc | tcaagcaatc | ctcccgcctg | agccttctga | 720 |
| gtagctgaga | ctacagatat | gggccaccac | acctggctat | ttttaacatt | ttttagtaga | 780 |
| gatgaagtct | tgctgtgttg | cccaggctgg | tcttaaactc | ctgggctcaa | gagctcctcc | 840 |
| tgccttggcc | tcccaaagtg | ctgggagtac | aggcatgagt | catggtgccc | agacggacat | 900 |
| tttttttaaaa | ataaaggaat | actcctgaaa | cgctgaagtc | ttctttgtac | ccctctgtga | 960 |
| taacatgaat | agcctcttaa | tgacaccaag | gagcaagaca | agttagtccc | aaagtagctc | 1020 |
| acatagatga | tgataaagga | atgaggggtg | ggtgtgatct | atgcaaaaaa | cccttactct | 1080 |
| ttaatgggtt | gctgtttcta | acataattgc | aacagtaccc | tacattgcta | taatgcatta | 1140 |
| tagttttcaa | agtgcttttg | tggcctccat | aatagagagg | ttgtgaggta | agcttcaacc | 1200 |
| acggctgccc | tactacccaa | gagtggacac | acaatgatga | ataggtcaat | ttctgcctct | 1260 |
| tagtttctta | gctagggagg | ggcacttact | ggaacagcac | agaaaacaga | gtctttggcc | 1320 |
| cagttggaga | atctttatca | ggttatgcta | cttcaagctt | tcctcctgtt | aaatgtgaga | 1380 |

```
ggaataaatc cctgttcctt ggatcagtgt gactctgaaa cagctggagg agagacagct    1440
ttaggcaggt tgaaacagag agctccagca tatgtacttt tttttttttt ttgagatgga    1500
gtctcgctct gtctcccagg ctggagtgca gtggctcgat cttggctcac tgcaagctct    1560
gcctcccagg ttcatgccat tctcccgcct cagcctccct agtagctggg actacaggct    1620
cccgccacca cgcccggcta attttttgt attttagta gagacagggt ttcaccatgt       1680
tggccaggcc agtcttgaac tcctgacctg aggtgatcca cctgcctcag tctcccaaag    1740
tgctgggatt acaggcgtga gccactgaac ttggccaagt gcactacttt taaaagttaa    1800
agtattatgc agccatgagg gaatattgtg caagaagaaa gcttttacaa gaaaaacttg    1860
aaacattggt attttttgcct ccttttttaac aactagagtc gttttgggag ttgtttcttg  1920
tcgaagaaac aacccatgtt tattttccca gtatggcagg accatgtagg aaagcaaaat    1980 taccccctcag gagaggaaat tctctgacac tctataaggc tccataaccc tcctctgaac   2040
tgtggccaac aagattgggt agcactttt aaggtagttt aagaaaaata ggctgtgcat     2100
ggtggtttat gcctgtaatc ccagcacttt gggaggccga ggtgagtgga tcacctgagg    2160
tcaggagttt gagaccagcc tgaccaatat ggtgaaaccc catctctact gaaaatacaa    2220
aaattagccg ggtgtggtgg cgggcacctg tagtcccagc tactcgggag gctgaggcag    2280
gagaattgct tgaacctggg aggcggaggt tgcagtgagc cgagactgtg ccactgcact    2340
ccagcctggg tgacagagca ggactccatc tcaaaaaaaa aaaaaaaaaa aagaaagaaa    2400
gaaaaatata tagtgagccc aataaagctg tataatctaa atcaaacatg acttgcatgc    2460
ctggagactt tgcactagaa aaatatttct acctaaaaaa tcaaatttta ttttctttct    2520
cacaaatatt caatctgctt tcatctcagt tcttcctacc ttgtcaaacc tctccccaca    2580
tttcctattc ttttctctc cagcctgata tctctcatta tactgcttaa gagaaatgtt     2640
atgttactat tctttctcc cagaactgtt tctctggttc tttaaggtgt ctgagtacac     2700
actgtgcctt cttcctttta gccctctctt ctccttgttc cctgagcctt acctttatga    2760
ccttagaact tcaagttccc actacaattt taaatataga ctattttgct tttcctccta    2820
ctagggagct taaattgcct ctaattacac tgttttcccg agtccttcct ctcctttgca    2880
atttagatat agcacagaag cacattttgc ttgactgtcc tctgaactgt catgctgttt    2940
tgatgtggtt ctattgtcca agagtcttgg ttaaataata gcccagcatc ccacctgtgt    3000 ttaaagaac tgcttcacag gcaaatcaaa aagcccatgg atccgaagtc acaatgggcg     3060
ttgctattca aacagcacca gattgctatt caacgcttgg ttgaaaaata aatttcagtt    3120
tcattcacct aatatatttc cttctatttt gtaggatggt atgctcttac ttcaatttgg    3180
acttgttcac aattgaacgt taacatagcc ttatagatta gcctgttttc attggtccag    3240
agtattctcc aaataaagca gggtctgtgc attttaagca actcccctga acaatttcat    3300
gggcattctc aaatttgaga actacctgaa agctgtgtt ggagaaaaga caaccaatg      3360 aatgtggcag gacagaatat tgaacattaa cttcccttttt cctcttctcc catctgttct   3420
cttccattat ccctacccgt ccgctcagtc tcgttattca ggcaacagtt attttgccat    3480
tatttcctca agaaaggaac aaaagtaaac acaattgctt tctgattttt ttttttttt     3540 tgcattttaa aatggacttt gaaccataa gcaaagaggt gtttaagagt ctttccaaag     3600
ccaaaaatga aggttttgaa atttcaaagt cactgccttg aagagactcg aggtttggag    3660
tgtgtacagt atgtcggagc tggacttttc tccttcctga gactagataa cggtctgaat    3720
```

```
ccaagacagt tttcatgatt tcagaggaag tggtcaagtg gtctgtgagg tagaccttct   3780
gcttaagagc agtcaggagg ccgggtgccg tggctcacgc ctgtaatccc agcactttgg   3840
gagaccgagg tgggcggatc acctgaggtc aggagttcaa gacaagcctg accaacatgc   3900
agaaaccctg tctctactaa aaatacaaaa aattggccgg gcacggtggc acatgcactc   3960
cagcctgggc aacaatagtg aaactccatc tcaaaaaaaa aacaaaaaaa agagaagaaa   4020
agaaaagaaa aggagcagtc aggatgtgtg cctccaaagc tgaggtagac aaaaagatac   4080
cagagttcta gaggcctgcc aggcacagca gcagcagcag aaggaaggtg tgggcgagaa   4140
cagggcagcc aggcgtgtgc cacctcccag acacaattat tgggaatgga gggcaagtgg   4200
tgatgggaga aaatcttgac ttaattgatg tcaagattaa agaaatgcca cctggtggca   4260
tttaagttca cacataggta aagaaagtta tgcatttact gtgaaagtca tcccactatt   4320
tagtagaaac aggagatctg gattctggtc aagagtctct tttgccaact gtggcaccac   4380
tgagcagcgg cacagctttt gtgaatcctg ggttcttcat tattaaaatg gggacattag   4440
cgttgggttg agtataagaa atggacattt ttgcaggtca aaaatggttg aatatttgca   4500
ttttcatatg attcaaccga atacttactt cacaggcata aggaaaaaaa tagaataaca   4560
tactaacaac tgtccctgga gtaagtactt aacaaataca tgatttataa agaagatatg   4620
tgaaagatat ttgtaagtac atgatttata gaaagtatg aaagtatgta aaccccttgtg   4680 gtctaatggt cacagaataa tctgagctta atatccctgc tccctaccat acagaaggca   4740
aaatgcctat taggggtttt ctttcttcac cctctccttc ttttcctcc tcctcttgac   4800 tcctcctcat cctcctcttt cttcttcccc ttattaatgt ctaaaaaggg gctgagcatg   4860
gtggctcatg cctgtaatcc tagcactctg ggaagctgcg gcaggtggat cacctgaggc   4920
caggagtttg aaaccagcct ggtcaacatg gcaaaacccc atccctacta aaaatacaaa   4980
aattacccag gtgtggtggc aggcacctgt aattccaact acccgggagg ctgaggcagg   5040
agaatcgctt aaacccggga ggcagaggtt gcagtgagcc aagattgtgc cactgttgtc   5100
catcctgggt gacagaggga gactctgtct caagataaat aataataata ataataattt   5160
ctaaaaaggt aatacatttt catagttcaa aaaccaaaag gtataaaagg aaatacagta   5220
aaaaatttcc tatcatatca ctgtctagag tactattcct tatatatttt cctgattttt   5280 gagtattta aaatgtgagt gttggatatg agtgttggat ttaaaaagtt ttatgataat   5340
ttgtgtatat ttgtgtgtgt gtgtgtgtgt gtgtgtgtgt atagtagtcc aagactatca   5400
gtttatgaat aataagagga gacccatgga aaaccagtcc ctttgaccaa gttcactcag   5460
ataatcagca gcagggcttg gacattaatt acagttatcc aacatccttt gaggtctcac   5520
atgcaaaatt acaaatatgg agtgtaaatg taacccactt tgctaggcaa aaaaagccct   5580 gttttttaa aaatatata ttttggctt atgggcaaca gaagccaggg agacgtacag   5640
tcaaacctca tttctcatgg ctttcatatc tgcaaattct cctactcatt aaaagttatt   5700
tataactccc gaatcaatac ccacagcact tttgtgatca ttggcagaca tgtgcagaaa   5760
agaaaaaaaa attgagttgt tgattgcaca cattcccagc tgaatttcaa caaagcaaca   5820
ctctgccttc ccacttcagc tttcttacta tatgtgtgtc cttttctgt ttatttagta   5880 ccatgttttt cacactttcg ttcttttttgg tggtgatttt gctgtttaaa atggccaaca   5940
agtgtagtgc taagtgctgc gtagggttct taagcacaag aaggctatga tgtgccttat   6000
ggagaaaata cgtgtgttgg atcagtttca ctcaagcatg agttatgcg ctattagctg   6060 tgagttcaat gttaacaaat caacaatata tgctaaagtg tctttaaaca gaaacacaca   6120
```

```
taaaacaagg ttatatgttt ggttggcaaa aatgttataa ccagaagctt gcagaaacct    6180
aaccctgtat ttcccttaag agcaatggtt cattattcac taattcaatg tttacagcaa    6240
ctttataaac tataactacc atgaataatg agaattgact atgttttaga tcataatacc    6300
tgaagtgaag ttttccatca tggttttttag ttcttagagt ccatttaagt ttttttaaaaa   6360 tatgatagct atcctatcac atcccacatt cttgagatta aaaaattaat cttttatttg    6420
gtacagaaaa ggctcctgcg tgcatttttg gaggggctgg accgctgagg aagtcatggt    6480
tggctcaagt ggtttaaatg cattgctaat ttcatagcct ctgaaccact tatgaaacaa    6540
tactgatgat atgtcagtag ctatgtttgc agctccttca ggaatgctta tatcttttac    6600
tgctggtaaa gaagaaattt atagtaatag attttttttt ttttttagata gagtctcact    6660 ctgtcgccta ggctggatta cagcggcttg atcacggttt actgcagcct ggatctccca    6720
ggctctccta ctgtagcctc cccagtaact agggccccca cacaggcatc accacaccca    6780
gctcattttt ttatgtttta tagagacagg gtcttactat gttttccagg ctggtctcaa    6840
acttctgggc tcaagcaatc ctcctacttt ggcctcccaa agtgctgaaa ttacaggcat    6900
gaaccactgc acctggttta tggtcatctt aagtagagac ttatgagtgc gtatcattgt    6960
atcaccaatc tgagactcaa ttttatcttt ctgttaatag acaatgcagt ttttctgtta    7020
attacaatga aaatcaaggg ttgcttagca agttttttact cataactcca gttttgtga    7080 cttatagtga gaaatgggta taattctttg tgatttgtta aaatgcagta tttcgaggag    7140
ggataacata taaaatttaa cagtttccta tcattatttt tatccttttg aaccactgta    7200
tactacagat agacaaaggc agctttggcc acttactcct cagtgtgact aagttgacca    7260
gatgttttcc agaccacagg ttctgtcaag agacagtgtg gagagaaatg ggtaggcagg    7320
tatggaaaga agagtcagaa acagatagtg agctaatctc tacaaatggc tcgttatggc    7380
ctgagctgtg ttctcctccc cgcaaaaaga tatgttggag tcgtaatccc cagtacctca    7440
gaatgtggcc ttatttggag attcgatatt tacagaggta agcaagttaa aatgagatca    7500
ctatagtggg tcctaattca atacgactgg tatccttaca aaaaggggaa atttaacca    7560 cagatacaga cacacacata gggagagtgc tagtgaaggt gaagtcagag attggaatga    7620
tgtagcagaa gcctaggaat gccaaagatt gccagcaaac caccagaagc tgggagagcc    7680
acatggaaca gattctcctt cacagtcccc tgaaagaacc aactctcctg cacctcgat    7740 ttcagacttc tagcctccag agctggggtc aatgagcttc tctcattaag ccatcatcca    7800
gtgtatggta ctttgttaca gcagtcttag caaatgcatg gttcctcact ggaaccatga    7860
atttccatgc atttatttca tttaaataat aaaacggatc cctttgtgg cttgtagttc    7920 tgttccattt caaaaatcca gaaaaaagat ttgttcagaa gctagaaatg atgaactgga    7980
tcttgcccaa ggtcataaaa ccacaaaacc ctttacagag cacaaaagtc tgatttttca    8040
aagcttctct caaagatgg gtcactcctt agtcatttag gccactgaca actgccctgg    8100
actctttatt tatttatttta tttatttatt tatttaattt ttttgagaca gagtcttgct    8160
ttgtcgccca ggctggagtg cagtggcgtg atctgagctc actgcaagcc ctgcctcccg    8220
ggttgacgcc attctcctgc ctcagcctcc caagtagctg ggactacagg cacccgccac    8280
cacgcccggc taattttttg tattttgttt agtagagaca gggtttcacc atgttagcca    8340
ggatggtctc gaggtcctga ccttgtgatc caccgcctt ggcctcccaa agtgctggga    8400
ttacaggcgt gagccactgc gcctggcctg gactcttaca tataataagc ttgacttatc    8460
```

```
gtacaactta taattgatgc tttcacgtca tgggaagatc aaattaatgc agagagcgac   8520
tacgtttctg gtgggagagc agcagggtc ttgagaggaa cagcagtgtt gactgtttcg    8580
ctacctactc tgggtgctga ttacatcttt ctttcgtgca ggcaaatcca cttggagcta   8640
ttttgggctc actgtgggca tcattctttg tatactctgc tcctttcccc catagtttct   8700
ctattgatgg gggattacta aagaatgaag aaaagaacaa aatgaaagtg cttttgaaa    8760
aattttaaat gactgtcact atgtaacata ttcattattt catgtctcca ctggacattt   8820
tggagatgtg agccttgcaa tacctacatg aatgcttcta tgattatgat tattgttttg   8880
ctcttcgcct aacaacttgc caagtattgt caacctcagt gtgtgagatg ggtccactc    8940
aaacatcagg gccgaagtca ggtagttcag ttaagtgaat ttgataccag gaactagtta   9000
caaaggagtt ggaagggctg gaaagccaaa ctggagaaga aggggaaccc cagagtaaca   9060
atagcaggaa gcctctaccg tctacctcta gaactgggga ggagctgagt taacagagtc   9120
ctggagccat tgctggggaa gaagaacccc aactgcagag gaaaagtggc cattgtgaag   9180
aaggtgatgg tggagaagtc gtctgaatca aaggggagag gatatgttgg ctcctttatc   9240
tttttatctt tcattgtcct aattccttct gggcatggtt aaatgagccc aggaaatgca   9300
gttggcagga atcagcttcc tgtgacatag acagagtaag agaaggacaa aaataatgaa   9360
tctgagagca agcaggcaaa tgaccagcac attaagccta gcacacagta tgttatacgg   9420
gatttggggt agcaaaagat gaaggcaggt cagagaagcc acaactaggg gatgggcaag   9480
gtcaatgagg tatgacgggt attgtataca ggaagagggt cataaacagg agtggagtca   9540
atacaggaga ctaacatata cacatcataa atattagtag agaagcataa aatagtctcc   9600
tggagatcag ggaaacagga aattataggt tttcaggata attcagccat atccaggaaa   9660
cacacacagt gaagtaacaa agagtcaata ggcttagagt ggtacaattc attatgcaca   9720
tgtaggaatt cattccaaat aataggctga aatgtagaca tgagaatcca aaaaagatgt   9780
tttcttagtt tttgccaata tcttagctac gttttttttg gttcaacaaa gtaagttaac   9840
agtcatatct gcttggaaat tgtatttagg ccaggtgcag tgtctcacgc ctgtaatccc   9900
agcacttggg gtggctgagg caggaggatc ccttgagccc aggagttaga ggctgcagtg   9960
agcgacaact acaccactgc attccagtct gggtgacaga acaaaaactt attaaaaaa    10020
gaaaaaaaaa aggtcgggcg cggtggctca cgcctgtaat cccagcactt tgggaggtcg   10080
aggtgggcgg atcacgagtc aagagatgga gaccatcttg gtcaacatgg tgaaacccca   10140
tctctactaa aaatacaaaa attagctggg catggtggca tgcacctgta gtcccaccta   10200
ttcaggaggc tgaggcagga gaatcgcttg aacccgggaa gcggaggttg cagtgagctg   10260
agattgcacc actgcactcc atcctgtcga gactctgtct caaaaagaaa aaaaggaaa    10320
agaaactatt gaaatagctg atattagttt gcttacttgt cgttactctt tttcatgatg   10380
gattataaag aaaagttata actatttgaa ttttctgctg atttgaagtc tctataaaca   10440
gtacattcct ttttggtaca cagagggcac ttatctgcaa gaaaggcaaa gaaaatggaa   10500
aagttaatga aagaggaatc atccaatcca cgaacagaat gaaaccacat acacagtgaa   10560
gaaacttgtc ttcatttttc ttccttatat tacttatcat tcatggtagt gactactttg   10620
gggcttgagt aaagcttctc taatttattc catgtagcat catatgtgaa aaagacaaat   10680
agatacttta gacatgataa taacacttta tttttatttt atttgtttat tttgagacag   10740
agttttgctc ttgttgccca ggctggagtg caatggtgca atctcagctc actgcaacct   10800
ctgcctcctg ggttcaagcg actctcctga ctcagcctcc caagtagctg ggattacagg   10860
```

```
cacgcatcac cacgcccagc taattttttg taatttagt agagacaggg tttctccgtg   10920
ttggccgggc tggcctcaaa ctcctgacct caggtgatcc acccaccttg gtctcccgaa   10980
gtgctgggat tataggtgtg agccaccatg cctggcccat aacaccttat ttaaaaataa   11040
tctgtctgga tccatacaac ttgtctggat aactaaattg gaaattattc cttgttttaa   11100
agtaattcaa ttgaaaattt ttaaattttt ttgttaatca agcactttt ggtggaatct    11160
aaattaacac atgtaggaga tgcctgtttc actaattaca caggcatctt gcagtaatta   11220
atgtctggga ggaaggaatg tcttttgctt actctcttct tcttcacaaa aatgtgaatt   11280
ttggaaagca ataatggaag catgtagaat tatagaaata caaatgtata taactatcac   11340
aaaaaaatga ggccaaagga ctattcagat ataattaggc tatggtagct gtaattatct   11400
aggaaattaa taaaattcat tcacctagaa attattagtg agcatcaaat atgtgtcagc   11460
actaggctag ggtctcagaa cgtacagata aatcatagtt ctggcttcag ggagttatat   11520
agattagaga taaaacctaa ctacaggggc tgggcacggt agctcatacc tgtaatccca   11580
ccactttggg aggccgaggc gggtggatcg cctgaggtca aggagtttga ccagcctg     11640
gccaacatga taaaatcctg tcactactaa aaatacaaaa gttagccggg aggtagtatg   11700
tgcacctgta atcccagcta ctcgggaggc tgaggcagga aatctcttg agcctgcggt    11760
ggaggttgtg gtgagctgag atcacgacac tgcactccaa tctgggcgag agagtgagac   11820
cctatctcaa aaccccaaac aaaacaaaca aaaaaaccaa acctaactac agggctatga   11880
gagatgacta ctggcaagga gccacaggta gaacaaaggg gatgtgtccc caggcaaagg   11940
gtagtcagca agcctgcaac ctcagggttc ccggatctga gcctctggct cttggctagg   12000
caggccccaa gcgttggcct cctgccatgg caagctccag cctggtctcc caccttgagc   12060
taacattcat atgttgtaga cacagccacg cttcctgctt acctgtcact tccagttctc   12120
gaaggcaccc ttttcaaatg aaaatccgcc ccttttcaca tcaaacagct catctggtcc   12180
tgtggattac atttctcaga aatgcctctg aacattcgcc tcctctccac ccccactgcc   12240
tctgctacag tgcaggtgct cgccatttct gatttgttct gtcacacact cgtttatcag   12300
gtctctccat ctcctgtttt gacatgctgt aaagcaattt gccactggaa aaagggctc    12360
tcttttttt tttgagacgg agtctcgctc tgctgcccag gctggagtgc aatggcatga    12420
tctcggctca ctgcaacctc tgcctcccaa gttcaagtga ttctcctgcc tcagcctccc   12480
taaagtctgg gattacaggt gcacgccacc aagcccggct aatttttgta ttttagtag   12540
acgtggggtt tcaccatatt ggccaagctg gtctcgaact cctgacctca ggtgatccac   12600
ccgcctcggc ctcccaaagt gctgggattt caggtgtgag catcgtgcc cggcctctct    12660
ttccaaagta tgttattatt tttcccaaga cccttgacg atcctcatt tcctacacac     12720
agtggttctc aaacttggat gtactccaga attacatagg aaattcttca tttttttaga   12780
cgaggtcttg ctatgtttct caggttggtc tcaaactctt gacctcgtgt gatcctccgg   12840
ccgcagtctc ccaagtagct gagattatag gcgtgccact gagcccagct ggaaatttt    12900
ttaaaacaca gattcctctg aatcaaaatt tctagaagtg aggtctgagc aatctgtatt   12960
tttaacaagt tatccagatg gctctttact gtcagtctgg ttccagctga gggagtttta   13020
gaattacaag gcaaagtcca aacttagcac acaaagtcat tcacatcaac tcttcccctg   13080
tacacaccct atgtcatagc cagagttgta acccatttct taaacaccca gggttctttt   13140
aagtctctgt gtcattgtat gttatttct ctagaattgc ctttaacctc ctttccaccc    13200
```

```
tggaaagcat tccctaagcc atctttgaag cttctttga tctctaactt agagtcctcc   13260
tctccttcta aagccctgtg ttaatcactt gtcatggtgt actttaattt ttacttgcct   13320
gtttctcttt acggtacttt gacttcaaag ggtggggctg caaattagtc atctccttag   13380
agtccagcct tgttcctagt tcctaactgg cacttaatat aaacgaatga atgaatggac   13440
aaatgaagag aatgctagtt atgataaaga attggccgtg tatgagacta cttctcttta   13500
tgaactaaat aattatatgc ctttcaataa aatactagta cacgtagcta gcacaagctc   13560
atcagcattt gagatgatat ggaaaccaaa ataaacaaat gctaccacaa aaacataatg   13620
actgctttcc ccagtgcagg actgatgaaa tcatcaaaca ttgagattaa tgtaatgttt   13680
ggcagatgtc cagtgttttt attttcatt tgcctttgtg ttcatttatg gactaacaat   13740
ataataaaca cacacatact cacagtacat ctttttttt ttttttttg caaagcccag     13800 ttttcttcat cgcatatctt tgttttcttc aagtatcccc ttacttaatg ttggtagtat   13860
tttttttaat gaaatataaa tccctaacca ccaagcaaga aatgagactc ttaattgcat   13920
cagtttacag tgcaatgtga gtgtaaatag tgtaaattga attttaatg gactttttt    13980 tttcccgttt ttgcttgcct tacattcatt atccctccct gggtaataaa catttatttt   14040 tcccttttgta accactcctc cccttctgtc catgtggttc tttttagtgg agctggtggt  14100
agggatgtgg catgagattc aagcttggcc acctggagtc actgtgttgt gctccagaag   14160
gacacctgat ccaagtcagc cagtaagagt gagccccagg attttttgctt ggaccactga  14220 ggaaaagtgt actctgccct gtggctgatc aaccattagg atataagcca ttgttgtagc   14280
tgtgtgagtc aagctacctg agaatgagga caacacagtg gcaagcaaca ccaagagaga   14340 aaagaggca gattctgatg acattttga gcctttgcat ccagctatgc ctgaatccaa     14400
tttatcccct ggaatttaca cttacttgag ctccacccac ttgaaagaaa acatttcttt   14460
ttattcttag cctgatttga atttggcctc tctcatttac tacccaaagt gtcttgacca   14520
ctagaatatt atgccagact ttacagcatc attgaatttg ccactttcca gaagagttgt   14580
gtgaattttc aatgtagctt ttaccttcta tgagtatcta gagatatatt taagtagaag   14640
tactccacta gtttgttgtg agatcttaag tcacttaatt tctctgtacc ctagttccct   14700
catttgctag acctagggag ctataatgtt ccttctgcaa aattcttatt ttgtgaaata   14760
ttctagaatg tctaactgat acactgctag aacaactgac tgctatttaa gaagagttga   14820 ctgctatttta aggatcataa ttctctaggc ataagtgctg tgacggcaca gcgtgtgcat   14880
cggggctgag gggtggggtg gagcagaaag taggaggaga aagtttgata aacttccttt   14940
tggataaatt gaaaacagtc aaataattta taatttctta tattatcatt attagcttct   15000
tctataatta ggagacttgt tccaaaatgt gagaattgtc acaagttgtc aaattcatca   15060
aaggaagaaa atggatgtct cacaaaaaag tatgctcagt ccaatttctt ctcgtcacac   15120
tggaacaaac tgaacagttt tacacagaga tgagaagcct ggacatttt caaatatgtt    15180 ttgaagagaa tggcaatgcc tgagacagaa gtaggaaaaa gcaatgaata tttaaaaatc   15240
tgagctggtg taaaactaga aatagtttta gtaagaacaa tgtgatgtgc tacactaagt   15300
gaaatgtata cattgggcca cattataatc aaaaataaga atgtacttt attcatcttt    15360 tatttaaaca ataatcaagg tggcgggcgc ggtggctcat gcctgtaatc ccagcacttt   15420
gggaggccaa ggtgggtgga tcatgaggtc aggagttcaa gaccagcctg acaacgtgg    15480 tgaaccccg tctctactaa aaatacaaaa attagctggg tggggtggca tatgcctgta    15540
ataccagctg ctcggggggc tgaggcagga gaatcgcttg aacttgggaa gtggaggttg   15600
```

```
cagtcagcca agattgtgcc attgcgctcc agcctgggtg acagagcaag agactctgtc    15660
tcaaaaggaa aaagaaaaa aaaaaaatca aggtaccatt tgtaccattt cctggaattt    15720
ctccaaagtg gcaaggtcac atgtttatac attagactcc cagtttaaca cacagcagac    15780
aataactttt ttttttttt tttgagatgg agtctcgctc tgtcacccag gctggagtgc    15840
agtggcacaa tcttggctga ctgcaacctc cgcttcccga gttcaagcga ttctcctgcc    15900
tcagcctccc gagtagctgg gattacaggc atatgccacc atgcccagct aattttgta    15960 tttttagtgg agatggggtt tcaccacatt gtccaggctg gtctcaaact cctgacctca    16020
taatccagcc acctcagcct cccgaagtgc tggtccaccc ttccttcttt tctcccttcc    16080
atccttctcc cttttattcc attttctaa atattagacc atagtacaaa tcaaaagtca    16140
caaactgata ggctgcaatg tagatacagc tgggaaaatg ttttgtttgc agaacactgg    16200
ggaaatttaa catgaaaaac tggaagatct caatccacat ggccacatgg taatattatt    16260
aatgttgcag gggcttttcca attcaacatg tcctctgcat ccctactatt tatactgcca    16320
ctcatccacc tttctgtatt actggcctat cacctataca cgtttgagtt tatattcttc    16380
tggctttact tagcaactta cctttttatat ttaacattac aacatggtat tatcaattag    16440
tattcgattc agttgcatat aaccaaaaat gccaaattat actggcttaa acactaagga    16500 tttattttc tgtcatataa aacaagtctg gaggtgggta gtccagggct aatatgacac    16560
tccagtgtca caaggtacct gggctccttc tatttatctt ttttttttt tttttgaga    16620 cggagtcttg ctctgtagcc caggctggag tgcagtggtg cgatctgggc tcactgcaag    16680
cttcgcctcc cgggttcaca ccattctcct gcctcagcct ccggagtagc tgggactaca    16740
ggcgcccgcc accacgcccg gctaatttt ttgttatttt taatagagac gaggtttaca    16800
ccgtgttagc caggatggtc tcgatctcct gacctcgtga tccactcatc tcggcctccc    16860
aaagtgctgg gattagaggc gtgagccacc gcgcctggcc ctatttatct tttataggac    16920
atggcttcca gtctcaagtt cagtttgtca cccataatgg ccaaagagca gtagtcacct    16980
tacctgtttc aggcaggaag ggcagagggc aagaaacaaa atggtgctcc tcctgattga    17040
gtcagcgttc tttaaagatg ttttccagat gttccaccca gccgcgtttt ttttttttg    17100 agagacaggg tcttgctctt gtcacccagg ctggagtaca gtggcatgat catggctcac    17160
tgaggcctca atctcccagg ctcaagcgat ccttccattt tagcctccca agtagctgga    17220
agtagctggg accacaggca catgccacca taccctgcta acttttttcat tttgtgtaga    17280 gacaaggtgt cactgtgttc tccaggctgg tctgcagttt ccaactcctg agtgcaagtg    17340
atcctcctgc tttggcctcc caaagggctg ggattacagg tgtgagccac tgtgtctggc    17400
caagctactt ctacttatat ctcattggtc ataacttgat cacacagcca catccagcta    17460
caatggagat tgagaaatgt agtcttttgg ctgggtacac agcatctgaa taaaatccag    17520
gcattgttac taaggaagaa ggagtaagtg tcaatctctg ctccataact ctctaggtta    17580
atacacacag atggaggaga ttgctagttg cccctcaaga tccagccttg ccttctgggc    17640
taagaaagcc cctgagattt acctggccat agtggcactg gaacaaaca atgtatttct    17700 aaatcttctg attttaaaat ctttcagaat cacgatttct ccgacatcag tatttttatg    17760
tctttagaat tcaacaaaat gaaattccta agtctaatat atgtgaatat taagttttag    17820
cagatactgc tacataactt tccagaaggg tgtggcaatt cacatctcca ccagtgatca    17880
gcatgttcat tttccataca gctctggata tttgtctat tttaaaatat cttcttctaa    17940
```

```
tctataattt aaaaatgtaa cttagtagga atttaattgt tcatgtaacc aaatcttccc   18000
attaatggct atgggtttct tcttttactt cagaaagtcc tccccacctt cagagtatat   18060
aaacattttt ttctaaattc ccttctaatt tcttataatt tatagtttta tttttgttat   18120
ttgattcatt tattctctca acagatattt attgagcact tattatacgt caggctctct   18180
tcaaactctg gtgagagtat tttctaactg ggagagacaa ccctagttga taagaaacaa   18240
acaaaccaat aagtaaataa gacatttccc ccagataatt aatacttggt gacgggggaa   18300
gacagtgaga caggctactt tacactggca ggtcaggaaa ggcttctctg aggaggcaag   18360
tgattcagga ttaattgatg actggtgagg aagtccgggg agtggacaca ggtgggaaca   18420
gcctggtggg tgtgaacagc aacaagaagg ttaatgtggc ttcatggaac agggtgaaga   18480
tgagacaagc tgaacactga ggtgggcacc agaacatgga gggctttgta ggtcccaata   18540
aggagtatgg atttttattgt atactggaga tttgtcatcc atctagaatc tgtttttata   18600
tataagaaaa ggtgtatatg tttgcgcaag tgtgtgtgtg tgtgtttggg ggggcggggt   18660
gggggcagac agggcgtaac ttttcttttaa attagagtca aaatttaatt aaactattca   18720
ttctttacag gcagtgaggg gattaggatc ttatcccaca gaatctcacc tcatttcaaa   18780
tgttgtacag atattatctg agatatattt tcaggccggg tgcggtggct cacgcctgta   18840
atctcagcac tttgggaagc cgaggcgggt ggatcatttg aggtcaggag ttcaagacca   18900
tcctggccaa catggtgaaa ccccatctct actaaaaata caaaaattag ccgggtgtgg   18960
tggtacacgt ctataatccc agctacttga gaggctgagg caggagaatc gcttgaatcc   19020
aggaggtgga gcttgcagtg agccgagaaa acgccactgc actccagcct gggcgacagg   19080
gcaagactct gtctcaaaaa aaaaaacgaa aaaagaaata tattttcaat gaaatcaagc   19140
atataatgac tattttttatc ccagcatctt ggcttcttca ggctgctata acaaagcatc   19200
cctagtggag catccctaat ctgaaaatcc aaaatccaaa acgttccaaa atctgaaacc   19260
ttctgaacac tgacatgaca ccacaaatgg aaaattctac atgtaaatac acgtaaatac   19320
aaactttgtt tcatgcacaa attaaaaata ttgtataaaa ttaccttcag gctatgcata   19380
taaggcatat atgaaatata aatgaatttt gtgtttaccc atgggtctca tccccaagat   19440
gtttcatttt gtatatgtgc atactcccaa atctgaaaaa atccaaaatc ttaaatatct   19500
gtagtcctaa gcattttaga taagggtatt tcaatcccctt atccataaac aatttattta   19560
taaacaacac aaatttaggc tttgtaaaaa atagaaattt ggccgggtgt ggtggctcac   19620
gcttgtaatc ccagcacttt gggaggccga ggcaggcaca tcacttgagc tcaggagttt   19680
gagaccagcc tggtcaacat ggtgaaacct tgtctctacc aaaaatacaa aaattagcag   19740
ggcttcgtgg catgcgcctg ttgtcccagc tactcgggag gctgaggcag gagaattgct   19800
tgaacccgga aggcagaggt tgcagtgagc caagattgag ccactgcact ccagcctggg   19860
ggacaagtga gactccacct caaaaaacaa acaatcaaac acaatataaa tttatttctc   19920
atagttctgc aagctgagaa gtccaagatc aagatgtgag cagatccacc tttggtgaag   19980
ggctgctttc catttgatag atggctgtct tcttgtgtcc tcacatggtg gaaagggtga   20040
ggcagttttt tgaggtctct tttaaaagag aactaatccc attcatgtgg gggtctgccc   20100
tcatgaccta atcactttcc aaaggcccca cttcctaata ccatcaccct gggggttaaa   20160
ttttcaacac acaaattggt tggagagtga gcgaacatag acattcagtc tatagccccc   20220
agggatgtag ccactgaata aaataatcta gaacttcatc tagaggcagt ttataagtca   20280
cataagaaaa ccagttttac ttatagtcac ataaaacttt tgataaaaaa caaccctagt   20340
```

```
tgataagcca tttgtttact ggacttggct ctgaagaaat gacttttggc taatcctcaa    20400
aatgaaatct actcacagag ggcaagatct gccaccagtg aagatgttta aaacaatgtg    20460
ctgtaggctt tgaaggcaag tctaaagaag agcttctaaa aatattttgc acaatggtag    20520
cattaaaaga gtaggcacat gggcccaag ataacatctg tgaagaggag gaccagtgtg     20580
tgtttccttt tgtatgttta agtactaagt cagtgattac tttataatta aaccatattc    20640
ctcttgatct gtccataata aggtcactct gtaatttata ataggcttct taccaaattc    20700
aagctttaca acaaccctat aggttaaata ttcctgtgaa ttttatagat gaagaaacag    20760
agtaagtgaa agagttcata ctcaattcaa gtctcttgag tctaaaatca gtgctctctc    20820
tacataagaa gttagttgct aagatcacac aacttgagaa gagagaagac agttttcaca    20880
gtccctcccc tctgaccact aggctgcttg gggtactttt acaacttacc tgctctgaat    20940
taaggctctc tgtgaatctg attcatctgc caatttgcaa acagtcagcc ctgtagtacg    21000
tacctaagtt gattttaaa atactatttc tcatcttaaa ataatggaaa ttgagtgaca    21060
taaatttcct ggacactttt taagatccaa agacaatttg ctaatttgtc gttacaatta    21120
aagagccccc caaaaggcgt aagaactgga ttttgacttg gacttctgtt ccttagtttc    21180
tttaacatat tgggggccgg gagtggtggc tcacacctgt aatcccagca ctttgggagg    21240
ccgaggcggg cagatcacga ggtcaggaga ttgagaccat cctggctaac acagtgaaac    21300
cccgtctcta caaaaaatac aaaaaaaaaa aaaaaaatt agccgggtat ggtggcgggc    21360
gcctgtagtc ccagctactc aggaggctga ggtaggagaa tggcatgaac ccaggaggca    21420
gagcttgcag tgagccgaga tcgcactaca ctgcactcca gcctgggcga cagagcaaga    21480
ttccatctca aaaaaaaaaa gaaaaagata ttgggaaaac tcacttaaac tctatgggct    21540
tctgtaccac taaggcttct caaatttgat gcaagtaatg ggaacttgct gtggctaact    21600
tgagccacag gagaaggata ctgcaagact cacaaatgct tgaaagtttc ggaacaggtt    21660
tggaaatggg taagaaccaa ggaccgggtt gacctgaact gaaaggaaat tgaggtgcta    21720
ttagggacaa atatgaaatg aaggatgaac tgtctctgac atcctttgct tctgtgtttg    21780
gagatgagta agcagggagt gggtgcatat gcaaacaggg tggtcagaaa tgctttggcc    21840
ggatgtgtga ctgaaggcta tgtgcagctg aggaaggctg ggccaccaca gtagcagaga    21900
ggctgaccaa tttggcatgc agcaagcagg aagtagaagg gatcttaagc aagcaaagtg    21960
tttgggtaga caagattatg aggaatgagc accaatgaca tttccaacaa gcactgaaag    22020
cttccaaatg cttctaacag ttactgcctg tacaaacaca ggacagtctt gactatgtga    22080
gactgtgaca gtttcctcat gcctatgaaa tgagagacag tacttagcac tgacatgagc    22140
ttcatatttg aaggcagcaa actactgaac cacatgtagc ttccgaaatc aaaagatgca    22200
aactggcaga ccacaggtca gatatgacat gcagaaaaaa attagttact atcttagcct    22260
agtttgtgct gcttacagaa tatcagagac tgggtacttt atagaaaca caattattt     22320 ttcatagttt tagaggctgg gaagtccaag atcaaagggc catcatctcg tgaaggcgtc    22380
cctgctgtgt caaaacatgg tggaaggcat cacatgggca aaagagagag agggaagcgg    22440
gggcaaactc cttttatca ggcacccagt cctgtgattc attcatgaag acagtgtcct     22500
cctggcctaa tcacctctta aagctcccac ctctcagcac tgttgcactg gaaattatat    22560
ttctcacaca tgaactttgg ggaacacatt caaaccatta cagttaccaa agataaaaat    22620
gcagatttca gatttctctt ggggaagaaa aaaggctctg gcaataccag ggctgtattt    22680
```

```
ccacatggca acagttgtct gttgccttct gttgggttgt gggctctcac attgccatac   22740
cctcctcatg gccccttca  ctcataacag tacctgccta gacctcgaag cactagtttc   22800
caaccctgct tgagttaact acttccatga caactgtgca aggccagagt gtgggcagct   22860
accttgaggg ccaccggcat gggctgccca agtgaccgag ggcactaacc tctgctctcg   22920
aaacttcttt ggtaggatct cttcactcct gacttactac ttgtaactgc tggaaacaac   22980
catttattct accccctacta aaccacatct gtcttttctg tcagagccaa tcttcaagca   23040
tatgcttcct caaaagactt taattaccag gtagtagaag cggcagcaaa gagtccccat   23100
ctagcatctt ctaaaatgta gtggagaaac caacgacaac gaatctgaga caaccagttg   23160
tttgacttct ctgaaaacaa cctctaaaaa aagccttctc tcgtgaatag ctgcagacat   23220
gctgggcact aattgatgat gatgcccttt agtgagtctc ctctgcacat acctgattcc   23280
atttggatgc tggccctcac atacttctat ctgcgaactc cggaacacag aatatcatac   23340
aatgtatgat tcaatctgga ctctgctgga gccattctct acaaagcaga cacaactttt   23400
tcttgcctaa atcctttcaa gttgctttat ttttatttt  aaactaatta ccataaatct   23460
aatttatcaa gctgctttta agataaactt taaaatgctt agagcagtct acaaattctt   23520
gcactgtttc actcttcctt atctctcagt cttcatctcc cattgcatct tctctgactc   23580
tttcatatgg atcttctttc aatttgtgga agaagccaag cttgttcctg cctcaggtcc   23640
ttgacacttg ctgttcactc tcctgggaga ctcttccccc catcttagct tttaaatacc   23700
agctggtcag actccttacc tgccttccac cttcctctca ttctcccact cctcgccttc   23760
atttctcaga gtcctccgct ctcttctttc tattgctctt aacacaattt gtctgttttc   23820
cgctaatctg taaactctac aagagcactt aactattttg catcccaccg aatattcgga   23880
gtcagcacag accccgtcat aatagagtag gtaagcaatg cttacctgtc aaatgaatga   23940
atgaaacacc cgattcatcc cccaagccag cttaatacat tagatgatct tatggactga   24000
ataagacatc cctccttta aagaatattt ttgttttagc ttcacatcag caaaccccga   24060
acggttcatc ctaagataag cctggtagag aggaaagata ctaaccttct agggtcctaa   24120
agtggaacta ggaacttatt agatatgcac attctcaggc attatttccg atagcccagt   24180
cagagaattc tgggggtatg gcccagcaat ctgtttaac  aaaccttca ggtaattctg    24240 atacacacta aagtttgaaa ggtttcttta aggcttccca gttttctttt ctttttgga    24300 gggatggggg ggggtctccc catgttgccc aggctggtct cgaactccta gcctcaagct   24360
atcctatcct cccacctcgg ccttccaaag cattgaaatt acaggcatga cccactgcgg   24420
ctcgcctccg tttctaactt aaaaaatttt tctttggagg ggagccttaa tccttttctat  24480 tatcctgcta gtagaatctt actactcctg agggtaatct ttgtcataat ccaaaagcct   24540
tgaataaagg cctatttgta tagttatgca gaatatattc ctgggaggtt tgccttccta   24600
ggagcacagg tcggccctgg gaggtggggg ttgggggca  gggctgcatt ctaaagtcct   24660
gtaacaacgc acaagtacaa ctgaatagaa ctcggaacaa aggcatcagg gccacggtgc   24720
aagtctttgt tcatccgttc cccgactgct caccctgtct gataccgctc ttttccaccc   24780
agaaaagcag ccactcaagt tttaagaatg gatgtatgcc gcggacgttt tcgattaggc   24840
cgttttctct caggcactgg aggatattcg tggctgcagg aggcgcttcc acccttcct    24900 caacctagca aagaagtaac tgaaactaac ccaagggtta caaccgaaaa gccccttcca   24960
gcttcagaag cagaactgga agctcggata gacttctccg cctctacact cctgaaaaac   25020
ccgcagtgga tttcaccaac ttcaggatcg gagcccaggc aggcgaacgt accttattgc   25080
```

-continued

```
gcatgctcgc tagcccctcc cgctcggagc ggaagggggga gcgctggggg cctgggcctg      25140
gcctggccgg ggcgtcggca ccggcggcca tcttggcttc ccggggaaag gcggcgtgag      25200
gggaagaagt tgtagggtgg gggcaggagt gaggaggagg gaagagagag ggggaggagg      25260
ccgcggcggg gcagggcggg gactgcctgc ctgcctgggt tgcggaagtg atagccgccg      25320
accgagcctg ctgctttctt gctactgctt cggcttcccg gctacccccc ggacggtgaa      25380
ggcggcccag ctgtggatgg tcagatagcc cttgtctccc gccgccaatc tctgccccct      25440
agcagcacgg agcagacggc ggcagcagca gcagcaggcg aggaggaaga tggcgggacg      25500
gctgccggcc tgtgtggtgg actgtggcac ggggtaaggg ggcttacggg cggggggtggg      25560 gaaactgagg cggaggaagg aagatggcgg gggagggagg aggccgggaa atgaatggtg      25620
cggcgaggtg ccgccgccgg ctgtcagtcc tagacccgcc ggccagcgag gggtggggcc      25680
cgcagccagg gcctcgcggg tcccctcgtt tctccctcct gggactgggg cggggggcgcg      25740 ggcccgagat tcaaccccca accctcccag cggctttctc cgcgcgaccc ctcccggccc      25800 ttccccccact acggtgggca gcgccgccca aagggcgctg gggacggtcg tcttggggggt      25860 ggtccccggg cccgacccat ccggctttcc tttccctccg cgcccgtttt tgccagtcgg      25920
tttggggacc caggggccga gctcggggac tggcctggca ggggagctag aaaagagaag      25980
cgctcctggt aggtttgaca agatcgctgt gacaacattc tgcccagggt gtgggtgggg      26040
aaagggaaga atcggactct gaaaatggga acctacagtg gggctttcat ttgaccaccc      26100
accttctcct ttcgactcct ggtcatttcc atctccctct gcgttttaac cggtgaacca      26160
agtcacattt taattcgagg gagaaagatg tcatgtgtta cttctgtagc ctcaaaaaag      26220 tccccccagtg agcaagcgcg ctgcaacttc cttagttttg tcaaagccgc ttcctgcttt      26280
cagtctttta taccctttata aggtagtttt tagtttccaa cctgagcaca tcttactaga      26340
acttttaagc aggttttaaa gagactgaat taccggtgct tggtgtccat ttatatgact      26400
taaaaaaatg tacttatgtt tcatggagtg ggggaaagga agcaccctgg aaaataaact      26460
aatttaagtt gtattcgttc attctgtgat ggtatcttga aggaagcagg aaggtataga      26520
ggtatatagg agggtgttta agttgcaaat agttactcgt agatatgtag ggtagtttgc      26580
gaaaatgtag agtggcttta aagtgtggtc gttcatttttg tattaataga cgttttagag      26640
agttgtacca cactcataac tgcatagaga atagactacc cttatttta tgtagaatca      26700 ctgcttcagg atgacatata ggaaagtggt ttttttttct gtgctgatga catctctcca      26760
attcccagaa cactcccagt tttttttttt tgagggggaa gtc                        26803
```

<210> SEQ ID NO 19
<211> LENGTH: 26803
<212> TYPE: DNA
<213> ORGANISM: Homo sapiens

<400> SEQUENCE: 19

```
gccgcaccta ccgctggcct cagacatcag caccccaaag ggtatgttgg agtcccatgg         60
tggaggtgcc ggccgctcct ccacgcactt gatgtatacc gaggatccca tgcttgacgt        120
cgcagggggc attagccagg agcacgttgc tgggatgcca gtccaggctg aggatggtgg        180
agccaatggg cttcttgatg tacttgcaca cccaccagtt attctcccgc tggaaataac        240
agatggcgat gacacacagc tgccgcccac agcaaacttg tcctgtgggc ccagcacaca        300
cagcaggcag tgggtgcggg cttaccctcc tggcccgtca gcgtccacac agaggccttg        360
```

```
tggcctgtgc cataggtcac gatgaggtta ctcttggagg cccagttgat gccttttacc    420
tgcccgttgt gctccttgag ctcgggcacc ttggcccact tggccccact cttacagctt    480
cgtggttgtt gaggcagatg gtggccatct gggtgcggcc cttgctccag gtttggcagc    540
aatgggttcc tgcagtcagc tgtgggaggc tgtagttgct ctccttttca gagtacccca    600
gctgcagact ctgggcagga cgcacccaac cagtgctctg gttttttgaa gtaaaaaatg    660
cataatgcaa ttttaccatc ttaaccattt tttaattatg aaatccggta gtgttaagta    720
taattgtgtt gttgtgaaac agatctccac aacttttca ttttgcaaaa ctaaataact     780
cctctttccc cctactccca agctccaggc agctaccatt tctgtttcta tgaatttgac    840
tacttatatt acctcatata aaggggttca taagtatttg tcttttcttg cttggttaca    900
tcacttagca tgatttctta agtttcattc atgttgtagc acatgtcaag atttccttt     960 tttttttaa aaaaaggat gaagactatt cgtttgtatg tatatgccac attttgttta    1020
tccatccatt tttcttcaaa tgtttgagtt gtgtgatgtt taattatgtg tcaccttgac   1080
ggggcaaagg gttcccaga cagctggtaa acattattg ctgggtatgt tagtgaggct    1140
gtttccagaa gagattagca tttgaattgg caggctgaat aatgaagatc tgccctcatc   1200
aatgtggatg ggccagaaca aaccaaaaag gtggagaaag gaccagttat ctccccacca   1260
cccctgtgcc ctttagctgg gacatccatc ttctgccatc agacatcaga gcttctggtt   1320
ctcaggcctt cagactccag aagttatacc agtggcttcc ctggcttttg gactcagact   1380
ggggtttcac tgtatgtttc cctgattctc aggcctttgg acttgaattg aattacagca   1440
tgaactttcc tagttctcta gcttgcatat ggcatattgt gggacttctt gacctccata   1500
atcatgtgag ctaattccca taataaatct cctcttatgt atctataatt catatagata   1560
tgatatctat atatcaatcc catagataaa tagatgtctc atatatatat caatgtctct   1620
atatgtagat gtctcatata tggtatctat gtatctgtat catctctata tatctaatca   1680
tctaatatag atgtctcatg atatctatat agatatatct atatcataga tgcagagata   1740
tcatatatat gtctgttct ttggagaatt ctgactgata caggttgctt ccgccttttg    1800
gctatcatga gtaatgccgc tgtaaccatg ggtatgcaaa acttctttg agaccctgct    1860 ctgagttctt ttgggtaaat acccagaagt ggattgctgg atgatttggt ggttctactt   1920 ttaattttt gaggaaatgc atactgtttt ccataatgg ttgcaccatt ttataatctc    1980
accaagagtg cacagggttt caatttctct acatccatac caacacttat tagtgtgtgt   2040
gtgtgtgtgt gtgtgtgttt aatggctgtc ctaatgggtg tgaggtgaca tttcactgtg   2100
gttctgattt gcacatctct gataattgct ggtgttgagc atccttccat atgcttgttg   2160
gtcatttata tatcatcttt ggaaaaaatg tctattcaag tcttttgtct attttttttc   2220
cttccaactt ttatttagg tctgggggta catgtgcagg tttgttacat ggataaattg    2280
tgtgtcatgg gggtttggtg tacagattat ttggtcgcct aggtaaatga gcatagtacc   2340
tgataggtag ttttttgacc ctccccttc tcccaccctc caccctgaag taggccccag    2400
tgtttattgt tcccttctta gcatctgtgt gtagtcaatg tttagctccc acttataagt   2460
gagaaaatgt ggtatttggt tttctgttct tacattaact tgcttagaat gatggcctcc   2520
agcagcatcc atgttgctgc aaaggacatg atttcgttct tcttatagct gtggtgtata   2580
tgtaccacat tttcttacc cagtccactg ctgatgggca tctaggttga ttccatgtct    2640
ttgatattgt gaatagtgct atgatgaaca tatgtgtgca tgtgtctttg tggcagaaca   2700 atttacatt ctttgggtat atatccagta atggggttgc taggtggaat gattaattca    2760
```

```
cttttaagtt ctttaagaaa tctctaaacc tctttcccca gtggctgaac taacttacat    2820
tcccaccagc agtgtccaag tgtttccttt tctgcacaac cttactaaca tctgttattt    2880 tttgacttt taatgatagc cattctgact catatgagat cgtatctctc tgtggttttg     2940
acttgcattt ctctgatgat tagtgatgta gagcattttt tcaaatgctt gttggccgca    3000
tgtgtcttct tttgagaagt gtctgctcct gtcatttgcc cacttttaa tgggcttgtt     3060 tgttttttgc ttgttaattt aagtttcatg tagattctgg atattagacc tttgtcaaat    3120
gcatagtttg tgaatatttt ctcccattcc ataggttgtt tactctgttg atagtttctt    3180
ttgctatgca gaagctcttt agtttagtta ggtactactt gtcaattttt gttttgttg     3240 ctttgtccat tttaaaaaat agagtaattt gattattttg ttgttgaatt gtaggaattc    3300
tttatatatt atggatgcta acatcttatc aaatatgatt tgcaaaacat tttccctcat   3360
tctgtaggtt gccttttcac tattgtgtcc ttcaatgaac aaaagttttt atgtttgatg    3420
cagtcccatt tgtccatttt ttttggttgc ctgtgatttt ggtgtcatat ccaagaatgt    3480
ggaatgtgtc atatccacat tcaatgtcct gacgatttt ttctatgttt tcttccagaa    3540
gttttattgc tttgggtctt tggtttaagt ctttagtcca ttttgagtta attttttgtat   3600 gtggtgtaag aaacaggtcc aactgcattg ttttgcatgt aaatatccag ttttcccagc    3660
atcatttgtt gaccagactg tcctttccc atttagtgct gttggagctc ttcttggagg    3720
tcagttggcc atgtgtacac aagtttattt ctgggctctt tattctgttc tattgatttg    3780
tatatctgtc tttattccag taccacactg ttttattctt ctttttcaaa attgtttgac    3840
tcttagggcc ctttgagatt ccatatcaat tttaggatga attcttctat ttctgcaaca    3900
aatgctattg gaatttttgat aaggattgaa ttgaatctgt agactgttt gagtgatatt    3960 aacatcttaa taatattaag tctaatccat gaatgtgaga tgtttctatt tatttatctc    4020
ttctttgatt tctttcagta atgttttata gttttcatta tataagtttt tacttcctta    4080
gtcaatttct aagaattgtt ttcttttttga tgccattgca acgggaatca ttttcttaat   4140
tttttcagat gctttcacta tttgtgtata gaaatgtaac tgattttttg tatgtgtgtt    4200
gattttgtat ctggtaactt tactgaattt ttaaatttgt tctaacctgt ttttttttt     4260 tggtggaatc tttaggattt tctgcatata agatcatgcc atctacaaac agaaattttt    4320 acttcttct tcccaatttg gatgccttt attgctttt cttgtctaat tgctttggac      4380
tggagttcca atactctgtt gaatagaagt gtccagaaca gacatttttg ccttgttctt    4440
aatcttagag gaaaagcttc cagttttca ctgagtatgc cgttagctgt ggacttttcc    4500
taaacaacct ttattatgtg caggtaattt ccttctcttt ccacttttga gtgttttttt    4560
tcttttcttt tctttttttg tgtgtgaaag gatattgaat tttgccaaat gcttttcctg    4620
catcagtgga gatggtcatg tgggttttgt cctttattct gtaaatgtgg tgtactacat    4680
tgattttcat atgttgaacc atccttgcat cccagggata aatcccactt gatcatggtg    4740
aatgatcttt tgagtgtgct gttgaattta ttttgctagt attttttga ctacgttcat     4800 cagacatatt gggtaattat ttattttttc ttgtagtatt tttgcctagc tttgatatca    4860
cactaatgct gccctcaaa gaatgacctt ggaagtattc ctttctcttc agttttggg     4920 ggattgatgt aaattctttt ttttttttt ttggagacag ggtctcactg tcacccaggc    4980
tggagtgcag cggcacaatc atagctcact gcagcctcta actcctgggc tcaagcaatt    5040
ctgcttcagc ctcctgagta gctgggacta taagcatgtg ccaccatgca cagctaattt    5100
```

```
atatatatat aatataatag ataaatatat atatatatat atatatatat atatattttt   5160
tttttttttt tttttttttt tttttttttt tgcagagaca aggtaggtct tgctatgttg   5220
cccaggctgg tctcagactc ctaggctcaa gtgaacctct cacctcagtc tcccaaagtt   5280
ctgggattac aggcatgagc caccacgtct ggccagtgtt aattcttcaa tatttggtag   5340
aattcttcag tgaagtcttc tagtcctggg cttttctttg ttgggaggtt tttaattacc   5400
aactcaattt ccttactagt tattggtcta tttatatctt ctatttcttc atgattcagt   5460
cttggcaggt ttggtgtttc tagaaattta tccatttctt ataggtcatc cagtttgttg   5520
gtatagttca tagtcttctc ttataatcct ttcttatctg tagctcagta cctcctatct   5580
ggagatgcag aattaggaat tgaaactata ataggccccc cttttataat ggggtgtcct   5640
tatttttacc ttctcacctt gcaataccct tgtcttgcta gtaaagaaag aagggaaatt   5700
tgattcagga ggtaatcata cttttcaatt tgtacaagat ctaatagcca tgaactccta   5760
tgtcattcct caccatccca taattcttag cccagccatc atccttacct caatccctgc   5820
tggtgcagcc tggtttattc tgttaatgtg ctgtactgca ttgaggtaag gacttctgct   5880
cagctttctt cttgatacca ttgtaccttg attcacactt cctcttgtga ataaagtttt   5940
agcatgaagc tgctttctta catattttaa gttcggctta aaggttttttc tgtacatcgt   6000 gaactgtaac aagtggaata taaccagacc gtagcttaca cttgtgccat ttaccaagtt   6060
ttggccaatc aaatgtagcc aactgtttga actgtattca aataagggaa atgctcagct   6120
gtaaccaagc caactgtttc tgtacctcac ttctgttttc tgtatgtcac tttccttttt   6180
ctgtccataa atcatcttcc atggcgtagg tgtgctggag tctcagagtc tattctggct   6240
caggaggctg cctgattttg aatcattcat ggctcaatta aacttcttta atttttttttt   6300 tttttgagat tgagtttcac ccttgttgcc caagttggag tgcaatggtg cagtctctgc   6360
tcactgcagc ctctgcctcc tgggttcaag cgattctcct gcctcagcct cctgagtagc   6420
tgagattaca ggcacatgcc accatgccca gctaatttttt ctatttttag tagagacagg   6480
gtttcgccat gttggccagg ctggtctcga actcctgacc tcagcctccc aaagtgctga   6540
gattacagat gtgagccact gcacctggct tcactccttc aaatttaatt cagctaaagt   6600
tttttatttt ttctctttct tttttttttt tttttttgag acagagtcac tgtcacccag   6660
gctgaagtgc agtggcacaa tctcggctca ctgcaacctc cgcctcccag actcaagcga   6720
tttctggcta atttttgtgt ttttagtaga gatgggtttt caccatattg gccaggctga   6780
tcttgaactc ctgaccctcag gtgatctgcc tgccttggcc tcccaaagtg ctaggattac   6840
aggcatgagc cactgtgccc agcctcaaat ttaagaagaa acagttaaca tggacttgca   6900
tacctccagg atattgtgaa tacctctcaa tatttttcta agttctcaaa gtcaaattag   6960
actctatgac aatcactcaa ggttcccttt gtttccaata tgttgatgac ctgctacttt   7020
gcaaccaaag caaacagggt gctcttctgg actcccttac tcaccttaag gcactgactg   7080
actaaggtta taaatcttcc aggtccaaat gccaacaggt acaaaaaatt cttacctact   7140
taggccataa aatatttag ggtactcaaa aactcgtccc aaaatgcctt gaatcaattt   7200
tattcattat ctctcaaaga caaacaatta cgtgaatttt taggagcaac tggatattgc   7260
caatggattc ccaattttgc tgcccatgtc taaccttat atgctgtcct cttagataca   7320
accacagagc actttacctg gtactctgag gcaccagcct ccttggaagc attgtccaca   7380
ccccagccct tcgactaccc aactttgaca atcttttta cctatattac tgtgaaaatg   7440
atgggattgt tgtgggtatc ttaggacaat cttttgtcc cataacatat ttctcatgtc   7500
```

```
aacctagata tgtcccacag tacctttctc atgttaagta gcatcaggca ttcctccatg    7560
cttatatgca atagacttag ctgccatcct aattgacaaa gcaagtattc ttatactgcc    7620
ccaccattca cctctctgtt ctccatgctg ttcctctaca ttggtatccc tttcaaagtg    7680
gatcttgcct caactaaccc ttaactgttt ttttttttgtt tttgttttttt gttttttgac    7740 aattctggca ctaccccaac acctgcttgt tccaatcttt caaagcctgg ccaccttaaa    7800
tagttaatct ggttactggt taggttaaca tctacataat gcagaagagt ttttgttcct    7860
accaatgtaa atatacctgg tgaacccatt ctggacaatg gatatataaa agcatatggt    7920
atccataagc aggaagacaa agtcactctg tctcctcctc tggtagatta atttggcact    7980
gggaagcctc catggaagct caaggtcagt gctttaccca agtaagacta ttggaaggaa    8040
atctctctac attgaaaata aatacagtac tggacctttt ctgggtaaca tttcaaaaat    8100
gtattgcaat caaattctgt gatttggctt cacagatggc actaaacaac cctccactgt    8160
cattgttact tggattataa ctaagtattt caatgtgagt gaatgtcaga ttacaggata    8220
atattcctgg tttgtaggaa aaagtagtgg gatatggaat agctcaagtg ttcccctagt    8280
tggcttgacc agcacccatg actatagttg atggatgga ccttaacttg gtcaataaat    8340
aaaatacatt tctatagtaa ccaaggctaa attaaagggt ttctctgcca ggtgtttcac    8400
aacctgtttt accctcatag cctaacagaa gcacattgga agtgaagatg tgcagatgcc    8460
aacatgattg atgataaggg ttgtgaaaga cacagaattc caacttggtt gttcacaggt    8520
tccaccacta tgaccttgtc tgtaaacaac actggtctct ctctcttttt ttttttttt    8580 agaaggaatc tcactctgtt acccaggctg gagggcagtg gcacaatctc agctcactgc    8640
accctccacc ttccggttca gcgattctc ctgcctcagt ctcccgagta gctgggagta    8700
caggtgccca ccaccatgcc cggcttattt ttgtagtttt agtagagaca ggatttctcc    8760
atgttggcca ggctggtctt cacctcaagt gatccgccag cctcggcctc ccaaagtgct    8820
gggattacaa gcgtgagcca ctgtgcctgg cctggtctca tttttatgta gcaataagat    8880
atataaaagg ttcccaccta agtggtcaga gaaatgtgaa gttggatatc tggtgccttc    8940
ccttaccaga tatcccactt tgaatgctag ccacattaca actggggttc ttttatatat    9000
aaattaatgc catgtagatg cacctgatga gacatcatag acaacgcact tatgtattgc    9060
aaccctaagt tctcagtaat gagaatgctt ttccaaagcc tggcaatgta cgatgtagaa    9120
agaacaatcc taagcattcc aaagtaatga acaagcatct ggtgccacta tacagactgg    9180
gaagcctgcc atttacaagt tagcagtgta gcctctgttg cactccaaaa ttgtgtccta    9240
gatatgctga ctgcccaaca gagaggagct tgtacaatca ctggcaacaa tgctacttct    9300
atataaatta gaaaggaaaa attgtgtcta atctatatca tttaaaaaga aaggttggcc    9360
gggcacggtg gctcacgcct gtaatcacag cacttcggga ggccgaagcg gcggatcat    9420 gaggtcaggg gatcgagacc atcctagcta acatggtgaa accctgtctc tactaaaaat    9480
acaaaaaatt agccaggcat ggtggcgggc acctgtagtc ccagctactt gggaggctga    9540
ggcaggagaa tggcgtgaac atgggaggcg gagcttgcag tgagcagaga tcacaccact    9600
gcaccccagc ctgggcgaca gaacgagact ccgtctcaaa aaaaaaaaaa aaaaaaaaa    9660 aaaaaaaaaa gaaaggtcaa cattctacgt taggtaaata aggcatagtc caattaactg    9720
aactgaactg acctattccc acgactggga gactggttca acagaatatg gaccagtgtg    9780
ttcagatttt tctctgttgt aatctatgtt cttctttcat tttgcagatc tcttacctcc    9840
```

```
cagcacctaa tatgagtctt ttctacatag gaaataatcc aaatatttgt gaaacttcat    9900
gtgaagtttc aaatggggga agtgaaggaa cgaacaaccc acctcctaac cccaatttat    9960
acccacctgt gttagttcat ttgtattgct atgaagagat acctggaggc tgggaaattt   10020
ataaagaaaa gaggcttaat tggctcacag ttctgcaggg tgtataggca tggcatcagt   10080
atgtgctcag ctcctggtga gggcttcagg gagcttacaa tcatagctga aggtgaaggg   10140
ggagcatgca tcttacatgg tgatagaggg agcaagagag agggtcgggg ggtgccaggc   10200
tctttaaaca accagctctc atgtgaaata ccagagccag aactcactca tcaccatggg   10260
gatggcacta agccattcat gagggatctg cctcatcacc caaacacttc ccagtaggcc   10320
ccacctccaa cttggggatt gtatttcaac atgacatttt gaggggacag atatccaata   10380
ttcaaaccat atcaccacca gaaaggcata aagattactt taaactgaaa atattggaac   10440
aaacaatcgc tgcggaaagc agccttatct gaccgaaagc agacctgtcc aagagttctg   10500
ctatcatcaa ctccttctga gggactttcc agacagcgag gtgacagatg tttacaaacg   10560
tgacgttaaa aaataaagtt gtgtaaatga gtcttatcag aaccttttat actttctcac   10620
tgaagcctca gttggtatat aaaccccttac cactggctgt ttgggaagtg actccttaca   10680
gagtgctccc tcaggcatgg agaataaact tttctcctgt taatgtattt tcaactaatt   10740
cgcaggccct agaccactca gatctaagtt gacagatgaa atgttttcct cccaacatga   10800
ccaagcttat agtgctttta tggtatatct gtagagattg cggtcaggca taacattgtt   10860
tgttagggtt gcagtacctt tcaggaaatg ctcaaagttt aattgattta ggggactttc   10920
actggatgag atgcctctct gagtcatcat aggttgcaaa gtattagttt tttgccactc   10980
actgtgtgtt gtgatatgac atactcataa tggggtagga caagatgtca gttttgcttc   11040
caaactttcc ttacttgttt cctttttggt tcaccactaa tgttgaagaa atgcaagatg   11100
gaaaatctca atagttgaca ctgattgatt gattgagatg gagtctcact ctgtcacctg   11160
ggctggagtg cagtggcgtg atatcggctc actgcaacct ccacctccca ggttcaagca   11220
gttctcctgc ctcagcctcc cgaacagctg ggattacagg tgcccgccac tactctcagc   11280
taattttttg tattttttagt agagatgggg tttcaccatg ttggccagac tagtctcgaa   11340
ttcctaacct tgtgattcgc ccgcctcggc ctcccaaggt gctgggatta caggcatgag   11400
tagttgacat ttattaagtg tttatatgtg ataagcactg ttagattatc ccatgtaata   11460
catcacttga ttgatttaag agattgtcat ttgaaagatt aaagaatatt tcccagaaag   11520
gatgcttggt caagcctcat catcctggga tggatgggac cttggttttg ggcaagttta   11580
ttacaattta agactattct aggtcatgga agtgtgtgtt aggacatata agtagttttc   11640
ttgtccagaa tactttgtaa taatataccc taagtttgat cagctttttg gcattcactt   11700
aattaaaatg ttcacaagta ggtacatttt tagaattgtt aagtaatata ctatttgtag   11760
tagcaaaaca ctacaaacaa atacctaata taataagagg gagtggttga ataaactagg   11820
gcatgtcaac taaaaaacat atttgaaatg cagggaaaat gcttactcta ggcaatagtt   11880 acaactttg tccattatag gtacataaag gaaaagagta cacaaagaat tctattaatg   11940
atgaaattag gaacaatgtt cccatcccca atttatacccc aaaagaaaat atgttctggc   12000
tgggcgcggt ggctcatgcc tgtaatccta gcagtttggg aggctgagac aggtggatcg   12060
cctgagctca ggagttcaaa accagtctgg gcaacatggc aaaacccgt ctccaccaaa    12120 aatacaaaaa attagccagg cgtgatgca catgcctgta ggtccagcta cttgggaggc   12180
cgaggtggga ggatcgcttg agctcgggat gtggaggctg cagtgagcaa agctcacacc   12240
```

```
actgcactct agcatgggtg acagagtgag accccgtctc aaataaataa ataaataaat  12300
gaaaacttat attctataac atgtattctt atgtctttgg ctaaaacaaa agagaagaaa  12360
aataagtaga gagctaagtg aagtgaagtg tcttgaaaca gataagccat aaagtgagat  12420
atatgagtaa atgagtagtt gctggcctag gaattgtttc tgatgttttc acctattgaa  12480 agaattttt tcttttttgta aatcttttt ttggtttgtt aaactgaaaa ataaaagcaa  12540
tgaagagata atattgctgt agtaatgtcc cttagtgcat ccttggagtt agttgtcttg  12600
aatttggcct gctctgattg tcatttgctg tttgctgcat gaaaaaatt tcagatttac  12660 aaaaatatgt gtgccagggt ggaggaaatt tttaacttga tgaattctca cctttaggac  12720
actgtctgct cttatatggc acttagcaag atgctgcaac aattgtccct gctcatactg  12780
ttggaggaag agggtatttg cagggagatt gctggagtca agatgatcca aatttaaatt  12840
gcagtggtga gcagtggcca ctagagggct gtgaagtact taattctaaa atttccacat  12900
tttaatctgg agcagaggaa actctggaag gaccactggg actaagggag ctcaatccca  12960
aacatcttta tctgagccct aaatgtcttc tacgttattc tttgacaata ctttgttaca  13020
tctcagaatt tgtagttttg aggtggaggt ttaagttaga aatagtttaa tatattctat  13080
tccagaatat aattcgcttt tttccaaatg aaactggcac taaaagcttt ttacttgaaa  13140
gcaaatacac ttcatatgct ttatgtattt ttgtccctat atcattgaaa tagtagattc  13200
aaggctgttt gtaaaaataa gtgactatac tgcatatagg aatagcccca ccttaaagac  13260 tttgattta aggacattaa gtgggagggt ctttttttgcc ttttttttt tgactatcaa  13320 aatactttca catttcttca attcaaagaa caactgttct aaatttagaa gacagacaag  13380
tgaaagagaa tatgctgcca tttccgatgg ttcttttta ctcttgatcc atcactctcc  13440
tgtctttggc tgactctttc tccaaaaagt accccttatt tttcctatgc ctttaacttc  13500
tgttttactt actctattgt agaactttga gaagttgtac accacattca ctgctacctc  13560
acattaactc tgcttactca ttgcagtctg ccttctgctc tcaatgatt gctcctgtga  13620 aggtcatctt tggtttagca cttgtttgaa atctaatagc ctaaatgcac atcgattact  13680
gtttagaatt caaacgacat ttatttattt actttgagat ggagtttcat tcttgtcgcc  13740
cagctggagt acaatggcat gatcttggct cactgcaacc tccacctccc aggttcaagc  13800
gattctcctg cctcagcctc ctgagtagct gggattacag gcaccctcaa ccacgcctgg  13860
ctaagttttg tattttttt agtagagatg gggtttcgcc atcttggcca ggctggtctc  13920
gaactcctga cctcaggtga tctgcctgcc tcagccccac aaagtgctgg gattacaagc  13980
gtgagccacc acgcccggcc caaatgacat ttatttttaa aagcaactaa accaggaaag  14040
accttcactc attcaatcaa aaaacatgca ttgaacacgt attcttggct agatccggtg  14100
ctgcaaagat gaaagacgcc actcctagcc tcaaggagct tgcagtttag tggtggcact  14160
ggatgtaaaa taatcataag atgtgaggtg aagactgatg aggtctattt tgttgacaca  14220
ggtaaacatt ctcagagaat atttaattag caacatgaca aaaattagtt gatttatttg  14280
aaggatattt aagtgaattt agagatgaga tttgttttta cttttttaat ttcagagagt  14340
tatgttggtt gcaaaaatct tgttttcta gtatctattt tataagccat ctgagaccag  14400 gatgtttct ttttaacatg taaacttgat gcagtctctt tgtaaagtaa tgaatccccc  14460
cgtgaacctc aaggagaaga aagtttagct tgaacactta atttcaagta ccttgagaag  14520
ggaacaggct gtattgctca gagaagaagg ctctattagc taaggtagaa ggacaatgta  14580
```

```
aaactcttgt gaagacacct aaatgtcatt ccactcaaag cccattatta ataatttgaa   14640
actgtctgct ctgtgaaggc aacgacctat ctttactcat ttttgactct gctaacattt   14700 cttttttatag ttgaactaga ggcaaggcaa ggaacttgac atgcttgttt tccctttaga   14760
ataaagtggc cagaagcagt ttcttctgtg tgatccaaca ctttcttatc cccagagcaa   14820
ctctgcatag tctagatgta ccagagccca gcagcctgtg aggtgatgtg atgtgatgtg   14880
atgtgaacag aaaggctcca tgttggatga tgcctatgaa tctaatcaga ttctcttttct   14940 tggtcattt gatttccaga gaaggcagta gaagcaggtt ctgtgtgtat aaccagagac   15000
tagagggagg aactgacagg gaagctgggt catgagagtg gtgtgctcag cagagtaggg   15060
agtaagagag agctggctcc agagaggatg acaaaatgcc catgtctcca gcacttcttt   15120
agcattctga gttcccatcc tatcatgaat aggaagagtt ttctagctct ccatgaagcc   15180
gaaataggtt tcagactttc ctttctttcc cacacacata ataaatacccc atcaggtaac   15240 ctgggcatgg ccttttattt aggcactaac aattctaaaa ggaattaata aatgcttcac   15300
tgccatttca cagtgtaaca gcatgccagt ttaccatacc attaacattt agcctcgtgg   15360
tatttctgtg tttttttcagt cagtaatgat ggcatttttg ccaagataat atagtgttaa   15420
actgtattgg ttgaaatcct aggctttta aatgtaaact agcactttac aaagtattac   15480
aaaggaaacg aaccagggaa acttgagaag gaactttctt atccacattg ttataggtta   15540
taaaatagtt cctatttaaa ttaaaatacc tactgttgca cttttatgtg tgtttttata   15600
tataaataac atctgggttg gcaaatatgt gattttcgtc aaataggctt tgattgaaga   15660
tgaaatattt ttgtaaaact agtcctttt taaagttaaa attttatgtt accacatgaa   15720
ttgatcagca gaaattttatt tacattatgt aaattgattt ttaagagtat ccacaaggtt   15780
ttagctatta ttttttgaact tgcttcctag cccacacaat taagtaataa gagtaagaaa   15840
aaagaaagca cacatccaaa tcatctatca aaacccagct tctacccaat gacacatcat   15900
tttatttctt gatcttgtaa tgttgagcac atgccttgga catattccta tatgtgggct   15960
ctattctctg cagcacgtca ctccctcttt tatccgcccc tcttatgtgc tcccactcct   16020
atcctcttca attaaaaatg cctctttctt tttttttaa gttaattaat taattaattt   16080 tttttttattg atcattcttg ggtgtttctc gcagaggggg atttggcagg gtcataggat   16140
aatagtggag ggaaggtcag cagataaaca agtgaacaaa ggtctctggt tttcctaggc   16200
agaggaccct gcgggcttcc acagtatttg tgtccctggg tacttgagat tagggagtgg   16260
tgatgactct taacgagtct gctgccttca agcatctgtt taacaaagca catcttgcat   16320
ggcccttaat ccatttaacc ctgagtggac acagcacatg tttcagagag cacagggttg   16380
ggggtaaggt catagatcaa cagcatccca aggcacagga attttctta gtacagaaca   16440 aaatgaagtc tcccatgtct acttctttct acacagacac agcaacaatc tgatttctct   16500
atcctttccc caccttccc cctttcctat tccacaaaaa ccgccatcgt catcatggcc   16560
cgttctcaat gagctgttgg gtacacctcc cagacggggt ggtggccggg cagaggggct   16620
cctcacttcc cagaaggggc ggccgggcag aggtgccccc cacctcccgg atgggcggc   16680 ggctgggtgg aggcgggccc ccacctccct cccagacggg gcggctggcc gggcggggc   16740 tgaccccccca cctgcctctg ggacggggcg gctggccggg cggggctga ccccccacct   16800 gcctccggga cagggtggct gctgggcaga ggggctcctc acttctcaga cggggcagct   16860
gccgggcgga gggctcctc acttctcaga cggggtggcc gggcagagac gctcctcacc   16920
tcccagacgg ggtcgcggct gggcagaggc gctcctcaca tcccagacgg ggcggcgggg   16980
```

```
cagaggcgct tcccgcatct cagacgatgg gcggccgggc agagacgctc ctcacttcct   17040
agacgtgatg gtggccggga agaggcgctc ctcacttccc agactgggca gccaggcaga   17100
ggggctcctc acatcccaga cgatgggcgg ccaggcagag acgctcctca cttcccagac   17160
ggggtggcgg ccaggcagag gctgcaatct cggcactttg ggaggccaag gcaggctgct   17220
gggaggtgga ggttgtagct agccgagatc acgccactgc actccagcct gggcaacatt   17280
gagcactgag tgaaccagac tccgtctgca atcccggcac ctcggaggc cgaggctggc    17340
ggatcactcg cggttaggag ctggagacca gcccggccaa cacagcgaaa ccctgtctcc   17400
accaaaaaaa tacgaaaacc agtcaggcgt ggcggcgcgc acctgcaatc ccaggcactc   17460
ggcaggctga ggcaggagaa tcaggcaggg aggttgcagt gagccgcgat ggcagcagta   17520
cagtccagct ttggctcggc atcagaggga taccgtggaa agagagggag agggagactg   17580
tggggagagg gagagggaga gaaaaatgcc tctttcaata tgtaaggtaa gattgataga   17640
tgattgcctt ccgtagttcc tcccaaaatt cataggttga aatcttagcc ctcagagtgg   17700
tggtattagg aagtatggag cctttgggag ataattagct caggagggtg gagccctccc   17760
gaataaattt aatgccttta taagcaagac cccagagagc cctttcaccc ttttctaccc   17820
tatgaggaca cagcgagaag acagctgtct gtgaaccagg aagcaggccc tcactacata   17880
ccgaatctac aagcaacttg atctcagact cccagtctc ctgaactgcg agatataaat    17940
gtttgctgtt taagtcaccc agtctaaggt attttgtta tagcagcctg aatggactca    18000
ggcggtaggc aagaggagga cagtgcacct gagttataca ttgggcaagt catttacctt   18060
cattggagcc tcggtttact tgtgttagat atgggaataa tgatagttac actgcagggt   18120
ggttgtgaag attagagaaa gtgcatatac tctgatcagc acagtgcatg gtacttcagt   18180
acacagtgtt aactgaagac acagtgttaa ctgaagacac agttgaaaac taaagatagc   18240
tagtgaaaca catgttctct gcacatcata cagtttcttg ggcagttttc aaagtgtgac   18300
tctgcagttc ataccaccat tatcacttag tctctaacaa ataatcatat ttgacacatt   18360
tggctgggac ttaataattt tatttgggca gcagctggtt tctggaagtg ttcatgggaa   18420
gaaaatgtat attaataaag ttagcaggta atgttctttg ttgaaatgtt ggatattgtg   18480
ggacacaaaa gagtcagggt aaatgtacat ttacagaatt gagcgtcaga gtgtcatagt   18540
tctctaatga tttacaaaga aagaattcct ggaacaagtg aaatacttaa taattaattc   18600
agcctgtatt tctgcaggta atcaactgca gtgataaaaa aataaaaatg gaactgtctt   18660
ttgctcattg gaaagatatt tgctgcattc aaagtcatca aaaaggcgaa gcaatgaaac   18720
ttaagacttt tgggttttaa taattaaaaa tccatcttaa agagaacctt gggctctggc   18780
acggtggctc attcttgtaa tcctagcact ttcggaggcc caggtgggcg gatcacttga   18840
ggtcaggagt ttgagaccag cctggttaac atggtgaaac cccatctcta ctaaaaatac   18900
aaaaattagc tgggtgtggt ggtgtgcgcc tgtaatccca gctacttggg aggctgaggc   18960
acgagaatca cttgaacctg ggagatggag gttgcagtga gccaagattg tgccactgca   19020
ttccagcctg ggtgacacag tgagactctg tcttgaaaaa aaaaaaaaga gagagagacc   19080
gtttgtgaag gtgtgttaca cagagaattc ctgattccta atctccagaa tagaaaaatt   19140
caaaggctca gaatcatccc aaatcaatta tccagtggca tctgcatttt ccgatttcat   19200
tctcactagc cgtgtgaaca tgggcatgac cccaggagcc aaggaattct ctaatgccta   19260
aggacagcca tgaggtcaat gaataacatg tgtcaggttt ccctggcaca gaggagcttc   19320
```

```
ccagtaaatg ttatttcct tagctatttc ccatttaaca tgtcaattat tcttagtgag    19380
tttccattca atatgagagt ttatataatt tgtcatattg aataggaact tgctaaggaa    19440
agctgtgtag cagaggaagc agccccaagt gacaggacat aaactttaaa ttcacaagat    19500
gcttgtatgt gaattatgat ggtatctgaa ttaacagtga tatttacagt ttagtaatac    19560
attttcttc ccttgtcttg ggctttataa aaaccctgta agtcatgtat gtcaggaatt    19620
ttatcctcat aattgagaga aaaatactcc atattttatt ggaaataaga tcagtagatt    19680
ctctgtatat catacaatgt cttgcctact taaattatca cccccttcc tatttcaaca    19740
aagactttct ctaagtaccc ctggcctctt gccctgatcc atactgttct ccttggtaat    19800
ggagtgagtt tcctgcctgg tgggtgcagc cattggccac atttctctag tgtatggaac    19860
tcaccggata aaaggcctca gatgtaggtc tctttctgct gtcttcaccc aggtgttgtg    19920
gagtgtgtct gtccttgagc actagctttc ccctgtgtgg gctgcctcaa ggcctgcatt    19980
catcaggtag ggactgttag ctggtagacc taagccacca ctccagtact gactgtcagt    20040
aaggaaggtg acatgctgac ctccatctgc tacatcattg tgtatatgtc ttcattagtt    20100
ctgcatattg gtgagaaaat ggatgctctg attcctcttg aaccccaaga gaatgaaggt    20160
aaaaaaattg aggtcctaat gcaaatttc ttagtacacc caaatctttg gatagagtcc    20220
tgcactcttt gagatatatc acacaatctg tctcactttc ttttcgcata tgttatatat    20280
tttaaaactt ttgtttttgg ggccaccact tactggctct gtgattttag gaaagctttt    20340
cagaccctca gaaccccagt ctcttcatct ctaaagtaat aaaatatatg taagaaacct    20400
atttcagcat gtgaattctg ttttcctttt tcctctagat gtatcatatc cagttaaaaa    20460
aaaatctact tgaactttgc aggtatcttc agtgtttatt acttctcatt tttaacattt    20520
attggaaatt agcatattgt cagaattgat ataatacaat atgtaacctc tttcattaag    20580
cttatcattt ttaaaataca aataactatt ctttacttaa attttatttt ctagacacag    20640
ggtcctgctc tctcgaaccc aggctggagt gcagtggcac aatcatagct cactgcagcc    20700
tcaaactctt gggcttaagt gatcctcctg cctcacactc tggagtagct gggattatag    20760
acctgagcca tggtgtccag catgacttaa attttgaata agttgcactt actaattaca    20820
cttacactgc tgcatctgaa agagtaatac aacaatagaa gccttttata gtaattattt    20880
gtggcaggta gactcctaaa atgactccca aatgacccac acccttgtac aatcaatacc    20940
ctgtcccttg agtgacagtg acttgctcta atcagttggc tttcagttaa tcaaaagaga    21000
gattatcttg ggctgaacta aactaatccc agcaagataa cagggacttc agtcttgcaa    21060
acagatatca tataaaggga atcatatctg cacatttgat tcttggaccc tgggtaggaa    21120
tttgttagag agcaaggatg tgaataaagg tgggaaataa aggtgtatct ggtgtctctg    21180
ctcaaaagct cacatgtagc tacaaggcag agatttaggg gagtggtatc cacagtcaag    21240
aagaattaat acatagtgtt tgagtctggc ttcttccaat tagcataatg cttttgaggt    21300
tcatccatat tgttgcatta ccagtagttt ttatttattt attttatcag tagtttctaa    21360
attgttgagt agtatattac attgtgtaga tatatcctgt gtgtttatcc atacacattt    21420
atggatattt gggagttgct agttttagc tattctatga gcattcacat acatgtcttt    21480
gtgtggaaat aggttttcat atctcttggg taaatatacg ggagtggaat tgctagatca    21540
tatggtaaat actctgtata cttaaaatga agagaaactg tcaaactatt ttccataatg    21600
gctctaccat acttgatgtt ttagaaaaga ggaaaaacac tagcaatttt gatgctgtat    21660
gtctacaacc taagagaatc taataatagc gtcctggtct gtcagtgtag gaattgccta    21720
```

```
ggtaatacat ggaaggtgtg gagggagcag gtacacagaa aatgtgcgtc agaaagtttt   21780
gcttttccta tcccacgtca tttctgagtc tgatcctccc tactcctcac aaataaattg   21840
gtagattcat ctgttttgg acccttttct gctctagtta ctgaactatc agagacttca    21900
ggaagagctt aagctaagct attccaggga agttttggtg ttactctgta cttacggact   21960
cctgcgtgtc tgtctctgtc accccagctg ccaactcaac ttagagttta ttagcctggc   22020
attgaccagc acactgtgat attctctgag gcacactgca tgctgctagt gtgccctggt   22080
tcataaagct gggccttcag cattgatccc actccaagtt ccttgctctg tcttcccaca   22140
gctgtcccct tggggatgt ggggggtctg acatcatttg cattattagt ctattccaag    22200
aaatgcacct gtgcactaat cagttcactt tttctgtctt agtcggcaga tctagccata   22260
gcccaatccc tcaatttcta tactaagcct tttatattag taaaactgtt atgttatcta   22320
gaaattcatc agtgggaaaa ctacttcaag ggaggtagtt agaggctgca aggtgctaaa   22380
tatttttctt tctttctttt taaatgtaac ttggatctaa agtaaggacg aatttccttt   22440
tattatttgt tcagaatata ccagctggtc ctgtgggcag aagtttgtta aggggcctgg   22500
atgtgaaata acagtgtatc tcgtgtctct gctcaagagc tcacatgtag ctacaaggca   22560
gagatttagg ggagtggcat atacggccaa ctgagaaata acaatattgt cagggactcc   22620
aaggcacttt ggaagatata aagaatttct taaattttct tgtagaattg ttgcaaaagg   22680
cagacatgct taaatgttta aataagcttc ttgaaaactc atggaacatt caatcacaac   22740
tccaacagtt ctccaaaatt tgatttattc tggccatatt atgcagcaaa gaaacacttg   22800
gctatttatc taaatctctt ctgtcttgta aatgatccta gaaaataatc tagaaataca   22860
ttttattaaa gtaatgcatg aggtacatat cgattaccag ccaatagttg aacttaaaca   22920
taatgcatgg gtgtgagggc tggcattgat gattcacaat gaacacagtt gaatatcact   22980
tccctgctga gactcgggta tcatcgcaaa accacagtga gcatcagtgg ggatctgcat   23040
gctctggtca agacagatct ccatgctgag tgtctgtttg ccatgatgaa gagaacagtc   23100
aacaggagtg tttgccatga tgtagagaac agtccgggag gagtgaatgg aggatggggg   23160
catgaggaaa gatgaggctt tctctagtta tgaccctttg tgtagaagtt aggagtaggg   23220
gataaatgtt tctgcctaat atttaacttg gaagagaaga tgtccatgtg aaaaactgct   23280
aaatactgaa acaagagagc atgtgactaa gcaataccat gtgtggcaca gaaaacaagt   23340
gcaatagcag tttagcaaag tgagttcagt gtaggctgaa ctggttagag caggtttccg   23400
ggtgaaggtg aggattggtg aggtttgga ttggtagaaa gagacgggga ggacatctca    23460
catcaagaag ttatgccagt ggatttcagg agaattgagt gtttgtgtct gaaaagcctg   23520
taagaatagg gcatgacagt gtggagaaat gcatgaaagt atgaaggatc gtgatatcca   23580
gtttgaggag tgctaactag aggctctgaa gatttgagaa gaaacataat gaaaggtgtt   23640
ctcagcctga tcttggtatg caggactggt aaacccaaa cacccttacca ttctattacc    23700
tctccctcaa ggaatgggtc ccttgataag aatttagtgt aaaaaagatt gtcaattcag   23760
tgctgctgct gagtgctagt ttcttttaaac acacacagtt ttcttttgag aatttttttt   23820
ctattagata gacgaactgt tatttaaatg aaaaaggcac atagtcccat aaaacaatta   23880
cacattcggg tgataacttc aaaaggagaa attaaaatgt tcttatgttt tgagcaagca   23940
tttccacttc cagactttgc tgcataaaca tctgtggtca tctagggaat gcctgacctg   24000
gttcagaggt gtcagagcaa tgtaaagtca cggaagtgct gcagttctat tctgggctct   24060
```

-continued

```
catcttttg cagcggtcca ttctctaatt ttcaaccaca tattaccaga caatctctta    24120
agtcatacac aacaaactga ttctgtttca atgcttagaa ttagaataaa aaagcctaag    24180
caaaaatagc acaaacattt gaaaaacact ccttttttct accactccct tcttagaaca    24240
gaaataaaag ccctgtactt taagaaaatg gatggaagaa ttttctttgt acttcttatt    24300
ctccaagtta catttactac ctgatagtgt taatacccttt ttgtagtacc tttctttaaa    24360
atatacaggg aaatgatctg ttccaagaaa ctgtgttttt aaatttaatt atagtgtgct    24420
atgatgattt aaaaaatggc cttttgagta aaggacacga acaagttatt taaaaagtga    24480
gcagtaagtg tggtcagtaa acacatcaaa aagttccctt cactaatatt caaagaaatg    24540
caaattagaa taataatacc cttgttgctt gtcaaattaa tactttaaca attattatgt    24600 aaatttatg gataggattg caaatcaaca caccttttcct ggccactggt gtacataata    24660
gaaattctaa aaatgttctt aggcttgacc aagcatttcc acttctagac tttgctgcac    24720
aaagatctgt ggtcatctag gagaaggctt gacctggttc agaggtatca gagcaatgca    24780
aagtcatgaa aatgctgcaa ttctatcctg gactgtcatc ttttttgtag tggtccattc    24840
tctaattttt caatgacgta gtaccagaca gtctcttaag tcaaatgtat ttgtagggct    24900
ctggatttga aattcaatct ggctttcagc cttgatgtgg ccactcccaa cttgtaaagg    24960
acctgtgaag acttagacac agaataaaac acagaagata agaaaaccaa ctttgaagaa    25020
aaatttattg tcaaaattgt actgggtcaa ttgagcaaaa acttcaaaga gcgttttcat    25080
attaaccaaa gcatccctcc tcaattgaaa catataaaga tattgttcac ccctatcctg    25140
actcagagat ccacaaatct gggcattcat catcaccata ttctgctggc aatagtttta    25200
agcagctaaa ttactgttct ctactcttga gtttcctcca tctcttcaga tacagaaagt    25260
tctagaatat attcaaataa tcaaatcttt aattcattcc atatatctgg ctcaagacag    25320
tgtcccaata accttattct agagaaagtc agatttagac ttgtgctcat catcatactc    25380
atgttcttga catcattta agctctgagg agacatctca cataactctc attgatacgt    25440
gtatacatct gtcactctgt gtttgtgctg tgatggatgg acttggatgt agatatgcat    25500
agatgatgaa gcagatagct atatatatgg tattgatgta gattcagtac agctgtataa    25560
ttgcatctgt gtttcacata tcttgtgtac tgtatcttga ctgtatctgt gtcaataccct    25620 aattgagtta taaggcataa atatgtggag ctcttagcac aatacctggc acactgcaat    25680
cagtcgatgt atgtgtttgt gtgtgtgcgt gtgtgtgtgt gtgatacaga cagaacctgc    25740
taatatgcat aatagtcagg ttgggttgtt ataacaaaat actatagact gtgtggctta    25800
aacggcagac atttgtttct cacagttctg gagtctggga atccaaggt caagattagt    25860 ttctggtgag agcagtcttc ctcttttgca gctccccatg gtttgcaaat cacagatttc    25920
tcgctgtatt ctcacatagt gtaggaggaa cagagggagg gaagggagga agtgcctaag    25980
gacactaatc ccatgatgag agttctatcc accatgacct aattacctcc taatgccacc    26040
atctccaaat actatcacac tgggaattag gtctttaaca tgtgaatcat ttggggtgga    26100
gaagacaaac attcagctca taacaggtaa ggtagaaaat ctcaagaatt tatattttgt    26160
atatgaaaga tcattaatga gcagaatttt aagtttaatg ccaattttaa tctattttta    26220
tcttttctac gattcttttt tacttttaa ttttaaact ttcatataca aaggataat    26280 atttggctaa atgttctctt cttttttgagc tctggatcat tgttacgatc accccataat    26340
tgtatgtgtg cagagatagt gctttataca ttttaaaac aatttatat acagtattaa    26400 attttatttt tcaataaaca atccatgaga tagaaagaac atatattttg ttttacagat    26460
```

```
aagctccagg gagagtctag ggtaccttag attgtatggg taaaacatgg tttatttaaa    26520
tcataaataa acagtcttat ttccctaaat gcacatacag gcatccacat caaatgaaat    26580
cacatcacat gaattgaaca ggcagttact gacttagaac tttgcactca caaaagacac    26640
actctcctaa atgtctccat catactatac tttttgtccc caaatgccta atcactgaag    26700
cttcagactt tgttgctttg attcccttag gaaaaattcc tggtgtttca gaaaaaaga     26760 gccatttaac tacattagaa gttaaccctc ctttaaaaat gtg                      26803

<210> SEQ ID NO 20
<211> LENGTH: 26803
<212> TYPE: DNA
<213> ORGANISM: Homo sapiens

<400> SEQUENCE: 20
cagttaaggt ggggcaggaa taaatcacaa tggtggaatg tcatcagtta aggcaggaac      60
tggccatttt cacttctttt gtgattcttc acttgcttca ggccatctgg atgtatatgt     120
gcaggtcaca gggcatacat tggcttagct tgggctcaga ggcctgacaa ggcacagaag     180
gagctgggat agaggtgcaa agtactcatg ctgacctgac atcccatgcc cacggcagac     240
atgactactt gatcggacaa tactttcttg gaatcaaaga cacaacttca cagtcctcag     300
catcatagtt caggcagcct gtatcagtag atcagagtgg gcacatggcc tggtgctatc     360
actccatcct gtgagggagg atgggattgg aatggaggtg gaggagtcac aggtggtcct     420
gatatcacag gcctgggagt ctgaaagaag tgcagtaggt agtattatgg ccctcaaaga     480
catctgtgtc ctactgtcta gagtcaatta aagtgttacc taacatagaa aaaaggattt     540
tgcaggtggg attaaactaa ggatctcaag atagaaagac tctcctggag tatccagttg     600
tgtccaatgt aagaacaagc gttctcaaaa tagggacaca ggagattgaa ttgcaaagga     660
gatgtgctga taaacggaga ggttggagtg atgccgccat gaggcaagga atgtgggtgg     720
cctctagcag ctagcaatga ttcggaaatg gattctcccc cagagtccag aaagatcaca     780
gcagtgctga caccttgatt tgagcccagt gtcacctctg tcagacttct gccctataga     840
actgtaagag gataaatttg tgttttaagg cacaaagttt atggtaattt gttatagcag     900
caatgggaaa ctaatacaag aagggttgtg ttatcaacag aaatacagca atcagaagaa     960
agatggttgg ggagagcaga gggtggggtg ggaaggtgat ggattctgtt tgggacattc    1020
tgggtgtcat atgaatatta ttggggaact gtccatcaaa agctcagact tcaaagaaag    1080
aaaggaagga gcaacaatat tttgaaaggg agaaagtagg taatattcaa tatgtgttga    1140
gtacctacaa ggttttttagt tcttcacca agttatttta tttaattttt atggcatcaa    1200
ggggtgtttt tttttttttct taaaccaaat tttctcagtt aagcatccca tgtaagtggc    1260
caggggttaa gagatgtgac taagactaga cagagtgatt ttcatcatta catggtacta    1320
tggttctact gaagcactga ggaaggaagt caagagagtt cctgagaaat gtctggagtc    1380
ttagtaacat gcaaagtgag gcagaggtat tgtcagtgtt agctggtcac tttgaaaggt    1440
tagaggtaaa taaagttcag ggcaatggta cttggagagg agtgaatctt tggtaacctg    1500
gaggagatgc ttctcagagg aaaatttctt cacagcatga agtcaccagc tctaagacta    1560
gtgggtgttc tggggatgt tagcagtgac tcactgactg ttggcccagt gaggggaggg     1620
atgaaaggct gggtagtggg tagagaatct gactcctcct gcccccacat gtctattcct    1680
gggccttctc ttggtggggg caaaaggtat gcaagggat ttccgcagtg tctgagtgct     1740
```

```
cccaggagac ggaaaagtaa ctgatgactt ggagttggag tcttgttggc tcaggcagct    1800
ggggcgtttt gggatttcaa cacctccctt tagtttctat gtatggtgct gagcaagtag    1860
tcaaagactt tggtcttgct ttacccagt  agcccacaag cctgagtaca tggctaacat    1920
ttattgggca cttagtgtgt gccaaagagc tttatgagac aggttctttt tgagtcccat    1980
tatactgata atgggactga taagaaacag aaggtcagaa aggcccagta acttgggcaa    2040
ggtcatgtag ctagtaagtg gtccagctga aatttaaaac caggtttatc caactccaaa    2100
tcccacatct gatttatttt gccatgaatt aaaacatagt tctgattttg agaaactccc    2160
agtcccagtg ggaaaacaga tggaatcaca aattaccata acacagtgta gtgatgtaga    2220 tataaaaca  aagacatggg aaccctgaaa ggaagttgta acaccaatag aggaatgcat    2280
ggaggagatc tttcagagga ggtagcctcg tagctgggct caggggtgga tgagtttctg    2340
gctagaagcg cattgtgggt agaggagaa  catatataga aaggcatgaa gatggtggac    2400
atgtttggaa agagtgagta ctagactgat gaacacgatg agtcaggagc ttatgacgtc    2460
aggggctact gctagcctag ctaatgactg aagattctgt gaaagaaaaa ccctaacatt    2520
tccagctgag tactagggcc atggtgatta tatatcatct ctcatgacaa cacaaatgtt    2580
tgggcttact tatcatcctg ctcagtaatc attatgtcac tcattaaaga tgtatcaggg    2640 taaatttag  gtgagaattg attagaaatg taaactctat atatgtagtt acaggcttca    2700
cagtttgcca ctcaaacaat atggtcatcc aatcatgagg cacaaccttc tgctcagaac    2760 tttttttataa ttgggagaaa gtgacatccg agttccatct cttctgagaa ctgtgcagct    2820
cagaaatctt cttccctttt ttgatccccc agttgggtga gatgacatta acagtgtgtt    2880
ataagcactt tcatgtttta ctacccata  ttcaaaatta agcatttcaa caactgtat     2940 aattgtctat aaatgtagca ttattagtta attttccttt taacacattg aggttacctc    3000 taatgtttg  ctatttttaa ctatgttgaa ataatcatgt ggtttttatt ctttgaatta    3060
ttttatattg taatgttccc tgaaatgaaa ttagttgatc aaaagatgag taatcttttc    3120
atgacttttg atacatgtca ctcaatcacc ttctggaaga gttggaacaa gagcctattg    3180
ctggcatccc atttcatagc catctcacca atgttggaaa atgggctttt cctatttttct    3240 gctaattcat tagttgttaa tggcttattt taactattaa tcccttgtta ttgatgaaag    3300
ttaagcattt tctgtatttt tatttctgt  ctaaattcta cttttttgcac aatttccttt    3360 gctcacttct tcactggaat ttagtatttt tctttccaat ttgtatgact ccaaaatcag    3420
tgataaaata agcaaagggt ctttcttaga ggctaaacaa gggaatgaat aaggaacaag    3480
aacagcaaag ggatagtgaa taaagataca aaataataac ttatttttat ttttgaagct    3540
ttccccaggc agtaattctt gacctttttta agattataaa ttattttgag atatgcattc    3600
ttatcctcaa aatgaattag tacataaaat ttaaatgggt tgatagatcc cctgaagtgt    3660
atccacaaaa tgctctcagg ttaagcaaca ttgttctata ataactgctt taaccaaaat    3720
gtttaattat tgcttgtgtt tacctgtcct agcaaagagc taattgttaa attttgtgtt    3780
agagggtcaa tattataaat aacttaatgt ggcctctctt tcctttcctt tttttgagag    3840
ttttgaggct atcactaagt gggctttaga gtaccaggtg ggaatctgac ctcactgctc    3900
aaactttcaa cttcaggcat gaagtggtcc cagtgatgtg ggaacctcag agtctaaaac    3960
aaaaatagta gactgaggcc ctcagaaacc agacttatca gattcagaat ttaatataac    4020
tatgtttgaa agatttaaag aaaataaatc aaattaaaaa gtgagcaaga agcaagaata    4080
acaaatgaac tggcatattt gagaaagaat tttgagcttt tagaaataat acatacactt    4140
```

```
attgaaataa aaactcaagt caataggttt aaacagcaaa atgaatatag ttaaagaaaa    4200
ctattgtgct gaaagattta aaaaactatt acacagaatg caaaatgatg aaataggta     4260 atttaatata tggcagatat gttaagacac tatgaggata gtatgagaag acctgataga    4320
catctaatca cagcacctta aggtgaaaat agagagagtg caccaatatt gaggagttaa    4380
tgtctgagac tattccagaa ctgataaata gatgaatcta cagatctcag aaacacagct    4440
tttacaaagg ataaatgaag agaaattcac cagagataca ttgtaatgaa tctgtaaatc    4500
accaaagcta aagatattat ttcacaagtg gaatgacagc tgacttctca caacaacga     4560 aagcaaggag acagttgaaa gacatcttga aaatggtgag agaaaaacta actgttaata    4620
taaaattgtg tacctatcaa aaatatcttt tggccaggcg tggtggctca cgcctataat    4680
cctagcactt tgggaagcca aggaacgtgg atcacttgag gtcaggagtt tgagaccgag    4740
accgtcctgg ccaacatggt gaaaccccat ctctactaaa aatacaaaaa aaaaaaaaa     4800 atagccatgt gtggtggtgt gcacctgtaa tcccagctac ttgggaggct gaggcaggag    4860
aatcgcttga acccaggagg tagaggttgc agtgagctga gatcatgctg ctgcactcca    4920
gtctgggtga cagagtgaga ctgcctcaaa accaaaccaa accaaaccaa accaatcttt    4980
caagaagtac accataaaga catttccgga taaacagtga atgagattac ttcctaaacg    5040
aatatgtaag gatgtttctt tttaaaattt tttttgggtg tattcatcac ctcaagcatt    5100 tattctttg tgttgttaca actgataaga atatctaagg atgtttcaaa aggaagaaaa     5160
atgatcccta aagtctggta tattagtttc ttattagttg ctctaagaaa ttactgcaaa    5220
cttagtggct ttaaaaaaca cgaaattatc tttcagttct gtaggtcaga aatttaacct    5280
cctgatttct ggtcagaagt cttactgggc taaaatcagg gtatcagcag gctgctgga     5340 ggctctggag atgatgtttc tctaatttct agaggcattt gcattcctta gctagtggct    5400
tcttcccaca tcttcaaagc taacagtggc agtcgagtcc ttctcttatc ttttttttt     5460 gggggggtt ataaattttt tttattatta ttatacttta agtttaggg tacatgtgca      5520 caacgtgcag gtttgttaca tatgtataca tgtgccacat tggtgtgctg cacccattaa    5580
ctcatcattt agcattaggt atatctccta atgctatccg tccccctcc cccaccccac     5640 aacagtcccc agtgtgtgat gttccccttc ccttctctta tcttatcact ctgacctctt    5700
ctgcctcctt tctctacttt taaggaccct tgtgattaga ttgggtccac ctaaataatc    5760
caggataatc tctttatttt aaggttagct gattagcaac ctcaattcca tctgtaacct    5820
taatttcttt tttgccatgt aacctaacat agtcacaggc ccaagggaat aataggatgt    5880
gggaattgcg ggtggtggag taggggcatt attctgctta ccacagggga ccttggatgt    5940
cagtaaaaaa tggtgaggaa gaaaacagga aacgtagaat aatctaaaca aatctttgaa    6000
aaataagttg aaatgtgggg ttagaaaaag ggcagaacta aatgttaag acaaattaaa     6060 atgttaagcc tataagttga gagggagatg atcaaggtta aaaatactca taaatcatat    6120 tttttgggt aggggggttag atatttatta attttagacc ctgagaagta aaatagtcat    6180
gacaaaaatt taatagtaac cactaaaaca agagaaacag agtatataac ttctaaatca    6240
atatgggaag gggaatggaa taagaaaaca atagcaacca ccaacacccc acccaaaata    6300
aataataagg tgagagagaa aaagaagcat tgaaaagggg ctaaaataaa ataaaaaatt    6360
aagtcatgcc cgtaatccca gcactttgag aggccaagat gggtggatca cctgaggtca    6420
ggagttcgag accagcctga ccaacatggg gaaacccccat ctctactaaa aattcaaaat    6480
```

```
tagctgggtg tggggtgca tgcctgtaat cccagctact ctggaggctg aggcaggaga    6540
atcgcttgaa cccaggaggc agaggttgtg gtgagcagag attgtgccat tgcattccag    6600
cctgggcagc aagagcgaaa cgccatctaa aaaaaaaaaa aaaaaaatta agatagtaaa    6660
acaaatccaa atacattaaa gattacaaaa aatgaaaatg aactaaactt cctagttgaa    6720
agacatattg tcagattgga ttttaaaatc tggcaatgat atttccagga cacagtccta    6780
aaatattaaa cacagaaaag ttgaaagtaa agggatggaa gaacacagtc aaactaacta    6840
gaagagagct gggttcaccc ttttatatca gagcagaatt tcactgagaa aacactaaca    6900
ggaaggggga aaggcacaac atagtgatga agcacttaat tctcaacaaa tgtatgacac    6960
ttctaaacta ttatgactgc aaaaaaaaaa aaaacctcag catatataaa attttggaag    7020
agccatggct atcagctgac atgcacttac catatttgca ttgtcctact acaaacttta    7080
cccatatgac caaggtgctg tcttcatccc cattttacag atggggaaat ttccccatag    7140
agaaaaagat ttgggccatg ccttggtttc ttcttgactc tgcttcctgc tgattgatcc    7200
tcacacctca cctggagacc tacttcacat tatccatcag gatgagaact ggtgtgcctt    7260
taccaaagga ccacagtcac cttcaaaacg tgtttagata gatctggatg gagacttatg    7320
tggttgcaga tgaaaaaaaa gtccccatgg tatatctgac tccatgtcat tcactgcatg    7380
aacactcaca cacatgcaca cgtacacagg caaacacaat cctgttctgg tccggcagta    7440
gtgccaacac tcaaatccca ggtcctactc tgaagccttt gaggaaacca ttgtcattct    7500
ggggtttatg ggaatatttc ttcttggtgc cccttgttcc tcacagaagc tttttttctg    7560
tgctgtgggc ttgctatcct agcttttcca gctatcctag ttttgcaaat ttctctgatc    7620
aatcacatca ggttcttgga tcatcccaaa attaagagg tacgttttgc tgcaagagac    7680
aaagacattc acctctcaca cagtttgaat tcctgggtag aaacagattt caatgctggc    7740
cagcctctgt agctcccagt gcccctcaa ttatgactcc cgaggcattg gagcaggatc    7800
ctcaccttgc gcaaagataa ttaggtgtgc tgaagaaagc cagacactgc tctttcttag    7860
ctctgcatcc ttaaaaagtt accactactc cttctctttg aatctttgac ttgtcaatgg    7920
taaagtgcct atgattctta aagggataaa aacgcaacct atataaagca cctggcatag    7980
tgcctggcac aggtgggtgt ttaacaaatg ttaactcctt tctatcccac tgtgggtgtc    8040
catatcctct tgggtaggct gcctctggtt tccattgtgt catcagagcc atactaaatc    8100
gatgtgttgg acatggatcc caagaactaa tttctggaat gagttatgcc taccaacttc    8160
cctgatactt acttctgtct ctccatttat caaatgaaa tgtttgcatt tggcctctgc    8220
cagttggagt aaccaaaagg cttagaggtt ttggagaggt cctacactgc catctgtttg    8280
accacatact gcctttcacg tgtaataagc attgttcttt acatttgtct aggaattagc    8340
agttcacaaa gcacattcgc atataagggc ttgttttgaa ttgatcttgg cagcaattct    8400
atgagacaag taaaggtag gtcaagcatt ataatcctca ttttaaatct gggaaaactg    8460
aatctcaaaa aggttgaaag acttgtctag gggacagtgt gtgggtaaat gagaagttaa    8520
gatttgctga actggcattt cctgactaca tatctagtgt ttatttatgg agaaggcact    8580
acggtggcca agtggctcag agtcacacag ctctgtgcct cagtttattt gtctgtaaaa    8640
tgaagataat aatatattct gaatactgtt gtggaatttc attgagatag ttcacataat    8700
ggcatggata ctgtagtaca ccgcctagat tcacaacccc acgactatcc atgagaatgg    8760
cccatagctc aagaggtcac attctttccc caggtgaagc ccgcatccaa tgactgctca    8820
gtgtgggtat ataaaggcct ggctcccttg ccagtgccac cctacctcct ggcgaatgga    8880
```

-continued

| | | |
|---|---|---|
| ctgaggcttg cattatgact gcattgcagc tcaactgttc tttccattca gtctttcctt | 8940 |
| tacactcaca caggtgagga cccagccatt aaatgcctca catgatgacc tctattgcat | 9000 |
| gctaggcttc gtgtgcacac acaaaaacca tcctctatca gtcaggcccc ttacttgcag | 9060 |
| aggcaaagag gccagtctgg gttagatgtg caccctgttt ttacaacaga acgagacaaa | 9120 |
| caggtcctcc ttaggtgtaa gttcatggcc ttggccccac ccctgaaact cagccatctg | 9180 |
| agacagtttt aggactgagg caaccccaga ctttgggttg ttgtttgctg ggcacagcct | 9240 |
| cctttttgcca atgttgcaat cctttgtaag agaccacagg ttgatcaccc gttcctgtta | 9300 |
| ctgagcacag agaggtttgt aggccagtct ctccaggaat tctgacgcac tgcaaaatcc | 9360 |
| catggtctga atgcttctac cttccctgtg aaagcccctg gcctcagaaa aggaagctgg | 9420 |
| tttaagtgac caacatttgg ggtggagctt ccgaggccc agccaccgtg ttacatgcaa | 9480 |
| caatcaacag agatattctt tggctagagt tgttttctg ggtataggac cctataatta | 9540 |
| aaatcagctc tccaacttcc cttcctccaa aaagtataca atgtaaggag gaaaatgcaa | 9600 |
| attgaaaagt tgctagccct tcccgccaga atgccacccc aagcctcccc tgcaggaagt | 9660 |
| tctggagtcc ccaactctgc cccaagcctg aggcccttga taaggtaaag ggatgtgagt | 9720 |
| gtggaggccg gagccccct cgccctgtag gctgctcccc ttgcttttcc ctttgaatgt | 9780 |
| tacagtttag ttctgtgact tacttataat tgcctgaatt ccccgcccac gctttctctt | 9840 |
| actttggggc ttctcaccgt tcctcttcct ccatcttcct cctctgaccc cactcccaag | 9900 |
| cctgaatggg gtgttcctct tccgtgctcc cacaaaaccc tgtgcctctt tcatcgttgc | 9960 |
| atatattatg ctgtaatgta gttttctgga ggtgtgaaga ctatgaatcc tatgaagaca | 10020 |
| aatacacacc taccttgctg accgttgtat cctcagaatc taatactgca cttggcacac | 10080 |
| agtggttggg agtaaatatt catgaggcaa acacacagga aggactcttt tgttatggtt | 10140 |
| gtttgttgtt gttgcaagta acataacccc accttgatct agctgactga cggctctacc | 10200 |
| accttgtctt ttgcagcaca agaggaatag gaactgcacc tcttccttca gtttcagctt | 10260 |
| gaataatatc aggaagattc gtatcggtct gagttgggtc acgtacccga cgtgctatag | 10320 |
| ctgaggatgg ggtaagctga ttggagtttg caacactgtt cacatagcca agatatggaa | 10380 |
| agaacctaaa tgtcaactgg tggatgaatg gataaagaaa ttgtggtata tacatacact | 10440 |
| ggaatattat tcaaccttaa aaagaaggaa atcctaacat ttgtgacaac atggatggac | 10500 |
| ctggagggaa ttatgctgag tgaaataaga cagacacaaa agacatttc ttgcaggagc | 10560 |
| tcacttatat gtggaatcta aaatagtcaa gcttaaagaa gagagtagac tactggttgt | 10620 |
| caggagcagg agaaaagtgg aaatgaagag gtgatagtta aagggtacaa agtttcagtt | 10680 |
| atacaagata aataagttct ggaggtttac tattaatata tcacatagta cctataagta | 10740 |
| acaatactgt attgtatact taaaattgct aagagggtat atcttatatg ttcttaccaa | 10800 |
| taataataat aatggtaata attaaggggc aggaggacac ttcaaaaggt gatggatatg | 10860 |
| tttatggcct tgatggtggt gatggtttca tgagagtata cttatcccca aactaattga | 10920 |
| gatgtaaata ttaaatatgt acagcttttt gtatgtcaat cgtacctcag taaagtagtt | 10980 |
| taaaaatggt tggactgaga aaggaggag ctgctcagca acatgaggct gggtgctggg | 11040 |
| cagacaaaac ctcacacatg cattactgaa cccacggact catgtctgtg agctttgtgg | 11100 |
| ctgtggatgc accatgccaa tgtagtcaag gattcttcaa tgtgtacctt actggattag | 11160 |
| ttccctctgt ttatttgtat tgactcctca gttcccttat gggttgcttg ttggctcttg | 11220 |

-continued

```
tggaattatt taagtaaggc tttggttgca ggagtcagac atgcttaagc tggttttggc    11280
tgtaatgggg aatttgtgag atgtgacaca gtgacaggaa gtgcagccag acgttgtgag    11340
aggcagtaac tgggaatagg aaagttatga gaagttaagg cagtagtaat tgtttctcta    11400
tcgaaggcca taatgttatc attcctgcct ctatctgttt gcttgttctt ctctctcagc    11460
agaatggtct tctctgcttc tctgtgcacc tgcagaaggt gaccacccta aggcttatgg    11520
attcaggagt cctcagtttg agagcagtta ccaaatgcct cgccctgtg aactctagtc     11580 ccagtttctt attcctggta ctggcttagt ttgaggcagc tgcccaccgt aagtccagtg    11640
agccatggcc tggggacaag gtcaggtaca tgtgtaatca gctgggtcta tgagttgtgg    11700
tggtggcgat ggaggtagct cccagaaaaa tggattacag gttaagaaga gtctatatat    11760
cttgaccaca tttgatgtga cttggaagtt tcaatgtgtg accacttaca aagttatgat    11820
caggtgtctc atttatttat ggtgatgtat gagtccgtgt gtgagtgtgt gtgtgtctgt    11880
gtttgtgtgt gtgtgtgaga gagagagaga gaatgagaat atgagtggtg gtttcccatt    11940
tatttttcta tgggccaaat cctgggctat gagctggaga tataagagta aacaaaatag    12000
acacggtgct tgctgtgacc tgccctggga gacagatatt acacggagga tcacataaat    12060
gcagagtctg agctgaggtc ttaagggtga ggataagtaa ctagtcagtg gagcagggga    12120
gggaagggtg ttccatgcct gtgtcaaggt cctgaggtga gagaaagagg tgaatttgag    12180
gaaccaaaag gagttcaggg aacaagaggg gctgtttcac aagctgagtc tggaagctga    12240
gcaggctgag cagattctta ggaactctgc aaaaacttaa gggcttgtct atgaccgtaa    12300
acaactacgg tcgtagataa acaagttggc aaacaactca aggatttaca gtcatcagaa    12360
ttgtaaaact gatcccatgt attttcaaac ctcaaatccc ttgctctgac cttgtgtgtc    12420
taagctagaa ggaagcagga tgcacctctc ccctggctgg aatgaaggga ttcacccaag    12480
ctctcagtct tctcacggca tccagggccc cctgcttgt gtgtggtcta gatttccatt     12540
cccatagtag gaattccttt gggagccttg gggtctctcc tgctagaggg cttcacctgt    12600
gactgtctca attcaaggga ggggttctaa taacattaaa cctcaatatc ttgctcttcc    12660
attcctgatg cctcccttc cttctaccct tcccctacct ccttctttcc tatgccacag      12720
gctggcaggt tagtgccaga gcaagtggcc agtcaccatc attggggttg tggatcctca    12780
gggttcttca gaagcccctt caccatgatc aagagtctcc agtcactcag aattccacgg    12840
ttcccaaatg ccagctctcc cactactccc agcgttctcc atctctggga tgttgggctc    12900
caggcttctc agatgcactg agtacccctag gctaagccac tgatccatca gaacttcata   12960
gcctgagagg agagggagac aggcttgcaa aggagagttc tgactagaca ctggggtgct    13020
acagatgccc gtaagttgtc cctttaccct cgatgtcccc agtgttggga ccacctggga    13080
atgcccagcc ttgtgtgctg attgacttgt agtcccctgg ccctgactgg aagcctagtt    13140
ttctctctca tgaccagcta ggcccctagc tccccaggga agaaatccaa tctatttcct    13200
ctgatagtaa tggctaatac ttaaataatg ccaaccacat gccaagcact ttacagttgt    13260
tagcccagtc ttcacaagca ccttgtgagg tgggcaagag tcttatctta ctctcatttt    13320
atagatgtgg cccaggatcc cacagctata gttcatggtg ctgggatttg aacctctggc    13380
caccagagcc caccttaatg tgtcctcctc ctgttgtcat aacagaaaag tacaacacca    13440
tgatgacaca tcaggctatc ctggcaggtt cccaggctgc cccaatgccc aactttctag    13500
gtttacaaag ttgacattta cgaagtttcc aggtttacaa atctagtttc tgattcttta    13560
gtcagcagga atttctctac aaaagctgct tcgaaaattt ccagccaaac cttacacacc    13620
```

```
ttggcattac atcttggtga gccaaggcgg aagagaacag gaagtgaagg ccccatggga    13680
agtccctgcg gtcgggagca cccaggcggg gcggggggtg gggggctttc ctgtggccgg    13740
ctccctgccc ctcccacccc cattcaggcc ctgtgagttg aatgaagaga ccctgggaat    13800
gagtccaggt ctgcagggtt agaggaaatt gaaggccctt accagatccc tgttgagaag    13860
tttatgaatt atgagccctt ctgcaaatga gagggttctt ccctgtcagg agggacagat    13920
tgtaggtggc aagattggtg gcagccagta ggctggtctg ctccttcctc tctatttcat    13980
atgtgtatga aggcattacc tgcagcaagg gcctgtgtaa atgcatgtga tttacagagc    14040
attttatgta ctgcgtgtca ttcatgcttc cggtgagccc taagtctaag atagggcaga    14100
tagcatcagg tccattttgc agctgtcaaa atgaggtctg aagggcagaa gtggtgtgcc    14160
cacacacaca caactggttg gctgcagacc tgggactag acccgggact tcgtcctgcc    14220
caggggtctc ttgccactgc tccccatcaa cttggatggc tttaagcatt tgtgagttgt    14280
ctgctccctg atggcagaat gcagagacat gaagctacaa gcaggttcgc tcccaacggc    14340
aaaaaggagg aggggtgttc agaacatcag gtgcttctag agaaagcagg gagagagtat    14400
ctggccttgt ggacaatgtc acggcagagg ccaggtatag ggcatggggg taactggaag    14460
cgggatggac cctgttattc cctaagacat ggcttccacg tagtgctcaa acaaggcctt    14520
tgcccttgct gttccctcca cctggaatat tcttcccctt ccttgacatt gctcaggtct    14580
ccactcttat gtcaccctct cagagagggc ttccctggcc actttcccta aaatagccac    14640
ccactcctag gtccctcaaa agcatatcct gctttggatt ttccctatag caatatgccc    14700
tatgaagtta ttttatttgc taacttgttt cttgtctgtt ttcctttgtt agagcgttgg    14760
ggaccttgtc tggcttgttc ccaatgcctg gaagagtgcc tggcacacag gattaagcca    14820
acacatatgt tttgaatgaa tgtgtgcaca catgcatgag ctggcggcag tcggggttgg    14880
ggtaagcacg aaggcccagc tcagttctct gcatgtgacc tcccatctta cgcagataag    14940
aaccagtttg gtttctgcta gcctgagtca ccctcctgga aactgggcct gcttggcatc    15000
aagtcagcca tcagccggcc catctcctca tgctggccaa ccctctgtga gtgtgtggga    15060
ggggaggctg ggctcctcct tgtactctct gaggtgctct ggaaggaggg gcagctccac    15120
cctgggaggg actgtggccc aggtactgcc cgggtgctac tttatgggca gcagctcagt    15180
tgagttagag tctggaagac ctcagaagac ctcctgtcct atgaggccct ccccatggct    15240
ttaggtaagc tccttccact ctcattttt cacctgagaa atgagagagg aaaatgtcta    15300
caattggtgt ttatcaaatg ctttcaggct ctggtgagca agcgtccagg aaaatgtcaa    15360
gcgcatggag ctccaggcct gtctggggga tctgggcacg gggaggcatc catgggagac    15420
catgcaggca ctctgaggca ggggctgcaa gcctagtgcc tgctggggca gcaggtgaac    15480
agagaggtgt aactgctgtg acagaagtca tggagtcctt ggagtgtgag ggtcattttc    15540
cactgttgat agaatagggg aattggtgaa atagccctgt aaatgagag aaagaacagt    15600 gtgagctcaa tgagaaatac taatagaatg tggcactgag ccacaaggtc tgaggcttga    15660
ttgataagga agggtgggga ctgtggagaa ttaagggctt ggcacaggtc agttccacca    15720
gttgtcacaa gagaatgcag gctcaggtgg ccagaacttc tcgcttttcc agaagagtcc    15780
gatattctga tttcattata tatagtattc tgattaaacc agacaataaa gcaagcagat    15840 aaaatatttta agtataagc tgccagtttg caacctccgg ttaggatttg tgtgggcaa    15900 agaaaaaaac tctcaggatc attggtatgt agactctaat tttaagtttc taatttaaaa    15960
```

```
ttggcccctg aggctgggcg tggtggctca cacctgtaat cccagcattt tgggaggcca   16020
aggtgggtgg atctcttgag gtcaagagtt caaggcctgc ctggccaaca tggtgaaacc   16080
ctgtctctat aaaaatacaa aaattagct gggcatggtg gtgcatgtct gcaatcttag    16140
ctacttgggt agctaaggca ggagaattgc tggaacccgg gaggtagagg ttgcagtgaa   16200
tggagatcac accactgcac tccagtctgg gcaatagaga gagacgctct ctctaaaaaa   16260
aaatatgtaa agataaataa aatgaaataa aataggcctc taatgagcag gccattctcc   16320
tttctgggtc ttactttcct tgcactcctt tctgggtgtt aagaggaggt ctagaggaag   16380
ctggacaact cttagcttgt agtaagcaca gtggaagtat cagctcttaa tgggtcatgg   16440
acacgttaca agctaggcgc cgtgctgagc actttacatg gtttatccca ctgaaccctc   16500
tcaataaccc tatgaggaag ggctattatt gctcacattt tcagaagagg aaatggatat   16560
agagagatta gataatttgc ccatggccag acagctagta taagaggagg aggtggattg   16620
actgcagaca ttctgtcttc aaaccactac actatgctat ggaggcacag agacttaatg   16680 aaaatcatgga gaggggaatt gctttgtcaa ccacaagcag ttattccggg ggcagcagat  16740
cctcccctgt cccccagtgg gtacaatggt ccctggtggg ttgtgctaca atgttagccc   16800
atggtcttat gtgttttttca aatgtgtaaa gtaggatgct ggaaccactc ttagaaccag   16860
ataccaatac attgtgaaga aataaatctc tgtgcttaaa actggttcat cccaaaatat    16920
tttgaactga cacacaatag gtgctaaata aatgtgtgtt aacttgaatt ggattgaatt   16980
cgggaaaaaa gtgcaataag cttagtgaag acaccatgtt ccctgggtag aggaaccaca   17040
ttctccatct aaggccagga gtatgggagg tatcaatgtt tgcccagcac agaacagggt   17100
gccaagaaga gaaagttga cggggtgcat actctgactg gaaactggaa gggtgagaac    17160
agagggtaaa ggatagagat ggaaccatgt gcatacactt tgtgttacct tggacaagtc   17220
attcatttct ctggacctct gctttctctc tacacaatgg ggtcccacca cttcccttac   17280
agctgacttg tatgaagaag gaggtggagg aggaggagaa ggtgaagaca atgctgactc   17340
aaagggtaaa ttatttttag gatccaagtt tgaaaacaat tttaggctac tagatatgaa   17400
caacatcttg attatgtagt tgaaggaaat taaagatgaa tggtttaatt aaaaattaat   17460
cagaatgaaa acgattgatt actaatatat ctgcaatggt ttattttcct gagtggcaga   17520
ctcactaagg ttttgaata ctcctgtgtg attgctctat gtatgtatgt atgtatgtat    17580
gtatgcatgt atctatctat ctgttgtcta ataaaatgga tcacatctct gctaataaaa   17640
acactacact ggcagggtac aattataatc attaactgtg cctggaattt gcagcagcag   17700
ccaccagagg taccagtgcc ctttaagggt tcataattta gaataatcca attatctgag   17760
tttttcaggg actgagggt ttggcaaggt gtagaacttt cagtaataaa gtcaagaaag   17820
tcctggacaa accaaggtag ttggtcactc tagtccataa ccaggtaaag agctttccct   17880
gtaacctgtg taaggtttta gaatcatttc tttccttatt accaaaaatc ctccccaaat   17940
tttcaagaaa ttatgaacta aatagttact ctatgagata ggagttcagc ccaaaagaaa   18000
caccataaga acaaatataa ttcttgctta tgttaaccat gcaatgaagc agagagaaaa   18060
agtcagtggc ctcttaggaa ggactgtagt gtgggaagaa ataactaaac tgggtttcaa   18120
tcctggcctg gccaggatct ggagcaagtg agttaatctt tctaagcctt gagtagtttc   18180
ttcttcttct tcttcttctt cctccccctt ctcctcttct tcttcctcct ccttctcctc   18240
ttcttcttct tcttcttctt cctcttcttc ttcttcctcc tcctcctcct cctcttcttc   18300
ttcttcctct tcctcttcct cttcctcttc ttcttcctcc tcttattctt cttcgtcgtc   18360
```

```
ttcgtcttct ttttattttc aaagtgaaag caagtttatt aagaaagtaa aggaataaaa   18420
gaatggccac tccatagaca gagtagcctg aaccttgagt tcttctataa agtcactatg   18480
aatttatact cattttgaaa gtgggtgtca atatgtctgt ccactttgca cagctgttat   18540
gtggacaaaa ggagatctgt gtgaaagtgt aacacagagc ctaaactata acaggtaagc   18600
aacacagttg tccccttccc catggtgtct gttcttctcc atttcctcct gtctgcaggg   18660
ggattataaa actaatcatc aaagccaaga aggcaagagc aagcatgtac cgctgaaaac   18720
acaagataac tgcataagta atgactttca gtgcagattc atagctaacc cataaactgc   18780 tgggcaaaa atcatcttgg aaggctctga acctcagaaa ggattcacag taagttaacc   18840
atgtagatct gagaggagag tagcttcttg tagataacag ttggattata taccatgtcc   18900 tgatccccctt catcatccag gagagcagag gtggtcaccc tgatagcagc aagcctgggg  18960
gctgcagctt ggtgggtaga ggtactcagg ggtacagatg tctccaaacc tgtcctgctg   19020
ccttagggag cttctaataa gttgatggat ttggttaaaa ttaacttggc tacttggcag   19080
gactgggtca gtgaggacca acaaaaagaa gacatcagat tatacccctgg gggtttgtat  19140 ttcttgtgtt tctttctctt ctttgtacta aaatatttac ccatgactgg gaaagagcaa   19200
ctggagtctt tgtagcatta tcttagcaaa aatttacaaa gtttggaaaa caatattgcc   19260
catattgtgt ggtgtgtcct gtgacactca ggattcaagt gttggccgaa gccactaaat   19320
gtgagatgaa gccattacaa ggcagtgtgc acatctgtcc acccaagctg gatgccaaca   19380
tttcacaaat agtgcttgcg tgacacaaat gcagttccag gaggcccaaa tgaaaatgtt   19440
tgtactgaaa tttgttaaag cttcccgaca aactagattt atcagtaagg attgttttct   19500
gcaaggggga tgaaacttgt ggggtgagcc atttgggctg aggaggaggg aggttggagc   19560
tgagaaatgt ggagacaatt tcccctttaga aggactgaat ctccctgcct ctctggggtg   19620
cggcagccag caggatccaa tggtgtatat gtctccccag ctccccattc agtgatatca   19680
tgtcagtagc ttgaaattat ccgtggtggg agtattatgt catggaaatt ggcaaatgga   19740
aacttttatt ggagattcaa ttgttaaact tttaccagca caacactgcc ctgccttcag   19800
agtcaatgac cctatccaag tttaatccat ctgtccactg tctccaacac gatctttata   19860
aaacacacct gacaacatta ccctttttatt cagttttta aaagataagt ttccagctca   19920
tcggggtggc tttaaaggcc atttctcctc tggacctcac ccaacttttc aaatcacttt   19980
tcctacccct acctctaaat gctactcaaa ctccagccat cctgaataat aagacttttg   20040
aaaagtagat tatgggctgg gcacagtggc tcacacctgt aatcccagca ctttgggagg   20100
ccaagatggg tggatcacct gaggtcggga gttcgagacc agcctgacta acatagtgaa   20160
accctgtctc tactaaaaat acaaaattag ttggggtgg tggcacaagc ctgtaatccc   20220
agctactcag gaggttgagg caggggaatt gcttgaacct gggaggcgga ggttgcggtg   20280
agcctagatt gctccactgc actccagcct gggcaacaag agcgaaactc catctcaaaa   20340
aaataaataa ataaataaag tagattacat cagatacctc tggcctaggt tgtttatgac   20400
caactctcct gctgagaata actagaaaag ctagacaaaa catatttcca aaagatctct   20460
ttggaggcat cagagaatgg ccaaggctgt aaggaactgc ctgagcccag agaggtggag   20520
cccagcactg gtgcccttta ctcctgggga catgtgctgg tttcaaaaac ttcagctgag   20580
cttttgagca ttcatggaac ttggtgggggg agatgaaatt tgtaccttaa atcctgccta   20640
cagggagggt ccctgataat ccccacccaa tttggaaatc tgggtcagcc ttcacaggta   20700
```

```
ctgaagccct cctctgaatg atctcaagtc ctgctagggt agaggttacc tgcttttgaa    20760
aggctcctgg cctacctgtg cagcaggagc aaaagtgaac catctcaggg tacagataac    20820
aatcatccag agccttgaat gacctctact gtgcttaata tatagtattc agcagtcagt    20880
aaaaaggatt taggcacatg caagatgacc tgtgtatcag ggagaaatag gcaataaatt    20940
gagatccagc agggatttga atcatggatt tgaatcaggg gcagccttcg aaagaactat    21000
ggagaatata ctcagattta aaacataaga ttggaatttt tggcagagaa ctaacaactg    21060
tacaaaaaag gaaccaaatg gaaatcctag aactgaaaga tgcaattaac cgatgttgag    21120
aaatagccaa catctattga acacttccca tgtggacagc tgtgctaaac actttacagg    21180
catcaacata agatgtgtcc ccttacagca gtgcagtgtc cctcctaaga catggacagc    21240
ctggtttccc tatctctctg cttcatcaaa accccttta c gtggggctta gacactcctg    21300
ttgtctctag tgtctagtag cacagggctc agcacatgga agccactaga tacaatttga    21360
tgaccaggac ctccgatgaa agccatgggt gctgattggg aaggcattgt cttttatgtg    21420
ctatggtctt aaagcttcat ccaggaagca gaactcgggg ggtgctgagg acccagaacc    21480
gagaataaga ttagtcagag atttcctgtg gcagaaatc ataaggacgc caactgtttg    21540
ggtgagataa gacgaaacca agagtggact tgtggccaga agcgtgagga agaggggagag    21600 agcttccctt gtccccttc ttcctctccc taagccacag tgattgacag ccccccccct    21660
ttggagtcag agcaggcttg agactggact gggaaaggag ggtgggtcag gatacagagc    21720
aggaaggctg ggagtgcagg gcaggagcaa ggggctgggg cattcattgt gcctgatctc    21780
tcccacttta cctggggtaa agaagcatat gcaaaagcca cggtgtgagt atttcccaag    21840
tgccagggtc agggcatgat tcatcacgtg cagcatttca ttcaatcctt atagtaaccg    21900
atgatgtggc ttctattatt agctctatca gataatgaaa ctgagaccaa gacaggctct    21960
gcacattgtg tggggtaatg acacaggggg attcagacct agactccata actcctgccc    22020
cagggaccac ccccaccctc accctgtgca tgtcgacaaa ggacagactg gccacttct    22080 caggacacag cggggaaatg acacagagca gggaggttcc aggagcccg agcgtctttt    22140 ctccaggaga atactctctg aattcagact ggggtcagag aaacatttac ccaggagccg    22200
cagtgtgggt ggggcttttt acttgaaacg ctgtctgaag gcagtggcca ggatggaact    22260
ctccacccta ccttggcaag ccacttctct tctgcaatct gtaaggacat tgttgagaga    22320
attatggtct tccaattccg gagggttgaa gaaagacaaa taggagagaa cctatcatag    22380
tcaggtgcta gctgccttct cttttcagaga gtgtgagaat aaagtgatac acttgattat    22440
tagcaaatac tttggaaatt ttaaacgcta atattcaaca cactctggaa gaggcaaata    22500
agtagacagg ttcatataca tcatctcctt cagctagtcc tcacaaaaac aaacaaatga    22560
ataaacaaaa ttcttctttg gccctcatag gaagacactg tttcttgaac gtgtttcaaa    22620
aaggatgggt gactcactca aggtcacact gtttatgagg acagtacagg aatacagaca    22680
tgccattttg cctgaaaaaa tccatcaccc agggaggtga cacaatttg cagaaatgtt    22740 ctatttcctc tgaaggatac attctttaaa cctttgggaa attcattcat agtcttcctc    22800
ctttgaagga ttaactctct ggacacaaag tgtttgattc tgatttgttg gttgaagat    22860 gtgttggttg agagaaagat tctgatttgt tggttgaaaa tagactcatc aagatcaact    22920
gctgtagtag taaatatttt gacatttgt ctgtattcct gtgctgccct cacaagctgc    22980
atcaccttga gtgagtcatt catacttttt tgtttgtttt tgtttggag atggagtctt    23040 actctgttgc ctaggctgga gtgcggtggc gtgatcttgg ctcactgcga cctccatctc    23100
```

```
ctgggttcaa gtgatcctcc tgcctcagcc tcccgagtag ctgggattac aggcacatgc   23160
caccatccct gctaattttt gcattttcag tagagacgga gtttcaccat gttggtcagg   23220
ttggtcttga actcctgacc tcaggtgatc cgcccacctc agcctcccca agtgctggga   23280
ttacaggtgt gagccaccgt gcccagccca gccatcattt ttgaaacacg tttgagaaac   23340
agtgtcttcc tttgagggcc aaggagacat ttttttttgtt tatttgtttg tttttgtgag   23400
gactagctga aggggtgat gtatattaac ctgcctactt atttgcctct tcccagagtg   23460
tgatgaatat tagggtttaa agtttctgaa gcatttgtta ataaagcccg gggctggagg   23520
tcagaagacc tggatttctc tgcatacttt tgccatcagc aagctgtgtg accttggaca   23580
gatccctttt ttgtctaaat ctttctgagt cttcttgaaa acaatgccag gttgggacag   23640
gatgattgcc aagctcccgt ccagctctaa aacactgcaa cgtatgcttc tgcaccagca   23700
ctgtccatcc tgtagatcat gcagaaattc tcttcaactt tttcctaccc ataaaatagg   23760
agcatgctta ccttttttcct aatgttccag gccccgggtc tagaatattg taagtaagga   23820
agttaatgtg tatcagagcc cattatgggc cagaagttct cctcttcctt cctacacctg   23880
cttcctccct ccctccctcc ctctttccct tccttccttc catccatttg tgaagaagac   23940
atgatcaccc tcattctgag agtgaagaga cagaggctca actaatgaaa tgatttgttc   24000
aaggtcacac gggtggcaca aggcaagtgg cagaggttga atttagaccc attcctgtcc   24060
aaatgctgag tttatgtcat cgtcccgaga ccataacttt aaagatgtaa gatagtggga   24120
aaagagttga tttcaaagca cctctcagaa ggactcactt tacatcaggg gtcagcagac   24180
tcaggccaaa tccggtccat tccccgcttt tgcaagaaa gttgtagtgg aacacagcta   24240
ggcttattga tttatggatt gccaacgtcc ttttgtgaaa cagacagctg agctgagtaa   24300
tcgtggcgca caaaacctaa aatatttact atctcgtcct ttacagaatg tttgccaatc   24360
tatggtccgg agtccaaggc tgtccatttt tcaaagaaca caaagtgaca tgagactgtc   24420
ccatgtgcag ggagccctat cattttatta tgaaaaaacg gcctttctgc tcaaatctgt   24480
tttttaaaaa gtcaacaaac agactctggg tacctgtcag gaacagtagg gagtttggtt   24540
tccattgtgc tcttcttccc aggaactcaa tgaaggggaa atagaaatct taattttggg   24600
gaaattgcac agggaaaaaa ggggagggaa tcagttacaa cactccattg cgacacttag   24660
tggggttgaa agtgacaaca gcaagggttt ctcttttttgg aaatgcgagg agggtatttc   24720
cgcttctcgc agtggggcag ggtggcagac gcctagcttg ggtgagtgac tatttctta   24780 taaaccacaa ctctgggccc gcaatggcag tccactgcct tgctgcagtc acagaatgga   24840
aatctgcaga ggcctccgca gtcacctaat cactctcctc ctcttcctgt tccattcaga   24900
gacgatctgc cgaccctctg ggagaaaatc cagcaagatg caagccttca ggtaaggcta   24960
ccccaaggag gagaaggtga gggtggatca gctggagact ggaaacatat cacagctgcc   25020
aggggctgcc aggcccccaga gggcctgaga actgggttttg ggctggagag gatgtccatt   25080
attcaagaaa gaggctgtta catgcatggg cttcaggact tgtgtttcaa aatatcccag   25140
atgtggatag tgcgaccgga gggctgtctt actttcccag agactcagga acccagtgag   25200
taatagatgc atgccaagga gtgggactgc gattcaggcc tagttgaatg tgctgacaga   25260
gaagcagaga ggggcaccag gggcacagcc cgaaggccca gactgatatg gcaaggcct   25320 gtctgtgctg acatgtcgga gggtcccact ctccagggac cttggtttcc ccgtctgtga   25380
catctgtgac atgagagtca cgataactcc ttgtgtgcct tacagggttg ttgtgaaaat   25440
```

```
taaatgcaca gataatagcg taacagtatt ccgtgcattg taaagagcct gaaaaccatt    25500
atgatttgaa aatggaatcg gctttgtgag accatcacta ttgtaaagat gtgatgctga    25560
tagaaatgac aggactgctt gtgcatgccc tctgcagtgt gacattccag cagtgaaatc    25620 atgttgggt gacttctccc ccactctgac ctttatgttt gtctgggccg aggctgcaag     25680
tcgggctctg tgggtgtatg agtgacaagt ctctcccttc cagatatggg gactgtctgc    25740
ttccctaggt tgcctctccc tgctctgatc agctagaagc tccaggagat cctcctggag    25800
gccccagcag gtgatgttta tccctccaga ctgaggctaa atctagaaac taggataatc    25860
acaaacaggc caatgctgcc atatgcaaag cactttggtt tgcctggcca ccctcgtcg     25920 agcatgtggg ctcttcagag ccacctgatg aggtgggtac agttagccac acttcacagg    25980
tgaagaggtg aggcacaggt cccaggtcag gctggccgga gctctgttta ttacgtctca    26040
cagctttgag tcctgctctc aaccagagag gcccttacc aagaagaaag gattgggacc     26100
cagaatcagg tcactggctg aggtagagag gaagccgggt tgttcccaag ggtagctgct    26160
cctgcaggac tctgagcagg tcaccagcta atggaggaaa ggctctaggg aaagacccctt   26220 ctggtctcag actcagagcg agttagctgc aaggtgttcc gtctcttgaa acttctacct    26280
aggtgctatg gtagccacta gtctcaggtg gctatttaaa tttatactta aatgaatgaa    26340
aatagaagaa aatttaaaat ccagacccctt ggtcacacta tccacattta aagaggtcaa   26400
tagccacatg tggttagtgg ccaccctatt gggcagtgca gctacagaac atttttgcat    26460
cccagaaagt tcttttggat gttgctgctc tacagcatgc tttgctgaaa cagaagtgcc    26520
ttccctggga atctcagatg ggaagcaagt aaggagggga gtcaaatgtg ggctcactgc    26580
tcaccagctg tgagggttgg gcctgcctct taaccattgt cagcctcagt cttctcatcc    26640
atgcatgccg tgggtatact aaaatactat acccctggaa gagctggatg caaatttgac    26700
aagttctggg ggacacagga aggtgccaag cacaaggctg ggcacatggt ggctgtgcac    26760
tacagctgag tccttttcct tttcagaatc tgggatgtta acc                      26803
```

<210> SEQ ID NO 21
<211> LENGTH: 177
<212> TYPE: PRT
<213> ORGANISM: Homo sapiens

<400> SEQUENCE: 21

```
Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
```

```
            130                 135                 140
Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                    165                 170                 175

Glu

<210> SEQ ID NO 22
<211> LENGTH: 159
<212> TYPE: PRT
<213> ORGANISM: Homo sapiens

<400> SEQUENCE: 22

Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
                20                  25                  30

Arg Asn Asn Gln Leu Val Ala Gly Tyr Leu Gln Gly Pro Asn Val Asn
                35                  40                  45

Leu Glu Glu Lys Ile Asp Val Val Pro Ile Glu Pro His Ala Leu Phe
50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser
                100                 105                 110

Gly Pro Thr Thr Ser Phe Glu Ser Ala Ala Cys Pro Gly Trp Phe Leu
                115                 120                 125

Cys Thr Ala Met Glu Ala Asp Gln Pro Val Ser Leu Thr Asn Met Pro
                130                 135                 140

Asp Glu Gly Val Met Val Thr Lys Phe Tyr Phe Gln Glu Asp Glu
145                 150                 155

<210> SEQ ID NO 23
<211> LENGTH: 180
<212> TYPE: PRT
<213> ORGANISM: Homo sapiens

<400> SEQUENCE: 23

Met Ala Leu Ala Asp Leu Tyr Glu Glu Gly Gly Gly Gly Gly Gly Glu
1               5                   10                  15

Gly Glu Asp Asn Ala Asp Ser Lys Glu Thr Ile Cys Arg Pro Ser Gly
                20                  25                  30

Arg Lys Ser Ser Lys Met Gln Ala Phe Arg Ile Trp Asp Val Asn Gln
                35                  40                  45

Lys Thr Phe Tyr Leu Arg Asn Asn Gln Leu Val Ala Gly Tyr Leu Gln
                50                  55                  60

Gly Pro Asn Val Asn Leu Glu Glu Lys Ile Asp Val Val Pro Ile Glu
65                  70                  75                  80

Pro His Ala Leu Phe Leu Gly Ile His Gly Gly Lys Met Cys Leu Ser
                85                  90                  95

Cys Val Lys Ser Gly Asp Glu Thr Arg Leu Gln Leu Glu Ala Val Asn
                100                 105                 110

Ile Thr Asp Leu Ser Glu Asn Arg Lys Gln Asp Lys Arg Phe Ala Phe
                115                 120                 125
```

Ile Arg Ser Asp Ser Gly Pro Thr Thr Ser Phe Glu Ser Ala Ala Cys
            130                 135                 140

Pro Gly Trp Phe Leu Cys Thr Ala Met Glu Ala Asp Gln Pro Val Ser
145                 150                 155                 160

Leu Thr Asn Met Pro Asp Glu Gly Val Met Val Thr Lys Phe Tyr Phe
                165                 170                 175

Gln Glu Asp Glu
            180

<210> SEQ ID NO 24
<211> LENGTH: 143
<212> TYPE: PRT
<213> ORGANISM: Homo sapiens

<400> SEQUENCE: 24

Met Gln Ala Phe Arg Ile Trp Asp Val Asn Gln Lys Thr Phe Tyr Leu
1               5                   10                  15

Arg Asn Asn Gln Leu Val Ala Gly Tyr Leu Gln Gly Pro Asn Val Asn
            20                  25                  30

Leu Glu Glu Lys Ile Asp Val Val Pro Ile Glu Pro His Ala Leu Phe
        35                  40                  45

Leu Gly Ile His Gly Gly Lys Met Cys Leu Ser Cys Val Lys Ser Gly
    50                  55                  60

Asp Glu Thr Arg Leu Gln Leu Glu Ala Val Asn Ile Thr Asp Leu Ser
65                  70                  75                  80

Glu Asn Arg Lys Gln Asp Lys Arg Phe Ala Phe Ile Arg Ser Asp Ser
                85                  90                  95

Gly Pro Thr Thr Ser Phe Glu Ser Ala Ala Cys Pro Gly Trp Phe Leu
            100                 105                 110

Cys Thr Ala Met Glu Ala Asp Gln Pro Val Ser Leu Thr Asn Met Pro
        115                 120                 125

Asp Glu Gly Val Met Val Thr Lys Phe Tyr Phe Gln Glu Asp Glu
    130                 135                 140

<210> SEQ ID NO 25
<211> LENGTH: 3804
<212> TYPE: DNA
<213> ORGANISM: Homo sapiens

<400> SEQUENCE: 25
taatttcagt gaattatat  aacttggtta catttaggtt acttattaca aatgaaaata      60
aatatactaa cagaagctgc ctcatatgca aatgagtaac atgttagaga ctaaaataca    120
caaaaaaatg catgtgcttt agctcatata acaatatac aggacaactt accgggtagc     180
ataaacaacc aacaacggac tatcaaaagg aacctcgtca tctagtaact ttaaccttgt    240
tggtagatct ccttttttcca tctccatata cacaggattg aacttgcca tttctgaaat    300 ataaagcata tccttttcca aactttatct cttaggcgga atattcaat ttatgaacat     360 gttcattcag caatcattag tcacgtacct actgtgtgga cctattatgt gcaaggccca    420
atattaagca ttacaagaga aacaaataaa agtacaagag atgtaatttc tacttttaag    480
aaccttaaaa tctaattggg aggcaaagca tattaaaagt tttaaataag acgaaggaac    540
atataattaa tacatcagtg actattactc ttaaaataat gagtatctag gcctatatat    600
agcaactgtc catataagca cacatcaaaa accaatatac atagctatca tcaatgccaa    660
gttgctcagt tttttctaga actagtattc ctactccatc ttttagaatt aaattcaatg    720

```
aaattaattt taaaatattt gaccttttt taaagttacc agtatagcaa atactcattc      780
tctgaagaac agaagatttg acttttgga atagccaaaa gtcacttaaa atcaagtctg      840
gtgaaaggag tgatgatcta aaactatttg tggtttaaaa aaaaaaagta tgaatctaaa     900
gtaaagtggg ttttttcca agtagttttc ttttttagtt ttttagaaac agggtctcat      960
tctgttgccc aggctggagt gcagtggtga tcactgcaac cttgaactcc tggctgtgtg    1020
tgtgtgtgtg tgtgtgtgca gcgacggggt cttcctacgt tgcctagctg cagtgcctgt    1080
gtgcacacat gcgcacatgc gtgtgtggag agacagggtc ttgctacgtt gcctagctgc    1140
aatacctggg tgtgtgcatg tgtgtgtgtg tagagacaag gtcttgaaac gttgtctagg    1200
ctggcatgtg tgtgtgtgtt tatatgtatg tgtgtgtaga cagggtcttg ctacattgca    1260
taggctggtg tgtgtgtttt tgtgtgtgta gagacggggt cttgctacgt tgcctaagct    1320
gggcaagtat ttttcaactg cctctgaaga caaatcccaa ataacagttc caaaagctgt    1380
ttcccataat tatcacatca ttagaagggt gaggcctact caccaggttc taagagccaa    1440
cattcatttt ctgatacatg cttttttaaa aaagtcattt ttccccagt ctcattgttt     1500
cccatttgac tgtgtcaggc aataagtact ttaaaggaat tcagaggagg aggccattca    1560
gaggtttggg gaagcctgat gactgcgcgg gagctaaacc agacatatcc acctaaattc    1620
aagtaagcag ccatatcact caaattgccc accatgcttc ctctagccag cactggtagt    1680
aacaactatc actctggctg atggagactc tttctgctc ttctgtgact gggtatgatc     1740
acataataga gacagataca gtaaatttcc aatgagtaat aatgtcacac atttgaactt    1800
acctgaggag aaatagcttg tttcttattt cacacaaaag acaatctacc tcaactcaga    1860
aaaaaaaaaa ttattatgct tttaactgct atatttgaat taaagcagat ctgtaactat    1920
agatccatgt ttctagaaag ctaaaatatc tttaagtaag atgacataaa aatgtatctc    1980
tattcacttt tggtaatgaa tgaaaagttg cttaaagtct aaagtattag aaatatggca    2040
tctgttattc aagtaggatt tggaattaag aaaattcact tcttcaaaaa catgggacta    2100
tggctgcaga aagggcaatg catatagttt ttagggtatg atagctggtt tctattatat    2160
gtcaggatga catatgcgac cttccgccaa ggtagatact gcgggctatg caccaaagtc    2220
tctgaggcag acatgtaagc gagctcttca cctatattca ttcttttcct cctggacagg    2280
ttacatttcc cagtttcctt tgcagttagt tgtggctata tgacagaatt ctcatcaatg    2340
gaaatgtaca cagaagagag gtaagccact accaggccag gcctataaga cagcactttc    2400
tacatgcttt ccccagacat agcaacccaa acatgaccac atcccttaag ggaagatgga    2460
gctgaaaata atggaaggaa cttggaatgc tagaatgctg aattaccacc tgggagacag    2520
ctacccactg acctggaata cctgtcctgg actgttacat gagcaagaaa tacacttcta    2580
tttatgtatg agttacttca ttatcagata tttattacag cagtttagct acctaagatc    2640
tctctctgcc tcagactgct tatctataaa atggaataac accatctact ccaaacatta    2700
ttgtaaggat gaaatgagac aatgctgaaa agtgtttacc ataatatctg ccacacaata    2760
agtaccccat atagtatttc tgtattagta agttacatga gagattttct tctttaata    2820
catctgcatt tataaacatt ttactttaac ctcaacttcc ccagcactgc tctaccattt    2880
tctgaatgtc attatgagag aaataaaact aatttctagg gccaggcatg gtggctcaca    2940
cctataatcc cagcattttg ggaggccaag gtgggaagac tgctttgagg tcaggatttc    3000
aagaccaacc tgggcaacac agtaagaccc catctctata aaaaaatgaa gaaatcagag    3060
```

| | |
|---|---|
| ggtacagtgg cacatgcctg taatcccacg actcagaaaa ctgaggcagg aggatcgctt | 3120 |
| gaacccaagg gatcaaggct acagtgagcc atgatcacac cactgcattc cagcctgggc | 3180 |
| acagagtgag accctgtctc taaaaataaa aaatagggcc aggcacagtg gttgatgcct | 3240 |
| gtgatcccaa cactttggga ggccaaggca ggtagatcac ttgaggtcag gcgtttgaga | 3300 |
| ccagcttggc cgacatggca aaaccctgtc tctactaaaa tacaaaaatt agctgggcgt | 3360 |
| ggtggtgcac gcctgcagtc ccagctactt gggaggctga ggcaagacaa tcacttgaac | 3420 |
| ccaggaggcg gaggttgcag tgagccaaga tggcgccact gcactcaaac agaatgaaac | 3480 |
| tctgtctcaa aaaaaataaa ataaataaaa atttaaaaac taatttctta taatccagtt | 3540 |
| gtgaatttaa ccaatgtctg aaagaactat taaaagttaa aatgaatgga aaacagaata | 3600 |
| aagggttgac cagaacagat gtgattttct acttaaatct ttttttaaa ccccaaaatt | 3660 |
| caaaactgct aatgtttttt aatacgaatt tctatctttg ataaggcaat ctgagtatta | 3720 |
| cctttcaatc cttcaataaa agtatcccaa acagaagggc tattactgta actaagcttg | 3780 |
| atactctcct tcgctctttt caag | 3804 |

<210> SEQ ID NO 26
<211> LENGTH: 3804
<212> TYPE: DNA
<213> ORGANISM: Homo sapiens
<220> FEATURE:
<221> NAME/KEY: misc_feature
<222> LOCATION: (2122)..(2131)
<223> OTHER INFORMATION: n is a, c, g, or t

<400> SEQUENCE: 26

| | |
|---|---|
| ggcttctggc tctgagtgag gtcctgctgc aaggtttcct agatgagcca ctgagactct | 60 |
| aataagatcc agtggaaata accaggctct cgtcggaata taagtcccaa gggaagctgt | 120 |
| gccagtcttg tgggcgactg cctgacttct cctttcattt cagcaccatg aagcttctca | 180 |
| cgggcctggt tttctgctcc ttggtcctgg gtgtcagcag ccgaagcttc ttttcgttcc | 240 |
| ttggcgaggc ttttgatggt aaggcttcag aaggtttgca ggatttctga agagaaacat | 300 |
| caccctggac ctgataaact ggggaaaatg atgctttcgg aaggctgctt ttgaaccaca | 360 |
| gagttgctag tgtctgcgtt gctgaggcct gccaggaact agggtttgct gggttgcctg | 420 |
| tctcgagtct ttcagagctg ctgggaatat cccctttccc cgtagtgcag cttctcagga | 480 |
| tgtgttaagt ggatggatca catttcagaa gccgctgcaa ggtgtatcaa aaacacatct | 540 |
| cctgagccgt aagggacggg gcatccagta acaacgcaca cggggtattt ttgggcttcc | 600 |
| ttaagatttg agccgctgcc ttaggttgtg ctgcccaatg tgcctgggga gctgctaaac | 660 |
| agattagaga gtcgaggatt gttgtcagtt actcagagaa agaacaatca tccttttccag | 720 |
| gagcacctga gctgtttgtt ttgcgtagaa gatgcaaaat aaggcctgca atgggtataa | 780 |
| aatgtccctc agcataaatc gcataggagt atgactaagg ctgttgactc ttctgtcttc | 840 |
| tttctccttc ctccttcgat ttcctagttg gataatgtac agggctcttt agcctcgctc | 900 |
| tgtcaggggc tcccttcctg gtttgttctg tttccattct tccttctcca gccttcttga | 960 |
| caagagctgg gaactaacgt gcctcaagcc cccacaagga ccacagcatt ttctcattta | 1020 |
| gtttcagaat gactctgtga cgcaatcttc ctctcttgga aggtgagaaa gctgatcttg | 1080 |
| gaaggtgaga aagctgagac ttagagcagc tgaagccaat gcccagggac ttactgccag | 1140 |
| tcagcaggtg gcagggcaga ggtttgagcc cggctgtgct tgaggtcagg gctcttgcca | 1200 |
| ggtagacgca tcactgacca cctcctagag gttgatggtt atgaatctca ggcacacctt | 1260 |

```
ggcatcacct gaaatacccca tgccttcaac tccccagcag agtctgcaga aactggcctg    1320
gggtgtggcc tgggcactgg gactttcagt ttctctctgg gtgattagaa agtgcagcca    1380
aggctcacgc ctgtaattcc agcactttgg gaggccaagg tggatgaatc acttgaggtc    1440
atgagttccg gagcagcctg gccaacatgg tgaaacccccg tctctactaa aaatactaaa    1500
atgtagccag gcgtggtggc aggcacctgt aatcccagct actcaggagg ctgaagcacg    1560
agaatcactt gaacccgaga agcagaggtt gcagtgacta gagatcgcac cagtgtcctc    1620
caacctgggt gacagagcga gactccatct aaaaaaaatg aaaagaaag tgcagccaag    1680 gcagagcacc actgccctat tgcttcctca agcaacccac agcatcagta cagcctacta    1740
agaaagtatt tagggacttt tatgctccta acagtcactg gaactcacgt cacaatgacg    1800
tgtattccat ttgcaagaat atatacttta ggtcggggtg cggtggctca cgcctgtaat    1860
cccagcactt tgggaggcca aggcaggggg atcacgaggt caggagttcg agaccagcct    1920
gaccaacatg gtgaaatccc cgtctctact aaaaatacaa aaattagcca ggcgtgatgg    1980
cgcatgcctg taatctcagc tactcaggag gctgaggcag aagaatctct tgaacctggg    2040
aggtggaggt tgcgatgagc tgagatagca ccactgcact ccagcctggg cgacagagca    2100
agactctgtc taaaaaaaaa annnnnnnnn naaaaaaaaa aaaaaaaaa aaaaaaaaa     2160 aaagaatata aactttagta gtcagggcag aagtactctg tgtctgccac ctttctcagc    2220
atcagtattc catgtcacta cctcattcat acacactcct ggatcttatc ataggcagct    2280
tcattctata gcagtggctc ttcaccaggg cacttgaaga agccaactag gataaaggaa    2340
tgtgcttctc aacccatggt atccaaggct gctatgatca caggctgaaa gcttgaagtc    2400
agtggaagat ttgtccttcc tcattcccct ctaaggtgtt gttggagtct ttatgttctc    2460
ctgatgtccc ttctgccttt cctttccttt ccaggggctc gggacatgtg gagagcctac    2520
tctgacatga gagaagccaa ttacatcggc tcagacaaat acttccatgc tcggggaac    2580 tatgatgctg ccaaaagggg acctgggggt gcctggctg cagaagtgat caggtaactg    2640
gagctcctgg gacgttaggg ctgggtgagc agagcttgcc tgccttggac agtcaggagg    2700
gagacgagct ccttgtggag aagttagagg ctgcggcccc tcctcctctt gccctctctc    2760
tgcctctgtg ctcagtgtga ggtctgagtg gatggtagga gtgagtgatt cctcatcctc    2820
cctctctggg tgctgttcat ccagcctagg ggtgcccagc ctggctgaat ggggtggtgc    2880
ccagtgtttt catccctcct tccttggcct ttctgggctc ctctctgagc cctcccttgg    2940
aacagggaga atgggagggt gggctattgc tcactggcct gattattaat ctccttcttg    3000
cctgccttga ttacagcgat gccagagaga atatccagag attctttggc catggtgcgg    3060
aggactcgct ggctgatcag gctgccaatg aatgggcag gagtggcaaa gaccccaatc    3120
acttccgacc tgctggcctg cctgagaaat actgagcttc ctcttcactc tgctctcagg    3180
agatctggct gtgaggccct cagggcaggg atacaaagcg gggagagggt acacaatggg    3240
tatctaataa atacttaaga ggtggaattt gtggaaactg ggtgttatac tttgtggtat    3300
agactgcctg tttagtatga aggggcgatc catgcacatc taagtgaacg tggaggctgg    3360
gtgggtggga gacgactcct gggcacacag ggcatcctgg gcatccctga ggcaaggaca    3420
tgatgagttc agtggccacc cccacaggat cccagggct tcagcagatc caccccctta    3480
ccccatgtga gcagctgccc agtgagtctg taggaacccg agccacattc ccagtgagtt    3540
caactgcacc ccggcacgtt ttgctagcac ctcaatggag agctccttgc ttgcagcttt    3600
```

```
ggcttgtggc acccagcaaa agcttcctgc cacccagtgg ctacagccac acactctcca    3660
gcaagattta atctcagcct tgtgaggagc cctttcccaa atttatttct ttctgtgttt    3720
tttatccctt agtagctaat ctcatgttag ccattaataa ctctctatgt taaacccttc    3780
cttttgtatc tgcggctaca ttga                                          3804
```

<210> SEQ ID NO 27
<211> LENGTH: 3804
<212> TYPE: DNA
<213> ORGANISM: Homo sapiens

<400> SEQUENCE: 27

```
gtataaatgc agaggtgcag taactgggct tttcaggata tccagatgga gttgtggtgt      60
tgttttgctt gtggttttta acgttaactt ttttttcccc tttatttaa  gagaagcaca    120 aaatgaacaa actagtgagc ccagcaacat ggatggaaat tccggagatg cagactgctt    180
tcagccagca gtcaaaaggg tatgggcaaa aaaatatgaa ccatttgggg ctcaagtttc    240
tccaaatact ttatgtgact gcaagtactg tatacgctta tttcctgtga ctcagttctt    300
ctaactaaga tgttaagcat ttggcttaaa gtgtatagca ttacaaagag tatttcccca    360
gctttggctt gccagccaac tttccattga ctctagcctg ttagccattt ttattgtttt    420
ttgtttgttt gtttgtttgt tttcctcaca tgtacacata catacagatt gttcttatat    480
gtgattttgt tctctgggaa taaaatcttc attcaacaga ggcaatatga cagaaaaacc    540
gaagtttcat gtatatgatt tttcaaagaa agtgaattgg ccctcatgtt aaacctagca    600
tttcagagct gaaagtgtct tctcattaaa tattgaagaa atcatttgag ggtgtggaga    660
aggatggaca gaattagctg cttgtgtatt tattcttctc ctgcaacttt gccacgctat    720
tttgtacctc ccttcctaat tatgataaag cttttcttaga gagcagtcag gcaatgtgta    780
ttaaatgttt aaagctttac acccttagtt ctacttgtgg acatttattt cttaagaaag    840
atgtatacta agatttagat agaaatattc attacagtat cataataaag acagtagcaa    900
ggattctgtt atctgtgttg cattaataca atagagattg atgcaactgt tcattatttt    960
gaaagcatta atgataatat tgcatcaaag agttcactga acagattgta cagtacagtt   1020
ttacacacaa aaaaaatagt ttgtgagctt taaaagggcc ttcaaatgaa tatgctaaac   1080
ggttatcttt caataaagag agtatgggta agtcttaatt tctttcattt atttcagtaa   1140
tttaatgttt ttgttgttgt tattgtttgt ttttttgaga cagagtcttg ctctgtcacc   1200
caggctggag tgcagtggtg caatctcagc tcactgcaat ctcggctcac tgcaacgtct   1260
gcctcctgga ttcaagcaat tcttctgcct cagcctccgg agtagctggg attacaggcg   1320
tgcaccacca tacctagcta atttttgtat ttttagtaga gacggagttt gccatattg   1380 gccaggctgg tgttgaactc ctggcctcat gtgatccgcc catctcagcc tcccaaagtg   1440
ctggggttac aggcatgagc cactgtgcca gcctatttca gtaacttaat gttttacag    1500 gcatgtatta cctataaaat taataaagcc agtgaggtat ttcttttttg aactaaagca   1560
aagctaataa taagttatag agaagttaga gaagaaatct attaagtgat actttctttg   1620
tatactgttg ggctgagtac ccttgattct tggtggtgaa caagttatca gaaatttctt   1680
ggccaggagc cgtggctcac acctgtagtc ccagcacttt gggagtccaa ggtgggtgga   1740
tcacttgagg tcagaatttc tagatcagcc tggccagcat ggtgaaaccc tgtctctatt   1800
aaaaatacag aaattagcca ggcatggtga cgtcgcctg taattccagc tacctgggag    1860
gctgaggcag caaaatcact tgaacctggc aggcggagtt cgcagtgagc tgggatcgcg   1920
```

```
tcgctgcact ccagcctgga tgacagagca agactccatc tcaaagaaaa aataaaaaag    1980
aaatttattt acttgtgtga atttttacaa tacagatgct tctcgactta aatggggcta    2040
catcccaata aactcataag ttgcaaatac tgtaaatcaa aaatgcattg aatacaccta    2100
atgtatggaa caccatagtt tagcctatcc tactttaaat gtgttccgaa cacttagatt    2160
agcctgtagt tgggcagcat tacctactat aaagtgtatt ttctaataaa atgttgaata    2220
tctcatgtaa ctcattgaat actgaaagtg aaaacaatg tatgggtact caaaatatgg     2280
tttctctact gaatgtgaat cactttgaca ccatcataaa gttgaaaaat tccaagtcaa    2340
accattgtaa gtcaggggct atcagtattc agtggtaaat gctggctcta actattcttc    2400
caagtcagtg gttgactgct gtttattcta taagggttta caatttatag attctctcac    2460
ttgtagaatg agagattcag aattaatagc agacagagtc cctaccttga tggagctttc    2520
atttaagtgt gaaagtcagg tgacctaaca aggccttggc ataagtttag gatttggatt    2580
gttatgggag cttgggtagg gacatgtcat aggtaaggca acagcagggg tagagataag    2640
cttgacatat gtcaaaaatc atgaagacat cagtaatcct tgaagttggc tgaaaggtat    2700
agagttgaga aagtagttaa aaaaaaaaaa gtcaggctga gtctaggtaa ggatgtgttt    2760
ctctgaggtc agatttgttc ctgtaccata aagggactat ttagaatctt aaagctggag    2820
caatttaaaa cgttaagttt tcagattgag gtcagatttg tgacttcatg tgaggtcaga    2880
tttgttcctg taccataaag ggactattta gaatcttaaa gctggagcaa tttaaaacgt    2940
taagttttca gattgacgtt ttttgaggta tagttaataa cctgaatgtt ctgattctag    3000
tcttggtagt caataagagt tgaccagatg aatttcatag ctttgtagag gatgaaatat    3060
ttcaaggctg atttgcacaa atgtttacat agatcatgta tctttcataa gtaatatgtt    3120
tgtattatta caaggctgta aaaatttaag caggttgtta atagcacagg gggtaacaga    3180
ttaataaaat taatgaataa aattactaaa agagtccaga agtaaaccca aatacgtgga    3240
ggaattaagc atatgtatga tacacatgac attttaaaaa tcagtgggaa aaggtaaatt    3300
atttttacaaa tggtgttaga agcactgatt gataattttg ttaaaagaaa cttagattcc    3360
ctattttact cctaatccaa aataaattct gagtggatct aagattaagc aaaaattaag    3420
ccggaagctg agcatggtag catgtgtctg taatctccgc aatttaggag actgagtttg    3480
gctgggagg tggtgatatg cgcctagaaa aaaaaaattt tttaagccac agatgtataa     3540
gcaaaagcg ggcaaagagg cggaattttt tttttttttt tttgatgaagt ctcacttgtc    3600
gcccaggctg gaacgcagtg gcgtgatctc agctcactgc aacctctgcc tcccgggttc    3660
aagcgattct cctgcctcag cctcccaagt agctgggatt acaggcacct gccgaggaga    3720
ggatttttt ataattaaaa caaaacaaaa caaaaaaaca ccaaactgga agataaagta    3780
tttacaacat gtaaaagact gttt                                          3804
```

<210> SEQ ID NO 28
<211> LENGTH: 122
<212> TYPE: PRT
<213> ORGANISM: Homo sapiens

<400> SEQUENCE: 28

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

-continued

Arg Asp Met Trp Arg Ala Tyr Ser Asp Met Arg Glu Ala Asn Tyr Ile
            35                  40                  45

Gly Ser Asp Lys Tyr Phe His Ala Arg Gly Asn Tyr Asp Ala Ala Lys
 50                  55                  60

Arg Gly Pro Gly Gly Ala Trp Ala Ala Glu Val Ile Ser Asp Ala Arg
 65                  70                  75                  80

Glu Asn Ile Gln Arg Phe Phe Gly His Gly Ala Glu Asp Ser Leu Ala
            85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
            115                 120

<210> SEQ ID NO 29
<211> LENGTH: 122
<212> TYPE: PRT
<213> ORGANISM: Homo sapiens

<400> SEQUENCE: 29

Met Lys Leu Leu Thr Gly Leu Val Phe Cys Ser Leu Val Leu Gly Val
 1               5                  10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
            35                  40                  45

Gly Ser Asp Lys Tyr Phe His Ala Arg Gly Asn Tyr Asp Ala Ala Lys
 50                  55                  60

Arg Gly Pro Gly Gly Ala Trp Ala Ala Glu Val Ile Ser Asp Ala Arg
 65                  70                  75                  80

Glu Asn Ile Gln Arg Phe Phe Gly His Gly Ala Glu Asp Ser Leu Ala
            85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
            115                 120

<210> SEQ ID NO 30
<211> LENGTH: 122
<212> TYPE: PRT
<213> ORGANISM: Homo sapiens

<400> SEQUENCE: 30

Met Lys Leu Leu Thr Gly Leu Val Phe Cys Ser Leu Val Leu Gly Val
 1               5                  10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
            35                  40                  45

Gly Ser Asp Lys Tyr Phe His Ala Arg Gly Asn Tyr Asp Ala Ala Lys
 50                  55                  60

Arg Gly Pro Gly Gly Ala Trp Ala Ala Glu Val Ile Ser Asp Ala Arg
 65                  70                  75                  80

Glu Asn Ile Gln Arg Phe Phe Gly His Gly Ala Glu Asp Ser Leu Ala
            85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
     115                 120

<210> SEQ ID NO 31
<211> LENGTH: 5687
<212> TYPE: DNA
<213> ORGANISM: Homo sapiens

<400> SEQUENCE: 31

| | | | | | |
|---|---|---|---|---|---|
| ctctctggtt | gcccttaaca | ttttttcctt | catttcaact | ttggtgggtc | tgatgattat | 60 |
| gtgtcttggg | gttgctcttc | tcgaggagta | tcttagtagt | attctctgta | tttcctgaat | 120 |
| ttgaatgttg | gcctgtcttt | ctaggttggg | gaagttctcc | tggataatat | cctgaagagt | 180 |
| attttcaac | ttggttctat | tctccttgtt | actttcaggt | acaccaatca | aacgtagatt | 240 |
| tggtcttgtc | acatagtccc | atatttcttg | gaggttttat | tcgttccttt | ttattctttt | 300 |
| ttctctagtt | ttgtcttctc | gctttatttc | actaagttga | tcttcaatct | ctgatatcct | 360 |
| tgcttctgct | tgattgattc | agctatcccc | cgctcgatat | acaaaccat | gtcacgaggc | 420 |
| gtggacaccc | cccatgatat | ggggagtatt | atcaccccc | tcttccccca | ctggatatta | 480 |
| caaaccatgt | catagggagg | tggacatccc | ccacaatatg | aggagtaata | tcacaccct | 540 |
| ttccccgcag | tggatattat | gaaccatgtc | acaggcggtt | aaacacccc | aacgatatgg | 600 |
| ggagtaatat | cacactcctc | tccccctgg | atattacgaa | ccatgtcatg | ggggtggac | 660 |
| acccttgca | atatggggag | taaaatcacc | ccctctccc | caactggat | attatgaacc | 720 |
| atgtcacagt | gggggaaaaa | tcctctgtga | tatgcagagt | aatatcaccc | cactctcacc | 780 |
| acctggatat | tacgaaccat | gtcacagggg | ggtggacacc | cccaagatg | ggggagtaat | 840 |
| atcacctcac | tctctgccac | cagatattac | aaactgtgtc | acagggggt | gaacaacccc | 900 |
| cacaatatgg | ggagcactat | cacccccctc | ccccagggta | ttatgatcca | tgtcacaggg | 960 |
| gggtggatac | cacccactat | atggggagta | atatcaccctt | tctctcccgc | cctggttttt | 1020 |
| atgaaccgtg | tcaggggg | gtggacaccc | cttgcgatat | ggggagtaat | atcaccccc | 1080 |
| tctccaccat | ctggatatta | cgaaccatgt | cacaggggg | tggacacccc | tgcgatatgg | 1140 |
| ggaggaatat | gccctctcc | ccacctggat | attacaaatc | atgtcacggg | ggacggacat | 1200 |
| ccccacaat | atgggagta | atatcaccac | actctcccct | gctggatatt | acgaaccata | 1260 |
| tcacaggcgg | ctggagacac | aaggcattaa | caatatttcg | agtaatatta | tctttccctt | 1320 |
| tgaacattat | gaacaatatg | acagagggt | gtacacctcc | tgcgatattg | ggagtaatgt | 1380 |
| catccctcc | cccactggat | attaggaacc | atattactgg | gggatgtatt | ccccttcta | 1440 |
| gattgggagg | aagatcatac | ttgccctccc | tgaatatttg | aaacaatatc | ataggggttt | 1500 |
| gtacactttt | acgatattgg | gagtaatatc | atcctttctc | ccctggaaa | ttaggaacaa | 1560 |
| tatcacaggg | gtggtgtaca | cccctgcaat | atttaggta | atattattgt | cttctccct | 1620 |
| cgatattagg | aacaatatta | caaggacggt | gtaaagtacc | tgccaaattg | gaaaaatac | 1680 |
| tatcctctcc | ctcttgtata | ttagaaacaa | taacacaggg | ggaatgtaca | cccactgcca | 1740 |
| tattgggagt | aatatcatac | tcgccccatc | cccagatat | taggaacaat | atcacagcag | 1800 |
| gggtgtacac | ttttacgata | ttgggagtaa | tatcatactc | tctccccctg | gaattagga | 1860 |
| ataatatcac | agagatggtg | tagaccctct | gcaatactta | ggataatatt | atcatctccc | 1920 |
| ccctcgatat | taggaacaat | attacgggga | gtgtaaatta | cctgccaaat | tggaggtaat | 1980 |
| cctctcctct | ctctcccctgt | atttagaaa | atataacaca | caggaaatgt | acaacactgc | 2040 |

```
gatattcgga gtaatatctt cttctcccca cctggatatt aggaacaata acacggacgg   2100
ggcgtacacc cctcgcgata ttgaatgtaa tgtcatcctc tccctccctt tatattacga   2160
acaatatcac agggggggtgt acaaccctg caatattgga agtagtatca tccattctcc   2220
catgaatatt aggaacaata tcacagggggt agagtacacc ctctgcaatt tcgggagtaa   2280
catcatcctc tcgttccctg gatattataa acaacaccac gggggggtgg gggtgtacac   2340 accccttcgat attgggagta atataatcct ttccctccct atatattaga agcaatatca   2400
caggggttgg tgtaaacttc ttgcgatatg gggattaata tcacccccct ctcctgccct   2460
ggatattatg aaccatatca cagggaggtg gacacacttt gcgatatggg gagtaatatc   2520
acgcccctct ccccccccgat attcgaacc atatcacaag ggagtggacc cccccacga   2580 tatggggagt aatatcaccc ccctctcccg ccctggatat tacgaaccat atcacagggg   2640
gatggacacc ccccgcgatg cggggagtaa tgtcacccc ttctgccccc taggatatta   2700
cgaaccatat catggacacc ctccacgata ttggaaataa tatcatcctc tcccccttgg   2760
atattaggaa caatatcaca ggggggttgta cacctcctat gatattggaa gtaatatcat   2820
cctctccctc ctggatatta gcaacaatat cacagggagt gtgtacaacc ccagcgatat   2880
ttggagtaat atcaccctct caccccatgg atatgagaaa caatatcaca ggggaggtgt   2940
acatcccacg tgatattgtg tgtaatatca ttcttcccca accccctgcaa tattgtggtg   3000 taatataatt ctctcccttc ctggacatta tgaacaatat cactactagg tgatacatta   3060
ggagtaatgt atccatagga tattatgagg aatatcacag ggtgtacacc cactgtgata   3120
ttagaggtaa tatctcccta aaatattaag aagaatatct tacacccact gtgactttag   3180
aagtaatatc tccctaaaac gttacaaata acatcgcagg gtgtacactc acagtgatat   3240
taggagtaat atctccctag aatattacaa atacacatgg tgtaaaccca ctgtgacttt   3300
agaagaacta tctccctaaa ataatacaaa aatatcgcag tgtataccat aatatcccct   3360
agaatatcat aaataatatc acagggtgta cacccactgt gataatagga ataataccac   3420
cccaggatat tatgaataat gtcacaggct gtacacccac tatgacatta ggagtaatat   3480
ctccctagga cactatgaat aacatcacag atttttacacc catggtgtgc acccactatg   3540
atattaggag taatatctgc acaggatata acaaataata gtacagggtg tacacatatg   3600
atatacaccc actgtgatat taggagaaat atatccctag gatattatga ataacctctc   3660
agagtacaca cacatggtat acaccctctg tggcattagg aacaataact ttctaaaaca   3720
ttacgaataa catcacagaa tgtacacaca tggtttacac ccactgtgac aggtgcaata   3780
tctcccttgg atattatgaa taacaacaaa ctatcactgt catattagga gtaatttctc   3840
cctagaatat tacaaataac atcacagggt gttcatttat ggtgcacacc cactgtgata   3900
ttaggagtaa tatctcccta ggatattact tttcatataa aagtgtgtac atccactgtg   3960
atattgggaa aaatatttct ctaggatatt atgaataata tcacagagcg tacacccact   4020
gtgatattag gagtaataat tccctgggtt attatgaata atatcacagg atgtacaacc   4080
actgtgatat taggagcaat atcttcctag gatattacaa ataatatcac agggtgtaca   4140
cccactgtga tattaaagta atttttaggt tattgtgaat aatatcacca agtgtacaaa   4200
catggtgtac actcactgtg atatcaggag taatatctca gtaaaatatt atgaataata   4260
tcacagggta tacacccact gtgatattag cagtagtatc tttgtaggat attacaaata   4320
atatcacagg gtgtatgccc actatgacat tagaagcaat atctccctag gatatcaaaa   4380
ataatatcac agggtgtaca acttctacat cccaggttct aagggattct cctgcttcag   4440
```

```
cctcctgagt ggctgggatt acagatgccc accaccacac ctggctaatt tcgtatttc      4500 agtagagatg gggtatcacc atgctggtca ggctggtctg gaacttctga cctcaggtga      4560
tccaccagcc tcggccttcc aaagtgctgg aatacaggt gtgagccaac gtgcttggca      4620
gagagttata tattaaataa atctggaaac atagctccca tgtttgagtg tgcatttact      4680
tttatgaaga aattatgtca gaaaacctaa ggatgataat aaatatgaaa agtaactggc      4740
atgtaaaaag gtcttttgat taagaactat aaggttcgat ttcatttta gataacgtga      4800 tcctagctct tgtatagtgc ttataaatat tctacatcaa aggaatttgt tgcacagtgt      4860
cagaataaaa taaagtgtat ttcactgctt cttaattttt aaattagact gagtttgttt      4920
tcctagagag agaagaacat ttttatttt ttctgaaaag agtaggccat attttactga      4980
gatcttagat ttgttatata ttaggttttg gtcttctaac attctccagt ggattttctc      5040
taaagtaggt atgcacagaa agagttgaat agcaaaaaag taaatcatgt aataattctg      5100
agattttggg gtttgtcaca actgagaaat attgctgagg gtgtatggtc ctcaagtgtg      5160
aaaatgttcc ttgtgaattg cttgtatccg aaatatacac acaacattaa gtcctggttt      5220 ttatcttta ttttttccaa tccttttttc ttctcaaggt gtccaagtca cacagagcca      5280
cagaatctca caggtgtctc agaattcctc ctcctgggac tctcagagga tccagaactg      5340
cagccactcc ttgctgggct gttcctatcc atgtgcctgg tcacgatgct ggggaacctg      5400
ctcatcatcc tggccgtcag ccctgactcc cacctccaca tccccatgta cttcttcctc      5460
tccaacctgt ccttgcctga cattggtttc accttggcca cggtccccaa gatgattgta      5520
gacatgcaat cacatagcag agtcatctcc catgcaggct gtctgacaca gatacctttc      5580
tttgtccttt tgtatgtat agatgacatg ctcctgactg tgatggccta tgactgattt      5640
gtggccatct gtcaccccct gcactaccca gtcatcatga atcctca                   5687
```

<210> SEQ ID NO 32
<211> LENGTH: 5687
<212> TYPE: DNA
<213> ORGANISM: Homo sapiens

<400> SEQUENCE: 32

```
attgaatttt atctcagagc ccacatgaag caggatcaaa gtcagtacac atgaaaacta      60
gagcccaaag actataaagc atgaaataag gatttaagct aaccctatct tgtaaggggt     120
ttgtaaagcc cagcttgcat ctgagctaca ctagcaccag gacagccact cagtaatggg     180
gtttctcaag gttattgctt ttcattcagt tgaaatgaga gtcatttctt acccttatgc     240
cctgtgagat ttcactggag gttgttcact gaaacatttt catatcattg catcaaccct     300
cttgaactca ctgtgcctgc ccccagttca gtctgtgact cacaagtacc ctgcagcaaa     360
agaaatccaa tagagggcaa atccctcacc ttaccttcct ttctaagacc tttgatgttc     420
tcatgtgtca tttcataatt gggattgtca attagtcgcc tcatctctgg tcctcacttt     480
cctctctccc agccaaactc aaccttcagc ccacacaatg gaattcaaca aaatgaggta     540
acagttttct gtgtgagtca ctctgggcaa ctctgttcac agagcactgt gaggtgagca     600
gccagaaccc aggcaagtgt ttcagccatc caagaactgg caggcagccc aagagacact     660
ctcacctgat gacagactag caggatgagt cctggaggaa atggttccca acagctgcag     720
aaggagtctc ttggctcatg cacagcaatg ctccttctcaa ttaaaaacgt tgtcattatt     780
gacactgcag tgtaaaatcc ttttacactg tgctcacatt tctacaggcc ttcacctgct     840
```

-continued

| | |
|---|---|
| ctgcccatta aagacaagac ccttccatga gatgatgaca tctctaagtt actgttccac | 900 |
| ccaaacagtc ctatataatg aagagaaaaa ttttgctggc cctcaaaagg caaacacaag | 960 |
| gagaaagatt tccacaagct gtttctcttt gctgagcact tagaggaaaa ctgtaagtgg | 1020 |
| ttggaagaag gctttgtttt ctacaagact tttagttatt cctcagaaat tttcctgctt | 1080 |
| attcccagag gaggtcatct cttagatgct gtcagtcaga tagggattgg cagccaagca | 1140 |
| gaggtgctca gagaggtttc caactaatgt ggccagcgga aaactgccaa gaagcaggg | 1200 |
| atccttagga caaataaact ggaagatatt ttggggataa aaataaatcc ttttgaaaat | 1260 |
| gaaagatgga gagtgctgt atatacaaat tgccctgttc tgaacaatgt tgtcactagg | 1320 |
| actggccctg agaccaatg atacaaacca aaatgttctc agacatgctt tgatggtctt | 1380 |
| tttctccaaa gttatctatt ctgtttccat ttcattctca caggacttgc catgggttc | 1440 |
| tcataagatt tcacattggt cataatccag gtggccctgg actgcaacct ctgagttggc | 1500 |
| aacatcagaa taggaattac gaaaaaccaa tttaaagtta aatacagaca caggcaaaag | 1560 |
| agagatgggt tgtcgaagct agtgcctagg tggacactgc ctcacatttt taattccaga | 1620 |
| agccatcagt actgagtgtc agatctcatt agtcaaacac agtgatcagg aatcctgttt | 1680 |
| tcctggagga tttccttgag ggagggacca ctcaagagtc tgaaatattt cacgtcatag | 1740 |
| agtatggatc tcacccccaac acccaatcag aaaataggga gaactggaaa ccaaaattcc | 1800 |
| ccctcccgct gtgaaggat gaaaccaga gtgttggagt tctgtcctga taatggagca | 1860 |
| gacagctagg cagcaatcaa tgagggccag tacaggaatt cagtgctaag tattgggtca | 1920 |
| taacagaagt agggaaggta ttaatccagt gctatatgag gatcctggga cactggctcc | 1980 |
| tagtaatcta gttataacta ttagcaaaaa agaaaaaaaa aatcagtgat gtgaagagat | 2040 |
| ggcctaaagg agctccagca atatagctaa gcagctggca agtggtctga ggagcattgc | 2100 |
| aattccaggc ctcctaaggt ggcagtacgg gcactggtaa gacattctgc tgtggtgaaa | 2160 |
| ctagtttacc atagaggatt cacaattaaa ataggcaaac aggaaatgca agacagaggc | 2220 |
| taacaaaggg ttttttttttt ggtgggggggg agttgtttgt ttgtttgttt gttttctgag | 2280 |
| acggagtctt cctctgttgc ccaggctgga atgcagtggc acgatctcag ctcactacaa | 2340 |
| cctctgcctc ccaggttcaa gcagttcttc tgcctcagcc tcccaggttc aagcagttct | 2400 |
| tctgcctcag cctcccaagt acctgggact atagctgtgt gccaccacat tgactaattt | 2460 |
| ttgtactttt agtacagact gggtttcacc atgttggcca ggctggtgtc gaactcctga | 2520 |
| cctcaagtaa tccccccgcc ttggcctccc aaagtgctgg aattacaggc atgagccacc | 2580 |
| acacctggcc agttttttggt aattcttaaa gaactcaatg agcaacactc aaacaaccat | 2640 |
| aaagactata gagctcatgg ttgaatttta gatagctaaa cagacaggag ttttttgtaag | 2700 |
| ttttgtaagt cttgctcatc cttccctctt ccatcctcta tctcaactat tctgtctacc | 2760 |
| attaaagcac cttagacctt gagtttggca atgcaacaag tgtgtgctca acacgaaata | 2820 |
| ggtaattcaa tagcaaagcc ctaaaacagc ctggcttgat tatttctcag ggcatgcagt | 2880 |
| tcctttgaag caggatcatt ttaataataa taataataga aataataata gaaattgaag | 2940 |
| acaattattt cacaatttcc atacacctaa gagctctaca tatgaatgat aatgcataat | 3000 |
| tgtaaagcat gcatattaca ggtaataaat atgttagcta attataaaca atgcccattt | 3060 |
| tcatatagtt tatccttgcc aaataaaact gtaaaaaaaa gacacctttc aaatgctgct | 3120 |
| aaggagtaat acctgaatga ggttgattta atggagtctt agttcctgca tgtgttctaa | 3180 |
| ttgaatagac tatgtagtaa ttcccttaca tacccatcca tgtccaagaa cagtgaagat | 3240 |

```
ctttatttaa tatgaattat tgcagatgat tagcacagtc tagccaaacc attccagtaa    3300
ttgtttttac ttgttatatt aatatataaa ttctcaaagg atataacagt gatgttgggt    3360
gaatttcact gaatgatagc tcaaacacct gaaatattga ctaagaaaac taatttatca    3420
atactgataa tcaattttaa tatgttaatt gattgtaata caggattctg tggttcaaaa    3480
aaaaagaaca agcaaaaaaa cttctcttcca tttccaaata ccaattaata gatctctact   3540
tccccttgga tttcttctta ccacctacca cctccaatct tcattctttc ctcacaaact    3600
aaacataaaa gttacctaca aagcatagaa tctgtgttaa aggatattct tgcttgtttt    3660
aagtccaaaa ttaaacagct ctgaattatt aaaaagcaca tgaattcaaa tgtcctattc    3720
taataagaaa atggtttaca tttctctatg ttcaaggaaa aaaatagtca agggtgtaca    3780
agtggggtaa aaattatttc cagtaggtta tgtgatttaa gttatagaaa cgaaccaggc    3840
aattcaatta aatgtcatgg aaagtaggtt ttttcttttc ctctttttt ctaatatgta    3900 cactttgtga agataaat ccatagtgtg ataatttgtc cactgggtcc atcagacact     3960
ggagacagct tcctaagaat tataaggctt ctaaaggctt ctaaagccta aattgcctag    4020
agcattttgt gtgccaggca ctttgctagg tgccctaggg atgcaagaag tataaatgtt    4080
ttatgagaat acaggctgga aatgtattct tgattattcc tgtggaattt ctaggcagaa    4140
aagagtctaa tggggtatag gtatatttc tcaacacaat tttctgagcc tttaccagat    4200
gcagttctat ggtttgaatg tgtccctcag agtttgtgtg ttggaaactt aatccccaat    4260
gcaataatgt tggtgaggcc taatgaaagc ctaataatgt aggtgaggcc taatgagagc    4320
tgtttagacc atgaaggctc ttccctcatg gatggattaa tgctgttatg gtgggaatgg    4380
gttcattatt actggggtgg gttcataata aaaagatgag tttggcctgc tattctctct    4440
ctttctcatc ctctcttcca ccatgggatg acacagcaag aaggcccctg caagatgccc    4500 tccccctcagt attggacttc acagcctcca ggaccataag ccaataaaatt tttgttcatt    4560 ataaatttcc cagtctgtgg tattctgtta tagcaacact caatttatgc attacttcca    4620
gattcttatg gctataccta cttctcacag tttgtattca cccctccttc aaccaagtac    4680
ccttaacaca gttcccatag tcacaaagcc aggtcactga agctgccctc tctccaacca    4740
cacacatata gatcaaatga ccccagacat agagctgatt gagaaggagg gaccagtacg    4800
agctctgctt ccccagcagc ttcctggaaa gaagaggcaa tacaacccaa cccaaaagtg    4860
caagagaagt aacacctcat gggatgagct taattaatca atgggagagg acactagaag    4920
acactagagg atctcccttc ctccctttct ttcccacttc accccctcca gtctctgaac    4980
catgagctat ttcaaaggtg cagtaatgct atatttggct tctctgaaga tatcctatga    5040
ggccaagtca tcagctttgt tcattatcta agagtggtgg ccagctcacc agcacttccc    5100
atcatgtttg ccctccctct ttcccttgtg ttacttccca ttttccctta cttctgcttt    5160
cttggcatta aattctactc tgcaatgtta ggatataagt ttttgcctca gattctgttt    5220
tctaggaaac ccatgctaag acaacactgg cagtggccct ggaaaagtaa acctcatgat    5280
ggatttggag ttggattgtt cactgatctg aaggacagag gactccactt aagtggtaag    5340
cagtgtagct atgaactctg ccacgcaggc ctcacaatta ctgaggcttc ttttacctgt    5400
ggttaactgg gacacagaac agcaggaaat tgagtgtaga ggttatcaag tagctgcttc    5460
acttaattgg tataatttta tggagttaac ctggtttaga gtccagagaa cattccacat    5520
agcctagaaa gggtagttat ttgtccttac cataatcaag tcatactttg aatatgagtt    5580
```

```
ttccttccct gttcagcacc acttctctta gacttaagaa tgcctgatct gttgatatta    5640
tgtcccatgt aacattgcct gagacaaaga tatccatgta ccttaaa                  5687
```

<210> SEQ ID NO 33
<211> LENGTH: 140
<212> TYPE: PRT
<213> ORGANISM: Homo sapiens

<400> SEQUENCE: 33

```
Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala Arg
        35                  40                  45

Leu Leu Leu Ala Ala Leu Val Gln Asp Tyr Val Gln Met Lys Ala Ser
    50                  55                  60

Glu Leu Glu Gln Glu Gln Glu Arg Glu Gly Ser Ser Leu Asp Ser Pro
65                  70                  75                  80

Arg Ser Lys Arg Cys Gly Asn Leu Ser Thr Cys Met Leu Gly Thr Tyr
                85                  90                  95

Thr Gln Asp Phe Asn Lys Phe His Thr Phe Pro Gln Thr Ala Ile Gly
            100                 105                 110

Val Gly Ala Pro Gly Lys Lys Arg Asp Met Ser Ser Asp Leu Glu Arg
        115                 120                 125

Asp His Arg Pro His Val Ser Met Pro Gln Asn Ala
    130                 135                 140
```

<210> SEQ ID NO 34
<211> LENGTH: 128
<212> TYPE: PRT
<213> ORGANISM: Homo sapiens

<400> SEQUENCE: 34

```
Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala Arg
        35                  40                  45

Leu Leu Leu Ala Ala Leu Val Gln Asp Tyr Val Gln Met Lys Ala Ser
    50                  55                  60

Glu Leu Glu Gln Glu Gln Glu Arg Glu Gly Ser Arg Ile Ile Ala Gln
65                  70                  75                  80

Lys Arg Ala Cys Asp Thr Ala Thr Cys Val Thr His Arg Leu Ala Gly
                85                  90                  95

Leu Leu Ser Arg Ser Gly Gly Val Val Lys Asn Asn Phe Val Pro Thr
            100                 105                 110

Asn Val Gly Ser Lys Ala Phe Gly Arg Arg Arg Arg Asp Leu Gln Ala
        115                 120                 125
```

<210> SEQ ID NO 35
<211> LENGTH: 141
<212> TYPE: PRT
<213> ORGANISM: Homo sapiens

<400> SEQUENCE: 35

```
Met Gly Phe Gln Lys Phe Ser Pro Phe Leu Ala Leu Ser Ile Leu Val
 1               5                  10                  15

Leu Leu Gln Ala Gly Ser Leu His Ala Ala Pro Phe Arg Ser Ala Leu
             20                  25                  30

Glu Ser Ser Pro Ala Asp Pro Ala Thr Leu Ser Glu Asp Glu Ala Arg
         35                  40                  45

Leu Leu Leu Ala Ala Leu Val Gln Asp Tyr Val Gln Met Lys Ala Ser
 50                  55                  60

Glu Leu Glu Gln Glu Gln Glu Arg Glu Gly Ser Ser Leu Asp Ser Pro
 65                  70                  75                  80

Arg Ser Lys Arg Cys Gly Asn Leu Ser Thr Cys Met Leu Gly Thr Tyr
                 85                  90                  95

Thr Gln Asp Phe Asn Lys Phe His Thr Phe Pro Gln Thr Ala Ile Gly
             100                 105                 110

Val Gly Ala Pro Gly Lys Lys Arg Asp Met Ser Ser Asp Leu Glu Arg
             115                 120                 125

Asp His Arg Pro His Val Ser Met Pro Gln Asn Ala Asn
             130                 135                 140

<210> SEQ ID NO 36
<211> LENGTH: 116
<212> TYPE: PRT
<213> ORGANISM: Homo sapiens

<400> SEQUENCE: 36

Ala Pro Phe Arg Ser Ala Leu Glu Ser Ser Pro Ala Asp Pro Ala Thr
 1               5                  10                  15

Leu Ser Glu Asp Glu Ala Arg Leu Leu Leu Ala Ala Leu Val Gln Asp
             20                  25                  30

Tyr Val Gln Met Lys Ala Ser Glu Leu Glu Gln Glu Gln Glu Arg Glu
             35                  40                  45

Gly Ser Ser Leu Asp Ser Pro Arg Ser Lys Arg Cys Gly Asn Leu Ser
 50                  55                  60

Thr Cys Met Leu Gly Thr Tyr Thr Gln Asp Phe Asn Lys Phe His Thr
 65                  70                  75                  80

Phe Pro Gln Thr Ala Ile Gly Val Gly Ala Pro Gly Lys Lys Arg Asp
             85                  90                  95

Met Ser Ser Asp Leu Glu Arg Asp His Arg Pro His Val Ser Met Pro
             100                 105                 110

Gln Asn Ala Asn
         115

<210> SEQ ID NO 37
<211> LENGTH: 187
<212> TYPE: PRT
<213> ORGANISM: Homo sapiens

<400> SEQUENCE: 37

Thr Ser Glu Glu Thr Ile Ser Thr Val Gln Glu Lys Gln Gln Asn Ile
 1               5                  10                  15

Ser Pro Leu Val Arg Glu Arg Gly Pro Gln Arg Val Ala Ala His Ile
             20                  25                  30

Thr Gly Thr Arg Gly Arg Ser Asn Thr Leu Ser Ser Pro Asn Ser Lys
             35                  40                  45

Asn Glu Lys Ala Leu Gly Arg Lys Ile Asn Ser Trp Glu Ser Ser Arg
 50                  55                  60
```

```
Ser Gly His Ser Phe Leu Ser Asn Leu His Leu Arg Asn Gly Glu Leu
 65                  70                  75                  80

Val Ile His Glu Lys Gly Phe Tyr Tyr Ile Tyr Ser Gln Thr Tyr Phe
                 85                  90                  95

Arg Phe Gln Glu Glu Ile Lys Glu Asn Thr Lys Asn Asp Lys Gln Met
            100                 105                 110

Val Gln Tyr Ile Tyr Lys Tyr Thr Ser Tyr Pro Asp Pro Ile Leu Leu
        115                 120                 125

Met Lys Ser Ala Arg Asn Ser Cys Trp Ser Lys Asp Ala Glu Tyr Gly
130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly
            180                 185
```

<210> SEQ ID NO 38
<211> LENGTH: 168
<212> TYPE: PRT
<213> ORGANISM: Homo sapiens

<400> SEQUENCE: 38

```
Val Arg Glu Arg Gly Pro Gln Arg Val Ala Ala His Ile Thr Gly Thr
  1               5                  10                  15

Arg Gly Arg Ser Asn Thr Leu Ser Ser Pro Asn Ser Lys Asn Glu Lys
             20                  25                  30

Ala Leu Gly Arg Lys Ile Asn Ser Trp Glu Ser Ser Arg Ser Gly His
         35                  40                  45

Ser Phe Leu Ser Asn Leu His Leu Arg Asn Gly Glu Leu Val Ile His
 50                  55                  60

Glu Lys Gly Phe Tyr Tyr Ile Tyr Ser Gln Thr Tyr Phe Arg Phe Gln
 65                  70                  75                  80

Glu Glu Ile Lys Glu Asn Thr Lys Asn Asp Lys Gln Met Val Gln Tyr
                 85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly
                165
```

COMPUTATIONAL ANALYSIS OF BIOLOGICAL DATA USING MANIFOLD AND A HYPERPLANE

RELATED APPLICATIONS

This application is division of U.S. patent application Ser. No. 16/355,984 filed on Mar. 18, 2019 which is a U.S. continuation of U.S. patent application Ser. No. 15/503,439 filed on Feb. 13, 2017, now U.S. Pat. No. 10,303,846, which is a National Phase of PCT Patent Application No. PCT/IL2015/050823 having International Filing Date of Aug. 12, 2015, which claims the benefit of priority under 35 USC § 119(e) of U.S. Provisional Patent Application Nos. 62/105,938 filed on Jan. 21, 2015 and 62/037,180 filed on Aug. 14, 2014. The contents of the above applications are all incorporated by reference as if fully set forth herein in their entirety.

SEQUENCE LISTING STATEMENT

The ASCII file, entitled 83217SequenceListing.txt, created on Aug. 20, 2020, comprising 190,563 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to computational analysis, and, more particularly, but not exclusively, to computational analysis of biological data, e.g., for the purpose of distinguishing between bacterial infection and non-bacterial disease, and/or between a bacterial infection and viral infection, and/or between an infectious and non-infectious disease.

Antibiotics (Abx) are the world's most prescribed class of drugs with a 25-30 billion $US global market. Abx are also the world's most misused drug with a significant fraction of all drugs (40-70%) being wrongly prescribed (Linder, J. A. and R. S. Stafford 2001; Scott, J. G. and D. Cohen, et al. 2001; Davey, P. and E. Brown, et al. 2006; Cadieux, G. and R. Tamblyn, et al. 2007; Pulcini, C. and E. Cua, et al. 2007), ("CDC—Get Smart: Fast Facts About Antibiotic Resistance" 2011).

One type of Abx misuse is when the drug is administered in case of a non-bacterial disease, such as a viral infection, for which Abx is ineffective. For example, according to the USA center for disease control and prevention CDC, over 60 Million wrong Abx prescriptions are given annually to treat flu in the US. The health-care and economic consequences of the Abx over-prescription include: (i) the cost of antibiotics that are unnecessarily prescribed globally, estimated at >$10 billion annually; (ii) side effects resulting from unnecessary Abx treatment are reducing quality of healthcare, causing complications and prolonged hospitalization (e.g. allergic reactions, Abx associated diarrhea, intestinal yeast etc.) and (iii) the emergence of resistant strains of bacteria as a result of the overuse (the CDC has declared the rise in antibiotic resistance of bacteria as "one of the world's most pressing health problems in the 21$^{st}$ century" (Arias, C. A. and B. E. Murray 2009; "CDC—About Antimicrobial Resistance" 2011).

Antibiotics under-prescription is not uncommon either. For example up to 15% of adult bacterial pneumonia hospitalized patients in the US receive delayed or no Abx treatment, even though in these instances early treatment can save lives and reduce complications (Houck, P. M. and D. W. Bratzler, et al. 2002).

Technologies for infectious disease diagnosis have the potential to reduce the associated health and financial burden associated with Abx misuse. Ideally, such a technology should: (i) accurately differentiate between a bacterial and viral infections; (ii) be rapid (within minutes); (iii) be able to differentiate between pathogenic and non-pathogenic bacteria that are part of the body's natural flora; (iv) differentiate between mixed co-infections and pure viral infections and (v) be applicable in cases where the pathogen is inaccessible (e.g. sinusitis, pneumonia, otitis-media, bronchitis, etc).

Current solutions (such as culture, PCR and immunoassays) do not fulfill all these requirements: (i) Some of the assays yield poor diagnostic accuracy (e.g. low sensitivity or specificity) (Uyeki et al. 2009), and are restricted to a limited set of bacterial or viral strains; (ii) they often require hours to days; (iii) they do not distinguish between pathogenic and non-pathogenic bacteria (Del Mar, C 1992), thus leading to false positives; (iv) they often fail to distinguish between a mixed and a pure viral infections and (v) they require direct sampling of the infection site in which traces of the disease causing agent are searched for, thus prohibiting the diagnosis in cases where the pathogen resides in an inaccessible tissue, which is often the case.

Consequentially, there still a diagnostic gap, which in turn often leads physicians to either over-prescribe Abx (the "Just-in-case-approach"), or under-prescribe Abx (the "Wait-and-see-approach") (Little, P. S. and I. Williamson 1994; Little, P. 2005; Spiro, D. M. and K. Y. Tay, et al. 2006), both of which have far reaching health and financial consequences.

Accordingly, a need exists for a rapid method that accurately differentiates between bacterial (including mixed bacterial plus viral infection), viral and non-bacterial, non-viral disease patients that addresses these challenges.

WO 2013/117746 teaches signatures and determinants for distinguishing between a bacterial and viral infection.

SUMMARY OF THE INVENTION

According to an aspect of some embodiments of the present invention there is provided a method of analyzing biological data, the biological data containing expression values of a plurality of polypeptides in the blood of a subject. The method comprises: calculating a distance between a segment of a curved line and an axis defined by a direction, the distance being calculated at a point over the curved line defined by a coordinate $\delta_1$ along the direction. The method further comprises correlating the distance to the presence of, absence of, or likelihood that the subject has a bacterial infection. The coordinate $\delta_1$ is defined by a combination of the expression values, wherein at least 90% of the segment is between a lower bound line $f(\delta_1)-\varepsilon_0$ and an upper bound line $f(\delta_1)+\varepsilon_1$, wherein the $g(\delta_0)$ equals $1/(1+\exp(\delta_1))$, and wherein each of the $\varepsilon_0$ and the $\varepsilon_1$ is less than 0.5.

According to some embodiments of the invention the method comprises obtaining the likelihood based on the distance, comparing the likelihood to a predetermined threshold, and, treating the subject for the bacterial infection when the likelihood is above the predetermined threshold.

According to an aspect of some embodiments of the present invention there is provided a method of analyzing biological data, the biological data containing expression values of a plurality of polypeptides in the blood of a subject.

The method comprises: calculating a distance between a segment of a curved line and an axis defined by a direction, the distance being calculated at a point over the curved line defined by a coordinate $\delta_0$ along the direction. The method further comprises correlating the distance to the presence of, absence of, or likelihood that the subject has a viral infection. The coordinate $\delta_0$ is defined by a combination of the expression values, wherein at least 90% of the segment is between a lower bound line $g(\delta_0)-\varepsilon_0$ and an upper bound line $g(\delta_0)+\varepsilon_1$, wherein the $f(\varepsilon_0)$ equals $1/(1+\exp(\delta_0))$, and wherein each of the $\varepsilon_0$ and the $\varepsilon_1$ is less than 0.5.

According to some embodiments of the invention the method comprises obtaining the likelihood based on the distance, comparing the likelihood to a predetermined threshold, and, treating the subject for the viral infection when the likelihood is above the predetermined threshold.

According to some embodiments of the invention the combination of the expression values comprises a linear combination of the expression values.

According to some embodiments of the invention the combination of the expression values includes at least one nonlinear term corresponding to at least one of the expression values.

According to an aspect of some embodiments of the present invention there is provided a method of analyzing biological data, the biological data containing expression values of a plurality of polypeptides in the blood of a subject. The method comprises: calculating a first distance between a segment of a curved surface and a plane defined by a first direction and a second direction. The first distance being calculated at a point over the surface defined by first coordinate $\delta_0$ along the first direction and a second coordinate $\delta_1$ along the second direction. The method further comprises correlating the first distance to the presence of, absence of, or likelihood that the subject has a bacterial infection. Each of the coordinates is defined by a different combination of the expression values, wherein at least 90% of the segment is between a lower bound surface $f(\delta_0,\delta_1)-\varepsilon_0$ and an upper bound surface $f(\delta_0,\delta_1)+\varepsilon_1$, wherein the $f(\delta_0,\delta_1)$ equals $\exp(\delta_1)/(1+\exp(\delta_0)+\exp(\delta_1))$, and wherein each of the $\varepsilon_0$ and the $\varepsilon_1$ is less than 0.5.

According to some embodiments of the invention for at least one of the coordinates, the combination of the expression values comprises a linear combination of the expression values.

According to some embodiments of the invention for at least one of the coordinates, the combination of the expression values includes at least one nonlinear term corresponding to at least one of the expression values.

According to some embodiments of the invention the method comprises obtaining the likelihood based on the first distance, comparing the likelihood to a predetermined threshold, and, treating the subject for the bacterial infection when the likelihood is above the predetermined threshold.

According to some embodiments of the invention the method comprises calculating a second distance between a segment of second curved surface and the plane; and correlating the second distance to the presence of, absence of, or likelihood that the subject has a viral infection. According to some embodiments of the invention at least 90% of the segment of the second surface is between a second lower bound surface $g(\delta_0,\delta_1)-\varepsilon_2$ and a second upper bound surface $g(\delta_0,\delta_1)+\varepsilon_3$, wherein the $g(\delta_0,\delta_1)$ equals $\exp(\delta_0)/(1+\exp(\varepsilon_0)+\exp(\varepsilon_1))$, and wherein each of the $\varepsilon_2$ and the $\varepsilon_3$ is less than 0.5.

According to some embodiments of the invention the method comprises obtaining the likelihood based on the second distance, comparing the likelihood to a second predetermined threshold, and, treating the subject for the viral infection when the likelihood is above the second predetermined threshold.

According to some embodiments of the invention the method comprises obtaining the likelihood that the subject has a bacterial infection based on the distance, obtaining the likelihood that the subject has a viral infection based on the second distance, comparing each of the likelihoods to a respective predetermined threshold, and, when each of the likelihoods is below the respective predetermined threshold, then determining that the patient is likely to have a non-infectious disease.

According to an aspect of some embodiments of the present invention there is provided a method of analyzing biological data, the biological data containing expression values of a plurality of polypeptides in the blood of a subject. The method comprises: calculating a distance between a segment of a curved surface and a plane defined by a first direction and a second direction. The distance is calculated at a point over the surface defined by first coordinate $\delta_0$ along the first direction and a second coordinate $\delta_1$ along the second direction. The method comprises correlating the distance to the presence of, absence of, or likelihood that the subject has, a viral infection; wherein each of the coordinates is defined by a different combination of the expression values, wherein at least 90% of the segment is between a lower bound surface $g(\delta_0,\delta_1)-\varepsilon_0$ and an upper bound surface $g(\delta_0,\delta_1)+\varepsilon_1$, wherein the $g(\delta_0,\delta_1)$ equals $\exp(\delta_0)/(1+\exp(\delta_0)+\exp(\delta_1))$, and wherein each of the $\varepsilon_0$ and the $\varepsilon_1$ is less than 0.5.

According to some embodiments of the invention each of the plurality of polypeptides is selected from the group consisting of CRP, IP-10, TRAIL, IL1ra, PCT and SAA.

According to some embodiments of the invention the plurality of polypeptides comprises at least three polypeptides.

According to some embodiments of the invention the plurality of polypeptides comprises at least three polypeptides selected from the group consisting of CRP, IP-10, TRAIL, IL1ra, PCT and SAA.

According to some embodiments of the invention the plurality of polypeptides comprises at least CRP and TRAIL.

According to some embodiments of the invention the plurality of polypeptides comprises at least CRP, TRAIL and IP-10.

According to some embodiments of the invention the method comprises generating an output of the likelihood, the output is presented as text.

According to some embodiments of the invention the method comprises generating an output of the likelihood, the output is presented graphically.

According to some embodiments of the invention the method comprises generating an output of the likelihood, the output is presented using a color index.

According to some embodiments of the invention the blood sample is whole blood.

According to some embodiments of the invention the blood sample is a fraction of whole blood.

According to some embodiments of the invention the blood fraction comprises serum or plasma.

According to some embodiments of the invention the method comprises determining the expression values, and wherein at least one of the expression values is determined electrophoretically or immunochemically.

According to some embodiments of the invention the immunochemical determination is effected by flow cytometry, radioimmunoassay, immunofluorescence or by an enzyme-linked immunosorbent assay.

According to some embodiments of the invention the calculating and the correlating is executed by a computer remote from the subject.

According to some embodiments of the invention the calculating and the correlating is executed by a computer near the subject.

According to some embodiments of the invention the calculating and the correlating is executed by a cloud computing resource of a cloud computing facility.

According to some embodiments of the invention the expression values are measured by a measuring system performing at least one automated assay selected from the group consisting of an automated ELISA, an automated immunoassay, and an automated functional assay, and the method comprises receiving said the biological data from said measuring system.

According to some embodiments of the invention the receiving is over an internet network via a network interface.

According to an aspect of some embodiments of the present invention there is provided a computer-implemented method for analyzing biological data. The method comprises: displaying on a display device a graphical user interface (GUI) having a calculation activation control; receiving expression values of polypeptides in the blood of a subject; responsively to an activation of the control by a user, automatically calculating a score based on the expression values; generating on the GUI a graphical scale having a first end identified as corresponding to a viral infection of the subject, and a second end identified as corresponding to a bacterial infection the subject; and generating a mark on the scale at a location corresponding to the score.

According to some embodiments of the invention the expression values are received by communicating with an external machine that measures the expression values.

According to some embodiments of the invention the GUI comprises a communication control, wherein the communication with the external machine is in response to an activation of the communication control by the user.

According to some embodiments of the invention the GUI comprises a plurality of an expression value input fields, wherein the expression values are received via the input fields.

According to some embodiments of the invention the score is a likelihood that the subject has bacterial infection.

According to some embodiments of the invention the score is a likelihood that the subject has viral infection.

According to an aspect of some embodiments of the present invention there is provided a computer software product, comprising a computer-readable medium in which program instructions are stored, which instructions, when read by a hardware processor, cause the hardware processor to receive expression values of a plurality of polypeptides in the blood of a subject who has an unknown disease, and to execute the method as delineated above and optionally as further detailed below.

According to an aspect of some embodiments of the present invention there is provided a system for analyzing biological data. The system comprises: a user interface configured to receive expression values of a plurality of polypeptides in the blood of a subject who has an unknown disease; and a hardware processor having a computer-readable medium storing the computer software product.

According to an aspect of some embodiments of the present invention there is provided a system for analyzing biological data. The system comprises: a first compartment configured to measure expression values of a plurality of polypeptides in the blood of a subject who has an unknown disease; a second compartment comprising a hardware processor having a computer-readable storing the computer software product.

According to some embodiments of the invention the first compartment, the second compartment and the display are mounted on or integrated with a body of a hand-held device.

According to an aspect of some embodiments of the present invention there is provided a method of analyzing a dataset. The method comprises: (a) accessing a dataset comprising classification groups based on expression values of a plurality of polypeptides in the blood of a subject who has an unknown disease in blood samples of multiple subjects, wherein the classification groups comprise a bacterial infection, a viral infection and a non-viral, non bacterial disease; and (b) analyzing the classification groups to provide at least a first probabilistic classification function $f(\delta_0, \delta_1)$ representing the likelihood that a particular subject has a bacterial infection, the first classification function being a function of a first coordinate $\delta_0$ and a second coordinate $\delta_1$, and wherein each of the coordinates is defined by a different combination of the expression values.

According to some embodiments of the invention the method further comprising calculating a second classification function $g(\delta_0, \delta_1)$ representing the likelihood that a particular subject has a viral infection, the second classification function being also a function of the first and the second coordinates.

According to some embodiments of the invention the method comprises calculating a third classification function $h(\delta_0, \delta_1)$ representing the likelihood that a particular subject has a non-viral, non bacterial disease, the third classification function being also a function of the first and the second coordinates.

According to some embodiments of the invention, for at least one of the coordinates, the combination of the expression values comprises a linear combination of the expression values.

According to some embodiments of the invention for at least one of the coordinates, the combination of the expression values includes at least one nonlinear term corresponding to at least one of the expression values.

According to some embodiments of the invention the method comprises generating an output of the analyzing.

According to some embodiments of the invention the dataset comprises one or more multidimensional entries.

According to some embodiments of the invention the method wherein each entry in the dataset comprises at least one clinical parameter of the respective subject.

According to some embodiments of the invention the method wherein the clinical parameter is selected from the group consisting of a sex, an age, a temperature, a time from symptoms onset and a weight.

According to some embodiments of the invention the analysis comprises machine learning.

According to some embodiments of the invention the machine learning comprises a supervised machine learning.

According to some embodiments of the invention the machine learning comprises at least one procedure selected from the group consisting of clustering, support vector machine, linear modeling, k-nearest neighbors analysis, decision tree learning, ensemble learning procedure, neural networks, probabilistic model, graphical model, Bayesian network, logistic regression and association rule learning.

According to some embodiments of the invention the method wherein the machine learning is selected from the group consisting of support vector machine, neural networks and logistic regression.

According to some embodiments of the invention the blood sample is whole blood.

According to some embodiments of the invention the blood sample is a fraction of whole blood.

According to some embodiments of the invention the blood fraction comprises serum or plasma.

According to some embodiments of the invention the expression value is determined electrophoretically or immunochemically.

According to some embodiments of the invention the immunochemical determination is effected by flow cytometry, radioimmunoassay, immunofluorescence or by an enzyme-linked immunosorbent assay.

According to an aspect of some embodiments of the present invention there is provided a method of predicting a prognosis for a disease. The method comprises measuring the TRAIL protein serum level in subject having the disease, wherein when the TRAIL level is below a predetermined level, the prognosis is poorer than for a subject having a disease having a TRAIL protein serum level above the predetermined level.

According to some embodiments of the invention the method wherein the disease is an infectious disease.

According to some embodiments of the invention the method wherein the disease is not an infectious disease.

According to an aspect of some embodiments of the present invention there is provided a method of determining a treatment course for a disease in a subject. The method comprises measuring the TRAIL protein serum level in the subject, wherein when the TRAIL level is below a predetermined level, the subject is treated with a treatment of last resort.

According to some embodiments of the invention the predetermined level is below 20 pg/ml.

According to an aspect of some embodiments of the present invention there is provided a method of determining an infection type in a female subject of fertility age.

The method comprises comparing the TRAIL protein serum level in the subject to a predetermined threshold, the predetermined threshold corresponding to the TRAIL protein serum level of a healthy female subject of fertility age, or a group of healthy female subjects of fertility age, wherein a difference between the TRAIL protein serum level and the predetermined threshold is indicative of an infection type.

According to an aspect of some embodiments of the present invention there is provided a method of determining an infection type in a male subject of fertility age.

The method comprises comparing the TRAIL protein serum level in the subject to a predetermined threshold, the predetermined threshold corresponding to the TRAIL protein serum level of a healthy male subject of fertility age, or a group of healthy male subjects of fertility age, wherein a difference between the TRAIL protein serum level and the predetermined threshold is indicative of an infection type.

According to some embodiments of the invention when the TRAIL protein serum level is above the predetermined threshold, the infection type is viral.

According to some embodiments of the invention when the TRAIL protein serum level is above the predetermined threshold, the infection type is not bacterial.

According to some embodiments of the invention when the TRAIL protein serum level is below the predetermined threshold, the infection type is bacterial.

According to some embodiments of the invention when the TRAIL protein serum level is below the predetermined threshold, the infection type is not viral.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1B. Study workflow. (A) An overview of the study workflow. $n_{Bacterial}$, $n_{Viral}$ and $n_{Control}$ represent the number of bacterial (including mixed bacterial plus viral co-infections), viral and control (with no apparent infectious disease) cases, respectively. (B) Proteins discovery and validation process.

FIGS. 2A-2C. The proteins TRAIL, IP-10 and CRP are differentially expressed in bacterial, viral and non-infectious patients. Box plots for TRAIL (A), IP-10 (B), and CRP (C), measured over the Majority cohort (n=765) are presented. Boxed line and circle correspond to group median and average respectively; t-test p-values between bacterial and viral groups and between infectious (bacterial and viral) vs. non-infectious (including healthy subjects) are depicted.

A. Major clinical syndromes; B. Specific clinical syndromes.

Figure 10:
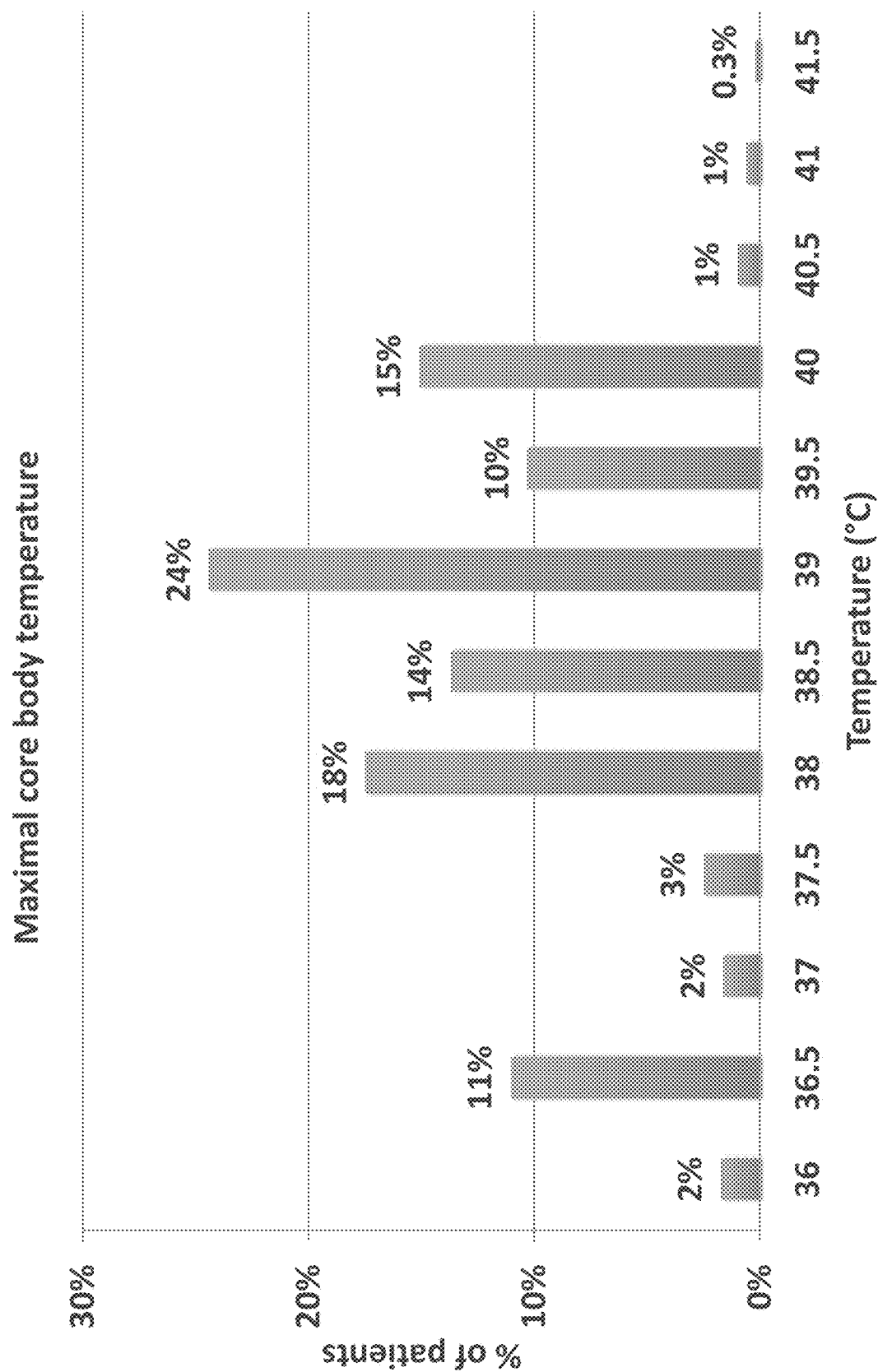

FIG. 10. Distribution of maximal body temperatures (n=794).

Figure 11:
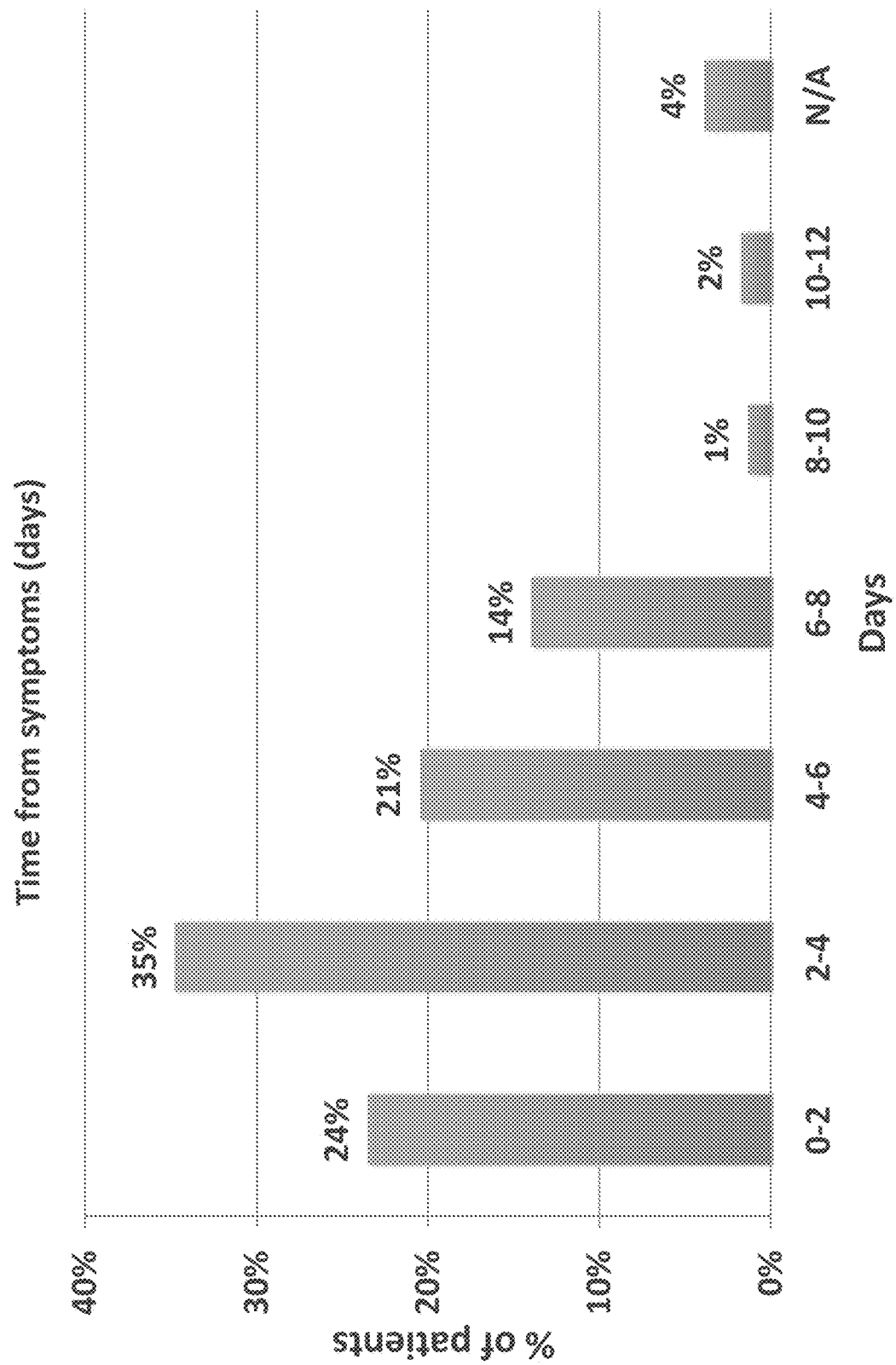

FIG. 11. Distribution of time from initiation of symptoms (n=794). N/A—healthy controls or patients for which data was not obtained.

Figure 12A:
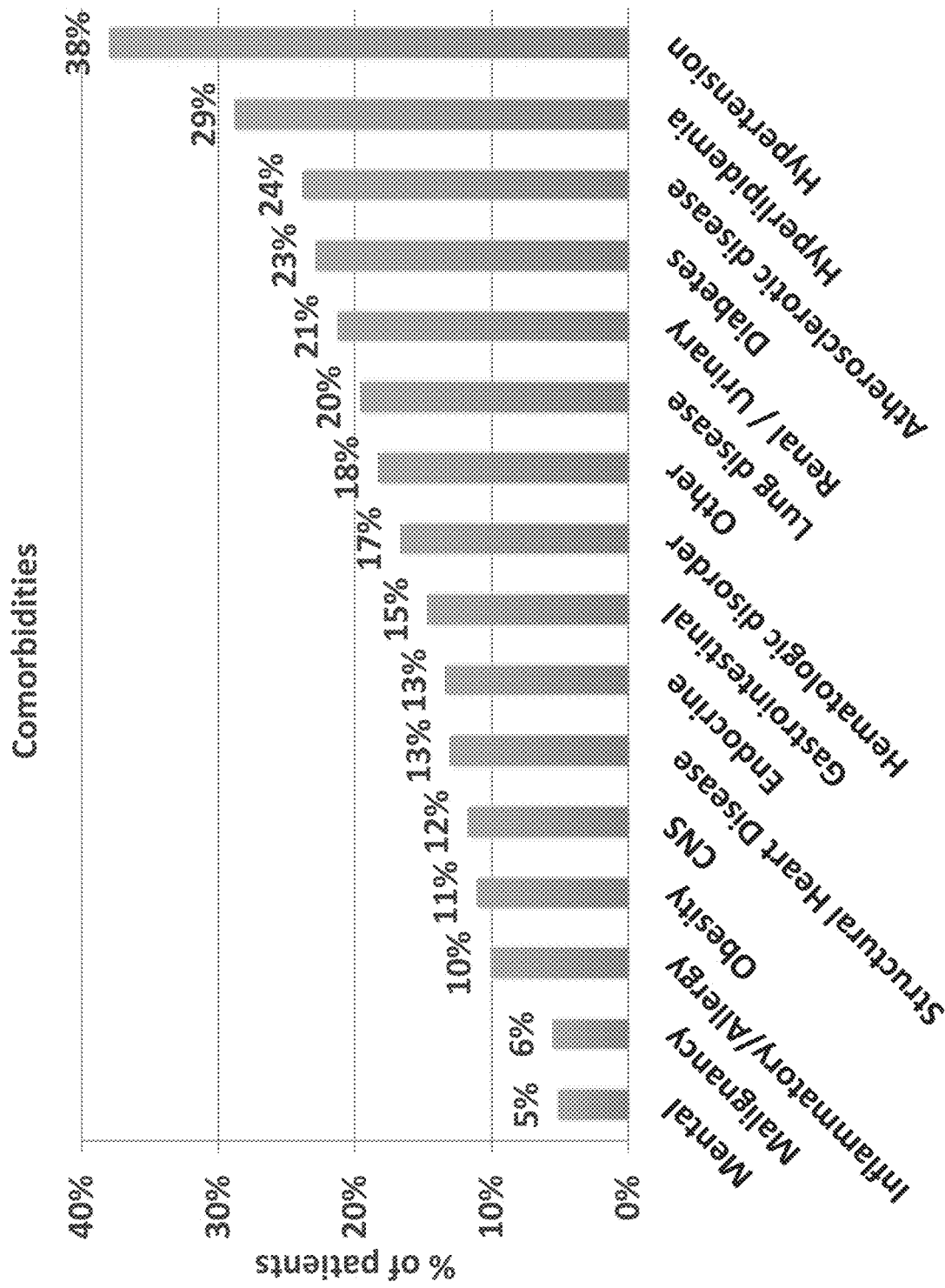
Figure 12B:
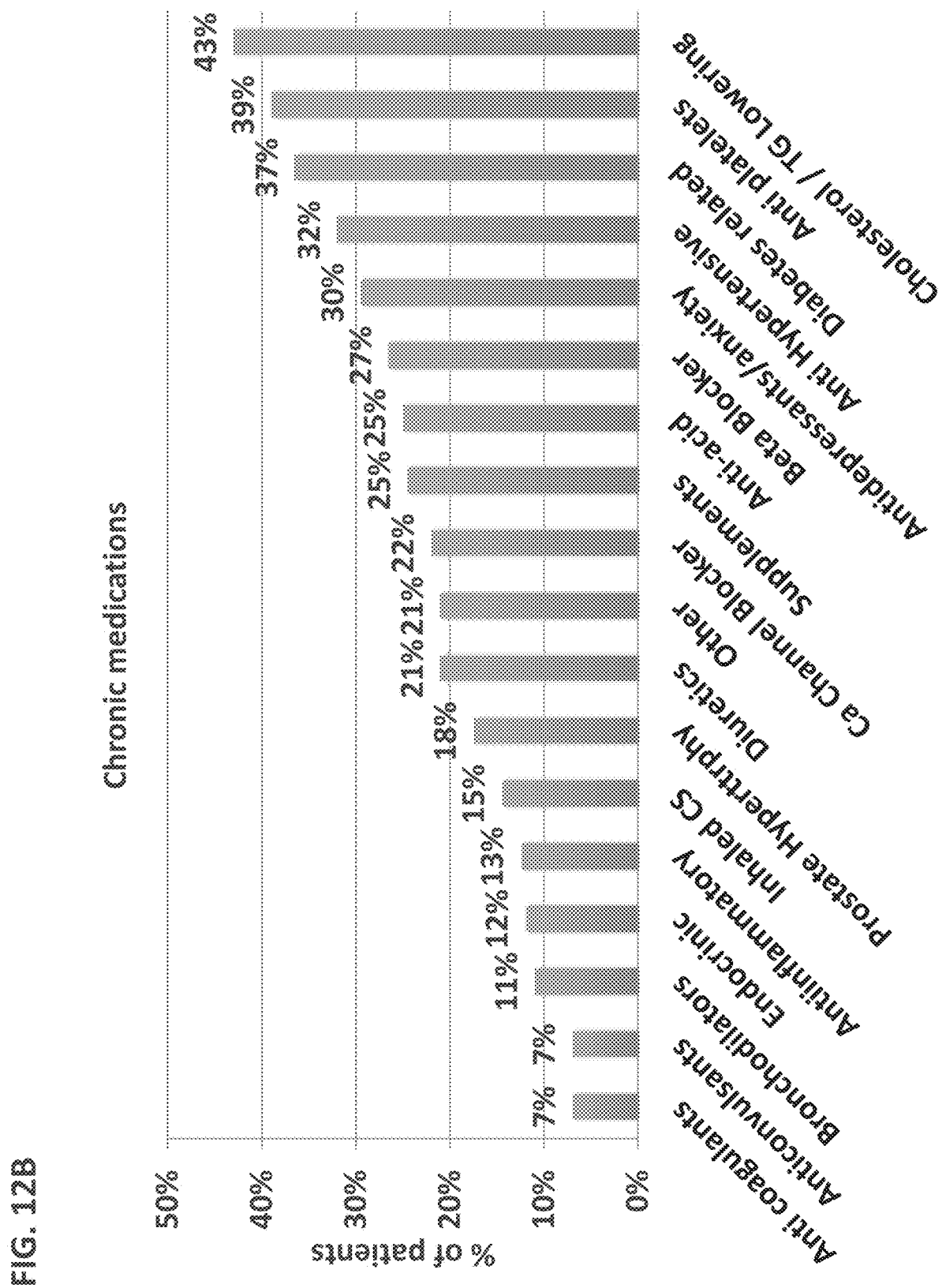

FIGS. 12A-12B. Comorbidities-related characterization of the patient population. A. Distribution of comorbidities (all chronically ill patients, n=305); B. Distribution of chronic medications (all chronically ill patients, n=305). Of note, some of the patients presented with several chronic diseases, and treated with several chronic medications.

Figure 13:
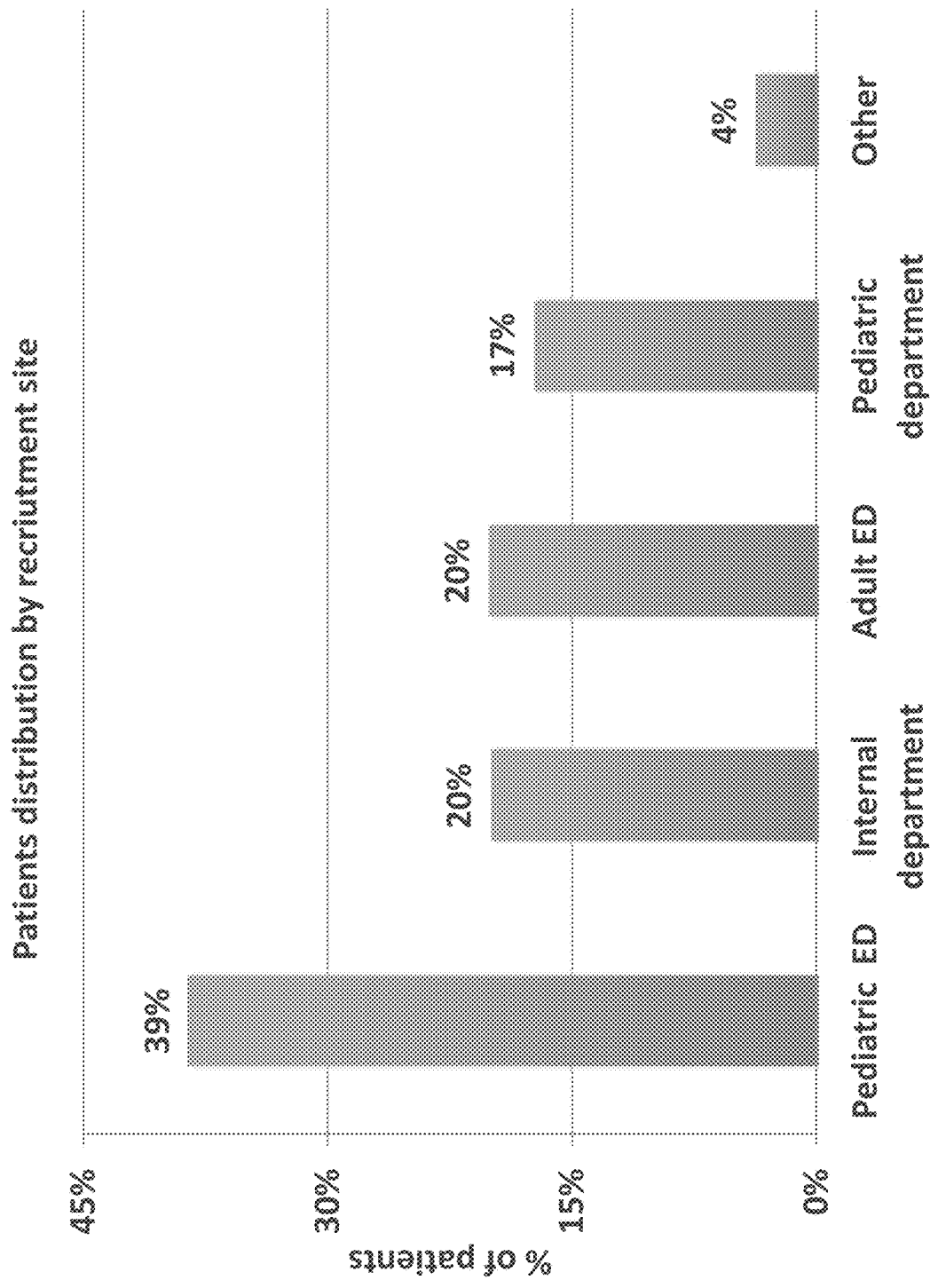

FIG. 13. Distribution of recruitment sites (diagnosed patients, n=794).

Figure 14A:
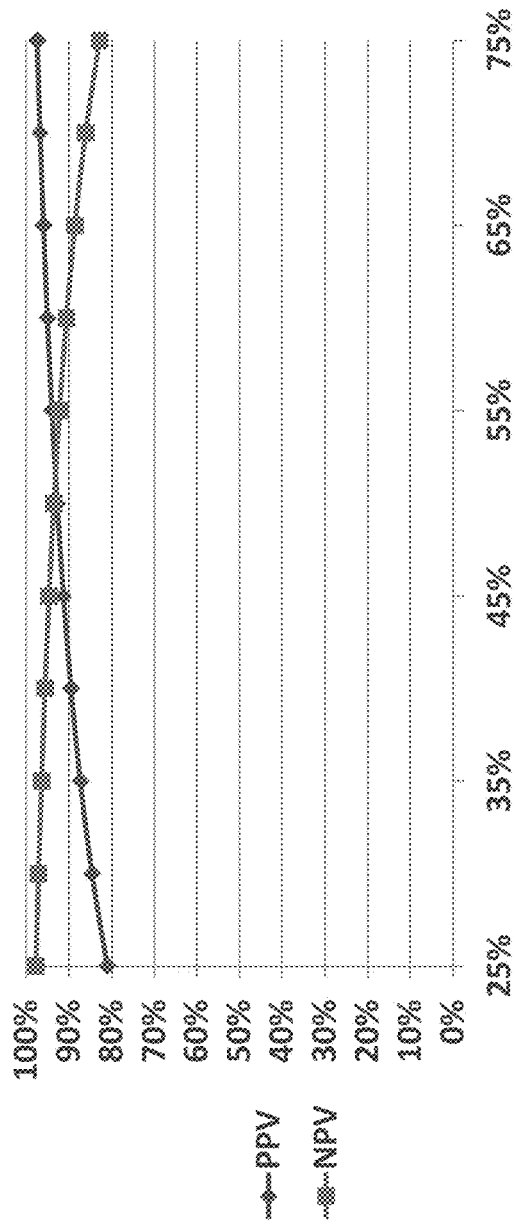
Figure 14B:
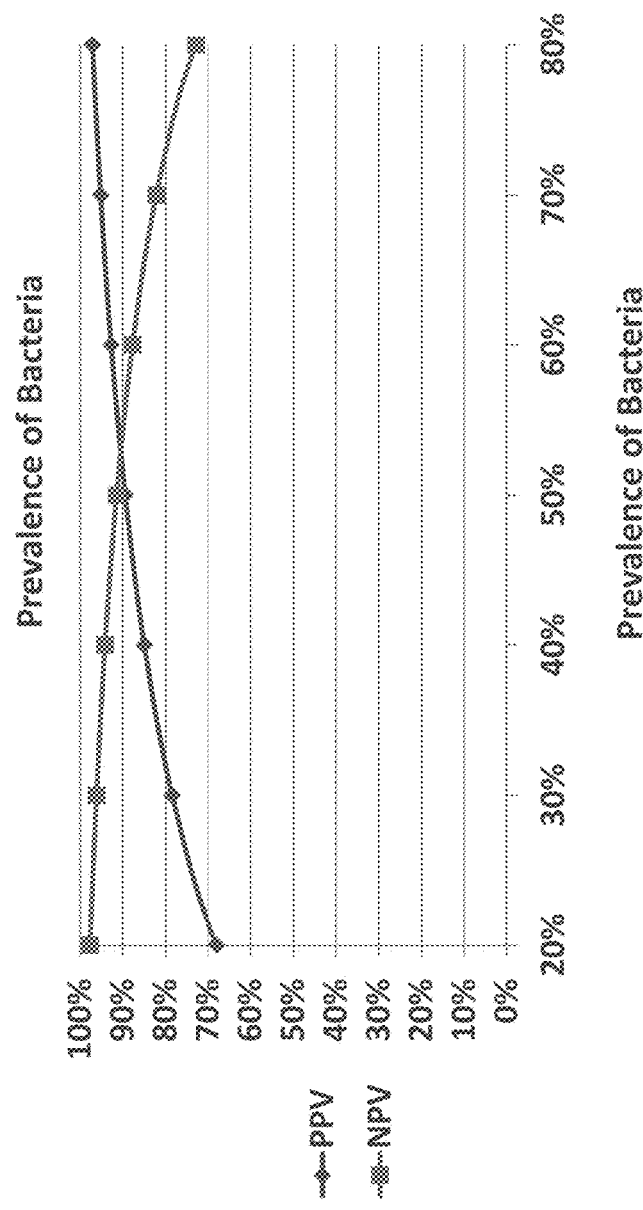

FIGS. 14A-14B. Extrapolated PPV and NPV values for the signature as a function of the prevalence of bacterial infections, A. Unanimous (bacterial, viral) cohort (n=527), B. Majority (bacterial, viral) cohort (n=653).

FIGS. 15A-15E. Scatter plots of clinical parameters and laboratory measurements in bacterial, viral, and non-infectious patients (as indicated) in the Majority (bacterial, viral, non-infectious) cohort (n=765). Boxed line and circle correspond to group median and average respectively. T-test p-values between bacterial and viral groups and between infectious (bacterial and viral) vs. non-infectious (including healthy subjects) are depicted.

Figure 16A:
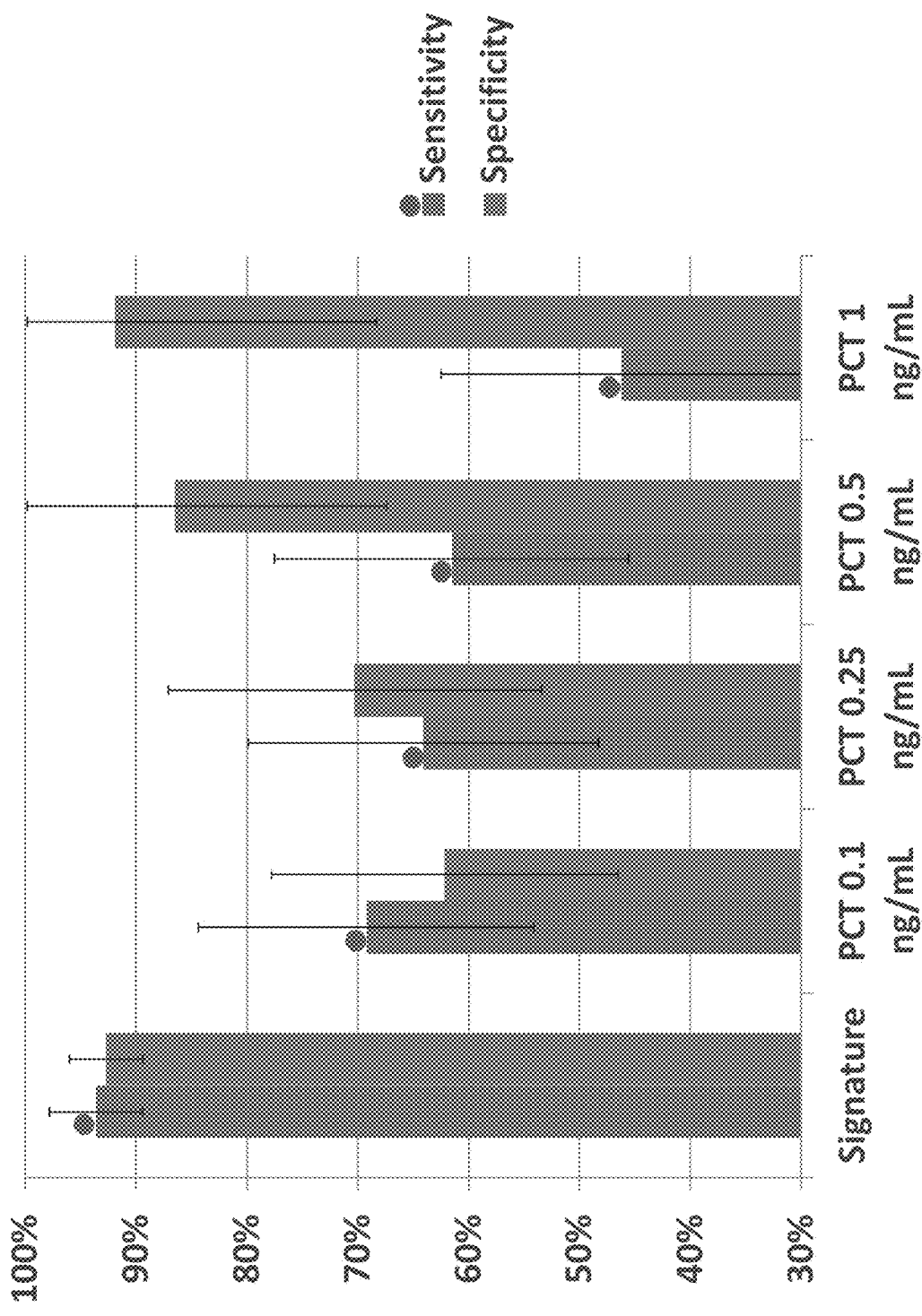
Figure 16B:
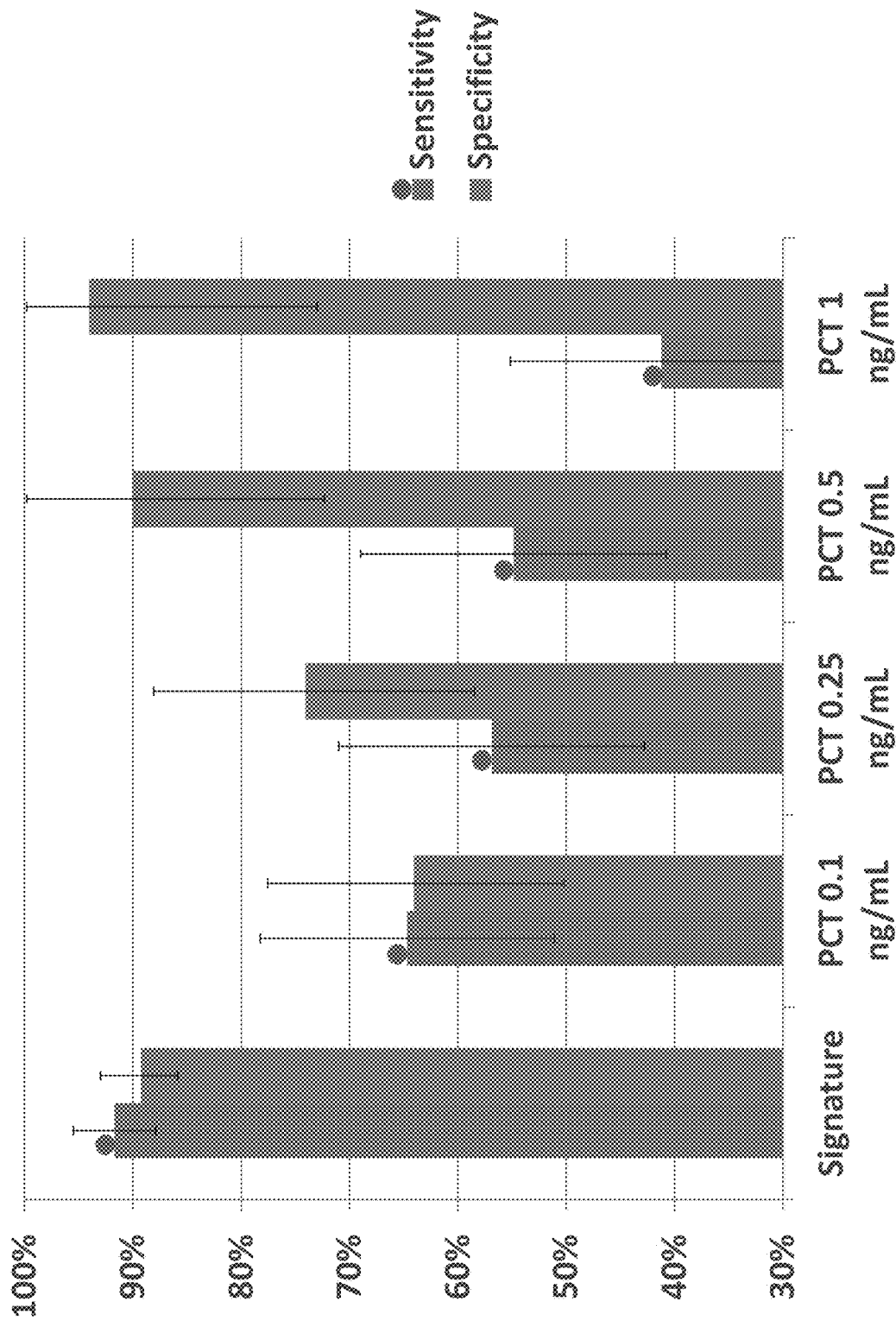

FIGS. 16A-16B. Comparison of the performance of the signature and PCT using different cutoffs. A. Performance measured in 76 patients from the Unanimous (bacterial, viral) cohort; B. Performance measured in 101 patients from the Majority (bacterial, viral) cohort. Error bars represent 95% CI. Signature sensitivity (left) and specificity (right) were calculated after filtering out 14% of the patients with a marginal immune response.

Figure 17A:
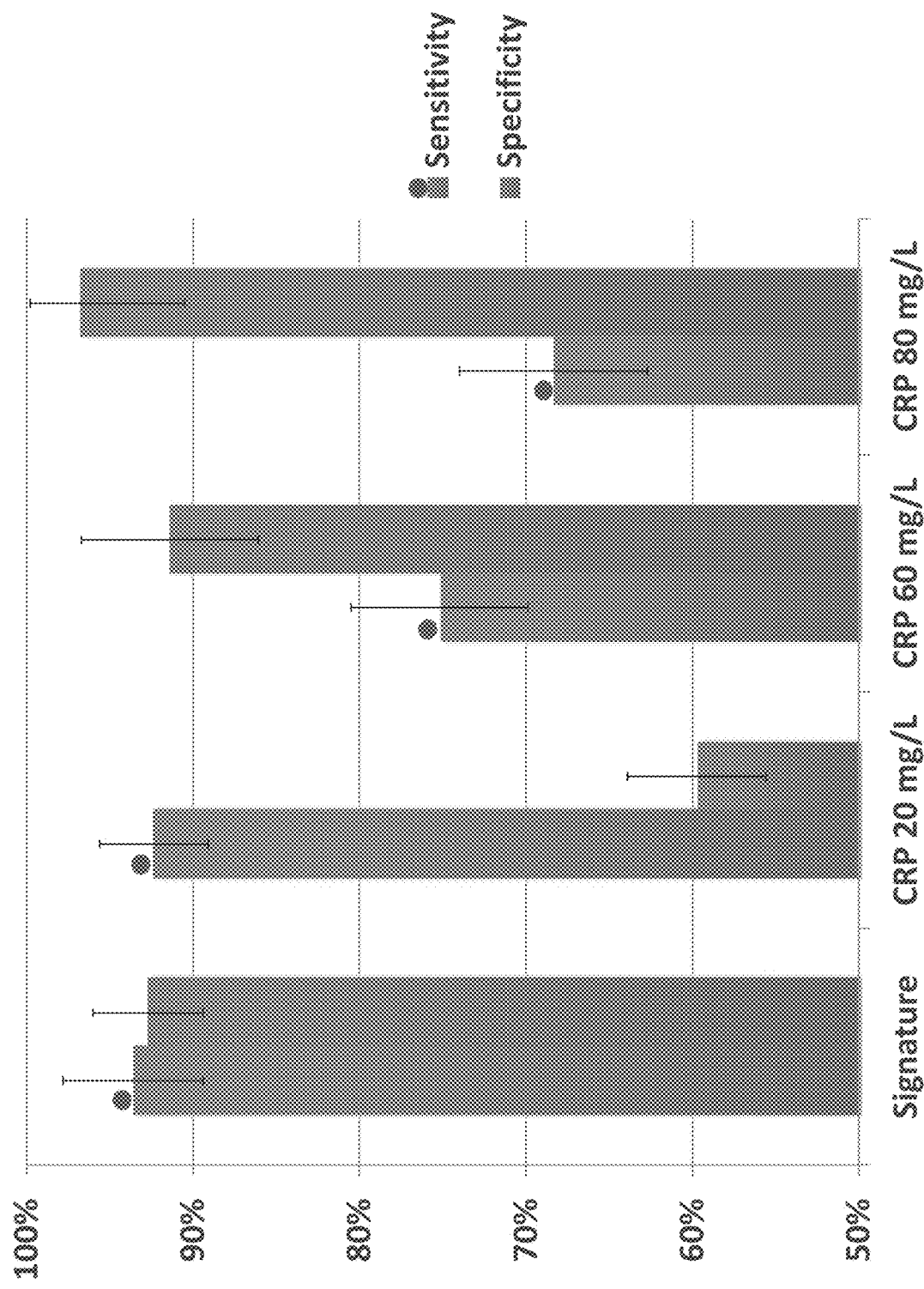
Figure 18A:
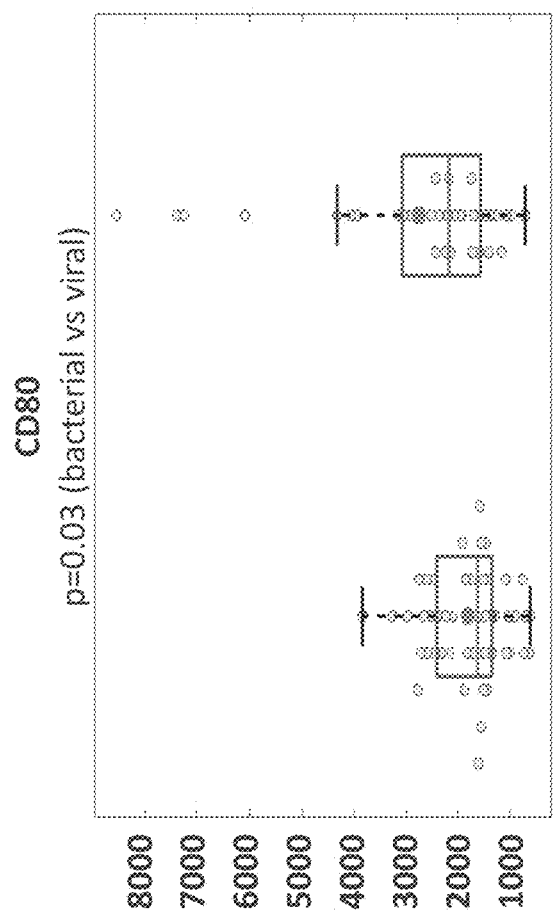
Figure 18B:
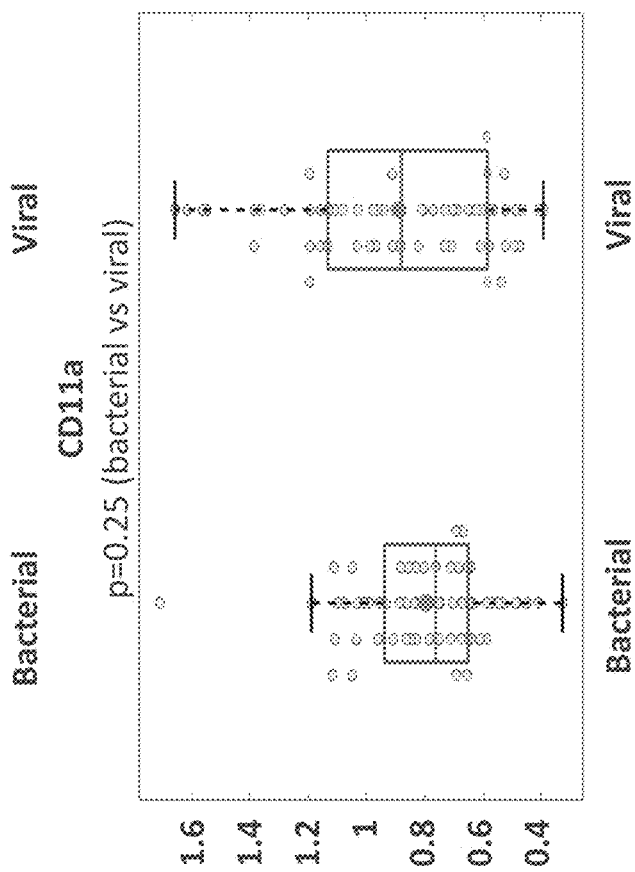
Figure 18C:
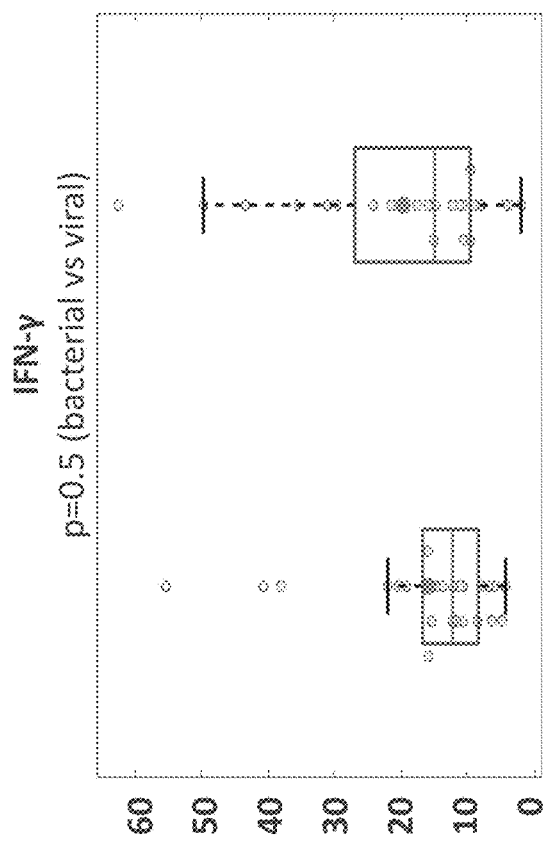
Figure 18D:
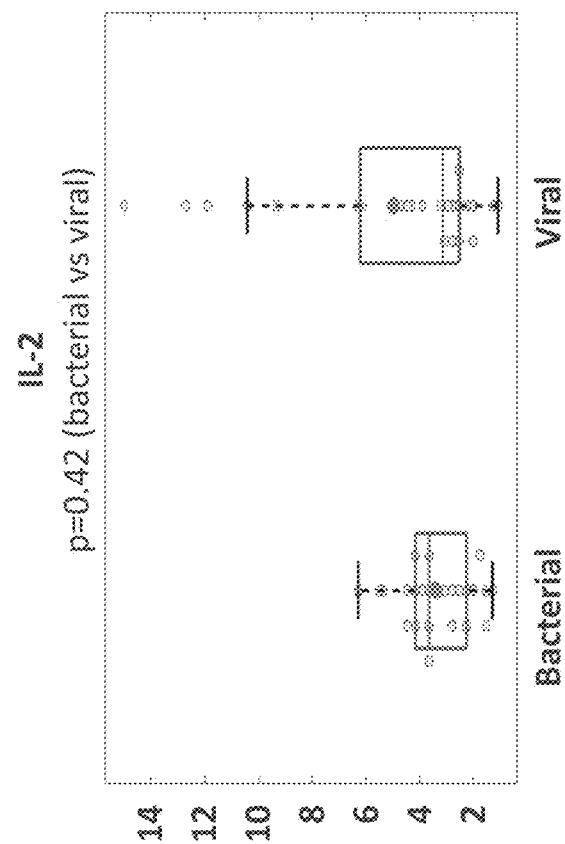
Figure 18E:
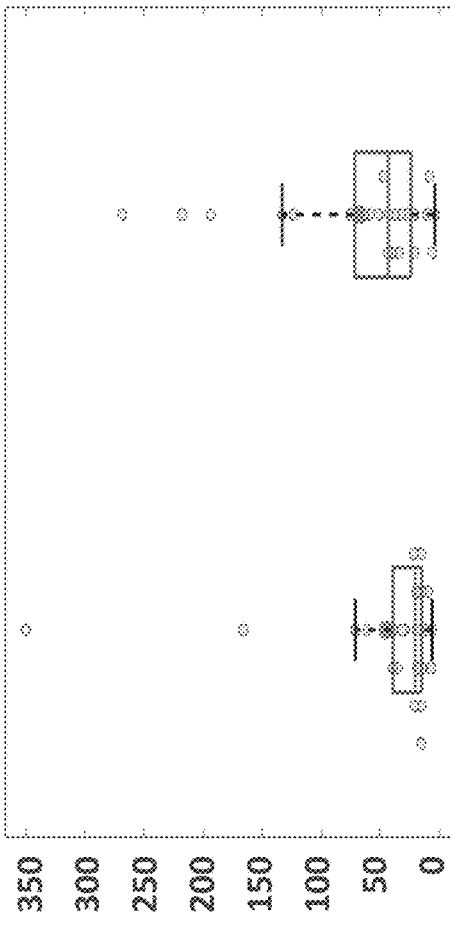
Figure 18F:
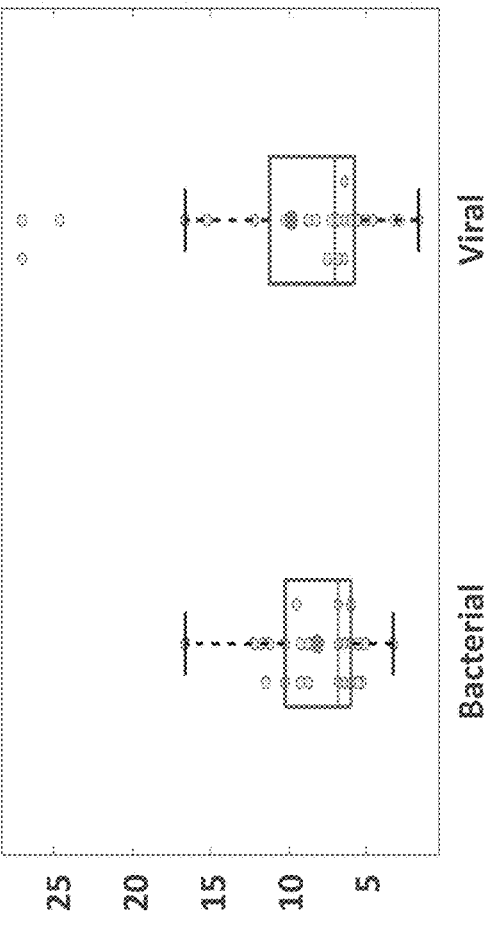
Figure 18G:
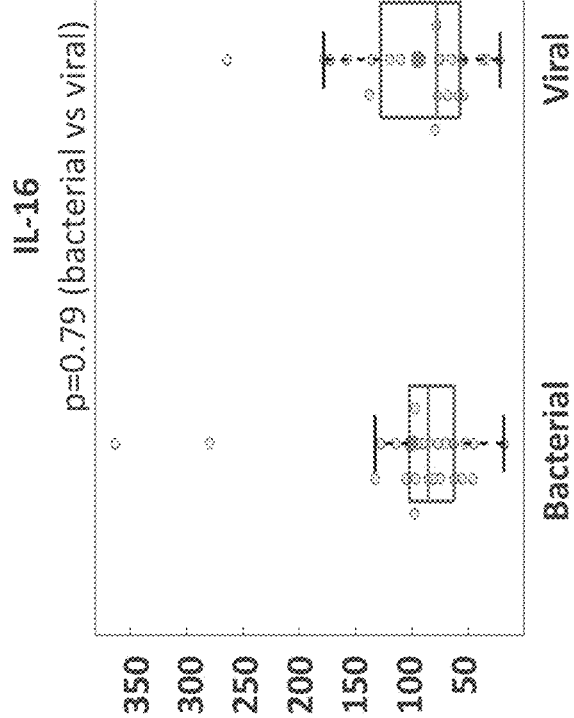
Figure 18H:
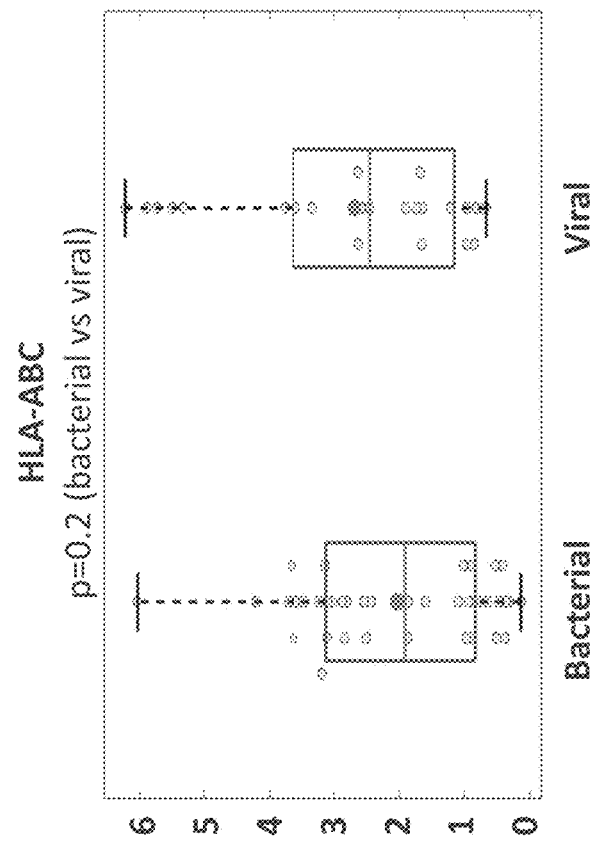

FIGS. 17A-17B. Comparison of the performance of the signature and CRP using different cutoffs. A. Performance measured in the Unanimous (bacterial, viral) cohort (n=527); B. Performance measured in the Majority (bacterial, viral) cohort (n=653). Error bars represent 95% CI. Signature sensitivity (left) and specificity (right) were calculated after filtering out 14% of the patients with a marginal immune response.

FIGS. 18A-18H. Scatter plots of levels of selected protein biomarkers (arbitrary units) in bacterial and viral patients. Boxed line and circle correspond to group median and average respectively. T-test p-values between bacterial and viral groups are depicted.

Figure 19A:
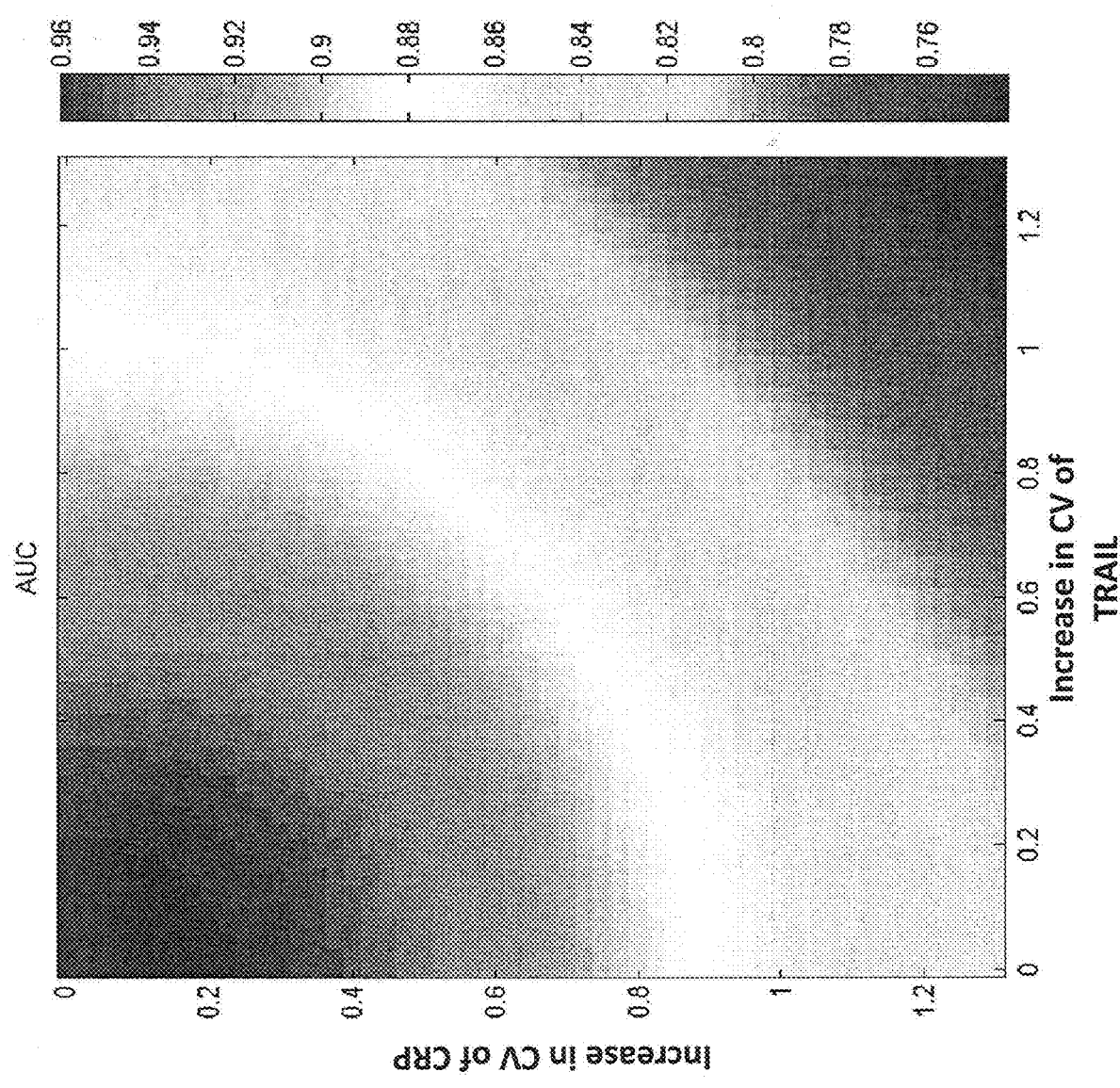
Figure 19B:
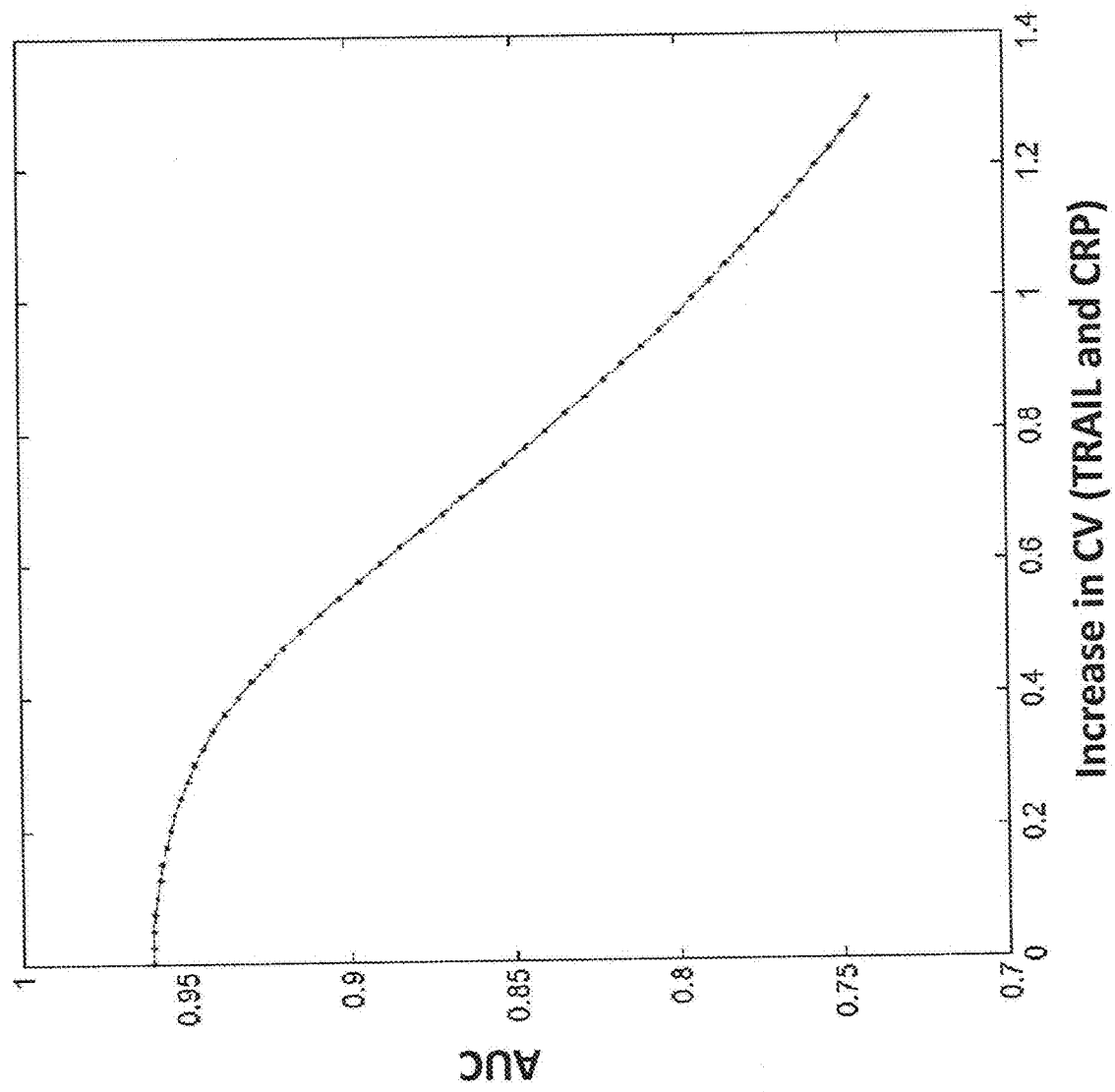

FIGS. 19A-19B. The clinical accuracy of the signature is robust to reduction in the technical accuracy of protein measurements. (A) The AUCs of the signature distinguishing bacterial from viral infection are estimated using a grayscale map as a function of CVs (std/mean) of TRAIL (y-axis) and CRP (x-axis) measurement. (B) AUC values on the diagonal of FIG. 19A a presented such that CV of TRAIL and CRP are equal.

Figure 20:
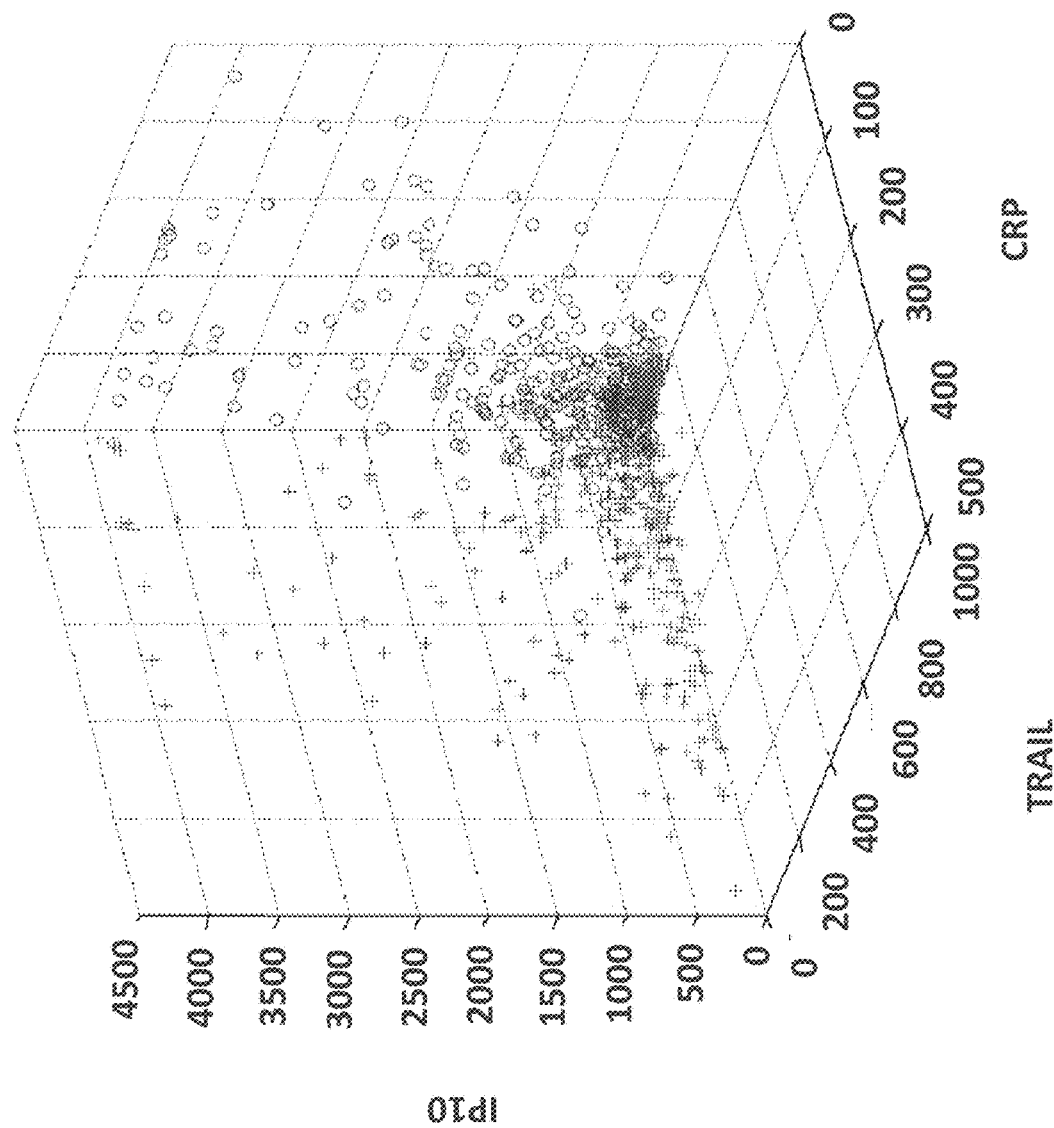

FIG. 20 is a 3-dimensional visualization of bacterial ('+'), viral ('o') and non-infectious ('^') patients. Different patients types are mapped to distinct regions in the CRP (μg/ml), TRAIL and IP-10 (pg/ml) concentration map.

Figures 21A, 21B, 21C:
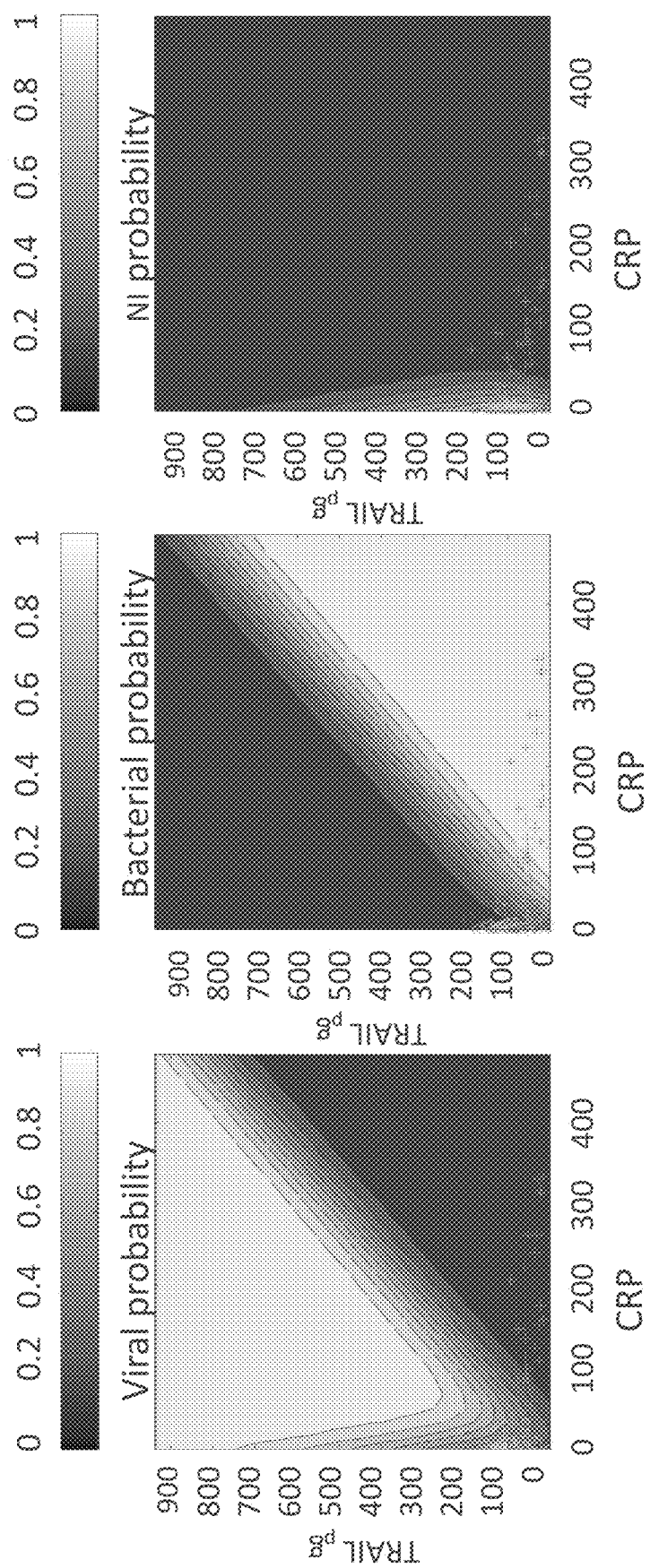

FIGS. 21A-21C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 0 to 100.

FIGS. 22A-22C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 100 to 200.

Figure 23A:
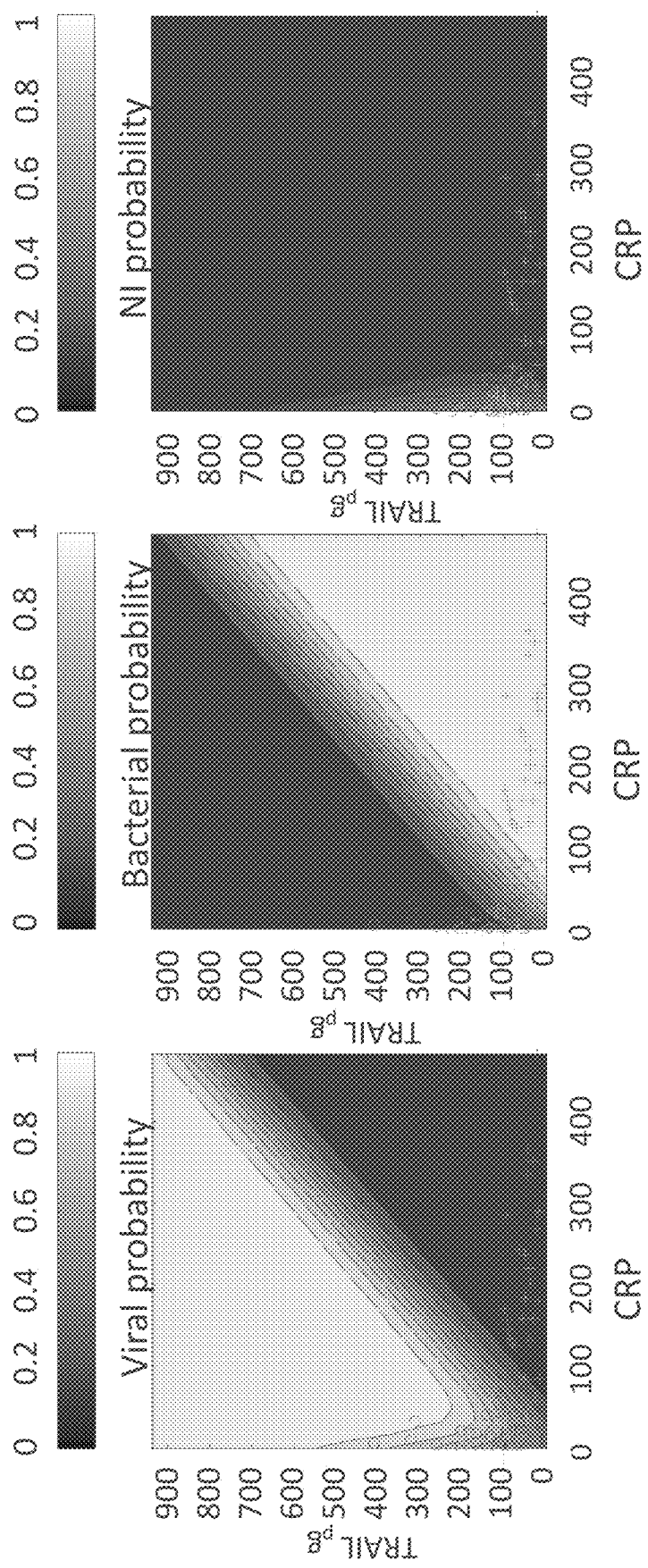
Figure 23B:
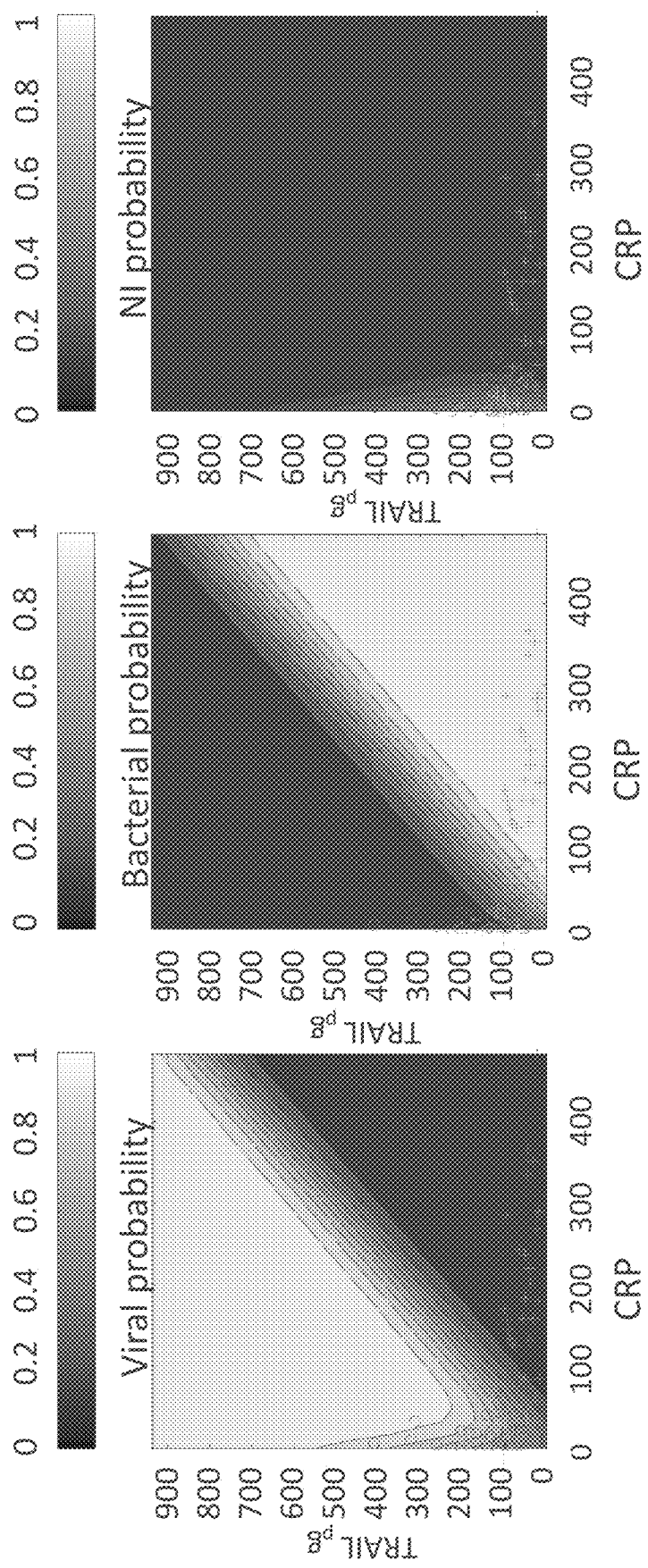
Figure 23C:
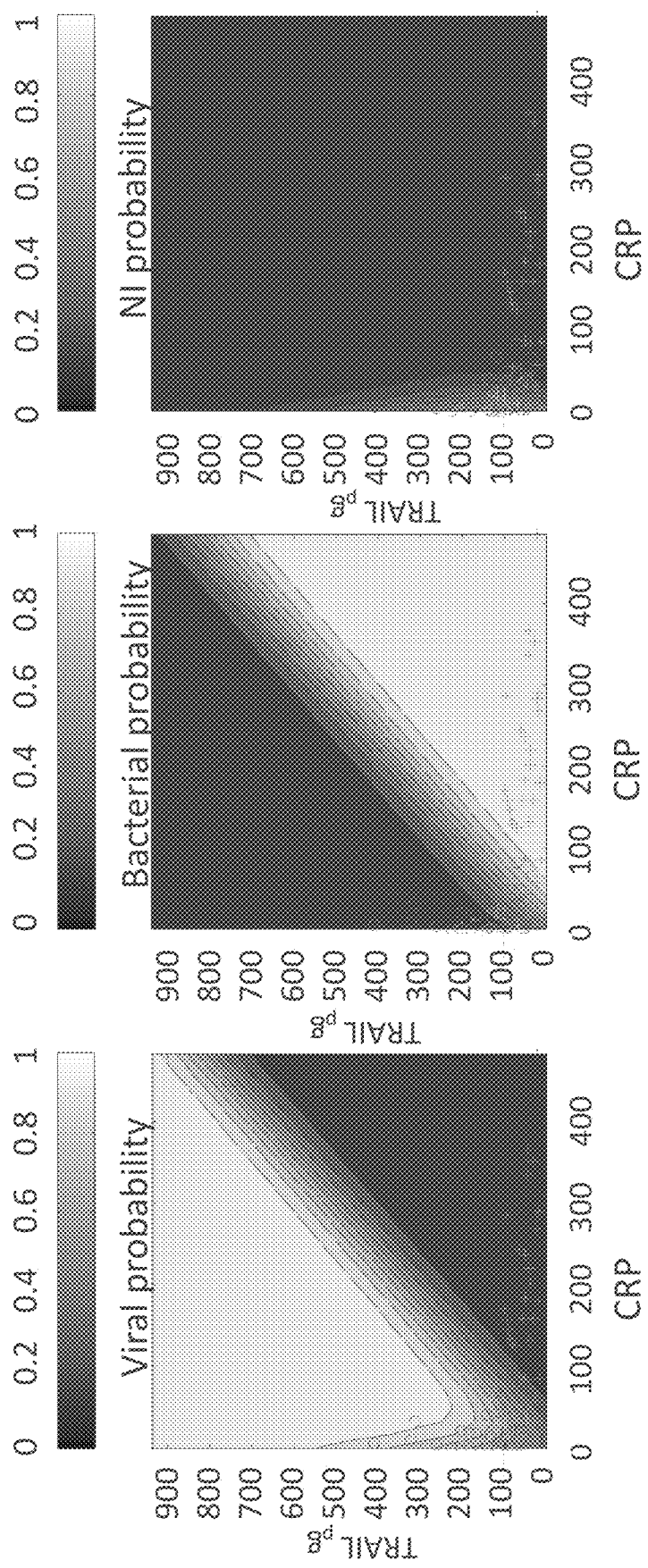

FIGS. 23A-23C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 200 to 300.

Figures 24A, 24B, 24C:
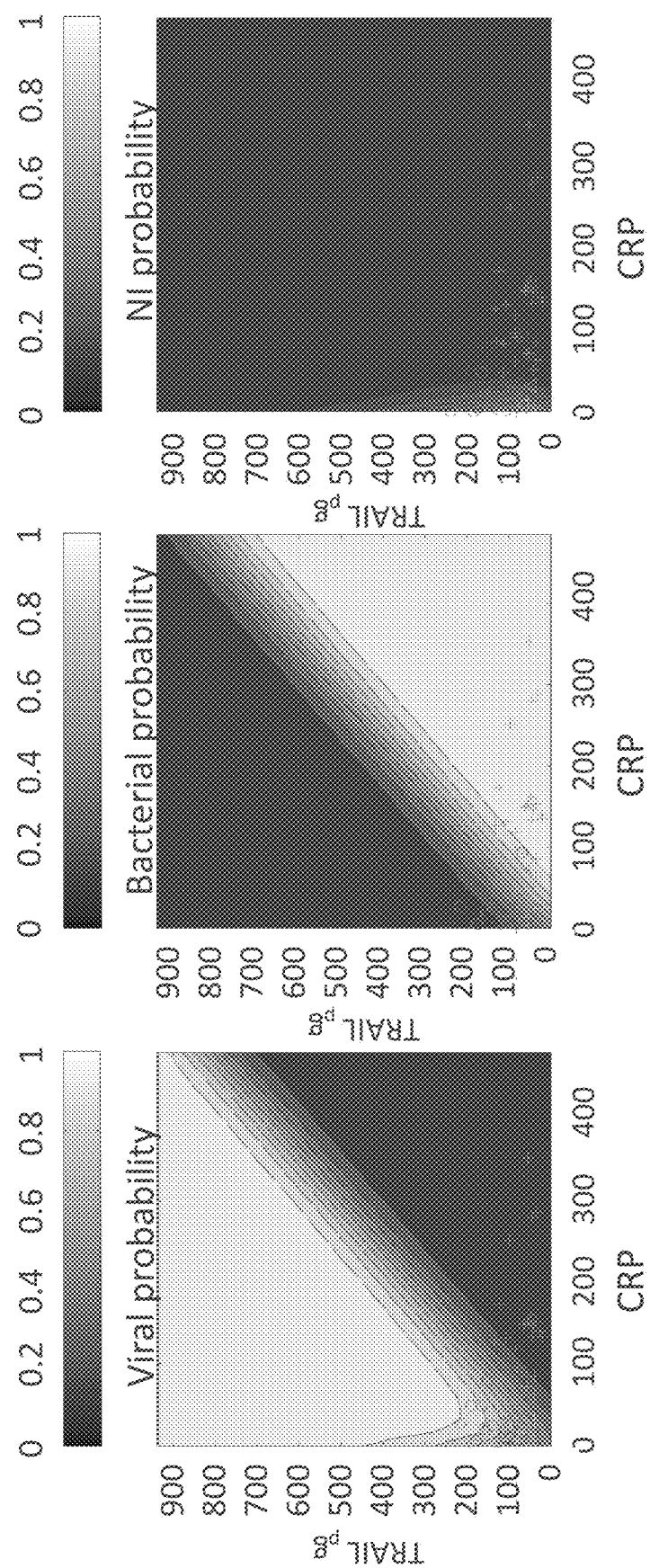

FIGS. 24A-24C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 300 to 400.

FIGS. 25A-25C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 400 to 500.

FIGS. 26A-26C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 500 to 1000.

Figures 27A, 27B, 27C:
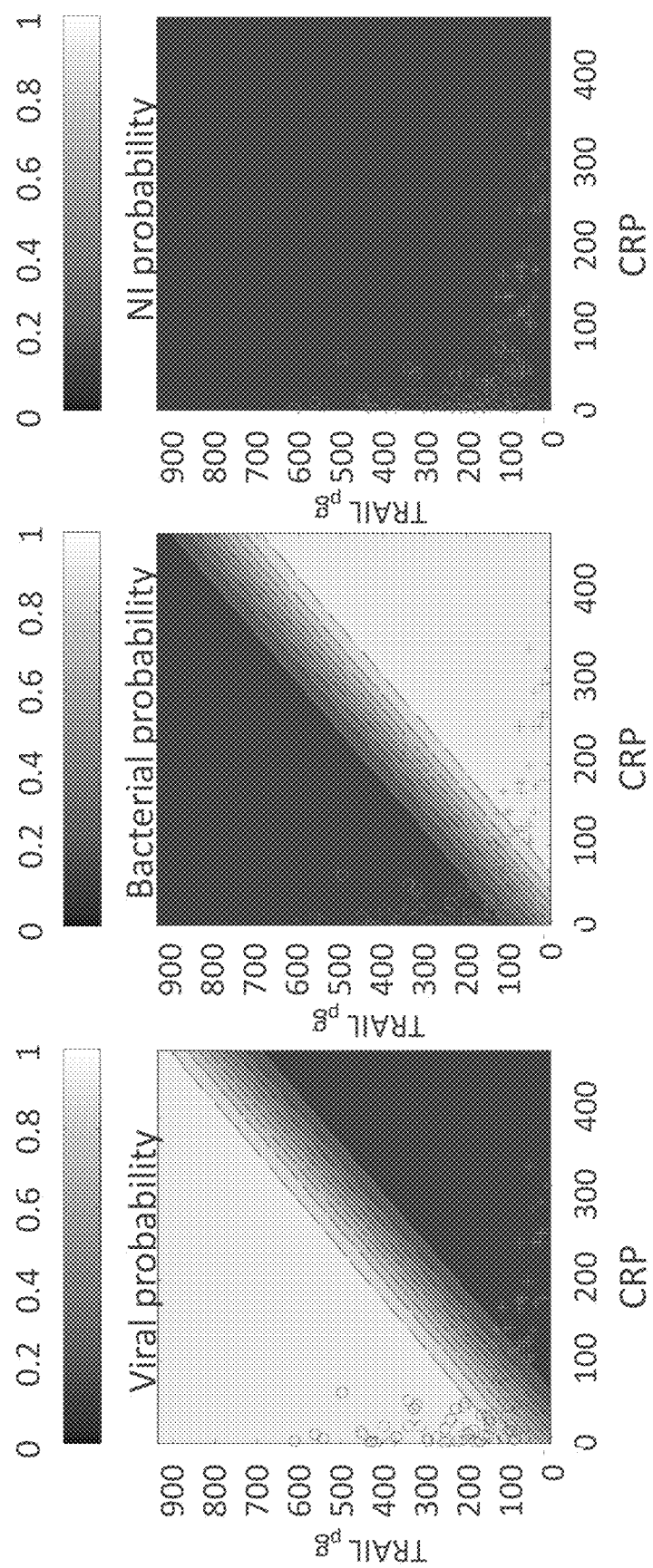
Figure 29F:
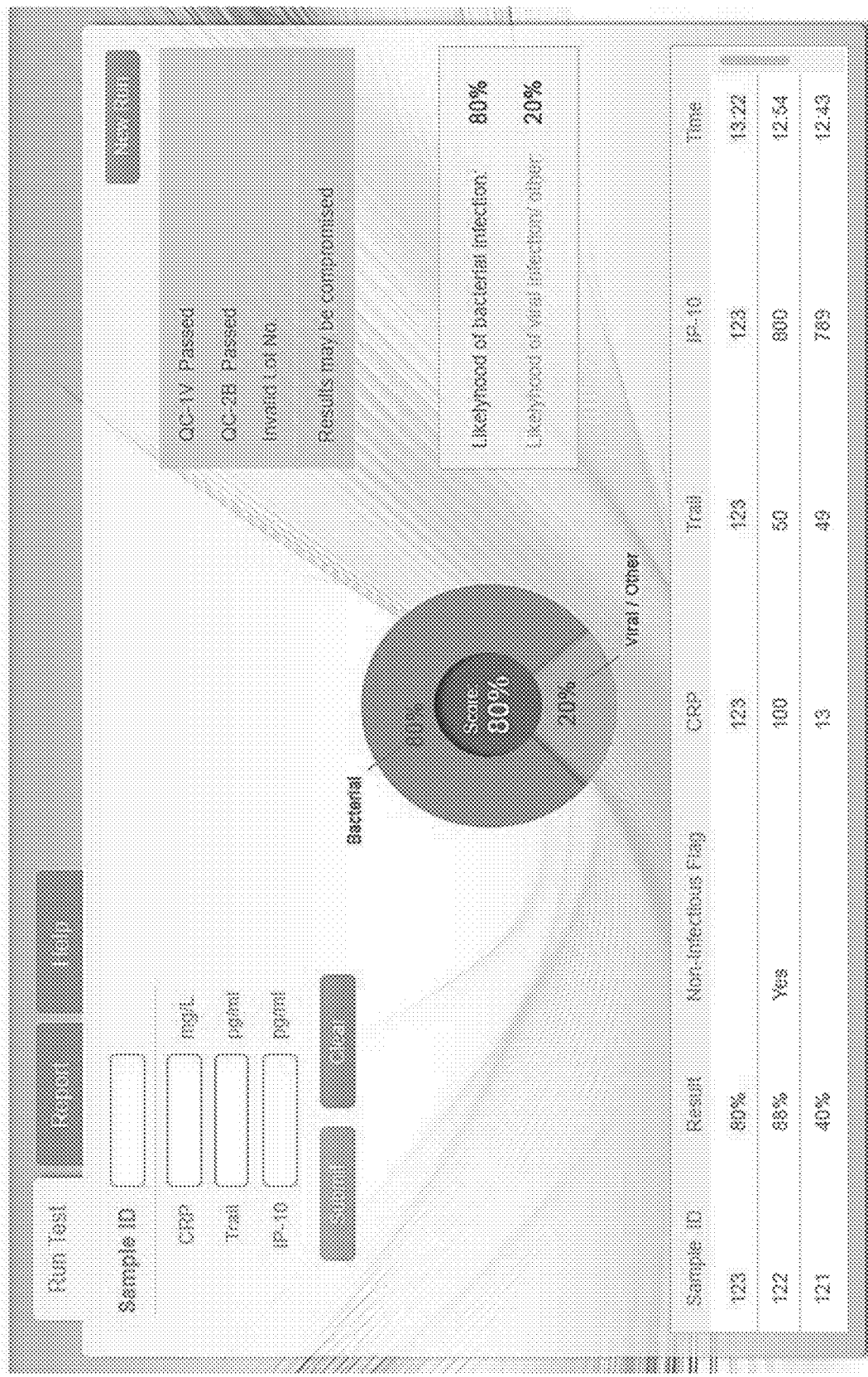

FIGS. 27A-27C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 1000 to 2000.

FIGS. 28A-28C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 which is 2000 or more.

FIGS. 29A-29F illustrate exemplary outputs of the method for distinguishing between bacterial and non-bacterial infection according to an embodiment of the present invention.

Figure 30A:
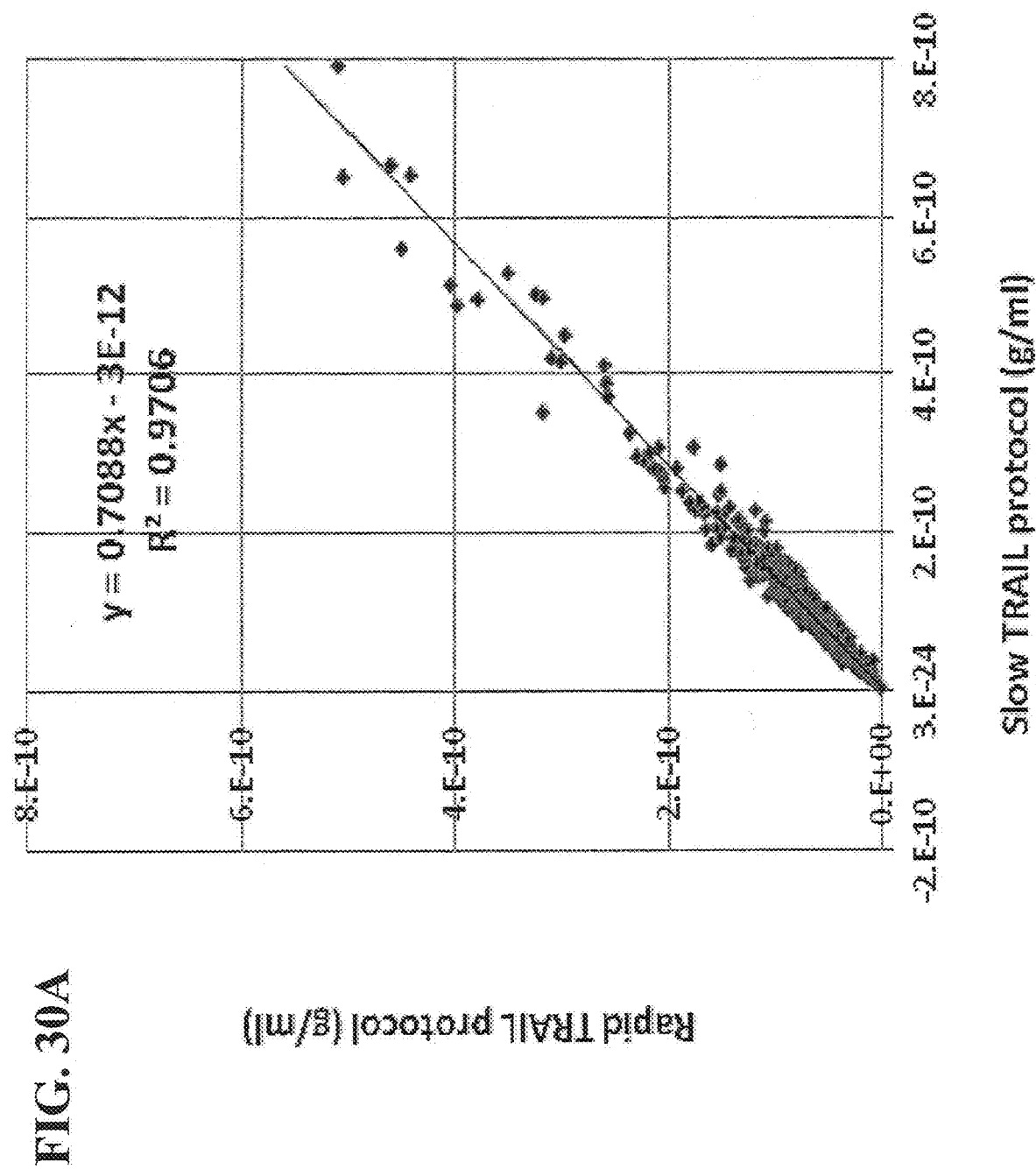
Figure 30B:
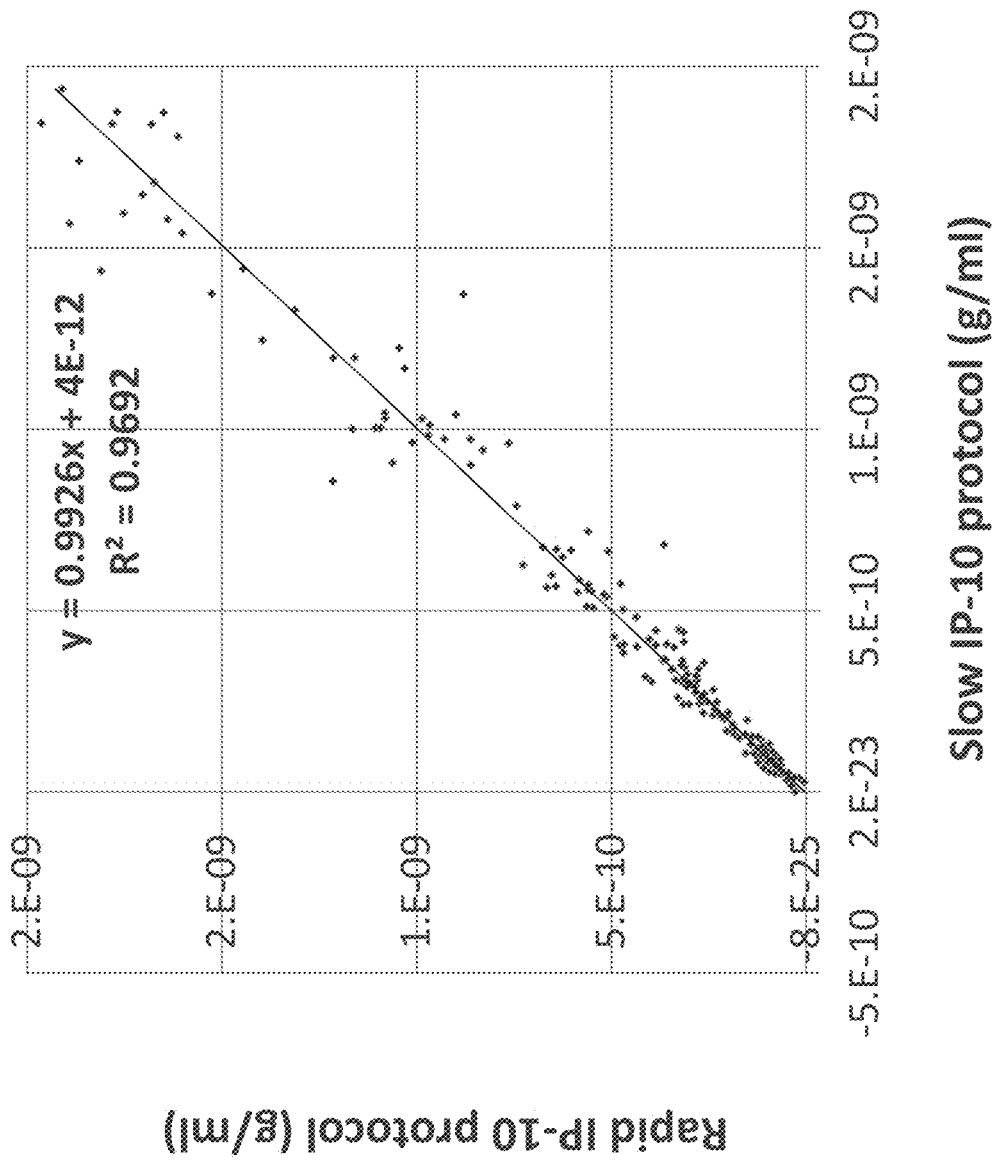

FIGS. 30A-30B are graphs illustrating the correlation between the rapid and slow protocol for measurement of TRAIL (FIG. 30A) and IP-10 (FIG. 30B).

FIG. 31 is a flowchart diagram of a method suitable for analyzing biological data obtained from a subject, according to various exemplary embodiments of the present invention.

Figure 32A:
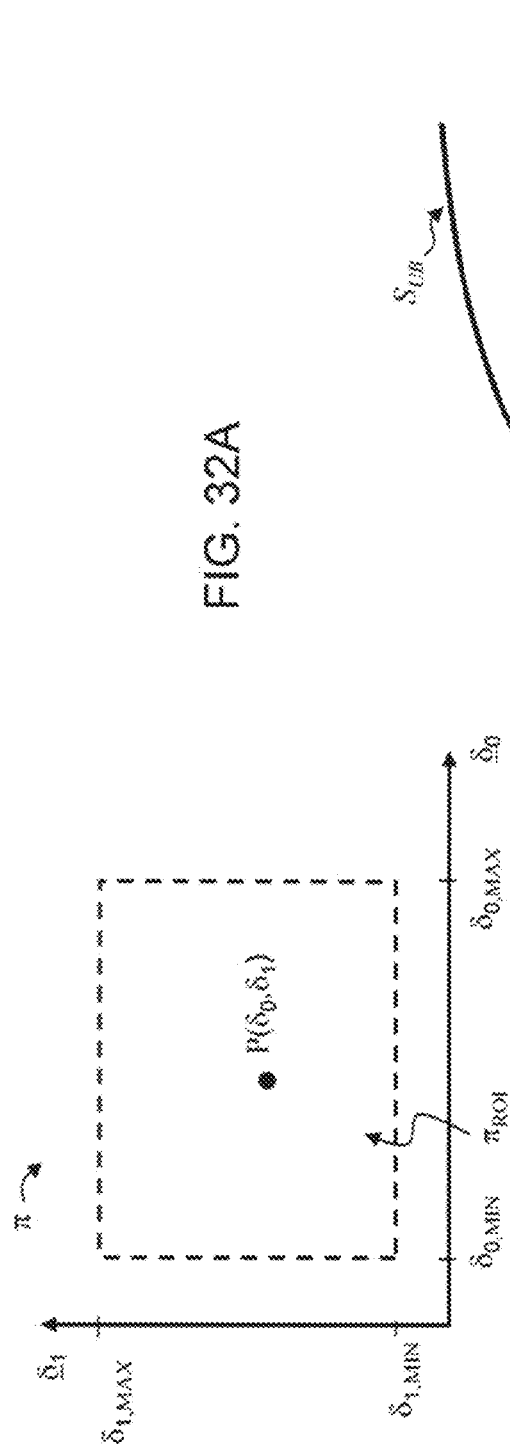
Figure 32B:
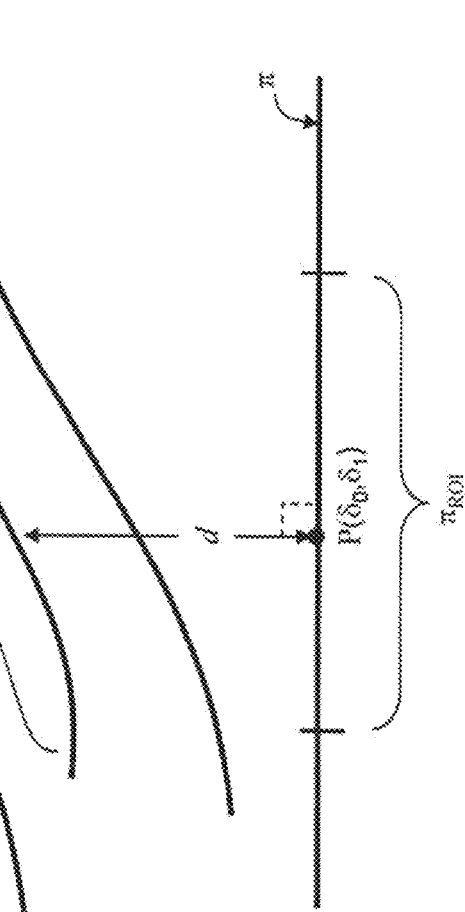

FIGS. 32A-32B are schematic illustrations describing a procedure for calculating a distance of a surface from a plane according to some embodiments of the present invention.

FIGS. 33A-33D are schematic illustrations describing a procedure for obtaining the smooth version of a segment of a surface, according to some embodiments of the present invention.

Figure 34:
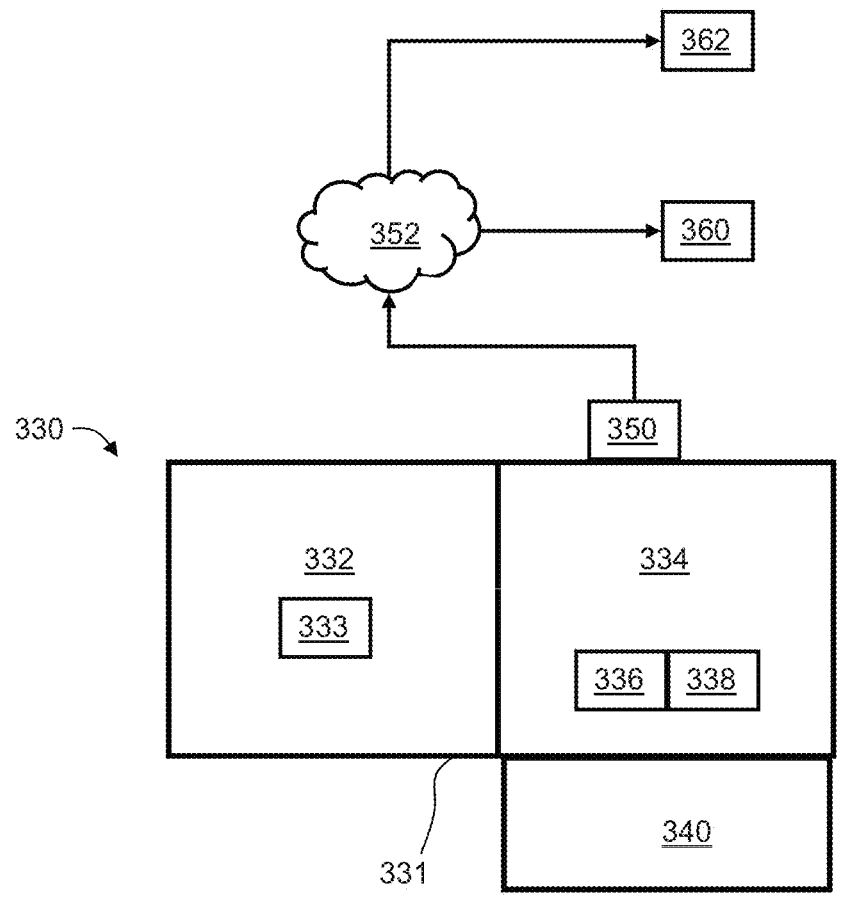
Figure 35A:
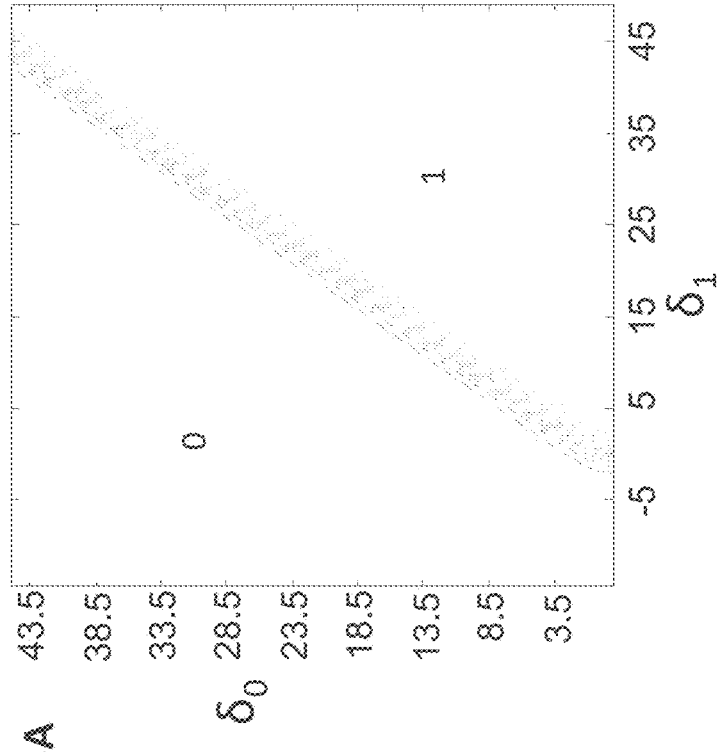
Figure 35B:
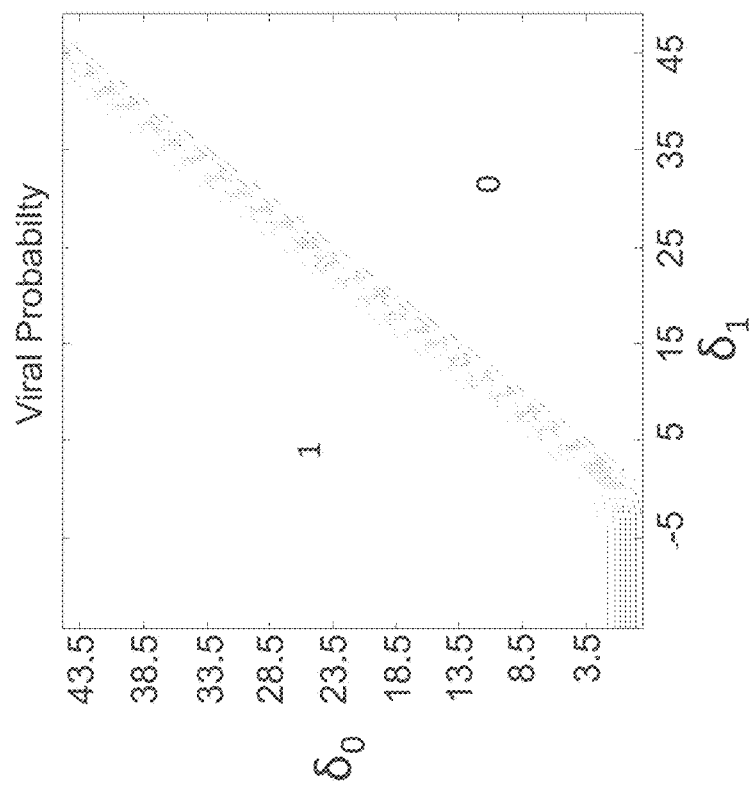
Figure 35C:
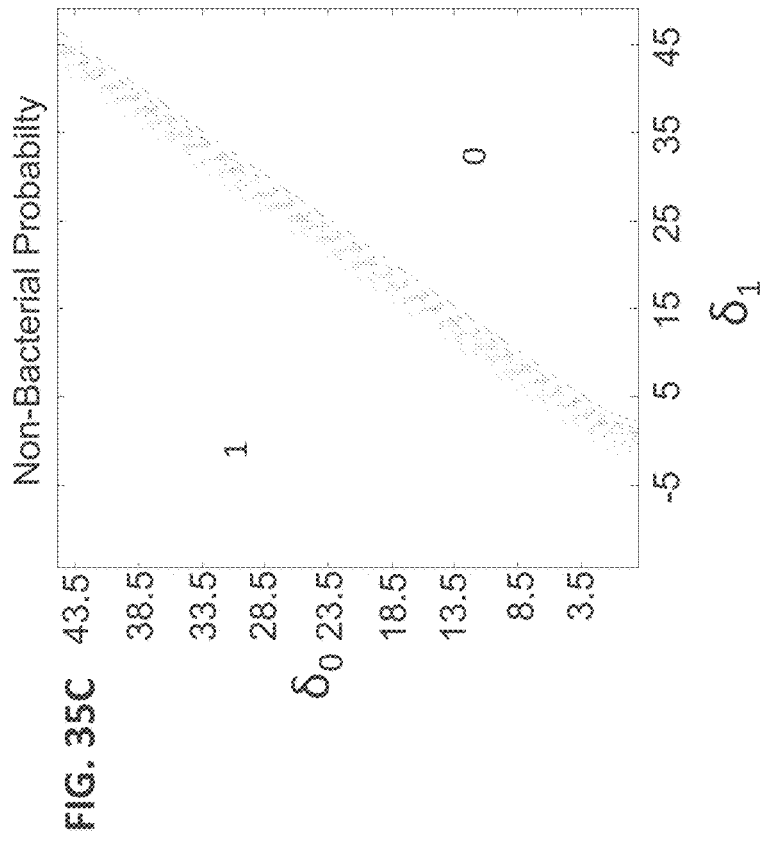
Figure 35D:
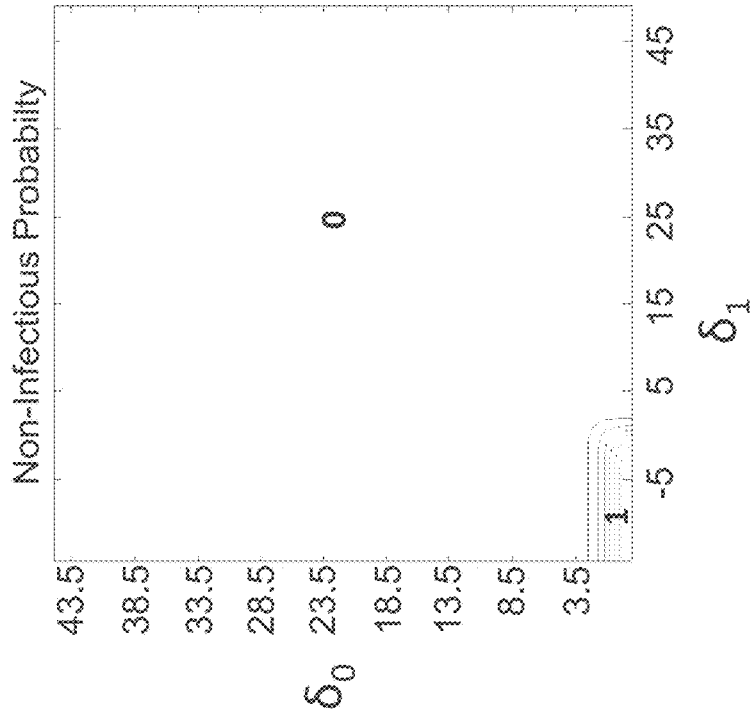

FIG. 34 is a schematic illustration of a block diagram of a system for analyzing biological data, according to some embodiments of the present invention.

FIGS. 35A-35D are contour plots describing the probability of bacterial (FIG. 35A), viral (FIG. 35B), non-bacterial (FIG. 35C), and non-infectious (FIG. 35D) etiologies as a function of the coordinates $\delta_0$ and $\delta_1$. The probability values range between 0% (black) to 100% (white).

Figure 36A:
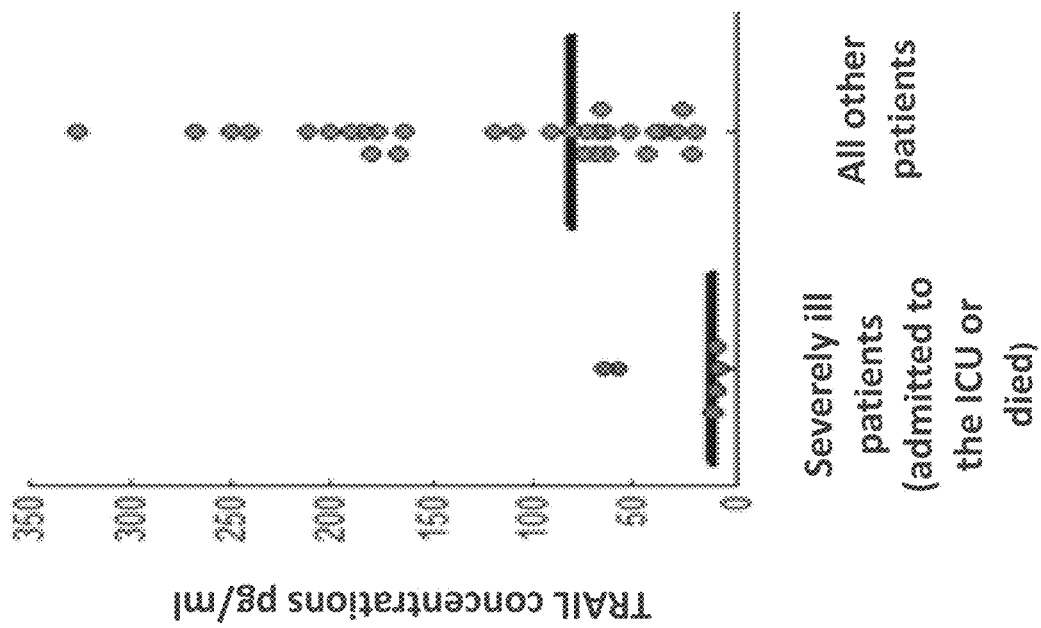
Figure 36B:
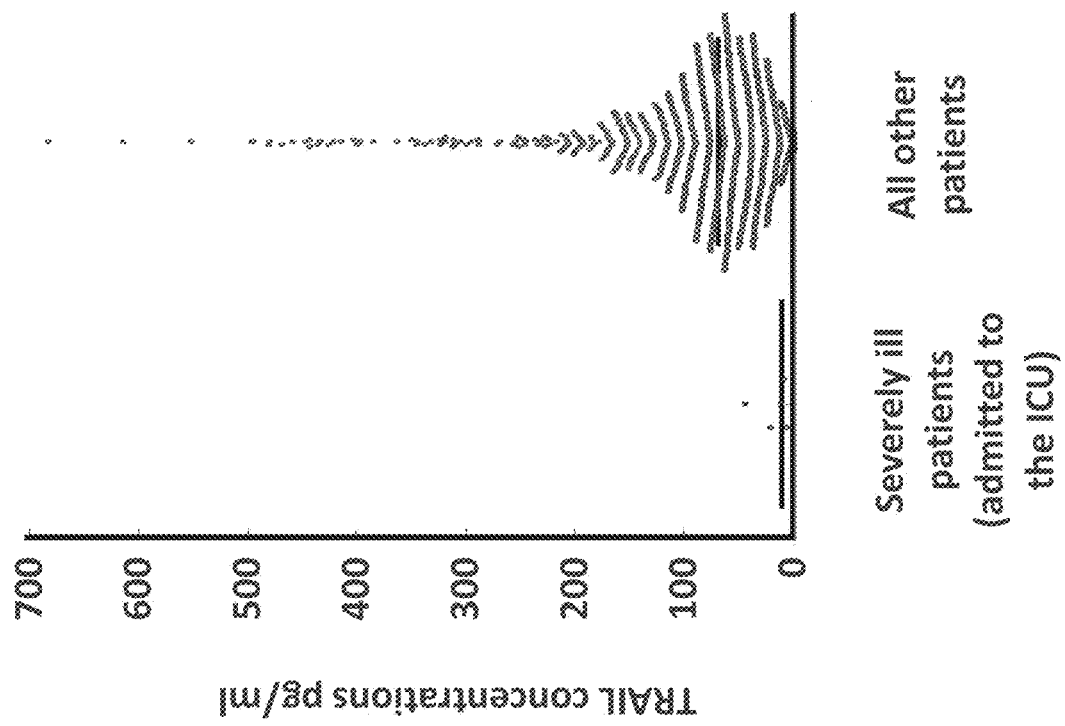

FIGS. 36A-36B. Low TRAIL levels are indicative or poor patient prognosis and outcome and high disease severity. (A) TRAIL concentrations in the serum of patients that were admitted to the ICU compared to all other patients (with infectious or non-infectious etiology). (B) TRAIL concentrations in the serum of pediatric patients that were admitted to the ICU or died compared to all other patients with infectious or non-infectious etiology.

Figure 37B:
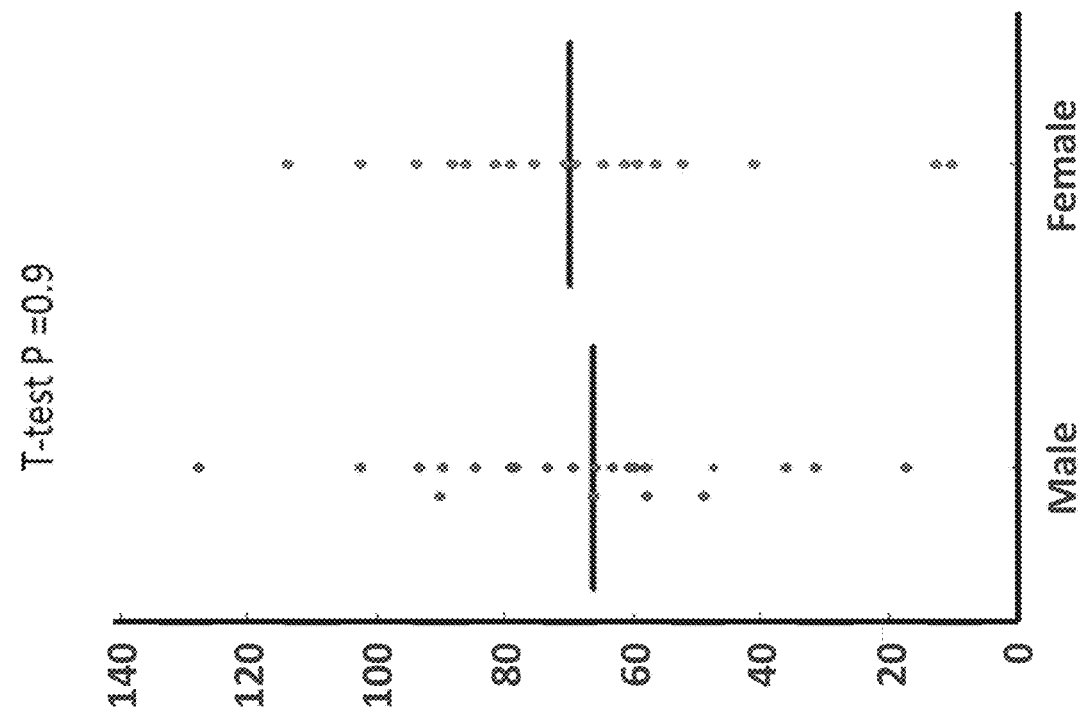
Figure 37A:
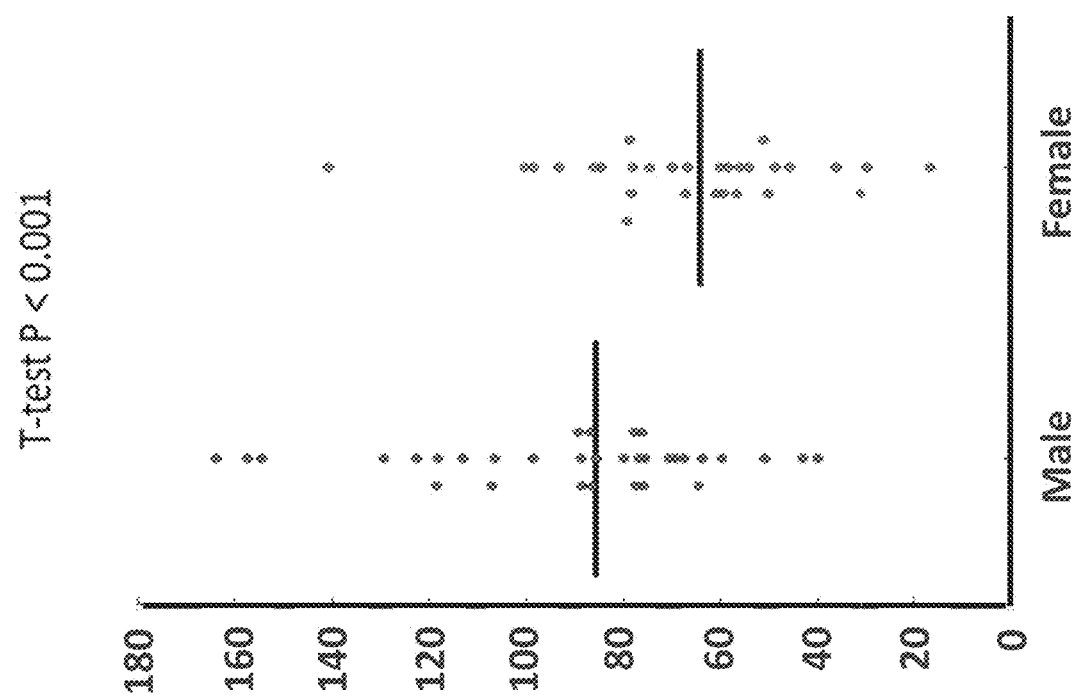

FIGS. 37A-37B are graphs illustrating the difference in TRAIL concentrations in males and females of fertility age.

FIGS. 38A-38E are screenshots of a graphical user interface (GUI) suitable for receiving user input in a computer-implemented method for analyzing biological data according to some embodiments of the present invention.

Figure 39A:
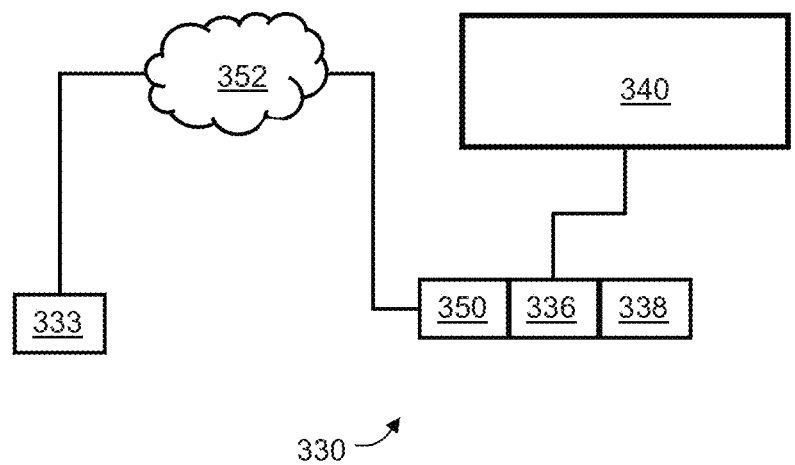
Figure 39B:
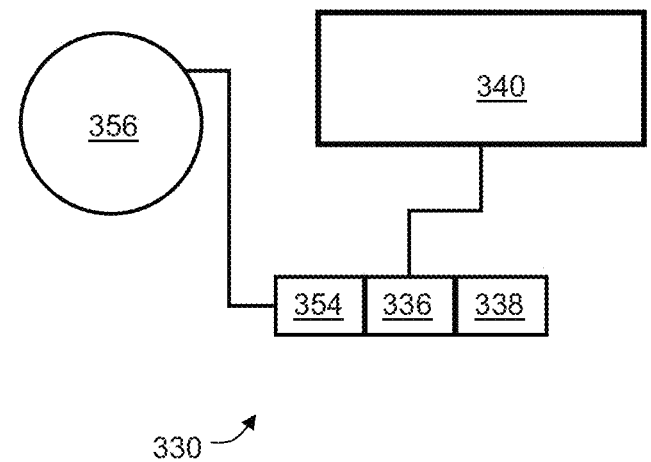

FIGS. 39A and 39B are schematic illustrations of a block diagram of a system for analyzing biological data, in embodiments of the invention in which the system comprises a network interface (FIG. 39A) and a user interface (FIG. 39B).

DESCRIPTION OF SPECIFIC EMBODIMENTS OF THE INVENTION

The present invention, in some embodiments thereof, relates to computational analysis, and, more particularly, but not exclusively, to computational analysis of biological data, e.g., for the purpose of distinguishing between bacterial infection and non-bacterial disease, and/or between a bacterial infection and viral infection, and/or between an infectious and non-infectious disease.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Different infectious agents have unique molecular patterns that can be identified and targeted by the immune system. Pathogen-associated molecular patterns (PAMPs) are an example of such molecules that are associated with different groups of pathogens and may be recognized by cells of the innate immune system using Toll-like receptors (TLRs) and other pattern recognition receptors (e.g. NOD proteins).

These patterns may vary considerably between different classes of pathogens and thus elicit different immune responses. For example, TLR-4 can recognize lipopolysaccharide, a constituent of gram negative bacteria, as well as lipoteichoic acids, constituent of gram positive bacteria, hence promoting an anti-microbial response of the immune system. TLR-3 can recognize single stranded RNA (often indicative of a viral infection) and thus prompt the appropriate anti-viral response. By distinguishing between different classes of pathogens (e.g bacterial versus viral) the immune system can mount the appropriate defense.

In the past few decades, several host markers have been identified that can be used for differential diagnosis of infection source in various indications. By measuring markers derived from the host rather than the pathogen, it is possible to minimize "false-positive" diagnoses due to non-pathogenic strains of bacteria that are part of the body's natural flora. One example is Procalcitonin (PCT), a precursor of the hormone calcitonin produced by the C-cells of the thyroid gland. PCT levels in the blood stream of healthy individuals is hardly detectable (in the pg/ml range) but it might increase dramatically, as a result of a severe infection with levels rising up to 100 ng/ml. PCT is heavily used to diagnose patients with systemic infection, sepsis, with sensitivity of 76% and specificity of 70%. However, studies that tested the diagnostic value of PCT in other non-systemic infection such as pneumonia or upper respiratory tract infections found it to be limited, especially when used in isolation.

The present inventors previously identified novel sets of biomarkers whose pattern of expression significantly correlates with infection type—as documented in International Patent Application WO2011132086 and WO2013/117746, both of which are incorporated herein by reference.

The present invention, in some embodiments thereof, is based on the use of signature of polypeptides for the diagnosis of bacterial infections, viral infections and non-bacterial, non-viral diseases. The methods of the present embodiments employ pattern recognition algorithms for the identification of the type of infection a subject is suffering from, which in turn allows for the selection of an appropriate treatment regimen. Various embodiments of the invention address limitations of current diagnostic solutions by: (i) allowing accurate diagnostics on a broad range of pathogens; (ii) enabling rapid diagnosis (within minutes); (iii) insensitivity to the presence of non-pathogenic bacteria and viruses (thus reducing the problem of false-positive); and (iv) eliminating the need for direct sampling of the pathogen, thus enabling diagnosis of inaccessible infections. Thus, some methods of the invention allow for the selection of subjects for whom antibiotic treatment is desired and prevent unnecessary antibiotic treatment of subjects having only a viral infection or a non-infectious disease. Some methods of the invention also allow for the selection of subjects for whom anti-viral treatment is advantageous.

To corroborate the findings in International Patent Application WO2013/117746, the present inventors have now increased the number of patients taking part in a multi-center clinical trial, enrolling 1002 hospital patients with different types of established infections as well as controls (patients with established non-viral/non-bacterial disease and healthy individuals).

Seeking to improve the level of accuracy and sensitivity of the previously described methods, the present inventors have now used a trinary classifier, which classifies patients (those having an established disease type) into one of three classes: bacterial infection, viral infection and non-bacterial, non-viral disease. Comparing the levels of a combination of polypeptides of a test subject with the expression patterns obtained in the study yielded superior results in terms of sensitivity and specificity compared to a binary classifier as summarized in Example 3 and Tables 9-12.

In the context of the present invention, the following abbreviations may be used: ANC=Absolute neutrophil count; ANN=Artificial neural networks; AUC=Area under the receiver operating curve; BP=*Bordetella pertussis*; CHF=Congestive heart failure; CI=Confidence interval; CID=Congenital immune deficiency; CLL=Chronic lymphocytic leukemia; CMV=Cytomegalovirus; CNS=Central nervous system; COPD=Chronic obstructive pulmonary disease; CP=*Chlamydophila* pneumonia; CRP=C-reactive protein; CSF=Cerebrospinal fluid; CV=Coefficient of variation; DOR=Diagnostic odds ratio; EBV=Epstein bar virus; eCRF=Electronic case report form; ED=Emergency department, ELISA=Enzyme-linked immunosorbent assay; FDR=False discovery rate; FMF=Familial Mediterranean fever; G-CSF=Granulocyte colony-stimulating factor; GM-CSF=Granulocyte-macrophage colony-stimulating factor; HBV=Hepatitis B virus; HCV=Hepatitis C virus; HI=*Haemophilus* influenza; HIV=Human immunodeficiency virus; IDE=Infectious disease experts; IL=Interleukin; IRB=institutional review board; IVIG=Intravenous immunoglobulin; KNN=K-nearest neighbors; LP=*Legionella pneumophila*; LR+=Positive likelihood ratio; LR-=Negative likelihood ratio; LRTI=Lower respiratory tract infections; mAb=Monoclonal antibodies; MDD=Minimum detectable dose; MDS=Myelodysplastic syndrome; MP=*Mycoplasma* pneumonia; MPD=Myeloproliferative disease; NPV=Negative predictive value; PCT=Procalcitonin; PED=Pediatric emergency department; PPV=Positive predictive value; QA=Quality assurance; RSV=Respiratory syncytial virus; RV=Rhinovirus; SIRS=systemic inflammatory syndrome; SP=*Streptococcus pneumonia*; STARD=Standards for Reporting of Diagnostic Accuracy; SVM=Support vector machine; TNF=Tumor necrosis factor; URTI=Upper respiratory tract infection; UTI=Urinary tract infection; WBC=White blood cell; WS=Wilcoxon rank-sum.

In the context of the present invention, the following statistical terms may be used:

"TP" is true positive, means positive test result that accurately reflects the tested-for activity. For example in the context of the present invention a TP, is for example but not limited to, truly classifying a bacterial infection as such.

"TN" is true negative, means negative test result that accurately reflects the tested-for activity. For example in the context of the present invention a TN, is for example but not limited to, truly classifying a viral infection as such.

"FN" is false negative, means a result that appears negative but fails to reveal a situation. For example in the context of the present invention a FN, is for example but not limited to, falsely classifying a bacterial infection as a viral infection.

"FP" is false positive, means test result that is erroneously classified in a positive category. For example in the context of the present invention a FP, is for example but not limited to, falsely classifying a viral infection as a bacterial infection.

"Sensitivity" is calculated by TP/(TP+FN) or the true positive fraction of disease subjects.

"Specificity" is calculated by TN/(TN+FP) or the true negative fraction of non-disease or normal subjects.

"Total accuracy" is calculated by (TN+TP)/(TN+FP+TP+FN).

"Positive predictive value" or "PPV" is calculated by TP/(TP+FP) or the true positive fraction of all positive test results. It is inherently impacted by the prevalence of the disease and pre-test probability of the population intended to be tested.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

"MCC" (Mathews Correlation coefficient) is calculated as follows: MCC=(TP*TN−FP*FN)/{(TP+FN)*(TP+FP)*(TN+FP)*(TN+FN)}^0.5
where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. MCC has been shown to be a useful for combining sensitivity and specificity into a single metric (Baldi, Brunak et al. 2000). It is also useful for measuring and optimizing classification accuracy in cases of unbalanced class sizes (Baldi, Brunak et al. 2000).

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), Mathews correlation coefficient (MCC), or as a likelihood, odds ratio, Receiver Operating Characteristic (ROC) curve, Area Under the Curve (AUC) among other measures.

"Analytical accuracy" refers to the reproducibility and predictability of the measurement process itself, and may be summarized in such measurements as coefficients of variation (CV), Pearson correlation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC and MCC, time to result, shelf life, etc. as relevant.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

Aspects of the invention will now be described in detail.

FIG. 31 is a flowchart diagram of a method suitable for analyzing biological data obtained from a subject, according to various exemplary embodiments of the present invention.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

In some embodiments of the present invention the subject has been previously treated with an antibiotic, and in some embodiments of the present invention the subject has not been previously treated with an antibiotic.

Any of the methods described herein can be embodied in many forms. For example, it can be embodied in on a tangible medium such as a computer for performing the method operations. It can be embodied on a computer readable medium, comprising computer readable instructions for carrying out the method operations. It can also be embodied in electronic device having digital computer capabilities arranged to run the computer program on the tangible medium or execute the instruction on a computer readable medium.

Computer programs implementing the method of the present embodiments can commonly be distributed to users on a distribution medium such as, but not limited to, CD-ROMs or flash memory media. From the distribution medium, the computer programs can be copied to a hard disk or a similar intermediate storage medium. In some embodiments of the present invention, computer programs implementing the method of the present embodiments can be distributed to users by allowing the user to download the programs from a remote location, via a communication network, e.g., the internet. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The computational operations of the method of the present embodiments can be executed by a computer, either remote from the subject or near the subject. When the computer is remote from the subject, it can receive the data over a network, such as a telephone network or the Internet. To this end, a local computer can be used to transmit the data to the remote computer. This configuration allows performing the analysis while the subject is at a different location (e.g., at home), and also allows performing simultaneous analyses for multiple subjects in multiple different locations.

The computational operations of the method can also be executed by a cloud computing resource of a cloud computing facility. The cloud computing resource can include a computing server and optionally also a storage server, and can be operated by a cloud computing client as known in the art.

The method according to some embodiments may be used to "rule in" a bacterial infection. Alternatively, the method may be used to rule out a non-bacterial infection. The method according to some embodiments can be used to "rule out" a bacterial infection and "rule in" a non-bacterial disease.

The method according to some embodiments may be used to "rule in" a viral infection. Alternatively, the method may be used to rule out a non-viral infection.

The method according to some embodiments can be used to "rule out" a viral infection and "rule in" a non-viral disease.

The method according to some embodiments may be used to "rule in" an infectious disease. Alternatively, the method may be used to rule out a non-infectious disease. The method according to some embodiments can be used to "rule out" an infectious disease and "rule in" a non-infectious disease.

The biological data analyzed by the method contain expression values of a plurality of polypeptides in the blood of a subject. In some embodiments the biological data comprises expression values of only two polypeptides, in some embodiments the biological data comprises expression values of at least three polypeptides, in some embodiments biological data comprises expression values of only three polypeptides, in some embodiments biological data comprises expression values of at least four polypeptides, in some embodiments biological data comprises expression values of only four polypeptides, in some embodiments biological data comprises expression values of at least five polypeptides, and in some embodiments biological data comprises expression values of only five polypeptides.

The present Inventors contemplate many types of polypeptides. Representative examples include, without limitation, CRP, IP-10, TRAIL, IL1ra, PCT and SAA. In some embodiments the plurality of polypeptides comprises at least CRP and TRAIL, and in some embodiments the plurality of polypeptides comprises at least CRP, TRAIL and IP-10.

In some embodiments of the present invention, the biological data is provided in the form of a subject-specific dataset, as further detailed herein.

According to a particular embodiment, the levels of secreted (i.e. soluble) polypeptides (e.g., TRAIL, CRP and IP-10) are analyzed by the method.

The term "subject" as used herein is preferably a human. A subject can be male or female. The subject may be a newborn, baby, infant or adult. A subject can be one who has been previously diagnosed or identified as having an infection, and optionally has already undergone, or is undergoing, a therapeutic intervention for the infection. Alternatively, a subject can also be one who has not been previously diagnosed as having an infection. For example, a subject can be one who exhibits one or more risk factors for having an infection. A subject may also have an infection but show no symptoms of infection.

The subject whose disease is being diagnosed according to some embodiments of the present invention is referred to below as the "test subject". The present Inventors have collected knowledge regarding the expression pattern of polypeptides, of a plurality of subjects whose disease has already been diagnosed, and have devised the analysis technique of the present embodiments based on the collected knowledge. This plurality of subjects is referred to below as "pre-diagnosed subjects" or "other subjects".

As used herein, the phrase "bacterial infection" refers to a condition in which a subject is infected with a bacterium. The infection may be symptomatic or asymptomatic. In the context of this invention, the bacterial infection may also comprise a viral component (i.e. be a mixed infection being the result of both a bacteria and a virus).

The bacterial infection may be acute or chronic.

An acute infection is characterized by rapid onset of disease, a relatively brief period of symptoms, and resolution within days. A chronic infection is an infection that develops slowly and lasts a long time. One difference between acute and chronic infection is that during acute infection the immune system often produces IgM+ antibodies against the infectious agent, whereas the chronic phase of the infection is usually characteristic of IgM−/IgG+ antibodies. In addition, acute infections cause immune mediated necrotic processes while chronic infections often cause inflammatory mediated fibrotic processes and scaring. Thus, acute and chronic infections may elicit different underlying immunological mechanisms.

The bacterial infection may be the result of gram-positive, gram-negative bacteria or atypical bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium complex, Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius, Streptococcus sanguis.*

The term "Gram-negative bacteria" as used herein refer to bacteria characterized by the presence of a double membrane surrounding each bacterial cell.

Representative Gram-negative bacteria include *Acinetobacter calcoaceticus, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio vulnificus, Yersinia enterocolitica* and *Yersinia pestis.*

The term "Atypical bacteria" refers to bacteria that do not fall into one of the classical "Gram" groups. Typically they are intracellular bacterial pathogens. They include, without limitations, Mycoplasmas spp., *Legionella* spp. Rickettsiae spp., and Chlamydiae spp.

The term "non-bacterial disease" as used herein, refers to any disease or condition that is not caused by infectious bacteria.

Referring to FIG. 31, the method begins at 310 and continues to 311 at which a first distance d between a segment $S_{ROI}$ of a first curved object S and a non-curved object π is calculated. Generally, the first curved object S is a manifold in n dimensions, where n is a positive integer, and the non-curved object π is a hyperplane in an n+1 dimensional space.

The concept of n-dimensional manifolds and hyperplanes in n+1 dimensions are well known to those skilled in the art of geometry. For example, when n=1 the first curved object is a curved line, and the non-curved object π is a hyperplane in 2 dimensions, namely a straight line defining an axis. When n=2, the first curved object is a curved surface, and the non-curved object π is a hyperplane in 3 dimensions, namely a flat plane, referred to below as "a plane".

The hyperplane π is defined by n directions. For example, when the non-curved object is an axis, it is defined by a single direction, and when the non-curved object is a plane it is defined by two directions, referred to as a first direction and a second direction.

The distance between the manifold S and hyperplane π is calculated at a point P over the hyperplane. P is defined by n coordinates. For example, when the hyperplane is an axis, P is defined by a single coordinate $\delta_1$, along the single direction, and when the hyperplane is a plane, P is define by a pair of coordinates denoted ($\delta_0$, $\delta_1$), where $\delta_0$ is referred to as "a first coordinate" and is defined along the first direction, and $\delta_1$ is referred to as "a second coordinate" and is defined along the second direction. Unless explicitly stated otherwise, a reference to coordinate $\delta_0$ describes an optional embodiment which is contemplated when S is a surface and π is a plane.

The directions are denoted using the same Greek letters as the respective coordinates, except that the directions are denoted by underlined Greek letters to indicate that these are vectors. Thus, the first direction is denoted $\underline{\delta}_0$, and the second direction is denoted $\underline{\delta}_1$.

FIG. 32A illustrates the hyperplane π for the case of n=2. In these embodiments, π is a plane defined by directions $\underline{\delta}_0$ and $\underline{\delta}_1$. Also shown is a point P at ($\delta_0$, $\delta_1$). Directions $\underline{\delta}_0$ and $\underline{\delta}_1$, are shown orthogonal to each other, but this need not necessarily be the case, since the angle between $\underline{\delta}_0$ and $\underline{\delta}_1$ can be different from 90°. Within the plane π, there is a planar region-of-interest $\pi_{ROI}$ spanning from a minimal first coordinate $\delta_{0,MIN}$ to a maximal first coordinate $\delta_{0,MAX}$ along direction $\underline{\delta}_0$, and from a minimal second coordinate $\delta_{1,MIN}$ to a maximal second coordinate $\delta_{1,MAX}$ along direction $\underline{\delta}_1$. The point P is within the region-of-interest $\pi_{ROI}$. When n=1 (not shown), π is an axis and the region-of-interest $\pi_{ROI}$ is a linear segment of π spanning from $\delta_{1,MIN}$ to $\delta_{1,MAX}$ along direction $\underline{\delta}_1$.

The calculation of the first distance d is illustrated in FIG. 32B which illustrates the hyperplane π and manifold S. The distance d is measured from S to the point P, perpendicularly to π. It is to be understood that while each of objects π and S is illustrated as a one dimensional line, this need not necessarily be the case, since S and π are generally n-dimensional mathematical objects. For example, when S is a surface and π is a plane both π and S are two dimensional mathematical objects. The segment $S_{ROI}$ of S is above a region-of-interest $\pi_{ROI}$. For example, when π is a plane $\pi_{ROI}$ is a planar region-of-interest, and when π is an axis, $\pi_{ROI}$ is a linear segment along the axis. Thus, $\pi_{ROI}$ is the projection of $S_{ROI}$ on π. For n=2, $S_{ROI}$ is preferably a non-planar segment of (the surface) S, and for n=1, $S_{ROI}$ is preferably a curved segment of (the curve) S.

Each of the n coordinates is defined by a combination of expression values of the polypeptides. For example, for n=1, the coordinate $\delta_1$ is defined by a combination of expression values of the polypeptides, and for n=2 each of the coordinates $\delta_0$ and $\delta_1$ is defined by a different combination of expression values of the polypeptides.

For example, $\delta_1$ and optionally also $\delta_0$ are combinations of the polypeptides, according to the following equation:

$$\delta_0 = a_0 + a_1 D_1 + a_2 D_2 + \ldots + \phi_0$$

$$\delta_1 = b_0 + b_1 D_1 + b_2 D_2 + \ldots + \phi_1,$$

where $a_0, a_1, \ldots$ and $b_0, b_1, \ldots$ are constant and predetermined coefficients, and each of the variables $D_1, D_2, \ldots$ is an expression levels of one of the polypeptides, and $\phi_0$ and $\phi_1$ are functions that are nonlinear with respect to at least one of the expression levels.

Each of the functions $\phi_0$ and $\phi_1$ is optional and may, independently, be set to zero (or, equivalently, not included in the calculation of the respective coordinate). When $\phi_0=0$ the coordinate $\delta_0$ is a combination of the polypeptides, and when $\phi_1=0$ the coordinate $\delta_1$ is a combination of the polypeptides.

The nonlinear functions $\phi_0$ and $\phi_1$ can optionally and preferably be expressed as a sub of powers of expression levels, for example, according to the following equations:

$$\phi_0 = \Sigma_i q_i X_i^{\gamma i}$$

$$\phi_1 = \Sigma_i r_i X_i^{\lambda i},$$

where i is a summation index, $q_i$ and $r_i$ are sets of coefficients, $X_i \in \{D_1, D_2, \ldots\}$, and each of γi and λi is a numerical exponent. Note that the number of terms in each of the nonlinear functions $\phi_0$ and $\phi_1$ does not necessarily equals the number of the polypeptides, and that two or more terms in each sum may correspond to the same polypeptide, albeit with a different numerical exponent.

Representative examples of coefficients suitable for the present embodiments are provided in the Examples section that follows (see Tables 3, 13-17, 29 and 31-36).

When $\phi_0=0$, $\phi_1=0$ and the polypeptides include TRAIL, $\delta_0$ is optionally and preferably an increasing function of an expression value of TRAIL, and $\delta_1$ is a decreasing function of TRAIL. When $\phi_0=0$, $\phi_1=0$ and the polypeptides include CRP, $\delta_1$ and optionally also $\delta_0$ are optionally and preferably increasing functions of an expression value of CRP. When the polypeptides include IP-10, $\delta_1$ and optionally also $\delta_0$ are optionally and preferably are increasing functions of an expression value of IP-10.

In embodiments in which $\phi_0=0$, $\phi_1=0$ and the polypeptides include TRAIL, CRP and IP-10, each $\delta_0$ and $\delta_1$ can be a linear combination of TRAIL, CRP and IP-10, according to the following equation:

$$\delta_0 = a_0 + a_1 C + a_2 I + a_3 T$$

$$\delta_1 = b_0 + b_1 C + b_2 I + b_3 T,$$

where C, I and T are, respectively, the expression levels of CRP, IP-10 and TRAIL.

Preferably, both $a_1$ and $b_1$ are positive. Preferably both $a_2$ and $b_2$ are positive.

Preferably, $a_3$ is positive, and $b_3$ is negative. Representative examples of coefficients suitable for the embodiments in which the combination is linear combination and the polypeptides are CRP, IP-10 and TRAIL are provided in the Examples section that follows (see Tables 3, 13-17 and 33).

In embodiments in which $\phi_0 \neq 0$, $\phi_1 \neq 0$ and the polypeptides include TRAIL, CRP and IP-10, each $\delta_0$ and $\delta_1$ can be a combination of TRAIL, CRP and IP-10, according to the following equations:

$$\delta_0 = a_0 + a_1 C + a_2 I + a_3 T + \phi_0$$

$$\delta_1 = b_0 + b_1 C + b_2 I + b_3 T + \phi_1,$$

where each of $\phi_0$ and $\phi_1$ is a nonlinear function of at least one or at least two of C, I and T. As a representative example, $\phi_0$ and $\phi_1$ can be expressed as:

$$\phi_0 = q_1 C^{\gamma 1} + q_2 C^{\gamma 2} + q_3 T^{\gamma 3}$$

$$\phi_1 = r_1 C^{\gamma 1} + r_2 C^{\gamma 2} + r_3 T^{\gamma 3}.$$

Representative examples of coefficients suitable for the embodiments in which the polypeptides are CRP, IP-10 and TRAIL and the nonlinear functions are not taken to be zero are provided in the Examples section that follows (see Table 36).

The boundaries $\delta_{0,MIN}$, $\delta_{0,MAX}$, $\delta_{1,MIN}$ and $\delta_{1,MAX}$ of $\pi_{ROI}$ preferably correspond to the physiologically possible ranges of the expression values of the polypeptides.

When measured using the protocols described in Example 8, more preferably Example 9, below, the physiologically possible ranges are typically from 0 to about 400 ug/ml (CRP), from 0 to about 3000 pg/ml (IP-10), and from 0 to about 700 pg/ml (TRAIL). Some subjects may exhibit concentrations that lie outside these ranges.—In various exemplary embodiments of the invention, when the expression values of TRAIL, CRP and IP-10 are measured according to the protocol described in Example 8, more preferably Example 9, below, the values of the coefficients $a_0, \ldots, a_3$ and $b_0, \ldots, b_3$ are taken from Table 3, below, and the boundaries of $\pi_{ROI}$ are: $\delta_{0,MIN}=-1.3$ $\delta_{0,MAX}=45$ $\delta_{1,MIN}N=-14.3$ and $\delta_{1,MAX}=49.6$.

When the expression values of TRAIL, CRP and IP-10 are measured by a protocol which is different from the protocol described in Example 8, more preferably Example 9, below, the values of the coefficients $a_0, \ldots, a_3$ and $b_0, \ldots, b_3$ are different from the values in Table 3 below, and therefore the boundaries of $\pi_{ROI}$ are also different from the above values. In such cases, the values of the coefficients and boundaries are correlative to the aforementioned values wherein the correlation for each coefficient and boundary is derived from the correlation between the expression value of the respective protein as measured according to the protocol described in Example 8, more preferably Example 9, and the expression value of the respective protein as actually measured.

At least a major part of the segment $S_{ROI}$ of curved object S is between two curved objects referred to below as a lower bound curved object $S_{LB}$ and an upper bound curved object $S_{UB}$.

As used herein "major part of the segment $S_{ROI}$" refers to a part of a smoothed version $S_{ROI}$ whose length (when n=1), surface area (when n=2) or volume (when n≥3) is 60% or 70% or 80% or 90% or 95% or 99% of a smoothed version of the length, surface area or volume of $S_{ROI}$, respectively.

As used herein, "a smooth version of the segment $S_{ROI}$" refers to the segment $S_{ROI}$, excluding regions of $S_{ROI}$ at the vicinity of points at which the Gaussian curvature is above a curvature threshold, which is X times the median curvature of $S_{ROI}$, where X is 1.5 or 2 or 4 or 8.

The following procedure can be employed for the purpose of determining whether the major part of the segment $S_{ROI}$ is between $S_{LB}$ and $S_{UB}$. Firstly, a smoothed version of the segment $S_{ROI}$ is obtained. Secondly, the length (when n=1), surface area (when n=2) or volume (when n≥3) $A_1$ of the smoothed version of the segment $S_{ROI}$ is calculated. Thirdly, the length (when n=1) surface area (when n=2) or volume (when n≥3) $A_2$ of the part of the smoothed version of the segment $S_{ROI}$ that is between $S_{LB}$ and $S_{UB}$ is calculated. Fourthly, the percentage of $A_2$ relative to $A_1$ is calculated.

FIGS. 33A-33D illustrates a procedure for obtaining the smooth version of $S_{ROI}$.

Figure 33A:
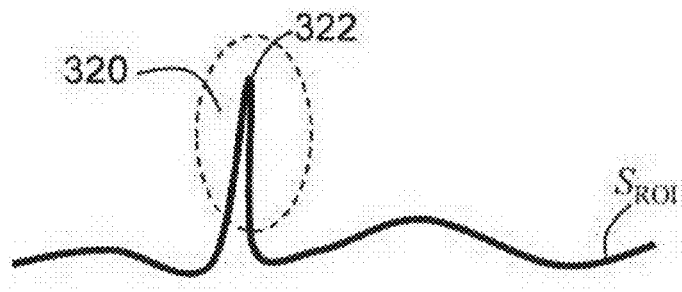
Figure 33B:
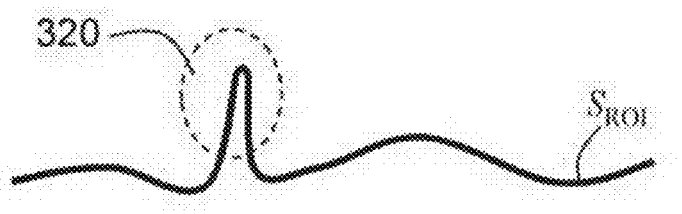
Figure 33C:
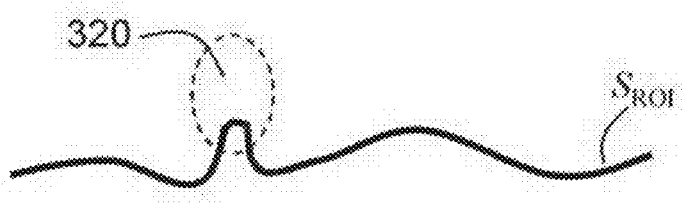
Figure 33D:
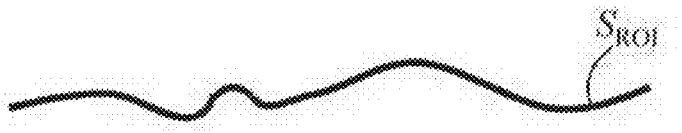

For clarity of presentation, $S_{ROI}$ is illustrated as a one dimensional segment, but the skilled person would understand that $S_{ROI}$ is generally an n-dimensional mathematical object. The Gaussian curvature is calculated for a sufficient number of sampled points on $S_{ROI}$. For example, when the manifold is represented as point cloud, the Gaussian curvature can be calculated for the points in the point cloud. The median of the Gaussian curvature is then obtained, and the curvature threshold is calculated by multiplying the obtained median by the factor X. FIG. 33A illustrates $S_{ROI}$ before the smoothing operation. Marked is a region 320 having one or more points 322 at which the Gaussian curvature is above the curvature threshold. The point or points at which with the Gaussian curvature is maximal within region 320 is removed and region 320 is smoothly interpolated, e.g., via polynomial interpolation, (FIG. 33B). The removal and interpolation is repeated iteratively (FIG. 33C) until the segment $S_{ROI}$ does not contain regions at which the Gaussian curvature is above the curvature threshold (FIG. 33D).

When n=1 (namely when S is a curved line), $S_{LB}$ is a lower bound curved line, and $S_{UB}$ an upper bound curved line. In these embodiments, $S_{LB}$ and $S_{UB}$ can be written in the form:

$$S_{LB}=f(\delta_1)-\varepsilon_0,$$

$$S_{UB}=f(\delta_1)-\varepsilon_1$$

where $f(\delta_1)$ is a probabilistic classification function of the coordinate $\delta_1$ (along the direction $\underline{\delta}_1$) which represents the likelihood that the test subject has a bacterial infection. In some embodiments of the invention $f(\delta_1)=1/(1+\exp(\delta_1))$. Both $S_{LB}$ and $S_{US}$ are positive for any value of $\delta_1$ within $\pi_{ROI}$. Also contemplated, are embodiments in which $f(\delta_1)$ is a probabilistic classification function which represents the likelihood that the test subject has a viral infection. Further contemplated, are embodiments in which $f(\delta_1)$ is a probabilistic classification function which represents the likelihood that the test subject has an infection.

When n=2 (namely when S is a curved surface), $S_{LB}$ is a lower bound curved surface, and $S_{UB}$ an upper bound curved surface. In these embodiments, $S_{LB}$ and $S_{UB}$ can be written in the form:

$$S_{LB}=f(\delta_0,\delta_1)-\varepsilon_0,$$

$$S_{UB}=f(\delta_0,\delta_1)+\varepsilon 1$$

where $f(\delta_0,\delta_1)$ is a probabilistic classification function of the first and second coordinates (along the first and second directions) which represents the likelihood that the test subject has a bacterial infection. In some embodiments of the invention $f(\delta_0,\delta_1)=\exp(\delta_1)/(1+\exp(\delta_0)+\exp(\delta_1))$. Both $S_{LB}$ and $S_{UB}$ are positive for any value of $\delta_0$ and $\delta_1$ within $\pi_{ROI}$.

In any of the above embodiments each of the parameters $\varepsilon_0$ and $\varepsilon_1$ is less than 0.5 or less than 0.4 or less than 0.3 or less than 0.2 or less than 0.1 or less than 0.05.

Referring again to FIG. 31, the method proceeds to 312 at which the calculated distance d is correlated to the presence of, absence of, or likelihood that the subject has, a disease or condition corresponding to the type of the probabilistic function f. For example, when the probabilistic function f represents the likelihood that the test subject has a bacterial infection, the calculated distance d is correlated to the presence of, absence of, or likelihood that the subject has, a bacterial infection.

In various exemplary embodiments of the invention the correlation includes determining that the distance d is the likelihood that the subject has a bacterial infection. The likelihood is optionally and preferably compared to a predetermined threshold $\omega_B$, wherein the method can determine that it is likely that the subject has a bacterial infection when the likelihood is above $\omega_B$, and that it is unlikely that the subject has a bacterial infection otherwise. Typical values for $\omega_B$ include, without limitation, about 0.2, about 0.3, about 0.4, about 0.5, about 0.6 and about 0.7. Other likelihood thresholds are also contemplated.

In some embodiments of the present invention, when the method determines that it is likely that the subject has a bacterial infection, the subject is treated (316) for the bacterial infection, as further detailed herein.

The present inventors found a probabilistic classification function $g(\delta_0,\delta_1)$ which represents the likelihood that the test subject has a viral infection. In various exemplary embodiments of the invention $g(\delta_0,\delta_1)$ equals $\exp(\delta_0)/(1+\exp(\delta_0)+\exp(\delta_1))$.

The function g can, according to some embodiments of the present invention, be utilized also for estimating the presence of, absence of, or likelihood that the subject has, a viral infection. Thus, in some embodiments, the method proceeds to 313 at which a second distance between a segment of a second curved surface and the plane π is calculated, and 314 at which the second distance is correlated to the presence of, absence of, or likelihood that the subject has, a viral infection. The procedure and definitions corresponding to 313 and 314 are similar to the procedure and definitions corresponding to 311 and 312 described above, mutatis mutandis. Thus, for example, a major part of the segment of the second surface is between a second lower bound surface $g(\delta_0,\delta_1)-\varepsilon_2$ and a second upper bound surface $g(\delta_0,\delta_1)+\varepsilon_3$, wherein each of $\delta_2$ and $\delta_3$ is less than 0.5 or less than 0.4 or less than 0.3 or less than 0.2 or less than less than 0.1 or less than 0.05.

In some embodiments of the present invention, when the method determines that it is likely that the subject has a viral infection, the subject is treated (316) for the viral infection, as further detailed herein.

In various exemplary embodiments of the invention the correlation includes determining that the second distance is the likelihood that the subject has a viral infection. The likelihood is optionally and preferably compared to a predetermined threshold $\omega_V$, wherein the method can determine that it is likely that the subject has a viral infection when the likelihood is above $\omega_V$, that it is unlikely that the subject has a viral infection otherwise. Typical values for $\omega_V$ include, without limitation, about 0.5, about 0.6 about 0.7 and about 0.8. Other likelihood thresholds are also contemplated.

In embodiments in which operations 313 and 314 are executed, operations 311 and 312 can be either executed or not executed. For example, the present embodiments contemplate a procedure in which operations 311 and 312 are not executed, and the method determines the likelihood that the subject has a viral infection, without calculating the first distance and without correlating the first distance to the presence of, absence of, or likelihood that the subject has, a bacterial infection.

Alternatively, all operations 311-314 can be executed, wherein 311 and 312 are executed irrespectively of the outcome of 314, and 313 and 314 are executed irrespectively of the outcome of 312. In these embodiments, the method optionally and preferably determines both the likelihood that the subject has a bacterial infection, and the likelihood that the subject has a viral infection. Each of these likelihoods can be compared to the respective predetermined threshold ($\omega_B$ or $\omega_V$). When each of the likelihoods is below the respective threshold, the method can determine that the patient is likely to have a non-bacterial and non-viral infectious disease. For example, the method can determine that it is likely that the subject has a non-infectious disease, a fungal disease or a parasitic disease.

Still alternatively, whether or not some operations are executed is dependent on the outcome of one or more other operations. For example, the method can execute 311 and 312, so as to determine the likelihood that the subject has a bacterial infection. Thereafter, the determined likelihood is compared to the threshold $\omega_B$. The method skips the execution of 313 and 314 if the determined likelihood is above $\omega_B$, and executes 313 and 314 otherwise. Another example of these embodiments is a procedure in which the method executes 313 and 314, so as to determine the likelihood that the subject has a viral infection. Thereafter, the determined likelihood is compared to the threshold $\omega_V$. The method skips the execution of 311 and 312 if the determined likelihood is above $\omega_V$, and executes 311 and 312 otherwise.

The method optionally and preferably continues to 315 at which an output of the likelihood(s) is generated. The output can be presented as text, and/or graphically and/or using a color index. The output can optionally include the results of the comparison to the threshold $\omega_B$. FIGS. 29A-29F and 38A-38E illustrate exemplary outputs suitable for distinguishing between bacterial and non-bacterial infection according to an embodiment of the present invention.

The method ends at 317.

FIGS. 38A-38E are screenshots of a graphical user interface (GUI) suitable for receiving user input in a computer-implemented method for analyzing biological data according to some embodiments of the present invention.

The GUI comprises a calculation activation control 390, that may be in the form of a button control. The GUI may also comprise a plurality of expression value input fields 380, wherein each expression value input field is configured for receiving from a user an expression value of a polypeptide in the blood of a subject. The user feeds into the input fields the expression values of the polypeptides. Alternatively, the expression values are can be received by establishing a communication between the computer and an external machine (not shown) that measures the expression values. In these embodiments, it is not necessary for the user to manually feed the expression values into the input fields. In some embodiments, the GUI comprises a communication control 392, e.g., in the form of a button control, wherein the communication with the external machine is in response to an activation of the communication control by the user.

Responsively to an activation of control 390 by the user, the computer calculates a score based on the expression values as received automatically or via fields 380. The core can be the likelihood that the subject has a bacterial infection and/or a viral infection. The score can be calculated for example, by calculating a distance between a curved surface and a plane defined by the two directions as further detailed hereinabove.

A graphical scale 382 can be generated on the GUI. The graphical scale can include a first end, identified as corresponding to a viral infection, and a second end, identified as corresponding to a bacterial infection.

Figure 38A:
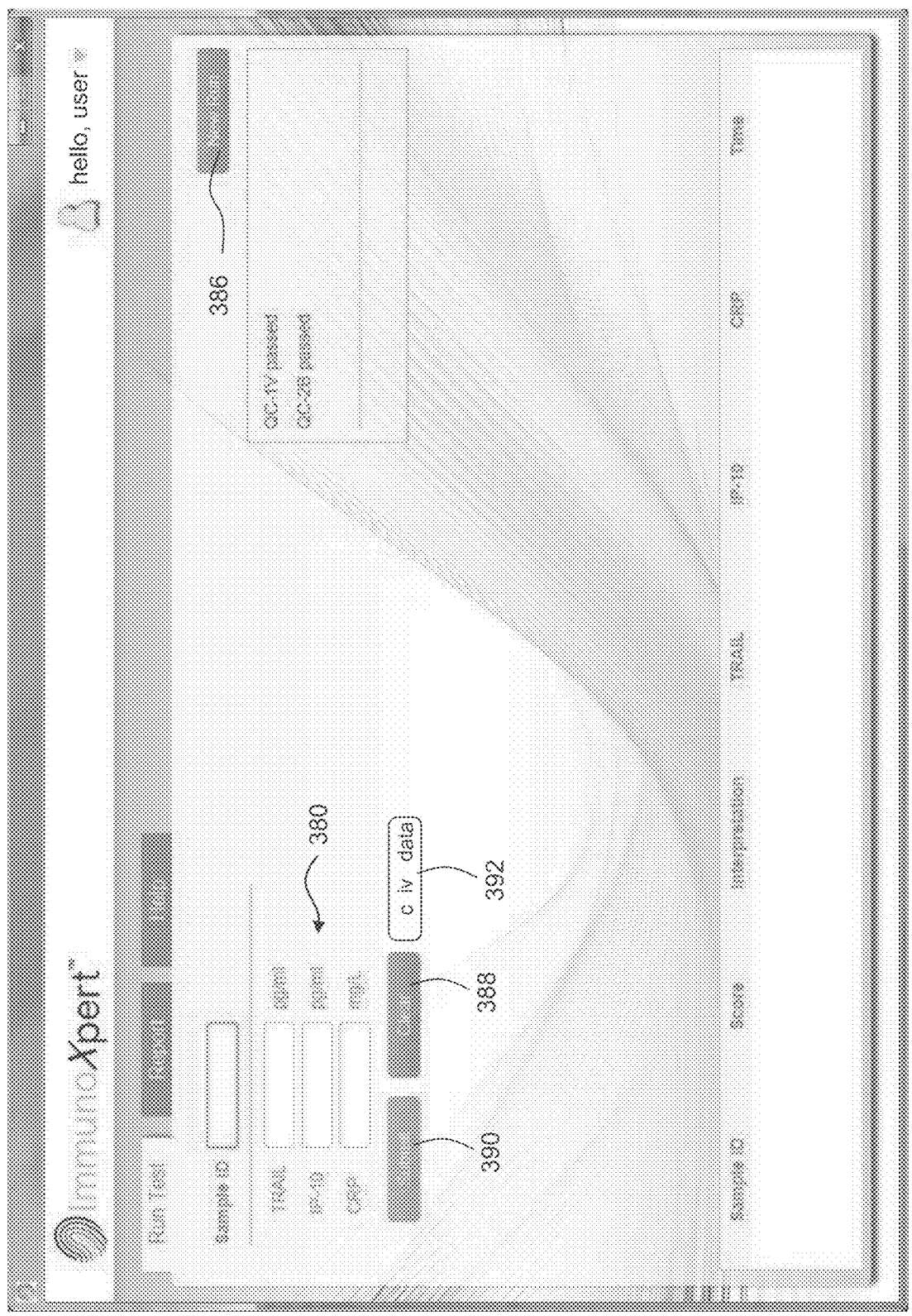
Figure 38B:
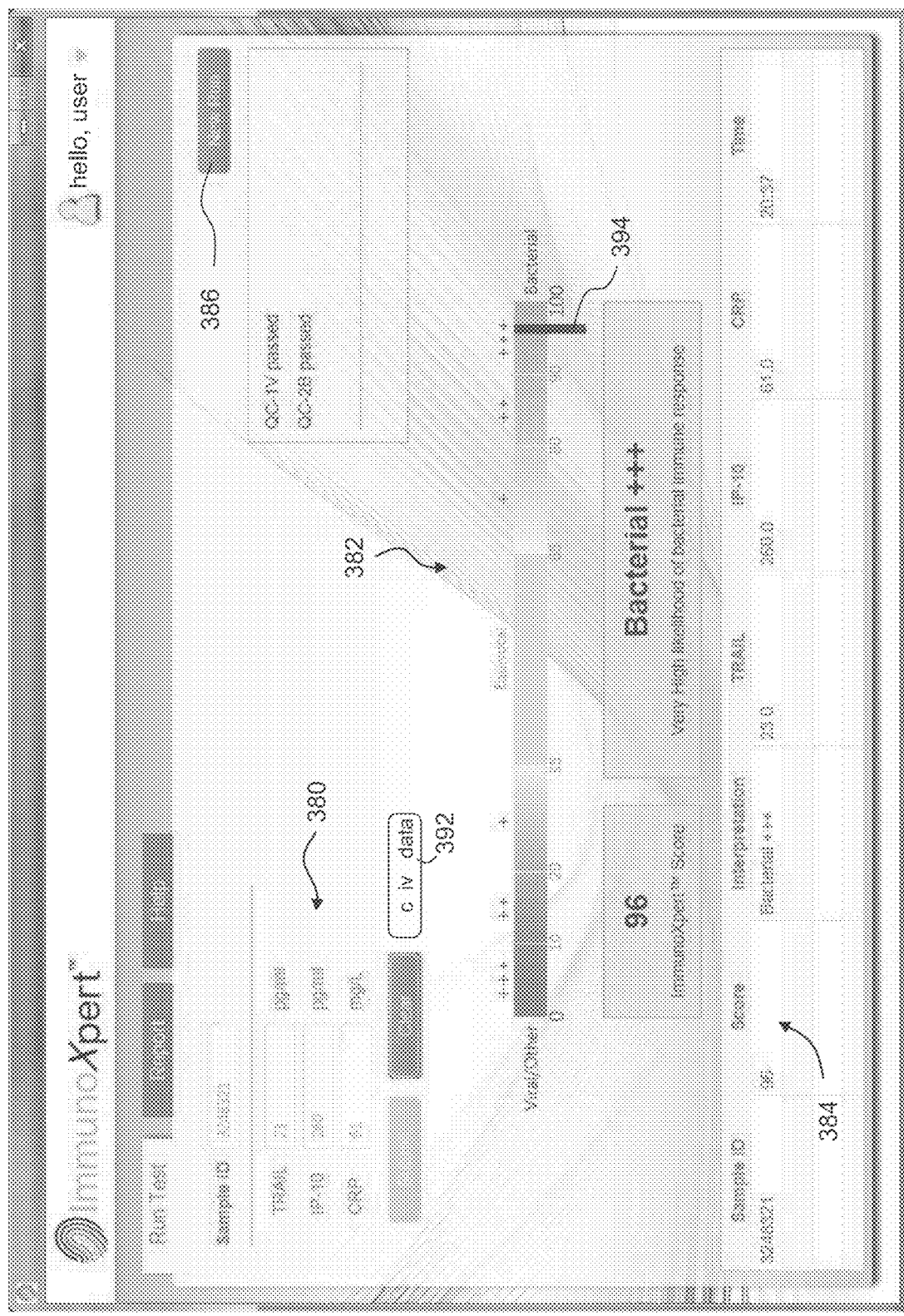
Figure 38C:
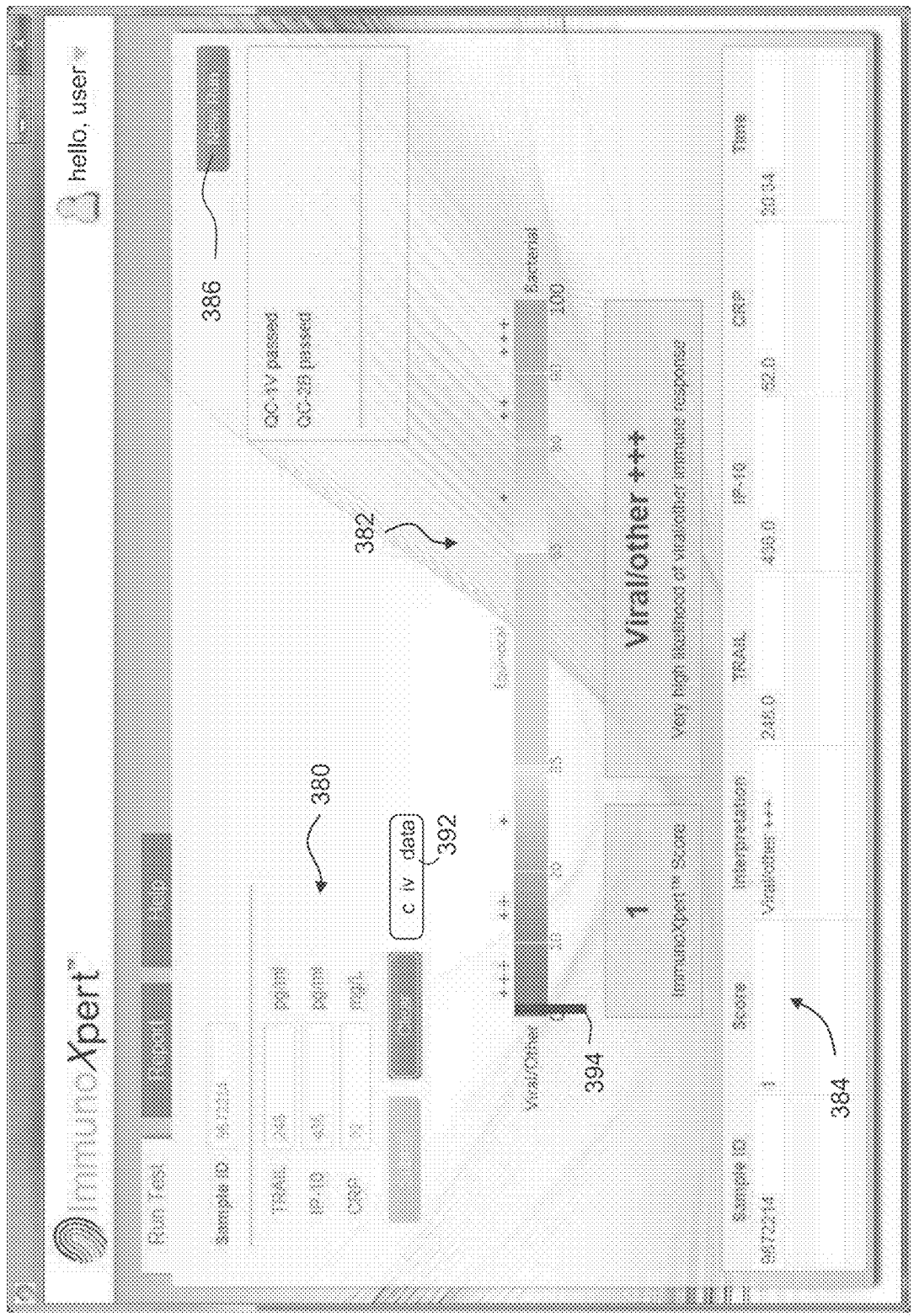
Figure 38D:
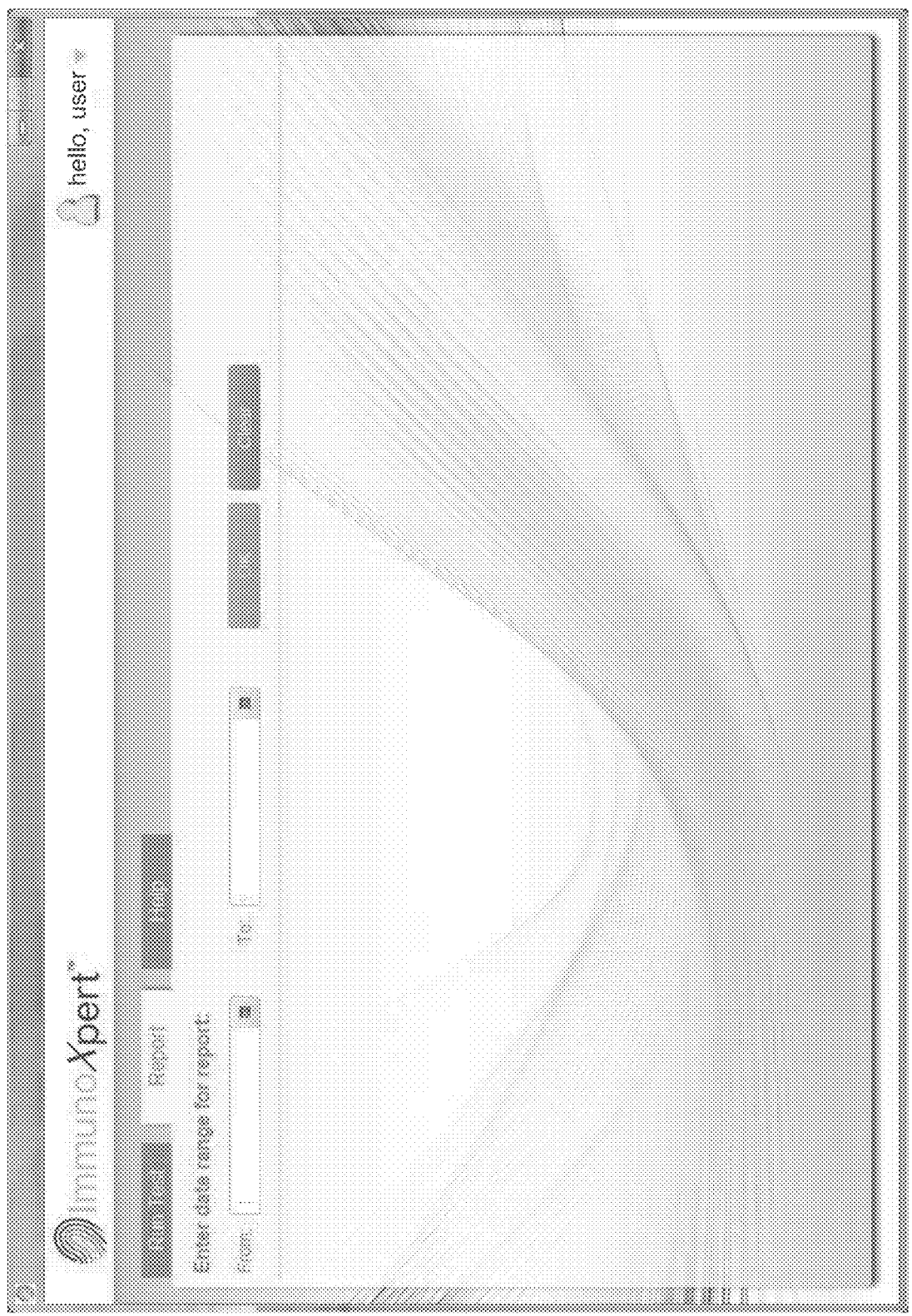
Figure 38E:

Once the score is calculated, a mark 394 can optionally and preferably be made on the graphical 382 at a location corresponding to the calculated likelihood. FIG. 38A shows the GUI before the values have been fed into the input fields, FIG. 38B shows mark 394 on scale 382 at a location that corresponds to a likelihood of 96% that the infection is bacterial, and FIG. 38C shows mark 394 on scale 382 at a location that corresponds to a likelihood of 1% that the infection is bacterial (or, equivalently, likelihood of 99% that the infection is viral). Optionally, the GUI also displays the calculated score numerically.

The GUI optionally and preferably includes one or more additional controls 386, 388 that may be in the form of button controls. For example, control 388 can instruct the computer to clear the input fields 380 when the user activates the control 388. This allows the user to feed values that correspond to a different sample. In some embodiments, the GUI also generates an output 384 that summarizes the results of the previous samples. Control 386 can instruct the computer to clear the input fields 380 as well as the output 384 when the user activates the control 386. This allows the user to begin a new run (optionally with multiple samples) without logging out of the GUI.

A representative example of a protocol suitable for the present embodiments is as follows.

The GUI presents an authenticated user with a dialog that allows the user to feed in quality control (QC) values of an experiment. The QC is validated, and the GUI in FIG. 38A is generated. The user feeds in the expression values in fields 380 and activate control 390 to receive the result (e.g., FIGS. 38B and 38C). To feed in expression values of another blood sample the user activates control 388. The result of each sample is added to output 384 which can be, for example, in the form of a table. To enter a new experiment without closing the software or logging out the user activates control 386 to clear output 384 and enter new QC values. Preferably, all the operations are logged in one or more log files.

In some embodiments of the present invention GUI also includes a report screen (FIGS. 38D and 38E) that displays the results of previous experiments, for example, in response to a date based request.

It will be appreciated that the polypeptide names presented herein are given by way of example. Many alternative names, aliases, modifications, isoforms and variations will be apparent to those skilled in the art. Accordingly, it is intended to embrace all the alternative protein names, aliases, modifications isoforms and variations.

Gene products, are identified based on the official letter abbreviation or gene symbol assigned by the international Human Genome Organization Naming Committee (HGNC) and listed at the date of this filing at the US National Center for Biotechnology Information (NCBI) web site also known as Entrez Gene.

TRAIL:

The protein, TNF Related Apoptosis Inducing Ligand (TRAIL), encoded by this gene is a cytokine that belongs to the tumor necrosis factor (TNF) ligand family. Additional names of the gene include without limitations APO2L, TNF-related apoptosis-inducing ligand, TNFSF10 and CD253. TRAIL exists in a membrane bound form and a soluble form, both of which can induce apoptosis in different cells, such as transformed tumor cells. This protein binds to several members of the TNF receptor superfamily such as TNFRSF10A/TRAILR1, NFRSF10B/TRAILR2, NFRSF10C/TRAILR3, TNFRSF10D/TRAILR4, and possibly also to NFRSF11B/OPG. The activity of this protein may be modulated by binding to the decoy receptors such as NFRSF10C/TRAILR3, TNFRSF10D/TRAILR4, and NFRSF11B/OPG that cannot induce apoptosis. The binding of this protein to its receptors has been shown to trigger the activation of MAPK8/JNK, caspase 8, and caspase 3. Alternatively spliced transcript variants encoding different isoforms have been found for this gene. TRAIL can be proteolytically cleaved from the cell surface to produce a soluble form that has a homotrimeric structure.

According to a particular embodiment, the level of the soluble (i.e. secreted) form of TRAIL is measured.

According to another embodiment, the membrane form of TRAIL is measured.

According to still another embodiment, both the membrane form of TRAIL and the secreted form of TRAIL are measured.

According to another aspect of the present invention there is provided a method of determining an infection type in a subject comprising measuring the concentration of soluble TRAIL and insoluble TRAIL, wherein the concentration is indicative of the infection type.

In one embodiment, when the concentration of the soluble TRAIL is higher than a pre-determined threshold value, a bacterial infection is ruled out for the subject.

In another embodiment, when the concentration of the soluble TRAIL is higher than a pre-determined threshold value, a viral infection is ruled in for the subject.

Exemplary protein sequences for soluble TRAIL are set forth in SEQ ID NO: 37 and SEQ ID NO: 38.

An exemplary mRNA sequence of membrane human TRAIL is set forth in SEQ ID NO: 1.

An exemplary amino acid sequences of membrane human TRAIL is set forth in SEQ ID NOs: 4.

Other exemplary cDNA and amino acid sequences for TRAIL are set forth in SEQ ID NOs: 2, 3 and 5-8.

IP10: This gene encodes a chemokine of the CXC subfamily and ligand for the receptor CXCR3. Binding of this protein to CXCR3 results in pleiotropic effects, including stimulation of monocytes, natural killer and T-cell migration, and modulation of adhesion molecule expression. Additional names of the gene include without limitations: IP-10, CXCL10, Gamma-IP10, INP10 and chemokine (C-X-C motif) ligand 10.

Exemplary cDNA sequence of human IP10 is set forth in SEQ ID NOs: 9-12.

An exemplary amino acid sequence of human IP10 is set forth in SEQ ID NO: 13.

CRP:

C-reactive protein; additional aliases of CRP include without limitation RP11-419N10.4 and PTX1. The protein encoded by this gene belongs to the pentaxin family. It is involved in several host defense related functions based on its ability to recognize foreign pathogens and damaged cells of the host and to initiate their elimination by interacting with humoral and cellular effector systems in the blood. Consequently, the level of this protein in plasma increases greatly during acute phase response to tissue injury, infection, or other inflammatory stimuli. CRP displays several functions associated with host defense: it promotes agglutination, bacterial capsular swelling, phagocytosis and complement fixation through its calcium-dependent binding to phosphorylcholine.

Exemplary cDNA sequence of human CRP is set forth in SEQ ID NOs: 14-16.

An exemplary amino acid sequence of human CRP is set forth in SEQ ID NO: 17.

IL1RA:

The protein encoded by this gene is a cytokine receptor that belongs to the interleukin 1 receptor family. This protein is a receptor for interleukin alpha (IL1A), interleukin beta (IL1B), and interleukin 1 receptor, type I (IL1R1/IL1RA). It is an important mediator involved in many cytokine induced immune and inflammatory responses. Additional names of the gene include without limitations: CD121A, IL-1RT1, p80, CD121a antigen, CD121A, IL1R and IL1ra.

Exemplary cDNA sequences of human IL1RA are set forth in SEQ ID NOs: 18, 19 and 20.

Exemplary amino acid sequences of human IL1RA are set forth in SEQ ID NOs:21-24.

PCT:

Procalcitonin (PCT) is a peptide precursor of the hormone calcitonin, the latter being involved with calcium homeostasis. Procalcitonin ("pCT") is a protein consisting of 116 amino acids and having a molecular weight of about 13,000 dalton. It is the prohormone of calcitonin which under normal metabolic conditions is produced and secreted by the C cells of the thyroid. pCT and calcitonin synthesis is initiated by translation of preprocalcitonin ("pre-pCT"), a precursor peptide comprising 141 amino acids. The amino acid sequence of human pre-pCT was described by Moullec et al. in FEBS Letters, 167:93-97 in 1984. pCT is formed after cleavage of the signal peptide (first 25 amino acids of pre-pCT).

Exemplary cDNA sequences of human PCT are set forth in SEQ ID NOs: 31-32.

Exemplary amino acid sequences of human PCT are set forth in SEQ ID NOs:33-36.

SAA:

encodes a member of the serum amyloid A family of apolipoproteins. The encoded protein is a major acute phase protein that is highly expressed in response to inflammation and tissue injury. This protein also plays an important role in HDL metabolism and cholesterol homeostasis. High levels of this protein are associated with chronic inflammatory diseases including atherosclerosis, rheumatoid arthritis, Alzheimer's disease and Crohn's disease. This protein may also be a potential biomarker for certain tumors. Alternate splicing results in multiple transcript variants that encode the same protein.

Exemplary cDNA sequences of human SAA are set forth in SEQ ID NOs: 25-27.

Exemplary amino acid sequences of human SAA are set forth in SEQ ID NO:28-30.

It will be appreciated that since patient to patient DNA variations may give rise to SNPs which can cause differences in the amino acid sequence of the proteins, the present inventors also contemplate proteins having amino acid sequences at least 90%, 95% or 99% homologous to the sequences provided herein above.

Measuring the polypeptide (for example, TRAIL, IP-10 and CRP) levels is typically affected at the protein level as further described herein below.

Methods of Detecting Expression and/or Activity of Proteins

Expression and/or activity level of proteins expressed in the cells of the cultures of some embodiments of the invention can be determined using methods known in the arts and typically involve the use of antibodies. Such methods may be referred to as immunoassays. Immunoassays may be run in multiple steps with reagents being added and washed away or separated at different points in the assay. Multi-step assays are often called separation immunoassays or heterogeneous immunoassays. Some immunoassays can be carried out simply by mixing the reagents and sample and making a physical measurement. Such assays are called homogenous immunoassays or less frequently non-separation immunoassays. The use of a calibrator is often employed in immunoassays. Calibrators are solutions that are known to contain the analyte in question, and the concentration of that analyte is generally known. Comparison of an assay's response to a real sample against the assay's response produced by the calibrators makes it possible to interpret the signal strength in terms of the presence or concentration of analyte in the sample.

The antibody may be monoclonal, polyclonal, chimeric, or a fragment of the foregoing, and the step of detecting the reaction product may be carried out with any suitable immunoassay.

Suitable sources for antibodies for the detection of the polypeptides include commercially available sources such as, for example, Abazyme, Abnova, AssayPro, Affinity Biologicals, AntibodyShop, Aviva bioscience, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, against any of the polypeptides described herein.

Polyclonal antibodies for measuring polypeptides include without limitation antibodies that were produced from sera by active immunization of one or more of the following: Rabbit, Goat, Sheep, Chicken, Duck, Guinea Pig, Mouse, Donkey, Camel, Rat and Horse.

Examples of additional detection agents, include without limitation: scFv, dsFv, Fab, sVH, F(ab')$_2$, Cyclic peptides, Haptamers, A single-domain antibody, Fab fragments, Single-chain variable fragments, Affibody molecules, Affilins, Nanofitins, Anticalins, Avimers, DARPins, Kunitz domains, Fynomers and Monobody.

Enzyme Linked Immunosorbent Assay (ELISA):

Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed with a mild detergent solution to remove any proteins or antibodies that are aspecifically bound. After the final wash step, the plate is developed by adding an enzymatic substrate to produce a visible signal, which indicates the quantity of antigen in the sample.

Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot:

This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Fluorescence Activated Cell Sorting (FACS):

This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Automated Immunoassay:

An automated analyzer applied to an immunoassay (often called "Automated Immunoassay") is a medical laboratory instrument designed to measure different chemicals and other characteristics in a number of biological samples quickly, with minimal human assistance. These measured properties of blood and other fluids may be useful in the diagnosis of disease. Many methods of introducing samples into the analyzer have been invented. This can involve placing test tubes of sample into racks, which can be moved along a track, or inserting tubes into circular carousels that rotate to make the sample available. Some analyzers require samples to be transferred to sample cups. However, the effort to protect the health and safety of laboratory staff has prompted many manufacturers to develop analyzers that feature closed tube sampling, preventing workers from direct exposure to samples. Samples can be processed singly, in batches, or continuously. Examples of automated immunoassay machines include, without limitation, ARCHITECT ci4100, ci8200 (2003), ci16200 (2007), ARCHITECT i1000SR, ARCHITECT i2000, i2000SR, i4000SR, AxSYM/AxSYM Plus, 1994 U.S., DS2, AIMS, AtheNA, DSX, ChemWell, UniCel Dxl 860i Synchron Access Clinical System, UniCel DxC 680i Synchron Access Clinical System, Access/Access 2 Immunoassay System, UniCel Dxl 600 Access Immunoassay System, UniCel DxC 600i Synchron Access Clinical System, UniCel Dxl 800 Access Immunoassay System, UniCel DxC 880i Synchron Access Clinical System, UniCel Dxl 660i Synchron Access Clinical System, SPA PLUS (Specialist Protein Analyzer), VIDAS Immunoassay Analyzer, BioPlex 2200, PhD System EVOLIS PR 3100TSC Photometer, MAGO 4S/2011 Mago Plus Automated EIA Processor, LIAISON XL/2010 LIAISON, ETI-MAX 3000 Agility, Triturus, HYTEC 288 PLUSDSX, VITROS ECi Immunodiagnostic System, VITROS 3600 Immunodiagnostic System, Phadia Laboratory System 100E, Phadia Laboratory System 250, Phadia Laboratory System 1000, Phadia Laboratory System 2500, Phadia Laboratory System 5000, cobas e 602/2010, cobas e411, cobas e601, MODULAR ANALYTICS E170, Elecsys 2010, Dimension EXL 200/2011, Dimension Xpand Plus Integrated Chemistry System, Dimension RxL Max/Max Suite Integrated Chemistry System; Dimension RxL Integrated Chemistry System, Dimension EXL with LM Integrated Chemistry System, Stratus CS Acute Care Diagnostic System, IMMULITE 2000 XPi Immunoassay System, ADVIA Centaur CP Immunoassay System, IMMULITE 2000, IMMULITE 1000, Dimension Vista 500 Intelligent Lab System, Dimension Vista 1500 Intelligent Lab System, ADVIA Centaur XP, AIA-900, AIA-360, AIA-2000, AIA-600 II, AIA-1800. Measurements of CRP, IP-10 and TRAIL can also be performed on a Luminex machine.

Lateral Flow Immunoassays (LFIA):

This is a technology which allows rapid measurement of analytes at the point of care (POC) and its underlying principles are described below. According to one embodiment, LFIA is used in the context of a hand-held device.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex.

After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the wick, that simply acts as a waste container. Lateral Flow Tests can operate as either competitive or sandwich assays.

Immunohistochemical Analysis:

Immunoassays carried out in accordance with some embodiments of the present invention may be homogeneous assays or heterogeneous assays. In a homogeneous assay the immunological reaction usually involves the specific antibody (e.g., anti-TRAIL, CRP and/or IP-10 antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels, which may be employed, include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase.

According to a particular embodiment, the antibody is immobilized to a porous strip to form a detection site. The measurement or detection region of the porous strip may include a plurality of sites, one for TRAIL, one for CRP and one for IP-10. A test strip may also contain sites for negative and/or positive controls.

Alternatively, control sites can be located on a separate strip from the test strip. Optionally, the different detection sites may contain different amounts of antibodies, e.g., a higher amount in the first detection site and lesser amounts in subsequent sites. Upon the addition of test sample, the number of sites displaying a detectable signal provides a quantitative indication of the amount of polypeptides present in the sample. The detection sites may be configured in any suitably detectable shape and are typically in the shape of a bar or dot spanning the width of a test strip.

The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein, rhodamine) in accordance with known techniques.

Monoclonal antibodies for measuring TRAIL include without limitation: Mouse, Monoclonal (55B709-3) IgG; Mouse, Monoclonal (2E5) IgG1; Mouse, Monoclonal (2E05) IgG1; Mouse, Monoclonal (M912292) IgG1 kappa; Mouse, Monoclonal (IIIF6) IgG2b; Mouse, Monoclonal (2E1-1B9) IgG1; Mouse, Monoclonal (RIK-2) IgG1, kappa; Mouse, Monoclonal M181 IgG1; Mouse, Monoclonal VI10E IgG2b; Mouse, Monoclonal MAB375 IgG1; Mouse, Monoclonal MAB687 IgG1; Mouse, Monoclonal HS501 IgG1; Mouse, Monoclonal clone 75411.11 Mouse IgG1; Mouse, Monoclonal T8175-50 IgG; Mouse, Monoclonal 2B2.108 IgG1; Mouse, Monoclonal B-T24 IgG1; Mouse, Monoclonal 55B709.3 IgG1; Mouse, Monoclonal D3 IgG1; Goat, Monoclonal C19 IgG; Rabbit, Monoclonal H257 IgG; Mouse, Monoclonal 500-M49 IgG; Mouse, Monoclonal 05-607 IgG; Mouse, Monoclonal B-T24 IgG1; Rat, Monoclonal (N2B2), IgG2a, kappa; Mouse, Monoclonal (1A7-2B7), IgG1; Mouse, Monoclonal (55B709.3), IgG and Mouse, Monoclonal B-S23*IgG1, Human TRAIL/TNFSF10 MAb (Clone 75411), Mouse IgG1, Human TRAIL/TNFSF10 MAb (Clone 124723), Mouse IgG1, Human TRAIL/TNFSF10 MAb (Clone 75402), Mouse IgG1.

Antibodies for measuring TRAIL include monoclonal antibodies and polyclonal antibodies for measuring TRAIL. Antibodies for measuring TRAIL include antibodies that were developed to target epitopes from the list comprising of: Mouse myeloma cell line NS0-derived recombinant human TRAIL (Thr95-Gly281 Accession #P50591), Mouse myeloma cell line, NS0-derived recombinant human TRAIL (Thr95-Gly281, with an N-terminal Met and 6-His tag Accession #P50591), E. coli-derived, (Val114-Gly281, with and without an N-terminal Met Accession #:Q6IBA9), Human plasma derived TRAIL, Human serum derived TRAIL, recombinant human TRAIL where first amino acid is between position 85-151 and the last amino acid is at position 249-281.

Examples of monoclonal antibodies for measuring CRP include without limitation: Mouse, Monoclonal (108-2A2); Mouse, Monoclonal (108-7G41D2); Mouse, Monoclonal (12D-2C-36), IgG1; Mouse, Monoclonal (1G1), IgG1; Mouse, Monoclonal (5A9), IgG2a kappa; Mouse, Monoclonal (63F4), IgG1; Mouse, Monoclonal (67A1), IgG1; Mouse, Monoclonal (8B-5E), IgG1; Mouse, Monoclonal (B893M), IgG2b, lambda; Mouse, Monoclonal (C1), IgG2b; Mouse, Monoclonal (C11F2), IgG; Mouse, Monoclonal (C2), IgG1; Mouse, Monoclonal (C3), IgG1; Mouse, Monoclonal (C4), IgG1; Mouse, Monoclonal (C5), IgG2a; Mouse, Monoclonal (C6), IgG2a; Mouse, Monoclonal (C7), IgG1; Mouse, Monoclonal (CRP103), IgG2b; Mouse, Monoclonal (CRP11), IgG1; Mouse, Monoclonal (CRP135), IgG1; Mouse, Monoclonal (CRP169), IgG2a; Mouse, Monoclonal (CRP30), IgG1; Mouse, Monoclonal (CRP36), IgG2a; Rabbit, Monoclonal (EPR283Y), IgG; Mouse, Monoclonal (KT39), IgG2b; Mouse, Monoclonal (N-a), IgG1; Mouse, Monoclonal (N1G1), IgG1; Monoclonal (P5A9AT); Mouse, Monoclonal (S5G1), IgG1; Mouse, Monoclonal (SB78c), IgG1; Mouse, Monoclonal (SB78d), IgG1 and Rabbit, Monoclonal (Y284), IgG, Human C-Reactive Protein/CRP Biot MAb (Cl 232024), Mouse IgG2B, Human C-Reactive Protein/CRP MAb (Clone 232007), Mouse IgG2B, Human/Mouse/Porcine C-Reactive Protein/CRP MAb (Cl 232026), Mouse IgG2A.

Antibodies for measuring CRP include monoclonal antibodies for measuring CRP and polyclonal antibodies for measuring CRP.

Antibodies for measuring CRP also include antibodies that were developed to target epitopes from the list comprising of: Human plasma derived CRP, Human serum derived CRP, Mouse myeloma cell line NS0-derived recombinant human C-Reactive Protein/CRP (Phe17-Pro224 Accession #P02741).

Examples of monoclonal antibodies for measuring IP-10 include without limitation: IP-10/CXCL10 Mouse anti-Human Monoclonal (4D5) Antibody (LifeSpan BioSciences), IP-10/CXCL10 Mouse anti-Human Monoclonal (A00163.01) Antibody (LifeSpan BioSciences), MOUSE ANTI HUMAN IP-10 (AbD Serotec), RABBIT ANTI HUMAN IP-10 (AbD Serotec), IP-10 Human mAb 6D4 (Hycult Biotech), Mouse Anti-Human IP-10 Monoclonal Antibody Clone B-050 (Diaclone), Mouse Anti-Human IP-10 Monoclonal Antibody Clone B-055 (Diaclone), Human CXCL10/IP-10 MAb Clone 33036 (R&D Systems), CXCL10/INP10 Antibody 1E9 (Novus Biologicals), CXCL10/INP10 Antibody 2C1 (Novus Biologicals), CXCL10/INP10 Antibody 6D4 (Novus Biologicals), CXCL10 monoclonal antibody M01A clone 2C1 (Abnova Corporation), CXCL10 monoclonal antibody (M05), clone 1E9 (Abnova Corporation), CXCL10 monoclonal antibody, clone 1 (Abnova Corporation), IP10 antibody 6D4 (Abcam), IP10 antibody EPR7849 (Abcam), IP10 antibody EPR7850 (Abcam).

Antibodies for measuring IP-10 include monoclonal antibodies for measuring IP-10 and polyclonal antibodies for measuring IP-10.

Antibodies for measuring IP-10 also include antibodies that were developed to target epitopes from the list comprising of: Recombinant human CXCL10/IP-10, non-glycosylated polypeptide chain containing 77 amino acids (aa 22-98) and an N-terminal His tag Interferon gamma inducible protein 10 (125 aa long), IP-10 His Tag Human Recombinant IP-10 produced in E. Coli containing 77 amino acids fragment (22-98) and having a total molecular mass of 8.5 kDa with an amino-terminal hexahistidine tag, E. coli-derived Human IP-10 (Val22-Pro98) with an N-terminal Met, Human plasma derived IP-10, Human serum derived IP-10, recombinant human IP-10 where first amino acid is between position 1-24 and the last amino acid is at position 71-98.

It will be appreciated that the expression level of the polypeptides described herein can be an absolute expression level, a normalized expression and/or a relative expression level.

In general scientific context, normalization is a process by which a measurement raw data is converted into data that may be directly compared with other so normalized data. In the context of the present invention, measurements of expression levels are prone to errors caused by, for example, unequal degradation of measured samples, different loaded quantities per assay, and other various errors. More specifically, any assayed sample may contain more or less biological material than is intended, due to human error and equipment failures. Thus, the same error or deviation applies to both the polypeptide of the invention and to the control reference, whose expression is essentially constant. Thus, division of TRAIL, IP-10 or CRP raw expression value by the control reference raw expression value yields a quotient which is essentially free from any technical failures or inaccuracies (except for major errors which destroy the sample for testing purposes) and constitutes a normalized expression value of the polypeptide. Since control reference expression values are equal in different samples, they constitute a common reference point that is valid for such normalization.

According to a particular embodiment, each of the polypeptide expression values are normalized using the same control reference.

It will further be appreciated that absolute expression values are dependent upon the exact protocol used, since each protocol typically leads to different signal to noise ratios, and consequentially to different concentrations being measured. More specifically, while the overall trend of the biomarkers will be preserved regardless of the protocol (e.g. TRAIL increases in viral infections and decreases in bacterial), the measurement scale is protocol dependent.

Such alterations in measured concentrations of proteins across different protocols can be compensated for by correlating the measurements of the two protocols and computing a transformation function, as illustrated in Example 5 herein below.

Typically, the samples which are analyzed are blood sample comprising whole blood, serum, plasma, leukocytes or blood cells. Preferably, the sample is whole blood, serum or plasma.

Of note, TRAIL and IP-10 and CRP are highly expressed in other tissues and samples including without limitation CSF, saliva and epithelial cells, bone marrow aspiration, urine, stool, alveolar lavage, sputum. Thus, some embodiments of the present invention can be used to measure TRAIL, CRP and IP-10 in such tissues and samples.

Preferably, the level of the polypeptides is measured within about 24 hours after the sample is obtained. Alternatively, the concentration of the polypeptides is measured in a sample that was stored at 12° C. or lower, when storage begins less than 24 hours after the sample is obtained.

Once the tests are carried out to determine the level of the polypeptides, a subject specific dataset is optionally generated which contains the results of the measurements.

The subject-specific dataset may be stored in a computer readable format on a non-volatile computer readable medium, and is optionally and preferably accessed by a hardware processor, such as a general purpose computer or dedicated circuitry.

As mentioned, the levels of the polypeptides in the test subjects blood are compared to the levels of the identical polypeptides in a plurality of subjects' blood, when the subjects have already been verified as having a bacterial infection, viral infection or non-bacterial/non-viral disease on the basis of parameters other than the blood level of the polypeptides. The levels of the polypeptides of the plurality of subjects together with their verified diagnosis can be stored in a second dataset, also referred to herein as the "group dataset" or "prediagnosed dataset", as further described herein below.

The phrase "non-bacterial/non-viral disease" refers to disease that is not caused by a bacteria or virus. This includes diseases such as acute myocardial infarction, physical injury, epileptic attack, inflammatory disorders etc, fungal diseases, parasitic diseases etc.

The phrase "viral infection" as used herein refers to a disease that is caused by a virus and does not comprise a bacterial component.

Methods of analyzing a dataset, for example, for the purpose of calculating one or more probabilistic classification function representing the likelihood that a particular subject has a bacterial infection, or the likelihood that a particular subject has a viral infection or the likelihood that a particular subject has a non-bacterial non-viral disease, may be performed as described in Example 1 herein below. For example, diagnosis may be supported using PCR diagnostic assays such as (i) Seeplex® RV15 for detection of parainfluenza virus 1, 2, 3, and 4, coronavirus 229E/NL63, adenovirus A/B/C/D/E, bocavirus 1/2/3/4, influenza virus A and B, metapneumovirus, coronavirus OC43, rhinovirus A/B/C, respiratory syncytial virus A and B, and Enterovirus, or (ii) Seeplex® PB6 for detection of *Streptococcus pneumoniae*, *Haemophilus influenzae*, *Chlamydophila pneumoniae*, *Legionella pneumophila*, *Bordetella pertussis*, and *Mycoplasma pneumoniae*.

Blood cultures, urine cultures and stool cultures may be analyzed for *Shigella* spp., *Campylobacter* spp. and *Salmonella* spp.; serological testing (IgM and/or IgG) for cytomegalovirus (CMV), Epstein-Barr virus (EBV), *Mycoplasma* Pneumonia, and *Coxiella burnetii* (Q-Fever).

Radiological tests (e.g. chest X-ray for suspected lower respiratory tract infection [LRTI]) may be used to confirm chest infections.

Alternatively, or additionally at least one trained physician may be used to establish the diagnosis.

Methods of determining the expression level of the polypeptides in the pre-diagnosed subjects have been described herein above.

Preferably, the same method which is used for determining the expression level of the polypeptides in the pre-diagnosed subjects is used for determining the level of the polypeptides in the test subject. Thus, for example if an immunoassay type method is used for determining the expression level of the polypeptides in the pre-diagnosed subjects, then an immunoassay type method should be used for determining the level of the polypeptides in the test subject.

It will be appreciated that, the type of blood sample need not be identical in the test subject and the pre-diagnosed subjects. The present inventors were able to show that serum and plasma levels for TRAIL are very similar. Thus, for example, if a serum sample is used for determining the expression level of the polypeptides in the pre-diagnosed subjects, then a plasma sample may be used for determining the level of the polypeptides in the test subject.

The group dataset is preferably stored in a computer readable format on a non-volatile computer readable medium, and is optionally and preferably accessed by a hardware processor, such as a general purpose computer or dedicated circuitry. Both datasets can be stored on the same medium and are optionally and preferably accessed by the same hardware processor.

In the subject-specific dataset, each entry can optionally and preferably be described as a tuple (D, L) where D represents the polypeptide in the dataset and L represents the blood level of the polypeptide D. Thus, the dataset may be a two-dimensional dataset in which all the elements can be described by a vector in a two-dimensional space spanned by the polypeptide and respective response. In the group dataset, each entry can be described as a tuple (S, G, D, L) where S represents the particular subject, G represents the diagnosis of the subject S in the group dataset, D represents the polypeptide and L represents blood level of the polypeptide D. Thus, the exemplified illustration is of a four-dimensional dataset in which all the elements can be described by a vector in a four-dimensional space spanned by the subjects, diagnosis, polypeptide and respective responses. Some embodiments of the present invention contemplate use of datasets of higher dimensions. Such datasets are described hereinafter.

The group dataset may optionally and preferably also include one or more of, more preferably all, the entries of the subject-specific dataset. In embodiments in which group dataset includes all the entries of the subject-specific dataset, it is not necessary to use two separate datasets, since the entire dataset is contained in one inclusive dataset. Yet, such an inclusive dataset is optionally and preferably annotated in a manner that allows distinguishing between the portion of the inclusive dataset that is associated with the subject under analysis, and the portion of the inclusive dataset that is associated only with the other subjects. In the context of the present disclosure, the portion of the inclusive dataset that is associated with the subject under analysis is referred to as the subject-specific dataset even when it is not provided as a separate dataset. Similarly, the portion of the inclusive dataset that is associated only with the other subjects is referred to as the group dataset even when it is not provided as a separate dataset.

The group dataset preferably includes polypeptide levels of many subjects (e.g., at least 10 subjects being prediagnosed as having a viral infection, at least 10 subjects being prediagnosed as having a bacterial infection and at least 10 subjects being prediagnosed as having a non-bacterial/non-viral disease; or at least 20 subjects being prediagnosed as having a viral infection, at least 20 subjects being prediagnosed as having a bacterial infection and at least 20 subjects being prediagnosed as having a non-bacterial/non-viral disease; or at least 50 subjects being prediagnosed as having a viral infection, at least 50 subjects being prediagnosed as having a bacterial infection and at least 50 subjects being prediagnosed as having a non-bacterial/non-viral disease.

The group-specific dataset can include additional data that describes the subjects. Datasets that include additional data may be advantageous since they provide additional information regarding the similarities between the subject under analysis and the other subject, thereby increasing the accuracy of the predictability.

Representative examples of types of data other than the level of the polypeptides include, without limitation traditional laboratory risk factors and/or clinical parameters, as further described herein above.

The present embodiments contemplate subject-specific and group datasets that include additional data, aside from the polypeptides and respective levels. In some embodiments at least one of the datasets comprises one or more (e.g., a plurality of) multidimensional entries, each entry having at least three dimensions, in some embodiments at least one of the datasets comprises one or more (e.g., a plurality of) multidimensional entries, each entry having at least four dimensions, in some embodiments at least one of the datasets comprises one or more (e.g., a plurality of) multidimensional entries, each entry having at least five dimensions, and in some embodiments at least one of the datasets comprises one or more (e.g., a plurality of) multidimensional entries, each entry having more than five dimensions.

The additional dimensions of the datasets provides additional information pertaining to the subject under analysis, to the other subjects and/or to levels of polypeptides other than TRAIL, CRP and IP-10.

In some embodiments of the present invention the additional information pertains to at least one of traditional laboratory risk factors, clinical parameters, blood chemistry and/or a genetic profile.

"Traditional laboratory risk factors" encompass biomarkers isolated or derived from subject samples and which are currently evaluated in the clinical laboratory and used in traditional global risk assessment algorithms, such as absolute neutrophil count (abbreviated ANC), absolute lymphocyte count (abbreviated ALC), white blood count (abbreviated WBC), neutrophil % (defined as the fraction of white blood cells that are neutrophils and abbreviated Neu (%)), lymphocyte % (defined as the fraction of white blood cells that are lymphocytes and abbreviated Lym (%)), monocyte % (defined as the fraction of white blood cells that are monocytes and abbreviated Mon (%)), Sodium (abbreviated Na), Potassium (abbreviated K), Bilirubin (abbreviated Bili).

Preferably, at least one of the traditional laboratory risk factors of the subject under analysis is included in the subject specific dataset, and at least one of the traditional laboratory risk factors of one or more (more preferably all) of the other subjects is included in the group dataset. When the subject specific dataset includes at least one of the traditional laboratory risk factors, the risk factors can be included as a separate entry. When the group dataset includes the risk factors, the risk factors is optionally and preferably included per subject. Thus, for example, a group dataset entry can be described by the tuple (S, G, D, L {R}), where S, G, D and L have been introduced before and {R} is the at least one risk factor of subject S.

"Clinical parameters" encompass all non-sample or non-analyte biomarkers of subject health status or other characteristics, such as, without limitation, age (Age), ethnicity (RACE), gender (Sex), core body temperature (abbreviated "temperature"), maximal core body temperature since initial appearance of symptoms (abbreviated "maximal temperature"), time from initial appearance of symptoms (abbreviated "time from symptoms"), pregnancy, or family history (abbreviated FamHX).

Preferably, at least one of the clinical parameters of the subject under analysis is included in the subject specific dataset, and at least one of the clinical parameters of one or more (more preferably all) of the other subjects is included in the group dataset. When the subject specific dataset includes at least one of the clinical parameters, the clinical parameters can be included as a separate entry. When the group dataset includes the clinical parameters, the clinical parameters is optionally and preferably included per subject. Thus, for example, a group dataset entry can be described by the tuple (S, G, D, L {C}), where S, G, D and L have been introduced before and {C} is the clinical parameter of subject S.

As used herein "blood chemistry" refers to the concentration, or concentrations, of any and all substances dissolved in, or comprising, the blood. Representative examples of such substances, include, without limitation, albumin, amylase, alkaline phosphatase, bicarbonate, total bilirubin, BUN, C-reactive protein, calcium, chloride, LDL, HDL, total cholesterol, creatinine, CPK, γ-GT, glucose, LDH, inorganic phosphorus, lipase, potassium, total protein, AST, ALT, sodium, triglycerides, uric acid and VLDL.

According to one embodiment, the blood chemistry of the subject under analysis is included in the subject specific dataset, and the blood chemistry of one or more (more preferably all) of the other subjects is included in the group dataset. When the subject specific dataset includes the blood chemistry, the blood chemistry can be included as a separate entry. When the group dataset includes the blood chemistry, the blood chemistry is optionally and preferably included per subject. Thus, for example, a group dataset entry can be described by the tuple (S, G, D, L {C}), where S, G, D and L have been introduced before and {C} is the blood chemistry of subject S.

In some embodiments of the present invention the additional information pertains to a genetic profile of individual.

As used herein "genetic profile" refers to the analysis of a number of different genes. A genetic profile can encompass the genes in an entire genome of the individual, or it can encompass a specific subset of genes. The genetic profile may include genomic profile, a proteomic profile, an epigenomic profile and/or a transcriptomic profile.

Preferably, the genetic profile of the subject under analysis is included in the subject specific dataset, and the genetic profile of one or more (more preferably all) of the other subjects is included in the group dataset. When the subject specific dataset includes the genetic profile, the genetic profile can be included as a separate entry. When the group dataset includes the genetic profile, the genetic profile is optionally and preferably included per subject. Thus, for example, a group dataset entry can be described by the tuple (S, G, D, L {P}), where S, G, D and L have been introduced before and {P} is the genetic profile of subject S.

The method optionally and preferably continues to a step of storing the levels of the polypeptide, at least temporarily, on a non-volatile computer readable medium from which it can be extracted or displayed as desired.

Once the two datasets are accessed, the method continues to the analysis phase in order to diagnose the test subject.

The analysis is performed so as to compute one or more probabilistic classification functions $f(\delta_0,\delta_1)$, $g(\delta_0,\delta_1)$, $h(\delta_0,\delta_1)$, representing the likelihoods that a particular subject has a bacterial infection, viral infection or non-viral, non-bacterial disease, respectively. Typically, f, g and h satisfy the relation $f(\delta_0,\delta_1)+g(\delta_0,\delta_1)+h(\delta_0,\delta_1)=1$. Each classification function is a function of the first coordinate $\delta_0$ and the second coordinate $\delta_1$, wherein each of the coordinates $\delta_0$ and $\delta_1$ is defined by a different combination of the expression values as further detailed hereinabove.

The analysis can be executed in more than one way.

According to one embodiment, the analysis uses a binary or, more preferably, trinary classifier to compute one or more of the probabilistic classification functions.

Preferably, the analysis sums the probability of the viral and the non-viral, non-bacterial disease in order to assign the likelihood of a non-bacterial infection. In another preferred embodiment, the analysis sums the probability of the viral and bacterial to assign the likelihood of an infectious disease. Yet in another preferred embodiment the analysis ignores the probability of the non-viral, non-bacterial disease, and performs a direct comparison of the bacterial and the viral probabilities. Exemplified interpretation functions suitable for analyzing the datasets according to some embodiments of the present invention are provided hereinunder.

The analysis of the datasets according to some embodiments of the present invention comprises executing a machine learning procedure.

As used herein the term "machine learning" refers to a procedure embodied as a computer program configured to induce patterns, regularities, or rules from previously collected data to develop an appropriate response to future data, or describe the data in some meaningful way.

Use of machine learning is particularly, but not exclusively, advantageous when the dataset includes multidimensional entries.

The group and subject datasets can be used as a training set from which the machine learning procedure can extract parameters that best describe the dataset. Once the parameters are extracted, they can be used to predict the type of infection.

In machine learning, information can be acquired via supervised learning or unsupervised learning. In some embodiments of the invention the machine learning procedure comprises, or is, a supervised learning procedure. In supervised learning, global or local goal functions are used to optimize the structure of the learning system. In other words, in supervised learning there is a desired response, which is used by the system to guide the learning.

In some embodiments of the invention the machine learning procedure comprises, or is, an unsupervised learning procedure. In unsupervised learning there are typically no goal functions. In particular, the learning system is not provided with a set of rules. One form of unsupervised learning according to some embodiments of the present invention is unsupervised clustering in which the data objects are not class labeled, a priori.

Representative examples of "machine learning" procedures suitable for the present embodiments, including, without limitation, clustering, association rule algorithms, feature evaluation algorithms, subset selection algorithms, support vector machines, classification rules, cost-sensitive classifiers, vote algorithms, stacking algorithms, Bayesian networks, decision trees, neural networks, instance-based algorithms, linear modeling algorithms, k-nearest neighbors analysis, ensemble learning algorithms, probabilistic models, graphical models, logistic regression methods (including multinomial logistic regression methods), gradient ascent methods, singular value decomposition methods and principle component analysis. Among neural network models, the self-organizing map and adaptive resonance theory are commonly used unsupervised learning algorithms. The adaptive resonance theory model allows the number of clusters to vary with problem size and lets the user control the degree of similarity between members of the same clusters by means of a user-defined constant called the vigilance parameter.

Following is an overview of some machine learning procedures suitable for the present embodiments.

Association rule algorithm is a technique for extracting meaningful association patterns among features.

The term "association", in the context of machine learning, refers to any interrelation among features, not just ones that predict a particular class or numeric value. Association includes, but it is not limited to, finding association rules, finding patterns, performing feature evaluation, performing feature subset selection, developing predictive models, and understanding interactions between features.

The term "association rules" refers to elements that co-occur frequently within the datasets. It includes, but is not limited to association patterns, discriminative patterns, frequent patterns, closed patterns, and colossal patterns.

A usual primary step of association rule algorithm is to find a set of items or features that are most frequent among all the observations. Once the list is obtained, rules can be extracted from them.

The aforementioned self-organizing map is an unsupervised learning technique often used for visualization and analysis of high-dimensional data. Typical applications are focused on the visualization of the central dependencies within the data on the map. The map generated by the algorithm can be used to speed up the identification of association rules by other algorithms. The algorithm typically includes a grid of processing units, referred to as "neurons". Each neuron is associated with a feature vector referred to as observation. The map attempts to represent all the available observations with optimal accuracy using a restricted set of models. At the same time the models become ordered on the grid so that similar models are close to each other and dissimilar models far from each other. This procedure enables the identification as well as the visualization of dependencies or associations between the features in the data.

Feature evaluation algorithms are directed to the ranking of features or to the ranking followed by the selection of features based on their impact.

The term "feature" in the context of machine learning refers to one or more raw input variables, to one or more processed variables, or to one or more mathematical combinations of other variables, including raw variables and processed variables. Features may be continuous or discrete.

Information gain is one of the machine learning methods suitable for feature evaluation. The definition of information gain requires the definition of entropy, which is a measure of impurity in a collection of training instances. The reduction in entropy of the target feature that occurs by knowing the values of a certain feature is called information gain. Information gain may be used as a parameter to determine the effectiveness of a feature in explaining the type of infection. Symmetrical uncertainty is an algorithm that can be used by a feature selection algorithm, according to some embodiments of the present invention. Symmetrical uncertainty compensates for information gain's bias towards features with more values by normalizing features to a [0,1] range.

Subset selection algorithms rely on a combination of an evaluation algorithm and a search algorithm. Similarly to feature evaluation algorithms, subset selection algorithms rank subsets of features. Unlike feature evaluation algorithms, however, a subset selection algorithm suitable for the present embodiments aims at selecting the subset of features with the highest impact on the type of infection, while accounting for the degree of redundancy between the features included in the subset. The benefits from feature subset selection include facilitating data visualization and understanding, reducing measurement and storage requirements, reducing training and utilization times, and eliminating distracting features to improve classification.

Two basic approaches to subset selection algorithms are the process of adding features to a working subset (forward selection) and deleting from the current subset of features (backward elimination). In machine learning, forward selection is done differently than the statistical procedure with the same name. The feature to be added to the current subset in machine learning is found by evaluating the performance of the current subset augmented by one new feature using cross-validation. In forward selection, subsets are built up by adding each remaining feature in turn to the current subset while evaluating the expected performance of each new subset using cross-validation. The feature that leads to the best performance when added to the current subset is retained and the process continues. The search ends when none of the remaining available features improves the predictive ability of the current subset. This process finds a local optimum set of features.

Backward elimination is implemented in a similar fashion. With backward elimination, the search ends when further reduction in the feature set does not improve the predictive ability of the subset. The present embodiments contemplate search algorithms that search forward, backward or in both directions. Representative examples of search algorithms suitable for the present embodiments include, without limitation, exhaustive search, greedy hill-climbing, random perturbations of subsets, wrapper algorithms, probabilistic race search, schemata search, rank race search, and Bayesian classifier.

A decision tree is a decision support algorithm that forms a logical pathway of steps involved in considering the input to make a decision.

The term "decision tree" refers to any type of tree-based learning algorithms, including, but not limited to, model trees, classification trees, and regression trees.

A decision tree can be used to classify the datasets or their relation hierarchically. The decision tree has tree structure that includes branch nodes and leaf nodes. Each branch node specifies an attribute (splitting attribute) and a test (splitting test) to be carried out on the value of the splitting attribute, and branches out to other nodes for all possible outcomes of the splitting test. The branch node that is the root of the decision tree is called the root node. Each leaf node can represent a classification (e.g., whether a particular portion of the group dataset matches a particular portion of the subject-specific dataset) or a value. The leaf nodes can also contain additional information about the represented classification such as a confidence score that measures a confidence in the represented classification (i.e., the likelihood of the classification being accurate). For example, the confidence score can be a continuous value ranging from 0 to 1, which a score of 0 indicating a very low confidence (e.g., the indication value of the represented classification is very low) and a score of 1 indicating a very high confidence (e.g., the represented classification is almost certainly accurate).

Support vector machines are algorithms that are based on statistical learning theory. A support vector machine (SVM) according to some embodiments of the present invention can be used for classification purposes and/or for numeric prediction. A support vector machine for classification is referred to herein as "support vector classifier," support vector machine for numeric prediction is referred to herein as "support vector regression".

An SVM is typically characterized by a kernel function, the selection of which determines whether the resulting SVM provides classification, regression or other functions. Through application of the kernel function, the SVM maps input vectors into high dimensional feature space, in which a decision hyper-surface (also known as a separator) can be constructed to provide classification, regression or other decision functions. In the simplest case, the surface is a hyper-plane (also known as linear separator), but more complex separators are also contemplated and can be applied using kernel functions. The data points that define the hyper-surface are referred to as support vectors.

The support vector classifier selects a separator where the distance of the separator from the closest data points is as large as possible, thereby separating feature vector points associated with objects in a given class from feature vector points associated with objects outside the class. For support vector regression, a high-dimensional tube with a radius of acceptable error is constructed which minimizes the error of the data set while also maximizing the flatness of the associated curve or function. In other words, the tube is an envelope around the fit curve, defined by a collection of data points nearest the curve or surface.

An advantage of a support vector machine is that once the support vectors have been identified, the remaining observations can be removed from the calculations, thus greatly reducing the computational complexity of the problem. An SVM typically operates in two phases: a training phase and a testing phase. During the training phase, a set of support vectors is generated for use in executing the decision rule. During the testing phase, decisions are made using the decision rule. A support vector algorithm is a method for training an SVM. By execution of the algorithm, a training set of parameters is generated, including the support vectors that characterize the SVM. A representative example of a support vector algorithm suitable for the present embodiments includes, without limitation, sequential minimal optimization.

Regression techniques which may be used in accordance with the present invention include, but are not limited to linear Regression, Multiple Regression, logistic regression, probit regression, ordinal logistic regression ordinal Probit-Regression, Poisson Regression, negative binomial Regression, multinomial logistic Regression (MLR) and truncated regression.

A logistic regression or logit regression is a type of regression analysis used for predicting the outcome of a categorical dependent variable (a dependent variable that can take on a limited number of values, whose magnitudes are not meaningful but whose ordering of magnitudes may or may not be meaningful) based on one or more predictor variables. Logistic regressions also include a multinomial variant. The multinomial logistic regression model, is a regression model which generalizes logistic regression by allowing more than two discrete outcomes. That is, it is a model that is used to predict the probabilities of the different possible outcomes of a categorically distributed dependent variable, given a set of independent variables (which may be real-valued, binary-valued, categorical-valued, etc.).

The advantage of logistic regression is that it assigns an interpretable measure of prediction confidence—a probability. For example, patients predicted of having a bacterial infection with a probability of 75% and 99%, would both be assigned as bacterial when using an SVM interpretation function but the fact that the latter has a higher probability would be masked. Assigning the likelihood level of confidence adds valuable clinical information that may affect clinical judgment.

Importantly, calculating the likelihood of infection type for each patients, allows to rationally filter out patients for which the system knows that it cannot classify with high certainty. This is demonstrated in FIG. 5, herein. Thus, when the product assigns a likelihood of say 40% bacterial infection (40 out of 100 patients with the "40%" score will be bacterial).

Additionally, by using thresholds on the likelihood scores, one can assign non-binary classifications of the test-subject. By way of example a test-subject with a bacterial likelihood below 30% can be assigned a low probability of bacterial infection; between 30% and 70% an intermediate probability of bacterial infection and above 70% a high probability of a bacterial infections. Other thresholds may be used.

The Least Absolute Shrinkage and Selection Operator (LASSO) algorithm is a shrinkage and/or selection algorithm for linear regression. The LASSO algorithm may minimizes the usual sum of squared errors, with a regularization, that can be an L1 norm regularization (a bound on the sum of the absolute values of the coefficients), an L2 norm regularization (a bound on the sum of squares of the coefficients), and the like. The LASSO algorithm may be associated with soft-thresholding of wavelet coefficients, forward stagewise regression, and boosting methods. The LASSO algorithm is described in the paper: Tibshirani, R, Regression Shrinkage and Selection via the Lasso, J. Royal. Statist. Soc B., Vol. 58, No. 1, 1996, pages 267-288, the disclosure of which is incorporated herein by reference.

A Bayesian network is a model that represents variables and conditional interdependencies between variables. In a Bayesian network variables are represented as nodes, and nodes may be connected to one another by one or more links. A link indicates a relationship between two nodes. Nodes typically have corresponding conditional probability tables that are used to determine the probability of a state of a node given the state of other nodes to which the node is connected. In some embodiments, a Bayes optimal classifier algorithm is employed to apply the maximum a posteriori hypothesis to a new record in order to predict the probability of its classification, as well as to calculate the probabilities from each of the other hypotheses obtained from a training set and to use these probabilities as weighting factors for future predictions of the type of infection. An algorithm suitable for a search for the best Bayesian network, includes, without limitation, global score metric-based algorithm. In an alternative approach to building the network, Markov blanket can be employed. The Markov blanket isolates a node from being affected by any node outside its boundary, which is composed of the node's parents, its children, and the parents of its children.

Instance-based algorithms generate a new model for each instance, instead of basing predictions on trees or networks generated (once) from a training set.

The term "instance", in the context of machine learning, refers to an example from a dataset.

Instance-based algorithms typically store the entire dataset in memory and build a model from a set of records similar to those being tested. This similarity can be evaluated, for example, through nearest-neighbor or locally weighted methods, e.g., using Euclidian distances. Once a set of records is selected, the final model may be built using several different algorithms, such as the naive Bayes.

The present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like infection, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

A machine-readable storage medium can comprise a data storage material encoded with machine readable data or data arrays which, when using a machine programmed with instructions for using said data, is capable of use for a variety of purposes. Measurements of effective amounts of the biomarkers of the invention and/or the resulting evaluation of risk from those biomarkers can implemented in computer programs executing on programmable computers, comprising, inter alia, a processor, a data storage system (including volatile and non-volatile memory and/or storage elements), at least one input device, and at least one output device.

Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein.

The health-related data management system of the invention may also be considered to be implemented as a computer-readable storage medium, configured with a computer program, where the storage medium so configured causes a computer to operate in a specific and predefined manner to perform various functions described herein.

The recorded output may include the assay results, findings, diagnoses, predictions and/or treatment recommendations. These may be communicated to technicians, physicians and/or patients, for example. In certain embodiments, computers will be used to communicate such information to interested parties, such as, patients and/or the attending physicians. Based on the output, the therapy administered to a subject can be modified.

In one embodiment, the output is presented graphically. In another embodiment, the output is presented numerically (e.g. as a probability). In another embodiment, the output is generated using a color index (for example in a bar display) where one color indicates bacterial infection and another color non-bacterial infection. The strength of the color correlates with the probability of bacterial infection/non-infection. Such a graphic display is presented in FIGS. 29A-29F.

In some embodiments, the output is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In some embodiments, the methods described herein are carried out using a system 330, which optionally and preferably, but not necessarily, comprises a hand-held device, which comprises at least two compartments the first which measures the amount of polypeptides in the blood (e.g. using an immunohistochemical method) and the second which computationally analyzes the results measured in the first compartment and provides an output relating to the diagnosis.

A block diagram of representative example of system 330 according to some embodiments of the present invention is illustrated in FIG. 34. System 330 can comprise a device 331 which can be, but is not necessarily a hand-held device. Alternatively, device 331 which can be a desktop mountable or a desktop placeable device. System 330 can comprise a first compartment 332 having a measuring system 333 configured to measure the expression value of the polypeptides in the blood of a subject. Measuring system 333 can perform at least one automated assay selected from the group consisting of an automated ELISA, an automated immunoassay, and an automated functional assay. System 330 can also comprise a second compartment 334 comprising a hardware processor 336 having a computer-readable medium 338 for storing computer program instructions for executing the operations described herein (e.g., computer program instructions for defining the first and/or second coordinates, computer program instructions for defining the curved line and/or plane, computer program instructions for calculating the first and/or distances, computer program instructions for correlating the calculated distance(s) to the presence of, absence of, or likelihood that the subject has, a bacterial and/or viral infection). Hardware processor 336 is configured to receive expression value measurements from first compartment 332 and execute the program instructions responsively to the measurements. Optionally and preferably hardware processor 336 is also configured to output the processed data to a display device 340.

In some optional embodiments of the present invention, system 330 communicates with a communication network. In these embodiments, system 330 or hardware processor 336 comprises a network interface 350 that communicates with a communication network 352. In the representative illustration shown in FIG. 34, network 352 is used for transmitting the results of the analysis performed by hardware processor 336 (for example, the presence of, absence of, or likelihood that the subject has, a bacterial and/or viral infection) to one or more remote locations. For example, system 330 can transmit the analysis results to at least one of a laboratory information system 360, and/or a central server 362 that collects data from a plurality of systems like system 330.

FIG. 39A is a schematic illustration showing a block diagram of system 330 in embodiments in which communication network 352 is used for receiving expression value measurements. In these embodiments, system 330 can comprise computer-readable medium 338, as further detailed hereinabove, and a hardware processor, such as, but not limited to, processor 336. Hardware processor 336 can comprise network interface 350. Via interface 350, hardware processor 336 receives expression value measurements from a measuring system, such as, but not limited to, measuring system 333, and executes the computer program instructions in computer-readable medium 338, responsively to the received measurements. Hardware processor 336 can then output the processed data to display device 340.

Combinations of the embodiments shown in FIGS. 34 and 39A are also contemplated. For example, interface 350 can be used both for receiving expression value measurements from network 352 and for transmitting the results of the analysis to network 352.

In some embodiments of the present invention system 330 communicates with a user, as schematically illustrated in the block diagram of FIG. 39B. In these embodiments, system 330 can comprise computer-readable medium 338, as further detailed hereinabove, and a hardware processor, such as, but not limited to, processor 336. Hardware processor 336 comprises a user interface 354 that communicates with a user 356. Via interface 350, hardware processor 336 receives expression value measurements from user 356. User 356 can obtain the expression value from an external source, or by executing at least one assay selected from the group consisting of an immunoassay and a functional assay, or by operating system 333 (not shown, see FIGS. 39A and 34). Hardware processor 336 executes the computer program instructions in computer-readable medium 338, responsively to the received measurements. Hardware processor 336 can then output the processed data to display device 340.

Once the diagnosis has been made, it will be appreciated that a number of actions may be taken.

Thus, for example, if a bacterial infection is ruled in, then the subject may be treated with an antibiotic agent.

Examples of antibiotic agents include, but are not limited to Daptomycin; Gemifloxacin; Telavancin; Ceftaroline; Fidaxomicin; Amoxicillin; Ampicillin; Bacampicillin; Carbenicillin; Cloxacillin; Dicloxacillin; Flucloxacillin; Mezlocillin; Nafcillin; Oxacillin; Penicillin G; Penicillin V; Piperacillin; Pivampicillin; Pivmecillinam; Ticarcillin; Aztreonam; Imipenem; Doripenem; Meropenem; Ertapenem; Clindamycin; Lincomycin; Pristinamycin; Quinupristin; Cefacetrile (cephacetrile); Cefadroxil (cefadroxyl); Cefalexin (cephalexin); Cefaloglycin (cephaloglycin); Cefalonium (cephalonium); Cefaloridine (cephaloradine); Cefalotin (cephalothin); Cefapirin (cephapirin); Cefatrizine; Cefazaflur; Cefazedone; Cefazolin (cephazolin); Cefradine (cephradine); Cefroxadine; Ceftezole; Cefaclor; Cefamandole; Cefmetazole; Cefonicid; Cefotetan; Cefoxitin; Cefprozil (cefproxil); Cefuroxime; Cefuzonam; Cefcapene; Cefdaloxime; Cefdinir; Cefditoren; Cefetamet; Cefixime; Cefmenoxime; Cefodizime; Cefotaxime; Cefpimizole; Cefpodoxime; Cefteram; Ceftibuten; Ceftiofur; Ceftiolene; Ceftizoxime; Ceftriaxone; Cefoperazone; Ceftazidime; Cefclidine; Cefepime; Cefluprenam; Cefoselis; Cefozopran; Cefpirome; Cefquinome; Fifth Generation; Ceftobiprole; Ceftaroline; Not Classified; Cefaclomezine; Cefaloram; Cefaparole; Cefcanel; Cefedrolor; Cefempidone; Cefetrizole; Cefivitril; Cefmatilen; Cefmepidium; Cefovecin; Cefoxazole; Cefrotil; Cefsumide; Cefuracetime; Ceftioxide; Azithromycin; Erythromycin; Clarithromycin; Dirithromycin; Roxithromycin; Telithromycin; Amikacin; Gentamicin; Kanamycin; Neomycin; Netilmicin; Paromomycin; Streptomycin; Tobramycin; Flumequine; Nalidixic acid; Oxolinic acid; Piromidic acid; Pipemidic acid; Rosoxacin; Ciprofloxacin; Enoxacin; Lomefloxacin; Nadifloxacin; Norfloxacin; Ofloxacin; Pefloxacin; Rufloxacin; Balofloxacin; Gatifloxacin; Grepafloxacin; Levofloxacin; Moxifloxacin; Pazufloxacin; Sparfloxacin; Temafloxacin; Tosufloxacin; Besifloxacin; Clinafloxacin; Gemifloxacin; Sitafloxacin; Trovafloxacin; Prulifloxacin; Sulfamethizole; Sulfamethoxazole; Sulfisoxazole; Trimethoprim-Sulfamethoxazole; Demeclocycline; Doxycycline; Minocycline; Oxytetracycline; Tetracycline; Tigecycline; Chloramphenicol; Metronidazole; Tinidazole; Nitrofurantoin; Vancomycin; Teicoplanin; Telavancin; Linezolid; Cycloserine 2; Rifampin; Rifabutin; Rifapentine; Bacitracin; Polymyxin B; Viomycin; Capreomycin.

If a viral infection is ruled in, the subject may be treated with an antiviral agent. Examples of antiviral agents include, but are not limited to Abacavir; Aciclovir; Acyclovir; Adefovir; Amantadine; Amprenavir; Ampligen; Arbidol; Atazanavir; Atripla; Balavir; Boceprevirertet; Cidofovir; Combivir; Dolutegravir; Darunavir; Delavirdine; Didanosine; Docosanol; Edoxudine; Efavirenz; Emtricitabine; Enfuvirtide; Entecavir; Ecoliever; Famciclovir; Fomivirsen; Fosamprenavir; Foscarnet; Fosfonet; Fusion inhibitor; Ganciclovir; Ibacitabine; Imunovir; Idoxuridine; Imiquimod; Indinavir; Inosine; Integrase inhibitor; Interferon type III; Interferon type II; Interferon type I; Interferon; Lamivudine; Lopinavir; Loviride; Maraviroc; Moroxydine; Methisazone; Nelfinavir; Nevirapine; Nexavir; Oseltamivir; Peginterferon alfa-2a; Penciclovir; Peramivir; Pleconaril; Podophyllotoxin; Raltegravir; Reverse transcriptase inhibitor; Ribavirin; Rimantadine; Ritonavir; Pyramidine; Saquinavir; Sofosbuvir; StavudineTelaprevir; Tenofovir; Tenofovir disoproxil; Tipranavir; Trifluridine; Trizivir; Tromantadine; Truvada; traporved; Valaciclovir; Valganciclovir; Vicriviroc; Vidarabine; Viramidine; Zalcitabine; Zanamivir; Zidovudine; RNAi antivirals; inhaled rhibovirons; monoclonal antibody respigams; neuriminidase blocking agents.

The information gleaned using the methods described herein may aid in additional patient management options. For example, the information may be used for determining whether a patient should or should not be admitted to hospital. It may also affect whether or not to prolong hospitalization duration. It may also affect the decision whether additional tests need to be performed or may save performing unnecessary tests such as CT and/or X-rays and/or MRI and/or culture and/or serology and/or PCR assay for specific bacteria and/or PCR assays for viruses and/or perform procedures such as lumbar puncture.

It is often clinically useful to assess patient prognosis, disease severity and outcome. The present inventors have now found that low levels of TRAIL (lower than about 20pg/ml or about 15pg/ml or about 10pg/ml or about 5pg/ml or about 2 pg/ml) are significantly correlated with poor patient prognosis and outcome, and high disease severity. For example, the present inventors showed that adult patients in the intensive care unit (ICU), which are generally severely ill, had significantly lower TRAIL levels compared to all other patients, which were less ill regardless of whether they had an infectious or non-infectious etiology.

Thus, according to another aspect of the present invention there is provided a method of predicting a prognosis for a disease comprising measuring the TRAIL protein serum level in subject having the disease, wherein when the TRAIL level is below a predetermined level, the prognosis is poorer than for a subject having a disease having a TRAIL protein serum level above the predetermined level.

Methods of measuring TRAIL protein serum levels are described herein above.

The disease may be an infectious disease or a non-infectious disease. The subject may have a disease which has been diagnosed or non-diagnosed.

Particular examples of diseases include without limitation bacterial infections (e.g. bacteremia, meningitis, respiratory tract infections, urinal tract infections etc.), sepsis, physical injury and trauma, cardiovascular diseases, multi-organ failure associated diseases, drug-induced nephrotoxicity, acute kidney disease, renal injury, advanced cirrhosis and liver failure, acute or chronic left heart failure, pulmonary hypertension with/without right heart failure, and various types of malignancies.

According to another embodiment, additional polypeptides are measured which aid in increasing the accuracy of the prediction. Thus, for example, other polypeptide which may be measured include IP-10, CRP, IL1RA, PCT and SAA.

According to a particular embodiment, IP-10, CRP and TRAIL are measured.

According to another embodiment, only TRAIL is measured.

The present inventors have found that patients having very low levels of TRAIL (as classified herein above) have lower chance of recovery, and higher chance of complications. Accordingly, the present inventors propose that when it is found that a subject has very low levels of TRAIL they should be treated with agents that are only used as a last resort.

Such agents for example may be for example experimental agents that have not been given full FDA approval. Other last resort agents are those that are known to be associated with severe side effects. Another exemplary last resort agent is an antibiotic such as vancomycin (which is typically not provided so as to prevent the spread of antibiotic resistance).

It will be appreciated that agents that are not typically considered as last resort agents can also be provided, but in doses which exceed the clinically acceptable dose.

According to this aspect of the present invention, if the TRAIL level is above a predetermined level, then the patient should typically not be treated with a last resort agent.

The present inventors have now found that basal levels of TRAIL in healthy individuals or patients with a non-infectious disease are lower in females compared to males during fertility age (t-test P<0.001) (see FIG. 37A), but is invariant in pre- or post-fertility age (t-test P=0.9, FIG. 37A). This trend was not observed in patients with an infectious disease.

This age dependent dynamics can be used to improve models distinguishing between bacterial, viral and non-infectious or healthy individuals, as would be evident to one skilled in the art.

For example, the model can include age and gender parameters. If the subject's age is within a certain range indicative of fertility (e.g. about 13 to 45 years) and the subject is male, then TRAIL model coefficients of males at fertility age can be used. If the subject's age is within the range indicative of fertility and the subject is female then TRAIL model coefficients of females at fertility age can be used. If the subject's age is outside the range indicative of fertility then TRAIL model coefficients that are gender invariant can be used.

Thus, according to another aspect of the invention there is provided a method of determining an infection type in a female subject of fertility age, the method comprising comparing the TRAIL protein serum level in the subject to a predetermined threshold, said predetermined threshold corresponding to the TRAIL protein serum level of a healthy female subject of fertility age, or a group of healthy female subjects of fertility age, wherein a difference between said TRAIL protein serum level and said predetermined threshold is indicative of an infection type.

Thus, according to another aspect of the invention there is provided a method of determining an infection type in a male subject of fertility age, the method comprising comparing the TRAIL protein serum level in the subject to a predetermined threshold, said predetermined threshold corresponding to the TRAIL protein serum level of a healthy male subject of fertility age, or a group of healthy male subjects of fertility age, wherein a difference between said TRAIL protein serum level and said predetermined threshold is indicative of an infection type.

It will be appreciated that predetermined thresholds can be used to either rule in or rule out an infection type.

Thus, for example if the TRAIL protein serum level is above a first predetermined threshold, the infection type is viral.

If, for example the TRAIL protein serum level is above a second predetermined threshold, the infection type is not bacterial.

If for example, the TRAIL protein serum level is below a third predetermined threshold, the infection type is bacterial.

If for example the TRAIL protein serum level is below a fourth predetermined threshold, the infection type is not viral.

Typically, the healthy male or female subject, referred to herein has no known disease. According to a particular embodiment, the control subject has no infectious disease.

Typically, the difference between the TRAIL protein serum level of the subject and the predetermined threshold is a statistically significant difference, as further described herein above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

A Host-Proteome Signature for Distinguishing Between Bacterial and Viral Infections: a Prospective Multi-Center Observational Study Methods Study Population:

A total of 1002 patients took part in the study. Pediatric patients (≤18 years) were recruited from pediatric emergency departments (PED), pediatric wards and surgical departments, and adults (>18 years) from emergency departments (ED), internal medicine departments and surgical departments. Informed consent was obtained from each participant or legal guardian, as applicable. Inclusion criteria for the infectious disease cohort included: clinical suspicion of an acute infectious disease, peak fever >37.5° C. since symptoms onset, and duration of symptoms ≤12 days. Inclusion criteria for the control group included: clinical impression of a non-infectious disease (e.g. trauma, stroke and myocardial infarction), or healthy subjects. Exclusion criteria included: evidence of any episode of acute infectious disease in the two weeks preceding enrollment; diagnosed congenital immune deficiency; current treatment with immunosuppressive or immunomodulatory therapy; active malignancy, proven or suspected human immunodeficiency virus (HIV)-1, hepatitis B virus (HBV), or hepatitis C virus (HCV) infection (FIG. 1A). Importantly, in order to enable broad generalization, antibiotic treatment at enrollment did not cause exclusion from the study.

Enrollment Process and Data Collection:

For each patient, the following baseline variables were recorded: demographics, physical examination, medical history (e.g. main complaints, underlying diseases, chronically-administered medications, comorbidities, time of symptom onset, and peak temperature), complete blood count (CBC) obtained at enrollment, and chemistry panel (e.g. creatinine, urea, electrolytes, and liver enzymes). A nasal swab was obtained from each patient for further microbiological investigation, and a blood sample was obtained for protein screening and validation. Additional samples were obtained as deemed appropriate by the physician (e.g. urine and stool samples in cases of suspected urinary tract infection [UTI], and gastroenteritis [GI] respectively). Radiological tests were obtained at the discretion of the physician (e.g. chest X-ray for suspected lower respiratory tract infection [LRTI]). Thirty days after enrollment, disease course and response to treatment were recorded. All information was recorded in a custom electronic case report form (eCRF).

Microbiological Investigation:

Patients underwent two multiplex-PCR diagnostic assays from nasal swab samples: (i) Seeplex® RV15 (n=713), for detection of parainfluenza virus 1, 2, 3, and 4, coronavirus 229E/NL63, adenovirus A/B/C/D/E, bocavirus 1/2/3/4, influenza virus A and B, metapneumovirus, coronavirus OC43, rhinovirus A/B/C, respiratory syncytial virus A and B, and Enterovirus, and (ii) Seeplex® PB6 (n=633) for detection of *Streptococcus pneumoniae, Haemophilus influenzae, Chlamydophila pneumoniae, Legionella pneumophila, Bordetella pertussis,* and *Mycoplasma pneumoniae.* Multiplex-PCR assays were performed by a certified service laboratory. Patients were also tested for additional pathogens according to their suspected clinical syndrome, including: blood culture (n=420), urine culture (n=188) and stool culture for *Shigella* spp., *Campylobacter* spp. and *Salmonella* spp. (n=66); serological testing (IgM and/or IgG) for cytomegalovirus (CMV), Epstein-Barr virus (EBV), *Mycoplasma* Pneumonia, and *Coxiella burnetii* (Q-Fever) (n=167, n=130, n=206 and n=41 respectively).

Establishing the Reference Standard: The Clear Diagnosis, Unanimous and Majority Cohorts:

A rigorous composite reference standard was created following recommendations of the Standards for Reporting of Diagnostic Accuracy (STARD).[38] First, a thorough clinical and microbiological investigation was performed for each patient as described above. Then, all the data collected throughout the disease course was reviewed by a panel of three physicians. For adult patients (>18 years) the panel included the attending physician and two infectious disease specialists, while for children and adolescents (≤18 years) it included the attending pediatrician, an infectious disease expert and a senior attending pediatrician. Each panel member assigned one of the following diagnostic labels to each patient: (i) bacterial; (ii) viral; (iii) no apparent infectious disease or healthy (controls); and (iv) indeterminate. Patients with mixed infections (bacteria plus virus) were labeled as bacterial because they are managed similarly (e.g. treated with antibiotics). Importantly, the panel members were blinded to the labeling of their peers and to the results of the signature.

This process was used to create three cohorts with an increasing level of diagnostic certainty (FIG. 1A):
(i) Majority cohort: Patients were assigned the same label by at least two of the three panel members;
(ii) Unanimous cohort (a subgroup of the Majority cohort): Patients were assigned the same label by all three panel members (the terms "unanimous cohort" and "consensus cohort" are used herein interchangeably); and
(iii) Clear Diagnosis cohort (a subgroup of the Unanimous cohort): Bacterial labeled patients were unanimously diagnosed by all three panel members, had WBC>15,000/μl (a cutoff indicative of increased bacterial infection risk[11]) and one of the following microbiological confirmations: bacteremia (with positive blood culture), bacterial meningitis (with positive CSF culture), pyelonephritis (with positive urine culture and ultrasound demonstration of renal involvement), UTI (with positive urine culture), septic shock (with positive blood culture), or peritonsillar abscess (proven by surgical exploration or computerized tomography). Viral labeled patients were unanimously diagnosed by panel members and had and a positive test result of a virus.

Additionally, control labeled patients were unanimously diagnosed by all three panel members.

Samples, Procedures and Protein Measurements:

Venous blood samples were stored at 4° C. for up to 5 hours on site and subsequently fractionated into plasma, serum and total leukocytes and stored at −80° C. Nasal swabs and stool samples were stored at 4° C. for up to 72 hours and subsequently transported to a certified service laboratory for multiplex PCR-based assay. In the screening phase, host-proteins were measured in serum and leukocytes using enzyme linked immunosorbent assay (ELISA), Luminex technology, protein arrays and Flow cytometry (on freshly isolated leukocytes). After screening and signature construction (see Host-proteome screening section), three proteins were selected and measured as follows: CRP was measured via either Cobas 6000, Cobas Integra 400, Cobas Integra 800, or Modular Analytics P800 (Roche). TRAIL and IP-10 were measured using commercial ELISA kits (MeMed Diagnostics).

Statistical Analysis:

The primary analysis was based on area under the receiver operating characteristics curve (AUC), Sensitivity (TP/P), Specificity (TN/N), Positive likelihood ratio (LR+=Sensitivity/[1−Specificity]), Negative likelihood ratio (LR−=[1−Sensitivity]/Specificity) and Diagnostic odds ratio (DOR=LR+/LR−), where P, N, TP and TN correspond to positives (bacterial patients), negatives (viral patients), true positives (correctly diagnosed bacterial patients), and true negatives (correctly diagnosed viral patients), respectively. Statistical analysis was performed with MATLAB. Sample size calculations are presented in Example 2 herein below.

Figure 1B:
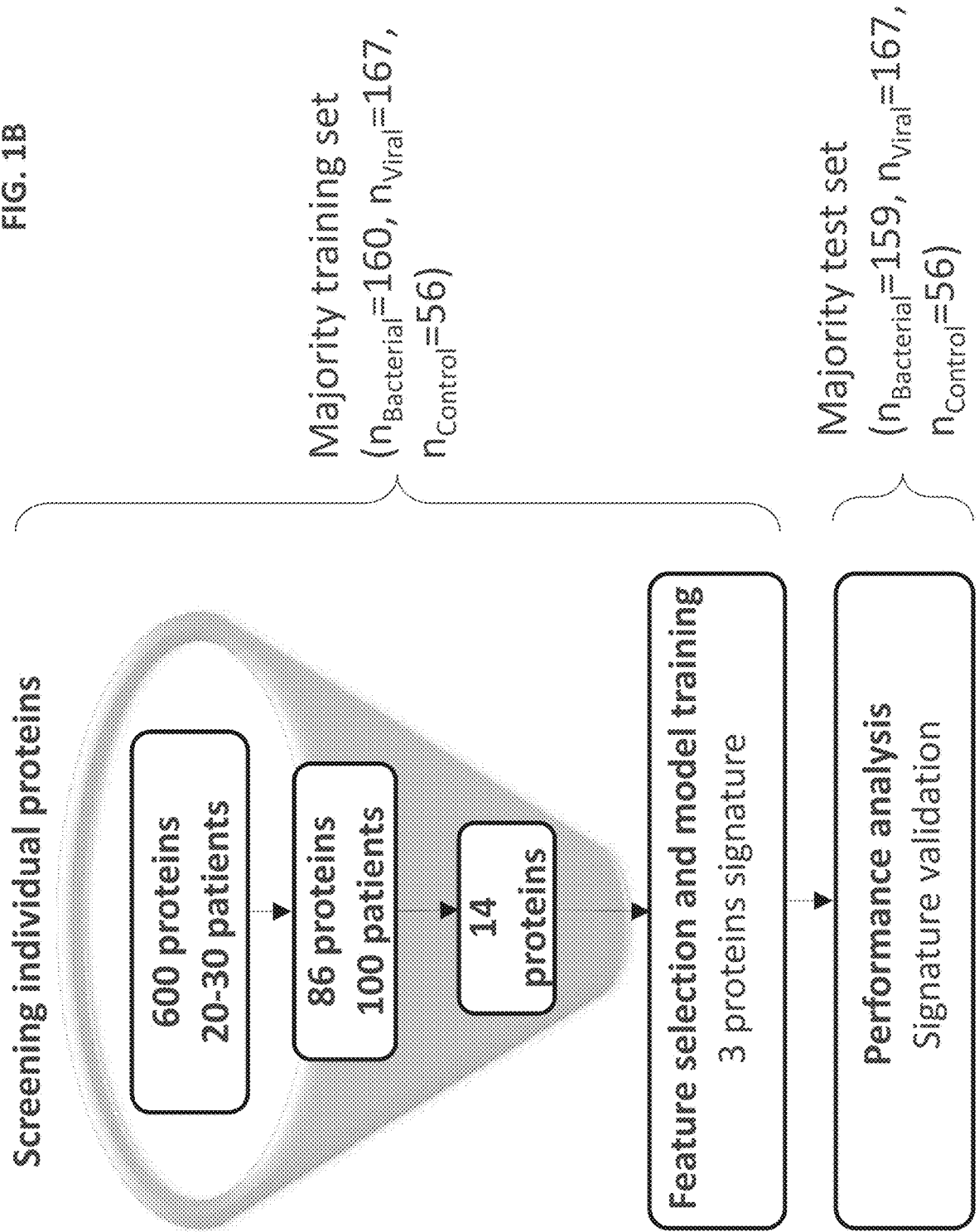

Host-Proteome Screening:

A general overview of the process for developing, training and testing the multivariate logistic model is depicted in FIG. 1B. Briefly, a systematic literature screen and bioinformatics analysis was performed that identified 600 protein candidates that were likely to be differentially expressed in peripheral blood samples of bacterial versus viral patients, some of which have a known role in the host immune response to infection and others with no direct link to the immune system. Next, each protein candidate was measured on 20-30 patients from the training set (50% viral and 50% bacterial) and a Wilcoxon rank-sum (WS) P-value<0.01 was used to screen proteins with statistically significant differential measurements. This resulted in a set of 86 proteins (false discovery rate [FDR] of 0.07). Each of these proteins was then evaluated in 100 additional patients (50% viral and 50% bacterial) and further screened using a t-test cutoff of $P<10^{-4}$, resulting in 14 proteins that were significantly differentially expressed in viral versus bacterial patients (FDR<0.001).

Signature Development and Validation:

A feature selection process was applied to identify the optimal combination of proteins. Two feature selection schemes were used: mutual-information min-max[39] and forward greedy wrapper[40], which use a series of iterations to add or remove features. The process was terminated when the increase in performance on the training set was no longer statistically significant (P>0.05). Both processes converged to the same final set of three proteins. To integrate the protein levels into a single score, multiple computational models were examined. Their performances were not significantly different (P>0.1 as further detailed in Example 2 herein below). A Multinomial Logistic Regression (MLR) model was chosen because provides a probabilistic interpretation by assigning a likelihood score to a patient's diagnosis. The signature uses this property to filter out patients whose probability of bacterial infection is intermediate: between 0.35 and 0.55. The term 'marginal immune response' is used to describe these patients because their profile borders between bacterial and viral host-responses. The patients in the Majority cohort were divided into training and test sets, each comprising 50% of the patients (FIG. 1B). The training set included the 120 patients who participated in the screening process and additional patients that were randomly assigned. The test set included the remaining patients and was used for independent assessment of the signature performance. Importantly, none of the test set patients were used to train the algorithms, or to select the proteins. A leave-10%-out cross-validation was used to estimate model performance. More details on the model construction are provided in Example 2 herein below).

Results

Figure 6A:
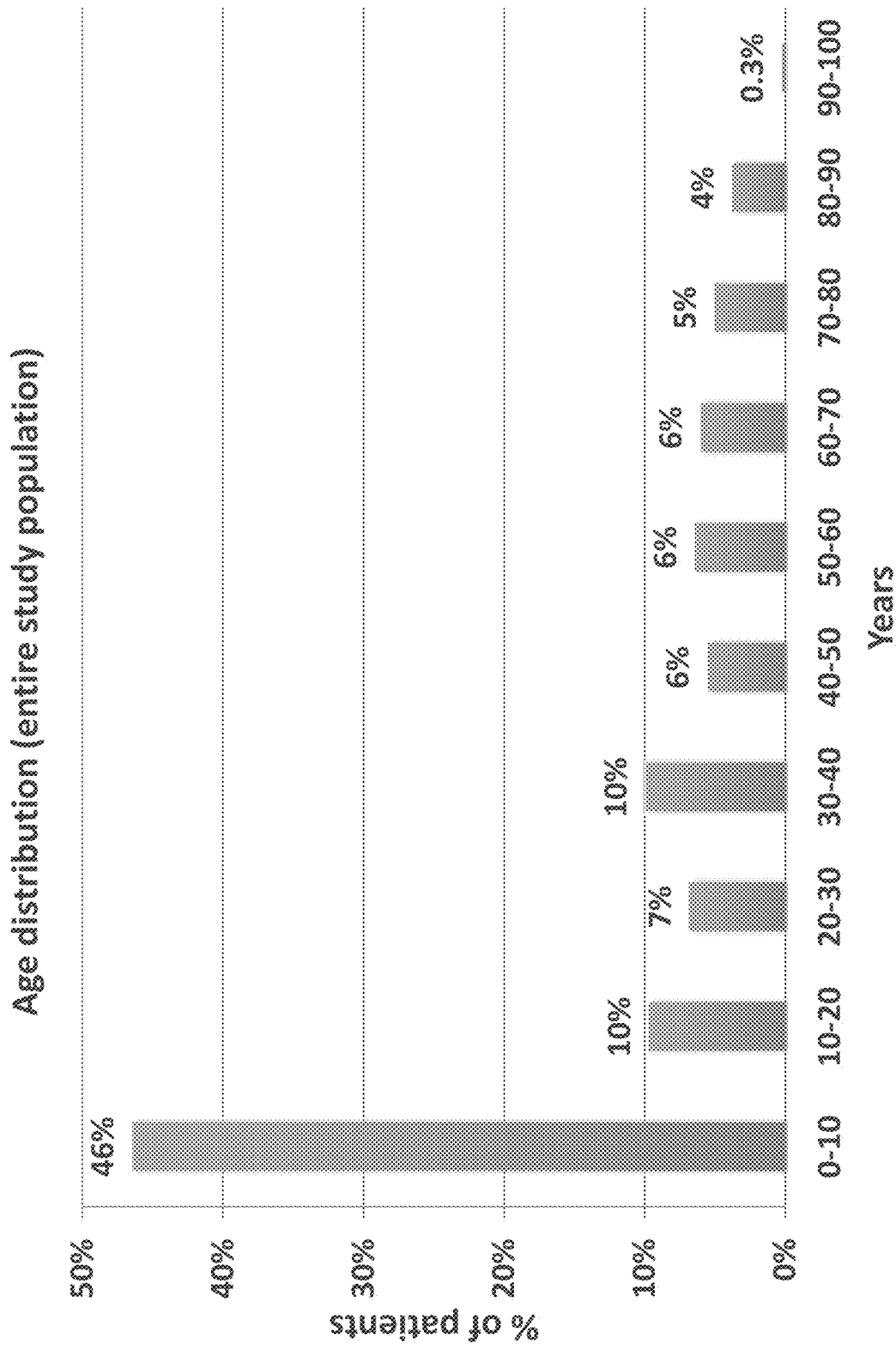
FIGS. 6A-6B. Age distribution of the diagnosed patients. A. The entire study population (n=794); B. Pediatric patients only (n=445).
Figure 6B:
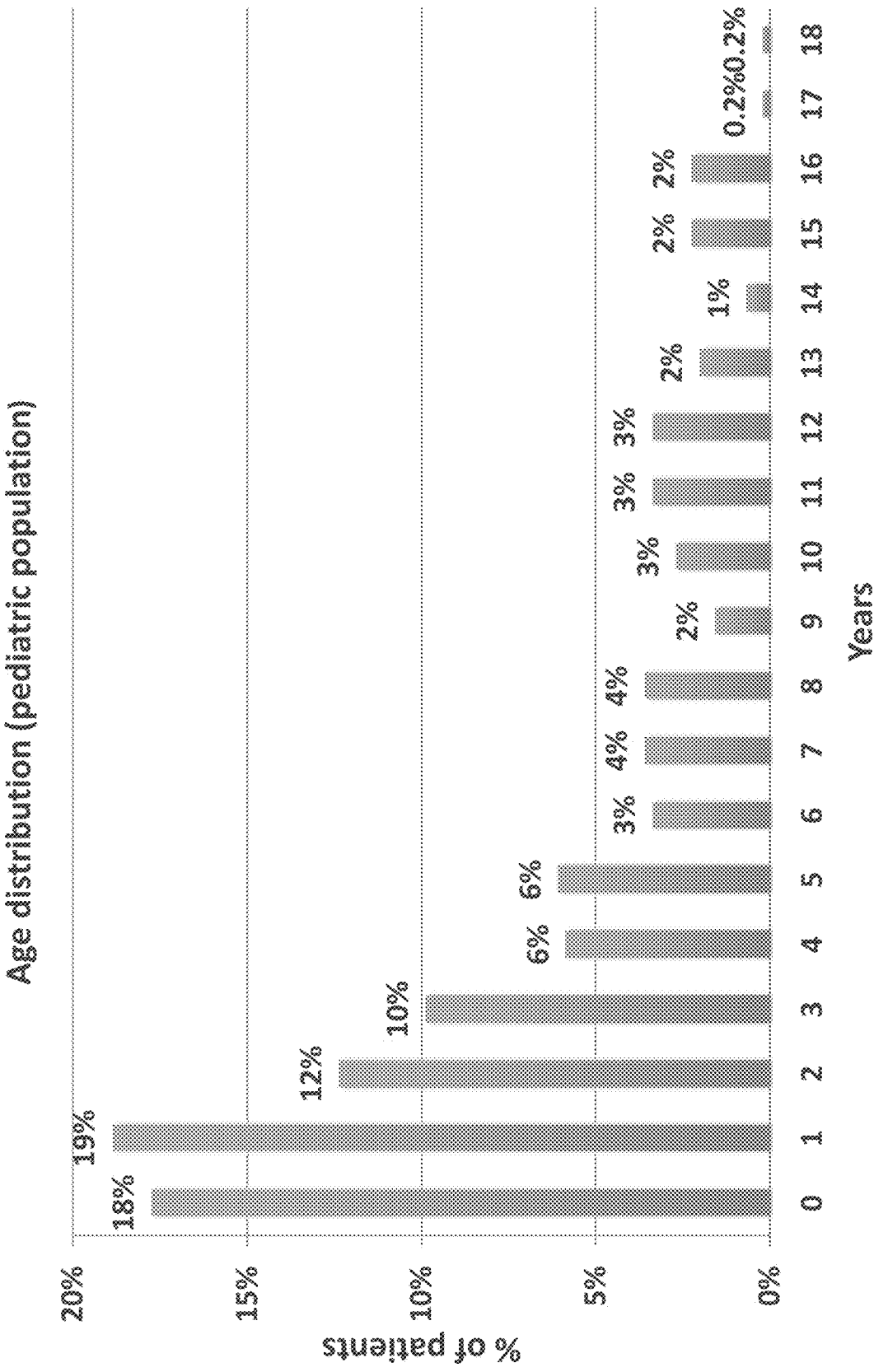
Figure 7A:
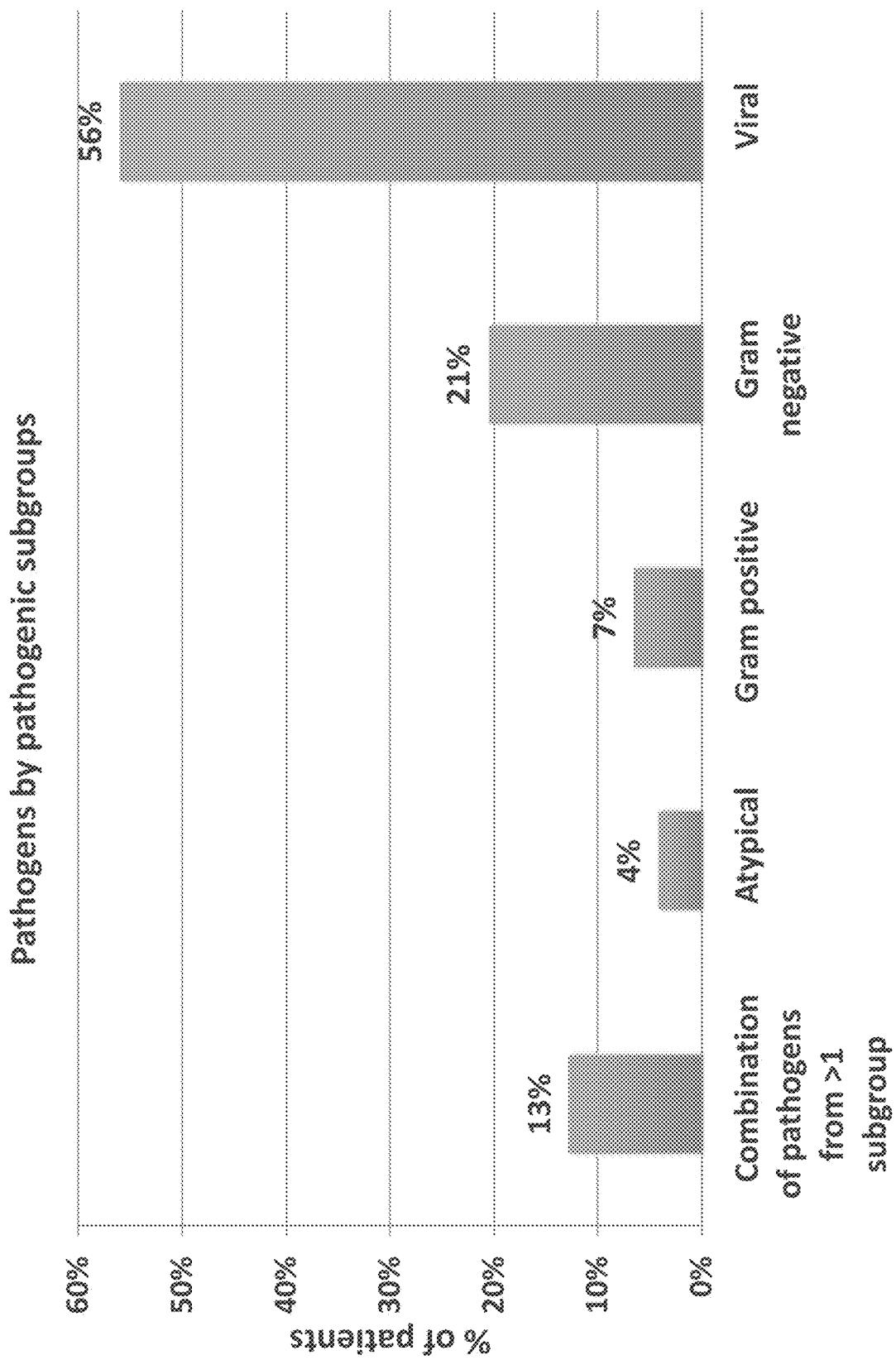
FIGS. 7A-7B. Distribution of detected pathogens in diagnosed patients (n=794). A. Distribution of detected pathogens by pathogenic subgroups; B. Distribution of detected pathogens by strain (strains detected from >1% of patients are presented). Distribution represents % of positive detections in patients with diagnosed infectious disease.
Figure 7B:
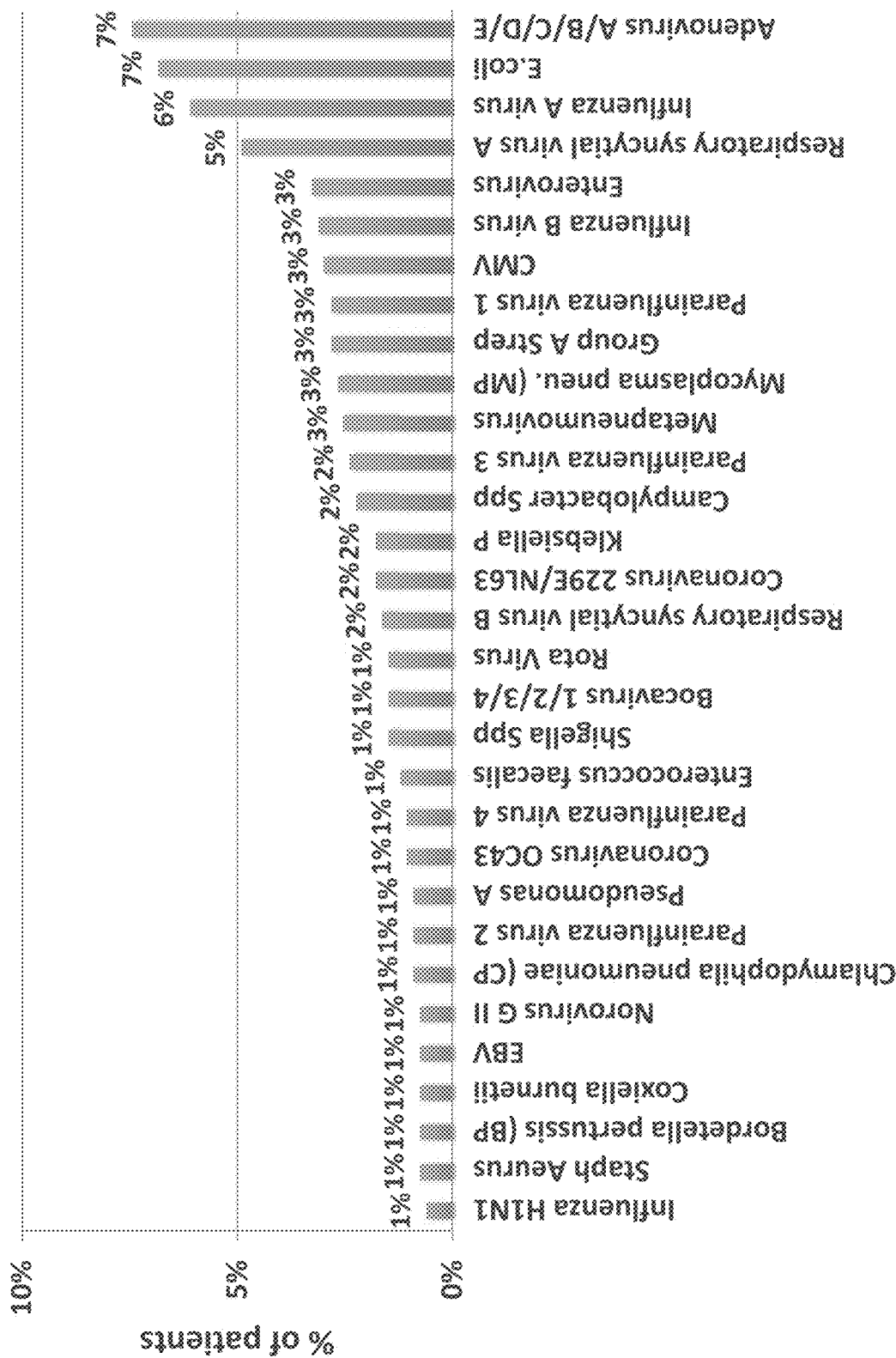

Patient Characteristics:

Three physicians independently assigned a label to each patient (either bacterial, viral, controls, or indeterminate). The labels were used to create three cohorts with increasing level of diagnostic certainty: Majority (n=765), Unanimous (n=639) and Clear Diagnosis (n=312) cohorts (FIG. 1A). Additionally, 98 patients were labeled as indeterminate, because the physicians could not establish disease etiology or there was no majority labeling. A detailed characterization of the Majority cohort is depicted in Table 1. Briefly, the cohort was balanced with respect to gender (47% females, 53% males) and included 56% pediatric patients (≤18 years) and 44% adults (>18 years). Patients presented with a wide range of clinical syndromes (e.g. RTI, UTI, and systemic infections), maximal temperatures (36-41.5° C.), time from symptoms onset (0-12 days), comorbidities, and medications (Table 1 and FIGS. 6A-12B). Altogether, 56 pathogen species were detected that are responsible for the vast majority of acute infectious diseases in the Western world (FIGS. 7A-7B).

TABLE 1

Baseline characteristics of the majority cohort patients.

| Criteria | | Total n = 765 | Children (≤18 years) n = 432 | Adults (>18 years) n = 333 |
|---|---|---|---|---|
| Age (years) | <3 | 211 (28) | | |
| | 3-6 | 93 (12) | | |
| | 6-9 | 46 (6) | | |
| | 9-18 | 82 (11) | | |
| | 18-30 | 55 (7) | | |
| | 30-60 | 161 (21) | | |
| | >60 | 117 (15) | | |
| Gender | Female | 363 (47) | 205 (47) | 158 (47) |
| Maximal Temperature (° C.) | <37.5 | 106 (14) | 28 (6) | 78 (23) |
| | 37.5-38.4 | 154 (20) | 68 (16) | 86 (26) |
| | 38.5-39.4 | 294 (38) | 164 (38) | 130 (39) |
| | 39.5-40.4 | 196 (26) | 157 (36) | 39 (12) |
| | >40.5 | 15 (2) | 15 (3) | 0 (0) |
| Time from symptoms onset (days) | 0-1 | 175 (24) | 118 (27) | 57 (17) |
| | 2-3 | 265 (36) | 161 (37) | 104 (31) |
| | 4-5 | 161 (22) | 89 (21) | 72 (22) |
| | 6-7 | 109 (15) | 52 (12) | 57 (17) |
| | 8-9 | 10 (1) | 2 (0.5) | 8 (2) |
| | 10-12 | 14 (2) | 2 (0.5) | 12 (4) |
| | N/A | 31 (4) | 8 (2) | 23 (7) |
| Clinical syndrome | Cellofills | 28 (4) | 7 (2) | 21 (6) |
| | CNS | 14 (2) | 9 (2) | 5 (2) |
| | GI | 89 (11.5) | 66 (15) | 23 (7) |
| | LRTI | 158 (21) | 84 (19) | 74 (22) |
| | Non-infectious | 112 (14.5) | 29 (7) | 83 (25) |
| | Other | 12 (1.5) | 4 (1) | 8 (2.5) |
| | Systemic | 150 (19.5) | 110 (26) | 40 (12) |
| | URTI | 145 (19) | 104 (24) | 41 (12) |
| | UTI | 57 (7) | 19 (4) | 38 (11) |
| Recruiting site | Pediatrics & Internal | 293 (38) | 137 (32) | 156 (47) |
| | PED & ED | 472 (62) | 295 (68) | 177 (53) |
| Hospitalization duration (days) | Not hospitalized | 272 (36) | 174 (40) | 98 (29) |
| | 1-2 | 206 (28) | 126 (29) | 80 (24) |
| | 3-4 | 170 (22) | 94 (22) | 76 (23) |
| | 5-6 | 53 (7) | 24 (6) | 29 (9) |
| | 7-8 | 31 (4) | 7 (1.5) | 24 (7) |
| | >8 | 33 (4) | 7 (1.5) | 26 (8) |
| Season | Autumn | 181 (24) | 111 (26) | 70 (21) |
| | Spring | 208 (27) | 124 (29) | 84 (25) |
| | Summer | 170 (22) | 98 (23) | 72 (22) |
| | Winter | 206 (27) | 99 (23) | 107 (32) |
| Smoking | Yes | 74 (10) | 0 (0) | 74 (22) |
| | No | 691 (90) | 432 (100) | 259 (78) |
| Antibiotic prescription | Yes | 432 (56) | 207 (48) | 225 (68) |
| | No | 333 (44) | 225 (52) | 108 (32) |
| Detected microorganisms | Not detected | 219 (29) | 79 (18) | 140 (42) |
| Viruses | Adenovirus A/B/C/D/E | 50 (7) | 47 (11) | 3 (1) |
| | Bocavtrus 1/2/3/4 | 9 (1) | 9 (2) | 0 (0) |
| | CMV & EBV | 25 (3) | 23 (5) | 2 (0.6) |
| | Coronavirus 229E/NL63/OC43 | 19 (2) | 14 (3) | 5 (2) |
| | Enteric viruses | 19 (2) | 16 (4) | 3 (1) |
| | Enterovirus | 21 (3) | 20 (5) | 1 (0.3) |
| | Influenza A virus | 45 (6) | 24 (6) | 21 (6) |
| | Influenza B virus | 19 (2) | 14 (3) | 5 (2) |
| | Metapneumovirus | 17 (2) | 13 (3) | 4 (1) |
| | Parainfluenza 1/2/3/4 | 48 (6) | 41 (9) | 7 (2) |

TABLE 1-continued

Baseline characteristics of the majority cohort patients.

|  | Criteria | Total n = 765 | Children (≤18 years) n = 432 | Adults (>18 years) n = 333 |
|---|---|---|---|---|
| Bacteria | Respiratory syncytial virus A/B | 40 (5) | 38 (9) | 2 (0.6) |
|  | Rhinovirus A/B/C | 87 (11) | 73 (17) | 14 (4) |
|  | Atypical bacteria | 27 (4) | 7 (2) | 20 (6) |
|  | E. coli | 44 (6) | 17 (4) | 27 (8) |
|  | Enterococcus faecalis | 10 (1) | 0 (0) | 10 (3) |
|  | Group A Step | 19 (2) | 16 (4) | 3 (1) |
|  | Haemophilus influenzae | 179 (23) | 148 (34) | 31 (9) |
|  | Streptococcus pneumoniae | 306 (40) | 207 (48) | 99 (30) |

Values are numbers (percentages). Only microorganisms that were detected in more than 5 patients are presented.
CNS—central nervous system,
GI—gastroenteritis,
LRTI—lower respiratory tract infection,
UTRI—upper respiratory tract infection,
UTI—urinary tract infection,
N/A—healthy controls or patients in which data was not obtained.
Influenza A subgroup included H1N1 strains. The atypical bacteria subgroup included *Chlamydophila pneumoniae*, *Mycoplasma pneumonia* and *Legionella pneumophila*. The Enteric viruses subgroup included Rota virus, Astrovirus, Enteric Adenovirus and Norovirus G I/II. In the clinical syndrome analysis the LRTI group included pneumonia, bronchiolitis, acute bronchitis, and laryngitis; URTI group included pharyngitis, acute otitis media, acute sinusitis and acute tonsillitis.

Figure 2B:
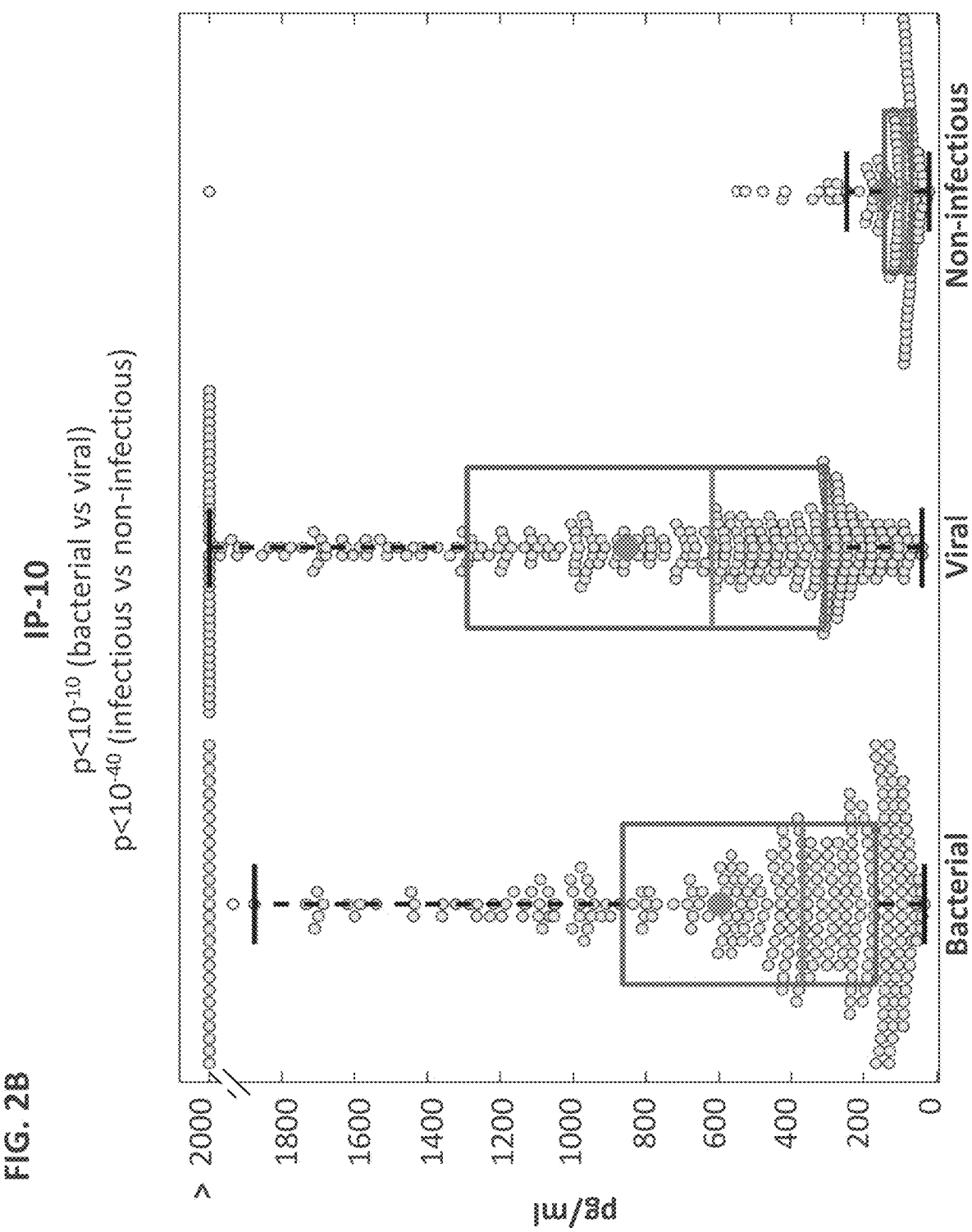

Signature Performance on the Clear Diagnosis, Unanimous and Majority Cohorts:

Of the 600 screened host-proteins and their combinations, the best signature for discriminating bacterial, viral and control patients in the Majority cohort training set included three soluble proteins: TNF-related apoptosis-inducing ligand (TRAIL), Interferon gamma-induced protein 10 (IP-10), and C-reactive protein (CRP) (FIGS. 2A-2C). Signature AUC for distinguishing between bacterial and viral infections on the test set of the Majority cohort was 0.94±0.04.

Similar results were obtained using leave-10%-out cross-validation on the entire Majority cohort (AUC=0.94±0.02). The signature significantly outperformed all the individual proteins evaluated in the screening phase ($P<10^{-6}$). The training and testing procedures were repeated on the Unanimous and Clear Diagnosis cohorts, yielding AUCs of 0.96±0.02 and 0.99±0.01, respectively. This stepwise increase in performance is aligned with the increased certainty of reference standard assignment in the three cohorts (Table 2, herein below).

TABLE 2

Signature measures of accuracy for diagnosing bacterial vs. viral infections

| B. Marginal immune response filter | | | A. All patients | | | |
|---|---|---|---|---|---|---|
| Majority cohort | Unanimous cohort | Clear diagnosis cohort | Majority cohort | Unanimous cohort | Clear diagnosis cohort | Accuracy measure |
| 0.94 | 0.97 | 0.99 | 0.94 | 0.96 | 0.99 | AUC |
| (0.92, 0.96) | (0.95, 0.99) | (0.98, 1.00) | (0.92, 0.96) | (0.94, 0.98) | (0.98, 1.00) | |
| 0.91 | 0.93 | 0.96 | 0.88 | 0.90 | 0.94 | Total |
| (0.88, 0.94) | (0.9, 0.96) | (0.93, 0.99) | (0.85, 0.90) | (0.87, 0.92) | (0.91, 0.97) | accuracy |
| 0.92 | 0.94 | 0.96 | 0.87 | 0.88 | 0.96 | Sensitivity |
| (0.88, 0.96) | (0.9, 0.98) | (0.88, 1.00) | (0.83, 0.91) | (0.84, 0.91) | (0.88, 1.00) | |
| 0.89 | 0.93 | 0.97 | 0.90 | 0.92 | 0.93 | Specificity |
| (0.86, 0.89) | (0.9, 0.96) | (0.89, 0.97) | (0.86, 0.93) | (0.89, 0.96) | (0.89, 0.97) | |
| 8.4 | 13.4 | 32.0 | 8.7 | 11.0 | 13.7 | LR+ |
| (6, 12) | (8, 21) | (13, 78) | (6, 12) | (7, 16) | (8, 24) | |
| 0.09 | 0.07 | 0.04 | 0.14 | 0.13 | 0.04 | LR− |
| (0.06, 0.13) | (0.04, 0.11) | (0.01, 0.26) | (0.11, 0.19) | (0.09, 0.18) | (0.01, 0.27) | |
| 93 | 208 | 776 | 60 | 84 | 319 | DOR |
| (53, 164) | (99, 436) | (92, 6528) | (37, 98) | (47, 150) | (43, 2383) | |

A. Performance estimates and their 95% CIs were obtained using a leave-10%-out cross-validation on all patients in the Clear Diagnosis cohort ($n_{Bacterial}$=27, $n_{Viral}$=173), Unanimous ($n_{Bacterial}$=256, $n_{Viral}$=271), and Majority ($n_{Bacterial}$=319, $n_{Viral}$=334) cohorts. B. The analysis was repeated after filtering out patients with a marginal immune response (Clear Diagnosis [$n_{Bacterial}$=27, $n_{Viral}$=159, $n_{marginal}$=14], Unanimous [$n_{Bacterial}$=233, $n_{Viral}$=232, $n_{marginal}$=62], and Majority [$n_{Bacterial}$=290, $n_{Viral}$=277, $n_{marginal}$=88]), which resembles the way clinicians are likely to use the signature.

Next, the present inventors used the signature to distinguish between infectious (bacterial or viral) and non-infectious controls on the Majority cohort test set, yielding an AUC of 0.96±0.02. Further evaluation using leave-10%-out cross-validation gave similar results (AUC=0.96±0.01). The signature outperformed any of the individual proteins ($P<10^{-8}$). Again, evaluation on the Unanimous and Clear Diagnosis cohorts showed improved AUCs of 0.97±0.02, and 0.97±0.03, respectively. To obtain conservative estimations of signature performance, the analysis that follows focuses on the Majority cohort.

Figure 3A:
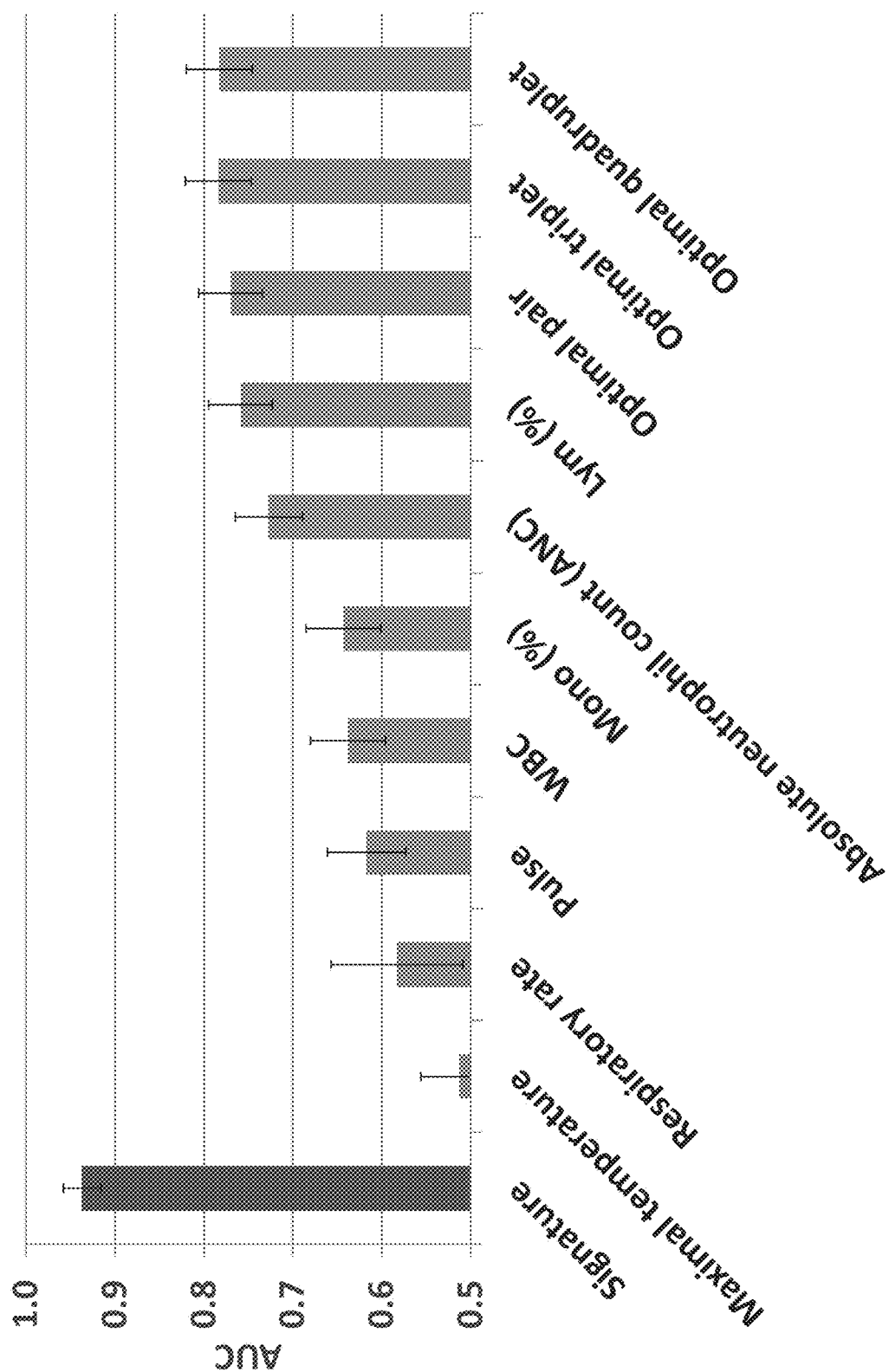
FIGS. 3A-3B. Comparison of the signature to lab parameters and protein biomarkers for diagnosing bacterial vs. viral patients. (A) Performance of clinical and lab parameters as well as the best performing pair (ANC and Lym %), triplet (ANC, Lym % and Pulse), and quadruplets (ANC, Lym %, Pulse, Mono %) of parameters, the values of which were combined using a logistic regression. Comparison was done on the Majority cohort (bacterial and viral patients, n=653), apart from pulse (recorded in 292 bacterial and 326 viral patients), and respiratory rate (recorded in 292 bacterial and 326 viral patients). The signature performed significantly better ($P<10^{-15}$) than the optimal quadruplet. (B) The signature performed significantly better ($P<10^{-8}$) than biomarkers with a well-established role in the host response to infections. For each of the select biomarkers, analysis was performed in a subgroup of the Majority cohort ($43 \leq n \leq 154$ for each analysis, a convenience sample, n depended on the strength of the signal). Error bars represent 95% CI.
Figure 3B:
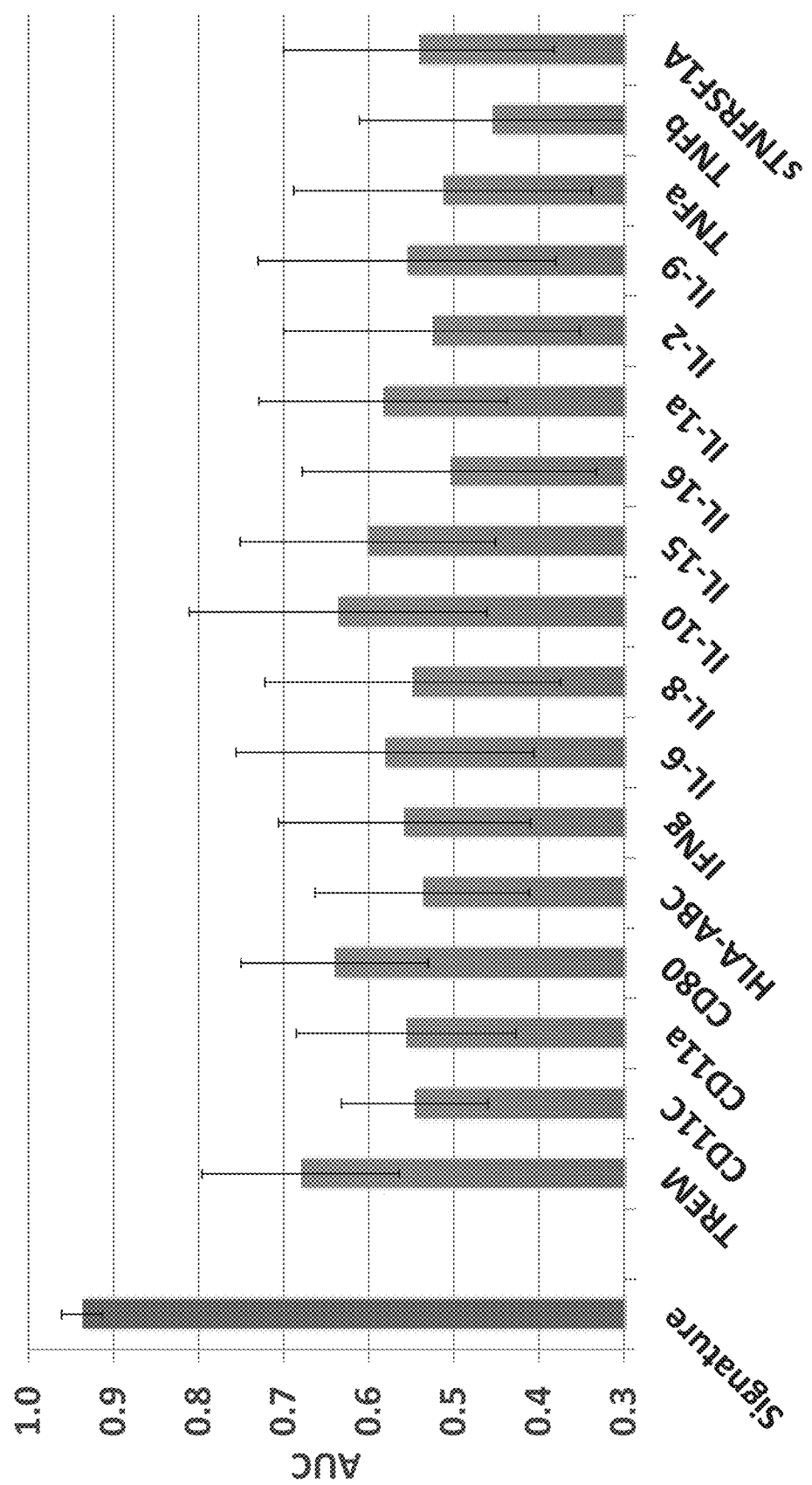

Comparison with Laboratory Measurements, Clinical Parameters, and Well-Established Biomarkers:

The signature was compared with well-established clinical parameters and laboratory measurements, including white blood count (WBC), absolute neutrophil count (ANC), percentage neutrophils, maximal temperature, pulse, and respiratory rate (FIG. 3A and Example 2). The signature surpassed all individual parameters ($P<10^{-18}$). Next, the signature was compared to a combination of several clinical parameters. To this end, multinomial logistic models were generated for all combinations of up to four clinical parameters. The best performing pair, triplet and quadruplet are depicted in FIG. 3A (adding a fifth parameter did not improve performance). The signature was significantly better than the best performing clinical parameters combination ($P<10^{-15}$), which consisted of ANC, pulse, % lymphocytes and % monocytes, (AUC=0.94±0.02 vs. 0.77±0.04). Next, the signature performance was compared to PCT and CRP, two proteins routinely used in clinical practice to diagnose sepsis and bacterial infections (Example 2). The signature performed significantly better than both proteins ($P<10^{-18}$ and $P<10^{-6}$, respectively). The signature also performed better than a wide range of host-proteins with an established role in the immune response to infection, including sepsis and bacterial-related (e.g. TREM, IL-6 and IL-8), virus-related (e.g. IFN-γ and IL-2), and inflammation-related (e.g. IL-1a and TNF-α) proteins ($P<10^{-8}$) (FIG. 3B and Example 2, herein below).

Figure 4:
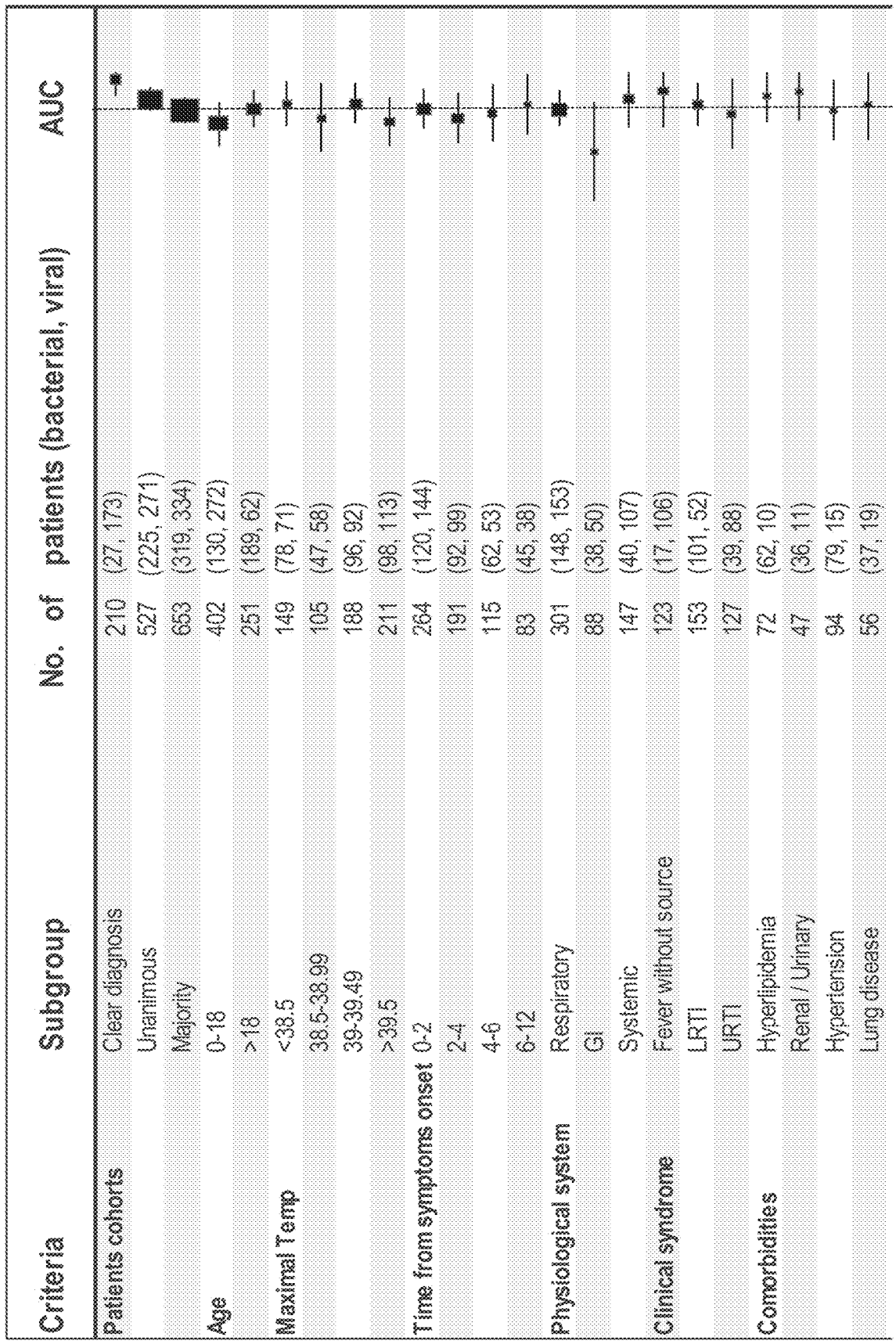
FIG. 4. Signature performance is robust across different patient subgroups. Signature AUC in subgroups of the Majority cohort (bacterial and viral) are depicted. Square size is proportional to number of patients and error bars represent 95% CI. In the Pathogens analysis, each virus was compared to bacteria affecting the same physiological system, indicated in brackets. R-respiratory, S-systemic, C-central nervous system, G-gastrointestinal, U-urinary, K-skin. Only pathogens detected in more than 5 patients are presented. For subgroup definitions see Table 1 in Example 1.

Signature Performance is Robust Across Different Patient Subgroups:

Patient and pathogen heterogeneity, which are inherent in real-life clinical settings, might negatively affect the diagnostic utility of any individual host-biomarker. To examine whether the signature, a combination of multiple biomarkers, can maintain steady performance despite patient-to-patient variability, subgroup analyses were performed. The signature was robust (AUCs between 0.87 and 1.0) across a wide range of patient characteristics, including age, clinical syndrome, time from symptom onset, maximal temperature, pathogen species, comorbidities, treatment with medications for chronic diseases, and clinical site (FIG. 4 and Example 2, herein below). The signature was also tested on the subgroup of patients who were technically excluded, but had unanimous labeling by the expert panel, which yielded an AUC of 0.96±0.06 ($n_{Bacterial}$=27, $n_{Viral}$=14). This might suggest that the signature is applicable more broadly to conditions that were initially excluded (e.g. sub-febrile patients).

Signature Performance Remains Unaffected by the Presence of Potential Colonizers:

Many disease-causing bacteria are also part of the natural flora, and are frequently found in asymptomatic subjects.[12,42-44] Such bacteria pose a considerable diagnostic challenge, because merely detecting them does not necessarily imply a causative role in the disease; therefore, appropriate treatment may remain unclear. The present inventors asked whether the signature performance is affected by their presence.

*Streptococcus pneumoniae* (SP) and *Haemophilus influenzae* (HI), detected by PCR on nasal swabs, were the two most common bacteria in the Majority group (Table 1, herein above). High rates of SP and HI were found amongst both bacterial and viral patients (SP: 36% and 47%; HI: 20% and 32%), substantiating the understanding that their mere presence does not necessarily cause a disease.[12] The patients were stratified based on whether or not they had SP (SP+: $n_{Bacterial}$=116, $n_{Viral}$=157; SP-: $n_{Bacterial}$=203, $n_{Viral}$=177) and AUC performance of the two groups was compared. A significant difference was not observed (0.93±0.03 vs. 0.94±0.02, P=0.31). The presence or absence of HI did not affect signature performance either (0.94±0.04 vs. 0.93±0.02; HI+: $n_{Bacterial}$=63, $n_{Viral}$=106; HI-: $n_{Bacterial}$=256, $n_{Viral}$=228, P=0.34). This indicates that the signature remains unaffected by carriage of SP and HI.

Discussion

A rigorous composite reference standard strategy was constructed that included the collection of clinical data, a chemistry panel, and a wide array of microbiological tests, followed by labeling by three independent physicians. This process generated a hierarchy of three sub-cohorts with decreasing size and increasing reference standard certainty: Majority, Unanimous and Clear Diagnosis. The respective signature AUCs were 0.94±0.02, 0.96±0.02, and 0.99±0.01. This stepwise increase in performance may be attributed to the increase in reference standard certainty. However, the increased accuracy, particularly in the Clear Diagnosis cohort, may also be partially due to a selection bias of patients with severe illness or straightforward diagnosis. Therefore, the primary analysis presented herein focused on the Majority cohort, which captures a wider spectrum of illness severity and difficult-to-diagnose cases. This cohort potentially includes some erroneous labeling, thereby leading to conservative estimations of the signature accuracy.

The signature addresses several challenges of current microbiological tests. (i) The difficulty of diagnosing inaccessible or unknown infection sites. The signature accurately diagnosed such cases, including lower respiratory tract infections (AUC 0.95±0.03, n=153) and fever without source (AUC=0.97±0.03, n=123). (ii) Prolonged time to results (hours to days). The signature measures soluble proteins, which are readily amenable to rapid measurement (within minutes) on hospital-deployed automated immunoassay machines and point-of-care devices. (iii) Mixed infections may lead to diagnostic uncertainty, because detection of a virus does not preclude bacterial co-infection.[14,15] The signature addresses this by classifying mixed infections together with pure bacterial infections, thus prompting physicians to manage both groups similarly with regard to antibiotics treatment. The fact that mixed co-infections elicited a proteome host-response that is similar to pure bacterial, rather than a mixture of responses, may indicate pathway dominance of bacterial over viral. (iv) A significant drawback of microbiological tests, PCRs in particular, is detection of potential colonizers in subjects with non-bacterial diseases.[12,13] The signature performance was unaffected by the presence or absence of potential colonizers.

Host-proteins, such as PCT, CRP and IL-6, are routinely used to assist in the diagnosis of bacterial infections because they convey additional information over clinical symptoms, blood counts and microbiology.[11] However, inter-patient and pathogen variability limit their usefullness.[21-27] Combinations of host-proteins have the potential to overcome this, but have thus far yielded insignificant-to-moderate diagnostic improvement over individual proteins.[11,35-37] This modest improvement may be due to the reliance on combinations of bacterial-induced proteins that are sensitive to the same factors, and are therefore less capable of compensating for one another. Accordingly, a larger improvement was observed in combinations that included host-proteins, clinical parameters and other tests.[11,35-37] Obtaining these multiple parameters in real-time, however, is often not feasible.

To address this, a combination of proteins with complementary behaviors was identified. Specifically, it was found that TRAIL was induced in response to viruses and suppressed by bacteria, IP-10 was higher in viral than bacterial infections, and CRP was higher in bacterial than viral infections. While the utility of elevated CRP to suggest bacterial infections is well established[31,45], the inclusion of novel viral-induced proteins, to complement routinely used bacterial-induced proteins, substantially contributed to the signature's robustness across a wide range of subgroups, including time from symptom onset, pathogen species and comorbidities among others. For example, adenoviruses, an important subgroup of viruses that cause 5%-15% of acute infections in children are particularly challenging to diagnose because they induce clinical symptoms that mimic a bacterial infection.[46] Routine laboratory parameters perform poorly on this subgroup compared to the signature (AUCs=0.60±0.10 [WBC], 0.58±0.10 [ANC], 0.88±0.05 [signature]; n=223).

Despite advances in infectious disease diagnosis, timely identification of bacterial infections remains challenging, leading to antibiotic misuse with its profound health and economic consequences. To address the need for better treatment guidance, the present inventors have developed and validated a signature that combines novel and traditional host-proteins for differentiating between bacterial and viral infections. The present finding in a large sample size of patients is promising, suggesting that this host-signature has the potential to help clinicians manage patients with acute infectious disease and reduce antibiotic misuse.

Example 2

A Host-Proteome Signature for Distinguishing Between Bacterial and Viral Infections: a Prospective Multi-Center Observational Study—Supplementary Material Measures of Accuracy The signature integrates the levels of three protein biomarkers measured in a subject, and computes a numerical score that reflects the probability of a bacterial vs. viral infection. To quantify the diagnostic accuracy of the signature a cutoff on the score was used and the following measures were applied: Sensitivity, specificity, positive predictive value (PPV), negative predictive value (NPV), total accuracy, positive likelihood ratio (LR+), negative likelihood ratio (LR−), and diagnostic odds ratio (DOR). These measures are defined as follows:

$$\text{Sensitivity} = \frac{TP}{TP + FN}$$

$$\text{Specificity} = \frac{TN}{TN + FP}$$

$$\text{total accuracy} = \frac{TP + FN}{TP + FN + TN + FP}$$

$$PPV = \frac{TP}{TP + FP} = \frac{\text{sensitivity} \cdot \text{prevalence}}{\text{sensitivity} \cdot \text{prevalence} + (1 - \text{specificity}) \cdot (1 - \text{prevalence})}$$

$$NPV = \frac{TN}{TN + FN} = \frac{\text{sensitivity} \cdot (1 - \text{prevalence})}{\text{specificity} \cdot (1 - \text{prevalence}) + (1 - \text{sensitivity}) \cdot (\text{prevalence})}$$

$$LR+ = \frac{\text{Sensitivity}}{1 - \text{Specificity}}$$

$$LR- = \frac{1 - \text{Sensitivity}}{\text{Specificity}}$$

$$DOR = \frac{LR+}{LR-}$$

P, N, TP, FP, TN, FN are positives, negatives, true-positives, false-positives, true-negatives, and false-negatives, respectively. Prevalence is the relative frequency of the positive class (i.e., prevalence=P/(P+N)). Unless mentioned otherwise, positives and negatives refer to patients with bacterial and viral infections, respectively.

The area under the receiver operating curve (AUC) was also used to perform cutoff independent comparisons of different diagnostic methods. For details on formulation and confidence interval (CI) computation of the AUC see Hanley and McNeil.[1] 95% CIs of the accuracy measures throughout this document are reported.

Sample Size:

The primary study objective was to obtain the performance of the signature for classifying patients with viral and bacterial etiologies. It was estimated that the sample size required to reject the null hypothesis that the sensitivity and specificity over the entire population, P, are lower than P0=75% with significance level of 1%, power of 90% for a difference of 15% (P1−P0≥15%), which yielded 394 patients (197 viral and 197 bacterial). Additionally it was anticipated that roughly 15% of the patients will have an indeterminate source of infection, 10% would be excluded for technical reasons and 10% will be healthy or non-infectious controls. Taken together, the study required the recruitment of at least 607 patients. This requirement was fulfilled because 1002 patients were recruited.

Constructing a Computation Model Logistic Model:

To integrate the protein levels into a single predictive score, multiple computational models were examined including Artificial Neural Networks (ANN), Support Vector Machines (SVM), Bayesian Networks (BN), K-Nearest Neighbor (KNN) and Multinomial Logistic Regression (MLR).[2,3] The AUCs for distinguishing between bacterial and viral infections obtained on the Majority cohort using a leave-10%-out cross validation were 0.93±0.02 (ANN), 0.93±0.02 (SVM [linear]), 0.94±0.02 [SVM (radial basis function)], 0.92±0.02 (BN), 0.91±0.02 (KNN) and 0.94±0.02 (MLR). Significant difference in the performances of ANN, SVM and MLR models (P>0.1 when comparing their AUCs) were not observed. The present inventors chose to use MLR because it provides a probabilistic interpretation by assigning a likelihood score to a patient's diagnosis.

The present inventors trained and tested the MLR signature for distinguishing between bacterial and non-bacterial etiologies. Since the prevalence of underlying etiologies varies across different clinical settings, the model priors were adjusted to reflect equal baseline prevalence (50% bacterial and 50% non-bacterial). Within the non-bacterial group the priors were adjusted to 45% viral and 5% non-infectious, to reflect the anticipated higher prevalence of viral versus non-infectious patients among subjects with suspicious for acute infection. The MLR weights and their respective 95% confidence intervals, as well as the p-values associated with each coefficient are summarized in Tables 3-4 herein below. In the bacterial versus viral infection analysis the probabilities were adjusted to sum up to 1 ($P_{b\_adjusted}=[P_b+P_v]$ and $P_{b\_adjusted}=[P_b+P_v]$, where $P_b$ and $P_v$ correspond to the probability of bacterial and viral infections respectively).

TABLE 3

MLR coefficients and their respective standard error

| Second Coordinate $\delta_1$ (bacterial) | First Coordinate $\delta_0$ (viral) | |
|---|---|---|
| $b_0 = -0.378 \pm 0.732$ | $a_0 = -1.299 \pm 0.651$ | Constant |
| $b_1 = -0.020 \pm 0.0084$ | $a_1 = 0.0088 \pm 0.0064$ | TRAIL |
| $b_2 = 0.0875 \pm 0.015$ | $a_2 = 0.0605 \pm 0.0145$ | CRP |
| $b_3 = 0.0050 \pm 0.0014$ | $a_3 = 0.0053 \pm 0.0014$ | IP-10 |

TABLE 4

The p-values associated with each MLR coefficient.

| Class (bacterial) | Class (viral) | |
|---|---|---|
| <0.001 | <0.001 | Constant |
| <0.001 | 0.008 | TRAIL |
| <0.001 | <0.001 | CRP |
| <0.001 | <0.001 | IP-10 |

Figure 5:
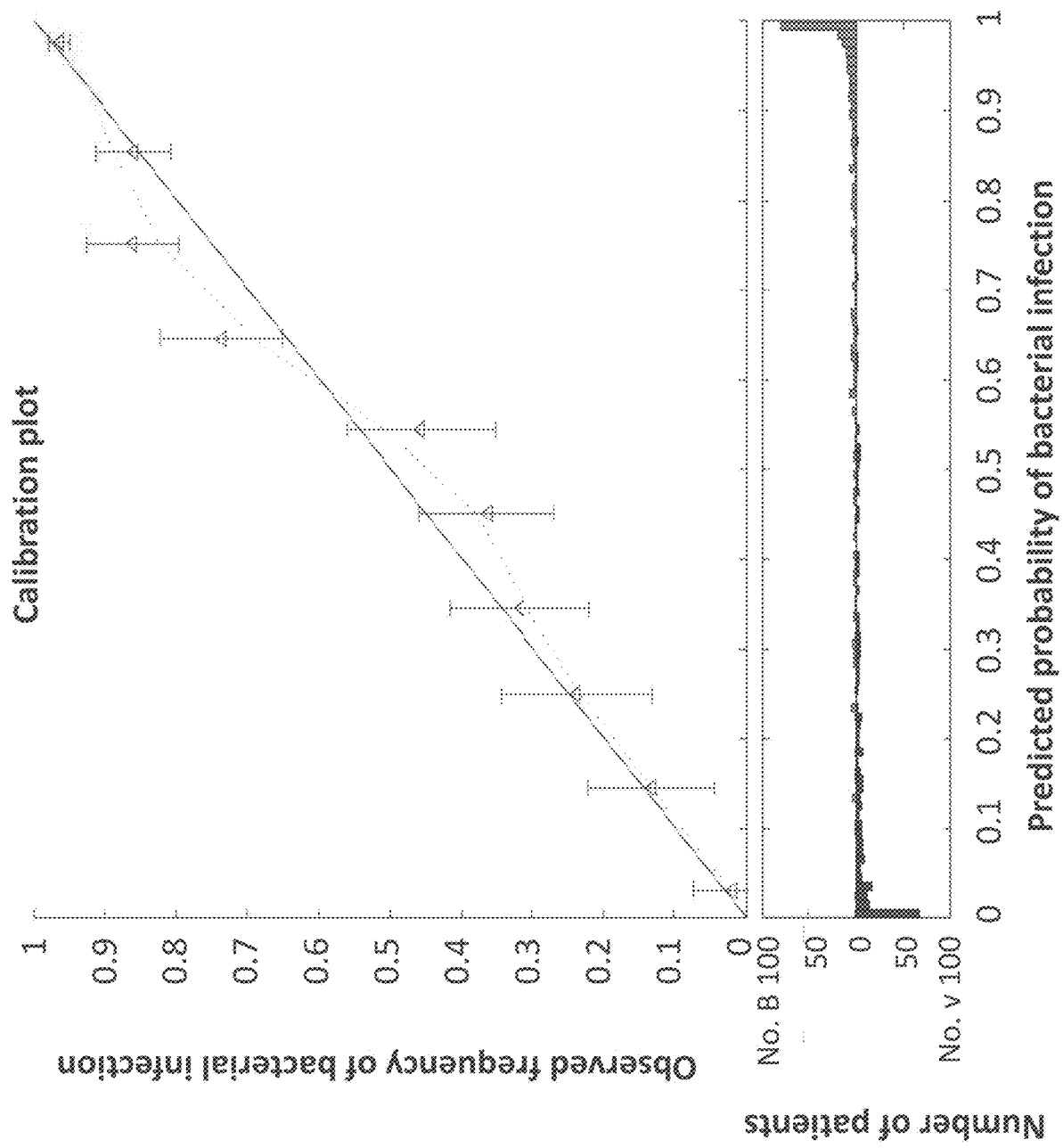
FIG. 5. Calibration plot of the MLR model. In the top panel patients were grouped into 10 bins based on their predicted probabilities of a bacterial infection (x-axis), and compared to the observed fraction of bacterial infections within each bin (y-axis). Dashed line is a moving average (of size 5 bins). The bottom panel shows the distribution of predicted probabilities for bacterial (upper bars) and viral (lower bars).

Logistic Calibration Curves:

In order to assess the validity of the MLR model, the calculated prediction probabilities were compared with the actually observed outcomes (FIG. 5). The predicted probabilities are highly compatible with the observed ones, further demonstrating the model validity.

Summary of the Patient Cohorts Used in this Study:

A total of 1002 patients were recruited and 892 were enrolled (110 were excluded based on pre-determined exclusion criteria). Based on the reference standard process described in the 'Methods' section of Example 1, patients were assigned to four different diagnosis groups: (i) bacterial; (ii) viral; (iii) no apparent infectious disease or healthy (controls); and (iv) indeterminate. Patients with mixed infections (bacteria plus virus) were labeled as bacterial because they are managed similarly (e.g. treated with antibiotics) (FIG. 1A). In total, 89% of all enrolled patients were assigned a diagnosis, a rate which approaches the literature-documented limit.[4-6] The following sections provide a detailed description of patient characteristics, which includes all the patients with a final diagnosis (n=794): 765 patients of the Majority cohort and 29 patients for which the serum samples were depleted during the screening phase (FIGS. 1A-1B).

Age and Gender Distribution:

Patients of all ages were recruited to the study. The patients with agreed diagnosis (diagnosed patients; n=794) included more pediatric (≤18 years) than adult (>18 years) patients (445 patients [56%] vs. 349 [44%]). The age distribution was relatively uniform for patients aged 20-80 years and peaked at <4 years of age for pediatric patients (FIGS. 6A-6B). The observed age distribution for pediatric patients is consistent with that expected and represents the background distribution in the inpatient setting[7] (e.g., the emergency department [ED], pediatrics departments, and internal departments). Patients of both genders were recruited to the study. The patient population was balanced in respect to gender distribution (47% females, 53% males).

Detected Pathogens:

A wide panel of microbiological tools were used in order to maximize pathogen detection rate. At least one pathogen was detected in 65% of patients with an acute infectious disease (56% of all 794 diagnosed patients). A total of 36 different pathogens were actively detected using multiplex PCR, antigen detection, and serological investigation. Additional 20 pathogens were detected using standard culture techniques or in-house PCR. Altogether, 56 different pathogens from all major pathogenic subgroups were detected (FIG. 7A). This rate of pathogen identification is similar to that reported in previously published studies and included pathogens from all major pathogenic subgroups (Gram-negative bacteria, Gram-positive bacteria, atypical bacteria, RNA viruses, and DNA viruses). In 13% of the patients, pathogens from more than one of the aforementioned pathogenic subgroups were detected (FIG. 7A).

The pathogenic strains found in this study are responsible for the vast majority of acute infectious diseases in the Western world and included key pathogens such as influenza A/B, respiratory syncytial virus (RSV), parainfluenza, *E. Coli*, Group A *Streptococcus*, etc. Notably, analysis of the detected pathogens revealed that none of the pathogens is dominant (FIG. 7B).

Figure 8:
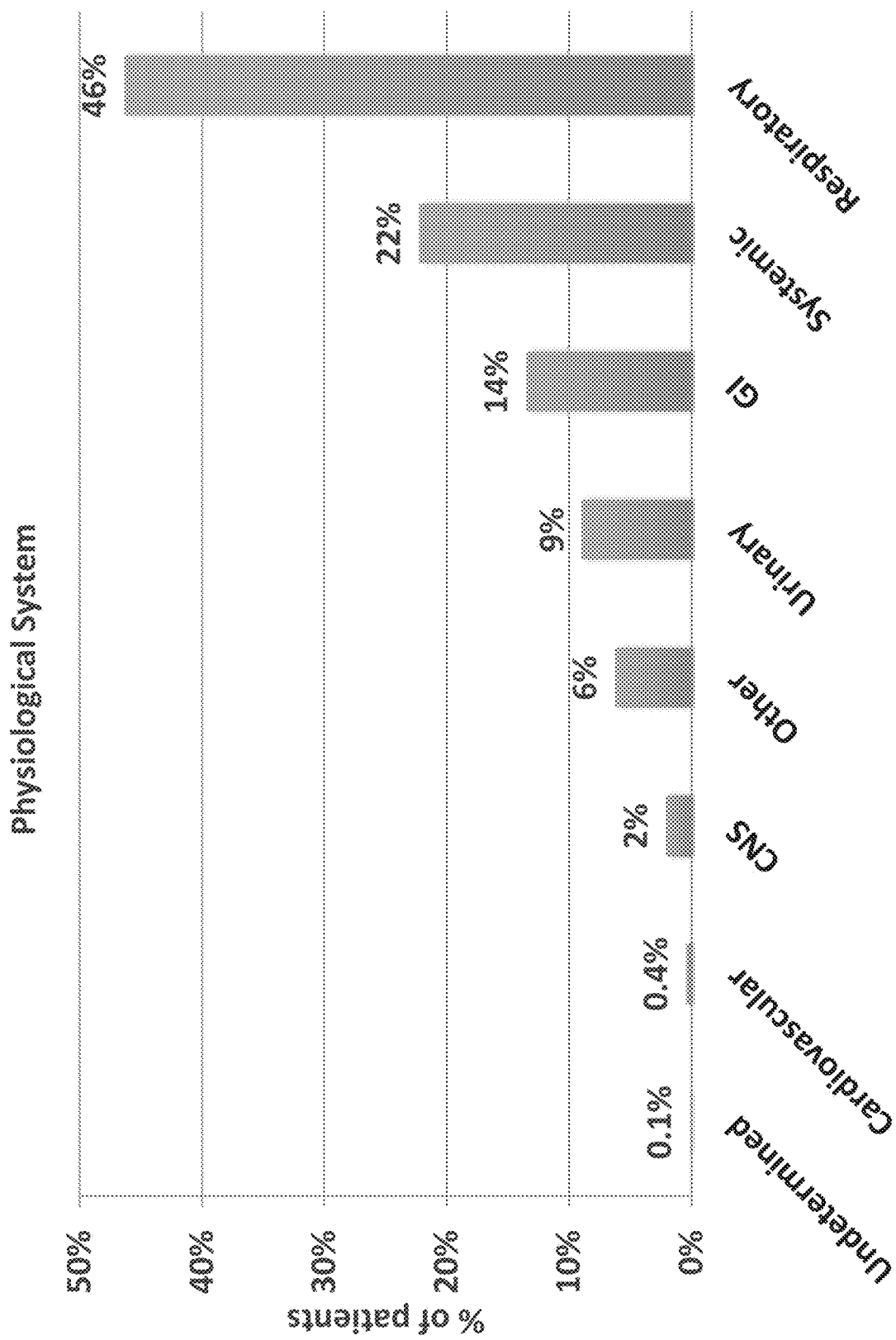
FIG. 8. Distribution of involved physiologic systems in patients diagnosed with an infectious disease (n=673).
Figure 9A:
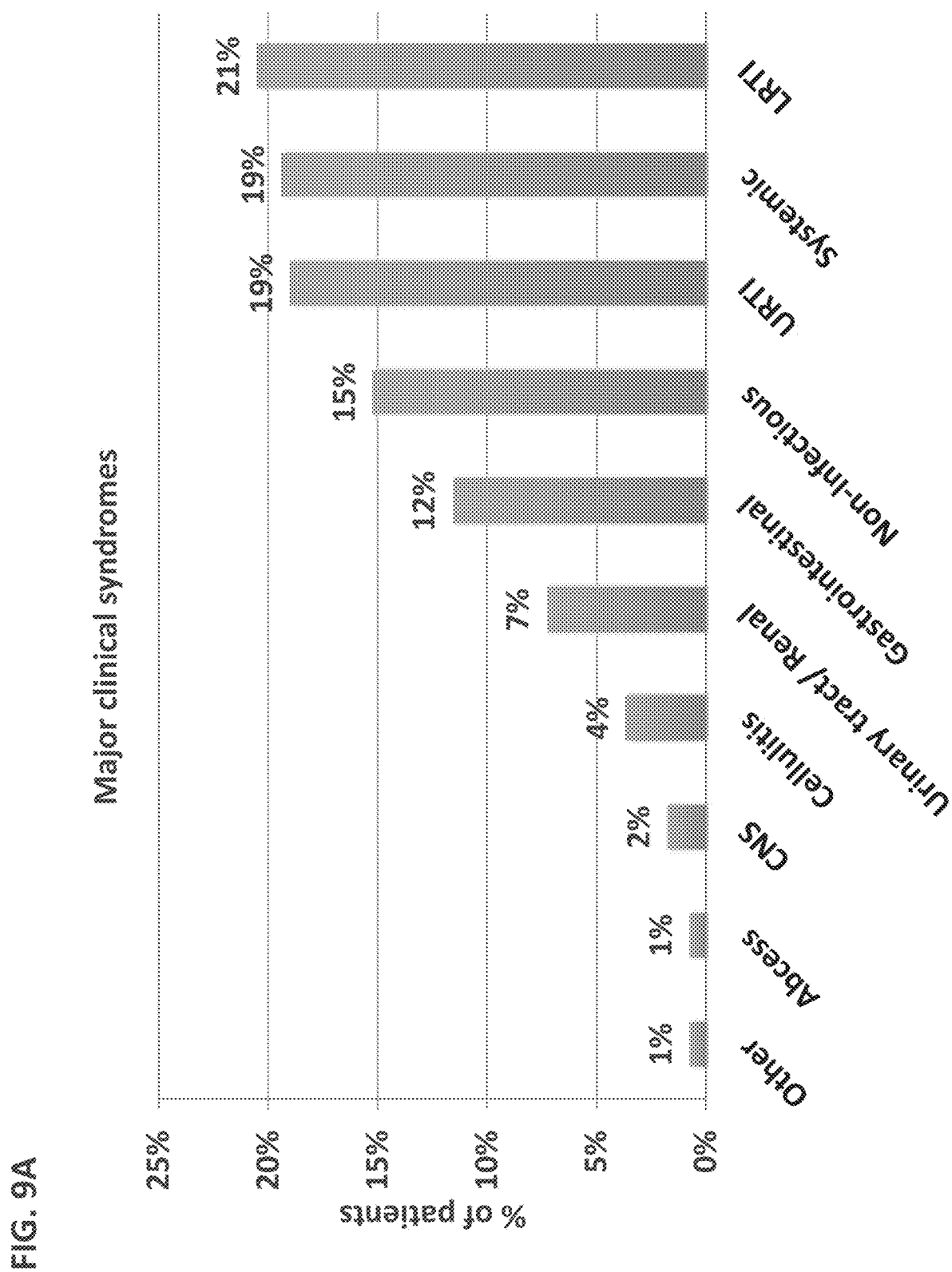
FIGS. 9A-9B. Distribution of clinical syndromes (all diagnosed patients, n=794).
Figure 9B:
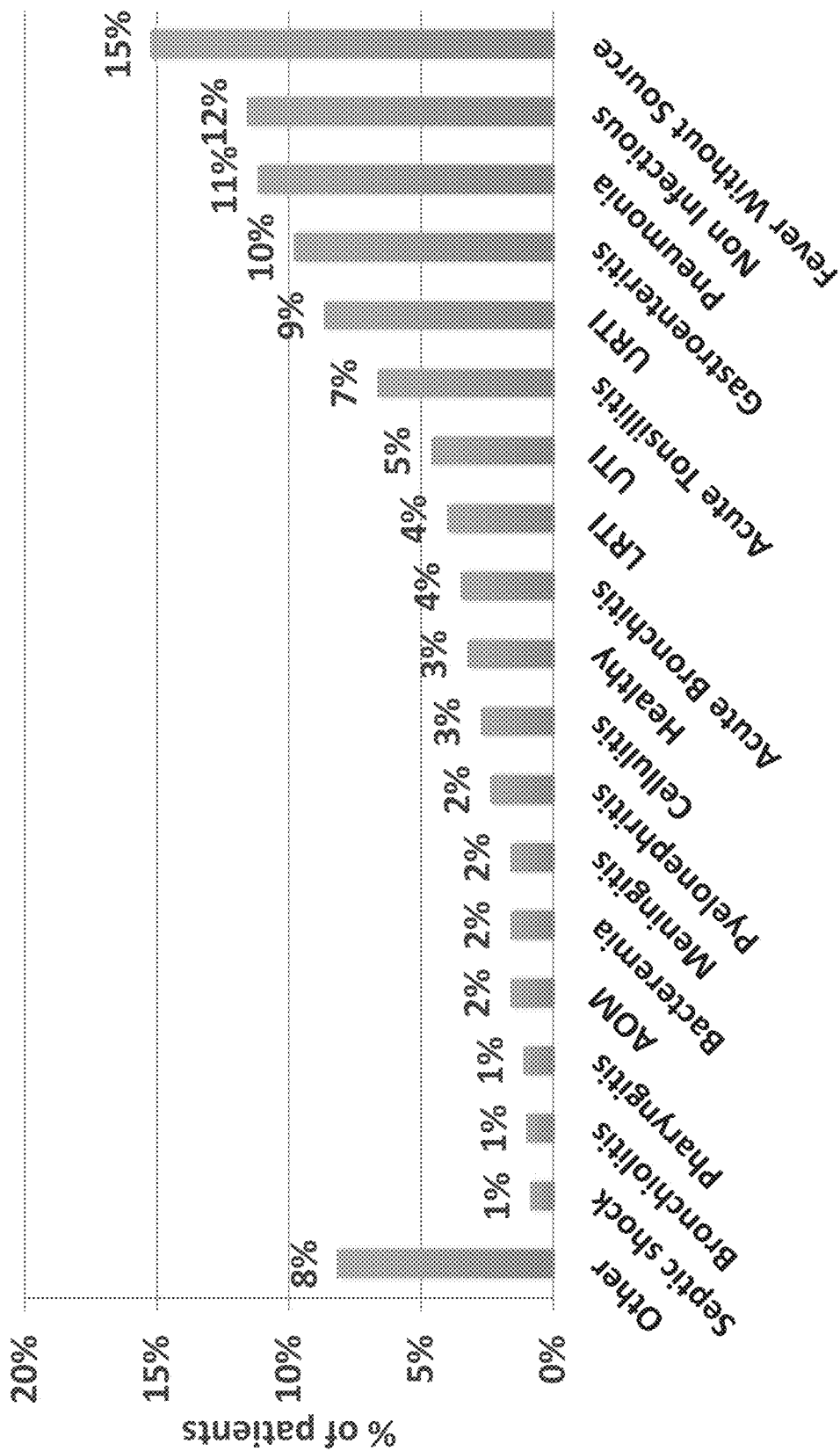

Involved Physiologic Systems and Clinical Syndromes:

The infectious disease patients (all diagnosed patients [n=794], excluding those with non-infectious diseases or healthy subjects, n=673) presented with infections in a variety of physiologic systems (FIG. 8). The most frequently involved physiologic system was the respiratory system (46%), followed by systemic infections (22%). All infections that did not involve the aforementioned systems and were not gastrointestinal, urinary, cardiovascular, or central nervous system (CNS) infections were categorized as 'Other' (e.g., cellulitis, abscess). The observed distribution of physiologic system involvement represents the natural distribution and is consistent with that reported for large cohorts of patients sampled year-round.

The diagnosed patients in the present study (n=794) presented with a variety of clinical syndromes (FIGS. 9A-9B) that reflects the expected clinical heterogeneity in a cohort of pediatric and adult patients collected year-round. The most frequent clinical syndrome was LRTI (21%) including mainly pneumonia, bronchitis, bronchiolitis, chronic obstructive pulmonary disease (COPD) exacerbation, and non-specific LRTI. The second most frequent syndrome was systemic infection (19%) including mainly fever without a source and occult bacteremia cases. Systemic infections were primarily detected in children <3 years of age but were also detected in a few adult patients. Systemic infections constitute a real clinical challenge as balancing between patient risk and the costs of testing/treatment is unclear. The third most frequent clinical syndrome was URTI (19%) including mainly acute tonsillitis, acute pharyngitis, non-specific URTI, acute sinusitis, and acute otitis media. The next most frequent syndromes were gastroenteritis (12%), UTI (7%), and cellulitis (4%). CNS infections (2%) included septic and aseptic meningitis. Additional clinical syndromes (1%) were classified as 'Other' and included less common infections (e.g., otitis externa, epididymitis, etc.). The observed pattern of clinical syndrome distribution represents most of the frequent and clinically relevant syndromes and is consistent with previously published large studies.

Core Body Temperature:

Core body temperature is an important parameter in evaluating infectious disease severity. The distribution of maximal body temperatures was examined in all of the diagnosed patients (n=794) using the highest measured body temperature (per-os or per-rectum). The distribution of the maximal body temperatures was relatively uniform between 38° C. and 40° C. with a peak of at 39° C. (FIG. 10). Body temperature <37.5° C. was reported for 15% of patients (the subgroup of patients with non-infectious diseases or healthy subjects). Body temperature ≥40.5° C. was rare (<3% of patients). Altogether, the observed distribution represents the normal range of temperatures in the clinical setting.

Time from symptoms onset: 'Time from symptoms' was defined as the duration (days) from the appearance of the first presenting symptom (the first presenting symptom could be fever but could also be another symptom such as nausea or headache preceding the fever). The distribution of 'time from symptoms' in our cohort (all diagnosed patients, n=794) peaked at 2-4 days after the initiation of symptoms (35% of patients) with substantial proportions of patients turning to medical assistance either sooner or later (FIG. 11).

Comorbidities and Chronic Drug Regimens:

Comorbidities and chronic drug regimens may, theoretically, affect a diagnostic test. Out of the diagnosed patients 62% had no comorbidities whereas 38% had ≥1 chronic disease. In addition, 75% of patients were not treated with chronic medications and 25% were treated with ≥1 chronic medication. The most frequent chronic diseases in our patient population were hypertension, hyperlipidemia, lung diseases (e.g., COPD, asthma, etc.), diabetes mellitus (mostly type 2), and ischemic heart disease, mirroring the most common chronic diseases in the Western world (FIG. 12A). The distribution of chronic drugs used by our patient population strongly correlated with the range of reported chronic diseases (e.g., 29% of the patients with comorbidities had hyperlipidemia and lipid lowering agents were the most frequently used drugs). Other frequently used drugs included aspirin, blood glucose control drugs, and beta blockers (FIG. 12B).

Patient Recruitment Sites:

Pediatric patients (≤18 years) were recruited from pediatric emergency departments (PED), pediatric wards and surgical departments, and adults (>18 years) from emergency departments (ED), internal medicine departments and surgical departments. The pediatric ED was the most common recruitment site (39%) and the other sites were comparable (17-20%) reflecting a relatively balanced recruitment process. The ratio between ED patients and hospitalized patients was ~1:1 for adults and ~2:1 for children (FIG. 13).

Characteristics of Excluded Patients:

Of the 1002 patients recruited for the study, 110 patients (11%) were excluded (some patients fulfilled more than one exclusion criterion). The most frequent reason for exclusion was having a fever below the study threshold of 37.5° C. (n=54), followed by time from symptom initiation of >12 days (n=26) and having a recent (in the preceding 14 days) infectious disease (n=22). Other reasons for exclusion included having an active malignancy (n=14), and being immunocompromised (e.g., due to treatment with an immunosuppressive drug; n=2).

Characteristics of Indeterminate Patients:

A total of 98 patients were defined as indeterminate based on the inability of the expert panel to reliably establish a composite reference standard, despite the rigorous collection of laboratory and clinical information. While it is not possible to directly examine the signature performance in these patients in the absence of a reference standard, it is possible to analyze their host-protein response in order to assess whether they differ from patients with a reference standard. We compared the distribution of TRAIL, IP-10 and CRP in acute infection patients with a reference standard (n=653) to those without a reference standard (n=98). No statistically significant difference was observed (Kolmogorov Smirnov test P=0.20, 0.25, 0.46 for TRAIL, IP-10 and CRP, respectively). The similarity in the host-protein response between patients with and without a reference standard implies that the present approach may be useful for diagnosing indeterminate patients in the clinical setting.

The Signature Performance Remains Robust Across Different Patient Subgroups:

In Example 1, the present inventors demonstrated that the signature remained robust across a wide range of patient characteristics including age, clinical syndrome, time from symptom onset, maximal temperature, pathogen species, comorbidities, and the clinical site with AUCs ranging from 0.87 to 1.0 (FIG. 4). In this Example, a review of the performance of the signature across additional patient subgroups is provided.

Stratification by Chronic Drug Regimens:

In real-world clinical practice, patients are often under various chronic drug regimens, which could, potentially, affect the level of proteins comprising the signature. The present inventors therefore examined whether the most used drugs (by categories) in our cohort impact the signature's performance. None of the evaluated drug groups were associated with significant alterations in the signature's accuracy (Table 5).

TABLE 5

Evaluation of the signature's sensitivity to various types of chronic drug regimens.

| Viral patients, n | Bacterial patients, n | Total patients, n | AUC [95% CI] | | Drug category |
|---|---|---|---|---|---|
| 7 | 43 | 50 | [0.90, 1.00] | 0.95 | Anti Hypertensive |
| 6 | 48 | 54 | [0.96, 1.00] | 0.99 | Anti platelets |
| 7 | 35 | 42 | [0.80, 1.00] | 0.90 | Anti-acid |
| 4 | 25 | 29 | [0.93, 1.00] | 0.98 | Antidepressants |
| 5 | 35 | 40 | [0.88, 1.00] | 0.95 | Beta Blocker |
| 5 | 34 | 39 | [0.86, 1.00] | 0.94 | Ca Channel Blocker |
| 11 | 53 | 64 | [0.89, 1.00] | 0.94 | Cholesterol/TG Lowering |
| 5 | 35 | 40 | [0.74, 1.00] | 0.87 | Diabetic |
| 5 | 25 | 30 | [0.83, 1.00] | 0.93 | Diuretics |
| 4 | 14 | 18 | [0.93, 1.00] | 0.98 | Hormonal |
| 8 | 18 | 26 | [0.87, 0.99] | 0.95 | Inhaled CS |
| 4 | 21 | 25 | [0.84, 1.00] | 0.94 | Prostate Hypertrophy |

Sepsis Based Stratification:

Sepsis is a potentially fatal medical condition characterized by a whole-body inflammatory state (called systemic inflammatory response syndrome [SIRS]) and the presence of a known or suspected infection. Patients with a bacterial sepsis benefit from early antibiotic therapy; delayed or misdiagnosis can have serious or even fatal consequences. The present inventors focused on adult patients for whom the definition of SIRS is clear and examined the ability of the signature to distinguish between adult patients with bacterial sepsis and those with viral infections as well as between adult patients with bacterial sepsis and those with viral sepsis.

Adult patients with bacterial sepsis were defined according to the American College of Chest Physicians and the Society of Critical Care Medicine. SIRS was defined by the presence of at least two of the following findings: (i) body temperature <36° C. or >38° C., (ii) heart rate >90 beats per minute, (iii) respiratory rate >20 breaths per minute or, on blood gas, a $PaCO_2$<32 mm Hg (4.3 kPa), and (iv) WBC <4,000 cells/mm$^3$ or >12,000 cells/mm$^3$ or >10% band forms. It was found that the signature achieved very high levels of accuracy in distinguishing between adult patients with bacterial sepsis and those with viral sepsis (AUC of 0.97 and 0.93 for the Unanimous [adult bacterial sepsis, adult viral sepsis] and the Majority [adult bacterial sepsis, adult viral sepsis] cohorts, respectively). These results demonstrate the utility of the signature in differentiating adult patients with bacterial sepsis from adult patients with viral infections.

TABLE 6

Signature accuracy in diagnosing bacterial sepsis vs. viral sepsis in adult patients

| Viral patients, n | Bacterial patients, n | Total patients, n | AUC [95% CI] | | |
|---|---|---|---|---|---|
| 21 | 93 | 114 | [0.94, 1.00] | 0.97 | Unanimous |
| 35 | 112 | 147 | [0.89, 0.97] | 0.93 | Majority |

Bacterial Vs. Non-Bacterial Patients Stratification:

Antibiotic misuse typically stems from the use of these drugs to treat non-bacterial (viral or non-infectious) patients or due to delayed or missed diagnosis of bacterial infections.

Therefore, the present inventors further examined the signature performance for distinguishing between bacterial and non-bacterial patients. The entire Majority cohort was evaluated using leave-10%-out cross-validation, yielding an AUC of 0.94±0.02. Improved performances were shown when evaluating the Unanimous cohort (AUC of 0.96±0.02), and after filtering out patients with a marginal immune response (Table 7).

TABLE 7

Signature measures of accuracy for diagnosing bacterial vs. non-bacterial (viral and non-infectious) patients.

| A. All patients | | B. Marginal immune response filter | | |
|---|---|---|---|---|
| Majority cohort | Unanimous cohort | Majority cohort | Unanimous cohort | Accuracy measure |
| 0.95 (0.93, 0.97) | 0.96 (0.94, 0.98) | 0.94 (0.92, 0.96) | 0.96 (0.94, 0.98) | AUC |
| 0.91 (0.89, 0.93) | 0.93 (0.91, 0.95) | 0.88 (0.85, 0.91) | 0.91 (0.89, 0.93) | Total accuracy |

TABLE 7-continued

Signature measures of accuracy for diagnosing bacterial vs. non-bacterial (viral and non-infectious) patients.

| A. All patients | | B. Marginal immune response filter | | |
|---|---|---|---|---|
| Majority cohort | Unanimous cohort | Majority cohort | Unanimous cohort | Accuracy measure |
| 0.91 (0.88, 0.95) | 0.92 (0.88, 0.95) | 0.87 (0.83, 0.91) | 0.88 (0.85, 0.91) | Sensitivity |
| 0.92 (0.89, 0.95) | 0.94 (0.91, 0.96) | 0.90 (0.87, 0.93) | 0.93 (0.91, 0.95) | Specificity |
| 11.4 (8, 16) | 15.3 (10, 23) | 8.7 (6, 12) | 12.6 (9, 18) | LR+ |
| 0.1 (0.07, 0.14) | 0.08 (0.05, 0.13) | 0.14 (0.11, 0.19) | 0.13 (0.09, 0.18) | LR− |
| 116 (67, 200) | 180 (94, 344) | 60 (38, 94) | 97 (56, 168) | DOR |

A. Performance estimates and their 95% CIs were obtained using a leave-10%-out cross-validation on all patients in the Unanimous ($n_{Bacterial}$ = 256, $n_{Non-bacterial}$ = 383), and Majority ($n_{Bacterial}$ = 319, $n_{Non-bacterial}$ = 446) cohorts. B. The analysis was repeated after filtering out patients with a marginal immune response (Unanimous [$n_{Bacterial}$ = 237, $n_{Non-bacterial}$ = 343, $n_{Marginal}$ = 59], and Majority [$n_{Bacterial}$ = 292, $n_{Non-bacterial}$ = 387, $n_{Marginal}$ = 86]), which resembles the way clinicians are likely to use the signature.

Figure 15A:
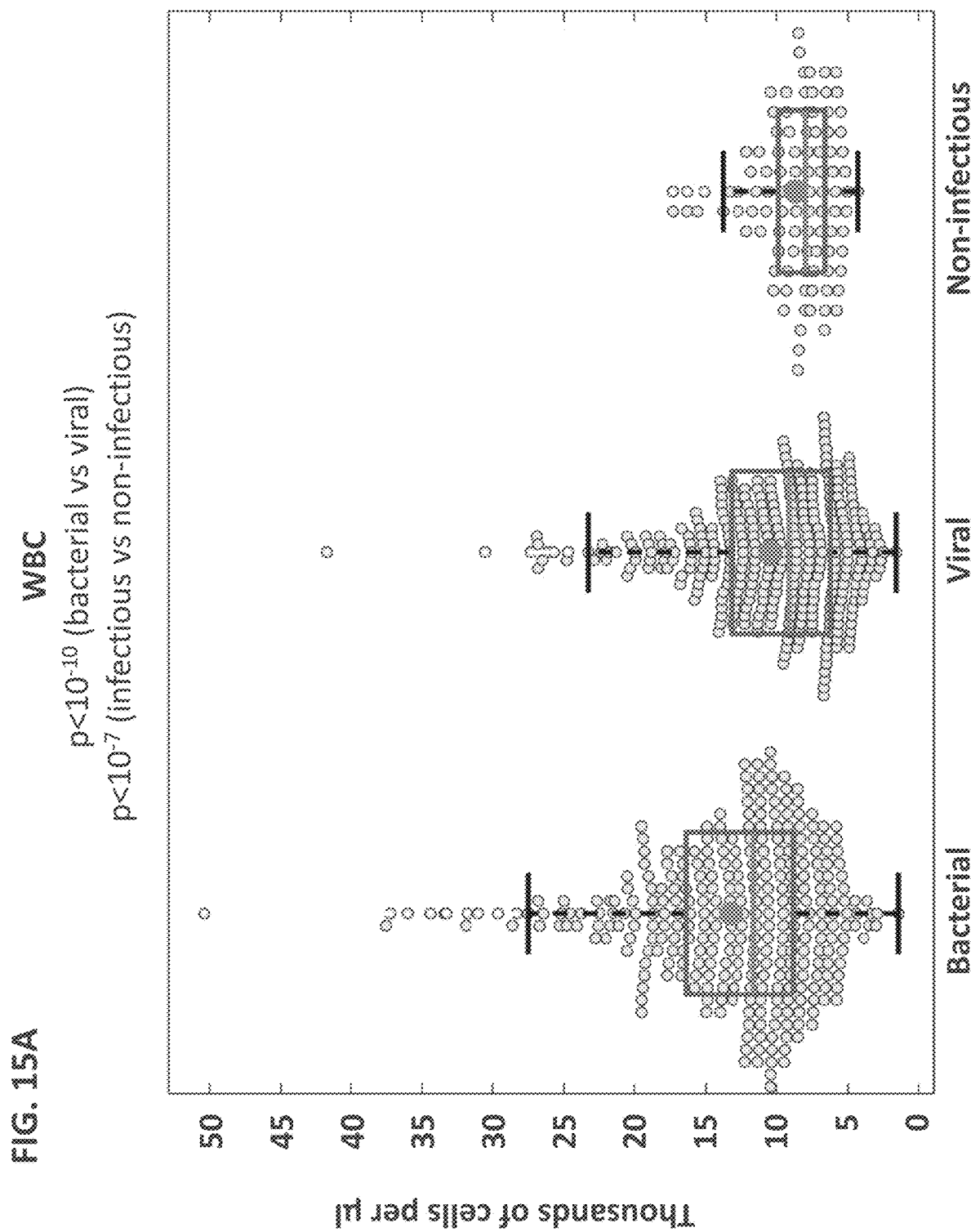
Figure 15C:
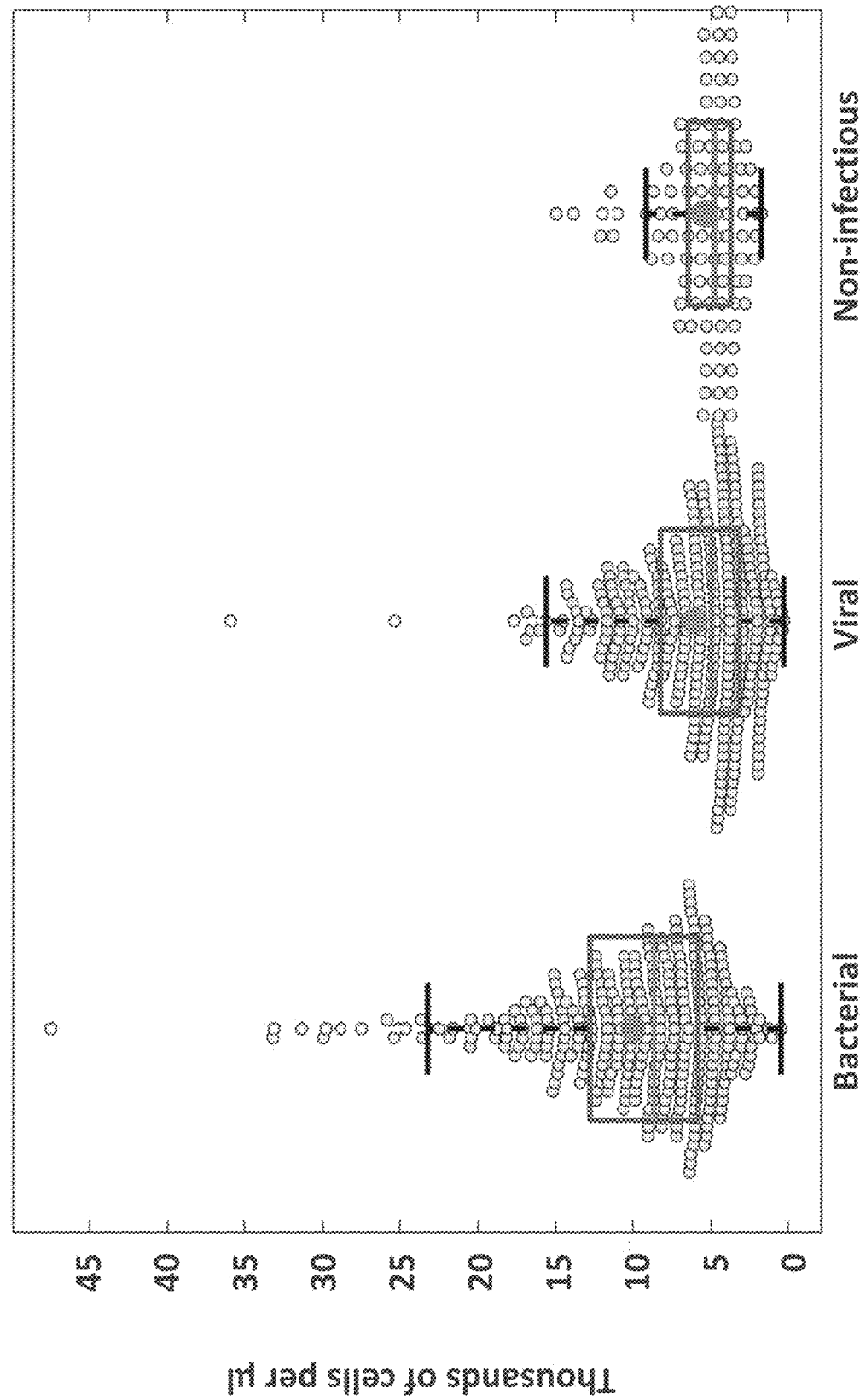
Figure 15D:
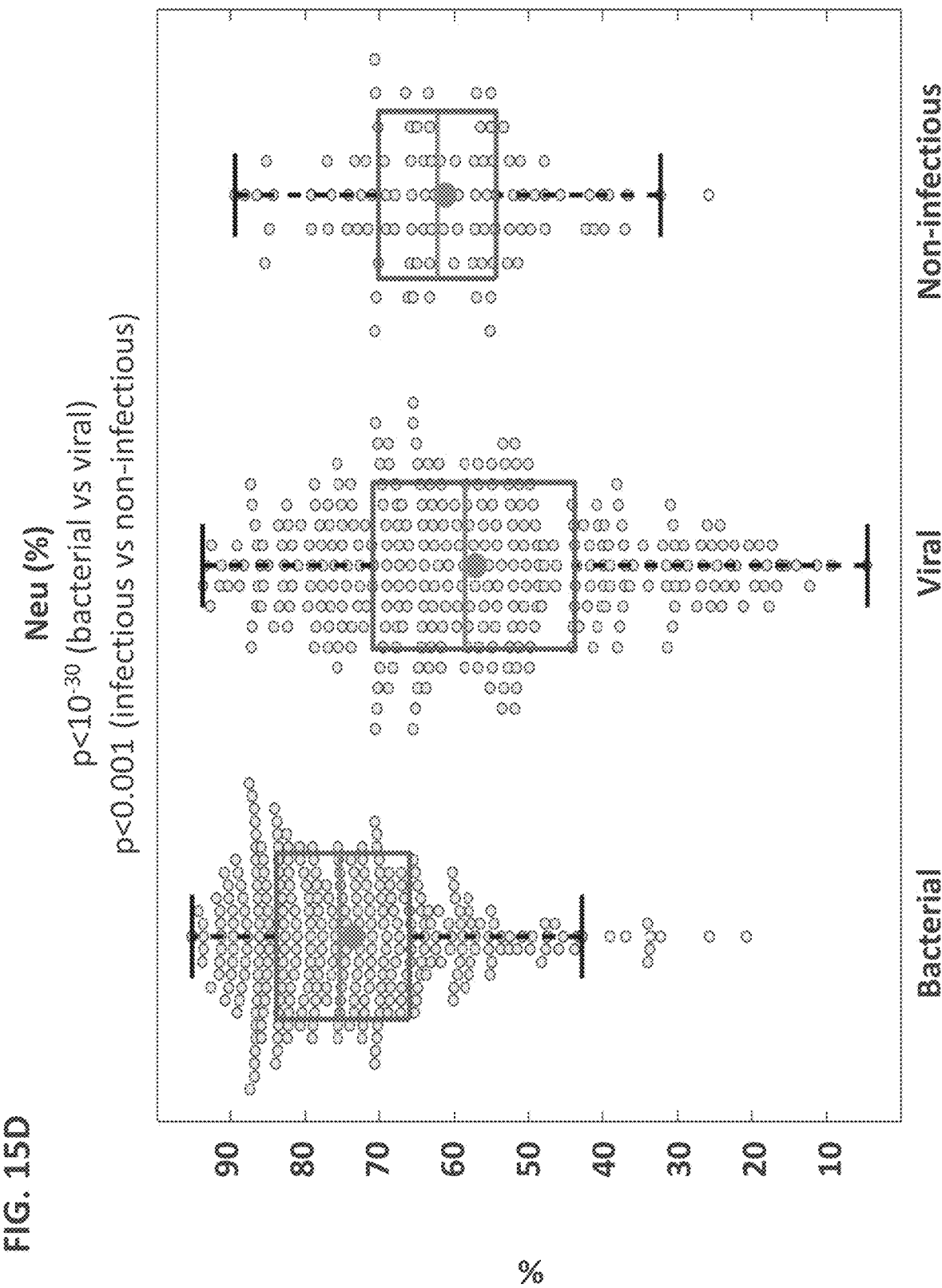
Figure 15E:
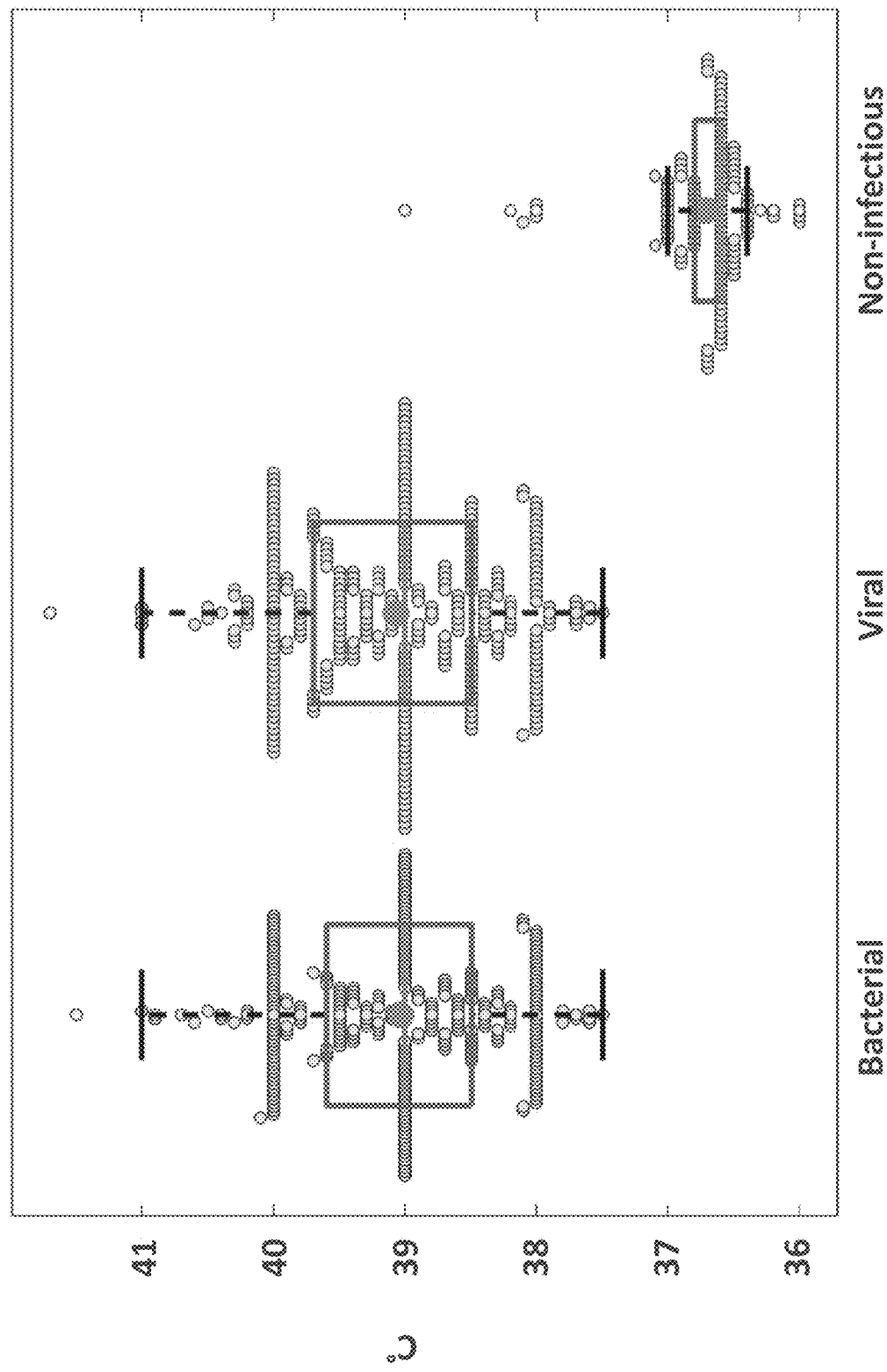

Protein Stability at Different Temperatures can Affect the Assay Performance:

The utility of a biomarker depends on its stability in real-life clinical settings (e.g., its decay rate when the sample is stored at room temperature prior to analyte measurement). To address this, we examined the stability of TRAIL, CRP and IP-10 in serum samples from four independent individuals during 24 hours at 4° C. and 25° C. Aliquots of 100 μl, from each plasma sample were pipetted into 0.2 mL tubes and kept at 4° C. or 25° C. from 0 to 24 hours. Subsequently, the levels of the analytes were measured (different time-points of the same analytes were measured using the same plate and reagents). The analyte half-lives at 4° and 25° C. were greater than 72 hours for TRAIL, CRP and IP-10 (FIGS. 15A-15C). Of note, in the real clinical setting, if the samples are stored at room temperature, the concentrations of TRAIL, IP-10 and CRP should be measured within about 24 after the sample is obtained. Preferably they should be measured within 5 hours, 4 hours, 3 hours, 2 hours, 1 hour, or even immediately after the sample was obtained. Alternatively, the sample should be stored at a temperature lower than 10° C., and then TRAIL can be measured more than 24 after obtaining the sample.

The Three Protein Combination Outperforms any Individual and Pairs of Proteins:

The combination of the three proteins outperforms that of the individual and pairs of proteins for distinguishing bacterial vs. viral and infectious vs. non-infectious patients.

TABLE 8

| | Bacterial vs. viral | | |
|---|---|---|---|
| AUC | Proteins #3 | Protein #2 | Protein #1 |
| 0.89 | — | — | TRAIL |
| 0.88 | — | — | CRP |
| 0.66 | — | — | IP-10 |
| 0.95 | — | CRP | TRAIL |
| 0.93 | — | IP-10 | CRP |
| 0.90 | — | IP-10 | TRAIL |
| 0.96 | IP-10 | CRP | TRAIL |

TABLE 9

| AUC | Proteins #3 | Protein #2 | Protein #1 |
|---|---|---|---|
| 0.60 | — | — | TRAIL |
| 0.87 | — | — | CRP |
| 0.89 | — | — | IP-10 |
| 0.90 | — | CRP | TRAIL |
| 0.95 | — | IP-10 | CRP |
| 0.89 | — | IP10 | TRAIL |
| 0.96 | IP-10 | CRP | TRAIL |

Performance Analysis as a Function of the Prevalence of Bacterial Infections:

The prevalence of bacterial and viral infections is setting dependent. For example, in the winter, a pediatrician in the outpatient setting is expected to encounter substantially more viral infections than a physician in the hospital internal department during the summer. Notably, some measures of diagnostic accuracy such as AUC, sensitivity, and specificity are invariant to the underlying prevalence, whereas other measures of accuracy, such as PPV and NPV are prevalence dependent. In this section, the expected signature performance in terms of PPV and NPV in clinical settings with different prevalence of bacterial and viral infections is reviewed.

As the basis for this analysis the signature accuracy measures were used that were obtained using the Unanimous (bacterial, viral) and Majority (bacterial, viral) cohorts. The prevalence of bacterial infections in the Unanimous cohort was 51.7% yielding a PPV of 93%±3% and NPV of 93%±3%. The prevalence of bacterial infections in the Majority cohort was 48.7% yielding a PPV of 89%±3% and NPV of 92%±3%.

The measured sensitivity and specificity was used to compute the expected changes in the signature PPV and NPV as a function of the prevalence of bacterial infections (FIGS. 14A-14B).

Examples of different clinical settings and the extrapolated signature PPV and NPV for each of them are presented in Table 10A.

TABLE 10A

Extrapolated signature PPV and NPV in different clinical settings, based on the Unanimous cohort.

| NPV | PPV | Prevalence of Bacterial infections* | Age | Setting |
|---|---|---|---|---|
| 98% | 76% | 20% | Children | Outpatient |
| 97% | 85% | 35% | Adults | Outpatient |
| 94% | 93% | 50% | Children | Inpatient |
| 78% | 98% | 80% | Adults | Inpatient |

*An average annual prevalence. Estimates of bacterial infection prevalence are based on data reported in the Bacterial etiology chapter, Part 7 of Harrison's Internal Medicine 17th Edition.

The signature outperforms standard laboratory and clinical parameters for diagnosing bacterial vs. viral infections: Standard laboratory and clinical parameters, some of which are routinely used in clinical practice to aid in the differential diagnosis of an infection source, were evaluated in the Majority cohort (bacterial, viral, non-infectious, n=765). The evaluated parameters included ANC, % neutrophils, % lymphocytes, WBC, and maximal temperature. In accordance with the well-established clinical role of these parameters, we observed a statistically significant difference in their levels between bacterial and viral patients (FIGS. 15A-15E). For example, bacterial patients had increased levels of ANC ($P<10^{-24}$), and WBC ($P<10^{-10}$), whereas viral patients had a higher % lymphocytes ($P<10^{-31}$). The signature was significantly more accurate than any of the individual features ($P<10^{-18}$) and their combinations ($P<10^{-15}$), see FIG. 3A).

The signature outperforms protein biomarkers with a well-established immunological role: The signature outperformed all clinical parameters and the 600 proteins that were evaluated during the screening phase (see FIGS. 3A-3B). The following section further compares the signature to selected proteins that are routinely used in the clinical setting or that have an immunological role.

One of the most widely used and useful protein biomarkers for differentiating sepsis from other non-infectious causes of SIRS in critically ill patients is procalcitonin (PCT). Whether PCT can be used to distinguish between local bacterial and viral infections is less clear. To test this, we measured PCT concentrations in 76 randomly selected patients from the Unanimous (bacterial, viral) cohort ($n_{Bacterial}$=39, $n_{Viral}$=37) and 101 randomly selected patients from the Majority (bacterial, viral) cohort ($n_{Bacterial}$=51, $n_{Viral}$=50) and compared the diagnostic accuracy based on PCT levels to that of the signature. PCT accuracy was calculated using the standard cutoffs routinely applied in the clinical setting (0.1 ng/mL, 0.25 ng/mL, 0.5 ng/mL, and 1 ng/mL).[19-23] Maximal PCT sensitivity of 69% was attained at a cutoff of 0.1 mg/mL and resulted in a specificity of 62% (for the Unanimous [bacterial, viral] cohort). For the same cohort, the signature showed significantly higher sensitivity of 94% (P<0.001) and specificity of 93% (P<0.001) (FIG. 16A). A comparison using the patients from the Majority (bacterial, viral) cohort showed similar results (FIG. 16B).

Overall, despite its high diagnostic and prognostic value for sepsis detection in critically ill patients, our results indicate that PCT is less accurate in distinguishing between patients with local infections (bacterial vs. viral).

Another protein biomarker used in the clinical setting is the C-reactive protein (CRP), an acute phase response protein that is up-regulated in infections and other inflammatory conditions. The performance of CRP was compared to that of the signature using the entire Unanimous (bacterial, viral) and Majority (bacterial, viral) cohorts. CRP accuracy was determined using several standard cutoffs applied in the clinical setting.[24-26] Maximal CRP sensitivity of 92% was attained at 20 mg/mL cutoff resulting in a specificity of 60% (for the Unanimous [bacterial, viral] cohort) (FIG. 17A). The signature had a similar sensitivity (94%) and a significantly higher specificity (93%, $P<10^{-9}$) in the same cohort. Similar results were observed using the Majority (bacterial, viral) cohort (FIG. 17B). Overall, the signature has a similar sensitivity to CRP with a 20 mg/L cutoff but a considerably higher specificity for distinguishing bacterial from viral patients.

Next, the differential response of protein biomarkers with a well-established role in the host response to infections was examined (Table 10B and FIGS. 18A-18H). Each biomarker was tested on at least 43 patients (about half bacterial and half viral), and if it showed promising results, it was further tested on additional patients (up to 150).

TABLE 10B

A list of protein biomarkers with a well-established role in the host response against infections, and the number of patients used to test each biomarker (for each analysis the analyzed patients included approximately half bacterial and half viral patients).

| No. of patients | Short description | Protein biomarker |
|---|---|---|
| 120 | CD11a is expressed by all leukocytes as part of the integrin lymphocyte function-associated antigen-1 (LFA-1). LFA-1 plays a central role in leukocyte intercellular adhesion through interactions with its ligands, ICAMs 1-3 (intercellular adhesion molecules 1 through 3). CD11a also functions in lymphocyte co-stimulatory signaling. | CD11a |
| 79 | CD11C is an integrin α X chain protein and mediates cell-cell interactions during inflammatory responses. | CD11C |
| 82 | CD80 is a membrane receptor involved in the co-stimulatory signal essential for T-lymphocyte activation. The binding of CD28 or CTLA-4 to CD80 induces T-cell proliferation and cytokine production. | CD80 |
| 65 | These are MHC class I antigens associated with β2-microglobulin and are expressed by all human nucleated cells. HLA-A, B, C are central in cell-mediated immune response and tumor surveillance. | HLA-A, B, C |
| 49 | IFN-γ is a soluble cytokine. IFN-γ participates in innate and adaptive immunity against viral and intracellular bacterial infections and in tumor control. | IFN-γ |
| 43 | IL-1a is a member of the IL-1 cytokine family. IL-1a is a pleiotropic cytokine involved in various immune responses, inflammatory processes, and hematopoiesis. IL-1a is produced by monocytes and macrophages as a proprotein, which is proteolytically processed and released in response to cell injury, thereby inducing apoptosis. | IL-1a |
| 49 | IL-2 is produced by T-cells in response to antigenic or mitogenic stimulation. IL-2 is required for T-cell proliferation and other activities crucial for regulation of the immune response. | IL-2 |
| 43 | IL-6 is a cytokine that functions in inflammation and maturation of B cells. IL-6 is an endogenous pyrogen capable of inducing fever in people with autoimmune diseases or infections. | IL-6 |
| 43 | IL-8 is a member of the CXC chemokine family and functions as one of the major mediators of the inflammatory response. | IL-8 |
| 43 | IL-9 is a cytokine that acts as a regulator of a variety of hematopoietic cells. IL-9 supports IL-2 independent and IL-4 independent growth of helper T-cells. | IL-9 |
| 48 | IL-10 is a cytokine produced primarily by monocytes and to a lesser extent by lymphocytes. IL-10 has pleiotropic effects in immunoregulation and inflammation. | IL-10 |
| 49 | IL-15 is a cytokine that stimulates the proliferation of T-lymphocytes. | IL-15 |
| 49 | IL-16 functions as a chemo-attractant, a modulator of T cell activation, and an inhibitor of HIV replication. | IL-16 |
| 54 | sTNFRSF1A is a receptor for TNFSF2/TNF-α and homo-trimeric TNFSF1/lymphotoxin-α that contributes to the induction of non-cytocidal TNF effects including anti-viral state and activation of the acid sphingomyelinase. | sTNFRSF1A |
| 43 | TNF-α is a cytokine secreted mainly by macrophages. TNF-α can induce cell death of certain tumor cell lines. It is a potent pyrogen causing fever directly or by stimulation of IL-1 secretion. | TNF-α |
| 43 | TNF-β is a potent mediator of inflammatory and immune responses. It is produced by activated T and B lymphocytes and is involved in the regulation of various biological processes including cell proliferation, differentiation, apoptosis, lipid metabolism, coagulation, and neurotransmission. | TNF-β |
| 150 | TREM is a pro-inflammatory amplifier present on neutrophils and monocytes. | TREM |

Since these biomarkers do not have a well-established cutoff in the clinical setting, we used their AUCs as a basis for comparison (FIG. 3B) The most informative biomarker was TREM (AUC of 0.68±0.09). The accuracy of TREM was significantly lower than that of the signature ($P<10^{-9}$ when comparing the two AUCs; FIG. 3B). These results demonstrate that mere participation of a protein in the host response to an infection does not necessarily imply diagnostic utility. For example, although IFN-γ has a well-established role in the immune response to viruses and intracellular bacteria, its short half-life (<20 h)[27] limits its diagnostic utility (as its concentration in the blood is highly dependent on the time from infection onset).

Example 3

Trinary Classifier Outperforms a Binary Classifier

In the binary model the classifier is trained by classifying all samples as either 'Bacterial' or 'Non-bacterial' ('Viral' and 'Non-infectious' are grouped). In the trinary model, the classifier learns to distinguish between three classes 'Bacterial', 'Viral' and 'Non-infectious'. The probability of the viral and the non-infectious are then grouped together to give the probability of 'non-bacterial'. This was demonstrated on the present data.

Both of the above classifiers were evaluated using a leave 10%-out cross-validation on both the Majority and Unanimous cohorts.

Results

Running the binary classifier on the majority cohort yields the results as summarized in Table 10C, herein below:

TABLE 10C

| Reference class | | |
|---|---|---|
| Bacterial (B) | Viral and non-infectious (V + NI) | |
| 63 | 411 | V + NI |
| 256 | 35 | B |

The sensitivity of the classifier on the Majority cohort is 80.3% and the specificity is 92.2%.

Running the multinomial based classifier on the same dataset yields the following results summarized in Table 10D.

TABLE 10D

| Reference class | | |
|---|---|---|
| (B) | (V + NI) | |
| 54 | 417 | V + NI |
| 265 | 29 | B |

It can be seen that this classifier outperforms the previous one both in terms of sensitivity and in terms of specificity. The sensitivity was improved to 83.1% and the specificity to 93.5%.

Running the binary classifier on the Unanimous cohort yields the results summarized in Table 11.

TABLE II

| Reference class | | |
|---|---|---|
| (B) | (V + NI) | |
| 39 | 358 | V + NI |
| 217 | 25 | B |

The sensitivity of the classifier on the Unanimous cohort is 84.8% and the specificity is 93.5%.

Running the multinomial based classifier on the same dataset yields the results summarized in Table 12.

TABLE 12

| Reference class | | |
|---|---|---|
| (B) | (V + NI) | |
| 38 | 364 | V + NI |
| 218 | 19 | B |

This classifier outperforms the previous one both in terms of sensitivity and in terms of specificity. The sensitivity was improved to 85.2% and the specificity to 95.0%.

In summary, the trinary classifier outperforms the binary based classifier both in terms of sensitivity and in terms of specificity on both datasets tested.

Example 4

The Clinical Accuracy of the Signature Remains Robust Even when Analytical Accuracy is Reduced It is important to assess how clinical accuracy is affected by the increase in the CV (std/mean) of the proteins measurements, because often different measurement devices, particularly those that are useful at the point-of-care, show increased CVs (i.e. reduced analytical accuracy).

The present inventors examined the change in AUC of the signature for distinguishing bacterial from viral infection as a function of the increase in CV of both TRAIL and CRP. This was done by taking the original patient data of the Unanimous cohort and simulating an increase in CV using monte-carlo simulations (FIGS. 19A-19B). Specifically, for each combination of TRAIL and CRP CVs, 100 simulated measurements were assigned to each of the patients and the AUC in each case was recomputed. The average AUC per CV combination is depicted. It can be seen that the signature clinical accuracy (in terms of AUC) is robust to the increases in technical CV. For example, increasing the ELISA CV by 0, 0.24 and 0.4 leads to a reduction in AUCs of 0.96, 0.95 and 0.94 respectively. Similar results are obtained when increasing the CV of IP-10, and when repeating the simulations on the Majority cohort.

This result may be explained by the usage of multiple biomarkers that compensate for one another. This surprising finding is useful because it opens the way to perform measurements of the proteins on cheap and rapid technologies (such as POC technologies), which often show reduced analytical sensitivity (compared for example to automated immunoassays or ELISA), without losing clinical accuracy.

Example 5

Different ELISA protocols can be applied for measuring TRAIL and IP-10, which would lead to different signal to noise ratios, and consequentially to different concentrations being measured. More specifically, while the overall trend of the biomarkers will be preserved regardless of the protocol (e.g. TRAIL increases in viral infections and decreases in bacterial), the measurement scale is protocol dependent. In the following subsections, examples of protocols are described that lead to different measured concentrations of IP-10 and TRAIL.

Measurements of Soluble IP-10 and TRAIL Using ELISA—Protocol No. 1:

To determine the concentrations of soluble IP-10 and TRAIL in human plasma and serum samples, a standard Sandwich ELISA (Enzyme-linked immunosorbent assay) was used. Briefly, the wells of 96-well plate were coated with capture-antibody specific to TRAIL and IP-10 and diluted in coating buffer (e.g. 1×PBS) followed by overnight incubation at 4° C. The wells were washed twice with washing buffer (e.g. 1×PBS with 0.2% Tween-20) and subsequently blocked with blocking buffer containing proteins (e.g. 1×PBS with 0.2% Tween-20 and 5% non-fat milk) for at least 2 hours at room temperature or overnight at 4° C. Wells were then washed twice with washing buffer. Protein standards and plasma or serum samples were incubated for two hour at room temperature. Then, the wells were washed three times with a washing buffer and subsequently incubated with an HRP conjugated detection-antibody specific to TRAIL and IP-10, diluted in blocking buffer for two hours at room temperature.

The wells were washed four times with a washing buffer and incubated with a reaction solution that contained an HRP substrate (e.g. TMB; 3, 3', 5,5'-Tetramethylbenzidine). After adequate color development, a stop solution was added to each well. The absorbance of the HRP reaction product in 450 nm was determined using standard spectrophotometer. This protocol took 5 (TRAIL) and 4.75 (IP10) hours respectively and is referred to herein as the slow protocol.

Measurements of Soluble IP-10 and TRAIL Using ELISA—Protocol No. 2:

Reducing assay time allows for increased clinical utility. To further reduce the protocol run time, the protocol was optimized for measuring TRAIL and IP10 and reduced to less than 100 minutes. The rapid protocol was performed as follows:

50 μl of assay diluent and 50 μl of Standards was added to samples or controls per well. The reaction was incubated for 30 minutes at room temperature on a horizontal orbital microplate shaker (3 mm orbit) set at 550 rpm. Each well was then aspirated and washed four times by using a wash buffer. Next, 200 μl of Conjugate was added to each well and the reactions were incubated for 45 minutes at room temperature on the shaker. The wells were washed four times with a washing buffer and incubated with a reaction solution that contained an HRP substrate (e.g. TMB; 3, 3', 5,5'-Tetramethylbenzidine). After 10-25 minutes, a stop solution was added to each well. The absorbance of the HRP reaction product in 450 nm was determined using a standard spectrophotometer. This protocol took 99 (TRAIL) and 85 (IP-10) minutes respectively and is referred to herein as the rapid protocol.

The slow and the rapid protocol measurements were compared using 357 samples for TRAIL and 189 samples for IP-10, and showed highly correlated results (FIGS. 30A-30B).

Of note, the average TRAIL concentration obtained using the rapid protocol was roughly 70 percent less than that obtained using the slow protocol concentration. Such alterations in measured concentrations of proteins across different protocols often occur and can be compensated for by correlating the measurements of the two protocols and computing a transformation function. For example, the transformation function y_slow=0.709×y_rapid−3e−12 may be used to translate the concentrations of the rapid protocol and the slow protocol. This translation preserves TRAIL's accuracy. Other, translation functions and protocols can be developed by one skilled in the art that also preserve the accuracy. In summary, the behavior of TRAIL remains the same across the two protocols (i.e. highest in viral, lower in non-infectious and lowest in bacterial), despite a shift in the calculated concentrations.

Different Protocols and Cohorts Lead to Different Model Coefficients:

An example of the multinomial logistic model coefficients generated on the majority patients cohort when measuring IP-10 and TRAIL with the slow protocol is shown in Table 13:

TABLE 13

| Second Coordinate $\delta_1$ (bacterial) | First Coordinate $\delta_0$ (viral) | |
|---|---|---|
| $b_0 = -1.5389 \pm 0.75676$ | $a_0 = -1.7331 \pm 0.62936$ | Const |
| $b_1 = 0.0851 \pm 0.015288$ | $a_1 = 0.0514 \pm 0.014896$ | CRP (mg/ml) |
| $b_2 = 0.0046 \pm 0.001372$ | $a_2 = 0.0049 \pm 0.001372$ | IP10 (pg/ml) |
| $b_3 = -0.0155 \pm 0.007056$ | $a_3 = 0.0048 \pm 0.005096$ | TRAIL (pg/ml) |

An example of the multinomial logistic model coefficients generated on the consensus patients cohort when measuring IP-10 and TRAIL with the slow protocol is shown in Table 14.

TABLE 14

| Second Coordinate $\delta_1$ (bacterial) | First Coordinate $\delta_0$ (viral) | |
|---|---|---|
| $b_0 = 2.6091 \pm 0.9357$ | $a_0 = -2.6866 \pm 0.75048$ | Const |
| $b_1 = 0.0866 \pm 0.016856$ | $a_1 = 0.0499 \pm 0.016464$ | CRP (mg/ml) |
| $b_2 = 0.0052 \pm 0.001568$ | $a_2 = 0.0059 \pm 0.001568$ | IP10 (pg/ml) |
| $b_3 = -0.0115 \pm 0.008232$ | $a_3 = 0.0084 \pm 0.005684$ | TRAIL (pg/ml) |

Since the frequency of the subgroups in the patient cohort deviates from the anticipated frequency in the general population, one can further adjust the model coefficients to reflect a predetermined prior probability using standard techniques for coefficient adjustment (for example see G. King and L Zeng, Statistics in Medicine 2002). For example, the following examples show multinomial logistic model coefficients generated on the majority patients cohort when measuring IP-10 and TRAIL with the slow protocol, reflecting prior probability of 45% bacterial, 45% viral and 10% non-infectious.

Model coefficients (trained on majority cohort) after prior adjustment are summarized in Table 15:

TABLE 15

| Second Coordinate $\delta_1$ (bacterial) | First Coordinate $\delta_0$ (viral) | |
|---|---|---|
| $b_0 = -1.1302 \pm 0.75676$ | $a_0 = -1.4151 \pm 0.62936$ | Const |
| $b_1 = 0.0851 \pm 0.015288$ | $a_1 = 0.0514 \pm 0.014896$ | CRP (mg/ml) |
| $b_2 = 0.0046 \pm 0.001372$ | $a_2 = 0.0049 \pm 0.001372$ | IP10 (pg/ml) |
| $b_3 = -0.0155 \pm 0.007056$ | $a_3 = 0.0048 \pm 0.005096$ | TRAIL (pg/ml) |

Model coefficients (trained on consensus cohort) after prior adjustment are summarized in Table 16.

TABLE 16

| Second Coordinate $\delta_1$ (bacterial) | First Coordinate $\delta_0$ (viral) | |
|---|---|---|
| $b_0 = -1.7833 \pm 0.9357$ | $a_0 = -2.083 \pm 0.75048$ | Const |
| $b_1 = 0.0866 \pm 0.016856$ | $a_1 = 0.0499 \pm 0.016464$ | CRP (mg/ml) |
| $b_2 = 0.0052 \pm 0.001568$ | $a_2 = 0.0059 \pm 0.001568$ | IP10 (pg/ml) |
| $b_3 = -0.0115 \pm 0.008232$ | $a_3 = 0.0084 \pm 0.005684$ | TRAIL (pg/ml) |

Of note, other combinations of coefficients can be chosen to produce similar results, as would be evident to one skilled in the art. Other protocols for measuring proteins that affect the measured protein concentrations would yield different model coefficients. For example, the rapid protocol for measuring TRAIL reduces the computed concentrations to roughly 70% of the concentrations computed in the slow protocol. Thus, one way to adjust for this is to alter the model coefficients of TRAIL to account for this change.

Another way is to divide the rapid protocol measurements of TRAIL by 70% and plug in to the above mentioned models that were developed for the slow protocol.

It is often preferable to use a log transformation on the protein measurements in order to improve model accuracy and calibration (i.e. better fit between the predicted risk of a certain infection and the observed risk).

An example of a model with log transformation of TRAIL and IP-10 is depicted in Table 17 (model was trained on the consensus cohort):

TABLE 17

| Second Coordinate $\delta_1$ (bacterial) | First Coordinate $\delta_0$ (viral) | |
|---|---|---|
| $b_0 = -5.9471 \pm 3.3391$ | $a_0 = -14.8487 \pm 3.3839$ | Const |
| $b_1 = 0.0833 \pm 0.016856$ | $a_1 = 0.0437 \pm 0.017052$ | CRP (mg/ml) |
| $b_2 = 1.3868 \pm 0.48608$ | $a_2 = 2.0148 \pm 0.4408$ | IP10 (pg/ml) |
| $b_3 = -0.788 \pm 0.60505$ | $a_3 = 0.8946 \pm 0.61348$ | TRAIL (pg/ml) |

Example 6

Hypersurface Parameterization

Given the concentrations of CRP [C], TRAIL [T] and IP-10 [P] we define:

$$\delta_0 = -1.299 + 0.0605 \times [C] + 0.0053 \times [P] + 0.0088 \times [T]$$

$$\delta_1 = -0.378 + 0.0875 \times [C] + 0.0050 \times [P] - 0.0201 \times [T]$$

The probabilities can then be calculated by:

$$P(\text{Viral}) = \frac{e^{\delta_0}}{1 + e^{\delta_0} + e^{\delta_1}}$$

$$P(\text{Bacterial}) = \frac{e^{\delta_1}}{1 + e^{\delta_0} + e^{\delta_1}}$$

$$P(\text{Non-intfectious}) = \frac{1}{1 + e^{\delta_0} + e^{\delta_1}}$$

We define the hyper surface in the [C], [T], [P] space:

$$\frac{e^{\delta_1}}{1 + e^{\delta_0} + e^{\delta_1}} = \omega$$

that is used to distinguish between bacterial and non-bacterial patients. In one preferred embodiment. In other preferred embodiments. Given a patient's [C], [T], [P] values that patient is classified as bacterial if $$\frac{e^{\delta_1}}{1 + e^{\delta_0} + e^{\delta_1}} > \omega,$$

else he/she are classified as non-bacterial.

We define the set all hyper plains that can be used to distinguish between bacterial and non-bacterial infections as those that reside within the following two hyper surfaces:

$$\frac{e^{\delta_1}}{1 + e^{\delta_0} + e^{\delta_1}} = \omega + \epsilon_1$$

$$\frac{e^{\delta_1}}{1 + e^{\delta_0} + e^{\delta_1}} = \omega - \epsilon_0$$

$\epsilon_1$ can be any number between 0 and 1-. In some preferred embodiments $\epsilon_1$ is smaller then 0.5, 0.4, 0.3, 0.2 or 0.1.
$\epsilon_0$ can be any number between 0 and $\omega$. In some preferred embodiments $\epsilon_0$ is smaller then 0.5, 0.4, 0.3, 0.2 or 0.1.

Illustrated examples of surfaces are provided in Example 7.

Example 7

Graphical Representation of Classification

FIG. 20 is a 3-dimensional visualization of bacterial ('+'), viral ('o') and non-infectious ('^') patients. Different patients types are mapped to distinct regions in the CRP (μg/ml), TRAIL and IP-10 (pg/ml) concentration map.

By way of example probability surfaces were generated using a multinomial logistic regression. Contour plots of the surfaces are shown in FIGS. 21A-28C, as a function of TRAIL (y-axis), CRP (x-axis), and IP-10 concentrations. FIGS. 21A, 22A, 23A, 24A, 25A, 26A, 27A, 28A, show probabilities of viral infectious, FIGS. 21B, 22B, 23B, 24B, 25B, 26B, 27B, 28B, show probabilities of bacterial or mixed infectious, and FIGS. 21C, 22C, 23C, 24C, 25C, 26C, 27C, 28C, show probabilities of non-infectious or healthy. FIGS. 21A-21C correspond to IP10$_p$g ranging from 0 to 100, FIGS. 22A-22C correspond to IP10$_p$g ranging from 100 to 200, FIGS. 23A-23C correspond to IP10$_p$g ranging from 200 to 300, FIGS. 24A-24C correspond to IP10$_p$g ranging from 300 to 400, FIGS. 25A-25C correspond to IP10$_p$g ranging from 400 to 500, FIGS. 26A-26C correspond to IP10$_p$g ranging from 500 to 1000, FIGS. 27A-27C correspond to IP10$_p$g ranging from 1000 to 2000 and FIGS. 28A-28C correspond to IP10$_p$g which is 2000 or above.

Patients with bacterial or mixed are marked with a '+'; viral with a 'o' and non-infectious or healthy with a '^'. It can be seen in that low levels of IP-10 are associated with non-infectious disease, higher levels with bacterial and highest with viral. Low levels of TRAIL are associated with bacterial infections, higher with non-infectious and healthy, and highest with viral. Low levels of CRP are associated with non-infectious disease and healthy subjects, higher with viral infection and highest with bacterial. The combination of the three proteins generates a probability function whose diagnostic performance outperforms any of the individual or pairs of proteins.

FIGS. 35A-35D are contour plots describing the probability of bacterial (FIG. 35A), viral (FIG. 35B), non-bacterial (FIG. 35C), and non-infectious (FIG. 35D) etiologies as a function of the coordinates $\delta_0$ and $\delta_1$. The probability values range between 0% (black) to 100% (white).

Example 8

Exemplified Protocols for Measuring Expression Levels

In general, without limitation expression value of TRAIL can be measured using an ELISA or automated immunoassay; expression value of IP-10 can be measured using an ELISA assay; and expression value of CRP can be measured using an ELISA or automated immunoassay. The expression value of CRP can also be measured using a functional assay based on its calcium-dependent binding to phosphorylcholine.

Protocol A:

Suitable Protocol for Measuring an Expression Value of TRAIL (a) immobilize TRAIL present in a sample using an antibody to a solid support;
(b) contact immobilized TRAIL with a second antibody that specifically binds to TRAIL; and
(c) quantify the amount of antibody that binds to the immobilized TRAIL.

Suitable Protocol for Measuring an Expression Value of IP-10

(a) immobilize IP-10 present in a sample using a capture antibody to a solid support;
(b) contact immobilized IP-10 with a second antibody that specifically binds to IP-10; and
(c) quantify the amount of antibody that binds to the immobilized IP-10.

Suitable Protocol for Measuring an Expression Value of CRP (a) immobilize CRP present in a sample using a capture antibody to a solid support;
(b) contact immobilized CRP with a second antibody that specifically binds to I CRP; and
(c) quantify the amount of antibody that binds to the immobilized CRP.

Protocol B:

Suitable Protocol for Measuring an Expression Value of TRAIL (a) Incubate a sample with a first antibody that specifically binds to TRAIL, wherein the said first antibody is immobilized to a solid phase;
(b) Wash;
(c) Add second antibody that specifically binds to TRAIL, wherein the second antibody is conjugated to an enzyme; wash
(d) Add enzyme substrate and quantify the amount of antibody that binds to the immobilized sample.

Suitable Protocol for Measuring an Expression Value of IP-10

(a) Incubate a sample with a first antibody that specifically binds to IP-10, wherein the said first antibody is immobilized to a solid phase;
(b) Wash;
(c) Add second antibody that specifically binds to IP-10, wherein the second antibody is conjugated to an enzyme; wash
(d) Add enzyme substrate and quantify the amount of antibody that binds to the immobilized sample.

Suitable Protocol for Measuring an Expression Value of CRP (a) Incubate a sample with a first antibody that specifically binds to CRP, wherein the said first antibody is immobilized to a solid phase;
(b) Wash;
(c) Add second antibody that specifically binds to CRP, wherein the second antibody is conjugated to an enzyme; wash
(d) Add enzyme substrate and quantify the amount of antibody that binds to the immobilized sample.

Protocol C:

Suitable Protocol for Measuring an Expression Value of CRP (a) measure the turbidity of a mixture of lipids;
(b) contact sample with a known amount of the lipids (preferably phosophorylcholine) in the presence of Calcium; and
(c) measure the turbidity of the solution, wherein increase in turbidity correlates with the amount of CRP.

Example 9

Detailed Description of ELISA for Analyzing the Amount of TRAIL and IP-10

Sample Collection and Storage:

Exposure of samples to room temperature should be minimized (less than 6 hours). A serum separator tube (SST) is used and the samples are allowed to clot for at least 30 minutes before centrifugation (5 minutes at 1200×g). Serum may be assayed immediately, or aliquoted and stored at 4-8° C. for up to 24 hours or at ≤−20° C. for up to 3 months. Repeated freeze-thaw cycles should be avoided.

Reagent Preparation:

All reagents should be brought to room temperature before use.

Substrate Solution:

Color Reagents A and B should be mixed together in equal volumes within 10 minutes of use. Protect from light.

QC-IV, QC-2B and Standards:

Thaw all QC and Standards and remove 150 uL from each vial to a separate marked Polypropylene test tube. Move back to −20° C. immediately after use.

Trail Measurements:

The materials used for analyzing TRAIL are provided in Table 18, herein below.

TABLE 18

| Storage conditions | Description | Part |
| --- | --- | --- |
| Store at 2-8° C. | 96 well microplate (12 strips of 8 wells) coated with anti-TRAIL antibody | TRAIL Microplate |
| | 21 ml of anti-TRAIL specific antibody conjugated to horseradish peroxidase with preservatives | TRAIL Conjugate |
| | 11 ml of a buffered protein base with preservatives | Assay diluent MM1S |
| | 21 mL of a 25-fold concentrated solution of buffered surfactant with preservative | Wash Buffer Concentrate |
| | 12 mL of stabilized hydrogen peroxide | Color reagent A |
| | 12 mL of tetramethylbenzidine (TMB) | Color reagent B |
| | 6 mL of 2N sulfuric acid | Stop solution |
| | 4 adhesive strips | Plate sealer |
| Store at −20° C. immediately after receiving. | 6 vials containing 0.7 ml of recombinant human TRAIL in buffered protein base with preservatives at the following concentrations 500, 250, 125, 62.5, 31.2 and 0 [pg/mL] | 6 TRAIL Standards |
| | 1 ml | QC-1V |
| | 1 ml | QC-2B |

TRAIL ELISA Procedure a) Prepare samples, reagents and standards as indicated above.
b) Remove excess microplate strips from the plate frame, return them to the foil pouch containing the desiccant pack, and reseal.

c) Add 50 µL of Assay Diluent MM1S to each well.
d) Add 50 µL of Standard, samples, or QC per well. Cover with the adhesive strip provided.
e) Incubate for 30 minutes at room temperature on a microplate shaker (3 mm orbit) set at 550 rpm.
f) Aspirate each well and wash, repeating the process 4 times. Wash by filling each well with Wash Buffer (300 µL). After the last wash, remove any remaining Wash Buffer by aspirating or decanting. Invert the plate and blot it against clean paper towels.
g) Add 200 µL of TRAIL Conjugate to each well. Cover with a new adhesive strip. Incubate for 45 minutes at room temperature on a microplate shaker (3 mm orbit) set at 550 rpm.
h) Repeat the aspiration/wash as in step (g).
i) Add 200 µL of Substrate solution to each well. Incubate for 24 to 30 minutes at room temperature. Protect from light.
j) Add 50 µL of Stop solution to each well. The color in the wells should change from blue to yellow. If the color in the wells is green or the color change does not appear uniform, gently tap the plate to ensure thorough mixing.
k) Determine the optical density of each well immediately, using a microplate reader set to 450 nm. Set wavelength correction to 570 nm, which will correct for optical imperfections in the plate.

TRAIL Calculation of Concentrations:

Average the duplicate readings for each sample and subtract the average zero standard optical density (O.D.). Create a standard curve by plotting the mean absorbance for each standard (y-axis) against the concentration (x-axis) and draw a best-fit linear curve. The minimal $r^2$ should not fall below 0.96. In case lower $r^2$ values are present, repeat the experiment to get reliable results.

Precision:

Precision was evaluated based on the CLSI (formerly NCCLS) EPOS-A2 guidelines. Three samples with concentrations at the low (11.4pg/ml), intermediate (58.8 pg/ml), and high (539.0 pg/ml) physiological concentrations were used to assess precision. Results are summarized in Table 19, where $S_r$ is within-run precision and $S_T$ is within-device precision:

TABLE 19

| High (539.0 pg/ml) | Medium (58.8 pg/ml) | Low (11.4 pg/ml) | |
|---|---|---|---|
| 18 | 18 | 18 | # of runs |
| 36 | 36 | 36 | # of duplicates |
| 13.2 | 2.45 | 0.84 | $S_r$ pg/mL |
| 2.5% | 4.2% | 7.3% | $S_r$ CV (%) |
| 29.7 | 3.6 | 1.3 | $S_T$ pg/mL |
| 5.5% | 6.1% | 11.5% | $S_T$ CV (%) |

Recovery:

Recovery was evaluated by spiking three levels of human recombinant TRAIL (250, 125 and 62.5 pg/mL) into 5 human serum samples with no detectable levels of TRAIL. The spiked values and the average recovery was then measured and calculated, as shown in Table 20 below.

TABLE 20

| Range | Average % Recovery | Sample |
|---|---|---|
| 75-78% | 77% | Serum (n = 5) |

Linearity:

To assess the linearity of the assay, five clinical samples containing high concentrations of TRAIL were serially diluted using a serum substitute to produce samples with values within the physiological range of the assay. Linearity was, on average, 97%, 100% and 105% for 1:2, 1:4 and 1:8 dilutions, respectively, as summarized in Table 21 below.

TABLE 21

| Serum (n = 5) | | |
|---|---|---|
| 97% | Average % of expected | 1:2 |
| 90-104% | Range % | |
| 100% | Average % of expected | 1:4 |
| 90-108% | Range % | |
| 105% | Average % of expected | 1:8 |
| 90-121% | Range % | |

Sensitivity:

To estimate the Limitation of Blank (LOB), we tested 72 blank samples of serum substitute. The mean of the blank samples was 0.78 pg/ml and the standard deviation was 1.39 pg/ml. Therefore, the calculated LOB is 3.07 pg/ml. To estimate the Limitation of Detection (LOD), the CLSI EP17-A guidelines were followed. Briefly, the measurement distribution around seven predetermined concentrations were characterized, each with 30 independent measurements (210 measurements) yielding an LOD of 10pg/ml.

Calibration:

This immunoassay is calibrated against a purified NS0-expressed recombinant human TRAIL.

Expected Values:

Samples from apparently healthy adult (>18 years) were measured for the presence of TRAIL. The range and mean values are summarized in Table 22.

TABLE 22

| Range pg/ml | Mean pg/ml | Sample Type |
|---|---|---|
| 17-157 | 90 | Serum (n = 34) |

Cross Reactivity and Interference:

This assay recognizes natural and recombinant human TRAIL. The factors 4-1BB Ligand, APRIL, BAFF/BLyS, CD27 Ligand, CD30 Ligand, CD40 Ligand, Fas Ligand, GITR Ligand, LIGHT, LT α1/β2,LT α2/β1,OPG,OX40 Ligand, TNF-α, TNF-β, TRAIL R3, TRAIL R4, TRANCE and TWEAK were prepared at 50 ng/mL in serum substitution and assayed for cross-reactivity. Additionally, preparations of these factors at 50 pg/mL in a mid-range recombinant human TRAIL control were tested for interference. No significant cross-reactivity or interference was observed.

Ip-10 Measurements:

The materials used for analyzing IP-10 are provided in Table 23, herein below.

TABLE 23

| Storage conditions | Description | Part |
|---|---|---|
| Store at 2-8° C. | 96 well microplate (12 strips of 8 wells) coated with anti-IP-10 antibody | IP-10 Microplate |
| | 21 ml of anti-IP-10 specific antibody conjugated to horseradish peroxidase with preservatives | IP-10 Conjugate |

TABLE 23-continued

| Storage conditions | Description | Part |
|---|---|---|
| | 11 ml of a buffered protein base with preservatives | Assay diluent MM56 |
| | 21 mL of a 25-fold concentrated solution of buffered surfactant with preservative | Wash Buffer Concentrate |
| | 12 mL of stabilized hydrogen peroxide | Color reagent A |
| | 12 mL of tetramethylbenzidine (TMB) | Color reagent B |
| | 6 mL of 2N sulfuric acid | Stop solution |
| | 4 adhesive strips | Plate sealer |
| Store at −20° C. immediately after receiving | 6 vials containing 0.7 ml of recombinant human IP-10 in buffered protein base with preservatives at the following concentrations 1000, 500, 250, 125, 62.5 and 0 [pg/mL] | 6 IP-10 Standards |
| | 1 ml | QC-1V |
| | 1 ml | QC-2B |

IP-10 ELISA Procedure
a) Prepare samples, reagents and standards as indicated herein above.
b) Remove excess microplate strips from the plate frame, return them to the foil pouch containing the desiccant pack, and reseal.
c) Add 50 μL of Assay Diluent MM56 to each well.
d) Add 50 μL of Standard, sample or QC per well. Cover with the adhesive strip provided.
e) Incubate for 30 minutes at room temperature on a microplate shaker (3 mm orbit) set at 550 rpm.
f) Aspirate each well and wash, repeating the process 4 times. Wash by filling each well with Wash Buffer (300 μL). After the last wash, remove any remaining Wash Buffer by aspirating or decanting. Invert the plate and blot it against clean paper towels.
g) Add 200 μL of IP-10 Conjugate to each well. Cover with a new adhesive strip. Incubate for 45 minutes at room temperature on a microplate shaker (3 mm orbit) set at 550 rpm.
h) Repeat the aspiration/wash as in step (g).
i) Add 200 μL of Substrate solution to each well. Incubate for 10 minutes at room temperature. Protect from light.
j) Add 50 μL of Stop solution to each well. The color in the wells should change from blue to yellow. If the color in the wells is green or the color change does not appear uniform, gently tap the plate to ensure thorough mixing.
k) Determine the optical density of each well immediately, using a microplate reader set to 450 nm. Set wavelength correction to 570 nm, which will correct for optical imperfections in the plate.

IP-10 Calculation of Concentrations:
Average the duplicate readings for each sample and subtract the average zero standard optical density (O.D.). Create a standard curve by plotting the mean absorbance for each standard (y-axis) against the concentration (x-axis) and draw a best-fit linear curve. The minimal $r^2$ should not fall below 0.96. In case lower $r^2$ values are present, repeat the experiment to get reliable results.

Precision:
Precision was evaluated based on the CLSI (formerly NCCLS) EP05-A2 guidelines. Three samples with concentrations at the low (69.4 pg/ml), intermediate (228.2 pg/ml), and high (641.5 pg/ml) physiological concentrations were used to assess precision. Results are summarized in Table 24 where $S_r$ is within-run precision and $S_T$ is within-device precision:

TABLE 24

| High (641.5 pg/ml) | Medium (228.2 pg/ml) | Low (69.4 pg/ml) | |
|---|---|---|---|
| 18 | 18 | 18 | # of runs |
| 36 | 36 | 36 | # of duplicates |
| 21.1 | 5.6 | 4.0 | $S_r$ pg/mL |
| 3.3% | 2.4% | 5.8% | $S_r$ CV (%) |
| 37.2 | 12.9 | 4.9 | $S_T$ pg/mL |
| 5.8% | 5.7% | 7.1% | $S_T$ CV (%) |

Recovery:
Recovery was evaluated by spiking three levels of human IP-10, 500, 250 and 125pg/mL into 5 human serum samples with no detectable levels of IP-10. The spiked values and the average recovery was than measured and calculated as illustrated in Table 25 below.

TABLE 25

| Range | Average % Recovery | Sample |
|---|---|---|
| 72-80% | 77 | Serum/plasma (n = 5) |

Linearity:
To assess the linearity of the IP-10 assay, 5 clinical samples containing high concentrations of IP-10 ranging between 873.7 to 1110.4 pg/mL were serially diluted with a serum substitute to produce samples with values within the physiological range of the assay. Linearity was, on average, 98%, 102% and 104% in 1:2, 1:4 and 1:8 dilutions, respectively, as summarized in Table 26 herein below.

TABLE 26

| Serum (n = 5) | | |
|---|---|---|
| 98% | Average % of expected | 1:2 |
| 93-102% | Range % | |
| 102% | Average % of expected | 1:4 |
| 97-107% | Range % | |
| 104% | Average % of expected | 1:8 |
| 96-111% | Range % | |

Sensitivity:
To estimate the Limitation of Blank (LOB), we tested 72 blank samples of serum substitute. The mean of the blank samples was 0.23pg/ml and the standard deviation was 1.26pg/ml, yielding an LOB of 2.29pg/ml.

To estimate the Limitation of Detection (LOD), the CLSI EP17-A guidelines were applied. Briefly, the measurement distribution around seven predetermined concentrations were characterized, each with 30 independent measurements (210 measurements) yielding an LOD of 10pg/ml.

Calibration:
This immunoassay is calibrated against a highly purified *E-coli*-expressed recombinant human IP-10.

Expected Values:
Samples from apparently healthy adult volunteers were measured for the presence of IP-10. The range and mean values are shown in Table 27 below.

TABLE 27

| Range pg/ml | Mean pg/ml | Sample Type |
|---|---|---|
| 29-525 | 119 | Serum (n = 34) |

Cross Reactivity and Interference:

This assay recognizes natural and recombinant human IP-10. The factors BLC/BCA-1,ENA-78,GCP-2,GROα, GRO γ,IFN-γ,IL-8,I-TAC,MIG,NAP-2,SDF-1a and SDF-1β were prepared at 50 ng/mL in serum substitution and assayed for cross-reactivity. Additionally, preparations of these factors at 50 pg/mL in a mid-range recombinant human IP-10 control were tested for interference. No significant cross-reactivity or interference was observed.

Example 10

Trail and Disease Prognosis

It is often clinically useful to assess patient prognosis, disease severity and outcome. The present inventors found that low levels of TRAIL are significantly correlated with poor patient prognosis and outcome, and high disease severity. For example, adult patients in the intensive care unit (ICU) had significantly lower TRAIL levels compared to all other patients, which were less ill regardless of whether they had an infectious or non-infectious etiology. Median serum concentrations were 9pg/ml vs. 80 pg respectively, (ranksum P<0.001, FIG. 36A), for severely ill and all other patients respectively.

40 Dutch pediatric patients, 3 months to 5 years of age. The TRAIL serum level was measured in 40 Dutch pediatric patients, 3 months to 5 years of age. It was found that those patients that were eventually admitted to the ICU (an indication of disease complication and poor prognosis) or even died had significantly lower TRAIL serum concentrations compared to the rest of the patients (median of 11 vs. 85, respectively; ranksum P<0.001) as depicted in FIG. 36B. Strikingly, the lowest TRAIL levels (<5 pgml) were measured in the only two children that died in the entire cohort. These results indicate that TRAIL could be used as a prognostic marker for predicting disease severity and outcome.

Example 11

Trail Age and Gender Parameters

Basal levels of TRAIL in healthy individuals or patients with a non-infectious disease are lower in females compared to males during fertility age (t-test P<0.001) (FIG. 37A), but is invariant in pre- or post-fertility age (t-test P=0.9, FIG. 37B). This trend was not observed in patients with an infectious disease.

Example 12

Exemplified Manifolds, Hyperplanes and Coordinates

One-Dimensional Manifold

When n=1, the manifold S is a curved line and the hyperplane π is an axis defining a single direction $\delta_1$. The coordinate $\delta_1$ in this Example is optionally and preferably a linear combination $b_0+b_1D_1+b_2D_2+\ldots$, of the polypeptides $D_1$, $D_2$, etc.

Table 28 below lists diagnostic performance (in AUCs) attained for n=1. The performance were computed using a leave-10%-out cross validation on the cohort specified in each row. In rows 1-4, the analyzed subjects had either bacterial or viral infections and the coordinate $\delta_1$ was calculated so that the probabilistic classification function $f(\delta_1)$ represented the likelihood that the test subject had a bacterial infection. In rows 5-8, the analyzed subjects were infectious or non-infections and the coordinate $\delta_1$ was calculated so that the probabilistic classification function $f(\delta_1)$ represented the likelihood that the test subject had an infection. In rows 10-12, the analyzed subjects had either bacterial or non-bacterial infection and the coordinate $\delta_1$ was calculated so that the probabilistic classification function $f(\delta_1)$ represented the likelihood that the test subject had a bacterial infection. In rows 1-4, the columns P and N correspond to the number of Bacterial and Viral patients respectively, in rows 5-8, the columns P and N correspond to the number of infectious and non-infectious patients, respectively, and in rows 9-12, the columns P and N correspond to the number Bacterial and non-Bacterial patients respectively. Majority and Consensus indicate the type of cohort on which the model was validated.

TABLE 28

| N | P | AUC | Polypeptides | | | Cohort | No. |
|---|---|---|---|---|---|---|---|
| 334 | 319 | 0.93 | | TRAIL | CRP | Majority | 1 |
| 334 | 319 | 0.94 | TRAIL | IP-10 | CRP | Majority | 2 |
| 271 | 256 | 0.95 | | TRAIL | CRP | Consensus | 3 |
| 271 | 256 | 0.96 | TRAIL | IP-10 | CRP | Consensus | 4 |
| 112 | 653 | 0.93 | | TRAIL | CRP | Majority | 5 |
| 112 | 653 | 0.96 | TRAIL | IP-10 | CRP | Majority | 6 |
| 112 | 527 | 0.93 | | TRAIL | CRP | Consensus | 7 |
| 112 | 527 | 0.97 | TRAIL | IP-10 | CRP | Consensus | 8 |
| 446 | 319 | 0.94 | | TRAIL | CRP | Majority | 9 |
| 446 | 319 | 0.94 | TRAIL | IP-10 | CRP | Majority | 10 |
| 383 | 256 | 0.95 | | TRAIL | CRP | Consensus | 11 |
| 383 | 256 | 0.96 | TRAIL | IP-10 | CRP | Consensus | 12 |

Table 29 below lists the coefficients $b_0$, $b_1$, $b_2$, etc that were used to define the coordinate $\delta_1$, for each of the 12 cases listed in Table 28, respectively. The first coefficient on the left is $b_0$, and then from left to right, the coefficients correspond to the order of the polypeptides in each row of Table 28. The coefficients correspond to the following concentration scales for each polypeptide: TRAIL (pg/ml), IP-10 (pg/ml) and CRP (ug/ml).

For a given set of polypeptides, the obtained coefficients have small variations among the different cohorts. Nevertheless, the coefficients for the probabilistic classification functions and coordinates of the present embodiments preferably correspond to those obtained for the Majority Cohort.

TABLE 29

| Coefficients | | | | No. |
|---|---|---|---|---|
| | −0.029953 | 0.027472 | 0.64814 | 1 |
| −0.029013 | −0.00028168 | 0.028119 | 0.71542 | 2 |
| | −0.033669 | 0.034565 | 0.636 | 3 |
| −0.03195 | −0.00058691 | 0.035748 | 0.79543 | 4 |
| | 0.016837 | 0.17237 | −2.0549 | 5 |
| 0.005213 | 0.00592 | 0.1263 | −2.3344 | 6 |
| | 0.018624 | 0.16625 | −2.3469 | 7 |
| 0.0079169 | 0.0061124 | 0.12261 | −2.7949 | 8 |
| | −0.027839 | 0.034954 | −0.08503 | 9 |
| −0.027916 | 2.2524e−05 | 0.034878 | −0.088207 | 10 |
| | −0.030997 | 0.044289 | −0.26606 | 11 |
| −0.03042 | −0.00018635 | 0.044938 | −0.23907 | 12 |

Table 30 below lists diagnostic performance (in AUCs) attained for one-dimensional manifold. The performance were computed using a leave-10%-out cross validation on the Majority cohort. In rows 1-55, the analyzed subjects had either bacterial or viral infections and the probabilistic classification function $f(\delta_1)$ represented the likelihood that the test subject had a bacterial infection. In rows 56-110, the analyzed subjects were infectious or non-infections and the probabilistic classification function $f(\delta_1)$ represented the likelihood that the test subject had an infection. In rows 1-55, the columns P and N correspond to the number of Bacterial and Viral patients respectively, and in rows 56-110, the columns P and N correspond to the number of infectious and noninfectious patients, respectively.

TABLE 30

| N | P | AUC | Polypeptides | | | | No. |
|---|---|---|---|---|---|---|---|
| 141 | 142 | 0.88 | | | | IL1ra | CRP 1 |
| 299 | 295 | 0.90 | | | | IP-10 | CRP 2 |
| 50 | 51 | 0.87 | | | | PCT | CRP 3 |
| 241 | 255 | 0.90 | | | | SAA | CRP 4 |
| 142 | 142 | 0.64 | | | | IP-10 | IL1ra 5 |
| 14 | 19 | 0.62 | | | | PCT | IL1ra 6 |
| 122 | 124 | 0.83 | | | | SAA | IL1ra 7 |
| 142 | 142 | 0.88 | | | | TRAIL | IL1ra 8 |
| 49 | 51 | 0.74 | | | | PCT | IP-10 9 |
| 242 | 251 | 0.85 | | | | SAA | IP-10 10 |
| 297 | 295 | 0.88 | | | | TRAIL | IP-10 11 |
| 40 | 45 | 0.78 | | | | SAA | PCT 12 |
| 50 | 51 | 0.87 | | | | TRAIL | PCT 13 |
| 244 | 255 | 0.90 | | | | TRAIL | SAA 14 |
| 141 | 142 | 0.90 | | | IP-10 | IL1ra | CRP 15 |
| 14 | 19 | 0.82 | | | PCT | IL1ra | CRP 16 |
| 121 | 124 | 0.89 | | | SAA | IL1ra | CRP 17 |
| 141 | 142 | 0.94 | | | TRAIL | IL1ra | CRP 18 |
| 49 | 51 | 0.89 | | | PCT | IP-10 | CRP 19 |
| 239 | 251 | 0.91 | | | SAA | IP-10 | CRP 20 |
| 40 | 45 | 0.88 | | | SAA | PCT | CRP 21 |
| 50 | 51 | 0.93 | | | TRAIL | PCT | CRP 22 |
| 241 | 255 | 0.94 | | | TRAIL | SAA | CRP 23 |
| 14 | 19 | 0.62 | | | PCT | IP-10 | IL1ra 24 |
| 122 | 124 | 0.85 | | | SAA | IP-10 | IL1ra 25 |
| 142 | 142 | 0.88 | | | TRAIL | IP-10 | IL1ra 26 |
| 13 | 17 | 0.76 | | | SAA | PCT | IL1ra 27 |
| 14 | 19 | 0.71 | | | TRAIL | PCT | IL1ra 28 |
| 122 | 124 | 0.92 | | | TRAIL | SAA | IL1ra 29 |
| 39 | 45 | 0.81 | | | SAA | PCT | IP-10 30 |
| 49 | 51 | 0.86 | | | TRAIL | PCT | IP-10 31 |
| 242 | 251 | 0.91 | | | TRAIL | SAA | IP-10 32 |
| 40 | 45 | 0.86 | | | TRAIL | SAA | PCT 33 |
| 14 | 19 | 0.83 | | PCT | IP-10 | IL1ra | CRP 34 |
| 121 | 124 | 0.92 | | SAA | IP-10 | IL1ra | CRP 35 |
| 141 | 142 | 0.94 | | TRAIL | IP-10 | IL1ra | CRP 36 |
| 13 | 17 | 0.74 | | SAA | PCT | IL1ra | CRP 37 |
| 14 | 19 | 0.90 | | TRAIL | PCT | IL1ra | CRP 38 |
| 121 | 124 | 0.94 | | TRAIL | SAA | IL1ra | CRP 39 |
| 39 | 45 | 0.88 | | SAA | PCT | IP-10 | CRP 40 |
| 49 | 51 | 0.92 | | TRAIL | PCT | IP-10 | CRP 41 |
| 239 | 251 | 0.94 | | TRAIL | SAA | IP-10 | CRP 42 |
| 40 | 45 | 0.92 | | TRAIL | SAA | PCT | CRP 43 |
| 13 | 17 | 0.70 | | SAA | PCT | IP-10 | IL1ra 44 |
| 14 | 19 | 0.70 | | TRAIL | PCT | IP-10 | IL1ra 45 |
| 122 | 124 | 0.91 | | TRAIL | SAA | IP-10 | IL1ra 46 |
| 13 | 17 | 0.82 | | TRAIL | SAA | PCT | IL1ra 47 |
| 39 | 45 | 0.85 | | TRAIL | SAA | PCT | IP-10 48 |
| 13 | 17 | 0.82 | SAA | PCT | IP-10 | IL1ra | CRP 49 |
| 14 | 19 | 0.75 | TRAIL | PCT | IP-10 | IL1ra | CRP 50 |
| 121 | 124 | 0.94 | TRAIL | SAA | IP-10 | IL1ra | CRP 51 |
| 13 | 17 | 0.78 | TRAIL | SAA | PCT | IL1ra | CRP 52 |
| 39 | 45 | 0.92 | TRAIL | SAA | PCT | IP-10 | CRP 53 |
| 13 | 17 | 0.62 | TRAIL | SAA | PCT | IP-10 | IL1ra 54 |
| 13 | 17 | 0.74 | TRAIL | SAA | PCT | IP-10 | IL1ra CRP 55 |
| 87 | 283 | 0.91 | | | | IL1ra | CRP 56 |
| 102 | 594 | 0.96 | | | | IP-10 | CRP 57 |
| 6 | 101 | 0.85 | | | | PCT | CRP 58 |
| 78 | 496 | 0.91 | | | | SAA | CRP 59 |

TABLE 30-continued

| N | P | AUC | Polypeptides | | | | No. |
|---|---|---|---|---|---|---|---|
| 87 | 284 | 0.89 | | | | IP-10 | IL1ra 60 |
| 6 | 33 | 0.79 | | | | PCT | IL1ra 61 |
| 64 | 246 | 0.91 | | | | SAA | IL1ra 62 |
| 87 | 284 | 0.86 | | | | TRAIL | IL1ra 63 |
| 6 | 100 | 0.73 | | | | PCT | IP-10 64 |
| 81 | 493 | 0.96 | | | | SAA | IP-10 65 |
| 107 | 592 | 0.91 | | | | TRAIL | IP-10 66 |
| 3 | 85 | 0.89 | | | | SAA | PCT 67 |
| 7 | 101 | 0.60 | | | | TRAIL | PCT 68 |
| 81 | 499 | 0.93 | | | | TRAIL | SAA 69 |
| 87 | 283 | 0.95 | | | IP-10 | IL1ra | CRP 70 |
| 6 | 33 | 0.76 | | | PCT | IL1ra | CRP 71 |
| 64 | 245 | 0.92 | | | SAA | IL1ra | CRP 72 |
| 87 | 283 | 0.93 | | | TRAIL | IL1ra | CRP 73 |
| 6 | 100 | 0.81 | | | PCT | IP-10 | CRP 74 |
| 78 | 490 | 0.97 | | | SAA | IP-10 | CRP 75 |
| 3 | 85 | 0.88 | | | SAA | PCT | CRP 76 |
| 6 | 101 | 0.87 | | | TRAIL | PCT | CRP 77 |
| 78 | 496 | 0.95 | | | TRAIL | SAA | CRP 78 |
| 6 | 33 | 0.77 | | | PCT | IP-10 | IL1ra 79 |
| 64 | 246 | 0.94 | | | SAA | IP-10 | IL1ra 80 |
| 87 | 284 | 0.90 | | | TRAIL | IP-10 | IL1ra 81 |
| 3 | 30 | 0.72 | | | SAA | PCT | IL1ra 82 |
| 6 | 33 | 0.67 | | | TRAIL | PCT | IL1ra 83 |
| 64 | 246 | 0.90 | | | TRAIL | SAA | IL1ra 84 |
| 3 | 84 | 0.98 | | | SAA | PCT | IP-10 85 |
| 6 | 100 | 0.68 | | | TRAIL | PCT | IP-10 86 |
| 81 | 493 | 0.96 | | | TRAIL | SAA | IP-10 87 |
| 3 | 85 | 0.98 | | | TRAIL | SAA | PCT 88 |
| 6 | 33 | 0.77 | | PCT | IP-10 | IL1ra | CRP 89 |
| 64 | 245 | 0.95 | | SAA | IP-10 | IL1ra | CRP 90 |
| 87 | 283 | 0.95 | | TRAIL | IP-10 | IL1ra | CRP 91 |
| 3 | 30 | 0.73 | | SAA | PCT | IL1ra | CRP 92 |
| 6 | 33 | 0.74 | | TRAIL | PCT | IL1ra | CRP 93 |
| 64 | 245 | 0.92 | | TRAIL | SAA | IL1ra | CRP 94 |
| 3 | 84 | 0.98 | | SAA | PCT | IP-10 | CRP 95 |
| 6 | 100 | 0.77 | | TRAIL | PCT | IP-10 | CRP 96 |
| 78 | 490 | 0.97 | | TRAIL | SAA | IP-10 | CRP 97 |
| 3 | 85 | 0.80 | | TRAIL | SAA | PCT | CRP 98 |
| 3 | 30 | 0.91 | | SAA | PCT | IP-10 | IL1ra 99 |
| 6 | 33 | 0.67 | | TRAIL | PCT | IP-10 | IL1ra100 |
| 64 | 246 | 0.94 | | TRAIL | SAA | IP-10 | IL1ra101 |
| 3 | 30 | 0.78 | | TRAIL | SAA | PCT | IL1ra102 |
| 3 | 84 | 0.65 | | TRAIL | SAA | PCT | IP-10 103 |
| 3 | 30 | 0.91 | SAA | PCT | IP-10 | IL1ra | CRP104 |
| 6 | 33 | 0.66 | TRAIL | PCT | IP-10 | IL1ra | CRP105 |
| 64 | 245 | 0.95 | TRAIL | SAA | IP-10 | IL1ra | CRP106 |
| 3 | 30 | 0.73 | TRAIL | SAA | PCT | IL1ra | CRP107 |
| 3 | 84 | 0.97 | TRAIL | SAA | PCT | IP-10 | CRP108 |
| 3 | 30 | 0.78 | TRAIL | SAA | PCT | IP-10 | IL1ra109 |
| 3 | 30 | 0.73 | TRAIL | SAA | PCT | IP-10 | IL1ra CRP110 |

Table 31 below list the coefficients $b_0, b_1, b_2$, etc that were used to define the coordinate $\delta_1$, for each of the 110 cases listed in Table 30, respectively. The first coefficient on the left is $b_0$, and then from left to right, the coefficients correspond to the order of the polypeptides in each row of Table 30. The coefficients correspond to the following concentration scales for each polypeptide: TRAIL (pg/ml), IP-10 (pg/ml), CRP (ug/ml), PCT (ng/ml), SAA (g/ml) and IL1ra (g/ml).

TABLE 31

| | | | | | | | Coefficients | | | | | | No. |
|---|---|---|---|---|---|---|---|
| | | | | | | −9849178.8 | 0.0363 | −1.997 | 1 |
| | | | | | | −0.0009 | 0.039722 | −1.6069 | 2 |
| | | | | | | 0.6405 | 0.054137 | −2.9681 | 3 |
| | | | | | | 1098.3777 | 0.034353 | −2.33196 | 4 |
| | | | | | | −0.00089 | 47954608.09 | 0.4715979 | 5 |
| | | | | | | 4.5607 | −69280395.624 | −0.74822 | 6 |
| | | | | | | 5283.68 | −33345728.8342 | −1.706206 | 7 |
| | | | | | | −0.03151 | 43833567.7377 | 3.0601663 | 8 |
| | | | | | | 0.86013 | −0.00060898 | −0.13268 | 9 |
| | | | | | | 4677.8311 | −0.0009684361 | −1.01872 | 10 |
| | | | | | | −0.0288 | 0.00031349 | 2.5632 | 11 |
| | | | | | | 2349.8702 | 1.1895403 | −1.35195 | 12 |
| | | | | | | −0.019169 | 0.4382 | 1.4742 | 13 |
| | | | | | | −0.02176 | 2962.7685 | 1.08972 | 14 |
| | | | | −0.00165 | 6.264E+7 | 0.039986 | −1.27532 | 15 |
| | | | | 1.07655 | −8.42E+7 | 0.0475326 | −2.3376 | 16 |
| | | | | 2098.4 | −2.22E+7 | 0.027867 | −2.23709 | 17 |
| | | | | −0.0266 | 2.0497E+7 | 0.030146 | 0.9001561 | 18 |
| | | | | 0.65349 | −0.0005 | 0.051698 | −2.5383 | 19 |
| | | | | 1378.2 | −0.00109 | 0.034481544 | −1.6940577 | 20 |
| | | | | −1243.01 | 1.4735726 | 0.054245413 | −2.7487888 | 21 |
| | | | | −0.010529 | 0.42793 | 0.04535 | −1.421 | 22 |
| | | | | −0.01891 | 183.3117 | 0.0312776 | 0.1044034 | 23 |
| | | | | 4.8755 | −0.001241 | −4107077 | −0.0013248 | 24 |
| | | | | 5777 | −0.001377 | 21179055 | −1.054077 | 25 |
| | | | | −0.03151 | −1.118−06 | 43882108 | 3.0605 | 26 |
| | | | | 4823 | 2.91 | −68741718 | −1.9806377 | 27 |
| | | | | −0.0342 | 1.941 | 113905139.6 | 2.844483 | 28 |
| | | | | −0.0264 | 3745.49 | −7296968.1 | 1.4399 | 29 |
| | | | | 2427.6 | 1.3263344 | −0.000765 | −0.8562752 | 30 |
| | | | | −0.020588 | 0.38993 | 0.00045394 | 1.357 | 31 |
| | | | | −0.021174 | 3048.4182 | −0.000163 | 1.0917705 | 32 |
| | | | | −0.013629 | 1431.011 | 0.89320046 | 0.48274 | 33 |
| | | | 1.5 | −0.003888 | 75533424 | 0.07214 | −0.6620 | 34 |
| | | | 2425.771 | −0.002 | 59894763 | 0.034006 | −1.433018 | 35 |
| | | | −0.0251 | −0.000084 | 50294164 | 0.03259 | 1.074937 | 36 |
| | | | 893.395 | 1.1316 | −70994467 | 0.038 | −2.302 | 37 |
| | | | −0.0477 | −0.084 | −81575254 | 0.061632 | 1.903272 | 38 |
| | | | −0.02483 | 1236 | 10145313 | 0.025 | 0.65146 | 39 |
| | | | −949.2 | 1.528887 | −5.5688E−4 | 0.04984696 | −2.32016 | 40 |
| | | | −0.011113 | 0.40033 | 0.00021523 | 0.045264 | −1.4662 | 41 |
| | | | −0.0177 | 329.7448 | −0.0003975 | 0.03169 | 0.14333 | 42 |
| | | | −0.011 | −1930.2 | 1.24 | 0.050385 | −1.109923 | 43 |
| | | | 6082.17 | 4.286 | −0.002014 | 2715886 | −1.087150 | 44 |
| | | | −0.0397 | 2.126 | 0.00092636 | −1508120 | 2.9154 | 45 |
| | | | −0.0252 | 4082.939 | −0.00062 | 17100158 | 1.55114 | 46 |
| | | | −0.0560 | 7639.7 | 0.68134 | −27909258 | 2.85226 | 47 |
| | | | −0.0134 | 1423.99 | 0.87764371 | 6.13e−05 | 0.446 | 48 |
| | | 4736.86 | 1.250 | −0.00652 | 172681901 | 0.07676 | −0.3021 | 49 |
| | | −0.044 | −0.121 | −0.000873 | −4.62E+7 | 0.0671 | 1.937 | 50 |
| | | −0.0219 | 1576.6 | −0.00134 | 54069432 | 0.029267 | 0.78878 | 51 |
| | | −0.055 | 3598 | −0.098620 | −74159142 | 0.041577 | 2.309 | 52 |
| | | −0.0116 | −2055 | 1.188 | 0.00023 | 0.0512 | −1.1542 | 53 |
| | | −0.055 | 8903.82 | 1.03 | −0.0012627 | 14035678 | 3.2 | 54 |
| −0.078 | 14133 | −0.687 | −0.009695 | 1.062E+8 | 0.10 | 5.59 | 55 |
| | | | | 3.996E+8 | 0.11089 | −1.021759 | 56 |
| | | | | 0.0063336 | 0.11347 | −1.9467 | 57 |
| | | | | 860.3249 | 0.0639025 | −84.98948 | 58 |
| | | | | 9898.8177 | 0.091563631 | −0.3299621 | 59 |
| | | | | 0.00721 | 107920251.6624 | −1.0006445 | 60 |
| | | | | 419.2 | 596535240 | −41.585735 | 61 |
| | | | | 14320 | 234257296.8937 | −0.4789050 | 62 |
| | | | | 0.00066 | 812307573.5455 | 0.09918792 | 63 |
| | | | | 1089.4251 | 0.00069423293 | −107.18015 | 64 |
| | | | | 12590.5 | 0.00967490979 | −2.05501 | 65 |
| | | | | −0.00905 | 0.0092076 | 0.19189 | 66 |
| | | | | 165893.71 | 122.7205081 | −11.30895 | 67 |
| | | | | 0.0041105 | 6.5788 | 0.98581 | 68 |
| | | | | 0.010541 | 19453.2163 | −1.366750 | 69 |
| | | | | 0.0062 | −77782071 | 0.10876 | −2.301980 | 70 |
| | | | | 393.7 | 559628637 | 0.048935 | −39.915 | 71 |
| | | | | 8656.83 | 244256710 | 0.0663 | −0.885780 | 72 |
| | | | | 0.0129 | 157875482 | 0.142003 | −2.694252 | 73 |
| | | | | 846.608 | 0.0014 | 0.07831107 | −84.66684 | 74 |
| | | | | 5900.1661 | 0.00927 | 0.081369191 | −2.5885198 | 75 |
| | | | | 131629 | 108.84 | 0.06793071342 | −10.12169 | 76 |
| | | | | 0.011421 | 822.6365 | 0.08303337 | −82.88872 | 77 |
| | | | | 0.013257 | 10662.5415 | 0.106214424 | −2.33978 | 78 |

TABLE 31-continued

| | | | Coefficients | | | No. |
|---|---|---|---|---|---|---|
| | | 417.43 | −0.000381 | 744190123.3893 | −41.369532 | 79 |
| | | 12128 | 0.0091619 | −130390666 | −2.266204 | 80 |
| | | −0.005459 | 0.007583 | 82287681 | −0.50010 | 81 |
| | | 377360 | −8.1908 | 6837963488 | −2.47028 | 82 |
| | | 0.00099 | 418.212 | 560182293 | −41.5502 | 83 |
| | | 0.011194 | 17111.2 | 29398797 | −1.8577 | 84 |
| | 21649017 | | 28.96307 | 0.4328 | −156.16 | 85 |
| | | 0.00330 | 1086.1672 | 0.00029753173 | −107.01823 | 86 |
| | | −9.3941e−05 | 12572.6828 | 0.00969 | −2.0464 | 87 |
| | | 24.2 | 80696477 | 471.6 | −2614.99 | 88 |
| | 392.929 | −0.0001 | 611767730 | 0.0491 | −39.82 | 89 |
| | 6854 | 0.00937 | −157521601 | 0.070555 | −2.81351 | 90 |
| | 0.005871 | 0.00552 | −61236289 | 0.118 | −2.9416 | 91 |
| | 403954 | −8.6576 | 7107285383 | −0.07356 | −2.349 | 92 |
| | 0.00857 | 373.75 | 383823513 | 0.05763 | −38.781 | 93 |
| | 0.013998 | 9692.125 | −4665192.1 | 0.0965657 | −2.782 | 94 |
| | 4998296 | −132.70 | 0.3202 | 10.567847038 | −132.7427 | 95 |
| | 0.00927 | 827.6066 | 0.000498 | 0.08349426 | −83.41464 | 96 |
| | 0.00369 | 6461.9905 | 0.008696 | 0.084631596 | −2.9639303 | 97 |
| | 2.32E+12 | 4.83248e+18 | −1.05E+14 | 9037614498892 | 1.185E+14 | 98 |
| | 9471186 | −296 | 0.196688 | 116933544267 | −99.64 | 99 |
| | 0.002761 | 413.88 | −0.00058 | 713679677.7954 | −41.177966 | 100 |
| | 0.00349 | 12684.8 | 0.0088176 | −124943185 | −2.6391378 | 101 |
| | 1.3718 | 8853215 | −272.0191 | 68076716508 | −163.16785 | 102 |
| | 0.9352 | 11007611 | 24.21772 | | 0.09197 | −134.8402 | 103 |
| 5448434 | −195 | 0.1975318 | 32157214873 | 5.367 | −82.7 | 104 |
| 0.024158 | 327.2 | −0.002344 | 823767988 | 0.0803 | −35.325 | 105 |
| 0.0065 | 7390.9 | 0.008791 | −151905670 | 0.080040 | −3.579 | 106 |
| 2.78 | −1129873 | −106.418 | 43593035460 | 29.2 | −338.972 | 107 |
| 1.563 | −96788.08 | −22.217 | 0.4843 | 8.2370 | −237.8248 | 108 |
| 4.06E+12 | 1.757e+18 | 2.798E+13 | 3.97E+12 | −5.96133e+22 | −8.51E+14 | 109 |
| 1.839 | −9.83E+5 | −16.687 | 0.58062 | −4575512593 | 9.549 | −276.3 | 110 |

Two-Dimensional Manifold

When n=2, the manifold S is a curved surface and the hyperplane π is a flat plane defined by the first direction $\delta_0$ and the second direction $\delta_1$. The coordinate $\delta_0$ in this Example is optionally and preferably a linear combination $a_0 + a_1 D_1 + a_2 D_2 + \ldots$, of the polypeptides $D_1$, $D_2$, etc; and the coordinate $\delta_1$ in this Example is optionally and preferably a linear combination $b_0 + b_1 D_1 + b_2 D_2 + \ldots$, of the polypeptides $D_1$, $D_2$, etc.

Tables 32-35 below list diagnostic performance (in AUCs) attained for n=2. The performance were computed using a leave-10%-out cross validation on a subset of the majority cohort that had sufficient serum to measure all the proteins. The coordinates $\delta_0$ and $\delta_1$ were calculated so that the probabilistic classification function $f(\delta_0, \delta_1)$ represented the likelihood that the test subject had a bacterial infection. The AUC values correspond to classifications according to Bacterial versus Viral (second column from right—B vs. V) and infectious vs. non-infectious (rightmost column—I vs. NI). Shown are results for the embodiments in which the plurality of polypeptides includes two polypeptides (Table 32), three polypeptides (Table 33), four polypeptides (Table 34) and five polypeptides (Table 35). The coefficients for the coordinates $\delta_0$ and $\delta_1$ are presented for each polypeptide, wherein "const" correspond to $a_0$ when applied to the coordinate $\delta_0$ and $b_0$ when applied to the coordinate $\delta_1$. The coefficients correspond to the following concentration scales for each protein: TRAIL (pg/ml), IP-10 (pg/ml), CRP (ug/ml), PCT (ng/ml), SAA (g/ml) and IL1ra (g/ml).

TABLE 32

| AUC (I vs. NI) | AUC (B vs. V) | | | | |
|---|---|---|---|---|---|
| 0.91 | 0.88 | TRAIL | IP-10 | Const | |
| | | 0.0006 | 0.0086 | −0.3333 | δ0 |
| | | −0.0294 | 0.0089 | 2.4481 | δ1 |
| 0.95 | 0.89 | IP-10 | CRP | Const | |
| | | 0.0055 | 0.0517 | −0.474 | δ0 |
| | | 0.0046 | 0.0902 | −1.9201 | δ1 |
| 0.96324 | 0.85647 | SAA | IP-10 | Const | |
| | | 9623.7195 | 0.0089 | −1.0634 | δ0 |
| | | 14280.3897 | 0.0079 | −2.0098 | δ1 |
| 0.89408 | 0.63901 | IP-10 | IL1ra | Const | |
| | | 0.0077 | 77589304.64 | −0.2347 | δ0 |
| | | 0.0069 | 122880671.4 | 0.3245 | δ1 |
| 0.735 | 0.70468 | PCT | IP-10 | Const | |
| | | 0.1778 | 0.0012 | 1.3717 | δ0 |
| | | 0.9426 | 0.0007 | 1.3073 | δ1 |
| 0.93 | 0.94 | TRAIL | CRP | Const | |
| | | 0.0129 | 0.0647 | −0.551 | δ0 |
| | | −0.0077 | 0.0953 | −0.1177 | δ1 |

TABLE 32-continued

| AUC (I vs. NI) | AUC (B vs. V) | | | | | |
|---|---|---|---|---|---|---|
| 0.92719 | 0.90714 | TRAIL | SAA | | Const | |
| | | 0.0146 | 15457.6689 | | −1.0101 | $\delta 0$ |
| | | −0.0081 | 18311.8735 | | 0.2736 | $\delta 1$ |
| 0.85523 | 0.88673 | TRAIL | IL1ra | | Const | |
| | | 0.0118 | 660539652.3 | | −0.1638 | $\delta 0$ |
| | | −0.0224 | 691029794.9 | | 3.3011 | $\delta 1$ |
| 0.69731 | 0.86706 | TRAIL | PCT | | Const | |
| | | 0.0095 | 0.6699 | | 0.7941 | $\delta 0$ |
| | | −0.0105 | 1.0871 | | 2.4419 | $\delta 1$ |
| 0.92 | 0.89 | SAA | CRP | | Const | |
| | | 7927.9578 | 0.0371 | | 0.9937 | $\delta 0$ |
| | | 9043.9184 | 0.0704 | | −1.2549 | $\delta 1$ |
| 0.93 | 0.87 | IL1ra | CRP | | Const | |
| | | 357544464 | 0.0549 | | 0.9321 | $\delta 0$ |
| | | 345095895 | 0.0895 | | −0.8849 | $\delta 1$ |
| 0.85 | 0.88 | PCT | CRP | | Const | |
| | | 0.1493 | 0.0543 | | 1.225 | $\delta 0$ |
| | | 0.71 | 0.1052 | | −1.48 | $\delta 1$ |
| 0.9154 | 0.82529 | SAA | IL1ra | | Const | |
| | | 11965 | 233885248 | | 0.9453 | $\delta 0$ |
| | | 17194.2625 | 201037678 | | −0.6599 | $\delta 1$ |
| 0.84314 | 0.78722 | SAA | PCT | | Const | |
| | | 6627 | −0.6192 | | 1.4185 | $\delta 0$ |
| | | 8964 | 0.2744 | | 0.1417 | $\delta 1$ |
| 0.82323 | 0.58647 | PCT | IL1ra | | Const | |
| | | −1.0932 | 601268546 | | 1.3547 | $\delta 0$ |
| | | 0.7431 | 600085479 | | 0.7175 | $\delta 1$ |

TABLE 33

| AUC (I vs. NI) | AUC (B vs. V) | | | | | |
|---|---|---|---|---|---|---|
| | | TRAIL | IP-10 | CRP | Const | |
| 0.96 | 0.94 | 0.005 | 0.0053 | 0.0555 | −1.0317 | $\delta 0$ |
| | | −0.0143 | 0.005 | 0.0884 | −0.6693 | $\delta 1$ |
| | | TRAIL | SAA | IP-10 | Const | |
| 0.96 | 0.91 | 0.0047 | 9804.469 | 0.0087 | −1.636 | $\delta 0$ |
| | | −0.0167 | 12810.9197 | 0.0085 | −0.435 | $\delta 1$ |
| | | TRAIL | IP-10 | IL1ra | Const | |
| 0.90 | 0.89 | 0.0056 | 0.0072 | 24233992.13 | −0.7474 | $\delta 0$ |
| | | −0.0282 | 0.0073 | 57162308.55 | 2.6252 | $\delta 1$ |
| | | TRAIL | PCT | IP-10 | Const | |
| 0.66 | 0.85 | 0.008 | 0.7463 | 0.0005 | 0.71 | $\delta 0$ |
| | | −0.0136 | 1.1103 | 0.001 | 2.1832 | $\delta 1$ |
| | | SAA | IP-10 | CRP | Const | |
| 0.97318 | 0.91325 | 4964.9078 | 0.0079 | 0.0389 | −1.1506 | $\delta 0$ |
| | | 6345.7097 | 0.0069 | 0.0729 | −2.7684 | $\delta 1$ |
| | | IP-10 | IL1ra | CRP | Const | |
| 0.95695 | 0.90645 | 0.0062 | −72572842.54 | 0.0635 | −0.5109 | $\delta 0$ |
| | | 0.0046 | −16278785.64 | 0.1025 | −1.6901 | $\delta 1$ |
| | | PCT | IP-10 | CRP | Const | |
| 0.8 | 0.88475 | 0.1083 | 0.0016 | 0.0598 | 0.1233 | $\delta 0$ |
| | | 0.6599 | 0.0011 | 0.1081 | −2.1504 | $\delta 1$ |
| | | SAA | IP-10 | IL1ra | Const | |
| 0.94944 | 0.85722 | 9571.3145 | 0.0094 | −141670519.4 | −0.97 | $\delta 0$ |
| | | 15309.775 | 0.008 | −119518794.5 | −1.932 | $\delta 1$ |

TABLE 33-continued

| AUC (I vs. NI) | AUC (B vs. V) | | | | | |
|---|---|---|---|---|---|---|
| | | SAA | PCT | IP-10 | Const | |
| 0.95635 | 0.79658 | 6137.1652 | −0.6596 | 0.0047 | −0.5085 | $\delta_0$ |
| | | 8580.4524 | 0.2775 | 0.004 | −1.3306 | $\delta_1$ |
| | | PCT | IP-10 | IL1ra | Const | |
| 0.73737 | 0.69549 | −1.1448 | 0.0005 | 540518195.3 | 1.0752 | $\delta_0$ |
| | | 0.7431 | −0.0003 | 578154355.6 | 0.9893 | $\delta_1$ |
| | | TRAIL | SAA | CRP | Const | |
| 0.94489 | 0.93838 | 0.0147 | 8741.563 | 0.0419 | −1.1898 | $\delta_0$ |
| | | −0.0045 | 8922.431 | 0.0715 | −0.9205 | $\delta_1$ |
| | | TRAIL | IL1ra | CRP | Const | |
| 0.92941 | 0.94316 | 0.0158 | 142723684.3 | 0.0735 | −1.1214 | $\delta_0$ |
| | | −0.0124 | 142922206.2 | 0.1005 | 0.254 | $\delta_1$ |
| | | TRAIL | PCT | CRP | Const | |
| 0.85644 | 0.91373 | 0.0132 | 0.3236 | 0.066 | −0.695 | $\delta_0$ |
| | | 0.0019 | 0.6114 | 0.1084 | −1.7666 | $\delta_1$ |
| | | TRAIL | SAA | IL1ra | Const | |
| 0.91298 | 0.91698 | 0.0165 | 13897.6693 | 19314215.49 | −1.1796 | $\delta_0$ |
| | | −0.0114 | 17471.1789 | −373899.4284 | 0.5955 | $\delta_1$ |
| | | TRAIL | SAA | PCT | Const | |
| 0.9451 | 0.85 | 0.0281 | 13902.8636 | −0.0348 | −2.1844 | $\delta_0$ |
| | | 0.0141 | 15302.3132 | 0.7361 | −1.6348 | $\delta_1$ |
| | | TRAIL | PCT | IL1ra | Const | |
| 0.73737 | 0.8797 | 0.0126 | 1.6517 | 445497461.8 | −0.3418 | $\delta_0$ |
| | | −0.0203 | 2.4203 | 638669048.4 | 2.2766 | $\delta_1$ |
| | | SAA | IL1ra | CRP | Const | |
| 0.91932 | 0.88856 | 7641.7563 | 224710899.2 | 0.0265 | 0.8638 | $\delta_0$ |
| | | 9730.7248 | 201425116.6 | 0.0536 | −1.256 | $\delta_1$ |
| | | SAA | PCT | CRP | Const | |
| 0.90588 | 0.88556 | 8520.704 | −1.4792 | 0.0207 | 1.1579 | $\delta_0$ |
| | | 7599.3621 | −0.2234 | 0.0695 | −1.3994 | $\delta_1$ |
| | | PCT | IL1ra | CRP | Const | |
| 0.84343 | 0.86842 | −0.6599 | 547844063.4 | 0.0388 | 0.8368 | $\delta_0$ |
| | | −0.1506 | 473174484.1 | 0.0873 | −1.6604 | $\delta_1$ |
| | | SAA | PCT | IL1ra | Const | |
| 0.9 | 0.81448 | 10349.4815 | −2.3088 | 565967860.9 | 1.0109 | $\delta_0$ |
| | | 15172.8663 | −0.2687 | 515166286.4 | −1.0283 | $\delta_1$ |

TABLE 34

| AUC (I vs. NI) | AUC (B vs. V) | | | | | | |
|---|---|---|---|---|---|---|---|
| | | TRAIL | SAA | IP-10 | CRP | Const | |
| 0.97 | 0.94 | 0.0058 | 5383.841 | 0.0075 | 0.0394 | −1.7981 | δ0 |
| | | −0.012 | 5731.9467 | 0.007 | 0.0702 | −1.5541 | δ1 |
| | | TRAIL | IP-10 | IL1ra | CRP | Const | |
| 0.96 | 0.94 | 0.0091 | 0.0053 | −6.995E+7 | 0.0703 | −1.5229 | δ0 |
| | | −0.0166 | 0.0046 | −3.228E+7 | 0.101 | −0.2128 | δ1 |
| | | TRAIL | PCT | IP-10 | CRP | Const | |
| 0.78667 | 0.903 | 0.0101 | 0.2921 | 0.0007 | 0.0651 | −0.6733 | δ0 |
| | | −0.0021 | 0.5293 | 0.001 | 0.1077 | −1.8383 | δ1 |
| | | TRAIL | SAA | IP-10 | IL1ra | Const | |
| 0.94957 | 0.91777 | 0.0091 | 10289.5699 | 0.0088 | 153195983.2 | −2.036 | δ0 |
| | | −0.0169 | 14282.9357 | 0.0082 | 138993063.2 | −0.2825 | δ1 |
| | | TRAIL | SAA | PCT | IP-10 | Const | |
| 0.93254 | 0.8433 | 0.0218 | 12161.0003 | −0.2264 | 0.0068 | −3.3387 | δ0 |
| | | 0.0083 | 13578.3133 | 0.5366 | 0.0068 | −2.9001 | δ1 |
| | | TRAIL | PCT | IP-10 | IL1ra | Const | |
| 0.65657 | 0.86842 | 0.0147 | 1.6805 | −0.0004 | 481673333.4 | −0.356 | δ0 |
| | | −0.0268 | 2.4993 | 0.001 | 491494579.8 | 2.4805 | δ1 |
| | | SAA | IP-10 | IL1ra | CRP | Const | |
| 0.95829 | 0.92002 | 6131.1692 | 0.0088 | −1.5446E+8 | 0.028 | −1.0249 | δ0 |
| | | 8579.4749 | 0.0067 | −9.6352E+7 | 0.0614 | −2.3655 | δ1 |
| | | SAA | PCT | IP-10 | CRP | Const | |
| 0.9881 | 0.8735 | 4377.1407 | −1.4641 | 0.0064 | 0.0419 | −1.4913 | δ0 |
| | | 3810.7522 | −0.1982 | 0.0059 | 0.0857 | −3.62 | δ1 |
| | | PCT | IP-10 | IL1ra | CRP | Const | |
| 0.74242 | 0.89098 | −0.4843 | 0.0004 | 4.54739E+8 | 0.0378 | 0.6379 | δ0 |
| | | −0.2044 | −0.0018 | 4.84865E+8 | 0.0969 | −0.7642 | δ1 |
| | | SAA | PCT | IP-10 | IL1ra | Const | |
| 0.94444 | 0.77828 | 4951.1109 | −2.8236 | 0.0095 | 212692846.6 | −0.802 | δ0 |
| | | 10430.5725 | −0.1446 | 0.008 | 210027138.1 | −2.0339 | δ1 |
| | | TRAIL | SAA | IL1ra | CRP | Const | |
| 0.92564 | 0.93742 | 0.0163 | 8701.5399 | 2.10729E+7 | 0.0386 | −1.3076 | δ0 |
| | | −0.0099 | 9890.6956 | 1.31614E+7 | 0.062 | −0.2694 | δ1 |
| | | TRAIL | SAA | PCT | CRP | Const | |
| 0.95294 | 0.91111 | 0.0253 | 11551.5028 | −1.3285 | 0.0278 | −1.8221 | δ0 |
| | | 0.0141 | 9802.9581 | −0.2648 | 0.0748 | −2.7829 | δ1 |
| | | TRAIL | PCT | IL1ra | CRP | Const | |
| 0.79798 | 0.89474 | 0.0137 | −0.1689 | 2.756E+8 | 0.0476 | −0.6344 | δ0 |
| | | −0.0264 | −0.236 | 2.7563E+8 | 0.0994 | 0.5587 | δ1 |
| | | TRAIL | SAA | PCT | IL1ra | Const | |
| 0.85556 | 0.92308 | 0.0343 | 12347.4916 | −0.5098 | 432026875.9 | −2.2741 | δ0 |
| | | −0.0152 | 19586.5686 | −0.4124 | 426850211.8 | 0.0383 | δ1 |
| | | SAA | PCT | IL1ra | CRP | Const | |
| 0.9 | 0.85068 | 2665.2949 | −0.5099 | 6.42961E+8 | 0.0552 | 0.5611 | δ0 |
| | | 3734.4091 | −0.3614 | 5.88426E+8 | 0.0941 | −1.8313 | δ1 |

TABLE 35

| AUC (I vs. NI) | AUC (B vs. V) | TRAIL | SAA | IP-10 | IL1ra | CRP | Const | |
|---|---|---|---|---|---|---|---|---|
| 0.95963 | 0.94381 | 0.0092 | 6688.18 | 0.0082 | −1.6265E+8 | 0.0336 | −2.1333 | $\delta_0$ |
| | | −0.0136 | 8261.93 | 0.0069 | −1.17187E+8 | 0.0619 | −1.1202 | $\delta_1$ |

| | | TRAIL | SAA | PCT | IP-10 | CRP | Const | |
|---|---|---|---|---|---|---|---|---|
| 0.95635 | 0.89972 | 0.0178 | 6302.89 | −1.297 | 0.0074 | 0.0517 | −3.4117 | $\delta_0$ |
| | | 0.0063 | 4437.96 | −0.249 | 0.0076 | 0.1 | −4.4957 | $\delta_1$ |

| | | TRAIL | PCT | IP-10 | IL1ra | CRP | Const | |
|---|---|---|---|---|---|---|---|---|
| 0.71717 | 0.88346 | 0.0246 | −0.2302 | −0.0017 | 5.4749E+8 | 0.0616 | −1.3864 | $\delta_0$ |
| | | −0.017 | −0.2819 | −0.0012 | 5.0261E+8 | 0.1096 | −0.1627 | $\delta_1$ |

| | | TRAIL | SAA | PCT | IP-10 | IL1ra | Const | |
|---|---|---|---|---|---|---|---|---|
| 0.85556 | 0.87783 | 0.0529 | 5922.72 | −0.7334 | 0.0149 | 2530173.292 | −6.1686 | $\delta_0$ |
| | | 0.0043 | 14225.92 | −0.282 | 0.0139 | 32115407.24 | −3.7073 | $\delta_1$ |

| | | SAA | PCT | IP-10 | IL1ra | CRP | Const | |
|---|---|---|---|---|---|---|---|---|
| 0.91111 | 0.819 | −22863.96 | −0.2611 | 0.0141 | −8.7081E+8 | 0.1586 | −2.8588 | $\delta_0$ |
| | | −18573.7 | −0.3918 | 0.008 | 7.27742E+8 | 0.2362 | −3.2596 | $\delta_1$ |

| | | TRAIL | SAA | PCT | IL1ra | CRP | Const | |
|---|---|---|---|---|---|---|---|---|
| 0.87778 | 0.90045 | 0.0397 | −7661.57 | −0.4075 | 6.98426E+8 | 0.1355 | −3.522 | $\delta_0$ |
| | | −0.008 | −4178.89 | −0.4915 | 6.53495E+8 | 0.1689 | −1.7514 | $\delta_1$ |

Example 13

Exemplified Coordinates that Include Nonlinear Functions

It was unexpectedly found by the present Inventor that incorporation of the nonlinear functions $\phi_0$ and $\phi_1$ in the calculation of the coordinates $\delta_1$ and $\delta_2$ captures more subtle trends in the data, while retaining a probabilistic framework that allows meaningful interpretation of the results. In this Example, the coordinates $\delta_0$ and $\delta_1$ were calculated according to the following equations:

$$\delta_0 = a_0 + a_1 C + a_2 I + a_3 T + \phi_0$$

$$\delta_1 = b_0 + b_1 C + b_2 I + b_3 T + \phi_1,$$

and the nonlinear functions were defined as:

$$\phi_0 = q_1 C^{\gamma_1} + q_2 C^{\gamma_2} + q_3 T^{\gamma_3}$$

$$\phi_1 = r_1 C^{\gamma_1} + r_2 C^{\gamma_2} + r_3 T^{\gamma_3}.$$

where $\gamma_1=0.5$, $\gamma_2=2$ and $\gamma_3=0.5$.

Table 36 details the coefficients and constants used in this Example.

TABLE 36

| First Coordinate $\delta_0$ (viral) | Second Coordinate $\delta_1$ (bacterial) | |
|---|---|---|
| $a_0 = -0.8388$ | $b_0 = 5.5123$ | Const |
| $a_1 = -0.0487$ | $b_1 = -0.0636$ | CRP (mg/ml) |

TABLE 36-continued

| First Coordinate $\delta_0$ (viral) | Second Coordinate $\delta_1$ (bacterial) | |
|---|---|---|
| $q_1 = 1.1367$ | $r_1 = 1.4877$ | $\text{CRP}^{0.5}$ (mg/ml)$^{0.5}$ |
| $q_2 = -5.14 \times 10^{-05}$ | $r_2 = 3.50 \times 10^{-05}$ | $\text{CRP}^2$ (mg/ml)$^2$ |
| $a_2 = 0.0089$ | $b_2 = 0.0085$ | IP10 (pg/ml) |
| $a_3 = 0.0408$ | $b_3 = 0.0646$ | TRAIL (pg/ml) |
| $q_3 = -0.6064$ | $r_3 = -1.8039$ | $\text{TRAIL}^{0.5}$ (pg/ml)$^{0.5}$ |

The performance of the model presented in Table 36 was examined on the Microbiologically Confirmed Cohort (AUC of 0.95±0.03), Unanimous Cohort (AUC of 0.95±0.02) and the Study cohort (AUC of 0.93±0.02). The signature performance improved as the size of the equivocal region increases.

Tables 37A-C below detail signature measures of accuracy for diagnosing bacterial versus viral infections when using the nonlinear model of the present Example. Performance estimates and their 95% CIs were obtained on the Microbiologically Confirmed sub-cohort (Table 37A; n=241), Unanimous sub-cohort (Table 37B; n=527), and Study Cohort (Table 37C; n=653), using different sizes of equivocal regions as indicated. Tables 37D-F below detail percentage of patients who had equivocal immune response in the Study Cohort when applying different thresholds, and Tables 37G-H below detail signature sensitivity and specificity when applying different equivocal immune response thresholds obtained on the Study Cohort. In Tables 37D-H the leftmost columns represents a minimal equivocal immune response threshold and the uppermost row represents a maximal equivocal immune response threshold.

TABLE 37A

| Equivocal immune response filter (10-90) | Equivocal immune response filter (20-80) | Equivocal immune response filter (30-70) | Equivocal immune response filter (35-65) | All patients | Accuracy measure |
|---|---|---|---|---|---|
| 0.98, (0.96, 1.00) | 0.96, (0.93, 0.99) | 0.94, (0.91, 0.97) | 0.93, (0.90, 0.97) | 0.89, (0.85, 0.93) | Total accuracy |
| 0.96, (0.90, 1.00) | 0.96, (0.91, 1.00) | 0.95, (0.89, 1.00) | 0.93, (0.87, 1.00) | 0.88, (0.80, 0.96) | Sensitivity |
| 0.99, (0.97, 1.00) | 0.96, (0.93, 0.99) | 0.94, (0.90, 0.98) | 0.94, (0.90, 0.97) | 0.90, (0.87, 0.94) | Specificity |
| 65% | 78% | 87% | 90% | 100% | % of patients included |

TABLE 37B

| Equivocal immune response filter (10-90) | Equivocal immune response filter (20-80) | Equivocal immune response filter (30-70) | Equivocal immune response filter (35-65) | All patients | Accuracy measure |
|---|---|---|---|---|---|
| 0.97, (0.95, 0.99) | 0.95, (0.93, 0.97) | 0.93, (0.90, 0.95) | 0.92, (0.89, 0.94) | 0.88, (0.85, 0.91) | Total accuracy |
| 0.96, (0.93, 0.99) | 0.93, (0.90, 0.97) | 0.91, (0.87, 0.95) | 0.90, (0.86, 0.94) | 0.85, (0.81, 0.89) | Sensitivity |
| 0.98, (0.96, 1.00) | 0.96, (0.93, 0.99) | 0.94, (0.91, 0.97) | 0.93, (0.90, 0.97) | 0.91, (0.87, 0.94) | Specificity |
| 63% | 76% | 86% | 90% | 100% | % of patients included |

TABLE 37C

| Equivocal immune response filter (10-90) | Equivocal immune response filter (20-80) | Equivocal immune response filter (30-70) | Equivocal immune response filter (35-65) | All patients | Accuracy measure |
|---|---|---|---|---|---|
| 0.95, (0.93, 0.98) | 0.92, (0.90, 0.95) | 0.90, (0.87, 0.92) | 0.89, (0.86, 0.91) | 0.85, (0.83, 0.88) | Total accuracy |
| 0.95, (0.91, 0.98) | 0.92, (0.88, 0.95) | 0.89, (0.85, 0.92) | 0.87, (0.83, 0.91) | 0.83, (0.79, 0.87) | Sensitivity |
| 0.95, (0.92, 0.98) | 0.93, (0.89, 0.96) | 0.91, (0.88, 0.95) | 0.90, (0.87, 0.94) | 0.87, (0.84, 0.91) | Specificity |
| 58% | 72% | 84% | 88% | 100% | % of patients included |

TABLE 37D

| 0.95 | 0.9 | 0.85 | 0.8 | 0.75 | 0.7 | 0.65 | 0.6 | 0.55 | 0.5 | 0.45 | 0.4 | 0.35 | 0.3 | 0.25 | 0.2 | 0.15 | 0.1 | |
|---|---|---|---|---|---|---|---|---|---|---|---|---|---|---|---|---|---|---|
| 52.8 | 47.2 | 44.0 | 40.9 | 38.6 | 36.3 | 34.8 | 33.2 | 31.2 | 29.1 | 26.3 | 24.0 | 22.7 | 20.5 | 17.6 | 13.9 | 10.4 | 6.6 | 0.05 |
| 46.2 | 40.6 | 37.4 | 34.3 | 32.0 | 29.7 | 28.2 | 26.6 | 24.7 | 22.5 | 19.8 | 17.5 | 16.1 | 13.9 | 11.0 | 7.4 | 3.8 | | 0.1 |
| 42.4 | 36.8 | 33.5 | 30.5 | 28.2 | 25.9 | 24.3 | 22.8 | 20.8 | 18.7 | 15.9 | 13.6 | 12.3 | 10.1 | 7.2 | 3.5 | | | 0.15 |
| 38.9 | 33.2 | 30.0 | 27.0 | 24.7 | 22.4 | 20.8 | 19.3 | 17.3 | 15.2 | 12.4 | 10.1 | 8.7 | 6.6 | 3.7 | | | | 0.2 |
| 35.2 | 29.6 | 26.3 | 23.3 | 21.0 | 18.7 | 17.2 | 15.6 | 13.6 | 11.5 | 8.7 | 6.4 | 5.1 | 2.9 | | | | | 0.25 |
| 32.3 | 26.6 | 23.4 | 20.4 | 18.1 | 15.8 | 14.2 | 12.7 | 10.7 | 8.6 | 5.8 | 3.5 | 2.1 | | | | | | 0.3 |
| 30.2 | 24.5 | 21.3 | 18.2 | 15.9 | 13.6 | 12.1 | 10.6 | 8.6 | 6.4 | 3.7 | 1.4 | | | | | | | 0.35 |
| 28.8 | 23.1 | 19.9 | 16.8 | 14.5 | 12.3 | 10.7 | 9.2 | 7.2 | 5.1 | 2.3 | | | | | | | | 0.4 |
| 26.5 | 20.8 | 17.6 | 14.5 | 12.3 | 10.0 | 8.4 | 6.9 | 4.9 | 2.8 | | | | | | | | | 0.45 |
| 23.7 | 18.1 | 14.9 | 11.8 | 9.5 | 7.2 | 5.7 | 4.1 | 2.1 | | | | | | | | | | 0.5 |
| 21.6 | 15.9 | 12.7 | 9.6 | 7.4 | 5.1 | 3.5 | 2.0 | | | | | | | | | | | 0.55 |
| 19.6 | 13.9 | 10.7 | 7.7 | 5.4 | 3.1 | 1.5 | | | | | | | | | | | | 0.6 |
| 18.1 | 12.4 | 9.2 | 6.1 | 3.8 | 1.5 | | | | | | | | | | | | | 0.65 |
| 16.5 | 10.9 | 7.7 | 4.6 | 2.3 | | | | | | | | | | | | | | 0.7 |
| 14.2 | 8.6 | 5.4 | 2.3 | | | | | | | | | | | | | | | 0.75 |
| 11.9 | 6.3 | 3.1 | | | | | | | | | | | | | | | | 0.8 |
| 8.9 | 3.2 | | | | | | | | | | | | | | | | | 0.85 |
| 5.7 | | | | | | | | | | | | | | | | | | 0.9 |

TABLE 37E

| 0.95 | 0.9 | 0.85 | 0.8 | 0.75 | 0.7 | 0.65 | 0.6 | 0.55 | 0.5 | 0.45 | 0.4 | 0.35 | 0.3 | 0.25 | 0.2 | 0.15 | 0.1 | |
|---|---|---|---|---|---|---|---|---|---|---|---|---|---|---|---|---|---|---|
| 53.6 | 43.6 | 38.2 | 33.5 | 29.5 | 26.0 | 23.5 | 21.6 | 18.8 | 16.6 | 13.8 | 11.3 | 10.3 | 9.1 | 7.5 | 5.3 | 3.4 | 2.5 | 0.05 |
| 51.1 | 41.1 | 35.7 | 31.0 | 27.0 | 23.5 | 21.0 | 19.1 | 16.3 | 14.1 | 11.3 | 8.8 | 7.8 | 6.6 | 5.0 | 2.8 | 0.9 | | 0.1 |
| 50.2 | 40.1 | 34.8 | 30.1 | 26.0 | 22.6 | 20.1 | 18.2 | 15.4 | 13.2 | 10.3 | 7.8 | 6.9 | 5.6 | 4.1 | 1.9 | | | 0.15 |
| 48.3 | 38.2 | 32.9 | 28.2 | 24.1 | 20.7 | 18.2 | 16.3 | 13.5 | 11.3 | 8.5 | 6.0 | 5.0 | 3.8 | 2.2 | | | | 0.2 |
| 46.1 | 36.1 | 30.7 | 26.0 | 21.9 | 18.5 | 16.0 | 14.1 | 11.3 | 9.1 | 6.3 | 3.8 | 2.8 | 1.6 | | | | | 0.25 |
| 44.5 | 34.5 | 29.2 | 24.5 | 20.4 | 16.9 | 14.4 | 12.5 | 9.7 | 7.5 | 4.7 | 2.2 | 1.3 | | | | | | 0.3 |
| 43.3 | 33.2 | 27.9 | 23.2 | 19.1 | 15.7 | 13.2 | 11.3 | 8.5 | 6.3 | 3.4 | 0.9 | | | | | | | 0.35 |
| 42.3 | 32.3 | 27.0 | 22.3 | 18.2 | 14.7 | 12.2 | 10.3 | 7.5 | 5.3 | 2.5 | | | | | | | | 0.4 |
| 39.8 | 29.8 | 24.5 | 19.7 | 15.7 | 12.2 | 9.7 | 7.8 | 5.0 | 2.8 | | | | | | | | | 0.45 |
| 37.0 | 27.0 | 21.6 | 16.9 | 12.9 | 9.4 | 6.9 | 5.0 | 2.2 | | | | | | | | | | 0.5 |
| 34.8 | 24.8 | 19.4 | 14.7 | 10.7 | 7.2 | 4.7 | 2.8 | | | | | | | | | | | 0.55 |
| 32.0 | 21.9 | 16.6 | 11.9 | 7.8 | 4.4 | 1.9 | | | | | | | | | | | | 0.6 |

TABLE 37E-continued

| 0.95 | 0.9 | 0.85 | 0.8 | 0.75 | 0.7 | 0.65 | 0.6 | 0.55 | 0.5 | 0.45 | 0.4 | 0.35 | 0.3 | 0.25 | 0.2 | 0.15 | 0.1 | |
|---|---|---|---|---|---|---|---|---|---|---|---|---|---|---|---|---|---|---|
| 30.1 | 20.1 | 14.7 | 10.0 | 6.0 | 2.5 | | | | | | | | | | | | | 0.65 |
| 27.6 | 17.6 | 12.2 | 7.5 | 3.4 | | | | | | | | | | | | | | 0.7 |
| 24.1 | 14.1 | 8.8 | 4.1 | | | | | | | | | | | | | | | 0.75 |
| 20.1 | 10.0 | 4.7 | | | | | | | | | | | | | | | | 0.8 |
| 15.4 | 5.3 | | | | | | | | | | | | | | | | | 0.85 |
| 10.0 | | | | | | | | | | | | | | | | | | 0.9 |

TABLE 37F

| 0.95 | 0.9 | 0.85 | 0.8 | 0.75 | 0.7 | 0.65 | 0.6 | 0.55 | 0.5 | 0.45 | 0.4 | 0.35 | 0.3 | 0.25 | 0.2 | 0.15 | 0.1 | |
|---|---|---|---|---|---|---|---|---|---|---|---|---|---|---|---|---|---|---|
| 52.1 | 50.6 | 49.4 | 47.9 | 47.3 | 46.1 | 45.5 | 44.3 | 43.1 | 41.0 | 38.3 | 36.2 | 34.4 | 31.4 | 27.2 | 22.2 | 17.1 | 10.5 | 0.05 |
| 41.6 | 40.1 | 38.9 | 37.4 | 36.8 | 35.6 | 35.0 | 33.8 | 32.6 | 30.5 | 27.8 | 25.7 | 24.0 | 21.0 | 16.8 | 11.7 | 6.6 | | 0.1 |
| 35.0 | 33.5 | 32.3 | 30.8 | 30.2 | 29.0 | 28.4 | 27.2 | 26.0 | 24.0 | 21.3 | 19.2 | 17.4 | 14.4 | 10.2 | 5.1 | | | 0.15 |
| 29.9 | 28.4 | 27.2 | 25.7 | 25.1 | 24.0 | 23.4 | 22.2 | 21.0 | 18.9 | 16.2 | 14.1 | 12.3 | 9.3 | 5.1 | | | | 0.2 |
| 24.9 | 23.4 | 22.2 | 20.7 | 20.1 | 18.9 | 18.3 | 17.1 | 15.9 | 13.8 | 11.1 | 9.0 | 7.2 | 4.2 | | | | | 0.25 |
| 20.7 | 19.2 | 18.0 | 16.5 | 15.9 | 14.7 | 14.1 | 12.9 | 11.7 | 9.6 | 6.9 | 4.8 | 3.0 | | | | | | 0.3 |
| 17.7 | 16.2 | 15.0 | 13.5 | 12.9 | 11.7 | 11.1 | 9.9 | 8.7 | 6.6 | 3.9 | 1.8 | | | | | | | 0.35 |
| 15.9 | 14.4 | 13.2 | 11.7 | 11.1 | 9.9 | 9.3 | 8.1 | 6.9 | 4.8 | 2.1 | | | | | | | | 0.4 |
| 13.8 | 12.3 | 11.1 | 9.6 | 9.0 | 7.8 | 7.2 | 6.0 | 4.8 | 2.7 | | | | | | | | | 0.45 |
| 11.1 | 9.6 | 8.4 | 6.9 | 6.3 | 5.1 | 4.5 | 3.3 | 2.1 | | | | | | | | | | 0.5 |
| 9.0 | 7.5 | 6.3 | 4.8 | 4.2 | 3.0 | 2.4 | 1.2 | | | | | | | | | | | 0.55 |
| 7.8 | 6.3 | 5.1 | 3.6 | 3.0 | 1.8 | 1.2 | | | | | | | | | | | | 0.6 |
| 6.6 | 5.1 | 3.9 | 2.4 | 1.8 | 0.6 | | | | | | | | | | | | | 0.65 |
| 6.0 | 4.5 | 3.3 | 1.8 | 1.2 | | | | | | | | | | | | | | 0.7 |
| 4.8 | 3.3 | 2.1 | 0.6 | | | | | | | | | | | | | | | 0.75 |
| 4.2 | 2.7 | 1.5 | | | | | | | | | | | | | | | | 0.8 |
| 2.7 | 1.2 | | | | | | | | | | | | | | | | | 0.85 |
| 1.5 | | | | | | | | | | | | | | | | | | 0.9 |

TABLE 37G

| 0.95 | 0.9 | 0.85 | 0.8 | 0.75 | 0.7 | 0.65 | 0.6 | 0.55 | 0.5 | 0.45 | 0.4 | 0.35 | 0.3 | 0.25 | 0.2 | 0.15 | 0.1 | |
|---|---|---|---|---|---|---|---|---|---|---|---|---|---|---|---|---|---|---|
| 98.0 | 98.3 | 98.5 | 98.6 | 98.7 | 98.7 | 98.8 | 98.8 | 98.8 | 98.9 | 95.6 | 92.9 | 92.0 | 90.7 | 89.2 | 87.1 | 85.4 | 84.6 | 0.05 |
| 92.9 | 94.1 | 94.6 | 95.0 | 95.3 | 95.5 | 95.6 | 95.7 | 95.9 | 96.0 | 92.9 | 90.4 | 89.5 | 88.3 | 86.8 | 84.8 | 83.2 | | 0.1 |
| 91.2 | 92.7 | 93.3 | 93.7 | 94.1 | 94.3 | 94.5 | 94.6 | 94.8 | 94.9 | 92.0 | 89.5 | 88.6 | 87.4 | 85.9 | 84.0 | | | 0.15 |
| 87.9 | 89.8 | 90.7 | 91.3 | 91.7 | 92.1 | 92.3 | 92.5 | 92.8 | 92.9 | 90.1 | 87.7 | 86.8 | 85.7 | 84.3 | | | | 0.2 |
| 84.3 | 86.8 | 87.8 | 88.6 | 89.2 | 89.6 | 89.9 | 90.1 | 90.5 | 90.7 | 88.0 | 85.7 | 84.8 | 83.8 | | | | | 0.25 |
| 81.9 | 84.7 | 85.8 | 86.7 | 87.4 | 87.9 | 88.3 | 88.5 | 88.9 | 89.2 | 86.5 | 84.3 | 83.5 | | | | | | 0.3 |
| 80.1 | 83.1 | 84.3 | 85.3 | 86.0 | 86.6 | 87.0 | 87.3 | 87.7 | 88.0 | 85.4 | 83.2 | | | | | | | 0.35 |
| 78.8 | 81.9 | 83.3 | 84.3 | 85.1 | 85.7 | 86.1 | 86.4 | 86.8 | 87.1 | 84.6 | | | | | | | | 0.4 |
| 75.5 | 79.0 | 80.5 | 81.6 | 82.5 | 83.2 | 83.7 | 84.0 | 84.5 | 84.8 | | | | | | | | | 0.45 |
| 72.1 | 76.0 | 77.6 | 78.9 | 79.9 | 80.6 | 81.1 | 81.5 | 82.1 | | | | | | | | | | 0.5 |
| 73.1 | 76.7 | 78.2 | 79.4 | 80.4 | 81.1 | 81.6 | 81.9 | | | | | | | | | | | 0.55 |
| 74.2 | 77.5 | 78.9 | 80.1 | 81.0 | 81.6 | 82.1 | | | | | | | | | | | | 0.6 |
| 74.9 | 78.0 | 79.4 | 80.5 | 81.3 | 82.0 | | | | | | | | | | | | | 0.65 |
| 75.8 | 78.7 | 80.0 | 81.0 | 81.8 | | | | | | | | | | | | | | 0.7 |
| 76.9 | 79.6 | 80.8 | 81.7 | | | | | | | | | | | | | | | 0.75 |
| 78.0 | 80.5 | 81.6 | | | | | | | | | | | | | | | | 0.8 |
| 79.3 | 81.5 | | | | | | | | | | | | | | | | | 0.85 |
| 80.5 | | | | | | | | | | | | | | | | | | 0.9 |

TABLE 37H

| 0.95 | 0.9 | 0.85 | 0.8 | 0.75 | 0.7 | 0.65 | 0.6 | 0.55 | 0.5 | 0.45 | 0.4 | 0.35 | 0.3 | 0.25 | 0.2 | 0.15 | 0.1 | |
|---|---|---|---|---|---|---|---|---|---|---|---|---|---|---|---|---|---|---|
| 97.5 | 94.5 | 92.3 | 89.7 | 88.6 | 86.7 | 85.7 | 83.9 | 82.1 | 79.2 | 80.1 | 80.8 | 81.3 | 82.1 | 83.1 | 84.2 | 85.2 | 86.3 | 0.05 |
| 97.9 | 95.5 | 93.6 | 91.4 | 90.5 | 88.8 | 88.0 | 86.4 | 84.9 | 82.3 | 83.0 | 83.5 | 83.9 | 84.5 | 85.3 | 86.1 | 86.9 | | 0.1 |
| 98.2 | 95.9 | 94.2 | 92.2 | 91.4 | 89.9 | 89.1 | 87.7 | 86.2 | 83.9 | 84.4 | 84.8 | 85.1 | 85.7 | 86.3 | 87.1 | | | 0.15 |
| 98.3 | 96.2 | 94.7 | 92.7 | 92.0 | 90.6 | 89.8 | 88.5 | 87.1 | 84.9 | 85.4 | 85.7 | 86.0 | 86.5 | 87.1 | | | | 0.2 |
| 98.4 | 96.5 | 95.0 | 93.2 | 92.5 | 91.1 | 90.5 | 89.2 | 87.9 | 85.8 | 86.2 | 86.5 | 86.8 | 87.2 | | | | | 0.25 |
| 98.5 | 96.7 | 95.3 | 93.5 | 92.9 | 91.6 | 90.9 | 89.7 | 88.5 | 86.4 | 86.8 | 87.1 | 87.3 | | | | | | 0.3 |
| 98.5 | 96.8 | 95.4 | 93.8 | 93.1 | 91.9 | 91.2 | 90.0 | 88.9 | 86.9 | 87.2 | 87.5 | | | | | | | 0.35 |
| 98.6 | 96.9 | 95.5 | 93.9 | 93.3 | 92.0 | 91.4 | 90.2 | 89.1 | 87.1 | 87.5 | | | | | | | | 0.4 |
| 98.6 | 96.9 | 95.6 | 94.0 | 93.4 | 92.2 | 91.6 | 90.4 | 89.3 | 87.4 | | | | | | | | | 0.45 |
| 98.7 | 97.0 | 95.8 | 94.2 | 93.6 | 92.4 | 91.8 | 90.7 | 89.6 | | | | | | | | | | 0.5 |
| 96.4 | 94.8 | 93.6 | 92.1 | 91.6 | 90.4 | 89.9 | 88.8 | | | | | | | | | | | 0.55 |
| 95.1 | 93.6 | 92.4 | 91.0 | 90.4 | 89.3 | 88.8 | | | | | | | | | | | | 0.6 |
| 93.9 | 92.4 | 91.3 | 89.9 | 89.3 | 88.3 | | | | | | | | | | | | | 0.65 |

TABLE 37H-continued

| | | | | | |
|---|---|---|---|---|---|
| 93.3 | 91.8 | 90.7 | 89.3 | 88.8 | 0.7 |
| 92.1 | 90.7 | 89.6 | 88.3 | | 0.75 |
| 91.6 | 90.2 | 89.1 | | | 0.8 |
| 90.2 | 88.8 | | | | 0.85 |
| 89.1 | | | | | 0.9 |

The signature performance was further examined on the Study Cohort when excluding the following two subgroups: (i) patients whose blood sample was taken after more than 3 days of antibiotic treatment in the hospital and (ii) patients with a suspected gastroenteritis. Details of the model performance on the Microbiologically Confirmed Cohort (AUC of 0.96±0.04), Unanimous Cohort (AUC of 0.96±0.02) and the Study cohort (AUC of 0.95±0.02) is further depicted in Table 38A-C.

Tables 38A-C detail signature measures of accuracy for diagnosing bacterial vs. viral infections using the non-linear MLR model. Performance estimates and their 95% CIs were obtained on the Microbiologically Confirmed sub-cohort (Table 38A; n=200), Unanimous sub-cohort (Table 38B; n=402), and Study Cohort (Table 38C; n=491), when excluding patients with over 3 days of antibiotics treatment at the hospital and/or suspicion of gastroenteritis.

TABLE 38A

| Equivocal immune response filter (10-90) | Equivocal immune response filter (20-80) | Equivocal immune response filter (30-70) | Equivocal immune response filter (35-65) | All patients | Accuracy measure |
|---|---|---|---|---|---|
| 0.98, (0.96, 1) | 0.96, (0.93, 0.99) | 0.95, (0.92, 0.99) | 0.95, (0.92, 1) | 0.91, (0.86, 0.95) | Total accuracy |
| 0.94, (87, 1) | 0.95, (0.89, 1) | 0.96, (0.89, 1) | 0.96, (0.89, 1) | 0.90, (0.82, 0.99) | Sensitivity |
| 1, (1, 1) | 0.97, (0.93, 1) | 0.95, (0.92, 0.99) | 0.95, (0.91, 0.99) | 0.91, (0.86, 0.95) | Specificity |
| 65% | 80% | 88% | 90% | 100% | % of patients included |

TABLE 38B

| Equivocal immune response filter (10-90) | Equivocal immune response filter (20-80) | Equivocal immune response filter (30-70) | Equivocal immune response filter (35-65) | All patients | Accuracy measure |
|---|---|---|---|---|---|
| 0.98, (0.96, 1) | 0.96, (0.94, 0.98) | 0.95, (0.93, 0.97) | 0.94, (0.92, 0.97) | 0.91, (0.88, 0.94) | Total accuracy |
| 0.98, (0.95, 1) | 0.95, (0.92, 0.99) | 0.94, (0.90, 0.98) | 0.93, (0.89, 0.97) | 0.89, (0.85, 0.94) | Sensitivity |
| 0.99, (0.97, 1) | 0.97, (0.94, 0.99) | 0.95, (0.93, 0.98) | 0.95, (0.92, 0.98) | 0.92, (0.88, 0.96) | Specificity |
| 65% | 79% | 88% | 91% | 100% | % of patients included |

TABLE 38C

| Equivocal immune response filter (10-90) | Equivocal immune response filter (20-80) | Equivocal immune response filter (30-70) | Equivocal immune response filter (35-65) | All patients | Accuracy measure |
|---|---|---|---|---|---|
| 0.97, (0.95, 0.99) | 0.94, (0.92, 0.97) | 0.93, (0.90, 0.95) | 0.91, (0.89, 0.94) | 0.88, (0.85, 0.91) | Total accuracy |
| 0.97, (0.94, 1) | 0.95, (0.91, 0.98) | 0.92, (0.88, 0.96) | 0.91, (0.87, 0.95) | 0.87, (0.83, 0.92) | Sensitivity |
| 0.97, (0.94, 1) | 0.94, (0.91, 0.97) | 0.93, (0.90, 0.96) | 0.92, (0.89, 0.96) | 0.89, (0.85, 0.92) | Specificity |
| 59% | 74% | 85% | 88% | 100% | % of patients included |

Example 14

Antibiotics Based Stratification

Of the 653 patients with suspicion of acute infection, 427 received antibiotics (299 had bacterial diagnosis and 128 had viral diagnosis). The AUC of the signature for distinguishing between the bacterial and viral infected patients in the antibiotics treated patients sub-cohort was 0.93±0.02. No statistically significant difference was observed between the performance on the antibiotics treated patients and the general cohort (0.94±0.02 versus 0.93±0.02; P=0.5).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of analyzing biological data, the biological data containing expression values of a plurality of polypeptides in the blood of a subject, the method comprising:

calculating by a hardware processor a distance between a segment of a curved surface and a plane defined by a first direction and a second direction, said distance being calculated at a point over said surface defined by first coordinate $\delta_0$ along said first direction and a second coordinate $\delta_1$ along said second direction; and correlating by said hardware processor said distance to the presence of, absence of, or likelihood that the subject has, a viral infection; and generating on a graphical user interface an output of said presence, absence or likelihood;

wherein each of said coordinates is defined by a different combination of said expression values, wherein at least 90% of said segment is between a lower bound surface $g(\delta_0,\delta_1)-\varepsilon_0$ and an upper bound surface $g(\delta_0,\delta_1)+\varepsilon_1$, wherein said $g(\delta_0,\delta_1)$ equals $\exp(\delta_0)/(1+\exp(\delta_0)+\exp(\delta_1))$, and wherein each of said $\varepsilon_0$ and said $\varepsilon_1$ is less than 0.5.

2. The method of claim 1, further comprising determining said expression values by a measuring system performing at least one assay selected from the group consisting of an automated ELISA, an automated immunoassay, and an automated functional assay, and the method comprises receiving said the biological data from said measuring system.

3. The method according to claim 1, wherein each of said plurality of polypeptides is selected from the group consisting of CRP, IP-10, TRAIL, IL1ra, PCT and SAA.

4. The method according to claim 1, wherein said plurality of polypeptides comprises at least three polypeptides.

5. The method according to claim 1, wherein said plurality of polypeptides comprises at least three polypeptides selected from the group consisting of CRP, IP-10, TRAIL, IL1ra, PCT and SAA.

6. The method according to claim 1, wherein said plurality of polypeptides comprises at least CRP and TRAIL.

7. The method according to claim 1, wherein said plurality of polypeptides comprises at least TRAIL and IP-10.

8. The method according to claim 1, wherein said plurality of polypeptides comprises at least CRP, TRAIL and IP-10.

9. A computer software product, comprising a computer-readable medium in which program instructions are stored, which instructions, when read by a hardware processor, cause the hardware processor to receive expression values of a plurality of polypeptides in the blood of a subject who has an unknown disease, and to execute the method according to claim 1.

10. A system for analyzing biological data, the system comprising:

a user and/or network interface which receives expression values of a plurality of polypeptides being measured in a blood sample of a subject who has an unknown disease by a measuring system performing at least one assay selected from the group consisting of an automated ELISA, an automated immunoassay, and an automated functional assay; and a hardware processor having a computer-readable medium storing the computer software product of claim 9.

11. A method of analyzing biological data, the biological data containing expression values of a plurality of polypeptides in the blood of a subject, the method comprising:

calculating by a hardware processor a distance between a segment of a curved line and an axis defined by a direction and storing said distance in a memory, said distance being calculated at a point over said curved line defined by a coordinate oi along said direction;

by said hardware processor, correlating said distance to the presence of, absence of, or likelihood that the subject has, a viral infection; and generating on a graphical user interface an output of said presence, absence or likelihood;

wherein said coordinate is defined by a combination of said expression values, wherein at least 90% of said segment is between a lower bound line $f(\delta_1)-\varepsilon_0$ and an upper bound line $f(\delta_1)+\varepsilon_1$, wherein said $f(\delta_1)$ equals $1/(1+\exp(\delta_1))$, and wherein each of said $\varepsilon_0$ and said $\varepsilon_1$ is less than 0.5.

12. The method according to claim 11, wherein each of said plurality of polypeptides is selected from the group consisting of CRP, IP-10, TRAIL, IL1ra, PCT and SAA.

13. The method according to claim 11, wherein said plurality of polypeptides comprises at least three polypeptides.

14. The method according to claim 11, wherein said plurality of polypeptides comprises at least three polypeptides selected from the group consisting of CRP, IP-10, TRAIL, IL1ra, PCT and SAA.

15. The method according to claim 11, wherein said plurality of polypeptides comprises at least CRP and TRAIL.

16. The method according to claim 11, wherein said plurality of polypeptides comprises at least TRAIL and IP-10.

17. The method according to claim 11, wherein said plurality of polypeptides comprises at least CRP, TRAIL and IP-10.

18. A computer software product, comprising a computer-readable medium in which program instructions are stored, which instructions, when read by a hardware processor, cause the hardware processor to receive expression values of a plurality of polypeptides in the blood of a subject who has an unknown disease, and to execute the method according to claim 11.

19. A system for analyzing biological data, the system comprising:

a user and/or network interface which receives expression values of a plurality of polypeptides being measured in a blood sample of a subject who has an unknown disease by a measuring system performing at least one assay selected from the group consisting of an automated ELISA, an automated immunoassay, and an automated functional assay; and a hardware processor having a computer-readable medium storing the computer software product of claim 18.

20. A method of treating a disease in a subject, the method comprising:

(a) measuring the amount of TRAIL protein in a blood sample of the subject, wherein when the amount of TRAIL in the subject is below a predetermined level, the method further comprises:

(b) treating the subject with a treatment of last resort, thereby treating the disease.

21. The method of claim 20, wherein said predetermined level is below about 20 pg/ml.

22. The method of claim 20, wherein said disease is a viral disease.

23. The method of claim 20, further comprising measuring the amount of CRP and IP10.

24. The method of claim 20, comprising treating the subject by an antiviral agent.

* * * * *